(12) United States Patent
Brånalt et al.

(10) Patent No.: US 12,729,196 B2
(45) **Date of Patent: *Sep. 8, 2026**

(54) N-(2-(4-CYANOTHIAZOLIDIN-3-YL)-2-OXOETHYL)-QUINOLINE-4-CARBOXAMIDES

(71) Applicant: AstraZeneca AB, Södertälje (SE)

(72) Inventors: Jonas Brånalt, Gothenberg (SE); Björn Holm, Gothenberg (SE); Maria Johansson, Gothenberg (SE); Olle Karlsson, Gothenberg (SE); Daniel Laurent Knerr, Gothenberg (SE); Anneli Nordqvist, Gothenberg (SE); Robert John Sheppard, Gothenberg (SE); Marianne Swanson, Gothenberg (SE); Anna Tomberg, Gothenberg (SE)

(73) Assignee: AstraZeneca AB, Södertälje (SE)

( * ) Notice: Subject to any disclaimer, the term of this patent is extended or adjusted under 35 U.S.C. 154(b) by 504 days.

This patent is subject to a terminal disclaimer.

(21) Appl. No.: 18/257,123

(22) PCT Filed: Dec. 16, 2021

(86) PCT No.: PCT/IB2021/061839

§ 371 (c)(1),
(2) Date: Jun. 13, 2023

(87) PCT Pub. No.: WO2022/130270

PCT Pub. Date: Jun. 23, 2022

(65) Prior Publication Data

US 2024/0101549 A1 Mar. 28, 2024

Related U.S. Application Data

(60) Provisional application No. 63/126,593, filed on Dec. 17, 2020.

(51) Int. Cl.

| | |
|---|---|
| ***C07D 417/12*** | (2006.01) |
| ***A61P 1/16*** | (2006.01) |
| ***C07D 417/14*** | (2006.01) |
| ***C07D 487/04*** | (2006.01) |
| ***C07D 487/10*** | (2006.01) |
| ***C07D 491/107*** | (2006.01) |
| ***C07D 491/113*** | (2006.01) |
| ***C07D 493/10*** | (2006.01) |
| ***C07D 495/10*** | (2006.01) |
| ***C07D 498/08*** | (2006.01) |

(52) U.S. Cl.

CPC .............. *C07D 417/12* (2013.01); *A61P 1/16* (2018.01); *C07D 417/14* (2013.01); *C07D 487/04* (2013.01); *C07D 487/10* (2013.01); *C07D 491/107* (2013.01); *C07D 491/113* (2013.01); *C07D 493/10* (2013.01); *C07D 495/10* (2013.01); *C07D 498/08* (2013.01)

(58) Field of Classification Search

CPC .. C07D 417/12; C07D 417/14; C07D 487/04; C07D 487/10; C07D 493/10; C07D 495/10; C07D 498/08; C07D 491/107; C07D 491/113; A61P 1/16

See application file for complete search history.

(56) References Cited

U.S. PATENT DOCUMENTS

| | | |
|---|---|---|
| 6,680,282 B2 | 1/2004 | Yamamoto et al. |
| 7,060,722 B2 | 6/2006 | Kitajima et al. |
| 7,067,668 B2 | 6/2006 | Yamamoto et al. |
| 7,074,794 B2 | 7/2006 | Kitajima et al. |

(Continued)

FOREIGN PATENT DOCUMENTS

| | | |
|---|---|---|
| AU | 2015315174 B2 | 9/2015 |
| CN | 108690043 A | 10/2018 |

(Continued)

OTHER PUBLICATIONS

Int'l Search Report and Written Opinion for PCT/IB2021/061839 mailed Mar. 9, 2022.

(Continued)

*Primary Examiner* — Rebecca L Anderson

(74) *Attorney, Agent, or Firm* — Arnold & Porter Kaye Scholer LLP

(57) ABSTRACT

Compounds having the structure of Formula (I): and pharmaceutically acceptable salts thereof, wherein $X^1$, $R^1$, $R^2$, $R^3$, $R^4$, $R^5$ and $R^6$ are as defined in the specification; pharmaceutical compositions comprising such compounds and salts; use of such compounds and salts to treat or prevent Prolyl endopeptidase fibroblast activation protein (FAP)-mediated conditions; kits comprising such compounds and salts; and methods for manufacturing such compounds and salts.

Formula (I)

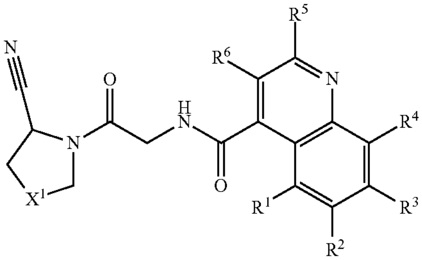

20 Claims, No Drawings

(56) References Cited

U.S. PATENT DOCUMENTS

| | | | | |
|---|---|---|---|---|
| 7,335,677 | B2 | 2/2008 | Evans et al. | |
| 7,345,180 | B2 | 3/2008 | Kakigami et al. | |
| 7,829,501 | B2 | 11/2010 | Nakamura et al. | |
| 8,039,420 | B2 | 10/2011 | Nakamura et al. | |
| 8,067,436 | B2 | 11/2011 | Bannen et al. | |
| 8,183,280 | B2 | 5/2012 | Evans et al. | |
| 9,346,814 | B2 | 5/2016 | Jansen et al. | |
| 10,266,526 | B2 | 4/2019 | Foley et al. | |
| 11,858,924 | B2 * | 1/2024 | Brånalt | C07D 498/08 |
| 2020/0157114 | A1 | 5/2020 | Kamioka et al. | |

FOREIGN PATENT DOCUMENTS

| | | | |
|---|---|---|---|
| EP | 1776011 | B1 | 8/2005 |
| EP | 1760076 | A1 | 3/2007 |
| EP | 3666770 | A1 | 6/2020 |
| JP | 2003026698 | A | 1/2003 |
| WO | 1998055460 | A1 | 12/1998 |
| WO | 2001002385 | A1 | 1/2001 |
| WO | 0134594 | A1 | 5/2001 |
| WO | 2001058871 | A1 | 8/2001 |
| WO | 2001081304 | A1 | 11/2001 |
| WO | 2001081337 | A1 | 11/2001 |
| WO | 2002014271 | A1 | 2/2002 |
| WO | 2003035057 | A1 | 5/2003 |
| WO | 2004067509 | A1 | 8/2004 |
| WO | 2004071454 | A2 | 8/2004 |
| WO | 2005087742 | A1 | 9/2005 |
| WO | 2006016708 | A1 | 2/2006 |
| WO | 2007017423 | A2 | 2/2007 |
| WO | 2007085895 | A2 | 8/2007 |
| WO | 2008064218 | A2 | 5/2008 |
| WO | 2011111875 | | 9/2011 |
| WO | 2013033396 | A2 | 3/2013 |
| WO | 2013050454 | A1 | 4/2013 |
| WO | 2013107820 | A1 | 7/2013 |
| WO | 2014016849 | A2 | 1/2014 |
| WO | 2015144093 | A1 | 10/2015 |
| WO | 2015164374 | A1 | 10/2015 |
| WO | 2016040505 | A1 | 3/2016 |
| WO | 2017189569 | A1 | 11/2017 |
| WO | 2018053267 | A1 | 3/2018 |
| WO | 2018111989 | A1 | 6/2018 |
| WO | 2018161033 | A1 | 9/2018 |
| WO | 2018195439 | A2 | 10/2018 |
| WO | 2018237349 | A1 | 12/2018 |
| WO | 2019031990 | A1 | 2/2019 |
| WO | 2019084271 | A1 | 5/2019 |
| WO | 2019118932 | A1 | 6/2019 |
| WO | 2019125849 | A1 | 6/2019 |
| WO | 2019154886 | A1 | 8/2019 |
| WO | 2020025517 | A1 | 2/2020 |
| WO | 2020032105 | A1 | 2/2020 |
| WO | 2020045334 | A1 | 3/2020 |
| WO | 2020132661 | A2 | 6/2020 |
| WO | 2021060453 | A1 | 4/2021 |
| WO | 2021090245 | A1 | 5/2021 |
| WO | 2022130270 | A1 | 6/2022 |

OTHER PUBLICATIONS

Int'l Search Report and Written Opinion for PCT/EP2023/066560 mailed Aug. 30, 2023.

Int'l Search Report and Written Opinion for PCT/EP2023/066561 mailed Aug. 30, 2023.

Dong, et al., Synthesis and biological activities of fluorescent acridine-containing HIV-1 nucleocapsid proteins for investigation of nucleic acid-NCp7 interactions, J. Peptide Res., 1997, v. 50, pp. 269-278.

Dwyer, et al., Discovery of pyrazolo[1,5-a]pyrimidine-based Pim inhibitors: A template-based approach, Bioorganic & Medicinal Chem. Ltrs., 2013, v. 23, pp. 6178-6182.

Jansen, et al., J. Med. Chem., Extended Structure—Activity Relationship and Pharmacokinetic Investigation of (4-Quinolinoyl)glycyl-2-cyanopyrrolidine Inhibitors of Fibroblast Activation Protein (FAP), J. Med. Chem., 2014, v.57, pp. 3053-3074.

Kushwaha, et al., Design, Synthesis, Biological Screening, and Molecular Docking Studies of Piperazine-Derived Constrained Inhibitors of DPP-IV for the Treatment of Type 2 Diabetes, Chem. Biol. Drug Des., 2015, v. 85, pp. 439-446.

Berge et al., "Pharmaceutical Salts," *Journal of Pharmaceutical Sciences*, 66(1), pp. 1-19 (Jan. 1977) (Amsterdam, Netherlands).

Bradbury et al., "New nonpeptide angiotensin II receptor antagonists. 2. Synthesis, biological properties, and structure-activity relationships of 2-alkyl-4-(biphenylylmethoxy)quinoline derivatives," *Journal of Medicinal Chemistry*, 35(22), pp. 4027-4038 (Oct. 1992) (Washington, DC).

Chalasani et al., "The diagnosis and management of nonalcoholic fatty liver disease: Practice guidance from the American Association for the Study of Liver Diseases," *Hepatology*, 67(1), pp. 328-357 (Jan. 2018) (Amsterdam, Netherlands).

De Willige et al., "Increased N-terminal cleavage of alpha-2-antiplasmin in patients with liver cirrhosis," *Journal of Thrombosis Haemostasis*, 11(11), pp. 2029-2036 (Nov. 2013) (Amsterdam, Netherlands).

Fan et al., "Fibroblast Activation Protein (FAP) Accelerates Collagen Degradation and Clearance from Lungs in Mice," *The Journal of Biological Chemistry*, 291(15), pp. 8070-8089 (Apr. 2016) (Rockville, Maryland).

Fredlund et al., "In Vitro Intrinsic Permeability: A Transporter-Independent Measure of Caco-2 Cell Permeability in Drug Design and Development," *Molecular Pharmaceutics*, 14(5), pp. 1601-1609 (May 2017) (Washington, DC).

Hamson et al., "Understanding fibroblast activation protein (FAP): substrates, activities, expression and targeting for cancer therapy," *Proteomics Clinical Applications*, 8(5-6), pp. 454-463 (Jun. 2014) (Hoboken, New Jersey).

Lee et al., "A novel plasma proteinase potentiates alpha2-antiplasmin inhibition of fibrin digestion," *Blood*, 103(10), pp. 3783-3788 (May 2004) (Washington, DC).

Levy et al., "Fibroblast activation protein: a cell surface dipeptidyl peptidase and gelatinase expressed by stellate cells at the tissue remodelling interface in human cirrhosis," *Hepatology*, 29(6), pp. 1768-1778 (Jun. 1999) (Alexandria, Virginia).

Lin et al., "Therapeutics targeting the fibrinolytic system," *Experimental & Molecular Medicine*, 52(3), pp. 367-379 (Mar. 2020) (Berlin, Germany).

Matsuda et al., "Insulin sensitivity indices obtained from oral glucose tolerance testing: comparison with the euglycemic insulin clamp," *Diabetes Care*, 22(9), pp. 1462-1470 (Sep. 1999) (Arlington, Virginia).

Matthews et al., "Homeostasis model assessment: insulin resistance and beta-cell function from fasting plasma glucose and insulin concentrations in man," *Diabetologia*, 28(7), pp. 412-419 (Jul. 1985) (Berlin, Germany).

Sohlenius-Sternbeck et al., "Evaluation of the human prediction of clearance from hepatocyte and microsome intrinsic clearance for 52 drug compounds," *Xenobiotica*, 40(9), pp. 637-649 (Sep. 2010) (London, United Kingdom).

Taylor et al., "Association Between Fibrosis Stage and Outcomes of Patients With Nonalcoholic Fatty Liver Disease: A Systematic Review and Meta-Analysis," *Gastroenterology*, 158(6), pp. 1611-1625.e12, (May 2020) (Amsterdam, Netherlands).

Truffi et al., "Inhibition of Fibroblast Activation Protein Restores a Balanced Extracellular Matrix and Reduces Fibrosis in Crohn's Disease Strictures Ex Vivo," *Inflammatory Bowel Diseases*, 24(2), pp. 332-345 (Jan. 2018) (Oxford, United Kingdom).

Williams et al., "Lower serum fibroblast activation protein shows promise in the exclusion of clinically significant liver fibrosis due to non-alcoholic fatty liver disease in diabetes and obesity," *Diabetes Research Clinical Practice*, 108(3), pp. 466-472 (Jun. 2015) (Amsterdam, Netherlands).

Winiwarter et al., "Time dependent analysis of assay comparability: a novel approach to understand intra- and inter-site variability over time," *Journal of Computer-Aided Molecular Design*, 29(9), pp. 795-807 (Sep. 2015) (Berlin, Germany).

(56) References Cited

OTHER PUBLICATIONS

Zhen et al., "Circulating FGF21 proteolytic processing mediated by fibroblast activation protein," *Biochemical Journal*, 473(5), pp. 605-614 (Mar. 2016) (London, United Kingdom).
Zientek et al., "In Vitro-In Vivo Correlation for Intrinsic Clearance for Drugs Metabolized by Human Aldehyde Oxidase," *Drug Metabolism and Disposition*, 38(8), pp. 1322-1327 (Aug. 2010) (Rockville, Maryland).

* cited by examiner

N-(2-(4-CYANOTHIAZOLIDIN-3-YL)-2-OXOETHYL)-QUINOLINE-4-CARBOXAMIDES

CROSS-REFERENCE TO RELATED APPLICATIONS

This application is a U.S. National Stage Application of International Application No. PCT/IB2021/061839, filed on Dec. 16, 2021, which claims the benefit under 35 U.S.C. § 119(e) of U.S. Provisional Application No. 63/126,593 filed on Dec. 17, 2020.

FIELD

The present disclosure relates generally to N-(2-(4-cyanothiazolidin-3-yl)-2-oxoethyl)-quinoline-4-carboxamides and pharmaceutically acceptable salts thereof. The specification further relates to pharmaceutical compositions comprising such compounds and salts; use of such compounds and salts to treat or prevent Prolyl endopeptidase fibroblast activation protein (FAP)-mediated conditions; kits comprising such compounds and salts; and methods for manufacturing such compounds and salts.

BACKGROUND

FAP, a type II transmembrane serine protease, is expressed by fibroblast like cells involved in tissue remodeling and healing. In the context of non-alcoholic steatohepatitis (NASH), FAP is upregulated on the cell surface of activated hepatic stellate cells involved in the fibrosis formation (*Hepatology* 1999, 29, 1768), a major aspect of NASH that predicts disease outcome (*Gastroenterology* 2020, 158, 1611). FAP also can be present as a shedded plasma protease. Increased levels of circulating FAP are associated with NASH disease severity (*Diabetes Res Clin Pract* 2015, 108, 466).

FAP has a consensus cleavage motif after Gly-Pro and exhibits both endopeptidase and exopeptidase activity. Known enzymatic activities include cleavage of collagens (*Hepatology* 1999, 29, 1768), α2-antiplasmin (α2AP) (*Blood* 2004 103, 3783), and fibroblast growth factor 21 (FGF21) (*Biochem J* 2016, 473, 605). FAP activity at the cell surface of activated fibroblasts (including cleavage of collagens) generates a pro-fibrotic environment. FAP cleavage of α2AP gives a more efficient cross-linking of α2AP to fibrin and results in reduced fibrin clearance. FAP cleavage of FGF21 inactivates FGF21 metabolic effects (*Biochem J* 2016, 473, 605). All these activities are associated with a worsening of NASH disease and inhibiting FAP has the potential to treat NASH and other conditions by affecting multiple mechanisms.

Inhibition of FAP activity is a presently unexploited therapeutic approach for treating NASH and other diseases associated with such activity. No approved pharmacological agents that inhibit FAP activity generally, or that inhibit FAP activity specifically, are currently available. Accordingly, there is a need for FAP inhibitors, particularly FAP inhibitors that have pharmacologically appropriate selectivity and bioavailability and therefore are suitable for administration to a subject in need of such treatment. The present disclosure addresses this large unmet need by providing such compounds together with corresponding pharmaceutical compositions and methods for the treatment or prevention of NASH and related conditions.

SUMMARY

In one aspect, the present disclosure provides compounds having the structure of Formula (I):

(I)

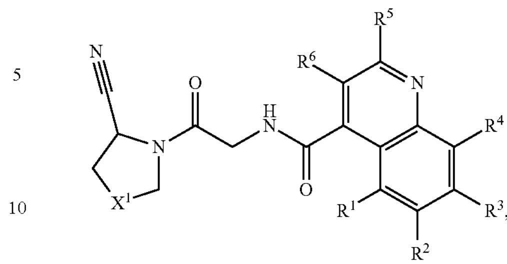

and pharmaceutically acceptable salts thereof, wherein:

$X^1$ is selected from the group consisting of —S—, —S(O)—, and —$S(O)_2$—;

$R^1$ is selected from the group consisting of hydrogen, halogen, hydroxy, $C_{1-3}$-alkyl, and $C_{1-6}$-alkoxy;

$R^2$ is selected from the group consisting of:

(a) heterocyclyl containing a total of 4 to 10 ring atoms, wherein the heterocyclyl ring: (i) is a saturated, partially saturated, or completely unsaturated monocyclic or fused bicyclic ring, (ii) has one, two, or three nitrogen ring atoms with the remaining ring atoms being carbon, and (iii) is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy;

(b) heterocyclyl containing a total of 5 to 10 ring atoms, wherein the heterocyclyl ring: (i) is a saturated, partially saturated, or completely unsaturated monocyclic or fused bicyclic ring, (ii) has (a) one nitrogen ring atom and one oxygen ring atom with the remaining ring atoms being carbon, or (b) one nitrogen ring atom and one sulfur ring atom with the remaining ring atoms being carbon, and (iii) is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen; and (c) spiro heterocyclyl containing a total of 6 to 11 ring atoms, wherein the spiro heterocyclyl: (i) comprises two saturated rings, (ii) has: (a) one or two nitrogen ring atoms with the remaining ring atoms being carbon, (b) one or two nitrogen ring atoms and one or two oxygen ring atoms with the remaining ring atoms being carbon, or (c) one nitrogen ring atom and one sulfur ring atom with the remaining ring atoms being carbon, and (iii) is optionally substituted with one or more substituents independently selected from the group consisting of halogen, oxo, $C_{1-6}$-alkyl, $C_{1-6}$-haloalkyl, $C_{1-6}$-alkoxy, $C_{1-6}$-haloalkoxy, and $C_{1-6}$-alkylcarbonyl;

$R^3$ is selected from the group consisting of hydrogen, halogen, and $C_{1-3}$-alkyl;

$R^4$ is selected from the group consisting of hydrogen, halogen, and $C_{1-3}$-alkyl;

$R^5$ is selected from the group consisting of hydrogen, halogen, and $C_{1-3}$-alkyl; and $R^6$ is selected from the group consisting of hydrogen, halogen, and $C_{1-3}$-alkyl.

In another aspect, the present disclosure provides compounds having the structure of Formulae (II), (III-A), (III-B), (III-C), (III-D), (III-E), (IV), (IV-A), (V), (VI), (VII), (VIII), (IX), (X), or (XI) as further defined herein, and pharmaceutically acceptable salts thereof.

In another aspect, the present disclosure provides pharmaceutical compositions comprising a therapeutically-effective amount of a compound having the structure of Formulae (I), (II), (III-A), (III-B), (III-C), (III-D), (III-E), (IV), (IV-A), (V), (VI), (VII), (VIII), (IX), (X), or (XI), or a pharmaceutically acceptable salt thereof, and a pharmaceutically acceptable carrier.

In another aspect, the present disclosure provides pharmaceutical compositions comprising therapeutically-effective amounts of a compound having the structure of Formulae (I), (II), (III-A), (III-B), (III-C), (III-D), (III-E), (IV), (IV-A), (V), (VI), (VII), (VIII), (IX), (X), or (XI), or a pharmaceutically acceptable salt thereof; a second pharmacological agent; and a pharmaceutically acceptable carrier.

In another aspect, the present disclosure provides methods for treating or preventing an FAP-mediated condition by administering a therapeutically effective amount of a compound having the structure of Formulae (I), (II), (III-A), (III-B), (III-C), (III-D), (III-E), (IV), (IV-A), (V), (VI), (VII), (VIII), (IX), (X), or (XI), or pharmaceutically acceptable salt thereof, to a subject in need thereof. In a further aspect, the FAP-mediated condition is selected from the group consisting of liver disease, type 2 diabetes mellitus, cardiovascular conditions, obesity, obesity-related conditions, fibrosis, keloid disorder, inflammation, and cancer. In a still further aspect, the FAP-mediated condition is liver disease, particularly nonalcoholic steatohepatitis (NASH).

In another aspect, the present disclosure provides compounds having the structure of Formulae (I), (II), (III-A), (III-B), (III-C), (III-D), (III-E), (IV), (IV-A), (V), (VI), (VII), (VIII), (IX), (X), or (XI), or pharmaceutically acceptable salts thereof, for use as medicaments for treating or preventing an FAP-mediated condition.

In another aspect, the present disclosure provides use of compounds having the structure of Formulae (I), (II), (III-A), (III-B), (III-C), (III-D), (III-E), (IV), (IV-A), (V), (VI), (VII), (VIII), (IX), (X), or (XI), or pharmaceutically acceptable salts thereof, to prepare medicaments for treating or preventing an FAP-mediated condition.

In another aspect, the present disclosure provides kits comprising a compound having the structure of Formulae (I), (II), (III-A), (III-B), (III-C), (III-D), (III-E), (IV), (IV-A), (V), (VI), (VII), (VIII), (IX), (X), or (XI), or pharmaceutically acceptable salt thereof.

In another aspect, the present disclosure provides methods for preparing compounds having the structure of Formulae (I), (II), (III-A), (III-B), (III-C), (III-D), (III-E), (IV), (IV-A), (V), (VI), (VII), (VIII), (IX), (X), or (XI), or pharmaceutically acceptable salts thereof.

DETAILED DESCRIPTION

Many embodiments are detailed throughout the specification and will be apparent to a reader skilled in the art. The specification is not to be interpreted as being limited to any particular embodiment(s) described herein.

I. Definitions

With respect to the embodiments disclosed in this specification, the following terms have the meanings set forth below:

Reference to "a" or "an" means "one or more." Throughout, the plural and singular should be treated as interchangeable, other than the indication of number.

Unless the context requires otherwise, the words "comprise" or "comprises" or "comprising" are used on the basis and clear understanding that they are to be interpreted inclusively, rather than exclusively, and that Applicants intend each of those words to be so interpreted in construing this patent, including the claims below.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I).

The term "hydroxy" (alone or in combination with another term(s)) means —OH.

The term "cyano" (alone or in combination with another term(s)) means —CN.

The term "oxo" (alone or in combination with another term(s)) means an oxo radical, and may be depicted as =O.

The term "alkyl" (alone or in combination with another term(s)) means a straight- or branched-chain saturated hydrocarbyl substituent (i.e., a substituent containing only carbon and hydrogen). Alkyl typically contains from 1 to about 20 carbon atoms, more typically from 1 to about 12 carbon atoms, even more typically from 1 to about 8 carbon atoms, and still even more typically from 1 to about 6 carbon atoms. Examples of such substituents include methyl, ethyl, n-propyl, isopropyl, n-butyl, isobutyl, sec-butyl, tert-butyl, pentyl, iso-amyl, 2,2,-dimethylpropyl, hexyl, heptyl, and octyl.

The term "cycloalkyl" (alone or in combination with another term(s)) means a saturated carbocyclyl substituent containing from 3 to about 14 carbon ring atoms, more typically from 3 to about 12 carbon ring atoms, and even more typically from 3 to about 8 carbon ring atoms. A cycloalkyl includes a single carbon ring, which typically contains from 3 to 6 carbon ring atoms. Examples of single-ring cycloalkyls include cyclopropyl, cyclobutyl, cyclopentyl, and cyclohexyl.

The term "cycloalkylalkyl" (alone or in combination with another term(s)) means an alkyl substituted with cycloalkyl.

Examples of such substituents include cyclopropylmethyl, cyclobutylmethyl, cyclopentylmethyl, and cyclohexylmethyl.

The term "alkoxy" (alone or in combination with another term(s)) means an alkylether substituent, i.e., alkyl-O—. Examples of alkoxy include methoxy ($CH_3$—O—), ethoxy, n-propoxy, iso-propoxy, n-butoxy, iso-butoxy, sec-butoxy, and tert-butoxy. Thus, for example:

(i) the term "alkoxyalkyl" (alone or in combination with another term(s)) means alkyl substituted with alkoxy such as "methoxymethyl" which may be depicted as:

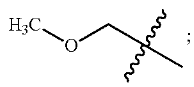

;

(ii) the term "cycloalkylalkoxy" (alone or in combination with another term(s)) means alkoxy substituted with cycloalkyl such as "cyclopropylmethoxy" which may be depicted as:

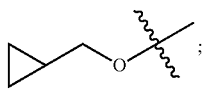 [SMILES: *OCC1CC1]

;

(iii) the term "alkoxyalkoxy" (alone or in combination with another term(s)) means alkoxy substituted with another alkoxy such as "methoxyethoxy" which may be depicted as:

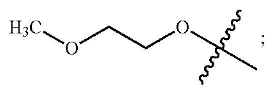 [SMILES: *OCCOC]

;

(iv) the term "alkoxyalkoxyalkyl" (alone or in combination with another term(s)) means alkyl substituted with alkoxyalkoxy such as "methoxyethoxymethyl" which may be depicted as:

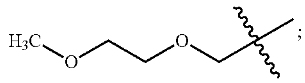 [SMILES: *COCCOC]

;

(v) the term "alkoxyphenyl" (alone or in combination with another term(s)) means phenyl substituted with alkoxy such as "4-methoxyphenyl" which may be depicted as:

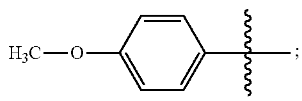 [SMILES: *c1ccc(OC)cc1]

;

and (vi) the term "alkoxyphenylalkyl" (alone or in combination with another term(s)) means alkyl substituted with alkoxyphenyl such as "4-methoxyphenylmethyl" which may be depicted as:

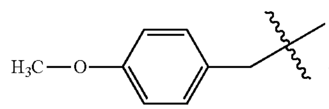

.

In some instances, the number of carbon atoms in a substituent (e.g., alkyl, cycloalkyl, etc.) is indicated by the prefix "$C_{x-y}$—", wherein x is the minimum and y is the maximum number of carbon atoms in the substituent. Thus, for example, "$C_{1-6}$-alkyl" refers to an alkyl substituent containing from 1 to 6 carbon atoms. Illustrating further, $C_{3-6}$-cycloalkyl refers to a cycloalkyl substituent containing from 3 to 6 carbon ring atoms.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Where there are more than one hydrogens replaced with halogens, the halogens may be the identical or different. Examples of haloalkyls include fluoromethyl, difluoromethyl, trifluoromethyl, difluoroethyl, 1,1,1-trifluoroethyl, pentafluoroethyl, difluoropropyl, heptafluoropropyl chloromethyl, dichloromethyl, trichloromethyl, difluorochloromethyl, dichlorofluoromethyl, and dichloropropyl. Similarly, "haloalkoxy" means an alkoxy substituent wherein at least one hydrogen radical is replaced by a halogen radical. Where there are more than one hydrogens replaced with halogens, the halogens may be the identical or different. Examples of haloalkoxy substituents include fluoromethoxy, difluoromethoxy, trifluoromethoxy (also known as "perfluoromethyloxy"), 1,1,1,-trifluoroethoxy, and chloromethoxy.

The term "carbonyl" (alone or in combination with another term(s)) means —C(O)—, which also may be depicted as:

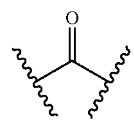

.

Thus, for example:

(i) the term "alkylcarbonyl" (alone or in combination with another term(s)) means alkyl-C(O)— such as "methylcarbonyl" (i.e., acetyl) which may be depicted as:

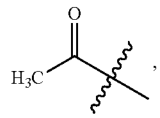 [SMILES: *C(C)=O]

, and other alkylcarbonyl substituents such as ethylcarbonyl, propylcarbonyl, butylcarbonyl, pentylcarbonyl, and hexylcarbonyl;

(ii) the term "alkylcarbonylalkyl" (alone or in combination with another term(s)) means alkyl substituted with alkylcarbonyl such as "methylcarbonylmethyl" which may be depicted as:

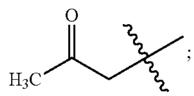

(iii) the term "cycloalkylcarbonyl" (alone or in combination with another term(s)) means cycloalkyl-C(O)— such as "cyclopropylcarbonyl" which may be depicted as:

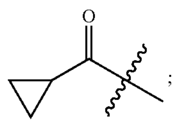 [SMILES: *C(=O)C1CC1]

and (iv) the term "cycloalkylcarbonylalkyl" (alone or in combination with another term(s)) means alkyl substituted with cycloalkylcarbonyl such as "cyclopropylcarbonylmethyl" which may be depicted as:

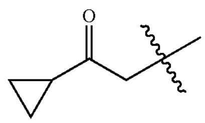

The term "thio" or "thia" (alone or in combination with another term(s)) means a divalent sulfur atom, which also may be depicted as —S—.

The term "sulfinyl" or "sulfoxido" (alone or in combination with another term(s)) means —S(O)—, which also may be depicted as:

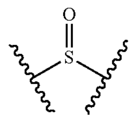 [SMILES: *S(*)=O]

The term "sulfonyl" (alone or in combination with another term(s)) means $—S(O)_2—$, which also may be depicted as:

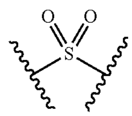

Thus, for example, "alkylsulfonyl" (alone or in combination with another term(s)) means alkyl-$S(O)_2$—. Examples of alkylsulfonyl substituents include methylsulfonyl, ethylsulfonyl, and propylsulfonyl. Similarly, the term "alkylsulfonylalkyl" (alone or in combination with another term(s)) means alkyl substituted with alkylsulfonyl such as "methylsulfonylmethyl" may be depicted as:

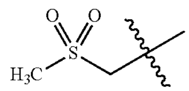

The term "alkylcarbonylaminoalkyl" (alone or in combination with another term(s)) means alkyl-C(O)—N(H)-alkyl- such as "methylcarbonylaminomethyl" which also may be depicted as:

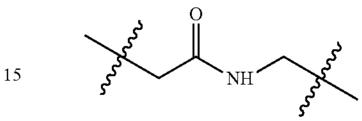

The term "heterocyclyl" (alone or in combination with another term(s)) means a saturated, partially saturated, or completely unsaturated (i.e., heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

Heterocyclyl includes monocyclic saturated, partially unsaturated, and completely unsaturated ring structures having, for example, 3 to 7 members, such as 3 to 6 members, 5 to 7 members such as 5 or 6 members, where at least one member and up to 4 members, particularly 1, 2 or 3 members of the ring are heteroatoms selected from N, O and S, and the remaining ring atoms are carbon atoms, in stable combinations known to those of skill in the art. Examples of monocyclic heterocyclyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, dioxazolyl, oxathiazolyl, oxathiolyl, oxathiolanyl, pyranyl, dihydropyranyl, pyridinyl, piperidinyl, pyridazinyl, pyrimidinyl, pyrazinyl, piperazinyl, triazinyl, oxazinyl, isoxazinyl, oxazolidinyl, isoxazolidinyl, oxathiazinyl, morpholinyl, azepinyl, oxepinyl, thiepinyl, and diazepinyl.

Heterocyclyl further includes bicyclic ring structures fused together (i.e., fused bicyclic) or two rings with only one common atom (i.e., spiro), wherein at least one such ring contains a heteroatom as a ring atom (i.e., nitrogen, oxygen, or sulfur). Examples of heterocyclyls having two ring structures fused together include indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other. Each substituent therefore may be identical to or different from the other substituent(s).

The term "pharmaceutically acceptable" is used adjectivally in this specification to mean that the modified noun is appropriate for use as a pharmaceutical product or as a part of a pharmaceutical product. For example, "pharmaceutically acceptable salts" are salts that are suitable for use in mammals, particularly humans, and include salts with an inorganic base, organic base, inorganic acid, organic acid, or basic or acidic amino acid that are suitable for use in mammals, particularly humans.

A "therapeutically effective amount" of a pharmacological agent is an amount that is sufficient to effect beneficial or desired results, including clinical results, and, as such, will depend upon the situation in which it is being administered. Where the pharmacological agent is being administered to treat liver disease, for example, a therapeutically effective amount of the agent is an amount of the agent that is sufficient, either alone or in combination with additional therapies, to provide an anti-liver disease effect in a subject as compared to the response obtained without administration of the agent.

The term "preventing" is readily understood by an ordinarily skilled physician and, with respect to treatment of a particular condition, can include is intended to have its normal meaning and includes primary prophylaxis to prevent the development of the condition and secondary prophylaxis whereby the condition has already developed and the patient is temporarily or permanently protected against exacerbation or worsening of the disease or the development of new symptoms associated with the condition.

The terms "treating" is readily understood by an ordinarily skilled physician and, with respect to treatment of a particular condition, can include (1) diminishing the extent or cause of the condition being treated, and/or (2) alleviating or ameliorating one or more symptoms associated with that condition. Treatment of liver disease, for example, can include stabilizing (i.e., not worsening), delaying, or slowing the spread or progression of the liver disease; prolonging survival as compared to expected survival if not receiving treatment; and/or otherwise ameliorating or palliating the cancer or the severity of the liver disease, in whole or in part.

II. Compounds

In one embodiment, the present disclosure provides compounds having the structure of Formula (I):

(I)

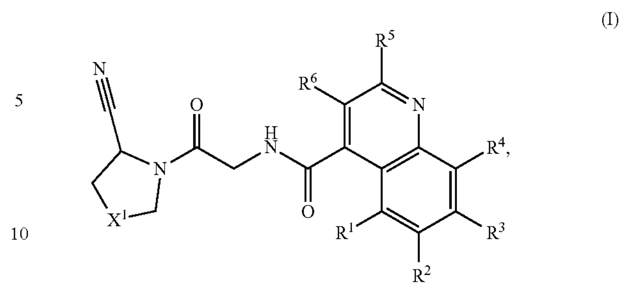

and pharmaceutically acceptable salts thereof, wherein:

$X^1$ is selected from the group consisting of —S—, —S(O)—, and —$S(O)_2$—;

$R^1$ is selected from the group consisting of hydrogen, halogen, hydroxy, $C_{1-3}$-alkyl, and $C_{1-6}$-alkoxy;

$R^2$ is selected from the group consisting of:

(a) heterocyclyl containing a total of 4 to 10 ring atoms, wherein the heterocyclyl ring: (i) is a saturated, partially saturated, or completely unsaturated monocyclic or fused bicyclic ring, (ii) has one, two, or three nitrogen ring atoms with the remaining ring atoms being carbon, and (iii) is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy;

(b) heterocyclyl containing a total of 5 to 10 ring atoms, wherein the heterocyclyl ring: (i) is a saturated, partially saturated, or completely unsaturated monocyclic or fused bicyclic ring, (ii) has (a) one nitrogen ring atom and one oxygen ring atom with the remaining ring atoms being carbon, or (b) one nitrogen ring atom and one sulfur ring atom with the remaining ring atoms being carbon, and (iii) is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen; and (c) spiro heterocyclyl containing a total of 6 to 11 ring atoms, wherein the spiro heterocyclyl: (i) comprises two saturated rings, (ii) has: (a) one or two nitrogen ring atoms with the remaining ring atoms being carbon, (b) one or two nitrogen ring atoms and one or two oxygen ring atoms with the remaining ring atoms being carbon, or (c) one nitrogen ring atom and one sulfur ring atom with the remaining ring atoms being carbon, and (iii) is optionally substituted with one or more substituents independently selected from the group consisting of halogen, oxo, $C_{1-6}$-alkyl, $C_{1-6}$-haloalkyl, $C_{1-6}$-alkoxy, $C_{1-6}$-haloalkoxy, and $C_{1-6}$-alkylcarbonyl;

$R^3$ is selected from the group consisting of hydrogen, halogen, and $C_{1-3}$-alkyl;

$R^4$ is selected from the group consisting of hydrogen, halogen, and $C_{1-3}$-alkyl;

$R^5$ is selected from the group consisting of hydrogen, halogen, and $C_{1-3}$-alkyl; and $R^6$ is selected from the group consisting of hydrogen, halogen, and $C_{1-3}$-alkyl.

In some embodiments, the present disclosure provides compounds having the structure of Formula (II):

(II)

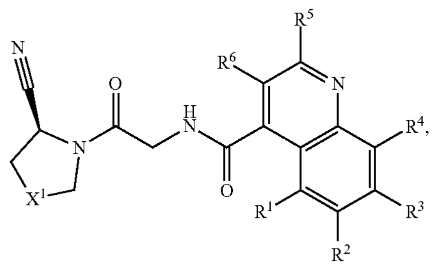

and pharmaceutically acceptable salts thereof, wherein $X^1$, $R^1$, $R^2$, $R^3$, $R^4$, $R^5$, and $R^6$ are as defined above for the compounds of Formula (I). In one aspect, $X^1$ is —S—. In another aspect, $X^1$ is —S(O)—. In another aspect, $X^1$ is —$S(O)_2$—.

In some embodiments, $R^1$ is selected from the group consisting of hydrogen, halogen, and $C_{1-3}$-alkyl. In one aspect, $R^1$ is selected from the group consisting of hydrogen, chloro, fluoro, and methyl. In another aspect, $R^1$ is hydrogen. In another aspect, $R^1$ is chloro. In another aspect, $R^1$ is fluoro. In another aspect, $R^1$ is methyl.

In some embodiments, $R^3$ is selected from the group consisting of hydrogen, halogen, and $C_{1-3}$-alkyl. In one aspect, $R^3$ is selected from the group consisting of hydrogen, chloro, fluoro, and methyl. In another aspect, $R^3$ is hydrogen. In another aspect, $R^3$ is chloro. In another aspect, $R^3$ is fluoro. In another aspect, $R^3$ is methyl.

In some embodiments, $R^4$ is selected from the group consisting of hydrogen, halogen, and $C_{1-3}$-alkyl. In one aspect, $R^4$ is hydrogen. In another aspect, $R^4$ is chloro. In another aspect, $R^4$ is fluoro. In another aspect, $R^4$ is methyl.

In some embodiments, $R^5$ is selected from the group consisting of hydrogen, halogen, and $C_{1-3}$-alkyl. In one aspect, $R^5$ is selected from the group consisting of hydrogen, chloro, fluoro, and methyl. In another aspect, $R^5$ is hydrogen. In another aspect, $R^5$ is fluoro. In another aspect, $R^5$ is chloro. In another aspect, $R^5$ is methyl.

In some embodiments, $R^6$ is selected from the group consisting of hydrogen, halogen, and $C_{1-3}$-alkyl. In one aspect, $R^6$ is selected from the group consisting of hydrogen, chloro, fluoro, and methyl. In another aspect, $R^6$ is hydrogen. In another aspect, $R^6$ is chloro. In another aspect, $R^6$ is fluoro. In another aspect, $R^6$ is methyl.

In some embodiments, one of the $R^1$, $R^3$, $R^4$, $R^5$, and $R^6$ substituents is selected from the group consisting of halogen and $C_{1-3}$-alkyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is selected from the group consisting of chloro and fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments, at least two of the $R^1$, $R^3$, $R^4$, $R^5$, and $R^6$ substituents are independently selected from the group consisting of halogen and $C_{1-3}$-alkyl, and the remaining $R^1$, $R^3$, $R^4$, $R^5$, and $R^6$ substituents are all hydrogen. In one aspect, two of the $R^1$, $R^3$, $R^4$, $R^5$, and $R^6$ substituents are independently selected from the group consisting of chloro, fluoro, and methyl, and the remaining $R^1$, $R^3$, $R^4$, $R^5$, and $R^6$ substituents are all hydrogen.

In some embodiments, at least one of the $R^1$, $R^3$, $R^4$, $R^5$, and $R^6$ substituents is chloro.

In some embodiments, at least one of the $R^1$, $R^3$, $R^4$, $R^5$, and $R^6$ substituents is fluoro.

In some embodiments, at least one of the $R^1$, $R^3$, $R^4$, $R^5$, and $R^6$ substituents is methyl.

In some embodiments, the present disclosure provides compounds having the structure of Formula (III-A):

(III-A)

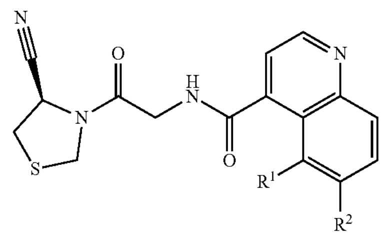

and pharmaceutically acceptable salts thereof, wherein $R^1$ and $R^2$ are as defined in the various embodiments above.

In some embodiments, the present disclosure provides compounds having the structure of Formula (III-B):

(III-B)

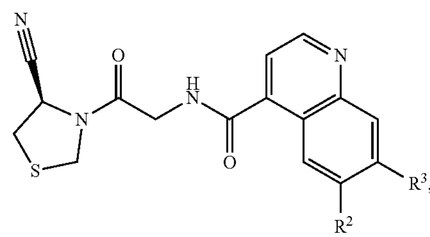

and pharmaceutically acceptable salts thereof, wherein $R^2$ and $R^3$ are as defined in the various embodiments above.

In some embodiments, the present disclosure provides compounds having the structure of Formula (III-C):

(III-C)

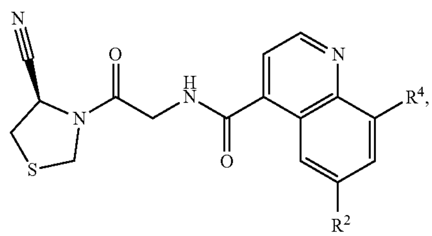

and pharmaceutically acceptable salts thereof, wherein $R^2$ and $R^4$ are as defined in the various embodiments above.

In some embodiments, the present disclosure provides compounds having the structure of Formula (III-D):

(III-D)

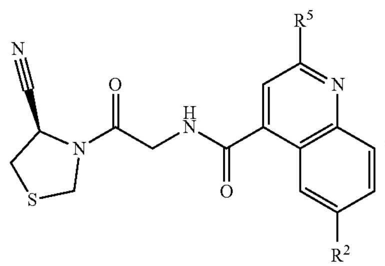

and pharmaceutically acceptable salts thereof, wherein $R^2$ and $R^5$ are as defined in the various embodiments above.

In some embodiments, the present disclosure provides compounds having the structure of Formula (III-E):

(III-E)

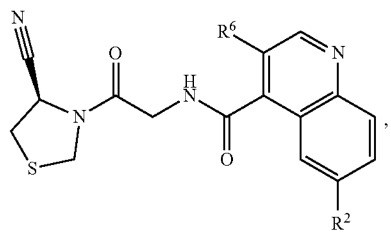

and pharmaceutically acceptable salts thereof, wherein $R^2$ and $R^6$ are as defined in the various embodiments above.

In some embodiments, the present disclosure provides compounds having the structure of Formula (IV):

(IV)

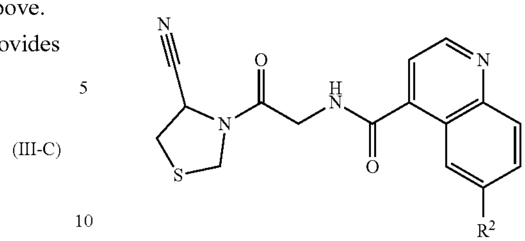

and pharmaceutically acceptable salts thereof, wherein $R^2$ is as defined above for the compounds of Formula (I).

In some embodiments, the present disclosure provides compounds having the structure of Formula (IV-A):

(IV-A)

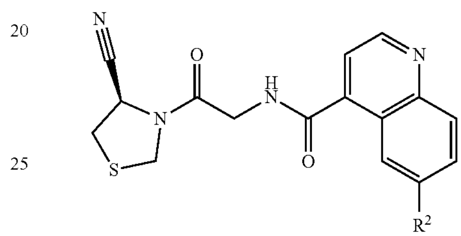

or pharmaceutically acceptable salts thereof, wherein $R^2$ is as defined above for the compounds of Formula (I).

A. $R^2$ is Monocyclic or Fused Bicyclic Heterocyclyl (Nitrogen and Carbon Ring Atoms)

In some embodiments, the present disclosure provides compounds having the structure of Formulae (I), (II), (III-A), (III-B), (III-C), (III-D), (III-E), (IV), or (IV-A), and pharmaceutically acceptable salts thereof, wherein $R^2$ is heterocyclyl containing a total of 4 to 10 ring atoms, wherein the heterocyclyl ring: (i) is a saturated, partially saturated, or completely unsaturated monocyclic or fused bicyclic ring, (ii) has one, two, or three nitrogen ring atoms with the remaining ring atoms being carbon, and (iii) is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy. In one aspect, the $R^2$ heterocyclyl ring is a saturated monocyclic ring. In another aspect, the $R^2$ heterocyclyl ring is a partially saturated monocyclic ring. In another aspect, the $R^2$ heterocyclyl ring is a completely unsaturated monocyclic ring. In another aspect, the $R^2$ heterocyclyl ring is a saturated fused bicyclic ring. In another aspect, the $R^2$ heterocyclyl ring is a partially saturated fused bicyclic ring. In another aspect, the $R^2$ heterocyclyl ring is a completely unsaturated fused bicyclic ring. In another aspect, the $R^2$ heterocyclyl ring has one nitrogen ring atom with the remaining ring atoms being carbon. In another aspect, the $R^2$ heterocyclyl ring has two nitrogen ring atoms with the remaining ring atoms being carbon. In another aspect, the $R^2$ heterocyclyl ring has three nitrogen ring atoms with the remaining ring atoms being carbon.

In some embodiments, the $R^2$ heterocyclyl ring is selected from the group consisting of:

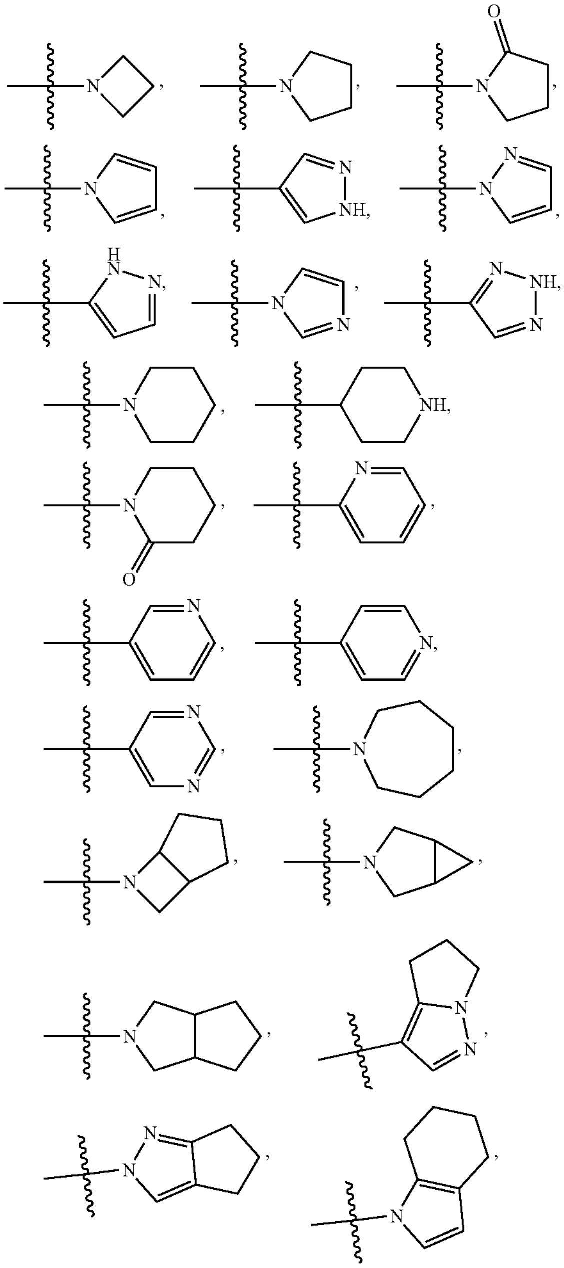

-continued

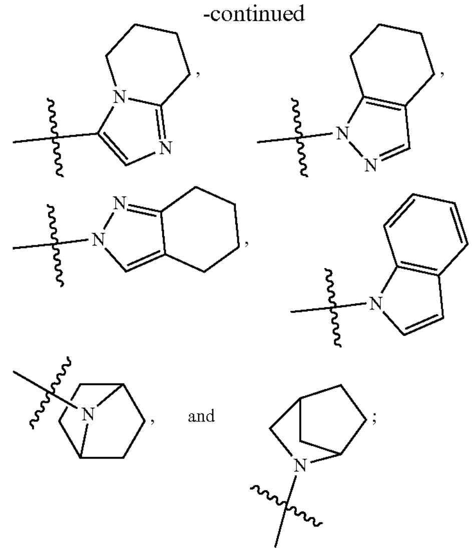

wherein the heterocyclyl ring is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy.

In some embodiments, the $R^2$ heterocyclyl ring is selected from the group consisting of:

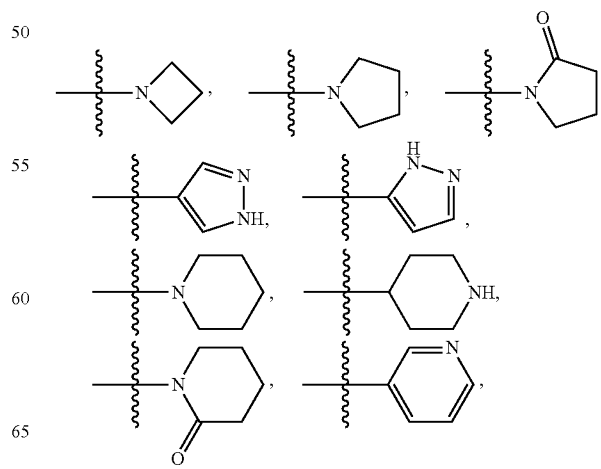

-continued

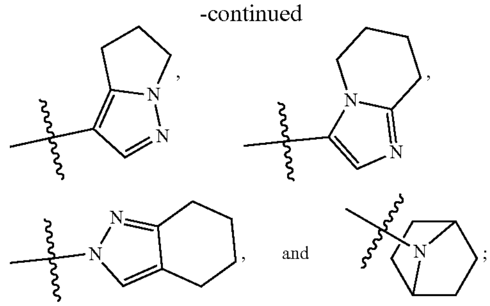

wherein the heterocyclyl ring is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy.

In some embodiments, the $R^2$ heterocyclyl ring is selected from the group consisting of:

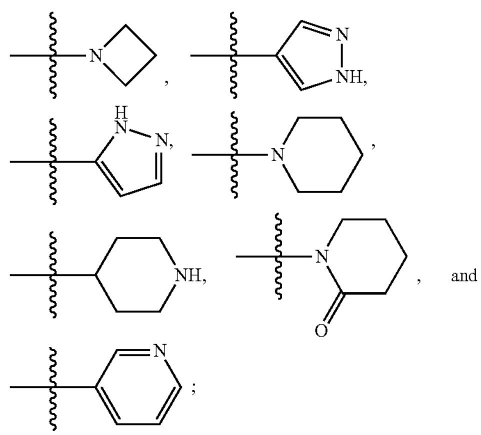

wherein the heterocyclyl ring is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy.

In some embodiments, the $R^2$ heterocyclyl ring is optionally substituted with one or more substituents independently selected from the group consisting of halogen, hydroxy, oxo, cyano, $C_{1-3}$-alkyl, $C_{3-6}$-cycloalkyl, $C_{1-3}$-alkoxy, $C_{1-3}$-alkylcarbonyl, $C_{3-6}$-cycloalkylcarbonyl, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkyl-carbonylamino-$C_{1-3}$-alkyl, $C_{1-3}$-alkylsulfonyl-$C_{1-3}$-alkyl, morpholinyl, tetrahydrofuranyl, tetrahydropyranyl, and tetrahydrooxepanyl, wherein the $C_{1-3}$-alkyl, $C_{3-6}$-cycloalkyl, $C_{1-3}$-alkoxy, $C_{1-3}$-alkylcarbonyl, $C_{3-6}$-cycloalkylcarbonyl, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylsulfonyl-$C_{1-3}$-alkyl, tetrahydrofuranyl, tetrahydropyranyl, and tetrahydrooxepanyl may be further substituted with one or more halogen.

In some embodiments, the $R^2$ heterocyclyl ring is optionally substituted with one or more substituents independently selected from the group consisting of halogen, hydroxy, oxo, $C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more halogen.

In some embodiments, the $R^2$ heterocyclyl ring is optionally substituted with one or more substituents independently selected from the group consisting of azetidinyl, pyrrolidinyl, piperidinyl, and morpholinyl, wherein the azetidinyl, pyrrolidinyl, piperidinyl, and morpholinyl may be further substituted with one or more halogen.

In some embodiments, the $R^2$ heterocyclyl ring is optionally substituted with one or more substituents independently selected from the group consisting of tetrahydrofuranyl, tetrahydropyranyl, and tetrahydrooxepanyl, wherein the tetrahydrofuranyl, tetrahydropyranyl, and tetrahydrooxepanyl may be further substituted with one or more halogen.

In some embodiments, the $R^2$ heterocyclyl ring is optionally substituted with one or more halogen. In one aspect, the $R^2$ heterocyclyl ring is optionally substituted with one or more chloro. In another aspect, the $R^2$ heterocyclyl ring is optionally substituted with one or more fluoro.

In some embodiments, the $R^2$ heterocyclyl ring is optionally substituted with one or more hydroxy.

In some embodiments, the $R^2$ heterocyclyl ring is optionally substituted with one or more oxo.

In some embodiments, the $R^2$ heterocyclyl ring is optionally substituted with one or more cyano.

In some embodiments, the $R^2$ heterocyclyl ring is optionally substituted with one or more $C_{1-3}$-alkyl, wherein the $C_{1-3}$-alkyl may be further substituted with one or more substituents independently selected from halogen and hydroxy.

In some embodiments, the $R^2$ heterocyclyl ring is optionally substituted with one or more $C_{3-6}$-cycloalkyl, wherein the $C_{3-6}$-cycloalkyl may be further substituted with one or more halogen.

In some embodiments, the $R^2$ heterocyclyl ring is optionally substituted with one or more $C_{3-6}$-cycloalkyl-$C_{1-3}$-alkyl, wherein the $C_{3-6}$-cycloalkyl-$C_{1-3}$-alkyl may be further substituted with one or more halogen.

In some embodiments, the $R^2$ heterocyclyl ring is optionally substituted with one or more $C_{1-3}$-alkoxy, wherein the $C_{1-3}$-alkoxy may be further substituted with one or more halogen.

In some embodiments, the $R^2$ heterocyclyl ring is optionally substituted with one or more $C_{3-6}$-cycloalkoxy, wherein the $C_{3-6}$-cycloalkoxy may be further substituted with one or more halogen.

In some embodiments, the $R^2$ heterocyclyl ring is optionally substituted with one or more $C_{1-3}$-alkoxy-$C_{1-3}$-alkyl, wherein the $C_{1-3}$-alkoxy-$C_{1-3}$-alkyl may be further substituted with one or more halogen.

In some embodiments, the $R^2$ heterocyclyl ring is optionally substituted with one or more $C_{1-3}$-alkoxy-$C_{2-3}$-alkoxy, wherein the $C_{1-3}$-alkoxy-$C_{2-3}$-alkoxy may be further substituted with one or more halogen.

In some embodiments, the $R^2$ heterocyclyl ring is optionally substituted with one or more $C_{1-3}$-alkoxy-$C_{2-3}$-alkoxy-$C_{1-3}$-alkyl, wherein the $C_{1-3}$-alkoxy-$C_{2-3}$-alkoxy-$C_{1-3}$-alkyl may be further substituted with one or more halogen.

In some embodiments, the $R^2$ heterocyclyl ring is optionally substituted with one or more $C_{1-3}$-alkylcarbonyl, wherein the $C_{1-3}$-alkylcarbonyl may be further substituted with one or more halogen.

In some embodiments, the $R^2$ heterocyclyl ring is optionally substituted with one or more $C_{3-6}$-cycloalkylcarbonyl, wherein the $C_{3-6}$-cycloalkylcarbonyl may be further substituted with one or more halogen.

In some embodiments, the $R^2$ heterocyclyl ring is optionally substituted with one or more $C_{1-3}$-alkyl-carbonylamino-$C_{1-3}$-alkyl, wherein the $C_{1-3}$-alkyl-carbonylamino-$C_{1-3}$-alkyl may be further substituted with one or more halogen.

In some embodiments, the $R^2$ heterocyclyl ring is optionally substituted with one or more $C_{1-3}$-alkylsulfonyl-$C_{1-3}$-alkyl, wherein the $C_{1-3}$-alkylsulfonyl-$C_{1-3}$-alkyl may be further substituted with one or more halogen.

In some embodiments, the $R^2$ heterocyclyl ring is optionally substituted with one or more substituents independently selected from the group consisting of phenyl, tolyl, $C_{1-3}$-alkoxyphenyl, phenyl-$C_{1-3}$-alkyl, and $C_{1-3}$-alkoxyphenyl-$C_{1-3}$-alkyl, wherein the phenyl, tolyl, phenyl-$C_{1-3}$-alkyl, and $C_{1-3}$-alkoxyphenyl-$C_{1-3}$-alkyl may be further substituted with one or more halogen.

In some embodiments, the $R^2$ heterocyclyl ring is optionally substituted with one or more substituents independently selected from the group consisting of azetidinyl, pyrrolidinyl, piperidinyl, and morpholinyl, wherein the azetidinyl, pyrrolidinyl, piperidinyl, and morpholinyl may be further substituted with one or more halogen.

In some embodiments, the $R^2$ heterocyclyl ring is optionally substituted with one or more substituents independently selected from the group consisting of tetrahydrofuranyl, tetrahydropyranyl, and tetrahydrooxepanyl, wherein the tetrahydrofuranyl, tetrahydropyranyl, and tetrahydrooxepanyl may be further substituted with one or more halogen.

In some embodiments, the $R^2$ heterocyclyl ring is optionally substituted with one or more substituents independently selected from the group consisting of fluoro, hydroxy, oxo, methyl, ethyl, propyl, isopropyl, cyclopropyl, fluoromethyl, difluoromethyl, trifluoromethyl, fluoroethyl, difluoroethyl, trifluoroethyl, difluoropropyl, trifluoropropyl, methoxy, ethoxy, isopropoxy, difluoromethoxy, trifluoromethoxy, methoxymethyl, trifluoromethoxymethyl, methylcarbonylaminomethyl, methylsulfonylmethyl, morpholinyl, and tetrahydropyranyl.

In some embodiments, the $R^2$ heterocyclyl ring is optionally substituted with one or more substituents independently selected from the group consisting of fluoro, hydroxy, methyl, fluoromethyl, difluoromethyl, trifluoromethyl, difluoroethyl, difluoropropyl, cyclopropyl, methoxy, trifluoromethoxy, ethoxy, and methoxymethyl.

In some embodiments, the $R^2$ heterocyclyl ring is:

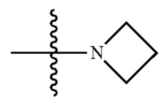

wherein the $R^2$ heterocyclyl ring is optionally substituted with one or more substituents independently selected from the group consisting of halogen, hydroxy, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, and morpholinyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, and morpholinyl may be further substituted with one or more halogen. In one aspect, the $R^2$ heterocyclyl ring is optionally substituted with one or more substituents independently selected from the group consisting of fluoro, hydroxy, $C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, isopropyl, fluoromethyl, difluoromethyl, trifluoromethyl, fluoroethyl, difluoroethyl, trifluoroethyl, difluoropropyl, trifluoropropyl, cyclopropyl, methoxy, ethoxy, difluoromethoxy, trifluoromethoxy, trifluoroethoxy, methoxymethyl, trifluoromethoxymethyl, methylamidomethyl, methylsulfonylmethyl, and morpholinyl. In another aspect, the $R^2$ heterocyclyl ring is optionally substituted with one or more substituents independently selected from the group consisting of fluoro, hydroxy, methyl, ethyl, cyclopropyl, fluoromethyl, difluoromethyl, trifluoromethyl, difluoroethyl, trifluoroethyl, difluoropropyl, trifluoropropyl, methoxy, ethoxy, trifluoromethoxy, trifluoromethoxymethyl, methoxymethyl, methylamidomethyl, and morpholinyl.

In some embodiments, the compounds and pharmaceutically acceptable salts are selected from the group consisting of:

(R)—N-(2-(4-Cyanothiazolidin-3-yl)-2-oxoethyl)-6-(2,2-dimethylazetidin-1-yl)-quinoline-4-carboxamide (Example 20);

(R)—N-(2-(4-Cyanothiazolidin-3-yl)-2-oxoethyl)-6-(3-fluoroazetidin-1-yl)quinoline-4-carboxamide (Example 21);

(R)—N-(2-(4-Cyanothiazolidin-3-yl)-2-oxoethyl)-6-(3,3-dimethylazetidin-1-yl)-quinoline-4-carboxamide (Example 22);

(R)—N-(2-(4-Cyanothiazolidin-3-yl)-2-oxoethyl)-6-(3,3-difluoroazetidin-1-yl)-quinoline-4-carboxamide (Example 23);

(R)—N-(2-(4-Cyanothiazolidin-3-yl)-2-oxoethyl)-6-(3-fluoro-3-methylazetidin-1-yl)-quinoline-4-carboxamide (Example 24);

(R)—N-(2-(4-Cyanothiazolidin-3-yl)-2-oxoethyl)-6-(3-methylazetidin-1-yl)quinoline-4-carboxamide (Example 25);

(R)—N-(2-(4-Cyanothiazolidin-3-yl)-2-oxoethyl)-6-(3-(trifluoromethyl)azetidin-1-yl)-quinoline-4-carboxamide (Example 26);

(R)—N-(2-(4-Cyanothiazolidin-3-yl)-2-oxoethyl)-6-(3-(fluoromethyl)-3-methylazetidin-1-yl)quinoline-4-carboxamide (Example 27);

(R)—N-(2-(4-Cyanothiazolidin-3-yl)-2-oxoethyl)-6-(3-(difluoromethyl)azetidin-1-yl)-quinoline-4-carboxamide (Example 28);

(R)—N-(2-(4-Cyanothiazolidin-3-yl)-2-oxoethyl)-6-(3-(methoxymethyl)-3-methyl-azetidin-1-yl)quinoline-4-carboxamide (Example 29);

N-(2-((R)-4-Cyanothiazolidin-3-yl)-2-oxoethyl)-6-((2S,3R)-3-methoxy-2-methyl-azetidin-1-yl)quinoline-4-carboxamide (Example 30);

(R)—N-(2-(4-Cyanothiazolidin-3-yl)-2-oxoethyl)-6-(3-cyclopropyl-3-fluoroazetidin-1-yl)quinoline-4-carboxamide (Example 31);

(R)—N-(2-(4-Cyanothiazolidin-3-yl)-2-oxoethyl)-6-(3-methoxyazetidin-1-yl)quinoline-4-carboxamide (Example 66);

(R)—N-(2-(4-Cyanothiazolidin-3-yl)-2-oxoethyl)-6-(3-(fluoromethyl)azetidin-1-yl)-quinoline-4-carboxamide (Example 113);

(R)—N-(2-(4-Cyanothiazolidin-3-yl)-2-oxoethyl)-6-(3-morpholinoazetidin-1-yl)-quinoline-4-carboxamide (Example 122);

(R)—N-(2-(4-Cyanothiazolidin-3-yl)-2-oxoethyl)-6-(3-((trifluoromethoxy)methyl)-azetidin-1-yl)quinoline-4-carboxamide (Example 130);

(R)—N-(2-(4-Cyanothiazolidin-3-yl)-2-oxoethyl)-6-(3-methyl-3-(2,2,2-trifluoroethyl)-azetidin-1-yl)quinoline-4-carboxamide (Example 131);

(R)—N-(2-(4-Cyanothiazolidin-3-yl)-2-oxoethyl)-6-(3-(trifluoromethoxy)azetidin-1-yl)quinoline-4-carboxamide (Example 132);

(R)—N-(2-(4-Cyanothiazolidin-3-yl)-2-oxoethyl)-6-(3-(2,2-difluoroethyl)-3-methyl-azetidin-1-yl)quinoline-4-carboxamide (Example 133);

(R)—N-(2-(4-Cyanothiazolidin-3-yl)-2-oxoethyl)-6-(3-cyclopropyl-3-methylazetidin-1-yl)quinoline-4-carboxamide (Example 134);

(R)—N-(2-(4-Cyanothiazolidin-3-yl)-2-oxoethyl)-6-(3-(difluoromethyl)-3-methyl-azetidin-1-yl)quinoline-4-carboxamide (Example 135);

(R)—N-(2-(4-Cyanothiazolidin-3-yl)-2-oxoethyl)-6-(3-(difluoromethoxy)azetidin-1-yl)quinoline-4-carboxamide (Example 136);

(R)—N-(2-(4-Cyanothiazolidin-3-yl)-2-oxoethyl)-6-(3-ethyl-3-methylazetidin-1-yl)-quinoline-4-carboxamide (Example 137);

(R)—N-(2-(4-Cyanothiazolidin-3-yl)-2-oxoethyl)-6-(3-ethyl-3-fluoroazetidin-1-yl)-quinoline-4-carboxamide (Example 138);

(R)—N-(2-(4-Cyanothiazolidin-3-yl)-2-oxoethyl)-6-(3-(2,2-difluoropropyl)azetidin-1-yl)quinoline-4-carboxamide (Example 140);

(R)—N-(2-(4-Cyanothiazolidin-3-yl)-2-oxoethyl)-6-(3-(3,3,3-trifluoropropyl)azetidin-1-yl)quinoline-4-carboxamide (Example 142);

(R)—N-(2-(4-Cyanothiazolidin-3-yl)-2-oxoethyl)-6-(3-fluoro-3-(trifluoromethyl)-azetidin-1-yl)quinoline-4-carboxamide (Example 143);

(R)—N-(2-(4-Cyanothiazolidin-3-yl)-2-oxoethyl)-6-(3-(2,2-difluoroethyl)azetidin-1-yl)-quinoline-4-carboxamide (Example 144);

(R)—N-(2-(4-Cyanothiazolidin-3-yl)-2-oxoethyl)-6-(3-cyclopropylazetidin-1-yl)-quinoline-4-carboxamide (Example 145);

(R)—N-(2-(4-Cyanothiazolidin-3-yl)-2-oxoethyl)-6-(3-(2-fluoroethyl)azetidin-1-yl)-quinoline-4-carboxamide (Example 146);

(R)—N-(2-(4-Cyanothiazolidin-3-yl)-2-oxoethyl)-6-(3-(1,1-difluoroethyl)azetidin-1-yl)-quinoline-4-carboxamide (Example 147);

(R)—N-(2-(4-Cyanothiazolidin-3-yl)-2-oxoethyl)-6-(3-isopropylazetidin-1-yl)quinoline-4-carboxamide (Example 148);

(R)—N-(2-(4-Cyanothiazolidin-3-yl)-2-oxoethyl)-6-(3-methoxy-3-methylazetidin-1-yl)-quinoline-4-carboxamide (Example 151);

(R)—N-(2-(4-Cyanothiazolidin-3-yl)-2-oxoethyl)-6-(3-ethoxy-3-methylazetidin-1-yl)-quinoline-4-carboxamide (Example 152);

(R)—N-(2-(4-Cyanothiazolidin-3-yl)-2-oxoethyl)-6-(3-ethyl-3-hydroxyazetidin-1-yl)-quinoline-4-carboxamide (Example 154);

(R)—N-(2-(4-Cyanothiazolidin-3-yl)-2-oxoethyl)-6-(3-fluoro-3-(fluoromethyl)azetidin-1-yl)quinoline-4-carboxamide (Example 157);

(R)—N-(2-(4-Cyanothiazolidin-3-yl)-2-oxoethyl)-6-(3-(2,2,2-trifluoroethyl)azetidin-1-yl)quinoline-4-carboxamide (Example 158);

N-(2-((R)-4-Cyanothiazolidin-3-yl)-2-oxoethyl)-6-(3,3-difluoro-2-methylazetidin-1-yl)quinoline-4-carboxamide (Example 159);

(R)—N-(2-(4-Cyanothiazolidin-3-yl)-2-oxoethyl)-6-(3-hydroxy-3-methylazetidin-1-yl)-quinoline-4-carboxamide (Example 165);

(R)-6-(3-(Acetamidomethyl)-3-methylazetidin-1-yl)-N-(2-(4-cyanothiazolidin-3-yl)-2-oxoethyl)quinoline-4-carboxamide (Example 181);

(R)—N-(2-(4-cyanothiazolidin-3-yl)-2-oxoethyl)-6-(3-fluoro-3-phenylazetidin-1-yl)-quinoline-4-carboxamide (Example 182);

(R)—N-(2-(4-Cyanothiazolidin-3-yl)-2-oxoethyl)-6-(3-(p-tolyl)azetidin-1-yl)quinoline-4-carboxamide (Example 183);

(R)—N-(2-(4-Cyanothiazolidin-3-yl)-2-oxoethyl)-6-(3-(4-fluorophenyl)azetidin-1-yl)-quinoline-4-carboxamide (Example 185);

(R)—N-(2-(4-Cyanothiazolidin-3-yl)-2-oxoethyl)-6-(3-(m-tolyl)azetidin-1-yl)quinoline-4-carboxamide (Example 186);

(R)-6-(3-(4-Chlorobenzyl)azetidin-1-yl)-N-(2-(4-cyanothiazolidin-3-yl)-2-oxoethyl)-quinoline-4-carboxamide (Example 187);

(R)—N-(2-(4-Cyanothiazolidin-3-yl)-2-oxoethyl)-6-(3-methyl-3-((methylsulfonyl)-methyl)azetidin-1-yl)quinoline-4-carboxamide (Example 188);

and pharmaceutically acceptable salts thereof.

In some embodiments, the compounds and pharmaceutically acceptable salts are selected from the group consisting of:

(R)—N-(2-(4-Cyanothiazolidin-3-yl)-2-oxoethyl)-6-(3,3-dimethylazetidin-1-yl)-quinoline-4-carboxamide (Example 22);

(R)—N-(2-(4-Cyanothiazolidin-3-yl)-2-oxoethyl)-6-(3-fluoro-3-methylazetidin-1-yl)-quinoline-4-carboxamide (Example 24);

(R)—N-(2-(4-Cyanothiazolidin-3-yl)-2-oxoethyl)-6-(3-(fluoromethyl)-3-methylazetidin-1-yl)quinoline-4-carboxamide (Example 27);

(R)—N-(2-(4-Cyanothiazolidin-3-yl)-2-oxoethyl)-6-(3-(difluoromethyl)azetidin-1-yl)-quinoline-4-carboxamide (Example 28);

(R)—N-(2-(4-Cyanothiazolidin-3-yl)-2-oxoethyl)-6-(3-(methoxymethyl)-3-methyl-azetidin-1-yl)quinoline-4-carboxamide (Example 29);

N-(2-((R)-4-Cyanothiazolidin-3-yl)-2-oxoethyl)-6-((2S,3R)-3-methoxy-2-methyl-azetidin-1-yl)quinoline-4-carboxamide (Example 30);

(R)—N-(2-(4-Cyanothiazolidin-3-yl)-2-oxoethyl)-6-(3-cyclopropyl-3-fluoroazetidin-1-yl)quinoline-4-carboxamide (Example 31);

(R)—N-(2-(4-Cyanothiazolidin-3-yl)-2-oxoethyl)-6-(3-methoxyazetidin-1-yl)quinoline-4-carboxamide (Example 66);

(R)—N-(2-(4-Cyanothiazolidin-3-yl)-2-oxoethyl)-6-(3-(fluoromethyl)azetidin-1-yl)-quinoline-4-carboxamide (Example 113);

(R)—N-(2-(4-Cyanothiazolidin-3-yl)-2-oxoethyl)-6-(3-(difluoromethyl)-3-methyl-azetidin-1-yl)quinoline-4-carboxamide (Example 135);

(R)—N-(2-(4-Cyanothiazolidin-3-yl)-2-oxoethyl)-6-(3-ethyl-3-fluoroazetidin-1-yl)-quinoline-4-carboxamide (Example 138);

(R)—N-(2-(4-Cyanothiazolidin-3-yl)-2-oxoethyl)-6-(3-(2,2-difluoropropyl)azetidin-1-yl)quinoline-4-carboxamide (Example 140);

(R)—N-(2-(4-Cyanothiazolidin-3-yl)-2-oxoethyl)-6-(3-fluoro-3-(trifluoromethyl)-azetidin-1-yl)quinoline-4-carboxamide (Example 143);

(R)—N-(2-(4-Cyanothiazolidin-3-yl)-2-oxoethyl)-6-(3-(1,1-difluoroethyl)azetidin-1-yl)-quinoline-4-carboxamide (Example 147);

(R)—N-(2-(4-Cyanothiazolidin-3-yl)-2-oxoethyl)-6-(3-methoxy-3-methylazetidin-1-yl)-quinoline-4-carboxamide (Example 151);

(R)—N-(2-(4-Cyanothiazolidin-3-yl)-2-oxoethyl)-6-(3-ethoxy-3-methylazetidin-1-yl)-quinoline-4-carboxamide (Example 152);

(R)—N-(2-(4-Cyanothiazolidin-3-yl)-2-oxoethyl)-6-(3-fluoro-3-(fluoromethyl)azetidin-1-yl)quinoline-4-carboxamide (Example 157);

(R)—N-(2-(4-Cyanothiazolidin-3-yl)-2-oxoethyl)-6-(3-hydroxy-3-methylazetidin-1-yl)-quinoline-4-carboxamide (Example 165);

and pharmaceutically acceptable salts thereof.

In some embodiments, the $R^2$ heterocyclyl ring is:

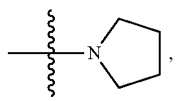 [SMILES: *N1CCCC1], wherein the $R^2$ heterocyclyl ring is optionally substituted with one or more substituents independently selected from the group consisting of halogen, hydroxy, oxo, $C_{1-6}$-alkyl, hydroxy-$C_{1-3}$-alkyl, $C_{3-6}$-cycloalkyl, $C_{1-6}$-alkoxy, and $C_{1-3}$-alkoxy-$C_{1-3}$-alkyl, wherein the $C_{1-6}$-alkyl, hydroxy-$C_{1-3}$-alkyl, $C_{3-6}$-cycloalkyl, $C_{1-6}$-alkoxy, and $C_{1-3}$-alkoxy-$C_{1-3}$-alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, hydroxy-$C_{1-3}$-alkyl, cyclopropyl, $C_{1-3}$-alkoxy, and $C_{1-3}$-alkoxy-$C_{1-3}$-alkyl, wherein the $C_{1-3}$-alkyl, hydroxy-$C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, fluoromethyl, difluoromethyl, trifluoromethyl, fluoroethyl, difluoroethyl, trifluoroethyl, difluoropropyl, hydroxymethyl, cyclopropyl, methoxy, ethoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, fluoromethyl, hydroxymethyl, methoxy, and trifluoromethoxy.

In some embodiments, the compounds and pharmaceutically acceptable salts are selected from the group consisting of:

(R)—N-(2-(4-Cyanothiazolidin-3-yl)-2-oxoethyl)-6-(3,3-difluoropyrrolidin-1-yl)-quinoline-4-carboxamide (Example 47);

(R)—N-(2-(4-Cyanothiazolidin-3-yl)-2-oxoethyl)-6-(3,3-dimethylpyrrolidin-1-yl)-quinoline-4-carboxamide (Example 48);

N-(2-((R)-4-Cyanothiazolidin-3-yl)-2-oxoethyl)-6-((3R,4S)-3,4-difluoropyrrolidin-1-yl)-quinoline-4-carboxamide (Example 50);

N-(2-((R)-4-Cyanothiazolidin-3-yl)-2-oxoethyl)-6-((S)-3-fluoropyrrolidin-1-yl)-quinoline-4-carboxamide (Example 51);

N-(2-((R)-4-Cyanothiazolidin-3-yl)-2-oxoethyl)-6-((R)-3-fluoropyrrolidin-1-yl)-quinoline-4-carboxamide (Example 52);

N-(2-((R)-4-Cyanothiazolidin-3-yl)-2-oxoethyl)-6-((S)-3-methylpyrrolidin-1-yl)-quinoline-4-carboxamide (Example 54);

N-(2-((R)-4-Cyanothiazolidin-3-yl)-2-oxoethyl)-6-((R)-3-methylpyrrolidin-1-yl)-quinoline-4-carboxamide (Example 55);

N-(2-((R)-4-Cyanothiazolidin-3-yl)-2-oxoethyl)-6-((S)-2-(trifluoromethyl)pyrrolidin-1-yl)quinoline-4-carboxamide (Example 56);

(R)—N-(2-(4-Cyanothiazolidin-3-yl)-2-oxoethyl)-6-(2,2-dimethylpyrrolidin-1-yl)-quinoline-4-carboxamide (Example 57);

N-(2-((R)-4-Cyanothiazolidin-3-yl)-2-oxoethyl)-6-((S)-2-methylpyrrolidin-1-yl)-quinoline-4-carboxamide (Example 65);

N-(2-((R)-4-Cyanothiazolidin-3-yl)-2-oxoethyl)-6-((R)-3-methoxypyrrolidin-1-yl)-quinoline-4-carboxamide (Example 161);

N-(2-((R)-4-Cyanothiazolidin-3-yl)-2-oxoethyl)-6-((R)-3-hydroxy-3-methylpyrrolidin-1-yl)quinoline-4-carboxamide (Example 167);

N-(2-((R)-4-Cyanothiazolidin-3-yl)-2-oxoethyl)-6-((S)-3-hydroxy-3-methylpyrrolidin-1-yl)quinoline-4-carboxamide (Example 168);

N-(2-((R)-4-Cyanothiazolidin-3-yl)-2-oxoethyl)-6-((RS)-3-fluoro-3-methylpyrrolidin-1-yl)quinoline-4-carboxamide (Example 198);

N-(2-((R)-4-Cyanothiazolidin-3-yl)-2-oxoethyl)-6-((R*)-2-cyclopropylpyrrolidin-1-yl)quinoline-4-carboxamide Isomer 1 (Example 199);

N-(2-((R)-4-Cyanothiazolidin-3-yl)-2-oxoethyl)-6-((R*)-2-cyclopropylpyrrolidin-1-yl)quinoline-4-carboxamide Isomer 2 (Example 200);

N-(2-((R)-4-Cyanothiazolidin-3-yl)-2-oxoethyl)-6-((S)-3-methoxypyrrolidin-1-yl)-quinoline-4-carboxamide (Example 207);

N-(2-((R)-4-cyanothiazolidin-3-yl)-2-oxoethyl)-6-((R)-2-methylpyrrolidin-1-yl)-quinoline-4-carboxamide (Example 211);

N-(2-((R)-4-Cyanothiazolidin-3-yl)-2-oxoethyl)-6-((S)-2-(methoxymethyl)pyrrolidin-1-yl)quinoline-4-carboxamide (Example 212);

N-(2-((R)-4-Cyanothiazolidin-3-yl)-2-oxoethyl)-6-((3S, 4S)-3,4-difluoropyrrolidin-1-yl)quinoline-4-carboxamide (Example 213);

N-(2-((R)-4-Cyanothiazolidin-3-yl)-2-oxoethyl)-6-((3R, 4R)-3,4-difluoropyrrolidin-1-yl)quinoline-4-carboxamide (Example 214);

N-(2-((R)-4-Cyanothiazolidin-3-yl)-2-oxoethyl)-6-((R)-3-(hydroxymethyl)pyrrolidin-1-yl)quinoline-4-carboxamide (Example 220);

N-(2-((R)-4-Cyanothiazolidin-3-yl)-2-oxoethyl)-6-((S)-3-(hydroxymethyl)pyrrolidin-1-yl)quinoline-4-carboxamide (Example 221);

N-(2-((R)-4-Cyanothiazolidin-3-yl)-2-oxoethyl)-6-((RS)-3, 3-difluoro-4-hydroxy-pyrrolidin-1-yl)quinoline-4-carboxamide (Example 224);

N-(2-((R)-4-Cyanothiazolidin-3-yl)-2-oxoethyl)-6-((3R*, 4R*)-3,4-dimethylpyrrolidin-1-yl)quinoline-4-carboxamide Isomer 1 (Example 225);

N-(2-((R)-4-Cyanothiazolidin-3-yl)-2-oxoethyl)-6-((3R*, 4R*)-3,4-dimethylpyrrolidin-1-yl)quinoline-4-carboxamide Isomer 2 (Example 226);

and pharmaceutically acceptable salts thereof.

In some embodiments, the $R^2$ heterocyclyl ring is:

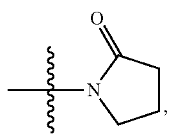

wherein the $R^2$ heterocyclyl ring is optionally substituted with one or more substituents independently selected from the group consisting of halogen, hydroxy, $C_{1-6}$-alkyl, $C_{3-6}$-cycloalkyl, $C_{1-6}$-alkoxy, and $C_{1-3}$-alkoxy-$C_{1-3}$-alkyl, and wherein the $C_{1-6}$-alkyl, $C_{3-6}$-cycloalkyl, $C_{1-6}$-alkoxy, and $C_{1-3}$-alkoxy-$C_{1-3}$-alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, fluoromethyl, difluoromethyl, trifluoromethyl, fluoroethyl, difluoroethyl, trifluoroethyl, difluoropropyl, cyclopropyl, methoxy, ethoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, fluoromethyl, methoxy, and trifluoromethoxy.

In some embodiments, the compounds and pharmaceutically acceptable salts are selected from the group consisting of:

(R)—N-(2-(4-Cyanothiazolidin-3-yl)-2-oxoethyl)-6-(2-oxopyrrolidin-1-yl)quinoline-4-carboxamide (Example 11);

(R)—N-(2-(4-Cyanothiazolidin-3-yl)-2-oxoethyl)-6-(3,3-dimethyl-2-oxopyrrolidin-1-yl)quinoline-4-carboxamide (Example 12);

N-(2-((R)-4-Cyanothiazolidin-3-yl)-2-oxoethyl)-6-((R*)-3-methyl-2-oxopyrrolidin-1-yl)quinoline-4-carboxamide Isomer 1 (Example 201);

N-(2-((R)-4-Cyanothiazolidin-3-yl)-2-oxoethyl)-6-((R*)-3-methyl-2-oxopyrrolidin-1-yl)quinoline-4-carboxamide Isomer 2 (Example 202);

and pharmaceutically acceptable salts thereof.

In some embodiments, the $R^2$ heterocyclyl ring is:

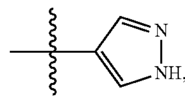 [SMILES: *c1cn[nH]c1]

wherein the $R^2$ heterocyclyl ring is optionally substituted with one or more substituents independently selected from the group consisting of halogen, hydroxy, $C_{1-6}$-alkyl, hydroxy-$C_{1-3}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkyl-carbonylamino-$C_{1-3}$-alkyl, $C_{1-3}$-alkylsulfonyl-$C_{1-3}$-alkyl, phenyl, tetrahydrofuranyl, tetrahydropyranyl, and tetrahydrooxepanyl, and wherein the $C_{1-6}$-alkyl, hydroxy-$C_{1-3}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkyl-carbonylamino-$C_{1-3}$-alkyl, $C_{1-3}$-alkylsulfonyl-$C_{1-3}$-alkyl, phenyl, tetrahydrofuranyl, tetrahydropyranyl, and tetrahydrooxepanyl may be further substituted with one or more halogen. In one aspect, the $R^2$ heterocyclyl ring is optionally substituted with one or more substituents independently selected from the group consisting of halogen, hydroxy, $C_{1-3}$-alkyl, $C_{3-6}$-cycloalkyl, cyclopropyl-$C_{1-3}$-alkyl, $C_{1-3}$-alkoxy, $C_{1-3}$-alkoxy-$C_{1-3}$-alkyl, tetrahydrofuranyl, tetrahydropyranyl, and tetrahydrooxepanyl, wherein the $C_{1-3}$-alkyl, $C_{3-6}$-cycloalkyl, cyclopropyl-$C_{1-3}$-alkyl, $C_{1-3}$-alkoxy, $C_{1-3}$-alkoxy-$C_{1-3}$-alkyl, and tetrahydropyranyl may be further substituted with one or more halogen. In another aspect, the $R^2$ heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, difluoropropyl, cyclopropyl, cyclopropylmethyl, methoxy, ethoxy, trifluoromethoxy, trifluoroethoxy, methoxymethyl, trifluoromethoxymethyl, and tetrahydropyranyl. In another aspect, the $R^2$ heterocyclyl ring is optionally substituted with one or more substituents independently selected from the group consisting methyl, ethyl, propyl, fluoromethyl, difluoromethyl, trifluoromethyl, fluoroethyl, difluoroethyl, trifluoroethyl, difluoropropyl, cyclopropyl, and tetrahydropyranyl.

In some embodiments, the compounds and pharmaceutically acceptable salts are selected from the group consisting of:

(R)—N-(2-(4-Cyanothiazolidin-3-yl)-2-oxoethyl)-6-(1-methyl-1H-pyrazol-4-yl)-quinoline-4-carboxamide (Example 129);

(R)—N-(2-(4-Cyanothiazolidin-3-yl)-2-oxoethyl)-6-(1-cyclopropyl-1H-pyrazol-4-yl)-quinoline-4-carboxamide (Example 170);

(R)—N-(2-(4-cyanothiazolidin-3-yl)-2-oxoethyl)-6-(1,3-dimethyl-1H-pyrazol-4-yl)-quinoline-4-carboxamide (Example 171);

(R)—N-(2-(4-Cyanothiazolidin-3-yl)-2-oxoethyl)-6-(3,5-dimethyl-1-(tetrahydro-2H-pyran-4-yl)-1H-pyrazol-4-yl) quinoline-4-carboxamide (Example 172);

(R)—N-(2-(4-cyanothiazolidin-3-yl)-2-oxoethyl)-6-(1-(tetrahydro-2H-pyran-4-yl)-1H-pyrazol-4-yl)quinoline-4-carboxamide (Example 173);

and pharmaceutically acceptable salts thereof.

In some embodiments, the $R^2$ heterocyclyl ring is:

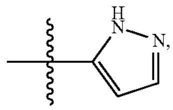 [SMILES: *c1ccn[nH]1]

wherein the $R^2$ heterocyclyl ring is optionally substituted with one or more substituents independently selected from the group consisting of halogen, hydroxy, $C_{1-6}$-alkyl, $C_{3-6}$-cycloalkyl, $C_{3-6}$-cycloalkyl $C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylsulfonyl-$C_{1-3}$-alkyl, phenyl, tetrahydrofuranyl, tetrahydropyranyl, and tetrahydrooxepanyl, and wherein the $C_{1-6}$-alkyl, $C_{3-6}$-cycloalkyl, $C_{3-6}$-cycloalkyl $C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylsulfonyl-$C_{1-3}$-alkyl, phenyl, tetrahydrofuranyl, tetrahydropyranyl, and tetrahydrooxepanyl may be further substituted with one or more halogen. In one aspect, the $R^2$ heterocyclyl ring is optionally substituted with one or more substituents independently selected from the group consisting of halogen, hydroxy, $C_{1-3}$-alkyl, $C_{3-6}$-cycloalkyl, cyclopropyl-$C_{1-3}$-alkyl, $C_{1-3}$-alkoxy, $C_{1-3}$-alkoxy-$C_{1-3}$-alkyl, tetrahydrofuranyl, tetrahydropyranyl, and tetrahydrooxepanyl, wherein the $C_{1-3}$-alkyl, $C_{3-6}$-cycloalkyl, cyclopropyl-$C_{1-3}$-alkyl, $C_{1-3}$-alkoxy, $C_{1-3}$-alkoxy-$C_{1-3}$-alkyl, and tetrahydropyranyl may be further substituted with one or more halogen. In another aspect, the $R^2$ heterocyclyl ring is optionally substituted with one or more substituents independently selected from the group consisting of fluoro, methyl, ethyl, propyl, isopropyl, fluoromethyl, difluoromethyl, trifluoromethyl, fluoroethyl, difluoroethyl, trifluoroethyl, difluoropropyl, cyclopropyl, methoxy, ethoxy, trifluoromethoxy, trifluoroethoxy, methoxymethyl, trifluoromethoxymethyl, and tetrahydropyranyl. In another aspect, the $R^2$ heterocyclyl ring is optionally substituted with one or more substituents independently selected from the group consisting methyl, ethyl, propyl, isopropyl, fluoromethyl, difluoromethyl, trifluoromethyl, fluoroethyl, difluoroethyl, trifluoroethyl, difluoropropyl, cyclopropyl, and tetrahydropyranyl.

In some embodiments, the compounds and pharmaceutically acceptable salts are selected from the group consisting of:

(R)—N-(2-(4-Cyanothiazolidin-3-yl)-2-oxoethyl)-6-(1-methyl-1H-pyrazol-5-yl)-quinoline-4-carboxamide (Example 174);

N-(2-((R)-4-Cyanothiazolidin-3-yl)-2-oxoethyl)-6-(1-(tetrahydro-2H-pyran-2-yl)-1H-pyrazol-5-yl)quinoline-4-carboxamide (Example 176);

(R)—N-(2-(4-Cyanothiazolidin-3-yl)-2-oxoethyl)-6-(1H-pyrazol-5-yl)quinoline-4-carboxamide (Example 196);

(R)—N-(2-(4-Cyanothiazolidin-3-yl)-2-oxoethyl)-6-(1-isopropyl-1H-pyrazol-5-yl)-quinoline-4-carboxamide (Example 197);

and pharmaceutically acceptable salts thereof.

In some embodiments, the $R^2$ heterocyclyl ring is:

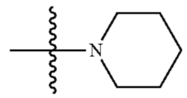

wherein the $R^2$ heterocyclyl ring is optionally substituted with one or more substituents independently selected from the group consisting of halogen, hydroxy, oxo, $C_{1-6}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, phenyl, tolyl, and $C_{1-3}$-alkoxyphenyl, and wherein the $C_{1-6}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, phenyl, tolyl, and $C_{1-3}$-alkoxyphenyl may be further substituted with one or more halogen. In one aspect, the $R^2$ heterocyclyl ring is optionally substituted with one or more substituents independently selected from the group consisting of fluoro, hydroxy, $C_{1-3}$-alkyl, cyclopropyl, cyclopropyl-$C_{1-3}$-alkyl, $C_{1-3}$-alkoxy, and $C_{1-3}$-alkoxy-$C_{1-3}$-alkyl, wherein the $C_{1-3}$-alkyl, cyclopropyl, cyclopropyl-$C_{1-3}$-alkyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, isopropyl, fluoromethyl, difluoromethyl, trifluoromethyl, fluoroethyl, difluoroethyl, trifluoroethyl, cyclopropyl, cyclopropylmethyl, methoxy, ethoxy, propoxy, isopropoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, propyl, isopropyl, fluoromethyl, difluoromethyl, trifluoromethyl, fluoroethyl, difluoroethyl, trifluoroethyl, cyclopropyl, methoxy, ethoxy, propoxy, isopropoxy, trifluoromethoxy, and trifluoroethoxy.

In some embodiments, the compounds and pharmaceutically acceptable salts are selected from the group consisting of:

N-(2-((R)-4-Cyanothiazolidin-3-yl)-2-oxoethyl)-6-((3S,4S,5R)-4-hydroxy-3,5-dimethylpiperidin-1-yl)quinoline-4-carboxamide (Example 7);

(R)—N-(2-(4-Cyanothiazolidin-3-yl)-2-oxoethyl)-6-(4-methoxypiperidin-1-yl)-quinoline-4-carboxamide (Example 8);

(R)—N-(2-(4-Cyanothiazolidin-3-yl)-2-oxoethyl)-6-(piperidin-1-yl)quinoline-4-carboxamide (Example 32);

(R)—N-(2-(4-Cyanothiazolidin-3-yl)-2-oxoethyl)-6-(4,4-dimethylpiperidin-1-yl)-quinoline-4-carboxamide (Example 33);

(R)—N-(2-(4-Cyanothiazolidin-3-yl)-2-oxoethyl)-6-(4-fluoro-4-methylpiperidin-1-yl)quinoline-4-carboxamide (Example 34);
(R)—N-(2-(4-Cyanothiazolidin-3-yl)-2-oxoethyl)-6-(4,4-difluoropiperidin-1-yl)-quinoline-4-carboxamide (Example 35);
(R)—N-(2-(4-Cyanothiazolidin-3-yl)-2-oxoethyl)-6-(3,3-difluoropiperidin-1-yl)-quinoline-4-carboxamide (Example 36);
(R)—N-(2-(4-Cyanothiazolidin-3-yl)-2-oxoethyl)-6-(4-(fluoromethyl)-4-methyl-piperidin-1-yl)quinoline-4-carboxamide (Example 37);
(R)—N-(2-(4-Cyanothiazolidin-3-yl)-2-oxoethyl)-6-(4,4-difluoro-3,3-dimethyl-piperidin-1-yl)quinoline-4-carboxamide (Example 38);
(R)—N-(2-(4-Cyanothiazolidin-3-yl)-2-oxoethyl)-6-(4-(trifluoromethyl)piperidin-1-yl)-quinoline-4-carboxamide (Example 39);
N-(2-((R)-4-Cyanothiazolidin-3-yl)-2-oxoethyl)-6-(3-fluoropiperidin-1-yl)quinoline-4-carboxamide (Example 40);
N-(2-((R)-4-Cyanothiazolidin-3-yl)-2-oxoethyl)-6-(3-methoxypiperidin-1-yl)-quinoline-4-carboxamide (Example 41);
(R)—N-(2-(4-Cyanothiazolidin-3-yl)-2-oxoethyl)-6-(4-methoxy-4-methylpiperidin-1-yl)quinoline-4-carboxamide (Example 42);
(R)—N-(2-(4-Cyanothiazolidin-3-yl)-2-oxoethyl)-6-(4-isopropoxypiperidin-1-yl)-quinoline-4-carboxamide (Example 43);
N-(2-((R)-4-Cyanothiazolidin-3-yl)-2-oxoethyl)-6-(4,4-difluoro-2-methylpiperidin-1-yl)quinoline-4-carboxamide (Example 44);
N-(2-((R)-4-Cyanothiazolidin-3-yl)-2-oxoethyl)-6-((S)-2-(fluoromethyl)piperidin-1-yl)quinoline-4-carboxamide (Example 45);
(R)—N-(2-(4-Cyanothiazolidin-3-yl)-2-oxoethyl)-6-(4-ethyl-4-hydroxypiperidin-1-yl)quinoline-4-carboxamide (Example 189);
(R)—N-(2-(4-Cyanothiazolidin-3-yl)-2-oxoethyl)-6-(4-hydroxy-4-methylpiperidin-1-yl)quinoline-4-carboxamide (Example 190);
(R)—N-(2-(4-Cyanothiazolidin-3-yl)-2-oxoethyl)-6-(4-ethyl-4-methoxypiperidin-1-yl)-quinoline-4-carboxamide (Example 191);
(R)—N-(2-(4-Cyanothiazolidin-3-yl)-2-oxoethyl)-6-(4-hydroxy-4-isopropylpiperidin-1-yl)quinoline-4-carboxamide (Example 192);
N-(2-((R)-4-Cyanothiazolidin-3-yl)-2-oxoethyl)-6-((3R,4S,5S)-4-hydroxy-3,4,5-trimethylpiperidin-1-yl)quinoline-4-carboxamide (Example 193);
(R)—N-(2-(4-Cyanothiazolidin-3-yl)-2-oxoethyl)-6-(4-fluoropiperidin-1-yl)quinoline-4-carboxamide (Example 205);
(R)—N-(2-(4-Cyanothiazolidin-3-yl)-2-oxoethyl)-6-(4-fluoro-4-phenylpiperidin-1-yl)-quinoline-4-carboxamide (Example 223);
and pharmaceutically acceptable salts thereof.

In some embodiments, the $R^2$ heterocyclyl ring is:

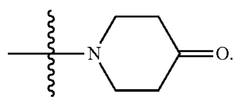 [SMILES: *N1CCC(=O)CC1]

In some embodiments, the compound or pharmaceutically acceptable salt is (R)—N-(2-(4-cyanothiazolidin-3-yl)-2-oxoethyl)-6-(4-oxopiperidin-1-yl)quinoline-4-carboxamide (Example 230), or a pharmaceutically acceptable salt thereof.

In some embodiments, the $R^2$ heterocyclyl ring is:

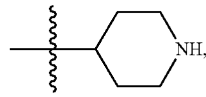 [SMILES: *C1CCNCC1]

wherein the $R^2$ heterocyclyl ring is optionally substituted with one or more substituents independently selected from the group consisting of halogen, hydroxy, oxo, $C_{1-6}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, and phenyl, and wherein the $C_{1-6}$-alkyl, $C_{3-6}$-cycloalkyl, $C_{3-6}$-cycloalkyl-$C_{1-3}$-alkyl, $C_{1-6}$-alkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, and phenyl may be further substituted with one or more halogen. In one aspect, the $R^2$ heterocyclyl ring is optionally substituted with one or more substituents independently selected from the group consisting of fluoro, hydroxy, oxo, $C_{1-3}$-alkyl, cyclopropyl, cyclopropyl-$C_{1-3}$-alkyl, $C_{1-3}$-alkoxy, and $C_{1-3}$-alkoxy-$C_{1-3}$-alkyl, wherein the $C_{1-3}$-alkyl, cyclopropyl, cyclopropyl-$C_{1-3}$-alkyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, oxo, methyl, ethyl, isopropyl, propyl, fluoromethyl, difluoromethyl, trifluoromethyl, fluoroethyl, difluoroethyl, trifluoroethyl, cyclopropyl, cyclopropylmethyl, methoxy, ethoxy, propoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, oxo, methyl, ethyl, propyl, isopropyl, fluoromethyl, difluoromethyl, trifluoromethyl, fluoroethyl, difluoroethyl, trifluoroethyl, cyclopropyl, methoxy, ethoxy, trifluoromethoxy, trifluoroethoxy, and methoxymethyl.

In some embodiments, the compound or pharmaceutically acceptable salt is (R)—N-(2-(4-cyanothiazolidin-3-yl)-2-oxoethyl)-6-(4-fluoro-1-methylpiperidin-4-yl)quinoline-4-carboxamide (Example 195), or a pharmaceutically acceptable salt thereof.

In some embodiments, the $R^2$ heterocyclyl ring is:

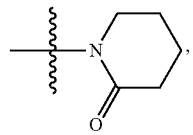 [SMILES: *N1CCCCC1=O]

wherein the $R^2$ heterocyclyl ring is optionally substituted with one or more substituents independently selected from the group consisting of halogen, hydroxy, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, isopropyl, fluoromethyl, difluoromethyl, trifluoromethyl, fluoroethyl, difluoroethyl, trifluoroethyl, cyclopropyl, methoxy, ethoxy, propoxy, isopropoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, propyl, isopropyl, fluoromethyl, difluoromethyl, trifluoromethyl, fluoroethyl, difluoroethyl, trifluoroethyl, cyclopropyl, methoxy, ethoxy, isopropoxy, trifluoromethoxy, trifluoroethoxy, and methoxymethyl.

In some embodiments, the compounds and pharmaceutically acceptable salts are selected from the group consisting of:

(R)—N-(2-(4-Cyanothiazolidin-3-yl)-2-oxoethyl)-6-(2-oxopiperidin-1-yl)quinoline-4-carboxamide (Example 14);

(R)—N-(2-(4-Cyanothiazolidin-3-yl)-2-oxoethyl)-6-(3,3-dimethyl-2-oxopiperidin-1-yl)-quinoline-4-carboxamide (Example 15);

N-(2-((R)-4-Cyanothiazolidin-3-yl)-2-oxoethyl)-6-((R*)-3-methyl-2-oxopiperidin-1-yl)quinoline-4-carboxamide Isomer 1 (Example 203);

N-(2-((R)-4-Cyanothiazolidin-3-yl)-2-oxoethyl)-6-((R*)-3-methyl-2-oxopiperidin-1-yl)quinoline-4-carboxamide Isomer 2 (Example 204);

and pharmaceutically acceptable salts thereof.

In some embodiments, the $R^2$ heterocyclyl ring is:

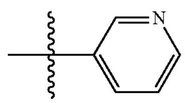 [SMILES: *c1cccnc1]

wherein the $R^2$ heterocyclyl ring is optionally substituted with one or more substituents independently selected from the group consisting of halogen, hydroxy, $C_{1-6}$-alkyl, hydroxy-$C_{1-3}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkyloxy, and $C_{1-3}$-alkoxy-$C_{2-3}$-alkyloxy-$C_{1-3}$alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkyloxy, and $C_{1-3}$-alkoxy-$C_{2-3}$-alkyloxy-$C_{1-3}$ alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, hydroxy-$C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting fluoro, hydroxy, methyl, ethyl, propyl, fluoromethyl, difluoromethyl, trifluoromethyl, hydroxymethyl, fluoroethyl, difluoroethyl, trifluoroethyl, cyclopropyl, methoxy, ethoxy, propoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting fluoro, hydroxy, methyl, ethyl, propyl, fluoromethyl, difluoromethyl, trifluoromethyl, fluoroethyl, difluoroethyl, trifluoroethyl, cyclopropyl, methoxy, ethoxy, trifluoromethoxy, trifluoroethoxy, and methoxymethyl.

In some embodiments, the compounds and pharmaceutically acceptable salts are selected from the group consisting of:

(R)—N-(2-(4-Cyanothiazolidin-3-yl)-2-oxoethyl)-6-(pyridin-3-yl)quinoline-4-carboxamide (Example 126);

(R)—N-(2-(4-Cyanothiazolidin-3-yl)-2-oxoethyl)-6-(2-methylpyridin-3-yl)quinoline-4-carboxamide (Example 128);

(R)—N-(2-(4-Cyanothiazolidin-3-yl)-2-oxoethyl)-6-(6-(difluoromethyl)pyridin-3-yl)-quinoline-4-carboxamide (Example 169);

(R)—N-(2-(4-Cyanothiazolidin-3-yl)-2-oxoethyl)-6-(6-methylpyridin-3-yl)quinoline-4-carboxamide (Example 177);

(R)—N-(2-(4-Cyanothiazolidin-3-yl)-2-oxoethyl)-6-(6-methoxypyridin-3-yl)quinoline-4-carboxamide (Example 178);

and pharmaceutically acceptable salts thereof.

In some embodiments, the $R^2$ heterocyclyl ring is:

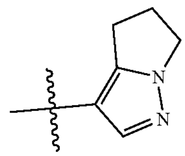

wherein the $R^2$ heterocyclyl ring is optionally substituted with one or more substituents independently selected from the group consisting of halogen, hydroxy, $C_{1-6}$-alkyl, hydroxy-$C_{1-3}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, hydroxy-$C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, fluoromethyl, difluoromethyl, trifluoromethyl, hydroxymethyl, fluoroethyl, difluoroethyl, trifluoroethyl, cyclopropyl, methoxy, ethoxy, propoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, propyl, fluoromethyl, difluoromethyl, trifluoromethyl, fluoroethyl, difluoroethyl, trifluoroethyl, cyclopropyl, methoxy, ethoxy, trifluoromethoxy, trifluoroethoxy, and methoxymethyl.

In some embodiments, the compound or pharmaceutically acceptable salt is (R)—N-(2-(4-cyanothiazolidin-3-yl)-2- oxoethyl)-6-(5,5-dimethyl-5,6-dihydro-4H-pyrrolo[1,2-b]pyrazol-3-yl)quinoline-4-carboxamide (Example 123), or a pharmaceutically acceptable salt thereof.

In some embodiments, the $R^2$ heterocyclyl ring is:

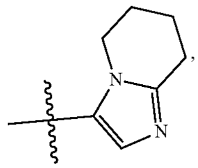 [SMILES: *c1cnc2n1CCCC2]

wherein the $R^2$ heterocyclyl ring is optionally substituted with one or more substituents independently selected from the group consisting of halogen, hydroxy, $C_{1-6}$-alkyl, hydroxy-$C_{1-3}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkoxy-$C_{2-3}$-alkoxy, and $C_{1-3}$-alkoxy-$C_{2-3}$-alkoxy-$C_{1-3}$-alkyl may be further substituted with one or more halogen. In one aspect, the $R^2$ heterocyclyl ring is optionally substituted with one or more substituents independently selected from the group consisting of fluoro, hydroxy, $C_{1-3}$-alkyl, hydroxy-$C_{1-3}$-alkyl, cyclopropyl, $C_{1-3}$-alkoxy, and $C_{1-3}$-alkoxy-$C_{1-3}$-alkyl, wherein the $C_{1-3}$-alkyl, cyclopropyl, $C_{1-3}$-alkoxy, and $C_{1-3}$-alkoxy-$C_{1-3}$-alkyl may be further substituted with one or more fluoro. In another aspect, the $R^2$ heterocyclyl ring is optionally substituted with one or more substituents independently selected from the group consisting of fluoro, hydroxy, methyl, ethyl, propyl, fluoromethyl, difluoromethyl, trifluoromethyl, hydroxymethyl, fluoroethyl, difluoroethyl, trifluoroethyl, cyclopropyl, methoxy, ethoxy, propoxy, trifluoromethoxy, trifluoroethoxy, methoxymethyl, and trifluoromethoxymethyl. In another aspect, the $R^2$ heterocyclyl ring is optionally substituted with one or more substituents independently selected from the group consisting of fluoro, hydroxy, methyl, ethyl, propyl, fluoromethyl, difluoromethyl, trifluoromethyl, fluoroethyl, difluoroethyl, trifluoroethyl, cyclopropyl, methoxy, ethoxy, trifluoromethoxy, trifluoroethoxy, and methoxymethyl.

In some embodiments, the compound or pharmaceutically acceptable salt is (R)—N-(2-(4-cyanothiazolidin-3-yl)-2-oxoethyl)-6-(5,6,7,8-tetrahydroimidazo[1,2-c]pyridin-3-yl)quinoline-4-carboxamide (Example 175) or a pharmaceutically acceptable salt thereof.

In some embodiments, the compounds and pharmaceutically acceptable salts are selected from the group consisting of:

N-(2-((R)-4-Cyanothiazolidin-3-yl)-2-oxoethyl)-6-((3S,4S,5R)-4-hydroxy-3,5-dimethylpiperidin-1-yl)quinoline-4-carboxamide (Example 7);

(R)—N-(2-(4-Cyanothiazolidin-3-yl)-2-oxoethyl)-6-(4-methoxypiperidin-1-yl)-quinoline-4-carboxamide (Example 8);

(R)—N-(2-(4-Cyanothiazolidin-3-yl)-2-oxoethyl)-6-(2-oxopyrrolidin-1-yl)quinoline-4-carboxamide (Example 11);

(R)—N-(2-(4-Cyanothiazolidin-3-yl)-2-oxoethyl)-6-(3,3-dimethyl-2-oxopyrrolidin-1-yl)quinoline-4-carboxamide (Example 12);

(R)—N-(2-(4-Cyanothiazolidin-3-yl)-2-oxoethyl)-6-(2-oxopiperidin-1-yl)quinoline-4-carboxamide (Example 14);

(R)—N-(2-(4-Cyanothiazolidin-3-yl)-2-oxoethyl)-6-(3,3-dimethyl-2-oxopiperidin-1-yl)-quinoline-4-carboxamide (Example 15);

(R)—N-(2-(4-Cyanothiazolidin-3-yl)-2-oxoethyl)-6-(2,2-dimethylazetidin-1-yl)-quinoline-4-carboxamide (Example 20);

(R)—N-(2-(4-Cyanothiazolidin-3-yl)-2-oxoethyl)-6-(3-fluoroazetidin-1-yl)quinoline-4-carboxamide (Example 21);

(R)—N-(2-(4-Cyanothiazolidin-3-yl)-2-oxoethyl)-6-(3,3-dimethylazetidin-1-yl)-quinoline-4-carboxamide (Example 22);

(R)—N-(2-(4-Cyanothiazolidin-3-yl)-2-oxoethyl)-6-(3,3-difluoroazetidin-1-yl)-quinoline-4-carboxamide (Example 23);

(R)—N-(2-(4-Cyanothiazolidin-3-yl)-2-oxoethyl)-6-(3-fluoro-3-methylazetidin-1-yl)-quinoline-4-carboxamide (Example 24);

(R)—N-(2-(4-Cyanothiazolidin-3-yl)-2-oxoethyl)-6-(3-methylazetidin-1-yl)quinoline-4-carboxamide (Example 25);

(R)—N-(2-(4-Cyanothiazolidin-3-yl)-2-oxoethyl)-6-(3-(trifluoromethyl)azetidin-1-yl)-quinoline-4-carboxamide (Example 26);

(R)—N-(2-(4-Cyanothiazolidin-3-yl)-2-oxoethyl)-6-(3-(fluoromethyl)-3-methylazetidin-1-yl)quinoline-4-carboxamide (Example 27);

(R)—N-(2-(4-Cyanothiazolidin-3-yl)-2-oxoethyl)-6-(3-(difluoromethyl)azetidin-1-yl)-quinoline-4-carboxamide (Example 28);

(R)—N-(2-(4-Cyanothiazolidin-3-yl)-2-oxoethyl)-6-(3-(methoxymethyl)-3-methyl-azetidin-1-yl)quinoline-4-carboxamide (Example 29);

N-(2-((R)-4-Cyanothiazolidin-3-yl)-2-oxoethyl)-6-((2S,3R)-3-methoxy-2-methyl-azetidin-1-yl)quinoline-4-carboxamide (Example 30);

(R)—N-(2-(4-Cyanothiazolidin-3-yl)-2-oxoethyl)-6-(3-cyclopropyl-3-fluoroazetidin-1-yl)quinoline-4-carboxamide (Example 31);

(R)—N-(2-(4-Cyanothiazolidin-3-yl)-2-oxoethyl)-6-(piperidin-1-yl)quinoline-4-carboxamide (Example 32);

(R)—N-(2-(4-Cyanothiazolidin-3-yl)-2-oxoethyl)-6-(4,4-dimethylpiperidin-1-yl)-quinoline-4-carboxamide (Example 33);

(R)—N-(2-(4-Cyanothiazolidin-3-yl)-2-oxoethyl)-6-(4-fluoro-4-methylpiperidin-1-yl)quinoline-4-carboxamide (Example 34);

(R)—N-(2-(4-Cyanothiazolidin-3-yl)-2-oxoethyl)-6-(4,4-difluoropiperidin-1-yl)-quinoline-4-carboxamide (Example 35);

(R)—N-(2-(4-Cyanothiazolidin-3-yl)-2-oxoethyl)-6-(3,3-difluoropiperidin-1-yl)-quinoline-4-carboxamide (Example 36);

(R)—N-(2-(4-Cyanothiazolidin-3-yl)-2-oxoethyl)-6-(4-(fluoromethyl)-4-methyl-piperidin-1-yl)quinoline-4-carboxamide (Example 37);

(R)—N-(2-(4-Cyanothiazolidin-3-yl)-2-oxoethyl)-6-(4,4-difluoro-3,3-dimethyl-piperidin-1-yl)quinoline-4-carboxamide (Example 38);

(R)—N-(2-(4-Cyanothiazolidin-3-yl)-2-oxoethyl)-6-(4-(trifluoromethyl)piperidin-1-yl)-quinoline-4-carboxamide (Example 39);

N-(2-((R)-4-Cyanothiazolidin-3-yl)-2-oxoethyl)-6-(3-fluoropiperidin-1-yl)quinoline-4-carboxamide (Example 40);

N-(2-((R)-4-Cyanothiazolidin-3-yl)-2-oxoethyl)-6-(3-methoxypiperidin-1-yl)-quinoline-4-carboxamide (Example 41);

(R)—N-(2-(4-Cyanothiazolidin-3-yl)-2-oxoethyl)-6-(4-methoxy-4-methylpiperidin-1-yl)quinoline-4-carboxamide (Example 42);

(R)—N-(2-(4-Cyanothiazolidin-3-yl)-2-oxoethyl)-6-(4-isopropoxypiperidin-1-yl)-quinoline-4-carboxamide (Example 43);

N-(2-((R)-4-Cyanothiazolidin-3-yl)-2-oxoethyl)-6-(4,4-difluoro-2-methylpiperidin-1-yl)quinoline-4-carboxamide (Example 44);

N-(2-((R)-4-Cyanothiazolidin-3-yl)-2-oxoethyl)-6-((S)-2-(fluoromethyl)piperidin-1-yl)quinoline-4-carboxamide (Example 45);

(R)—N-(2-(4-Cyanothiazolidin-3-yl)-2-oxoethyl)-6-(3,3-difluoropyrrolidin-1-yl)-quinoline-4-carboxamide (Example 47);

(R)—N-(2-(4-Cyanothiazolidin-3-yl)-2-oxoethyl)-6-(3,3-dimethylpyrrolidin-1-yl)-quinoline-4-carboxamide (Example 48);

N-(2-((R)-4-Cyanothiazolidin-3-yl)-2-oxoethyl)-6-((3R,4S)-3,4-difluoropyrrolidin-1-yl)quinoline-4-carboxamide (Example 50);

N-(2-((R)-4-Cyanothiazolidin-3-yl)-2-oxoethyl)-6-((S)-3-fluoropyrrolidin-1-yl)-quinoline-4-carboxamide (Example 51);

N-(2-((R)-4-Cyanothiazolidin-3-yl)-2-oxoethyl)-6-((R)-3-fluoropyrrolidin-1-yl)-quinoline-4-carboxamide (Example 52);

N-(2-((R)-4-Cyanothiazolidin-3-yl)-2-oxoethyl)-6-(hexahydrocyclopenta[c]pyrrol-2(1H)-yl)quinoline-4-carboxamide (Example 53);

N-(2-((R)-4-Cyanothiazolidin-3-yl)-2-oxoethyl)-6-((S)-3-methylpyrrolidin-1-yl)-quinoline-4-carboxamide (Example 54);

N-(2-((R)-4-Cyanothiazolidin-3-yl)-2-oxoethyl)-6-((R)-3-methylpyrrolidin-1-yl)-quinoline-4-carboxamide (Example 55);

N-(2-((R)-4-Cyanothiazolidin-3-yl)-2-oxoethyl)-6-((S)-2-(trifluoromethyl)pyrrolidin-1-yl)quinoline-4-carboxamide (Example 56);

(R)—N-(2-(4-Cyanothiazolidin-3-yl)-2-oxoethyl)-6-(2,2-dimethylpyrrolidin-1-yl)-quinoline-4-carboxamide (Example 57);

N-(2-((R)-4-Cyanothiazolidin-3-yl)-2-oxoethyl)-6-((R)-3-fluoroazepan-1-yl)quinoline-4-carboxamide (Example 59);

N-(2-((R)-4-Cyanothiazolidin-3-yl)-2-oxoethyl)-6-((S)-3-fluoroazepan-1-yl)quinoline-4-carboxamide (Example 60);

N-(2-((R)-4-Cyanothiazolidin-3-yl)-2-oxoethyl)-6-((S)-2-methylpyrrolidin-1-yl)-quinoline-4-carboxamide (Example 65);

(R)—N-(2-(4-Cyanothiazolidin-3-yl)-2-oxoethyl)-6-(3-methoxyazetidin-1-yl)quinoline-4-carboxamide (Example 66);

(R)—N-(2-(4-Cyanothiazolidin-3-yl)-2-oxoethyl)-6-(3-(fluoromethyl)azetidin-1-yl)-quinoline-4-carboxamide (Example 113);

(R)—N-(2-(4-Cyanothiazolidin-3-yl)-2-oxoethyl)-6-(4,5,6,7-tetrahydro-1H-indazol-1-yl)quinoline-4-carboxamide (Example 114);

(R)—N-(2-(4-Cyanothiazolidin-3-yl)-2-oxoethyl)-6-(4,5,6,7-tetrahydro-2H-indazol-2-yl)quinoline-4-carboxamide (Example 115);

(R)—N-(2-(4-Cyanothiazolidin-3-yl)-2-oxoethyl)-6-(5-methyl-3-(trifluoromethyl)-1H-pyrazol-1-yl)quinoline-4-carboxamide (Example 116);

(R)—N-(2-(4-Cyanothiazolidin-3-yl)-2-oxoethyl)-6-(6,6-dimethyl-5,6-dihydrocyclopenta[c]pyrazol-2(4H)-yl)quinoline-4-carboxamide (Example 117);

(R)—N-(2-(4-Cyanothiazolidin-3-yl)-2-oxoethyl)-6-(3-(trifluoromethyl)-1H-pyrazol-1-yl)quinoline-4-carboxamide (Example 118);

(R)—N-(2-(4-Cyanothiazolidin-3-yl)-2-oxoethyl)-6-(4,6-difluoro-1H-indol-1-yl)-quinoline-4-carboxamide (Example 119);

(R)—N-(2-(4-Cyanothiazolidin-3-yl)-2-oxoethyl)-6-(5-fluoro-1H-indol-1-yl)quinoline-4-carboxamide (Example 120);

(R)—N-(2-(4-Cyanothiazolidin-3-yl)-2-oxoethyl)-6-(3-methyl-1H-pyrrol-1-yl)-quinoline-4-carboxamide (Example 121);

(R)—N-(2-(4-Cyanothiazolidin-3-yl)-2-oxoethyl)-6-(3-morpholinoazetidin-1-yl)-quinoline-4-carboxamide (Example 122);

(R)—N-(2-(4-Cyanothiazolidin-3-yl)-2-oxoethyl)-6-(5,5-dimethyl-5,6-dihydro-4H-pyrrolo[1,2-b]pyrazol-3-yl) quinoline-4-carboxamide (Example 123);

(R)—N-(2-(4-Cyanothiazolidin-3-yl)-2-oxoethyl)-6-(2-fluoropyridin-4-yl)quinoline-4-carboxamide (Example 124);

(R)—N-(2-(4-Cyanothiazolidin-3-yl)-2-oxoethyl)-6-(5-fluoropyridin-2-yl)quinoline-4-carboxamide (Example 125);

(R)—N-(2-(4-Cyanothiazolidin-3-yl)-2-oxoethyl)-6-(pyridin-3-yl)quinoline-4-carboxamide (Example 126);

(R)—N-(2-(4-Cyanothiazolidin-3-yl)-2-oxoethyl)-6-(pyrimidin-5-yl)quinoline-4-carboxamide (Example 127);

R)—N-(2-(4-Cyanothiazolidin-3-yl)-2-oxoethyl)-6-(2-methylpyridin-3-yl)quinoline-4-carboxamide (Example 128);

(R)—N-(2-(4-Cyanothiazolidin-3-yl)-2-oxoethyl)-6-(1-methyl-1H-pyrazol-4-yl)-quinoline-4-carboxamide (Example 129);

(R)—N-(2-(4-Cyanothiazolidin-3-yl)-2-oxoethyl)-6-(3-((trifluoromethoxy)methyl)-azetidin-1-yl)quinoline-4-carboxamide (Example 130);

(R)—N-(2-(4-Cyanothiazolidin-3-yl)-2-oxoethyl)-6-(3-methyl-3-(2,2,2-trifluoroethyl)-azetidin-1-yl)quinoline-4-carboxamide (Example 131);

(R)—N-(2-(4-Cyanothiazolidin-3-yl)-2-oxoethyl)-6-(3-(trifluoromethoxy)azetidin-1-yl)quinoline-4-carboxamide (Example 132);

(R)—N-(2-(4-Cyanothiazolidin-3-yl)-2-oxoethyl)-6-(3-(2,2-difluoroethyl)-3-methyl-azetidin-1-yl)quinoline-4-carboxamide (Example 133);

(R)—N-(2-(4-Cyanothiazolidin-3-yl)-2-oxoethyl)-6-(3-cyclopropyl-3-methylazetidin-1-yl)quinoline-4-carboxamide (Example 134);

(R)—N-(2-(4-Cyanothiazolidin-3-yl)-2-oxoethyl)-6-(3-(difluoromethyl)-3-methyl-azetidin-1-yl)quinoline-4-carboxamide (Example 135);

(R)—N-(2-(4-Cyanothiazolidin-3-yl)-2-oxoethyl)-6-(3-(difluoromethoxy)azetidin-1-yl)-quinoline-4-carboxamide (Example 136);

(R)—N-(2-(4-Cyanothiazolidin-3-yl)-2-oxoethyl)-6-(3-ethyl-3-methylazetidin-1-yl)-quinoline-4-carboxamide (Example 137);

(R)—N-(2-(4-Cyanothiazolidin-3-yl)-2-oxoethyl)-6-(3-ethyl-3-fluoroazetidin-1-yl)-quinoline-4-carboxamide (Example 138);

(R)—N-(2-(4-Cyanothiazolidin-3-yl)-2-oxoethyl)-6-(3-(2,2-difluoropropyl)azetidin-1-yl)quinoline-4-carboxamide (Example 140);

(R)—N-(2-(4-Cyanothiazolidin-3-yl)-2-oxoethyl)-6-(3-(3,3,3-trifluoropropyl)azetidin-1-yl)quinoline-4-carboxamide (Example 142);

(R)—N-(2-(4-Cyanothiazolidin-3-yl)-2-oxoethyl)-6-(3-fluoro-3-(trifluoromethyl)-azetidin-1-yl)quinoline-4-carboxamide (Example 143);

(R)—N-(2-(4-Cyanothiazolidin-3-yl)-2-oxoethyl)-6-(3-(2,2-difluoroethyl)azetidin-1-yl)-quinoline-4-carboxamide (Example 144);

(R)—N-(2-(4-Cyanothiazolidin-3-yl)-2-oxoethyl)-6-(3-cyclopropylazetidin-1-yl)-quinoline-4-carboxamide (Example 145);

(R)—N-(2-(4-Cyanothiazolidin-3-yl)-2-oxoethyl)-6-(3-(2-fluoroethyl)azetidin-1-yl)-quinoline-4-carboxamide (Example 146);

(R)—N-(2-(4-Cyanothiazolidin-3-yl)-2-oxoethyl)-6-(3-(1,1-difluoroethyl)azetidin-1-yl)-quinoline-4-carboxamide (Example 147);

(R)—N-(2-(4-Cyanothiazolidin-3-yl)-2-oxoethyl)-6-(3-isopropylazetidin-1-yl)quinoline-4-carboxamide (Example 148);

(R)—N-(2-(4-Cyanothiazolidin-3-yl)-2-oxoethyl)-6-(3-methoxy-3-methylazetidin-1-yl)-quinoline-4-carboxamide (Example 151);

(R)—N-(2-(4-Cyanothiazolidin-3-yl)-2-oxoethyl)-6-(3-ethoxy-3-methylazetidin-1-yl)-quinoline-4-carboxamide (Example 152);

(R)—N-(2-(4-Cyanothiazolidin-3-yl)-2-oxoethyl)-6-(3-ethyl-3-hydroxyazetidin-1-yl)-quinoline-4-carboxamide (Example 154);

6-(6-Azabicyclo[3.2.0]heptan-6-yl)-N-(2-((R)-4-cyanothiazolidin-3-yl)-2-oxoethyl)-quinoline-4-carboxamide (Example 156);

(R)—N-(2-(4-Cyanothiazolidin-3-yl)-2-oxoethyl)-6-(3-fluoro-3-(fluoromethyl)azetidin-1-yl)quinoline-4-carboxamide (Example 157);

(R)—N-(2-(4-Cyanothiazolidin-3-yl)-2-oxoethyl)-6-(3-(2,2,2-trifluoroethyl)azetidin-1-yl)quinoline-4-carboxamide (Example 158);

N-(2-((R)-4-Cyanothiazolidin-3-yl)-2-oxoethyl)-6-(3,3-difluoro-2-methylazetidin-1-yl)quinoline-4-carboxamide (Example 159);

N-(2-((R)-4-Cyanothiazolidin-3-yl)-2-oxoethyl)-6-(6,6-difluoro-3-azabicyclo[3.1.0]hexan-3-yl)quinoline-4-carboxamide (Example 160);

N-(2-((R)-4-Cyanothiazolidin-3-yl)-2-oxoethyl)-6-((R)-3-methoxypyrrolidin-1-yl)-quinoline-4-carboxamide (Example 161);

(R)—N-(2-(4-Cyanothiazolidin-3-yl)-2-oxoethyl)-6-(3-hydroxy-3-methylazetidin-1-yl)-quinoline-4-carboxamide (Example 165);

N-(2-((R)-4-Cyanothiazolidin-3-yl)-2-oxoethyl)-6-((R)-3-hydroxy-3-methylpyrrolidin-1-yl)quinoline-4-carboxamide (Example 167);

N-(2-((R)-4-Cyanothiazolidin-3-yl)-2-oxoethyl)-6-((S)-3-hydroxy-3-methylpyrrolidin-1-yl)quinoline-4-carboxamide (Example 168);

(R)—N-(2-(4-Cyanothiazolidin-3-yl)-2-oxoethyl)-6-(6-(difluoromethyl)pyridin-3-yl)-quinoline-4-carboxamide (Example 169);

(R)—N-(2-(4-Cyanothiazolidin-3-yl)-2-oxoethyl)-6-(1-cyclopropyl-1H-pyrazol-4-yl)-quinoline-4-carboxamide (Example 170);

(R)—N-(2-(4-cyanothiazolidin-3-yl)-2-oxoethyl)-6-(1,3-dimethyl-1H-pyrazol-4-yl)-quinoline-4-carboxamide (Example 171);

(R)—N-(2-(4-Cyanothiazolidin-3-yl)-2-oxoethyl)-6-(3,5-dimethyl-1-(tetrahydro-2H-pyran-4-yl)-1H-pyrazol-4-yl)quinoline-4-carboxamide (Example 172);

(R)—N-(2-(4-cyanothiazolidin-3-yl)-2-oxoethyl)-6-(1-(tetrahydro-2H-pyran-4-yl)-1H-pyrazol-4-yl)quinoline-4-carboxamide (Example 173);

(R)—N-(2-(4-Cyanothiazolidin-3-yl)-2-oxoethyl)-6-(1-methyl-1H-pyrazol-5-yl)-quinoline-4-carboxamide (Example 174);

(R)—N-(2-(4-Cyanothiazolidin-3-yl)-2-oxoethyl)-6-(5,6,7,8-tetrahydroimidazo[1,2-c]-pyridin-3-yl)quinoline-4-carboxamide (Example 175);

N-(2-((R)-4-Cyanothiazolidin-3-yl)-2-oxoethyl)-6-(1-(tetrahydro-2H-pyran-2-yl)-1H-pyrazol-5-yl)quinoline-4-carboxamide (Example 176);

(R)—N-(2-(4-Cyanothiazolidin-3-yl)-2-oxoethyl)-6-(6-methylpyridin-3-yl)quinoline-4-carboxamide (Example 177);

(R)—N-(2-(4-Cyanothiazolidin-3-yl)-2-oxoethyl)-6-(6-methoxypyridin-3-yl)quinoline-4-carboxamide (Example 178);

(R)-6-(3-(Acetamidomethyl)-3-methylazetidin-1-yl)-N-(2-(4-cyanothiazolidin-3-yl)-2-oxoethyl)quinoline-4-carboxamide (Example 181);

(R)—N-(2-(4-cyanothiazolidin-3-yl)-2-oxoethyl)-6-(3-fluoro-3-phenylazetidin-1-yl)-quinoline-4-carboxamide (Example 182);

(R)—N-(2-(4-Cyanothiazolidin-3-yl)-2-oxoethyl)-6-(3-(p-tolyl)azetidin-1-yl)quinoline-4-carboxamide (Example 183);

(R)—N-(2-(4-Cyanothiazolidin-3-yl)-2-oxoethyl)-6-(3-(4-fluorophenyl)azetidin-1-yl)-quinoline-4-carboxamide (Example 185);

(R)—N-(2-(4-Cyanothiazolidin-3-yl)-2-oxoethyl)-6-(3-(m-tolyl)azetidin-1-yl)quinoline-4-carboxamide (Example 186);

(R)-6-(3-(4-Chlorobenzyl)azetidin-1-yl)-N-(2-(4-cyanothiazolidin-3-yl)-2-oxoethyl)-quinoline-4-carboxamide (Example 187);

(R)—N-(2-(4-Cyanothiazolidin-3-yl)-2-oxoethyl)-6-(3-methyl-3-((methylsulfonyl)-methyl)azetidin-1-yl)quinoline-4-carboxamide (Example 188);

(R)—N-(2-(4-Cyanothiazolidin-3-yl)-2-oxoethyl)-6-(4-ethyl-4-hydroxypiperidin-1-yl)-quinoline-4-carboxamide (Example 189);

(R)—N-(2-(4-Cyanothiazolidin-3-yl)-2-oxoethyl)-6-(4-hydroxy-4-methylpiperidin-1-yl)quinoline-4-carboxamide (Example 190);

(R)—N-(2-(4-Cyanothiazolidin-3-yl)-2-oxoethyl)-6-(4-ethyl-4-methoxypiperidin-1-yl)-quinoline-4-carboxamide (Example 191);

(R)—N-(2-(4-Cyanothiazolidin-3-yl)-2-oxoethyl)-6-(4-hydroxy-4-isopropylpiperidin-1-yl)quinoline-4-carboxamide (Example 192);

N-(2-((R)-4-Cyanothiazolidin-3-yl)-2-oxoethyl)-6-((3R,4S,5S)-4-hydroxy-3,4,5-trimethylpiperidin-1-yl)quinoline-4-carboxamide (Example 193);

(R)—N-(2-(4-Cyanothiazolidin-3-yl)-2-oxoethyl)-6-(4-fluoro-1-methylpiperidin-4-yl)-quinoline-4-carboxamide (Example 195);

(R)—N-(2-(4-Cyanothiazolidin-3-yl)-2-oxoethyl)-6-(1H-pyrazol-5-yl)quinoline-4-carboxamide (Example 196);

(R)—N-(2-(4-Cyanothiazolidin-3-yl)-2-oxoethyl)-6-(1-isopropyl-1H-pyrazol-5-yl)-quinoline-4-carboxamide (Example 197);

N-(2-((R)-4-Cyanothiazolidin-3-yl)-2-oxoethyl)-6-((RS)-3-fluoro-3-methylpyrrolidin-1-yl)quinoline-4-carboxamide (Example 198);

N-(2-((R)-4-Cyanothiazolidin-3-yl)-2-oxoethyl)-6-((R*)-2-cyclopropylpyrrolidin-1-yl)quinoline-4-carboxamide Isomer 1 (Example 199);

N-(2-((R)-4-Cyanothiazolidin-3-yl)-2-oxoethyl)-6-((R*)-2-cyclopropylpyrrolidin-1-yl)quinoline-4-carboxamide Isomer 2 (Example 200);

N-(2-((R)-4-Cyanothiazolidin-3-yl)-2-oxoethyl)-6-((R*)-3-methyl-2-oxopyrrolidin-1-yl)quinoline-4-carboxamide Isomer 1 (Example 201);

N-(2-((R)-4-Cyanothiazolidin-3-yl)-2-oxoethyl)-6-((R*)-3-methyl-2-oxopyrrolidin-1-yl)quinoline-4-carboxamide Isomer 2 (Example 202);

N-(2-((R)-4-Cyanothiazolidin-3-yl)-2-oxoethyl)-6-((R*)-3-methyl-2-oxopiperidin-1-yl)quinoline-4-carboxamide Isomer 1 (Example 203);

N-(2-((R)-4-Cyanothiazolidin-3-yl)-2-oxoethyl)-6-((R*)-3-methyl-2-oxopiperidin-1-yl)quinoline-4-carboxamide Isomer 2 (Example 204);

(R)—N-(2-(4-Cyanothiazolidin-3-yl)-2-oxoethyl)-6-(4-fluoropiperidin-1-yl)quinoline-4-carboxamide (Example 205);

6-(3-Azabicyclo[3.1.0]hexan-3-yl)-N-(2-((R)-4-cyanothiazolidin-3-yl)-2-oxoethyl)-quinoline-4-carboxamide (Example 206);

N-(2-((R)-4-Cyanothiazolidin-3-yl)-2-oxoethyl)-6-((S)-3-methoxypyrrolidin-1-yl)-quinoline-4-carboxamide (Example 207);

N-(2-((R)-4-Cyanothiazolidin-3-yl)-2-oxoethyl)-6-((1R,5S,6R)-6-(trifluoromethyl)-3-azabicyclo[3.1.0]hexan-3-yl) quinoline-4-carboxamide (Example 208);

(R)-6-(7-Azabicyclo[2.2.1]heptan-7-yl)-N-(2-(4-cyanothiazolidin-3-yl)-2-oxoethyl)-quinoline-4-carboxamide (Example 209);

6-(2-Azabicyclo[2.2.1]heptan-2-yl)-N-(2-((R)-4-cyanothiazolidin-3-yl)-2-oxoethyl)-quinoline-4-carboxamide (Example 210);

N-(2-((R)-4-cyanothiazolidin-3-yl)-2-oxoethyl)-6-((R)-2-methylpyrrolidin-1-yl)-quinoline-4-carboxamide (Example 211);

N-(2-((R)-4-Cyanothiazolidin-3-yl)-2-oxoethyl)-6-((S)-2-(methoxymethyl)pyrrolidin-1-yl)quinoline-4-carboxamide (Example 212);

N-(2-((R)-4-Cyanothiazolidin-3-yl)-2-oxoethyl)-6-((3S,4S)-3,4-difluoropyrrolidin-1-yl)quinoline-4-carboxamide (Example 213);

N-(2-((R)-4-Cyanothiazolidin-3-yl)-2-oxoethyl)-6-((3R,4R)-3,4-difluoropyrrolidin-1-yl)quinoline-4-carboxamide (Example 214);

(R)—N-(2-(4-Cyanothiazolidin-3-yl)-2-oxoethyl)-6-(2-phenyl-1H-imidazol-1-yl)-quinoline-4-carboxamide (Example 217);

(R)—N-(2-(4-Cyanothiazolidin-3-yl)-2-oxoethyl)-6-(3-phenyl-1H-pyrrol-1-yl)-quinoline-4-carboxamide (Example 218);

(R)—N-(2-(4-Cyanothiazolidin-3-yl)-2-oxoethyl)-6-(4,5,6,7-tetrahydro-1H-indol-1-yl)quinoline-4-carboxamide (Example 219);

N-(2-((R)-4-Cyanothiazolidin-3-yl)-2-oxoethyl)-6-((R)-3-(hydroxymethyl)pyrrolidin-1-yl)quinoline-4-carboxamide (Example 220);

N-(2-((R)-4-Cyanothiazolidin-3-yl)-2-oxoethyl)-6-((S)-3-(hydroxymethyl)pyrrolidin-1-yl)quinoline-4-carboxamide (Example 221);

(R)—N-(2-(4-Cyanothiazolidin-3-yl)-2-oxoethyl)-6-(4-fluoro-4-phenylpiperidin-1-yl)-quinoline-4-carboxamide (Example 223);

N-(2-((R)-4-Cyanothiazolidin-3-yl)-2-oxoethyl)-6-((RS)-3,3-difluoro-4-hydroxy-pyrrolidin-1-yl)quinoline-4-carboxamide (Example 224);

N-(2-((R)-4-Cyanothiazolidin-3-yl)-2-oxoethyl)-6-((3R*,4R*)-3,4-dimethylpyrrolidin-1-yl)quinoline-4-carboxamide Isomer 1 (Example 225);

N-(2-((R)-4-Cyanothiazolidin-3-yl)-2-oxoethyl)-6-((3R*,4R*)-3,4-dimethylpyrrolidin-1-yl)quinoline-4-carboxamide Isomer 2 (Example 226);

(R)—N-(2-(4-Cyanothiazolidin-3-yl)-2-oxoethyl)-6-(4-oxopiperidin-1-yl)quinoline-4-carboxamide (Example 230);

and pharmaceutically acceptable salts thereof.

In some embodiments, the compounds and pharmaceutically acceptable salts are selected from the group consisting of:

N-(2-((R)-4-Cyanothiazolidin-3-yl)-2-oxoethyl)-6-((3S,4S,5R)-4-hydroxy-3,5-dimethylpiperidin-1-yl)quinoline-4-carboxamide (Example 7);

(R)—N-(2-(4-Cyanothiazolidin-3-yl)-2-oxoethyl)-6-(4-methoxypiperidin-1-yl)-quinoline-4-carboxamide (Example 8);

(R)—N-(2-(4-Cyanothiazolidin-3-yl)-2-oxoethyl)-6-(3,3-dimethyl-2-oxopyrrolidin-1-yl)quinoline-4-carboxamide (Example 12);

(R)—N-(2-(4-Cyanothiazolidin-3-yl)-2-oxoethyl)-6-(3,3-dimethyl-2-oxopiperidin-1-yl)quinoline-4-carboxamide (Example 15);

(R)—N-(2-(4-Cyanothiazolidin-3-yl)-2-oxoethyl)-6-(3,3-dimethylazetidin-1-yl)-quinoline-4-carboxamide (Example 22);

(R)—N-(2-(4-Cyanothiazolidin-3-yl)-2-oxoethyl)-6-(3-fluoro-3-methylazetidin-1-yl)-quinoline-4-carboxamide (Example 24);

(R)—N-(2-(4-Cyanothiazolidin-3-yl)-2-oxoethyl)-6-(3-(fluoromethyl)-3-methylazetidin-1-yl)quinoline-4-carboxamide (Example 27);

(R)—N-(2-(4-Cyanothiazolidin-3-yl)-2-oxoethyl)-6-(3-(difluoromethyl)azetidin-1-yl)quinoline-4-carboxamide (Example 28);

(R)—N-(2-(4-Cyanothiazolidin-3-yl)-2-oxoethyl)-6-(3-(methoxymethyl)-3-methyl-azetidin-1-yl)quinoline-4-carboxamide (Example 29);

N-(2-((R)-4-Cyanothiazolidin-3-yl)-2-oxoethyl)-6-((2S,3R)-3-methoxy-2-methyl-azetidin-1-yl)quinoline-4-carboxamide (Example 30);

(R)—N-(2-(4-Cyanothiazolidin-3-yl)-2-oxoethyl)-6-(3-cyclopropyl-3-fluoroazetidin-1-yl)quinoline-4-carboxamide (Example 31);

(R)—N-(2-(4-Cyanothiazolidin-3-yl)-2-oxoethyl)-6-(piperidin-1-yl)quinoline-4-carboxamide (Example 32);

(R)—N-(2-(4-Cyanothiazolidin-3-yl)-2-oxoethyl)-6-(4-fluoro-4-methylpiperidin-1-yl)quinoline-4-carboxamide (Example 34);

N-(2-((R)-4-Cyanothiazolidin-3-yl)-2-oxoethyl)-6-(3-methoxypiperidin-1-yl)-quinoline-4-carboxamide (Example 41);

(R)—N-(2-(4-Cyanothiazolidin-3-yl)-2-oxoethyl)-6-(4-methoxy-4-methylpiperidin-1-yl)quinoline-4-carboxamide (Example 42);

(R)—N-(2-(4-Cyanothiazolidin-3-yl)-2-oxoethyl)-6-(4-isopropoxypiperidin-1-yl)-quinoline-4-carboxamide (Example 43);

N-(2-((R)-4-Cyanothiazolidin-3-yl)-2-oxoethyl)-6-((3R, 4S)-3,4-difluoropyrrolidin-1-yl)quinoline-4-carboxamide (Example 50);

N-(2-((R)-4-Cyanothiazolidin-3-yl)-2-oxoethyl)-6-((R)-3-fluoropyrrolidin-1-yl)-quinoline-4-carboxamide (Example 52);

(R)—N-(2-(4-Cyanothiazolidin-3-yl)-2-oxoethyl)-6-(3-methoxyazetidin-1-yl)quinoline-4-carboxamide (Example 66);

(R)—N-(2-(4-Cyanothiazolidin-3-yl)-2-oxoethyl)-6-(3-(fluoromethyl)azetidin-1-yl)-quinoline-4-carboxamide (Example 113);

(R)—N-(2-(4-Cyanothiazolidin-3-yl)-2-oxoethyl)-6-(3-(difluoromethyl)-3-methyl-azetidin-1-yl)quinoline-4-carboxamide (Example 135);

(R)—N-(2-(4-Cyanothiazolidin-3-yl)-2-oxoethyl)-6-(3-ethyl-3-fluoroazetidin-1-yl)-quinoline-4-carboxamide (Example 138);

(R)—N-(2-(4-Cyanothiazolidin-3-yl)-2-oxoethyl)-6-(3-(2, 2-difluoropropyl)azetidin-1-yl)quinoline-4-carboxamide (Example 140);

(R)—N-(2-(4-Cyanothiazolidin-3-yl)-2-oxoethyl)-6-(3-fluoro-3-(trifluoromethyl)-azetidin-1-yl)quinoline-4-carboxamide (Example 143);

(R)—N-(2-(4-Cyanothiazolidin-3-yl)-2-oxoethyl)-6-(3-(1, 1-difluoroethyl)azetidin-1-yl)quinoline-4-carboxamide (Example 147);

(R)—N-(2-(4-Cyanothiazolidin-3-yl)-2-oxoethyl)-6-(3-methoxy-3-methylazetidin-1-yl)quinoline-4-carboxamide (Example 151);

(R)—N-(2-(4-Cyanothiazolidin-3-yl)-2-oxoethyl)-6-(3-ethoxy-3-methylazetidin-1-yl)-quinoline-4-carboxamide (Example 152);

(R)—N-(2-(4-Cyanothiazolidin-3-yl)-2-oxoethyl)-6-(3-fluoro-3-(fluoromethyl)azetidin-1-yl)quinoline-4-carboxamide (Example 157);

N-(2-((R)-4-Cyanothiazolidin-3-yl)-2-oxoethyl)-6-((R)-3-methoxypyrrolidin-1-yl)-quinoline-4-carboxamide (Example 161);

(R)—N-(2-(4-Cyanothiazolidin-3-yl)-2-oxoethyl)-6-(3-hydroxy-3-methylazetidin-1-yl)-quinoline-4-carboxamide (Example 165);

(R)—N-(2-(4-Cyanothiazolidin-3-yl)-2-oxoethyl)-6-(6-(difluoromethyl)pyridin-3-yl)-quinoline-4-carboxamide (Example 169);

(R)—N-(2-(4-Cyanothiazolidin-3-yl)-2-oxoethyl)-6-(3,5-dimethyl-1-(tetrahydro-2H-pyran-4-yl)-1H-pyrazol-4-yl) quinoline-4-carboxamide (Example 172);

(R)—N-(2-(4-Cyanothiazolidin-3-yl)-2-oxoethyl)-6-(5,6,7, 8-tetrahydroimidazo[1,2-a]pyridin-3-yl)quinoline-4-carboxamide (Example 175);

(R)—N-(2-(4-Cyanothiazolidin-3-yl)-2-oxoethyl)-6-(4-ethyl-4-hydroxypiperidin-1-yl)quinoline-4-carboxamide (Example 189);

(R)—N-(2-(4-Cyanothiazolidin-3-yl)-2-oxoethyl)-6-(4-hydroxy-4-methylpiperidin-1-yl)quinoline-4-carboxamide (Example 190);

(R)—N-(2-(4-Cyanothiazolidin-3-yl)-2-oxoethyl)-6-(4-fluoro-1-methylpiperidin-4-yl)-quinoline-4-carboxamide (Example 195);

N-(2-((R)-4-Cyanothiazolidin-3-yl)-2-oxoethyl)-6-((RS)-3-fluoro-3-methylpyrrolidin-1-yl)quinoline-4-carboxamide (Example 198);

N-(2-((R)-4-Cyanothiazolidin-3-yl)-2-oxoethyl)-6-((R*)-3-methyl-2-oxopyrrolidin-1-yl)quinoline-4-carboxamide Isomer 1 (Example 201);

N-(2-((R)-4-Cyanothiazolidin-3-yl)-2-oxoethyl)-6-((R*)-3-methyl-2-oxopyrrolidin-1-yl)quinoline-4-carboxamide Isomer 2 (Example 202);

N-(2-((R)-4-Cyanothiazolidin-3-yl)-2-oxoethyl)-6-((R*)-3-methyl-2-oxopiperidin-1-yl)quinoline-4-carboxamide Isomer 1 (Example 203);

N-(2-((R)-4-Cyanothiazolidin-3-yl)-2-oxoethyl)-6-((R*)-3-methyl-2-oxopiperidin-1-yl)quinoline-4-carboxamide Isomer 2 (Example 204);

(R)—N-(2-(4-Cyanothiazolidin-3-yl)-2-oxoethyl)-6-(4-fluoropiperidin-1-yl)quinoline-4-carboxamide (Example 205);

N-(2-((R)-4-Cyanothiazolidin-3-yl)-2-oxoethyl)-6-((S)-3-methoxypyrrolidin-1-yl)-quinoline-4-carboxamide (Example 207);

N-(2-((R)-4-Cyanothiazolidin-3-yl)-2-oxoethyl)-6-((3S, 4S)-3,4-difluoropyrrolidin-1-yl)quinoline-4-carboxamide (Example 213);

N-(2-((R)-4-Cyanothiazolidin-3-yl)-2-oxoethyl)-6-((S)-3-(hydroxymethyl)pyrrolidin-1-yl)quinoline-4-carboxamide (Example 221);

N-(2-((R)-4-Cyanothiazolidin-3-yl)-2-oxoethyl)-6-((RS)-3, 3-difluoro-4-hydroxy-pyrrolidin-1-yl)quinoline-4-carboxamide (Example 224);

and pharmaceutically acceptable salts thereof.

B. $R^2$ is Monocyclic or Fused Bicyclic Heterocyclyl (Nitrogen, Oxygen (or Sulfur), and Carbon Ring Atoms)

In some embodiments, the present disclosure provides compounds having the structure of Formulae (I), (II), (III-A), (III-B), (III-C), (III-D), (III-E), (IV), or (IV-A), and pharmaceutically acceptable salts thereof, wherein $R^2$ is heterocyclyl containing a total of 5 to 10 ring atoms, wherein the heterocyclyl ring: (i) is a saturated, partially saturated, or completely unsaturated monocyclic or fused bicyclic ring, (ii) has (a) one nitrogen ring atom and one oxygen ring atom with the remaining ring atoms being carbon, or (b) one nitrogen ring atom and one sulfur ring atom with the remaining ring atoms being carbon, and (iii) is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is a saturated monocyclic ring. In another aspect, the $R^2$ heterocyclyl ring is a partially saturated monocyclic ring. In another aspect, the $R^2$ heterocyclyl ring is a completely unsaturated monocyclic ring. In another aspect, the $R^2$ heterocyclyl ring is a saturated fused bicyclic ring. In another aspect, the $R^2$ heterocyclyl ring is a partially saturated fused bicyclic ring. In another aspect, the $R^2$ heterocyclyl ring is a completely unsaturated fused bicyclic ring. In another aspect, the $R^2$ heterocyclyl ring has one nitrogen ring atom and one oxygen ring atom with the remaining ring atoms being carbon. In another aspect, the $R^2$ heterocyclyl ring has one nitrogen ring atom and one sulfur ring atom with the remaining ring atoms being carbon.

In some embodiments, the $R^2$ heterocyclyl ring contains a total of 6 to 10 ring atoms.

In some embodiments, the $R^2$ heterocyclyl ring is selected from the group consisting of:

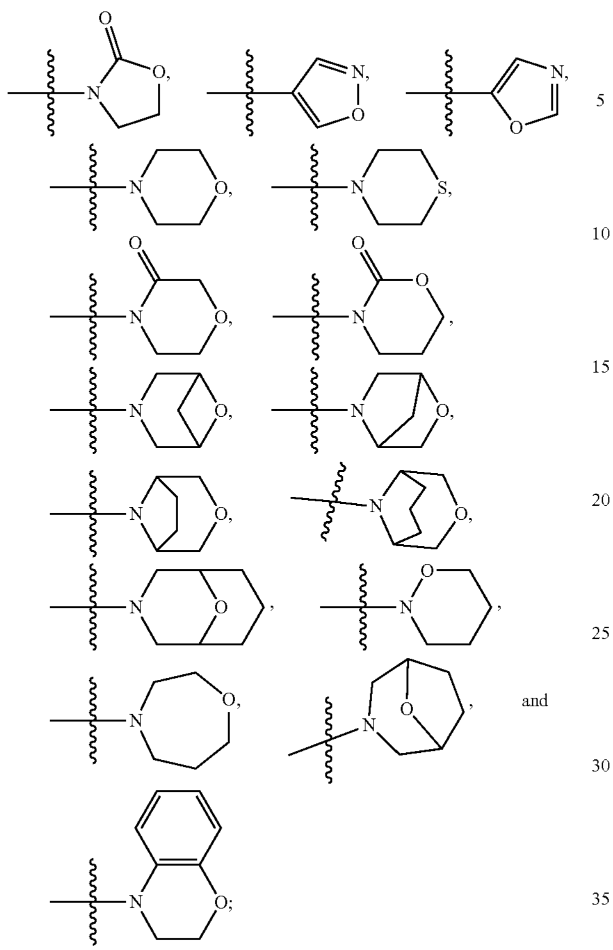

and wherein the heterocyclyl ring is optionally substituted with one or more substituents independently selected from the group consisting of halogen, cyano, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{1-6}$-alkoxy, $C_{1-3}$-alkoxy-$C_{1-3}$-alkyl, $C_{3-6}$-cycloalkyl, $C_{1-3}$-alkylcarbonyl-$C_{1-3}$-alkyl, and $C_{1-3}$-alkylsulfonyl-$C_{1-3}$-alkyl may be further substituted with one or more halogen.

In some embodiments, the $R^2$ heterocyclyl ring is selected from the group consisting of:

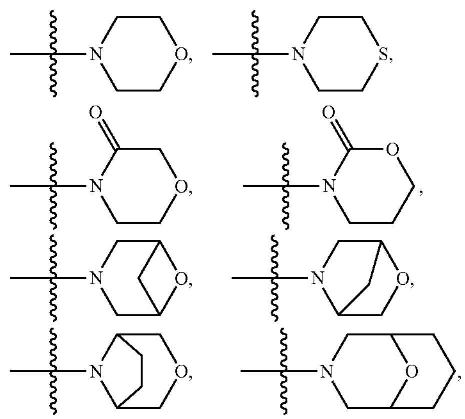

-continued

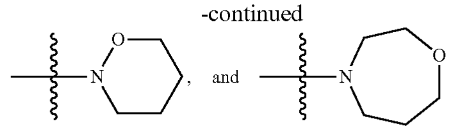

and wherein the heterocyclyl ring is optionally substituted with one or more substituents independently selected from the group consisting of halogen, cyano, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{1-6}$-alkoxy, $C_{1-3}$-alkoxy-$C_{1-3}$-alkyl, $C_{3-6}$-cycloalkyl, $C_{1-3}$-alkylcarbonyl-$C_{1-3}$-alkyl, and $C_{1-3}$-alkylsulfonyl-$C_{1-3}$-alkyl may be further substituted with one or more halogen.

In some embodiments, the $R^2$ heterocyclyl ring is selected from the group consisting of:

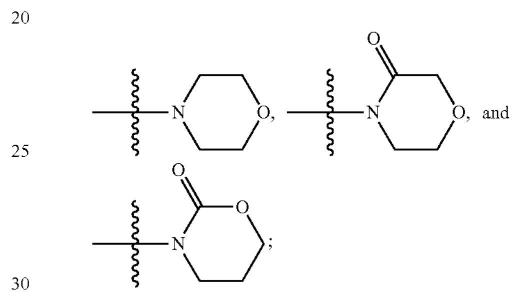

and wherein the heterocyclyl ring is optionally substituted with one or more substituents independently selected from the group consisting of halogen, cyano, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen.

In some embodiments, the $R^2$ heterocyclyl ring is optionally substituted with one or more substituents independently selected from the group consisting of halogen, cyano, $C_{1-3}$-alkyl, $C_{3-5}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{1-3}$-alkoxy, $C_{1-3}$-alkoxy-$C_{1-3}$-alkyl, $C_{1-3}$-alkylcarbonyl-$C_{1-3}$-alkyl, $C_{3-5}$-cycloalkyl, and $C_{1-3}$-alkylsulfonyl-$C_{1-3}$-alkyl may be further substituted with one or more halogen.

In some embodiments, the $R^2$ heterocyclyl ring is optionally substituted with one or more substituents independently selected from the group consisting of halogen, cyano, $C_{1-2}$-alkyl, $C_{3-4}$-cycloalkyl, $C_{1-2}$-alkoxy, $C_{1-2}$-alkoxy-$C_{1-3}$-alkyl, $C_{1-2}$-alkylcarbonyl-$C_{1-2}$-alkyl, and $C_{1-2}$-alkylsulfonyl-$C_{1-2}$-alkyl, wherein the $C_{1-2}$-alkyl, $C_{3-4}$-cycloalkyl, $C_{1-2}$-alkoxy, $C_{1-2}$-alkoxy-$C_{1-2}$-alkyl, $C_{1-2}$-alkylcarbonyl-$C_{1-2}$-alkyl, and $C_{1-2}$-alkylsulfonyl-$C_{1-2}$-alkyl may be further substituted with one or more halogen.

In some embodiments, the $R^2$ heterocyclyl ring is optionally substituted with one or more halogen. In one aspect, the $R^2$ heterocyclyl ring is optionally substituted with one or more fluoro.

In some embodiments, the $R^2$ heterocyclyl ring is optionally substituted with one or more $C_{1-3}$-alkyl, wherein the $C_{1-3}$-alkyl may be further substituted with one or more halogen.

In some embodiments, the $R^2$ heterocyclyl ring is optionally substituted with one or more $C_{3-6}$-cycloalkyl, wherein the $C_{3-6}$-cycloalkyl may be further substituted with one or more halogen.

In some embodiments, the $R^2$ heterocyclyl ring is optionally substituted with one or more $C_{1-3}$-alkoxy-$C_{1-3}$-alkyl, wherein the $C_{1-3}$-alkoxy-$C_{1-3}$-alkyl may be further substituted with one or more halogen.

In some embodiments, the $R^2$ heterocyclyl ring is optionally substituted with one or more $C_{1-3}$-alkylsulfonyl-$C_{1-3}$-alkyl, wherein the $C_{1-3}$-alkylsulfonyl-$C_{1-3}$-alkyl may be further substituted with one or more halogen.

In some embodiments, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, isopropoxy, trifluoromethoxy, trifluoroethoxy, methoxymethyl, methoxyethyl, trifluoromethoxymethyl, and methylsulfonylmethyl.

In some embodiments, the $R^2$ heterocyclyl ring is optionally substituted with one or more substituents independently selected from the group consisting of fluoro, methyl, ethyl, isopropyl, cyclopropyl, fluoromethyl, difluoropropyl, methoxy, and trifluoromethoxy.

In some embodiments, the $R^2$ heterocyclyl ring is:

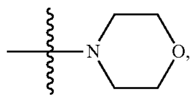

wherein the $R^2$ heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-5}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-5}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of fluoro, cyano, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, methoxyethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, trifluoromethyl, difluoropropyl, methoxy, trifluoromethoxy, and methoxymethyl.

In some embodiments, the compounds and pharmaceutically acceptable salts are selected from the group consisting of:

(R)—N-(2-(4-Cyanothiazolidin-3-yl)-2-oxoethyl)-3-fluoro-6-morpholinoquinoline-4-carboxamide (Example 2);

(R)—N-(2-(4-Cyanothiazolidin-3-yl)-2-oxoethyl)-6-(2,2-difluoromorpholino)quinoline-4-carboxamide (Example 4);

(R)—N-(2-(4-Cyanothiazolidin-3-yl)-2-oxoethyl)-6-(2,2,6,6-tetrafluoromorpholino)-quinoline-4-carboxamide (Example 5);

(R)—N-(2-(4-Cyanothiazolidin-3-yl)-2-oxoethyl)-8-methyl-6-morpholinoquinoline-4-carboxamide (Example 9);

(R)—N-(2-(4-Cyanothiazolidin-3-yl)-2-oxoethyl)-7-methyl-6-morpholinoquinoline-4-carboxamide (Example 10);

(R)—N-(2-(4-Cyanothiazolidin-3-yl)-2-oxoethyl)-6-(2,2-dimethyl-3-oxomorpholino)-quinoline-4-carboxamide (Example 16);

(R)—N-(2-(4-Cyanothiazolidin-3-yl)-2-oxoethyl)-6-morpholinoquinoline-4-carboxamide (Example 67);

N-(2-((R)-4-Cyanothiazolidin-3-yl)-2-oxoethyl)-6-((2R,6S)-2,6-dimethylmorpholino)-quinoline-4-carboxamide (Example 68);

N-(2-((R)-4-Cyanothiazolidin-3-yl)-2-oxoethyl)-6-((R)-2-(fluoromethyl)morpholino)-quinoline-4-carboxamide (Example 69);

N-(2-((R)-4-Cyanothiazolidin-3-yl)-2-oxoethyl)-6-((2R,6R)-2,6-dimethylmorpholino)-quinoline-4-carboxamide (Example 70);

N-(2-((R)-4-Cyanothiazolidin-3-yl)-2-oxoethyl)-6-((S)-2-(fluoromethyl)morpholino)-quinoline-4-carboxamide (Example 71);

N-(2-((R)-4-Cyanothiazolidin-3-yl)-2-oxoethyl)-6-((R)-2-methylmorpholino)-quinoline-4-carboxamide (Example 72);

N-(2-((R)-4-Cyanothiazolidin-3-yl)-2-oxoethyl)-6-((R)-2-(trifluoromethyl)-morpholino)quinoline-4-carboxamide (Example 73);

N-(2-((R)-4-Cyanothiazolidin-3-yl)-2-oxoethyl)-6-((S)-2-(trifluoromethyl)-morpholino)quinoline-4-carboxamide (Example 74);

N-(2-((R)-4-Cyanothiazolidin-3-yl)-2-oxoethyl)-6-((2S,6S)-2,6-dimethylmorpholino)-quinoline-4-carboxamide (Example 78);

N-(2-((R)-4-Cyanothiazolidin-3-yl)-2-oxoethyl)-6-((S)-2-methylmorpholino)-quinoline-4-carboxamide (Example 80);

N-(2-((R)-4-Cyanothiazolidin-3-yl)-2-oxoethyl)-6-((2R,3S)-2,3-dimethyl-morpholino)quinoline-4-carboxamide (Example 81);

N-(2-((R)-4-Cyanothiazolidin-3-yl)-2-oxoethyl)-6-((2S,3S)-2,3-dimethylmorpholino)quinoline-4-carboxamide (Example 82);

N-(2-((R)-4-Cyanothiazolidin-3-yl)-2-oxoethyl)-6-((2R,3R)-2,3-dimethyl-morpholino)quinoline-4-carboxamide (Example 83);

N-(2-((R)-4-Cyanothiazolidin-3-yl)-2-oxoethyl)-6-((R*)-3-(trifluoromethyl)-morpholino)quinoline-4-carboxamide Isomer 1 (Example 84);

N-(2-((R)-4-Cyanothiazolidin-3-yl)-2-oxoethyl)-6-((R*)-3-(trifluoromethyl)-morpholino)quinoline-4-carboxamide Isomer 2 (Example 85);

N-(2-((R)-4-Cyanothiazolidin-3-yl)-2-oxoethyl)-6-((2R,5R)-2,5-dimethylmorpholino)quinoline-4-carboxamide (Example 87);

(R)—N-(2-(4-Cyanothiazolidin-3-yl)-2-oxoethyl)-6-(2,2-dimethylmorpholino)-quinoline-4-carboxamide (Example 88);

N-(2-((R)-4-Cyanothiazolidin-3-yl)-2-oxoethyl)-6-((S)-3-(methoxymethyl)-morpholino)quinoline-4-carboxamide (Example 89);

N-(2-((R)-4-Cyanothiazolidin-3-yl)-2-oxoethyl)-6-((3S,5R)-3,5-dimethyl-morpholino)quinoline-4-carboxamide (Example 90);

N-(2-((R)-4-Cyanothiazolidin-3-yl)-2-oxoethyl)-6-((R)-2-((methylsulfonyl)-methyl)morpholino)quinoline-4-carboxamide (Example 92);

N-(2-((R)-4-Cyanothiazolidin-3-yl)-2-oxoethyl)-6-((S)-2-(methoxymethyl)-morpholino)quinoline-4-carboxamide (Example 93);

N-(2-((R)-4-Cyanothiazolidin-3-yl)-2-oxoethyl)-6-((S)-2-((methylsulfonyl)-methyl)morpholino)quinoline-4-carboxamide (Example 94);

N-(2-((R)-4-Cyanothiazolidin-3-yl)-2-oxoethyl)-6-((R)-3-(2-methoxyethyl)-morpholino)quinoline-4-carboxamide (Example 95);

N-(2-((R)-4-Cyanothiazolidin-3-yl)-2-oxoethyl)-6-((2S,3S)-3-(methoxymethyl)-2-methylmorpholino)quinoline-4-carboxamide (Example 96);

N-(2-((R)-4-Cyanothiazolidin-3-yl)-2-oxoethyl)-6-((2R,3R)-3-(methoxymethyl)-2-methylmorpholino)quinoline-4-carboxamide (Example 97);

7-Bromo-N-(2-((R)-4-cyanothiazolidin-3-yl)-2-oxoethyl)-6-((3S,5R)-3,5-dimethylmorpholino)quinoline-4-carboxamide (Example 100);

(R)-5-Chloro-N-(2-(4-cyanothiazolidin-3-yl)-2-oxoethyl)-6-morpholinoquinoline-4-carboxamide (Example 101);

N-(2-((R)-4-Cyanothiazolidin-3-yl)-2-oxoethyl)-6-((S)-3-methylmorpholino)-quinoline-4-carboxamide (Example 102);

N-(2-((R)-4-Cyanothiazolidin-3-yl)-2-oxoethyl)-6-((3S,5S)-3,5-dimethylmorpholino)-quinoline-4-carboxamide (Example 103);

N-(2-((R)-4-Cyanothiazolidin-3-yl)-2-oxoethyl)-6-((3R,5R)-3,5-dimethylmorpholino)-quinoline-4-carboxamide (Example 105);

N-(2-((R)-4-Cyanothiazolidin-3-yl)-2-oxoethyl)-6-((S)-3-ethylmorpholino)quinoline-4-carboxamide (Example 106);

(R)—N-(2-(4-Cyanothiazolidin-3-yl)-2-oxoethyl)-6-(3,3-dimethylmorpholino)-quinoline-4-carboxamide (Example 107);

N-(2-((R)-4-Cyanothiazolidin-3-yl)-2-oxoethyl)-6-((R)-3-methylmorpholino)-quinoline-4-carboxamide (Example 108);

(R)—N-(2-(4-Cyanothiazolidin-3-yl)-2-oxoethyl)-2-methyl-6-morpholinoquinoline-4-carboxamide (Example 109);

(R)-7-Chloro-N-(2-(4-cyanothiazolidin-3-yl)-2-oxoethyl)-6-morpholinoquinoline-4-carboxamide (Example 179);

(R)-8-Chloro-N-(2-(4-cyanothiazolidin-3-yl)-2-oxoethyl)-6-morpholinoquinoline-4-carboxamide (Example 180);

and pharmaceutically acceptable salts thereof.

In some embodiments, the compounds and pharmaceutically acceptable salts are selected from the group consisting of:

(R)—N-(2-(4-Cyanothiazolidin-3-yl)-2-oxoethyl)-8-methyl-6-morpholinoquinoline-4-carboxamide (Example 9);

(R)—N-(2-(4-Cyanothiazolidin-3-yl)-2-oxoethyl)-6-morpholinoquinoline-4-carboxamide (Example 67);

N-(2-((R)-4-Cyanothiazolidin-3-yl)-2-oxoethyl)-6-((2R,6S)-2,6-dimethylmorpholino)-quinoline-4-carboxamide (Example 68);

N-(2-((R)-4-Cyanothiazolidin-3-yl)-2-oxoethyl)-6-((R)-2-(fluoromethyl)morpholino)-quinoline-4-carboxamide (Example 69);

N-(2-((R)-4-Cyanothiazolidin-3-yl)-2-oxoethyl)-6-((2R,6R)-2,6-dimethylmorpholino)-quinoline-4-carboxamide (Example 70);

N-(2-((R)-4-Cyanothiazolidin-3-yl)-2-oxoethyl)-6-((S)-2-(fluoromethyl)morpholino)-quinoline-4-carboxamide (Example 71);

N-(2-((R)-4-Cyanothiazolidin-3-yl)-2-oxoethyl)-6-((R)-2-methylmorpholino)-quinoline-4-carboxamide (Example 72);

N-(2-((R)-4-Cyanothiazolidin-3-yl)-2-oxoethyl)-6-((R)-2-(trifluoromethyl)-morpholino)quinoline-4-carboxamide (Example 73);

N-(2-((R)-4-Cyanothiazolidin-3-yl)-2-oxoethyl)-6-((S)-2-(trifluoromethyl)-morpholino)quinoline-4-carboxamide (Example 74);

N-(2-((R)-4-Cyanothiazolidin-3-yl)-2-oxoethyl)-6-((2S,6S)-2,6-dimethylmorpholino)-quinoline-4-carboxamide (Example 78);

N-(2-((R)-4-Cyanothiazolidin-3-yl)-2-oxoethyl)-6-((S)-2-methylmorpholino)-quinoline-4-carboxamide (Example 80);

N-(2-((R)-4-Cyanothiazolidin-3-yl)-2-oxoethyl)-6-((2R,3S)-2,3-dimethylmorpholino)-quinoline-4-carboxamide (Example 81);

N-(2-((R)-4-Cyanothiazolidin-3-yl)-2-oxoethyl)-6-((2S,3S)-2,3-dimethylmorpholino)-quinoline-4-carboxamide (Example 82);

(R)—N-(2-(4-Cyanothiazolidin-3-yl)-2-oxoethyl)-6-(2,2-dimethylmorpholino)-quinoline-4-carboxamide (Example 88);

N-(2-((R)-4-Cyanothiazolidin-3-yl)-2-oxoethyl)-6-((S)-3-(methoxymethyl)-morpholino)quinoline-4-carboxamide (Example 89);

N-(2-((R)-4-Cyanothiazolidin-3-yl)-2-oxoethyl)-6-((S)-2-(methoxymethyl)-morpholino)quinoline-4-carboxamide (Example 93);

N-(2-((R)-4-Cyanothiazolidin-3-yl)-2-oxoethyl)-6-((2R,3R)-3-(methoxymethyl)-2-methylmorpholino)-quinoline-4-carboxamide (Example 97);

N-(2-((R)-4-Cyanothiazolidin-3-yl)-2-oxoethyl)-6-((S)-3-methylmorpholino)-quinoline-4-carboxamide (Example 102);

N-(2-((R)-4-Cyanothiazolidin-3-yl)-2-oxoethyl)-6-((S)-3-ethylmorpholino)quinoline-4-carboxamide (Example 106);

(R)—N-(2-(4-Cyanothiazolidin-3-yl)-2-oxoethyl)-6-(3,3-dimethylmorpholino)-quinoline-4-carboxamide (Example 107);

and pharmaceutically acceptable salts thereof.

In some embodiments, the $R^2$ heterocyclyl ring is:

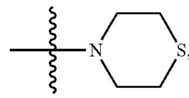

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$- alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of halogen, cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, isopropyl, cyclopropyl, fluoromethyl, difluoropropyl, methoxy, and trifluoromethoxy.

In some embodiments, the compound or pharmaceutically acceptable salt is (R)—N-(2-(4-cyanothiazolidin-3-yl)-2-oxoethyl)-6-thiomorpholinoquinoline-4-carboxamide (Example 3), or a pharmaceutically acceptable salt thereof.

In some embodiments, the $R^2$ heterocyclyl ring is:

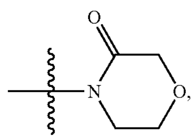 [SMILES: *N1CCOCC1=O]

wherein the heterocyclyl ring is optionally substituted with one or more substituents independently selected from the group consisting of halogen, cyano, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, isopropyl, cyclopropyl, fluoromethyl, difluoropropyl, methoxy, and trifluoromethoxy.

In some embodiments, the compound or pharmaceutically acceptable salt is (R)—N-(2-(4-cyanothiazolidin-3-yl)-2-oxoethyl)-6-(2,2-dimethyl-3-oxomorpholino)quinoline-4-carboxamide (Example 16), or a pharmaceutically acceptable salt thereof.

In some embodiments, the $R^2$ heterocyclyl ring is:

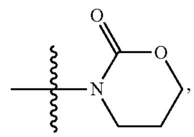 [SMILES: *N1CCCOC1=O]

wherein the heterocyclyl ring is optionally substituted with one or more substituents independently selected from the group consisting of halogen, cyano, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, isopropyl, cyclopropyl, fluoromethyl, difluoropropyl, methoxy, and trifluoromethoxy. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compound or pharmaceutically acceptable salt is (R)—N-(2-(4-cyanothiazolidin-3-yl)-2-oxoethyl)-6-(6,6-dimethyl-2-oxo-1,3-oxazinan-3-yl)quinoline-4-carboxamide (Example 112), or a pharmaceutically acceptable salt thereof.

In some embodiments, the $R^2$ heterocyclyl ring is:

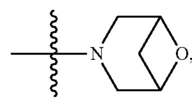 [SMILES: *N1CC2CC(C1)O2]

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, isopropyl, fluoromethyl, difluoropropyl, methoxy, and trifluoromethoxy.

In some embodiments, the compound or pharmaceutically acceptable salt is 6-(6-oxa-3-azabicyclo[3.1.1]heptan-3-yl)-N-(2-((R)-4-cyanothiazolidin-3-yl)-2-oxoethyl)quinoline-4-carboxamide (Example 77), or a pharmaceutically acceptable salt thereof.

In some embodiments, the $R^2$ heterocyclyl ring is:

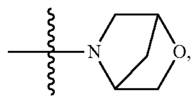

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compounds and pharmaceutically acceptable salts are selected from the group consisting of:

6-((1S,4S)-2-oxa-5-azabicyclo[2.2.1]heptan-5-yl)-N-(2-((R)-4-cyanothiazolidin-3-yl)-2-oxoethyl)quinoline-4-carboxamide (Example 75);

6-((1R,4R)-2-oxa-5-azabicyclo[2.2.1]heptan-5-yl)-N-(2-((R)-4-cyanothiazolidin-3-yl)-2-oxoethyl)quinoline-4-carboxamide (Example 76);

and pharmaceutically acceptable salts thereof.

In some embodiments, the $R^2$ heterocyclyl ring is:

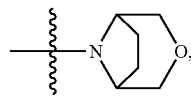 [SMILES: *N1C2CCC1COC2]

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compound or pharmaceutically acceptable salt is 6-(3-oxa-8-azabicyclo[3.2.1]octan-8-yl)-N-(2-((R)-4-cyanothiazolidin-3-yl)-2-oxoethyl)quinoline-4-carboxamide (Example 98), or a pharmaceutically acceptable salt thereof.

In some embodiments, the $R^2$ heterocyclyl ring is:

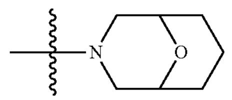

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$- alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, isopropyl, fluoromethyl, difluoropropyl, methoxy, and trifluoromethoxy.

In some embodiments, the compound or pharmaceutically acceptable salt is 6-((1R,5S)-9-oxa-3-azabicyclo[3.3.1]nonan-3-yl)-N-(2-((R)-4-cyanothiazolidin-3-yl)-2-oxoethyl)quinoline-4-carboxamide (Example 194), or a pharmaceutically acceptable salt thereof.

In some embodiments, the $R^2$ heterocyclyl ring is:

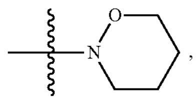 [SMILES: *N1CCCCO1]

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compound or pharmaceutically acceptable salt is (R)—N-(2-(4-cyanothiazolidin-3-yl)-2-oxoethyl)-6-(1,2-oxazinan-2-yl)quinoline-4-carboxamide (Example 1), or a pharmaceutically acceptable salt thereof.

In some embodiments, the $R^2$ heterocyclyl ring is:

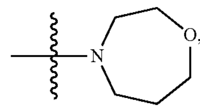 [SMILES: *N1CCCOCC1]

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compounds and pharmaceutically acceptable salts are selected from the group consisting of:

N-(2-((R)-4-Cyanothiazolidin-3-yl)-2-oxoethyl)-6-((R)-7-methyl-1,4-oxazepan-4-yl)quinoline-4-carboxamide (Example 61);

N-(2-((R)-4-Cyanothiazolidin-3-yl)-2-oxoethyl)-6-((S)-7-methyl-1,4-oxazepan-4-yl)quinoline-4-carboxamide (Example 62);

N-(2-((R)-4-Cyanothiazolidin-3-yl)-2-oxoethyl)-6-((S)-3-methyl-1,4-oxazepan-4-yl)quinoline-4-carboxamide (Example 63);

N-(2-((R)-4-Cyanothiazolidin-3-yl)-2-oxoethyl)-6-((R)-2-methyl-1,4-oxazepan-4-yl)quinoline-4-carboxamide (Example 64);

(R)—N-(2-(4-Cyanothiazolidin-3-yl)-2-oxoethyl)-6-(1,4-oxazepan-4-yl)quinoline-4-carboxamide (Example 91);

and pharmaceutically acceptable salts thereof.

In some embodiments, the $R^2$ heterocyclyl ring is:

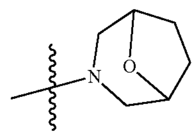

wherein the heterocyclyl ring is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkyl-carbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In one aspect, the $R^2$ heterocyclyl ring is optionally substituted with one or more substituents independently selected from the group consisting of halogen, cyano, $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, wherein the $C_{1-3}$-alkyl, $C_{3-6}$-cycloalkyl, $C_{1-3}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen. In another aspect, the $R^2$ heterocyclyl ring is optionally substituted with one or more substituents independently selected from the group consisting of cyano, fluoro, methyl, ethyl, propyl, isopropyl, cyclopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methoxymethyl, trifluoromethoxymethyl, and methylsulfonylmethyl. In another aspect, the $R^2$ heterocyclyl ring is optionally substituted with one or more substituents independently selected from the group consisting of fluoro, methyl, ethyl, fluoromethyl, difluoropropyl, methoxy, and trifluoromethoxy.

In some embodiments, the compound or pharmaceutically acceptable salt is 6-(8-Oxa-3-azabicyclo[3.2.1]octan-3-yl)-N-(2-((R)-4-cyanothiazolidin-3-yl)-2-oxoethyl)quinoline-4-carboxamide (Example 79), or a pharmaceutically acceptable salt thereof.

In some embodiments, the compounds and pharmaceutically acceptable salts are selected from the group consisting of:

(R)—N-(2-(4-Cyanothiazolidin-3-yl)-2-oxoethyl)-6-(1,2-oxazinan-2-yl)quinoline-4-carboxamide (Example 1);

(R)—N-(2-(4-Cyanothiazolidin-3-yl)-2-oxoethyl)-3-fluoro-6-morpholinoquinoline-4-carboxamide (Example 2);

(R)—N-(2-(4-Cyanothiazolidin-3-yl)-2-oxoethyl)-6-thiomorpholinoquinoline-4-carboxamide (Example 3);

(R)—N-(2-(4-Cyanothiazolidin-3-yl)-2-oxoethyl)-6-(2,2-difluoromorpholino)quinoline-4-carboxamide (Example 4);

(R)—N-(2-(4-Cyanothiazolidin-3-yl)-2-oxoethyl)-6-(2,2,6,6-tetrafluoromorpholino)-quinoline-4-carboxamide (Example 5);

(R)—N-(2-(4-Cyanothiazolidin-3-yl)-2-oxoethyl)-6-(2,3-dihydro-4H-benzo[b][1,4]oxazin-4-yl)quinoline-4-carboxamide (Example 6);

(R)—N-(2-(4-Cyanothiazolidin-3-yl)-2-oxoethyl)-8-methyl-6-morpholinoquinoline-4-carboxamide (Example 9);

(R)—N-(2-(4-Cyanothiazolidin-3-yl)-2-oxoethyl)-7-methyl-6-morpholinoquinoline-4-carboxamide (Example 10);

(R)—N-(2-(4-Cyanothiazolidin-3-yl)-2-oxoethyl)-6-(5,5-dimethyl-2-oxooxazolidin-3-yl)quinoline-4-carboxamide (Example 13);

(R)—N-(2-(4-Cyanothiazolidin-3-yl)-2-oxoethyl)-6-(2,2-dimethyl-3-oxomorpholino)-quinoline-4-carboxamide (Example 16);

N-(2-((R)-4-Cyanothiazolidin-3-yl)-2-oxoethyl)-6-((R)-7-methyl-1,4-oxazepan-4-yl)-quinoline-4-carboxamide (Example 61);

N-(2-((R)-4-Cyanothiazolidin-3-yl)-2-oxoethyl)-6-((S)-7-methyl-1,4-oxazepan-4-yl)-quinoline-4-carboxamide (Example 62);

N-(2-((R)-4-Cyanothiazolidin-3-yl)-2-oxoethyl)-6-((S)-3-methyl-1,4-oxazepan-4-yl)-quinoline-4-carboxamide (Example 63);

N-(2-((R)-4-Cyanothiazolidin-3-yl)-2-oxoethyl)-6-((R)-2-methyl-1,4-oxazepan-4-yl)-quinoline-4-carboxamide (Example 64);

(R)—N-(2-(4-Cyanothiazolidin-3-yl)-2-oxoethyl)-6-morpholinoquinoline-4-carboxamide (Example 67);

N-(2-((R)-4-Cyanothiazolidin-3-yl)-2-oxoethyl)-6-((2R,6S)-2,6-dimethylmorpholino)-quinoline-4-carboxamide (Example 68);

N-(2-((R)-4-Cyanothiazolidin-3-yl)-2-oxoethyl)-6-((R)-2-(fluoromethyl)-morpholino)quinoline-4-carboxamide (Example 69);

N-(2-((R)-4-Cyanothiazolidin-3-yl)-2-oxoethyl)-6-((2R,6R)-2,6-dimethylmorpholino)-quinoline-4-carboxamide (Example 70);

N-(2-((R)-4-Cyanothiazolidin-3-yl)-2-oxoethyl)-6-((S)-2-(fluoromethyl)-morpholino)quinoline-4-carboxamide (Example 71);

N-(2-((R)-4-Cyanothiazolidin-3-yl)-2-oxoethyl)-6-((R)-2-methylmorpholino)-quinoline-4-carboxamide (Example 72);

N-(2-((R)-4-Cyanothiazolidin-3-yl)-2-oxoethyl)-6-((R)-2-(trifluoromethyl)-morpholino)quinoline-4-carboxamide (Example 73);

N-(2-((R)-4-Cyanothiazolidin-3-yl)-2-oxoethyl)-6-((S)-2-(trifluoromethyl)-morpholino)quinoline-4-carboxamide (Example 74);

6-((1S,4S)-2-Oxa-5-azabicyclo[2.2.1]heptan-5-yl)-N-(2-((R)-4-cyanothiazolidin-3-yl)-2-oxoethyl)quinoline-4-carboxamide (Example 75);

6-((1R,4R)-2-Oxa-5-azabicyclo[2.2.1]heptan-5-yl)-N-(2-((R)-4-cyanothiazolidin-3-yl)-2-oxoethyl)quinoline-4-carboxamide (Example 76);

6-(6-Oxa-3-azabicyclo[3.1.1]heptan-3-yl)-N-(2-((R)-4-cyanothiazolidin-3-yl)-2-oxoethyl)quinoline-4-carboxamide (Example 77);

N-(2-((R)-4-Cyanothiazolidin-3-yl)-2-oxoethyl)-6-((2S,6S)-2,6-dimethylmorpholino)-quinoline-4-carboxamide (Example 78);

6-(8-Oxa-3-azabicyclo[3.2.1]octan-3-yl)-N-(2-((R)-4-cyanothiazolidin-3-yl)-2-oxoethyl)quinoline-4-carboxamide (Example 79);

N-(2-((R)-4-Cyanothiazolidin-3-yl)-2-oxoethyl)-6-((S)-2-methylmorpholino)-quinoline-4-carboxamide (Example 80);

N-(2-((R)-4-Cyanothiazolidin-3-yl)-2-oxoethyl)-6-((2R,3S)-2,3-dimethylmorpholino)-quinoline-4-carboxamide (Example 81);

N-(2-((R)-4-Cyanothiazolidin-3-yl)-2-oxoethyl)-6-((2S,3S)-2,3-dimethylmorpholino)-quinoline-4-carboxamide (Example 82);

N-(2-((R)-4-Cyanothiazolidin-3-yl)-2-oxoethyl)-6-((2R,3R)-2,3-dimethylmorpholino)-quinoline-4-carboxamide (Example 83);

N-(2-((R)-4-Cyanothiazolidin-3-yl)-2-oxoethyl)-6-((R*)-3-(trifluoromethyl)-morpholino)quinoline-4-carboxamide Isomer 1 (Example 84);

N-(2-((R)-4-Cyanothiazolidin-3-yl)-2-oxoethyl)-6-((R*)-3-(trifluoromethyl)-morpholino)quinoline-4-carboxamide Isomer 2 (Example 85);

6-(3-Oxa-9-azabicyclo[3.3.1]nonan-9-yl)-N-(2-((R)-4-cyanothiazolidin-3-yl)-2-oxoethyl)quinoline-4-carboxamide (Example 86);

N-(2-((R)-4-Cyanothiazolidin-3-yl)-2-oxoethyl)-6-((2R,5R)-2,5-dimethylmorpholino)-quinoline-4-carboxamide (Example 87);

(R)—N-(2-(4-Cyanothiazolidin-3-yl)-2-oxoethyl)-6-(2,2-dimethylmorpholino)-quinoline-4-carboxamide (Example 88);

N-(2-((R)-4-Cyanothiazolidin-3-yl)-2-oxoethyl)-6-((S)-3-(methoxymethyl)-morpholino)quinoline-4-carboxamide (Example 89);

N-(2-((R)-4-Cyanothiazolidin-3-yl)-2-oxoethyl)-6-((3S,5R)-3,5-dimethyl-morpholino)quinoline-4-carboxamide (Example 90);

(R)—N-(2-(4-Cyanothiazolidin-3-yl)-2-oxoethyl)-6-(1,4-oxazepan-4-yl)quinoline-4-carboxamide (Example 91);

N-(2-((R)-4-Cyanothiazolidin-3-yl)-2-oxoethyl)-6-((R)-2-((methylsulfonyl)-methyl)morpholino)quinoline-4-carboxamide (Example 92);

N-(2-((R)-4-Cyanothiazolidin-3-yl)-2-oxoethyl)-6-((S)-2-(methoxymethyl)-morpholino)quinoline-4-carboxamide (Example 93);

N-(2-((R)-4-Cyanothiazolidin-3-yl)-2-oxoethyl)-6-((S)-2-((methylsulfonyl)-methyl)morpholino)quinoline-4-carboxamide (Example 94);

N-(2-((R)-4-Cyanothiazolidin-3-yl)-2-oxoethyl)-6-((R)-3-(2-methoxyethyl)-morpholino)quinoline-4-carboxamide (Example 95);

N-(2-((R)-4-Cyanothiazolidin-3-yl)-2-oxoethyl)-6-((2S,3S)-3-(methoxymethyl)-2-methylmorpholino)quinoline-4-carboxamide (Example 96);

N-(2-((R)-4-Cyanothiazolidin-3-yl)-2-oxoethyl)-6-((2R,3R)-3-(methoxymethyl)-2-methylmorpholino)quinoline-4-carboxamide (Example 97);

6-(3-Oxa-8-azabicyclo[3.2.1]octan-8-yl)-N-(2-((R)-4-cyanothiazolidin-3-yl)-2-oxoethyl)quinoline-4-carboxamide (Example 98);

7-Bromo-N-(2-((R)-4-cyanothiazolidin-3-yl)-2-oxoethyl)-6-((3S,5R)-3,5-dimethyl-morpholino)quinoline-4-carboxamide (Example 100);

(R)-5-Chloro-N-(2-(4-cyanothiazolidin-3-yl)-2-oxoethyl)-6-morpholinoquinoline-4-carboxamide (Example 101);

N-(2-((R)-4-Cyanothiazolidin-3-yl)-2-oxoethyl)-6-((S)-3-methylmorpholino)-quinoline-4-carboxamide (Example 102);

N-(2-((R)-4-Cyanothiazolidin-3-yl)-2-oxoethyl)-6-((3S,5S)-3,5-dimethylmorpholino)-quinoline-4-carboxamide (Example 103);

N-(2-((R)-4-Cyanothiazolidin-3-yl)-2-oxoethyl)-6-((3R,5R)-3,5-dimethylmorpholino)-quinoline-4-carboxamide (Example 105);

N-(2-((R)-4-Cyanothiazolidin-3-yl)-2-oxoethyl)-6-((S)-3-ethylmorpholino)quinoline-4-carboxamide (Example 106);

(R)—N-(2-(4-Cyanothiazolidin-3-yl)-2-oxoethyl)-6-(3,3-dimethylmorpholino)-quinoline-4-carboxamide (Example 107);

N-(2-((R)-4-Cyanothiazolidin-3-yl)-2-oxoethyl)-6-((R)-3-methylmorpholino)-quinoline-4-carboxamide (Example 108);

(R)—N-(2-(4-Cyanothiazolidin-3-yl)-2-oxoethyl)-2-methyl-6-morpholinoquinoline-4-carboxamide (Example 109);

(R)—N-(2-(4-Cyanothiazolidin-3-yl)-2-oxoethyl)-6-(6,6-dimethyl-2-oxo-1,3-oxazinan-3-yl)quinoline-4-carboxamide (Example 112);

(R)-7-Chloro-N-(2-(4-cyanothiazolidin-3-yl)-2-oxoethyl)-6-morpholinoquinoline-4-carboxamide (Example 179);

(R)-8-Chloro-N-(2-(4-cyanothiazolidin-3-yl)-2-oxoethyl)-6-morpholinoquinoline-4-carboxamide (Example 180);

6-((1R,5S)-9-Oxa-3-azabicyclo[3.3.1]nonan-3-yl)-N-(2-((R)-4-cyanothiazolidin-3-yl)-2-oxoethyl)quinoline-4-carboxamide (Example 194);

(R)—N-(2-(4-Cyanothiazolidin-3-yl)-2-oxoethyl)-6-(2,4-dimethyloxazol-5-yl)quinoline-4-carboxamide (Example 215);

(R)—N-(2-(4-Cyanothiazolidin-3-yl)-2-oxoethyl)-6-(3,5-dimethylisoxazol-4-yl)-quinoline-4-carboxamide (Example 216);

and pharmaceutically acceptable salts thereof.

In some embodiments, the compounds and pharmaceutically acceptable salts are selected from the group consisting of:

(R)—N-(2-(4-Cyanothiazolidin-3-yl)-2-oxoethyl)-6-(1,2-oxazinan-2-yl)quinoline-4-carboxamide (Example 1);

(R)—N-(2-(4-Cyanothiazolidin-3-yl)-2-oxoethyl)-3-fluoro-6-morpholinoquinoline-4-carboxamide (Example 2);

(R)—N-(2-(4-Cyanothiazolidin-3-yl)-2-oxoethyl)-6-(2,2-difluoromorpholino)quinoline-4-carboxamide (Example 4);

(R)—N-(2-(4-Cyanothiazolidin-3-yl)-2-oxoethyl)-8-methyl-6-morpholinoquinoline-4-carboxamide (Example 9);

(R)—N-(2-(4-Cyanothiazolidin-3-yl)-2-oxoethyl)-6-morpholinoquinoline-4-carboxamide (Example 67);

N-(2-((R)-4-Cyanothiazolidin-3-yl)-2-oxoethyl)-6-((2R,6S)-2,6-dimethylmorpholino)-quinoline-4-carboxamide (Example 68);

N-(2-((R)-4-Cyanothiazolidin-3-yl)-2-oxoethyl)-6-((R)-2-(fluoromethyl)morpholino)-quinoline-4-carboxamide (Example 69);

N-(2-((R)-4-Cyanothiazolidin-3-yl)-2-oxoethyl)-6-((2R,6R)-2,6-dimethylmorpholino)-quinoline-4-carboxamide (Example 70);

N-(2-((R)-4-Cyanothiazolidin-3-yl)-2-oxoethyl)-6-((S)-2-(fluoromethyl)morpholino)-quinoline-4-carboxamide (Example 71);

N-(2-((R)-4-Cyanothiazolidin-3-yl)-2-oxoethyl)-6-((R)-2-methylmorpholino)-quinoline-4-carboxamide (Example 72);

N-(2-((R)-4-Cyanothiazolidin-3-yl)-2-oxoethyl)-6-((R)-2-(trifluoromethyl)-morpholino)quinoline-4-carboxamide (Example 73);

N-(2-((R)-4-Cyanothiazolidin-3-yl)-2-oxoethyl)-6-((S)-2-(trifluoromethyl)-morpholino)quinoline-4-carboxamide (Example 74);

6-((1S,4S)-2-Oxa-5-azabicyclo[2.2.1]heptan-5-yl)-N-(2-((R)-4-cyanothiazolidin-3-yl)-2-oxoethyl)quinoline-4-carboxamide (Example 75);

6-((1R,4R)-2-Oxa-5-azabicyclo[2.2.1]heptan-5-yl)-N-(2-((R)-4-cyanothiazolidin-3-yl)-2-oxoethyl)quinoline-4-carboxamide (Example 76);

6-(6-Oxa-3-azabicyclo[3.1.1]heptan-3-yl)-N-(2-((R)-4-cyanothiazolidin-3-yl)-2-oxoethyl)quinoline-4-carboxamide (Example 77);

N-(2-((R)-4-Cyanothiazolidin-3-yl)-2-oxoethyl)-6-((2S,6S)-2,6-dimethylmorpholino)-quinoline-4-carboxamide (Example 78);

6-(8-Oxa-3-azabicyclo[3.2.1]octan-3-yl)-N-(2-((R)-4-cyanothiazolidin-3-yl)-2-oxoethyl)quinoline-4-carboxamide (Example 79);

N-(2-((R)-4-Cyanothiazolidin-3-yl)-2-oxoethyl)-6-((S)-2-methylmorpholino)-quinoline-4-carboxamide (Example 80);

N-(2-((R)-4-Cyanothiazolidin-3-yl)-2-oxoethyl)-6-((2R, 3S)-2,3-dimethylmorpholino)-quinoline-4-carboxamide (Example 81);

N-(2-((R)-4-Cyanothiazolidin-3-yl)-2-oxoethyl)-6-((2S, 3S)-2,3-dimethylmorpholino)-quinoline-4-carboxamide (Example 82);

(R)—N-(2-(4-Cyanothiazolidin-3-yl)-2-oxoethyl)-6-(2,2-dimethylmorpholino)-quinoline-4-carboxamide (Example 88);

N-(2-((R)-4-Cyanothiazolidin-3-yl)-2-oxoethyl)-6-((S)-3-(methoxymethyl)-morpholino)quinoline-4-carboxamide (Example 89);

N-(2-((R)-4-Cyanothiazolidin-3-yl)-2-oxoethyl)-6-((S)-2-(methoxymethyl)-morpholino)quinoline-4-carboxamide (Example 93);

N-(2-((R)-4-Cyanothiazolidin-3-yl)-2-oxoethyl)-6-((2R, 3R)-3-(methoxymethyl)-2-methylmorpholino)quinoline-4-carboxamide (Example 97);

6-(3-Oxa-8-azabicyclo[3.2.1]octan-8-yl)-N-(2-((R)-4-cyanothiazolidin-3-yl)-2-oxoethyl)quinoline-4-carboxamide (Example 98);

N-(2-((R)-4-Cyanothiazolidin-3-yl)-2-oxoethyl)-6-((S)-3-methylmorpholino)-quinoline-4-carboxamide (Example 102);

N-(2-((R)-4-Cyanothiazolidin-3-yl)-2-oxoethyl)-6-((S)-3-ethylmorpholino)quinoline-4-carboxamide (Example 106);

(R)—N-(2-(4-Cyanothiazolidin-3-yl)-2-oxoethyl)-6-(3,3-dimethylmorpholino)-quinoline-4-carboxamide (Example 107);

(R)—N-(2-(4-Cyanothiazolidin-3-yl)-2-oxoethyl)-2-methyl-6-morpholinoquinoline-4-carboxamide (Example 109);

(R)—N-(2-(4-Cyanothiazolidin-3-yl)-2-oxoethyl)-6-(6,6-dimethyl-2-oxo-1,3-oxazinan-3-yl)quinoline-4-carboxamide (Example 112);

and pharmaceutically acceptable salts thereof.

C. $R^2$ is Spiro Heterocyclyl

In some embodiments, the present disclosure provides compounds having the structure of Formulae (I), (II), (III-A), (III-B), (III-C), (III-D), (IV), or (IV-A), or pharmaceutically acceptable salts thereof, wherein $R^2$ is spiro heterocyclyl containing a total of 6 to 11 ring atoms, wherein the spiro heterocyclyl: (i) comprises two saturated rings, (ii) has: (a) one or two nitrogen ring atoms with the remaining ring atoms being carbon, (b) one or two nitrogen ring atoms and one or two oxygen ring atoms with the remaining ring atoms being carbon, or (c) one nitrogen ring atom and one sulfur ring atom with the remaining ring atoms being carbon, and (iii) is optionally substituted with one or more substituents independently selected from the group consisting of halogen, oxo, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl has: (a) one or two nitrogen ring atoms with the remaining ring atoms being carbon, or (b) one or two nitrogen ring atoms and one or two oxygen ring atoms with the remaining ring atoms being carbon. In another aspect, the $R^2$ spiro heterocyclyl has one or two nitrogen ring atoms and, optionally, one or two oxygen ring atoms with the remaining ring atoms being carbon. In another aspect, the $R^2$ spiro heterocyclyl has one nitrogen ring atom with the remaining ring atoms being carbon. In another aspect, the $R^2$ spiro heterocyclyl has two nitrogen ring atoms with the remaining ring atoms being carbon. In another aspect, the $R^2$ spiro heterocyclyl has one nitrogen ring atom and one oxygen ring atom with the remaining ring atoms being carbon. In another aspect, the $R^2$ spiro heterocyclyl has one nitrogen ring atom and two oxygen ring atoms with the remaining ring atoms being carbon.

In some embodiments, the two saturated rings of the $R^2$ spiro heterocyclyl are selected from the group consisting of:

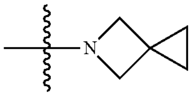, 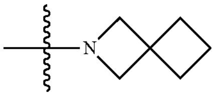,

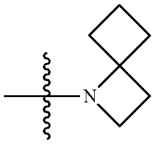, 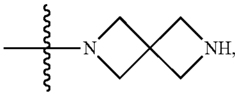

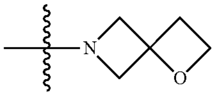, 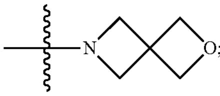

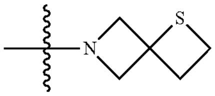, 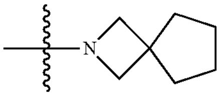,

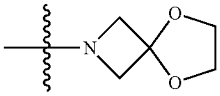, 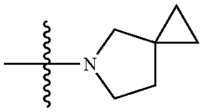,

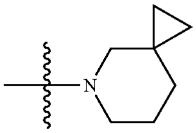, 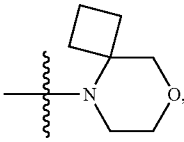

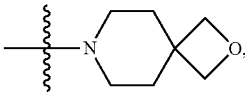 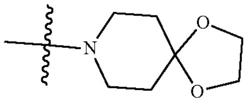,

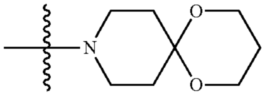, 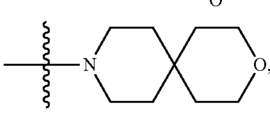

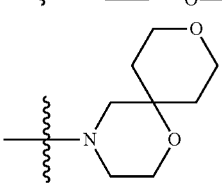, 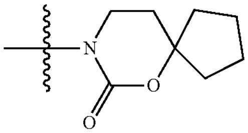, and

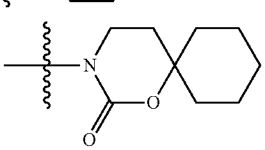

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl.

In some embodiments, the two saturated rings of the $R^2$ spiro heterocyclyl are selected from the group consisting of:

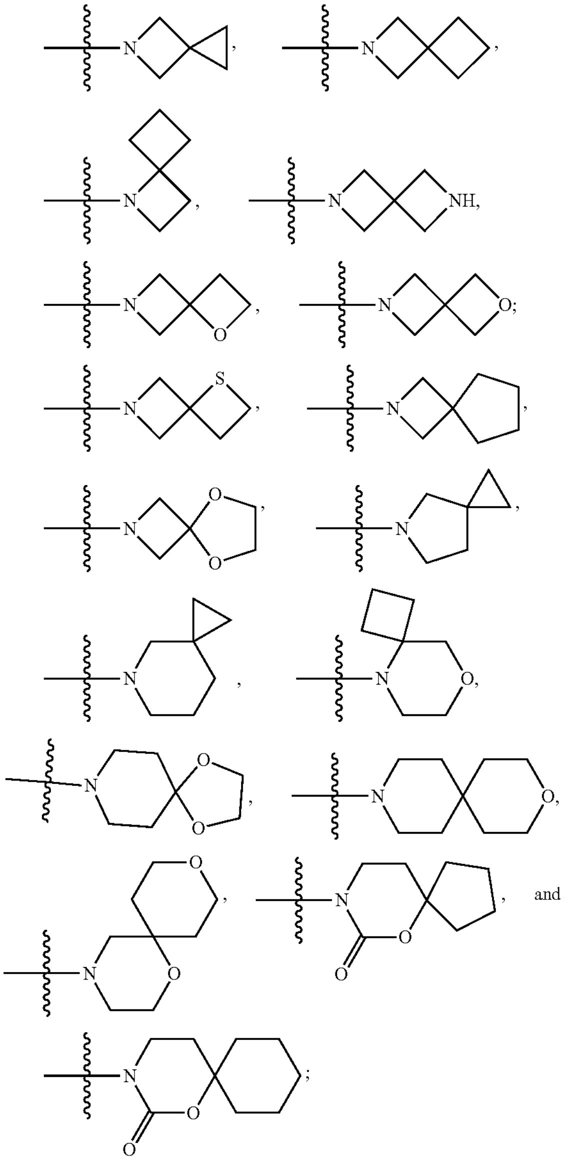

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl.

In some embodiments, the two saturated rings of the $R^2$ spiro heterocyclyl are selected from the group consisting of:

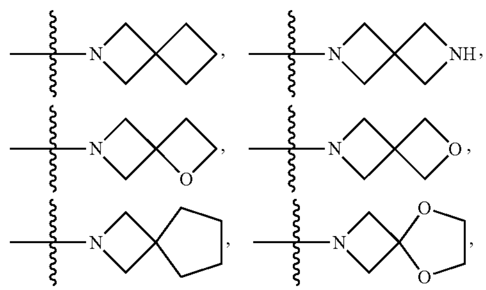

-continued

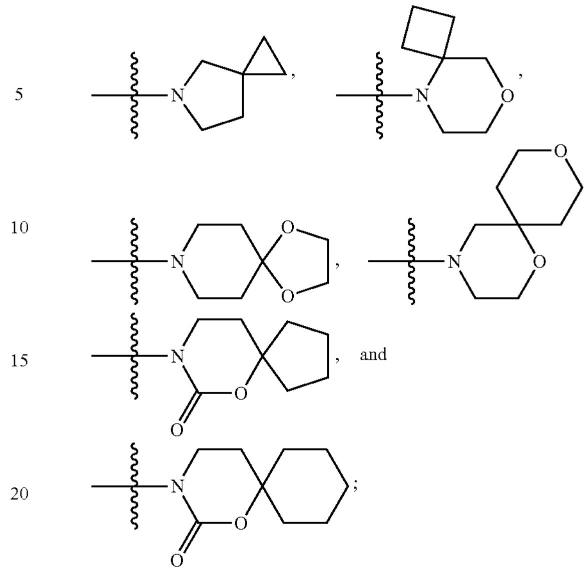

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl.

In some embodiments, the two saturated rings of the $R^2$ spiro heterocyclyl are selected from the group consisting of:

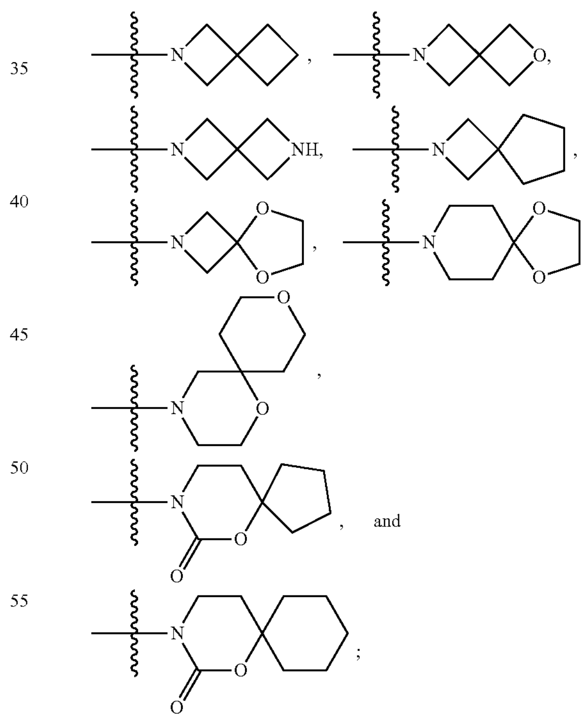

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl.

In some embodiments, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl.

In some embodiments, the $R^2$ spiro heterocyclyl ring is optionally substituted with one or more halogen. In one aspect, the $R^2$ spiro heterocyclyl ring is optionally substituted with one or more fluoro.

In some embodiments, the $R^2$ spiro heterocyclyl ring is optionally substituted with one or more $C_{1-3}$-alkyl.

In some embodiments, the $R^2$ spiro heterocyclyl ring is optionally substituted with one or more $C_{1-3}$-haloalkyl.

In some embodiments, the $R^2$ spiro heterocyclyl ring is optionally substituted with one or more $C_{1-3}$-alkoxy.

In some embodiments, the $R^2$ spiro heterocyclyl ring is optionally substituted with one or more $C_{1-3}$-haloalkoxy.

In some embodiments, the $R^2$ spiro heterocyclyl ring is optionally substituted with one or more $C_{1-3}$-alkylcarbonyl. In one aspect, the $R^2$ spiro heterocyclyl ring is optionally substituted with one or more methylcarbonyl.

In some embodiments, the $R^2$ spiro heterocyclyl ring is optionally substituted with one or more substituents independently selected from the group consisting of fluoro, methyl, ethyl, propyl, isopropyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, ethylcarbonyl, and isopropylcarbonyl.

In some embodiments, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the two saturated rings of the $R^2$ spiro heterocyclyl are:

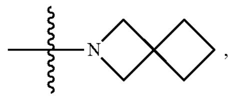 [SMILES: *N1CC2(CCC2)C1], wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, and trifluoroethoxy. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compounds and pharmaceutically acceptable salts are selected from the group consisting of:

(R)—N-(2-(4-Cyanothiazolidin-3-yl)-2-oxoethyl)-6-(2-azaspiro[3.3]heptan-2-yl)-quinoline-4-carboxamide (Example 17);

(R)—N-(2-(4-Cyanothiazolidin-3-yl)-2-oxoethyl)-6-(6-fluoro-2-azaspiro[3.3]heptan-2-yl)quinoline-4-carboxamide (Example 155);

(R)—N-(2-(4-Cyanothiazolidin-3-yl)-2-oxoethyl)-6-(6-(trifluoromethyl)-2-azaspiro[3.3]heptan-2-yl)quinoline-4-carboxamide (Example 150);

(R)—N-(2-(4-Cyanothiazolidin-3-yl)-2-oxoethyl)-6-(6-methyl-2-azaspiro[3.3]heptan-2-yl)quinoline-4-carboxamide (Example 149);

and pharmaceutically acceptable salts thereof.

In some embodiments, the two saturated rings of the $R^2$ spiro heterocyclyl are:

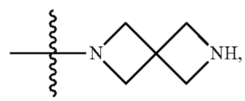 [SMILES: *N1CC2(CNC2)C1]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, and methylcarbonyl. In another aspect, the $R^2$ spiro heterocyclyl ring is optionally substituted with one or more substituents independently selected from the group consisting of fluoro, methyl, ethyl, fluoromethyl, difluoromethyl, trifluoromethyl, and methylcarbonyl.

In some embodiments, the compound or pharmaceutically acceptable salt is (R)-6-(6-acetyl-2,6-diazaspiro[3.3]heptan-2-yl)-N-(2-(4-cyanothiazolidin-3-yl)-2-oxoethyl)quinoline-4-carboxamide (Example 184), or a pharmaceutically acceptable salt thereof.

In some embodiments, the two saturated rings of the $R^2$ spiro heterocyclyl are:

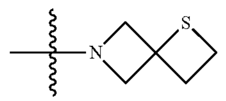, wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(1-thia-6-azaspiro[3.3]heptan-6-yl)quinoline-4-carboxamide (Example 222), or a pharmaceutically acceptable salt thereof.

In some embodiments, the two saturated rings of the $R^2$ spiro heterocyclyl are:

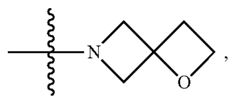

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compounds and pharmaceutically acceptable salts are selected from the group consisting of:

(R)—N-(2-(4-Cyanothiazolidin-3-yl)-2-oxoethyl)-6-(3,3-dimethyl-1-oxa-6-azaspiro[3.3]heptan-6-yl)quinoline-4-carboxamide (Example 18);

(R)—N-(2-(4-Cyanothiazolidin-3-yl)-2-oxoethyl)-6-(1-oxa-6-azaspiro[3.3]heptan-6-yl)quinoline-4-carboxamide (Example 153);

and pharmaceutically acceptable salts thereof.

In some embodiments, the two saturated rings of the $R^2$ spiro heterocyclyl are:

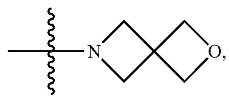 [SMILES: *N1CC2(COC2)C1]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(2-oxa-6-azaspiro[3.3]heptan-6-yl)quinoline-4-carboxamide (Example 166), or a pharmaceutically acceptable salt thereof.

In some embodiments, the two saturated rings of the $R^2$ spiro heterocyclyl are:

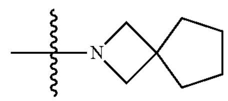

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compounds and pharmaceutically acceptable salts are selected from the group consisting of:

(R)—N-(2-(4-Cyanothiazolidin-3-yl)-2-oxoethyl)-6-(2-azaspiro[3.4]octan-2-yl)quinoline-4-carboxamide (Example 139);

(R)—N-(2-(4-Cyanothiazolidin-3-yl)-2-oxoethyl)-6-(5,5-difluoro-2-azaspiro[3.4]octan-2-yl)quinoline-4-carboxamide (Example 141);

and pharmaceutically acceptable salts thereof.

In some embodiments, the two saturated rings of the $R^2$ spiro heterocyclyl are:

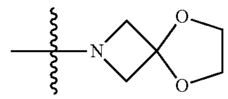

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(5,8-dioxa-2-azaspiro[3.4]octan-2-yl)quinoline-4-carboxamide (Example 163), or a pharmaceutically acceptable salt thereof.

In some embodiments, the two saturated rings of the $R^2$ spiro heterocyclyl are:

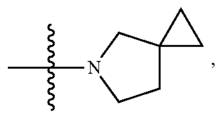 [SMILES: *N1CCC2(CC2)C1]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, and trifluoroethoxy. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the two saturated rings of the $R^2$ spiro heterocyclyl are:

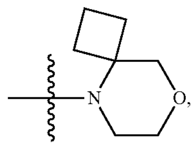 [SMILES: *N1CCOCC12CCC2]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(8-oxa-5-azaspiro[3.5]nonan-5-yl)quinoline-4-carboxamide (Example 104), or a pharmaceutically acceptable salt thereof.

In some embodiments, the two saturated rings of the $R^2$ spiro heterocyclyl are:

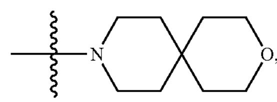

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(3-oxa-9-azaspiro[5.5]undecan-9-yl)quinoline-4-carboxamide (Example 162), or a pharmaceutically acceptable salt thereof.

In some embodiments, the two saturated rings of the $R^2$ spiro heterocyclyl are:

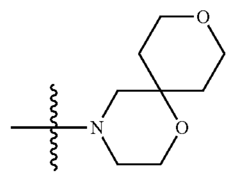

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(1,9-dioxa-4-azaspiro[5.5]undecan-4-yl)quinoline-4-carboxamide (Example 99), or a pharmaceutically acceptable salt thereof.

In some embodiments, the two saturated rings of the $R^2$ spiro heterocyclyl are:

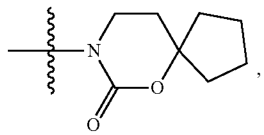 [SMILES: *N1CCC2(CCCC2)OC1=O]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, and trifluoroethoxy. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(7-oxo-6-oxa-8-azaspiro[4.5]decan-8-yl)quinoline-4-carboxamide (Example 111), or a pharmaceutically acceptable salt thereof.

In some embodiments, the two saturated rings of the $R^2$ spiro heterocyclyl are:

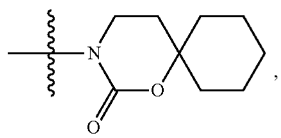 [SMILES: *N1CCC2(CCCCC2)OC1=O]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-haloalkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, and trifluoroethoxy. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(2-oxo-1-oxa-3-azaspiro[5.5]undecan-3-yl)quinoline-4-carboxamide (Example 110), or a pharmaceutically acceptable salt thereof.

In some embodiments, the two saturated rings of the $R^2$ spiro heterocyclyl are:

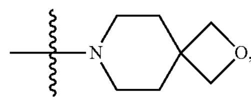 [SMILES: *N1CCC2(CC1)COC2]

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(2-oxa-7-azaspiro[3.5]nonan-7-yl)quinoline-4-carboxamide (Example 229), or a pharmaceutically acceptable salt thereof.

In some embodiments, the two saturated rings of the $R^2$ spiro heterocyclyl are:

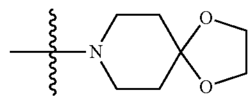

wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(1,4-dioxa-8-azaspiro[4.5]decan-8-yl)quinoline-4-carboxamide (Example 228), or a pharmaceutically acceptable salt thereof. In some embodiments, the two saturated rings of the $R^2$ spiro heterocyclyl are:

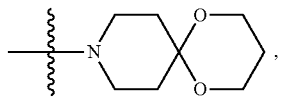 [SMILES: *N1CCC2(CC1)OCCCO2], wherein one or both of the rings are optionally substituted with one or more substituents independently selected from the group consisting of halogen, $C_{1-6}$-alkyl, $C_{1-6}$-haloalkyl, $C_{1-6}$-alkoxy, $C_{1-6}$-haloalkoxy, and $C_{1-6}$-alkylcarbonyl. In one aspect, the $R^2$ spiro heterocyclyl ring is optionally substituted with one or more substituents independently selected from the group consisting of halogen, $C_{1-3}$-alkyl, $C_{1-3}$-alkoxy, $C_{1-3}$-haloalkoxy, and $C_{1-3}$-alkylcarbonyl. In another aspect, the $R^2$ spiro heterocyclyl ring is optionally substituted with one or more substituents independently selected from the group consisting of fluoro, methyl, ethyl, propyl, fluoromethyl, difluoromethyl, trifluoromethyl, fluoroethyl, difluoroethyl, trifluoroethyl, trifluoropropyl, methoxy, ethoxy, trifluoromethoxy, trifluoroethoxy, methylcarbonyl, and ethylcarbonyl. In another aspect, the $R^2$ spiro heterocyclyl ring is optionally substituted with one or more substituents independently selected from the group consisting of fluoro, methyl, ethyl, fluoromethyl, difluoromethyl, and trifluoromethyl.

In some embodiments, the compound or pharmaceutically acceptable salt is (R)—N-(2-(4-cyanothiazolidin-3-yl)-2-oxoethyl)-6-(1,5-dioxa-9-azaspiro[5.5]undecan-9-yl)quinoline-4-carboxamide (Example 227), or a pharmaceutically acceptable salt thereof.

In some embodiments, the compounds and pharmaceutically acceptable salts are selected from the group consisting of:

(R)—N-(2-(4-Cyanothiazolidin-3-yl)-2-oxoethyl)-6-(2-azaspiro[3.3]heptan-2-yl)quinoline-4-carboxamide (Example 17);

(R)—N-(2-(4-Cyanothiazolidin-3-yl)-2-oxoethyl)-6-(3,3-dimethyl-1-oxa-6-azaspiro[3.3]heptan-6-yl)quinoline-4-carboxamide (Example 18);

(R)—N-(2-(4-Cyanothiazolidin-3-yl)-2-oxoethyl)-6-(1-azaspiro[3.3]heptan-1-yl)quinoline-4-carboxamide (Example 19);

(R)—N-(2-(4-Cyanothiazolidin-3-yl)-2-oxoethyl)-6-(5-azaspiro[2.5]octan-5-yl)quinoline-4-carboxamide (Example 46);

(R)—N-(2-(4-Cyanothiazolidin-3-yl)-2-oxoethyl)-6-(5-azaspiro[2.4]heptan-5-yl)quinoline-4-carboxamide (Example 49);

N-(2-((R)-4-Cyanothiazolidin-3-yl)-2-oxoethyl)-6-((R)-6-(fluoromethyl)-5-azaspiro[2.4]heptan-5-yl)quinoline-4-carboxamide (Example 58);

(R)—N-(2-(4-Cyanothiazolidin-3-yl)-2-oxoethyl)-6-(1,9-dioxa-4-azaspiro[5.5]undecan-4-yl)quinoline-4-carboxamide (Example 99);

(R)—N-(2-(4-Cyanothiazolidin-3-yl)-2-oxoethyl)-6-(8-oxa-5-azaspiro[3.5]nonan-5-yl)quinoline-4-carboxamide (Example 104);

(R)—N-(2-(4-Cyanothiazolidin-3-yl)-2-oxoethyl)-6-(2-oxo-1-oxa-3-azaspiro[5.5]undecan-3-yl)quinoline-4-carboxamide (Example 110);

(R)—N-(2-(4-Cyanothiazolidin-3-yl)-2-oxoethyl)-6-(7-oxo-6-oxa-8-azaspiro[4.5]decan-8-yl)quinoline-4-carboxamide (Example 111);

(R)—N-(2-(4-Cyanothiazolidin-3-yl)-2-oxoethyl)-6-(2-azaspiro[3.4]octan-2-yl)quinoline-4-carboxamide (Example 139);

(R)—N-(2-(4-Cyanothiazolidin-3-yl)-2-oxoethyl)-6-(5,5-difluoro-2-azaspiro[3.4]octan-2-yl)quinoline-4-carboxamide (Example 141);

(R)—N-(2-(4-Cyanothiazolidin-3-yl)-2-oxoethyl)-6-(6-methyl-2-azaspiro[3.3]heptan-2-yl)quinoline-4-carboxamide (Example 149);

(R)—N-(2-(4-Cyanothiazolidin-3-yl)-2-oxoethyl)-6-(6-(trifluoromethyl)-2-azaspiro[3.3]heptan-2-yl)quinoline-4-carboxamide (Example 150);

(R)—N-(2-(4-Cyanothiazolidin-3-yl)-2-oxoethyl)-6-(1-oxa-6-azaspiro[3.3]heptan-6-yl)quinoline-4-carboxamide (Example 153);

(R)—N-(2-(4-Cyanothiazolidin-3-yl)-2-oxoethyl)-6-(6-fluoro-2-azaspiro[3.3]heptan-2-yl)quinoline-4-carboxamide (Example 155);

(R)—N-(2-(4-Cyanothiazolidin-3-yl)-2-oxoethyl)-6-(3-oxa-9-azaspiro[5.5]undecan-9-yl)quinoline-4-carboxamide (Example 162);

(R)—N-(2-(4-Cyanothiazolidin-3-yl)-2-oxoethyl)-6-(5,8-dioxa-2-azaspiro[3.4]octan-2-yl)quinoline-4-carboxamide (Example 163);

(R)—N-(2-(4-Cyanothiazolidin-3-yl)-2-oxoethyl)-6-(5-azaspiro[2.3]hexan-5-yl)quinoline-4-carboxamide (Example 164);

(R)—N-(2-(4-Cyanothiazolidin-3-yl)-2-oxoethyl)-6-(2-oxa-6-azaspiro[3.3]heptan-6-yl)quinoline-4-carboxamide (Example 166);

(R)-6-(6-Acetyl-2,6-diazaspiro[3.3]heptan-2-yl)-N-(2-(4-cyanothiazolidin-3-yl)-2-oxoethyl)quinoline-4-carboxamide (Example 184);

(R)—N-(2-(4-Cyanothiazolidin-3-yl)-2-oxoethyl)-6-(1-thia-6-azaspiro[3.3]heptan-6-yl)quinoline-4-carboxamide (Example 222);

(R)—N-(2-(4-Cyanothiazolidin-3-yl)-2-oxoethyl)-6-(1,5-dioxa-9-azaspiro[5.5]undecan-9-yl)quinoline-4-carboxamide (Example 227);

(R)—N-(2-(4-Cyanothiazolidin-3-yl)-2-oxoethyl)-6-(1,4-dioxa-8-azaspiro[4.5]decan-8-yl)quinoline-4-carboxamide (Example 228);

(R)—N-(2-(4-Cyanothiazolidin-3-yl)-2-oxoethyl)-6-(2-oxa-7-azaspiro[3.5]nonan-7-yl)quinoline-4-carboxamide (Example 229);

and pharmaceutically acceptable salts thereof.

In some embodiments, the compounds and pharmaceutically acceptable salts are selected from the group consisting of:

(R)—N-(2-(4-Cyanothiazolidin-3-yl)-2-oxoethyl)-6-(3,3-dimethyl-1-oxa-6-azaspiro[3.3]heptan-6-yl)quinoline-4-carboxamide (Example 18);

(R)—N-(2-(4-Cyanothiazolidin-3-yl)-2-oxoethyl)-6-(1,9-dioxa-4-azaspiro[5.5]undecan-4-yl)quinoline-4-carboxamide (Example 99);

(R)—N-(2-(4-Cyanothiazolidin-3-yl)-2-oxoethyl)-6-(2-oxo-1-oxa-3-azaspiro[5.5]undecan-3-yl)quinoline-4-carboxamide (Example 110);

(R)—N-(2-(4-Cyanothiazolidin-3-yl)-2-oxoethyl)-6-(6-(trifluoromethyl)-2-azaspiro[3.3]heptan-2-yl)quinoline-4-carboxamide (Example 150);

(R)—N-(2-(4-Cyanothiazolidin-3-yl)-2-oxoethyl)-6-(1-oxa-6-azaspiro[3.3]heptan-6-yl)quinoline-4-carboxamide (Example 153);

(R)—N-(2-(4-Cyanothiazolidin-3-yl)-2-oxoethyl)-6-(5,8-dioxa-2-azaspiro[3.4]octan-2-yl)quinoline-4-carboxamide (Example 163);

(R)—N-(2-(4-Cyanothiazolidin-3-yl)-2-oxoethyl)-6-(2-oxa-6-azaspiro[3.3]heptan-6-yl)quinoline-4-carboxamide (Example 166);

(R)—N-(2-(4-Cyanothiazolidin-3-yl)-2-oxoethyl)-6-(1-thia-6-azaspiro[3.3]heptan-6-yl)quinoline-4-carboxamide (Example 222);

and pharmaceutically acceptable salts thereof.

D. $R^2$ is Azetidinyl

In some embodiments, the present disclosure provides compounds having the structure of Formula (V):

(V)

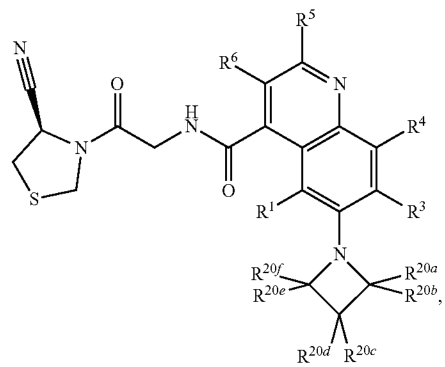

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{20a}$ and $R^{20b}$ are independently selected from the group consisting of hydrogen and $C_{1-3}$-alkyl;

$R^{20c}$ and $R^{20d}$ are independently selected from the group consisting of hydrogen, fluoro, hydroxy, $C_{1-3}$-alkyl, $C_{3-6}$-cycloalkyl, $C_{3-6}$-cycloalkyl-$C_{1-3}$-alkyl, $C_{1-3}$-alkoxy, $C_{3-6}$-cycloalkoxy, $C_{1-3}$-alkoxy-$C_{1-3}$-alkyl, phenyl, tolyl, phenyl-$C_{1-3}$-alkyl, morpholinyl, $C_{1-3}$-alkylsulfonyl-$C_{1-3}$-alkyl, and $C_{1-3}$-alkyl-carbonylamino-$C_{1-3}$-alkyl; and wherein the $C_{1-3}$-alkyl, $C_{3-6}$-cycloalkyl, $C_{3-6}$-cycloalkyl-$C_{1-3}$-alkyl, $C_{1-3}$-alkoxy, $C_{3-6}$-cycloalkoxy, $C_{1-3}$-alkoxy-$C_{1-3}$-alkyl, phenyl, and phenyl-$C_{1-3}$-alkyl may be further substituted with one or more halogen; and $R^{20e}$ and $R^{20f}$ are independently selected from the group consisting of hydrogen and In some embodiments of the compounds having the structure of Formula (V), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (V), $R^1$, $R^3$, $R^4$, $R^5$, and $R^6$ are all hydrogen.

In some embodiments of the compounds having the structure of Formula (V):

$R^{20a}$ and $R^{20b}$ are independently selected from the group consisting of hydrogen and methyl;

$R^{20c}$ and $R^{20d}$ are independently selected from the group consisting of hydrogen, fluoro, hydroxy, $C_{1-3}$-alkyl, $C_{3-6}$-cycloalkyl, $C_{1-3}$-alkoxy, $C_{1-3}$-alkoxy-$C_{1-3}$-alkyl, morpholinyl, $C_{1-3}$-alkylsulfonyl-$C_{1-3}$-alkyl, and $C_{1-3}$-alkyl-carbonylamino-$C_{1-3}$-alkyl; and wherein the $C_{1-3}$-alkyl, $C_{3-6}$-cycloalkyl, $C_{1-3}$-alkoxy, and $C_{1-3}$-alkoxy-$C_{1-3}$-alkyl may be further substituted with one or more halogen; and $R^{20e}$ and $R^{20f}$ are independently selected from the group consisting of hydrogen and methyl.

In some embodiments of the compounds having the structure of Formula (V), $R^{20c}$ and $R^{20d}$ are independently selected from the group consisting of hydrogen, fluoro, $C_{1-3}$-alkyl, $C_{1-3}$-alkoxy, morpholinyl, and $C_{1-3}$-alkyl-carbonylamino-$C_{1-3}$-alkyl; and wherein the $C_{1-3}$-alkyl and $C_{1-3}$-alkoxy may be further substituted with one or more halogen.

In some embodiments, the compounds and pharmaceutically acceptable salts are selected from the group consisting of:

(R)—N-(2-(4-Cyanothiazolidin-3-yl)-2-oxoethyl)-6-(3-(fluoromethyl)-3-methylazetidin-1-yl)quinoline-4-carboxamide (Example 27);

(R)—N-(2-(4-Cyanothiazolidin-3-yl)-2-oxoethyl)-6-(3-(fluoromethyl)azetidin-1-yl)quinoline-4-carboxamide (Example 113);

(R)—N-(2-(4-Cyanothiazolidin-3-yl)-2-oxoethyl)-6-(3-methoxy-3-methylazetidin-1-yl)quinoline-4-carboxamide (Example 151);

and pharmaceutically acceptable salts thereof.

E. $R^2$ is Morpholinyl

In some embodiments, the present disclosure provides compounds having the structure of Formula (VI):

(VI)

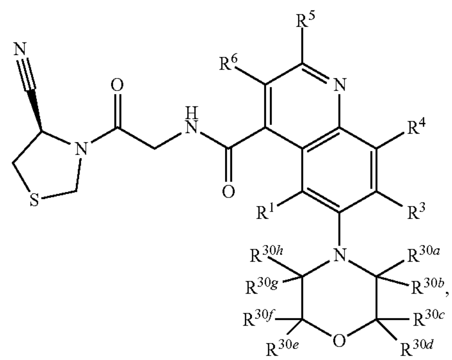

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{30a}$ and $R^{30b}$ are independently selected from the group consisting of hydrogen, $C_{1-3}$-alkyl, and $C_{1-3}$-alkoxy-$C_{1-3}$-alkyl;

$R^{30c}$ and $R^{30d}$ are independently selected from the group consisting of hydrogen, halogen, $C_{1-3}$-alkyl, halo-$C_{1-3}$-alkyl, $C_{1-3}$-alkoxy-$C_{1-3}$-alkyl, and $C_{1-3}$-alkylsulfonyl-$C_{1-3}$-alkyl;

$R^{30e}$ and $R^{30f}$ are independently selected from the group consisting of hydrogen, halogen, $C_{1-3}$-alkyl, halo-$C_{1-3}$-alkyl, $C_{1-3}$-alkoxy-$C_{1-3}$-alkyl, and $C_{1-3}$-alkylsulfonyl-$C_{1-3}$-alkyl; and $R^{30g}$ and $R^{30h}$ are independently selected from the group consisting of hydrogen, $C_{1-3}$-alkyl, halo-$C_{1-3}$-alkyl, and $C_{1-3}$-alkoxy-$C_{1-3}$-alkyl.

In some embodiments of the compounds having the structure of Formula (VI), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (VI), $R^1$, $R^3$, $R^4$, $R^5$, and $R^6$ are all hydrogen.

In some embodiments of the compounds having the structure of Formula (VI):

$R^{30a}$ and $R^{30b}$ are independently selected from the group consisting of hydrogen, $C_{1-2}$-alkyl, halo-$C_{1-2}$-alkyl, and $C_{1-2}$-alkoxy-$C_{1-2}$-alkyl;

$R^{30c}$ and $R^{30d}$ are independently selected from the group consisting of hydrogen, halogen, $C_{1-2}$-alkyl, halo-$C_{1-2}$-alkyl, $C_{1-2}$-alkoxy-$C_{1-2}$-alkyl, and $C_{1-2}$-alkylsulfonyl-$C_{1-2}$-alkyl;

$R^{30e}$ and $R^{30f}$ are independently selected from the group consisting of hydrogen, halogen, $C_{1-2}$-alkyl, halo-$C_{1-2}$-alkyl, $C_{1-2}$-alkoxy-$C_{1-2}$-alkyl, and $C_{1-2}$-alkylsulfonyl-$C_{1-2}$-alkyl; and $R^{30g}$ and $R^{30h}$ are independently selected from the group consisting of hydrogen, $C_{1-2}$-alkyl, halo-$C_{1-2}$-alkyl, and $C_{1-2}$-alkoxy-$C_{1-2}$-alkyl.

In some embodiments, the compounds and pharmaceutically acceptable salts are selected from the group consisting of:

(R)—N-(2-(4-Cyanothiazolidin-3-yl)-2-oxoethyl)-8-methyl-6-morpholinoquinoline-4-carboxamide (Example 9);

(R)—N-(2-(4-Cyanothiazolidin-3-yl)-2-oxoethyl)-6-morpholinoquinoline-4-carboxamide (Example 67);

N-(2-((R)-4-Cyanothiazolidin-3-yl)-2-oxoethyl)-6-((2R, 6S)-2,6-dimethylmorpholino)-quinoline-4-carboxamide (Example 68);

N-(2-((R)-4-Cyanothiazolidin-3-yl)-2-oxoethyl)-6-((R)-2-(fluoromethyl)morpholino)-quinoline-4-carboxamide (Example 69);

N-(2-((R)-4-Cyanothiazolidin-3-yl)-2-oxoethyl)-6-((2R, 6R)-2,6-dimethylmorpholino)-quinoline-4-carboxamide (Example 70);

N-(2-((R)-4-Cyanothiazolidin-3-yl)-2-oxoethyl)-6-((S)-2-(fluoromethyl)morpholino)-quinoline-4-carboxamide (Example 71);

N-(2-((R)-4-Cyanothiazolidin-3-yl)-2-oxoethyl)-6-((R)-2-methylmorpholino)-quinoline-4-carboxamide (Example 72);

N-(2-((R)-4-Cyanothiazolidin-3-yl)-2-oxoethyl)-6-((S)-2-methylmorpholino)-quinoline-4-carboxamide (Example 80);

and pharmaceutically acceptable salts thereof.

F. $R^2$ is Piperidin-1-yl

In some embodiments, the present disclosure provides compounds having the structure of Formula (VII):

(VII)

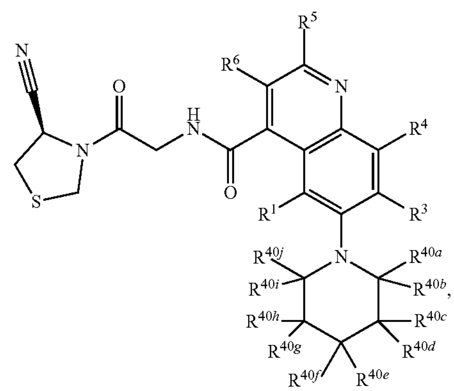

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{40a}$ and $R^{40b}$ are independently selected from the group consisting of hydrogen, $C_{1-3}$-alkyl, and halo-$C_{1-3}$-alkyl;

$R^{40c}$ and $R^{40d}$ are independently selected from the group consisting of hydrogen, fluoro, $C_{1-3}$-alkyl, halo-$C_{1-3}$-alkyl, and $C_{1-3}$-alkoxy;

$R^{40e}$ and $R^{40f}$ are independently selected from the group consisting of hydrogen, fluoro, hydroxy, oxo, $C_{1-3}$-alkyl, halo-$C_{1-3}$-alkyl, cyclopropyl, and $C_{1-3}$-alkoxy;

$R^{40g}$ and $R^{40h}$ are independently selected from the group consisting of hydrogen, fluoro, $C_{1-3}$-alkyl, halo-$C_{1-3}$-alkyl, and $C_{1-3}$-alkoxy; and $R^{40i}$ and $R^{40j}$ are independently selected from the group consisting of hydrogen, $C_{1-3}$-alkyl, and halo-$C_{1-3}$-alkyl.

In some embodiments of the compounds having the structure of Formula (VII), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (VII), $R^1$, $R^3$, $R^4$, $R^5$, and $R^6$ are all hydrogen.

In some embodiments of the compounds having the structure of Formula (VII):

$R^{40a}$ and $R^{40b}$ are independently selected from the group consisting of hydrogen, $C_{1-3}$-alkyl, and halo-$C_{1-3}$-alkyl;

$R^{40c}$ and $R^{40d}$ are independently selected from the group consisting of hydrogen, fluoro, $C_{1-3}$-alkyl, halo-$C_{1-3}$-alkyl, and $C_{1-3}$-alkoxy;

$R^{40e}$ and $R^{40f}$ are independently selected from the group consisting of hydrogen, fluoro, hydroxy, $C_{1-3}$-alkyl, halo-$C_{1-3}$-alkyl, cyclopropyl, and $C_{1-3}$-alkoxy;

$R^{40g}$ and $R^{40h}$ are independently selected from the group consisting of hydrogen, fluoro, $C_{1-3}$-alkyl, halo-$C_{1-3}$-alkyl, and $C_{1-3}$-alkoxy; and $R^{40i}$ and $R^{40j}$ are independently selected from the group consisting of hydrogen, $C_{1-3}$-alkyl, and halo-$C_{1-3}$-alkyl.

In some embodiments of the compounds having the structure of Formula (VII):

$R^{40a}$ and $R^{40b}$ are independently selected from the group consisting of hydrogen, $C_{1-2}$-alkyl, and halo-$C_{1-2}$-alkyl;

$R^{40c}$ and $R^{40d}$ are independently selected from the group consisting of hydrogen, fluoro, $C_{1-2}$-alkyl, halo-$C_{1-2}$-alkyl, and $C_{1-2}$-alkoxy;

$R^{40e}$ and $R^{40f}$ are independently selected from the group consisting of hydrogen, fluoro, hydroxy, $C_{1-2}$-alkyl, halo-$C_{1-2}$-alkyl, and $C_{1-2}$-alkoxy;

$R^{40g}$ and $R^{40h}$ are independently selected from the group consisting of hydrogen, fluoro, $C_{1-2}$-alkyl, halo-$C_{1-2}$-alkyl, and $C_{1-2}$-alkoxy; and $R^{40i}$ and $R^{40j}$ are independently selected from the group consisting of hydrogen, $C_{1-2}$-alkyl, and halo-$C_{1-2}$-alkyl.

In some embodiments, the compounds and pharmaceutically acceptable salts are selected from the group consisting of:

(R)—N-(2-(4-Cyanothiazolidin-3-yl)-2-oxoethyl)-6-(4-methoxypiperidin-1-yl)quinoline-4-carboxamide (Example 8);

(R)—N-(2-(4-Cyanothiazolidin-3-yl)-2-oxoethyl)-6-(4-methoxy-4-methylpiperidin-1-yl)quinoline-4-carboxamide (Example 42);

(R)—N-(2-(4-Cyanothiazolidin-3-yl)-2-oxoethyl)-6-(4-fluoropiperidin-1-yl)quinoline-4-carboxamide (Example 205);

(R)—N-(2-(4-cyanothiazolidin-3-yl)-2-oxoethyl)-6-(4-oxopiperidin-1-yl)quinoline-4-carboxamide (Example 230)

and pharmaceutically acceptable salts thereof.

G. $R^2$ is Piperidin-4-yl

In some embodiments, the present disclosure provides compounds having the structure of Formula (VIII):

(VIII)

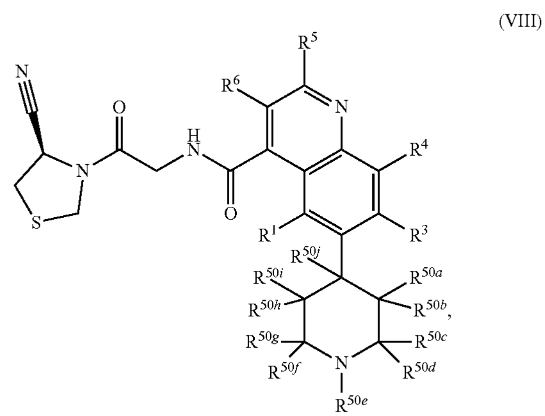

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{50a}$ and $R^{50b}$ are independently selected from the group consisting of hydrogen, fluoro, $C_{1-3}$-alkyl, halo-$C_{1-3}$-alkyl, and $C_{1-3}$-alkoxy;

$R^{50c}$ and $R^{50d}$ are independently selected from the group consisting of hydrogen, $C_{1-3}$-alkyl, and halo-$C_{1-3}$-alkyl, or together are oxo;

$R^{50e}$ is selected from the group consisting of hydrogen, $C_{1-3}$-alkyl, halo-$C_{1-3}$-alkyl, $C_{1-3}$-alkoxy-$C_{2-3}$-alkyl, $C_{1-3}$-alkyl-carbonyl, and $C_{3-6}$-cycloalkyl-carbonyl;

$R^{50f}$ and $R^{50g}$ are independently selected from the group consisting of hydrogen, $C_{1-3}$-alkyl, and halo-$C_{1-3}$-alkyl, or together are oxo;

$R^{50h}$ and $R^{50i}$ are independently selected from the group consisting of hydrogen, fluoro, $C_{1-3}$-alkyl, halo-$C_{1-3}$-alkyl, and $C_{1-3}$-alkoxy; and $R^{50j}$ is selected from the group consisting of hydrogen and fluoro.

In some embodiments of the compounds having the structure of Formula (VIII), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (VIII), R', $R^3$, $R^4$, $R^5$, and $R^6$ are all hydrogen.

In some embodiments of the compounds having the structure of Formula (VIII):

$R^1$, $R^3$, $R^4$, $R^5$, and $R^6$ are independently selected from the group consisting of hydrogen, fluoro, and methyl;

$R^{50a}$ and $R^{50b}$ are independently selected from the group consisting of hydrogen, fluoro, $C_{1-2}$-alkyl, halo-$C_{1-2}$-alkyl, and $C_{1-2}$-alkoxy;

$R^{50c}$ and $R^{50d}$ are independently selected from the group consisting of hydrogen, $C_{1-2}$-alkyl, and halo-$C_{1-2}$-alkyl;

$R^{50e}$ is selected from the group consisting of hydrogen, $C_{1-2}$-alkyl, halo-$C_{1-2}$-alkyl, and $C_{1-2}$-alkoxy-$C_{2-3}$-alkyl;

$R^{50f}$ and $R^{50g}$ are independently selected from the group consisting of hydrogen, $C_{1-2}$-alkyl, and halo-$C_{1-2}$-alkyl;

$R^{50h}$ and $R^{50i}$ are independently selected from the group consisting of hydrogen, fluoro, $C_{1-2}$-alkyl, halo-$C_{1-2}$-alkyl, and $C_{1-2}$-alkoxy; and $R^{50j}$ is selected from the group consisting of hydrogen and fluoro.

In some embodiments of the compounds having the structure of Formula (VIII), at least one of $R^{50a}$, $R^{50b}$, $R^{50h}$, $R^{50i}$, and $R^{50j}$ is fluoro.

H. $R^2$ is 3-Oxomorpholinyl

In some embodiments, the present disclosure provides compounds having the structure of Formula (IX):

(IX)

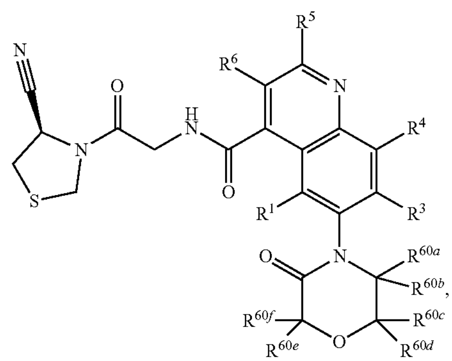

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{60a}$ and $R^{60b}$ are independently selected from the group consisting of hydrogen and $C_{1-3}$-alkyl;

$R^{60c}$ and $R^{60d}$ are independently selected from the group consisting of hydrogen and $C_{1-3}$-alkyl; and $R^{60e}$ and $R^{60f}$ are independently selected from the group consisting of hydrogen and $C_{1-3}$-alkyl.

In some embodiments of the compounds having the structure of Formula (IX), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (IX), $R^1$, $R^3$, $R^4$, $R^5$, and $R^6$ are all hydrogen.

In some embodiments of the compounds having the structure of Formula (IX):

$R^4$ is methyl; and $R^1$, $R^3$, $R^5$, and $R^6$ are all hydrogen.

In some embodiments of the compounds having the structure of Formula (IX):

$R^1$, $R^3$, $R^4$, $R^5$, and $R^6$ are independently selected from the group consisting of hydrogen, fluoro, and methyl;

$R^{60a}$ and $R^{60b}$ are independently selected from the group consisting of hydrogen and $C_{1-2}$-alkyl;

$R^{60c}$ and $R^{60d}$ are independently selected from the group consisting of hydrogen and $C_{1-2}$-alkyl; and $R^{60e}$ and $R^{60f}$ are independently selected from the group consisting of hydrogen and $C_{1-2}$-alkyl.

I. $R^2$ is 5,8-Dioxa-2-azaspiro[3.4]octan-2-yl

In some embodiments, the present disclosure provides compounds having the structure of Formula (X):

(X)

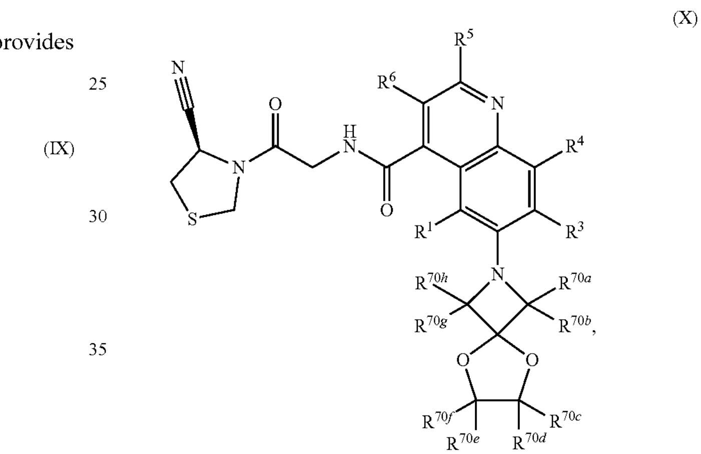

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{70a}$ and $R^{70b}$ are independently selected from the group consisting of hydrogen and $C_{1-3}$-alkyl;

$R^{70c}$ and $R^{70d}$ are independently selected from the group consisting of hydrogen and $C_{1-3}$-alkyl;

$R^{70e}$ and $R^{70f}$ are independently selected from the group consisting of hydrogen and $C_{1-3}$-alkyl; and $R^{70g}$ and $R^{70h}$ are independently selected from the group consisting of hydrogen and $C_{1-3}$-alkyl.

In some embodiments of the compounds having the structure of Formula (X), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (X), $R^1$, $R^3$, $R^4$, $R^5$, and $R^6$ are all hydrogen.

In some embodiments of the compounds having the structure of Formula (X):

$R^1$, $R^3$, $R^4$, $R^5$, and $R^6$ are independently selected from the group consisting of hydrogen, fluoro, and methyl;

$R^{70a}$ and $R^{70b}$ are independently selected from the group consisting of hydrogen and $C_{1-2}$-alkyl;

$R^{70c}$ and $R^{70d}$ are independently selected from the group consisting of hydrogen and $C_{1-2}$-alkyl;

$R^{70e}$ and $R^{70f}$ are independently selected from the group consisting of hydrogen and $C_{1-2}$-alkyl; and $R^{70g}$ and $R^{70h}$ h are independently selected from the group consisting of hydrogen and $C_{1-2}$-alkyl.

J. $R^2$ is Pyridin-3-yl

In some embodiments, the present disclosure provides compounds having the structure of Formula (XI):

(XI)

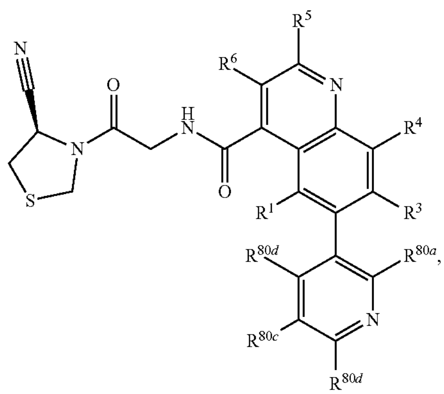

and pharmaceutically acceptable salts thereof, wherein:

$R^1$, $R^3$, $R^4$, $R^5$, and $R^6$ are independently selected from the group consisting of hydrogen, chloro, fluoro, and methyl;

$R^{80a}$ is selected from the group consisting of hydrogen, fluoro, $C_{1-3}$-alkyl, halo-$C_{1-3}$-alkyl, and $C_{1-3}$-alkoxy;

$R^{80b}$ is selected from the group consisting of hydrogen, fluoro, $C_{1-3}$-alkyl, halo-$C_{1-3}$-alkyl, and $C_{1-3}$-alkoxy;

$R^{80c}$ is selected from the group consisting of hydrogen, fluoro, $C_{1-3}$-alkyl, halo-$C_{1-3}$-alkyl, and $C_{1-3}$-alkoxy; and $R^{80d}$ is selected from the group consisting of hydrogen, fluoro, $C_{1-3}$-alkyl, halo-$C_{1-3}$-alkyl, and $C_{1-3}$-alkoxy.

In some embodiments of the compounds having the structure of Formula (XI), one of the $R^1$, $R^3$, $R^4$, $R^5$, and $R^6$ substituents is selected from the group consisting of chloro, fluoro, and methyl, and the remaining $R^1$, $R^3$, $R^4$, $R^5$, and $R^6$ substituents are all hydrogen. In one aspect, one of the $R^1$, $R^3$, $R^4$, $R^5$, and $R^6$ substituents is chloro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is fluoro, and the remaining $R^1$, $R^3$, $R^4$, $R^5$, and $R^6$ substituents are all hydrogen. In another aspect, one of the $R^1$, $R^3$, $R^4$, $R^5$, and $R^6$ substituents is methyl, and the remaining $R^1$, $R^3$, $R^4$, $R^5$, and $R^6$ substituents are all hydrogen.

In some embodiments of the compounds having the structure of Formula (XI), $R^1$, $R^3$, $R^4$, $R^5$, and $R^6$ are all hydrogen.

In some embodiments of the compounds having the structure of Formula (XI):

$R^1$, $R^3$, $R^4$, $R^5$, and $R^6$ are independently selected from the group consisting of hydrogen, fluoro, and methyl;

$R^{80a}$ is selected from the group consisting of hydrogen, fluoro, $C_{1-2}$-alkyl, halo-$C_{1-2}$-alkyl, and $C_{1-2}$-alkoxy;

$R^{80b}$ is selected from the group consisting of hydrogen, fluoro, $C_{1-2}$-alkyl, halo-$C_{1-2}$-alkyl, and $C_{1-2}$-alkoxy;

$R^{80c}$ is selected from the group consisting of hydrogen, fluoro, $C_{1-2}$-alkyl, halo-$C_{1-2}$-alkyl, and $C_{1-2}$-alkoxy; and $R^{80d}$ is selected from the group consisting of hydrogen, fluoro, $C_{1-2}$-alkyl, halo-$C_{1-2}$-alkyl, and $C_{1-2}$-alkoxy.

In some embodiments, the compound or pharmaceutically acceptable salt is (R)—N-(2-(4-cyanothiazolidin-3-yl)-2-oxoethyl)-6-(6-(difluoromethyl)pyridin-3-yl)quinoline-4-carboxamide (Example 169), or a pharmaceutically acceptable salt thereof.

K. Additional Embodiments

Any embodiment of the compounds described in the present disclosure can be combined with any other suitable embodiment described herein to provide additional embodiments. For example, where one embodiment individually or collectively describes possible groups for $R^1$, $R^3$, $R^4$, $R^5$, and/or $R^6$ and a separate embodiment describes possible groups for $R^2$, it is understood that these embodiments can be combined to provide an additional embodiment describing the possible groups described for $R^1$, $R^3$, $R^4$, $R^5$, and/or $R^6$ together with the possible groups described for $R^2$. In other words, for any of the embodiments of the compounds described in the present disclosure, the $R^2$ substituent can be as defined in any of the embodiments of $R^2$ described below.

The compounds of the present disclosure have a pharmaceutically acceptable FAP inhibitory activity measured as described for the hFAP inhibition assay (tight binders) reported in the Examples below. In one aspect, the compounds have an FAP inhibitory activity at $IC_{50}$ concentrations below about 100 nM. In another aspect, the compounds have an FAP inhibitory activity at $IC_{50}$ concentrations below about 50 nM. In another aspect, the compounds have an FAP inhibitory activity at $IC_{50}$ concentrations below about 10 nM. In another aspect, the compounds have an FAP inhibitory activity at $IC_{50}$ concentrations below about 1 nM.

In some embodiments, the compounds of the present disclosure possess a pharmaceutically acceptable surface plasmon resonance (SPR) $pK_d$ value measured as described for the SPR assay reported in the Examples below. In one aspect, the compounds have a surface plasmon resonance (SPR) $pK_d$ value greater than about 7. In another aspect, the compounds have a surface plasmon resonance (SPR) $pK_d$ value greater than about 8. In another aspect, the compounds have an SPR $pK_d$ value greater than about 9. In another aspect, the compounds have an SPR $pK_d$ value greater than about 10.

In some embodiments, the compounds of the present disclosure have a pharmaceutically acceptable selectivity for FAP relative to PREP measured as described for the hFAP inhibition assay (tight binders) and the hPREP inhibition assay reported in the Examples below. In one aspect, the compounds are at least about 50 times more selective for FAP relative to PREP. In another aspect, the compounds are at least about 100 times more selective for FAP relative to PREP. In another aspect, the compounds are at least about 1,000 times more selective for FAP relative to PREP. In another aspect, the compounds are at least about 10,000 times more selective for FAP relative to PREP. In another aspect, the compounds have a PREP $IC_{50}$ value greater than about 0.1 μM. In another aspect, the compounds have a PREP $IC_{50}$ value greater than about 1.0 μM. In another aspect, the compounds have a PREP $IC_{50}$ value greater than about 10.0 μM.

In some embodiments, the compounds of the present disclosure have a pharmaceutically acceptable selectivity for FAP relative to DPP7 measured as described for the hFAP inhibition assay (tight binders) and the DPP7 selectivity assay reported in the Examples below. In one aspect, the compounds are at least about 50 times more selective for FAP relative to DPP7. In another aspect, the compounds are at least about 100 times more selective for FAP relative to DPP7. In another aspect, the compounds are at least about 1,000 times more selective for FAP relative to DPP7. In another aspect, the compounds are at least about 10,000 times more selective for FAP relative to DPP7. In another aspect, the compounds have an $IC_{50}$ value for DPP7 that is greater than about 0.1 μM. In another aspect, the compounds have an $IC_{50}$ value for DPP7 that is greater than about 1 μM. In another aspect, the compounds have an $IC_{50}$ value for DPP7 that is greater than about 10 μM.

In some embodiments, the compounds of the present disclosure have a pharmaceutically acceptable selectivity for FAP relative to DPP8 and/or DPP9 measured as described for the hFAP inhibition assay (tight binders), DPP8 selectivity assay, and DPP9 selectivity assay reported in the Examples below. In one aspect, the compounds are selective for FAP relative to DPP8. In another aspect, the compounds are selective for FAP relative to DPP9. In another aspect, the compounds are selective for FAP relative to both DPP8 and DPP9. In one aspect, the compounds are at least about 50 times more selective for FAP relative to DPP8 and/or DPP9. In another aspect, the compounds are at least about 100 times more selective for FAP relative to DPP8 and/or DPP9. In another aspect, the compounds are at least about 500 times more selective for FAP relative to DPP8 and/or DPP9. In another aspect, the compounds are at least about 1,000 times more selective for FAP relative to DPP8 and/or DPP9. In another aspect, the compounds have an $IC_{50}$ value for DPP8 and/or DPP9 that is greater than about 0.01 μM. In another aspect, the compounds have an $IC_{50}$ value for DPP8 and/or DPP9 that is greater than about 0.1 μM. In another aspect, the compounds have an $IC_{50}$ value for DPP8 and/or DPP9 that is greater than about 0.4 μM.

In some embodiments, the compounds of the present disclosure have a pharmaceutically acceptable metabolic stability measured as described for the human liver microsomes (HLM) assay reported in the Examples below. In one aspect, the compounds have an HLM $CL_{int}$ value less than about 300 μL/min/mg. In another aspect, the compounds have an HLM $CL_{int}$ value less than about 100 μL/min/mg. In another aspect, the compounds have an HLM $CL_{int}$ value less than about 50 μL/min/mg.

In some embodiments, the compounds of the present disclosure have a pharmaceutically acceptable metabolic stability measured as described for the rat hepatocytes (rHep) assay reported in the Examples below. In one aspect, the compounds have an rHep $CL_{int}$ value less than about 300 μL/min/$10^6$ cells. In another aspect, the compounds have an rHep $CL_{int}$ value less than about 100 μL/min/$10^6$ cells. In another aspect, the compounds have an rHep $CL_{int}$ value less than about 50 μL/min/$10^6$ cells.

In some embodiments, the compounds of the present disclosure have a pharmaceutically acceptable Caco-2 AB intrinsic permeability measured as described for the Caco-2 AB intrinsic permeability assay reported in the Examples below. In one aspect, the compounds have a Caco-2 intrinsic apparent permeability of at least about $0.1\times10^6$ cm/s. In another aspect, the compounds have a Caco-2 intrinsic apparent permeability of at least about 6 cm/s. In another aspect, the compounds have a Caco-2 intrinsic apparent permeability of at least about $1\times10^6$ cm/s.

In some embodiments, the compounds of the present disclosure have a pharmaceutically acceptable Caco-2 bidirectional (ABBA) A to B apparent permeability measured as described for the Caco-2 bidirectional (ABBA) A to B apparent permeability assay reported in the Examples below. In one aspect, the compounds have a Caco-2 bidirectional (ABBA) A to B apparent permeability of at least about $0.1\times10^6$ cm/s. In another aspect, the compounds have a Caco-2 bidirectional (ABBA) A to B apparent permeability of at least about $0.25\times10^6$ cm/s. In another aspect, the compounds have a Caco-2 bidirectional (ABBA) A to B apparent permeability of at least about $0.5\times10^6$ cm/s.

In some embodiments, the compounds of the present disclosure have a pharmaceutically acceptable kinetic solubility measured as described for the kinetic solubility assay reported in the Examples below. In one aspect, the compounds have a kinetic solubility of at least about 1 μM. In another aspect, the compounds have a kinetic solubility of at least about 10 μM. In another aspect, the compounds have a kinetic solubility of at least about 25 μM. In another aspect, the compounds have a kinetic solubility of at least about 50 μM.

L. Salts

The compounds of the present disclosure may exist in salt form or in non-salt form (i.e., as a free base), and the present disclosure covers both salt forms and non-salt forms. The compounds may form acid addition salts or base addition salts. In general, an acid addition salt can be prepared using various inorganic or organic acids. Such salts can typically be formed by, for example, mixing the compound with an acid (e.g. a stoichiometric amount of an acid) using various methods known in the art. This mixing may occur in water, an organic solvent (e.g. ether, ethyl acetate, ethanol, methanol, isopropanol, or acetonitrile), or an aqueous/organic mixture. In another aspect, the acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example *J Pharm Sci.* 1977 66, 1. Examples of pharmaceutically acceptable salts are also described in "Handbook of Pharmaceutical Salts: Properties, Selection, and Use" by Stahl and Wermuth (Wiley-VCH, Weinheim, Germany, 2002).

M. Isomers

The compounds and salts of the present disclosure may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods. In some embodiments, a single stereoisomer is obtained by isolating it from a mixture of isomers (e.g., a racemate) using, for example, chiral chromatographic separation. In other embodiments, a single stereoisomer is obtained through direct synthesis from, for example, a chiral starting material.

A particular enantiomer of a compound described herein may be more active than other enantiomers of the same compound. In one embodiment, the compound, or a pharmaceutically acceptable salt thereof, is a single enantiomer being in an enantiomeric excess (% ee) of ≥90, ≥95%, ≥96%, ≥97, ≥98% or ≥99%. In one aspect, the single enantiomer is present in an enantiomeric excess (% ee) of ≥99%.

In another embodiment, the present disclosure relates to a pharmaceutical composition comprising a compound, or a pharmaceutically acceptable salt thereof, which is a single enantiomer being in an enantiomeric excess (% ee) of ≥90, ≥95%, ≥96%, ≥97, ≥98% or ≥99%, or a pharmaceutically acceptable salt thereof, in association with one or more pharmaceutically acceptable excipients. In one aspect, the single enantiomer is present in an enantiomeric excess (% ee) of ≥99%.

N. Additional Forms

The compounds and salts of the present disclosure may exist in various tautomeric forms and the specification encompasses all such tautomeric forms. "Tautomers" are structural isomers that exist in equilibrium resulting from the migration of a hydrogen atom. The compounds of the present disclosure, and pharmaceutically acceptable salts thereof, may exist as solvates (such as a hydrates) as well as unsolvated forms, and the present specification covers all such solvates.

The compounds of the present disclosure, and pharmaceutically acceptable salts thereof, may exist in crystalline or amorphous form, and the present specification covers all such forms.

Compounds and salts of the present disclosure may be isotopically-labeled (or "radio-labeled"). In that instance, one or more atoms are replaced by an atom having an atomic mass or mass number different from the atomic mass or mass number typically found in nature. The specification encompasses isotopically-labelled forms of compounds disclosed herein. Examples of isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{18}O$ and $^{36}Cl$. The isotope that is used will depend on the specific application of that radio-labeled derivative. For example, for in vitro receptor labeling and competition assays, $^{3}H$ or $^{14}C$ are often useful. For radio-imaging applications, $^{11}C$ is often useful. In some embodiments, the radionuclide is $^{3}H$. In some embodiments, the radionuclide is $^{14}C$. In some embodiments, the radionuclide is $^{11}C$.

O. Intermediates

In some embodiments, the present disclosure provides additional compounds that are useful as intermediates for preparing the compounds of the present disclosure, and pharmaceutically acceptable salts thereof.

III. Methods of Use

The disclosed compounds of the present disclosure, and pharmaceutically acceptable salts thereof, are inhibitors of Prolyl endopeptidase fibroblast activation protein (FAP) activity. FAP is an endopeptidase that enzymatically cleaves substrates involved in glucose and lipid metabolism, fibrinolysis, and collagen production.

FAP is believed to cleave and inactivate human Fibroblast Growth Factor 21 (FGF-21) (*Biochem J* 2016, 473, 605), a protein involved in the regulation of glucose and lipid metabolism. It is hypothesized that inhibition of FAP increases endogenous FGF-21 levels and signaling, and results, for example, in decreased steatosis, improved insulin sensitivity, improved glucose tolerance, reduced body weight, and/or reduced cardiovascular disease mortality.

FAP is also believed to cleave human α2-Antiplasmin (α2AP) (*Blood* 2004 103, 3783), a protein involved in the regulation of fibrosis and fibrinolysis. Tissue repair involves coagulation which results in fibrin deposition. The fibrin of a clot is usually lysed, primarily by plasmin when converted from its inactive form (plasminogen) by plasminogen activators. Fibrinolysis is inhibited by Plasminogen Activator Inhibitor-1 (PAI-1), Plasminogen Activator Inhibitor-2 (PAI-2), and α2AP, (*Experimental & Molecular Medicine* 2020, 52, 367) all of which are induced by tissue trauma. FAP converts α2AP into a more active form that decreases plasmin activity and increases fibrin deposition at the site of an injury. It is hypothesized that inhibition of FAP increases fibrinolysis and improves tissue regeneration at the site of injury (*J Thromb Haemost* 2013, 11, 2029; Proteomics Clin. Appl. 2014, 8, 454).

FAP is further believed to promote collagen production and deposition and to play a role in increased fibrosis through altered extracellular matrix (ECM) turnover (*J Biol Chem* 2016, 8, 291). It is hypothesized that inhibition of FAP results in a decrease in collagen deposition and a reduction in inflammation (Inflamm Bowel Dis. 2018, 18, 332).

In view of the above, it is hypothesized that inhibition of FAP collectively reduces fibrosis and inflammation by decreasing hepatic stellate cell activity and increasing fibrinolysis, and further provides positive metabolic effects through increased FGF21 signaling and improved glucose tolerance.

In some embodiments, therefore, the present disclosure provides a method for treating or preventing an FAP-mediated condition in a subject in need thereof by administering to the subject a therapeutically effective amount of a compound of Formula I, or a pharmaceutically acceptable salt thereof.

In some embodiments, the present disclosure provides a method for treating or preventing a condition characterized by overexpression of FAP in a subject in need thereof by administering to the subject a therapeutically effective amount of a compound of the present disclosure, or a pharmaceutically acceptable salt thereof.

In some embodiments, the present disclosure provides a method for treating or preventing liver disease in a subject in need thereof by administering to the subject a therapeutically effective amount of a compound of the present disclosure, or a pharmaceutically acceptable salt thereof. In one aspect, the liver disease is a fatty liver disease. In another aspect, the liver disease is Nonalcoholic Fatty Liver Disease (NAFLD). In another aspect, the NAFLD is selected from the group consisting of isolated steatosis, Nonalcoholic Steatohepatitis (NASH), liver fibrosis, and cirrhosis. In another aspect, the liver disease is end stage liver disease. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating liver disease in a subject in need thereof by administering to the subject a therapeutically effective amount of a compound of the present disclosure, or a pharmaceutically acceptable salt thereof, wherein the subject has a body mass index (BMI) of 27 $kg/m^2$ to 40 $kg/m^2$. In one aspect, the subject has a PMI of 30 $kg/m^2$ to 39.9 $kg/m^2$. In another aspect, the subject has a BMI of at least 40 $kg/m^2$. In another aspect, the subject is overweight. In another aspect, the subject is obese. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to dyslipidemia. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to insulin resistance. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to at least one of Type 2 diabetes and renal insufficiency. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to Type 2 diabetes. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for treating liver disease in a subject in need thereof by administering to the subject a therapeutically effective amount of a compound of the present disclosure, or a pharmaceutically acceptable salt thereof, wherein the subject is also suffering from or susceptible to renal insufficiency. In another aspect, the liver disease is NAFLD. In another aspect, the liver disease is NASH. In another aspect, the liver disease is liver fibrosis. In another aspect, the liver disease is cirrhosis.

In some embodiments, the present disclosure provides a method for reducing liver fat in a subject in need thereof by administering to the subject a therapeutically effective amount of a compound of the present disclosure, or a pharmaceutically acceptable salt thereof. In one aspect, the subject is suffering from or susceptible to NAFLD. In another aspect, the subject is suffering from or susceptible to NASH. In another aspect, the subject is suffering from or susceptible to liver fibrosis. In another aspect, the subject is suffering from or susceptible to cirrhosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing Nonalcoholic Fatty Liver Disease (NAFLD) in a subject in need thereof by administering to the subject a therapeutically effective amount of a compound of the present disclosure, or a pharmaceutically acceptable salt thereof. In one aspect, the NAFLD is Stage 1 NAFLD. In another aspect, the NAFLD is Stage 2 NAFLD. In another aspect, the NAFLD is Stage 3 NAFLD. In another aspect, the NAFLD is Stage 4 NAFLD. See, e.g., "The Diagnosis and Management of Nonalcoholic Fatty Liver Disease: Practice Guidance From the American Association for the Study of Liver Diseases," *Hepatology,* 2018, Vol, 67, No. 1. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing Nonalcoholic Steatohepatitis (NASH) in a subject in need thereof by administering to the subject a therapeutically effective amount of a compound of the present disclosure, or a pharmaceutically acceptable salt thereof. In one aspect, the NASH is Stage 1 NASH, In another aspect, the NASH is Stage 2 NASH. In another aspect, the NASH is Stage 3 NASH. In another aspect, the NASH is Stage 4 NASH. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing liver fibrosis in a subject in need thereof by administering to the subject a therapeutically effective amount of a compound of the present disclosure, or a pharmaceutically acceptable salt thereof. In one aspect, the subject is suffering from Stage 3 liver fibrosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing cirrhosis in a subject in need thereof by administering to the subject a therapeutically effective amount of a compound of the present disclosure, or a pharmaceutically acceptable salt thereof. In one aspect, the subject is suffering from stage F4 cirrhosis. In another aspect, the subject is also suffering from or susceptible to one or more conditions selected from the group consisting of obesity, dyslipidemia, insulin resistance, Type 2 diabetes, and renal insufficiency.

In some embodiments, the present disclosure provides a method for treating or preventing type 2 diabetes mellitus in a subject in need thereof by administering to the subject a therapeutically effective amount of a compound of the present disclosure, or a pharmaceutically acceptable salt thereof. In one aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of improving glycemic control in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 kg/m 2. In another aspect, the subject has a BMI of at least 40 $kg/m^2$. In another aspect, the subject is overweight. In another aspect, the subject is obese.

In some embodiments, the present disclosure provides a method of improving glycemic control in a subject with type 2 diabetes and diabetic kidney disease by administering to the subject a therapeutically effective amount of a compound of the present disclosure, or a pharmaceutically acceptable salt thereof. In one aspect, the administration of the compound is an adjunct to diet and exercise. In another aspect, the administration of the compound also reduces body weight and/or treats obesity. In another aspect, the subject has a. BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of improving glycemic control in a subject with type 2 diabetes and renal insufficiency by administering to the subject a therapeutically effective amount of a compound of the present disclosure, or a pharmaceutically acceptable salt thereof. In one aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese.

In some embodiments, the present disclosure provides a method of treating or preventing insulin resistance in a subject thereof by administering to the subject a therapeutically effective amount of a compound of the present disclosure, or a pharmaceutically acceptable salt thereof. In another aspect, the subject is a subject is suffering from type 2 diabetes. In another aspect, the subject is a subject is suffering from diabetic kidney disease. In another aspect, the subject is suffering from renal insufficiency. Insulin resistance can be measured, for example, using the Homeostatic Model Assessment of Insulin Resistance (HOMA-IR) and/or the MATSUDA index. The HOMA-IR is explained, for example, in *Diabetologia* 1985, 28, 412, which is herein incorporated by reference in its entirety. The MATSUDA index is explained, for example, in *Diabetes Care* 1999, 22, 1462, which is herein incorporated by reference in its entirety.

In some embodiments, the present disclosure provides a method of treating or preventing glucose intolerance in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency.

In some embodiments, the present disclosure provides a method of treating a cardiovascular condition in a subject in need of treatment by administering to the subject a therapeutically effective amount of a compound of the present disclosure, or a pharmaceutically acceptable salt thereof. In one aspect, the cardiovascular condition is selected from the group consisting of heart failure, cardiomyopathy, atherosclerosis, venous thromboembolism, and atrial fibrillation. In one aspect, the cardiovascular condition is heart failure. In another aspect, the cardiovascular condition is heart failure with preserved ejection fraction (HFpEF). In another aspect, the cardiovascular condition is cardiomyopathy. In another aspect, the cardiomyopathy is selected from the group consisting of hypertrophic cardiomyopathy, dilated cardiomyopathy, restrictive cardiomyopathy, hypertrophic cardiomyopathy, ischemic cardiomyopathy, ischemic cardiomyopathy, dilated cardiomyopathy, and idiopathic cardiomyopathy. In another aspect, the cardiovascular condition is atherosclerosis. In another aspect, the cardiovascular condition is venous thromboembolism. In another aspect, the cardiovascular condition is atrial fibrillation.

In some embodiments, the present disclosure provides a method of treating obesity or an obesity-related condition in a subject in need thereof by administering to the subject a therapeutically effective amount of a compound of the present disclosure, or a pharmaceutically acceptable salt thereof. In one aspect, the obesity-related condition is an obesity-related metabolic condition. In another aspect, the obesity-related condition is selected from the group consisting of insulin resistance, pre-diabetes, type 2 diabetes, glucose intolerance, increased fasting glucose, and glucagonomas. In another aspect, the obesity-related condition is dyslipidemia. In another aspect, the obesity-related condition is a cardiovascular condition is selected from the group consisting of heart failure, cardiomyopathy, atherosclerosis, venous thromboembolism, and atrial fibrillation. In another aspect, the obesity-related condition is renal disease.

In some embodiments, the present disclosure provides a method of reducing body weight in a subject in need thereof by administering to the subject a therapeutically effective amount of a compound of the present disclosure, or a pharmaceutically acceptable salt thereof. In one aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 40 $kg/m^2$. In another aspect, the subject has a BMI of 30 $kg/m^2$ to 39.9 $kg/m^2$. In another aspect, the subject has a BMI of at least 40 $kg/m^2$. In another aspect, the subject is overweight. In another aspect, the subject is obese. In another aspect, the subject's weight is reduced, for example, by at least about 5%, 10%, 15%, 20%, 25%, 30%, 35%, or 40%.

In some embodiments, the present disclosure provides a method of reducing body fat in a subject in need of treatment by administering to the subject a therapeutically effective amount of a compound of the present disclosure, or a pharmaceutically acceptable salt thereof. In another aspect, the subject is a subject is suffering from type 2 diabetes. In another aspect, the subject is a subject is suffering from diabetic kidney disease. In another aspect, the subject is suffering from renal insufficiency. In another aspect, the administration of the compound is an adjunct to diet and exercise. In another aspect, the administration of the compound also reduces body weight and/or treats obesity. In another aspect, the subject has a BMI of 27 $kg/m^2$ to 4.0 $kg/m^2$. In another aspect, the subject has a MAI of 30 $kg/m^2$ to 39.9 $kg/m^2$. In another aspect, the subject has a of at least 40 $kg/m^2$. In another aspect, the subject is overweight. In another aspect, the subject is obese. In another aspect, the fat is liver fat.

In some embodiments, the present disclosure provides a method for treating or preventing fibrosis in a subject in need thereof by administering to the subject a therapeutically effective amount of a compound of the present disclosure, or a pharmaceutically acceptable salt thereof. In one aspect, the fibrosis is interstitial lung disease. In another aspect, the fibrosis is interstitial lung disease with progressive fibrosis. In another aspect, the interstitial lung disease is pulmonary fibrosis. In another aspect, the interstitial lung disease is idiopathic pulmonary fibrosis (IPF).

In some embodiments, the present disclosure provides a method for promoting tissue remodeling in a subject in need thereof by administering to the subject a therapeutically effective amount of a compound of the present disclosure, or a pharmaceutically acceptable salt thereof. In one aspect, the subject has suffered cardiac tissue damage due to a myocardial infarction.

In some embodiments, the present disclosure provides a method of promoting wound healing and/or reducing adhesions in a subject in need thereof by administering to the subject a therapeutically effective amount of a compound of the present disclosure, or a pharmaceutically acceptable salt thereof. In one aspect, the administration of the compound promotes wound healing and/or reduces adhesions through increased fibrinolysis.

In some embodiments, the present disclosure provides a method for treating or preventing a keloid disorder in a subject in need thereof by administering to the subject a therapeutically effective amount of a compound of the present disclosure, or a pharmaceutically acceptable salt thereof. In one aspect, the keloid disorder is selected from the group consisting of scar formation, keloid tumors, and keloid scar.

In some embodiments, the present disclosure provides a method for treating or preventing inflammation in a subject in need thereof by administering to the subject a therapeutically effective amount of a compound of the present disclosure, or a pharmaceutically acceptable salt thereof. In one aspect, the inflammation is chronic inflammation. In one aspect, the chronic inflammation is selected from the group consisting of rheumatoid arthritis, osteoarthritis, and Crohn's disease. In another aspect, the chronic inflammation is rheumatoid arthritis.

In some embodiments, the present disclosure provides a method of treating cancer in a subject in need of treatment by administering to the subject a therapeutically effective amount of a compound of the present disclosure, or a pharmaceutically acceptable salt thereof. In one aspect, the cancer is selected from the group consisting of breast cancer, pancreatic cancer, small intestine cancer, colon cancer, rectal cancer, lung cancer, head and neck cancer, ovarian cancer, hepatocellular carcinoma, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer. In another aspect, the cancer is hepatocellular carcinoma.

The subject treated typically will be a human or non-human mammal, particularly a human. Suitable subjects can also include domestic or wild animals; companion animals (including dogs, cats, and the like); livestock (including horses, cows and other ruminants, pigs, poultry, rabbits, and the like); primates (including monkeys such as rhesus monkeys, cynomolgus (also known as crab-eating or long-tailed) monkeys, marmosets, tamarins, chimpanzees, macaques, and the like); and rodents (including rats, mice, gerbils, guinea pigs, and the like).

In some embodiments, the present disclosure provides the compounds of the present disclosure, or pharmaceutically acceptable salts thereof, for use as medicaments.

In some embodiments, the present disclosure provides for the use of the compounds of the Formula I, or pharmaceutically acceptable salts thereof, for treating or preventing an FAP-mediated condition as discussed above.

In some embodiments, the present disclosure provides for the use of the compounds of the Formula I, or pharmaceutically acceptable salts thereof, for the manufacture of medicaments for treating or preventing an FAP-mediated condition as discussed above.

IV. Combination Therapies and Fixed-Dose Combinations

The compounds of the present disclosure may be used in the methods described above as either as single pharmacological agents or in combination with other pharmacological agents or techniques. Such combination therapies may be achieved by way of the simultaneous, sequential or separate dosing of the individual components of the treatment. These combination therapies (and corresponding combination products) employ the compounds of the present disclosure within the dosage ranges described in this application and the other pharmacological agent(s), typically within its approved dosage range(s).

In some embodiments, the present disclosure provides a combination suitable for use in the treatment of a condition selected from the previously discussed conditions, wherein the combination comprises a compound of the present disclosure, or a pharmaceutically acceptable salt thereof, and a sodium-glucose transport protein 2 (SGLT2) inhibitor. In one aspect, the SGLT2 inhibitor is selected from the group consisting of canagliflozin, dapagliflozin, empagliflozin, ertugliflozin, ipragliflozin, luseogliflozin, and remogliflozin. In another aspect, the SGLT2 inhibitor is dapagliflozin.

In some embodiments, the present disclosure provides a combination suitable for use in the treatment of a condition selected from the previously discussed conditions, wherein the combination comprises a compound of the present disclosure, or a pharmaceutically acceptable salt thereof, and metformin.

In some embodiments, the present disclosure provides a combination suitable for use in the treatment of a condition selected from the previously discussed conditions, wherein the combination comprises a compound of the present disclosure, or a pharmaceutically acceptable salt thereof, and a glucagon-like peptide-1 receptor (GLP1) agonist. In one aspect, the SGLT2 inhibitor is selected from the group consisting of exenatide, liraglutide, lixisenatide, albiglutide, dulaglutide, and semaglutide.

In some embodiments, the present disclosure provides a combination suitable for use in the treatment of a condition selected from the previously discussed conditions, wherein the combination comprises a compound of the present disclosure, or a pharmaceutically acceptable salt thereof, and a dipeptidyl peptidase 4 (DPP4) inhibitor. In one aspect, the DPP4 inhibitor is selected from the group consisting of sitagliptin, vildagliptin, saxagliptin, linagliptin, gemigliptin, anagliptin, teneligliptin, alogliptin, trelagliptin, omarigliptin, evogliptin, gosogliptin, and dutogliptin.

In some embodiments, the present disclosure provides a combination suitable for use in the treatment of a condition selected from the previously discussed conditions, wherein the combination comprises a compound of the present disclosure, or a pharmaceutically acceptable salt thereof, and a peroxisome proliferator-activated receptor (PPAR) agonist. In one aspect, the PPAR agonist is a PPARα agonist. In another aspect, the PPAR agonist is a PPARγ agonist. In another aspect, the PPAR agonist is a PPARα/γ agonist. In another aspect, the PPAR agonist is selected from the group consisting of clofibrate, gemfibrozil, ciprofibrate, bezafibrate, and fenofibrate. In another aspect, the PPAR agonist is a thiazolidinedione. In another aspect, the thiazolidinedione is selected from the group consisting of pioglitazone, rosiglitazone, lobeglitazone, and rivoglitazone. In another aspect, the PPAR agonist stimulates liver expression of FGF21.

In some embodiments, the present disclosure provides a pharmaceutical composition comprising a compound of the present disclosure, or a pharmaceutically acceptable salt thereof; one or more pharmacological agents selected from SGLT2 inhibitors, metformin, GLP1 agonists, DPP4 inhibitors, and PPAR agonists; and a pharmaceutically acceptable diluent or carrier. Such a combination can be used for the manufacture of a medicament for use in the treatment of a condition selected from the previously discussed conditions. In one aspect, the pharmaceutical composition comprises an SGLT2 inhibitor. In another aspect, the pharmaceutical composition comprises metformin. In another aspect, the pharmaceutical composition comprises a GLP1 agonist. In another aspect, the pharmaceutical composition comprises a DPP4 inhibitor. In another aspect, the pharmaceutical composition comprises a PPAR agonist.

In some embodiments, the present disclosure provides a combination suitable for use in the treatment of cancer, wherein the combination comprises a compound of the present disclosure, or a pharmaceutically acceptable salt thereof, and an immune checkpoint inhibitor. In one aspect, the immune checkpoint inhibitor is selected from the group consisting of anti-PD-1 antibodies, anti-PD-L1 antibodies, anti-CTLA4 antibodies, TLR7 agonists, CD40 agonists, Lag-3 antagonists, and OX40 agonists. In another aspect, the immune checkpoint inhibitor is an anti-PD-1 antibody (e.g., pembrolizumab (Keytruda), nivolumab (Opdivo), cemiplimab (Libtayo), etc.). In another aspect, the immune checkpoint inhibitor is an anti-PD-L1 antibody (e.g., atezolizumab (Tecentriq), avelumab (Bavencio), durvalumab (Imfinzi), etc.). In another aspect, the immune checkpoint inhibitor is an anti-CTLA4 antibody (e.g., ipilimumab (Yervoy), tremelimumab, etc.). In another aspect, the cancer is selected from the group consisting of pancreatic cancer, colon cancer, and rectal cancer.

V. Pharmaceutical Compositions

The compounds of the present disclosure, and pharmaceutically acceptable salts thereof, may be administered as pharmaceutical compositions, comprising one or more pharmaceutically acceptable excipients. Therefore, in some embodiments the present disclosure provides pharmaceutical compositions comprising a compound of the present disclosure, or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth Edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more coloring, sweetening, flavoring and/or preservative agents.

The total daily dose will necessarily be varied depending upon the subject treated, the particular route of administration, any therapies being co-administered, and the severity of the illness being treated, and may include single or multiple doses. Specific dosages can be adjusted, for example, depending upon the condition being treated; the age, body weight, general health condition, sex, and diet of the subject; administration routes; dose intervals; excretion rate; and other drugs being co-administered to the subject. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. The compound of the present disclosure, or a pharmaceutically acceptable salt thereof, typically will be administered to a warm-blooded animal at a unit dose within the range 2.5 to 5000 $mg/m^2$ body area of the animal, or approximately 0.05 to 100 mg/kg, and this normally provides a therapeutically-effective dose. A unit dose form such as a tablet or capsule can contain, for example, 0.1 to 500 mg, 0.1 to 250 mg, 0.1 to 100 mg, of active ingredient.

In some embodiments, the present disclosure provides pharmaceutical compositions for use in therapy, comprising a compound of the present disclosure, or a pharmaceutically acceptable salt thereof, and at least one pharmaceutically acceptable excipient.

In some embodiments, the present disclosure provides pharmaceutical compositions for use in the treatment of an FAP-mediated condition, comprising a compound of the present disclosure, or a pharmaceutically acceptable salt thereof, and at least one pharmaceutically acceptable excipient. In one aspect, the FAP-mediated condition is selected from the group consisting of liver disease, type 2 diabetes mellitus, cardiovascular conditions, obesity, obesity-related conditions, fibrosis, keloid disorder, inflammation, and cancer.

VI. Kits

The present disclosure further provides kits comprising a unit dosage form comprising a compound of the present disclosure, or a pharmaceutically acceptable salt thereof, contained within a packaging material and a label or package insert which indicates that the unit dosage form can be used for treating one or more of the previously described conditions.

In some embodiments, the kit comprises a unit dosage form comprising a compound of the present disclosure, or a pharmaceutically acceptable salt thereof, contained within a packaging material and a label or package insert which indicates that the pharmaceutical composition can be used for treating an FAP-mediated condition. In another aspect, the FAP-mediated condition is liver disease. In another aspect, the liver disease is selected from the group consisting of fatty liver disease, end stage liver disease, and cirrhosis. In another aspect, the liver disease is selected from the group consisting of Nonalcoholic Steatohepatitis (NASH) and Nonalcoholic Fatty Liver Disease (NAFLD).

In some embodiments, kit comprises: (a) a first unit dosage form comprising a compound of the present disclosure, or a pharmaceutically acceptable salt thereof; (b) a second unit dosage form comprising a pharmacological agent selected from the group consisting of SGLT2 inhibitors, metformin, GLP1 agonists, DPP4 inhibitors, and PPAR agonists; (c) a container means for containing said first and second dosage forms; and (d) a label or package insert which indicates that the first unit dosage form and second unit dosage form can be used for treating an FAP-mediated condition.

VII. Methods of Preparation

The present disclosure further provides processes for the preparation of the compounds of Formulae (I), (II), (III-A), (III-B), (III-C), (III-D), (III-E), (IV), (IV-A), (V), (VI), (VII), (VIII), (IX), (X), and (XI), and pharmaceutically acceptable salts thereof.

Schemes 1 to 14 below illustrate synthetic routes to compounds of Formula (II) wherein $R^1$, $R^2$, $R^3$, $R^4$, $R^5$, $R^6$ and $X^1$ are as defined in formula (I), $R^7$ is an alkyl group (e.g., methyl, ethyl, or tert-butyl), and $X^2$, $X^3$ and $X^4$ are leaving groups (e.g., Cl, Br, I, or OTf). One of skill in the art will appreciate that these methods are representative and are not inclusive of all possible methods for preparing the compounds of the present disclosure. The $R^X$ substituents in each Scheme are as defined for the compounds of the present disclosure unless otherwise stated. It is understood that the processes for preparation described in Schemes 1 to 14 can be performed starting from any enantiomer, or a racemic mixture, of compounds of formula (2), (4), (6), (8), (9), (10), (11), (12), (13) or (14), to give compounds of Formula (II) or any stereoisomer of Formula (II).

SCHEME 1

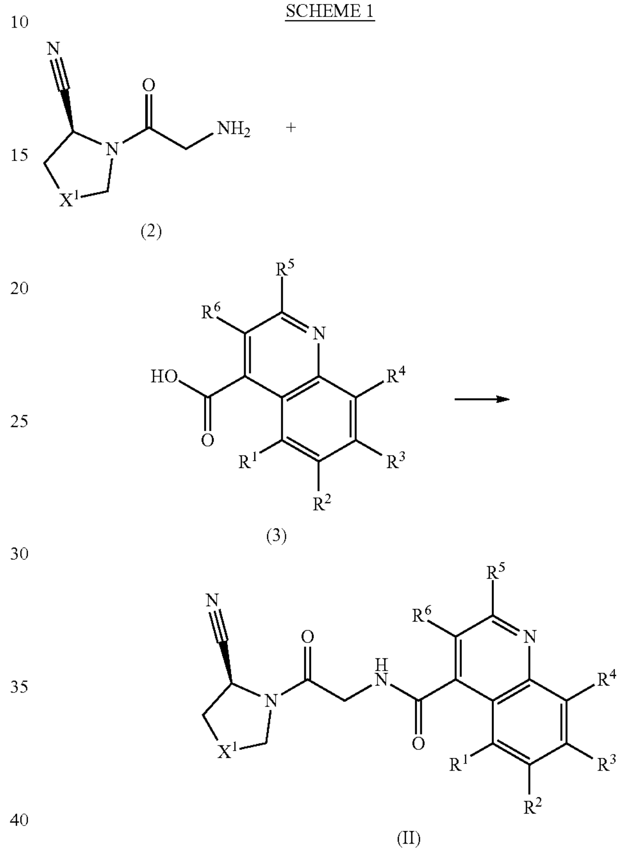

(2) + (3) → (II)

Scheme 1 illustrates synthetic routes to certain compounds of formula (II). A compound of formula (2) may be reacted with a compound of formula (3) to give a compound of formula (II). The reaction may be performed using suitable coupling reagents (e.g., HATU, HOBt/EDC, or T3P) in the presence of a base (typically an organic base such as DIPEA or TEA) using a solvent such as DCM, DMF, EtOAc or MeCN, or mixtures thereof, and at temperatures ranging from typically 0° C. to 60° C.

SCHEME 2

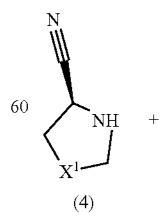

(4) +

-continued

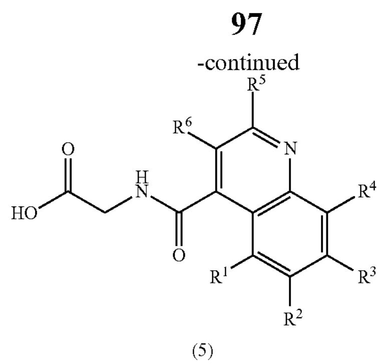

(5)

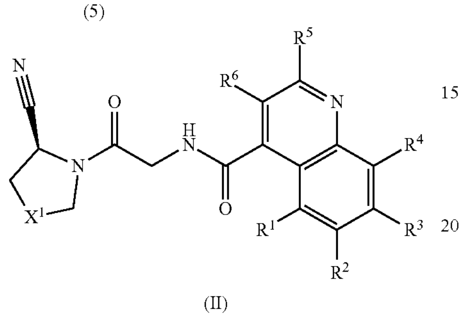

(II)

Scheme 2 illustrates additional synthetic routes to certain compounds of formula (II). A compound of formula (4) may be reacted with a compound of formula (5) to give a compound of formula (II). The reaction may be performed using suitable coupling reagents (e.g., HATU, HOBt/EDC, or T3P) in the presence of a base (typically an organic base, such as DIPEA or TEA) using a solvent such as DCM, DMF, EtOAc or MeCN, or mixtures thereof, and at temperatures ranging from typically 0° C. to 60° C.

SCHEME 3

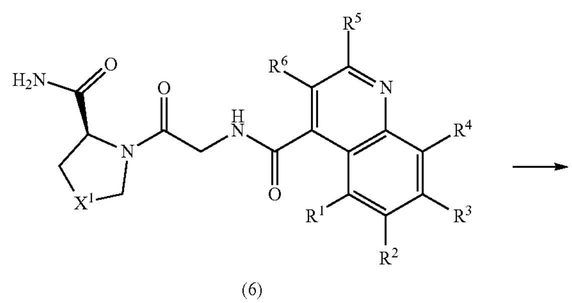

(6)

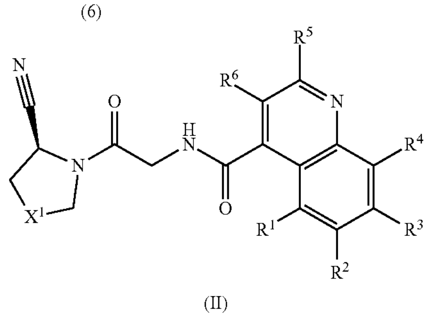

(II)

Scheme 3 illustrates additional synthetic routes to certain compounds of formula (II). A compound of formula (6) may be transformed into a compound of formula (II) by dehydration using a suitable reagent (typically TFAA or T3P) in a solvent such as DCM, DMF, EtOAc or MeCN, or mixtures thereof, and at a temperature ranging from typically 0° C. to 120° C.

SCHEME 4

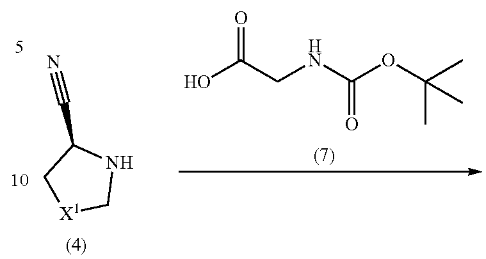

(4) (7)

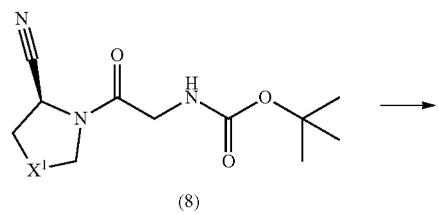

(8)

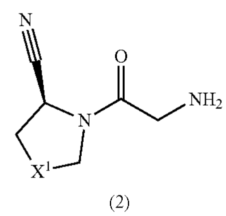

(2)

Scheme 4 illustrates synthetic routes to certain compounds of formula (2). A compound of formula (4) may be reacted with (tert-butoxycarbonyl)-glycine (7) to give a compound of formula (8). The reaction may be performed using suitable coupling reagents (e.g., HATU, HOBt/EDC or T3P) in the presence of a base (typically an organic base, such as DIPEA or TEA) using a solvent such as DCM, DMF, EtOAc or MeCN, or mixtures thereof, and at temperatures ranging from typically 0° C. to 120° C.

A compound of formula (2) may be formed by reacting a compound of formula (8) with a suitable acid (e.g., HCl) in a solvent such as 1,4-dioxane, EtOAc, MeOH or water, or mixtures thereof. Alternatively, the reaction may be performed using acids such as TFA, neat or in a solvent such as DCM, at temperatures ranging from typically 0° C. to 60° C.

SCHEME 5

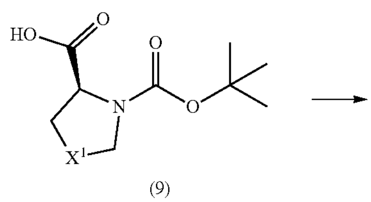

(9)

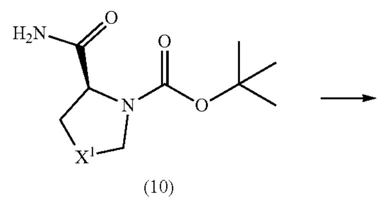

(10)

-continued

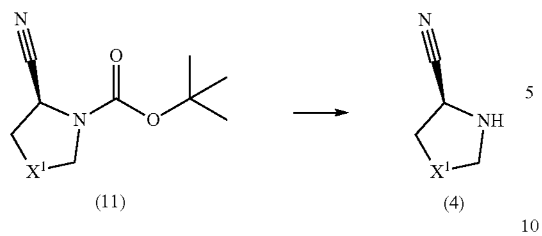

(11)

(4)

Scheme 5 illustrates synthetic routes to certain compounds of formula (4). A compound of formula (10) may be formed by reacting a compound of formula (9) with $NH_3$, either neat or as a solution, e.g. in water or MeOH, or with an ammonia synthetic equivalent (e.g., $NH_4Cl$). The reaction may be performed using suitable coupling reagents (e.g., HATU, HOBt/EDC, T3P or $Boc_2O$) in the presence of a base (typically an organic base, such as DIPEA or TEA) using a solvent such as THF, DMF, EtOAc or MeCN, or mixtures thereof, and at temperatures ranging from typically 0° C. to 120° C.

A compound of formula (10) may be transformed into a compound of formula (11) by dehydration using a suitable reagent (typically TFAA or T3P) in a solvent such as DCM, DMF, EtOAc or MeCN, or mixtures thereof, and at a temperature ranging from typically 0° C. to 120° C.

A compound of formula (4) may be formed by reacting a compound of formula (11) with a suitable acid (e.g., HCl or TsOH) in a solvent such as MeCN, 1,4-dioxane, EtOAc, MeOH or water, or mixtures thereof. Alternatively, the reaction may be performed using acids such as TFA, neat or in a solvent such as DCM, at temperatures ranging from typically 0° C. to 60° C.

SCHEME 6

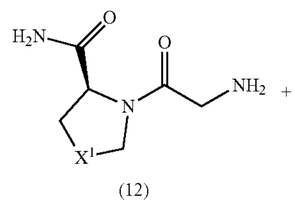

(12)

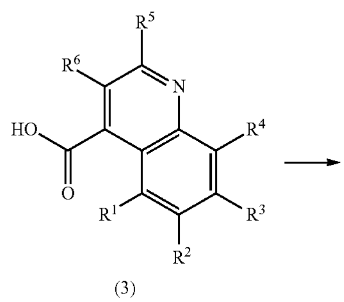

(3)

-continued

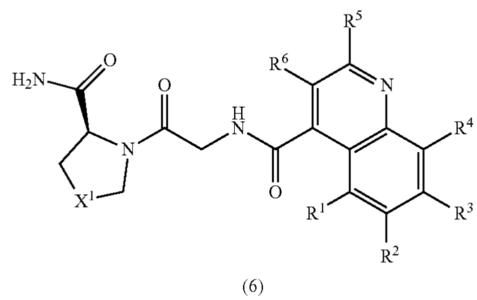

(6)

Scheme 6 illustrates synthetic routes to certain compounds of formula (6). A compound of formula (12) may be reacted with a compound of formula (3) to give a compound of formula (6). The reaction may be performed under conditions described for the analogous reaction described in Scheme 1.

SCHEME 7

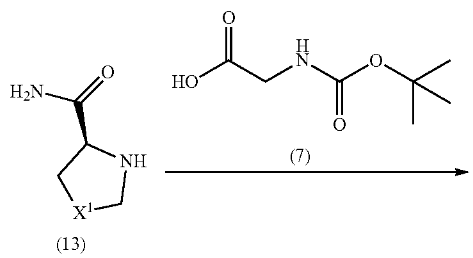

(13)

(7)

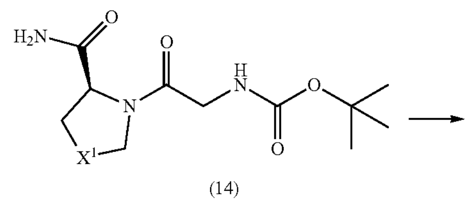

(14)

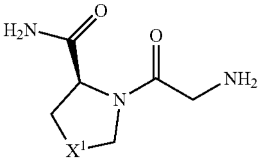

(12)

Scheme 7 illustrates synthetic routes to certain compounds of formula (12). A compound of formula (12) may be formed from compounds of formula (13) and (7), via a compound of formula (14). The reactions may be performed under conditions described for the analogous reactions described in Scheme 4.

SCHEME 8

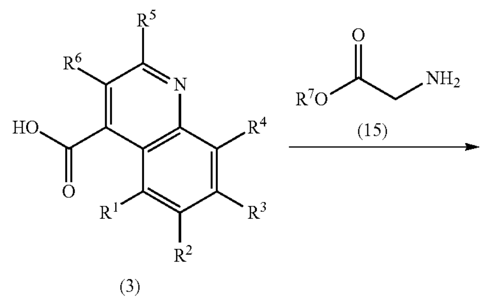

(3)

-continued

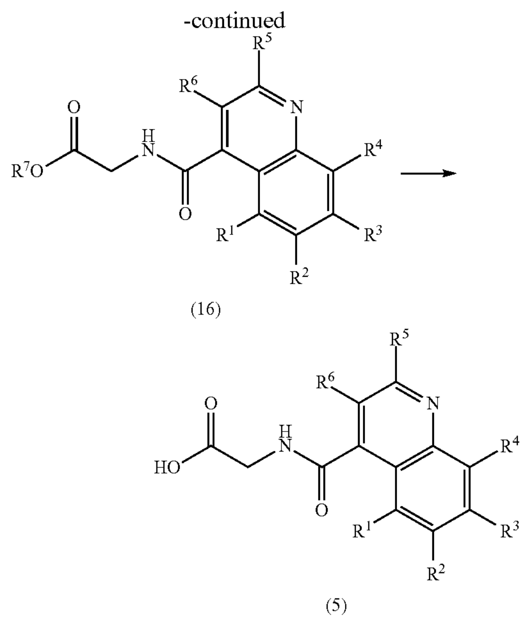

(16)

(5)

Scheme 8 illustrates synthetic routes to certain compounds of formula (5). A compound of formula (3) may be reacted with a compound of formula (15) to give a compound of formula (16). The reaction may be performed using suitable coupling reagents (e.g., HATU, HOBt/EDC or T3P) in the presence of a base (typically an organic base such as DIPEA or TEA) using a solvent such as DCM, DMF, EtOAc or MeCN, or mixtures thereof, and at temperatures ranging from typically 0° C. to 120° C.

A compound of formula (5) may be formed by reacting a compound of formula (16) with a base (e.g., NaOH or LiOH) in an organic solvent (e.g., dioxane, THF, or MeOH, or mixtures thereof), and optionally in the presence of water. The reaction may be performed in a temperature interval from 0° C. to reflux. Alternatively, for compounds of formula (16) where $R^7$=tert-butyl, the reaction may be performed with a suitable acid (e.g., HCl) in a solvent such as 1,4-dioxane, EtOAc, MeOH or water, or mixtures thereof. Alternatively, the reaction may be performed using acids such as TFA, neat or in a solvent such as DCM, at temperatures ranging from typically 0° C. to 60° C.

SCHEME 9

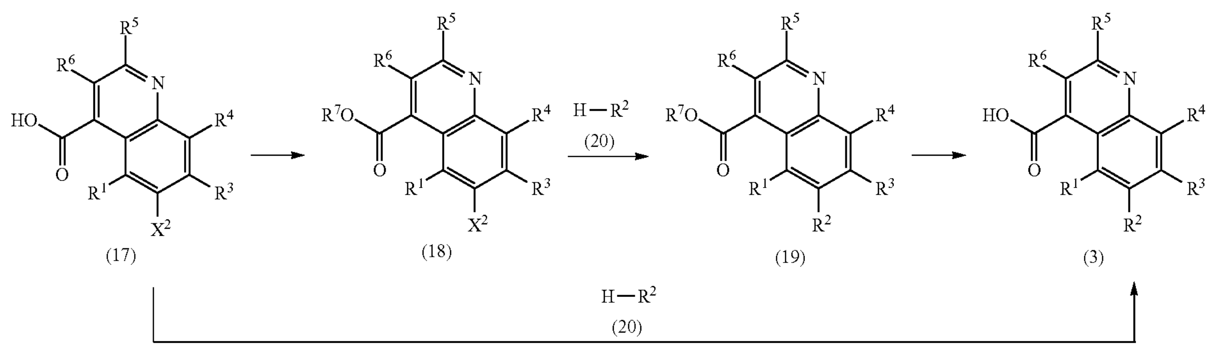

(17) (18) (19) (3)

Scheme 9 illustrates synthetic routes to certain compounds of formula (3). A compound of formula (18) may be formed by reacting a compound of formula (17) with an alcohol (e.g., MeOH or EtOH) in the presence of an acid (e.g., HCl or $H_2SO_4$) in a suitable solvent, or using the alcohol as solvent. Alternatively, the reaction may be promoted by reagents such as $SOCl_2$ in a suitable solvent, or using the alcohol (e.g., MeOH or EtOH) as solvent. Alternatively, a compound of formula (18) may be reacted with an alcohol (e.g., MeOH or EtOH) promoted by coupling reagents (e.g., EDC or TBTU) in the presence of base (such as DIPEA, TEA, or DMAP) using a solvent such as DCM, DMF, EtOAc or MeCN, or mixtures thereof, and at temperatures ranging from typically 0° C. to 120° C.

A compound of formula (19) wherein $R^2$ is as defined in Formula (I), and where the attachment point to the quinoline is through a nitrogen atom, may be formed by reacting a compound of formula (18) with an amine H—$R^2$ (20), wherein $R^2$ is as defined in Formula (I). The reaction may be catalyzed with a suitable Pd-reagent, e.g. $Pd_2(dba)_3$ with a suitable phosphine ligand (e.g., XPhos, CPhos, SPhos, RuPhos, DavePhos or XantPhos) in the presence of a base (such as $Cs_2CO_3$) in a suitable solvent (such as 1,4-dioxane), optionally in the presence of water, at temperatures ranging from room temperature to reflux.

A compound of formula (19) wherein $R^2$ is as defined in formula (I), and where the attachment point to the quinoline is through a nitrogen atom, may be formed by reacting a compound of formula (18) with an amine H—$R^2$ (20), wherein $R^2$ is as defined in formula (I). The reaction may be catalyzed with a suitable Cu-reagent (e.g., CuI or $Cu_2O$) in the presence of a base (such as $K_2CO_3$ or $Cs_2CO_3$) in a suitable solvent (such as DMF) at temperatures ranging from room temperature to 160° C.

A compound of formula (3) may be formed by reacting a compound of formula (19) with a base (e.g., NaOH or LiOH) in an organic solvent (e.g., 1,4-dioxane, THF, or MeOH, or mixtures thereof), and optionally in the presence of water. The reaction may be performed in a temperature interval from 0° C. to reflux. Alternatively, for compounds of formula (19) where $R^7$=tert-butyl, the reaction may be performed with a suitable acid (e.g., HCl) in a solvent such as 1,4-dioxane, EtOAc, MeOH or water, or mixtures thereof. Alternatively, for compounds of formula (19) where $R^7$=tert-butyl, the reaction may be performed using acids such as TFA, neat or in a solvent such as DCM, at temperatures ranging from typically 0° C. to 60° C.

Alternatively, a compound of formula (3) wherein $R^2$ is as defined in Formula (I), and where the attachment point to the quinoline is through a nitrogen atom, may be formed directly from a compound of formula (17) by reaction with an amine H—$R^2$ (20), wherein $R^2$ is as defined in formula (I). The reaction may be performed under conditions described for the analogous reactions described above in Scheme 9.

SCHEME 10

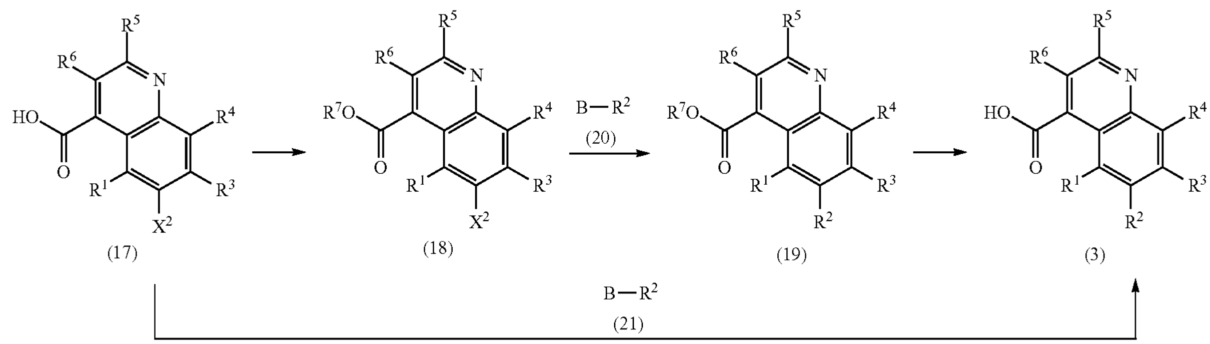

(17) (18) (19) (3)

Scheme 10 illustrates synthetic routes to certain compounds of formula (3). A compound of formula (19) wherein $R^2$ is as defined in formula (I), and where the attachment point to the quinoline is through a carbon atom, may be formed by reacting a compound of formula (18) with a compound B—$R^2$ (21), wherein B is a boronic acid, boronate ester or trifluoroborate salt, and wherein $R^2$ is as defined in formula (I). The reaction may be catalyzed with a suitable Pd-reagent (e.g., $Pd(dppf)Cl_2$) in the presence of a base (such as $Na_2CO_3$ or $K_2CO_3$) in a suitable solvent (such as 1,4-dioxane), optionally in the presence of water, at temperatures ranging from room temperature to reflux.

A compound of formula (3) may be formed by reacting a compound of formula (19) under conditions described for the analogous reactions described in Scheme 9. Alternatively, a compound of formula (3) wherein $R^2$ is as defined in Formula (I), and where the attachment point to the quinoline is through a carbon atom, may be formed directly from a compound of formula (17) by reaction with a compound B—$R^2$ (21), wherein B is a boronic acid, boronate ester or trifluoroborate salt, and wherein $R^2$ is as defined in formula (I). The reaction may be performed under conditions described for the analogous reaction described above in Scheme 10.

SCHEME 11

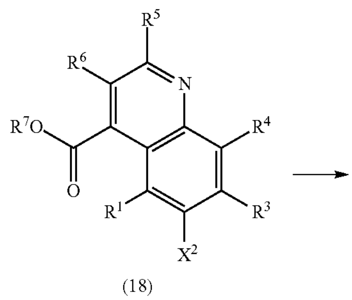

(18)

-continued

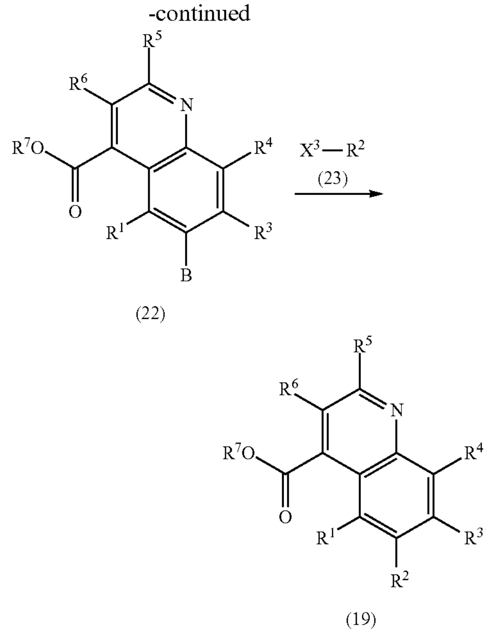

(22)

(19)

Scheme 11 illustrates synthetic routes to certain compounds of formula (19). A compound of formula (22), wherein B is a boronic acid, boronate ester or trifluoroborate salt, may be formed by reacting a compound of formula (18) with a bis-boronic species (e.g., $B_2(OH)_4$ (hypodiboric acid) or $B_2pin_2$ (4,4,4',4',5,5,5',5'-octamethyl-2,2'-bi(1,3,2-dioxaborolane)). The reaction may be catalyzed with a suitable Pd-reagent (e.g., $Pd(dppf)Cl_2$) in the presence of a base (such as $Na_2CO_3$ or $K_2CO_3$) in a suitable solvent (such as ethanol or 1,4-dioxane), optionally in the presence of water, at temperatures ranging from room temperature to reflux.

A compound of formula (19) wherein $R^2$ is as defined in formula (I), and where the attachment point to the quinoline is through a carbon atom, may be formed by reacting a compound of formula (22) with an arylhalide or aryl pseudohalide of formula (23), wherein $R^2$ is as defined in formula (I) and X 3 is attached to $R^2$ via a carbon atom. The reaction may be catalyzed with a suitable Pd-reagent (e.g., $Pd(dppf)Cl_2$) in the presence of a base (such as $Na_2CO_3$ or $K_2CO_3$) in a suitable solvent (such as 1,4-dioxane), optionally in the presence of water, at temperatures ranging from room temperature to reflux.

SCHEME 12

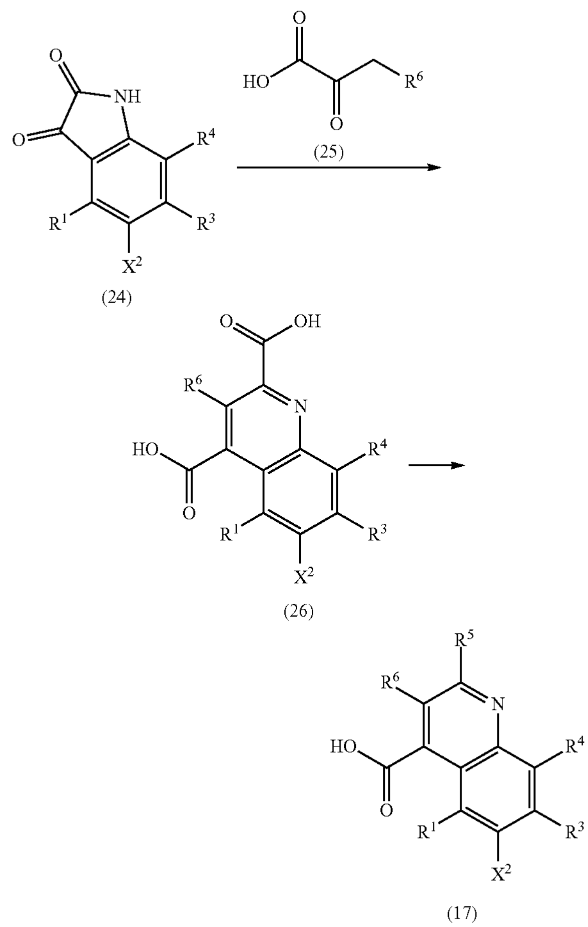

(24) (25) (26) (17)

Scheme 12 illustrates synthetic routes to certain compounds of formula (17). A compound of formula (26) may be formed by reacting a compound of formula (24) with a 2-ketocarboxylic acid of formula (25), or a salt thereof (e.g., a sodium salt), in the presence of a base (e.g., NaOH) in water at reflux temperature, or at elevated temperatures ranging from typically 100° C. to 160° C. in a sealed vessel, or in a sealed tube in a microwave reactor. A compound of formula (17) may be formed by heating a compound of formula (26), either neat, or in a suitable solvent (e.g., water) at elevated temperatures ranging from typically 150° C. to 250° C. in a sealed vessel, or in sealed tube in a microwave reactor.

SCHEME 13

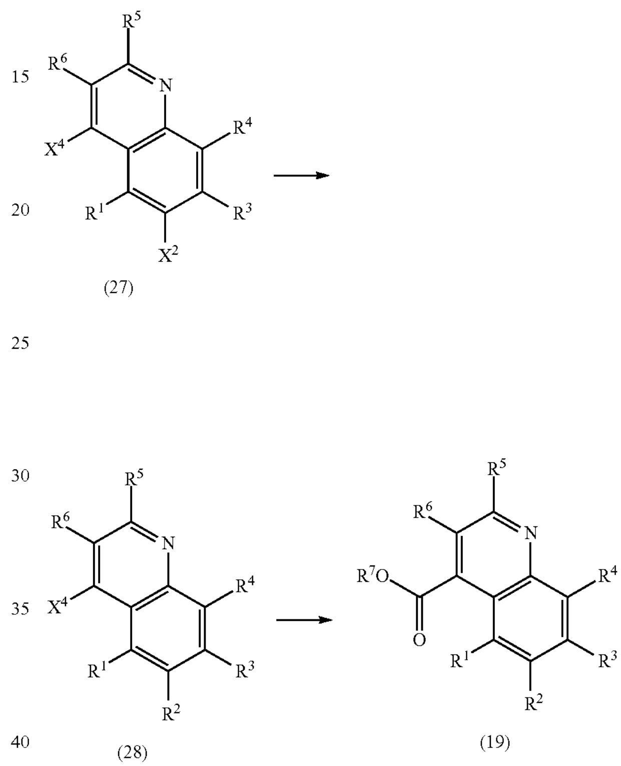

(27) (28) (19)

Scheme 13 illustrates synthetic routes to certain compounds of formula (19). A compound of formula (28) wherein $R^2$ is as defined in formula (I), and where the attachment point to the quinoline is through a nitrogen atom or a carbon atom, may be formed from a compound of formula (27) using synthetic methodology performed under conditions described for the analogous reactions described in Scheme 9, 10 and 11.

A compound of formula (19) may be formed by reacting a compound of formula (28) with carbon monoxide (1-10 atm), typically at a pressure of 10 atm, at a temperature ranging from typically 80° C. to 120° C. in a sealed vessel. The reaction may be catalyzed with a suitable Pd-reagent (e.g., $Pd(dppf)Cl_2$) in the presence of a base (e.g., TEA) in the presence of a suitable alcohol (such as MeOH or EtOH) in a suitable solvent, or using the alcohol as solvent.

SCHEME 14

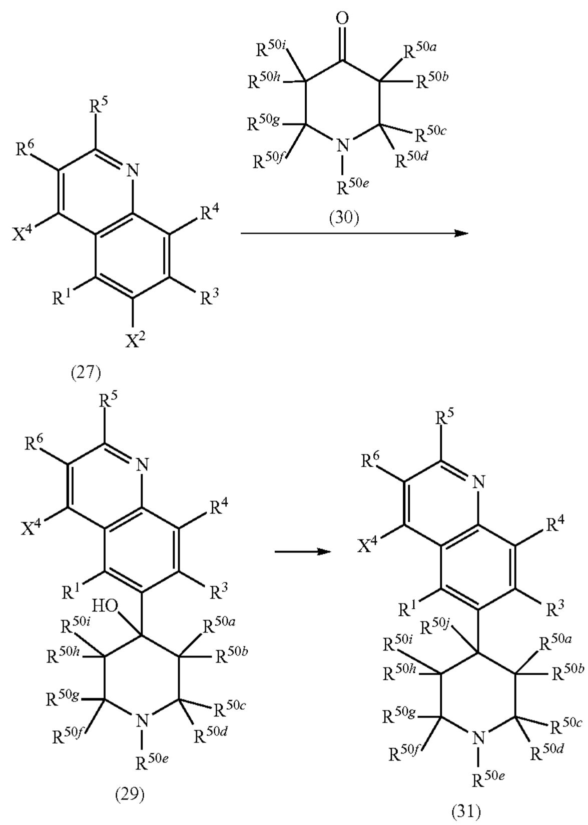

(30) (27) (29) (31)

Scheme 14 illustrates synthetic routes to certain compounds of formula (31). A compound of formula (29) in which $R^{50}$ is as defined in Formula (VIII) may be formed from a compound of formula (27) by metal halogen exchange using an organometallic reagent (e.g., BuLi) followed by reaction with an electrophile such as a ketone of formula (30). The reaction may be performed in a solvent such as THF at a temperature ranging from typically −78° C. to room temperature.

A compound of formula (31) in which $R^{50j}$ is a fluorine, may be formed by reacting a compound of formula (29) with a fluorinating agent (e.g., DAST) in a solvent such as DCM at a temperature ranging from typically −20° C. to reflux.

A compound of formula (31) may be converted into a compound of formula (VIII) using synthetic methodology analogous to those described in Scheme 13, 10 and 1.

It should be understood that: (i) the organic reactions described in this disclosure are performed according to laboratory practice known to person skilled in the art; (ii) some of the reactions described in this disclosure may optionally be performed in different orders than laid out herein; (iii) chiral isomers of compounds in this disclosure can be resolved at any stage in the synthetic process using chiral resolving agents described in the literature and known to person skilled in the art, or using chiral chromatography methods described in the literature and known to person skilled in the art, or as described further in the Examples; (iv) additional and/or other protective groups may optionally be needed in some of the steps described above, and (v) a deprotection step therefore optionally may be performed, using method described in the literature and known to person skilled in the art. The protection and deprotection of functional groups is described in "*Protective Groups in Organic Synthesis*" 3$^{rd}$ Ed, T. W. Greene and P. G. M. Wutz, Wiley-Interscience (1999), which publication is incorporated herein by reference.

VIII. Examples

The following descriptions of experiments, procedures, examples, and intermediates are intended to exemplify embodiments of the disclosure and are in no way intended to be limiting. Other compounds of this disclosure may be prepared using the methods illustrated in these examples, either alone or in combination with techniques generally known in the art.

A. General Conditions

Unless stated otherwise:

(i) operations were carried out at room temperature (rt), i.e., in the range 17 to 25° C. and under an atmosphere of an inert gas such as $N_2$ unless otherwise stated;

(ii) where reactions refer to the use of a microwave reactor, one of the following microwave reactors were used: Biotage Initiator, Personal Chemistry Emrys Optimizer, Personal Chemistry Smith Creator or CEM Explorer;

(iii) in general, the course of reactions was followed by thin layer chromatography (TLC) and/or analytical high performance liquid chromatography (HPLC or UPLC) which was usually coupled to a mass spectrometer (LCMS).

(iv) when necessary, organic solutions were dried over anhydrous $MgSO_4$ or $Na_2SO_4$, or by using ISOLUTE® Phase Separator, and work-up procedures were carried out using traditional phase separating techniques.

(v), evaporations were carried out either by rotary evaporation in vacuo or in a Genevac HT-4/EZ-2 or Biotage V10;

(vi) unless otherwise stated, flash column chromatography was performed on straight phase silica, using either Merck Silica Gel (Art. 9385) or pre-packed cartridges such as Biotage® SNAP cartridges (40-63 μm silica, 4-330 g), Biotage® Sfar Silica HC D cartridges (20 μm, 10-100 g), Interchim PuriFlash™ cartridges (25 μm, 4-120 g), Interchim PuriFlash™ cartridges (50 μm, 25-330 g), Grace™ GraceResolv™ Silica Flash Cartridges (4-120 g) or Agela Flash Colum Silica-CS cartridges (80-330 g), or on reversed phase silica using Agela Technologies C-18, spherical cartridges (20-35 μm, 100A, 80-330 g), manually or automated using a Grace Reveleris® X2 Flash system or similar system;

(vii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section, and one of the following methods as described below;

HPLC Prep Methods: PrepMethod A: The compound was purified by preparative HPLC on a YMC-Actus Triart C18 ExRS column (5 μm, 150×30 mm ID) using a gradient of MeCN in $H_2O/NH_4HCO_3$ (10 mM) as mobile phase; PrepMethod B: The compound was purified by preparative HPLC on a XBridge™ C18 OBD column (5 μm, 150×30 mm ID) using a gradient of MeCN in a $H_2O/NH_4HCO_3$ (10 mM)/$NH_3$ (0.1%, aq) buffer system as mobile phase; PrepMethod C: The compound was purified by preparative HPLC on a XSelect CSH OBD column (5 μm, 150×30 mm ID) using a gradient of MeCN in $H_2O$/FA (0.1%) as mobile phase; PrepMethod D: The compound was purified by preparative HPLC on a XSelect CSH C18 OBD column (5 μm, 250×19 mm ID) using a gradient of MeCN in $H_2O$/FA (0.1%) as mobile phase; PrepMethod E: The compound was purified by preparative HPLC on a Kromasil $C_8$ column (10 μm, 250×20 mm ID) using a gradient of MeCN in $H_2O$/MeCN/FA (95/5/0.2) as mobile phase; PrepMethod F: The compound was purified by preparative HPLC on a Waters™ Sunfire™ C18 OBD column (5 μm, 150×30 mm ID) using a gradient of MeCN in $H_2O$/FA (0.1%) as mobile phase; PrepMethod G: The compound was purified by preparative HPLC on a Kromasil $C_8$ column (10 μm, 250×50 mm ID) using a gradient of MeCN in $H_2O$/MeCN/FA (95/5/0.2) as mobile phase; PrepMethod H: The compound was purified by preparative HPLC on a XBridge™ C18 column (10 μm, 250×50 mm ID) using a gradient of MeCN in $H_2O$/MeCN/$NH_3$ (95/5/0.2) as mobile phase; PrepMethod I: The compound was purified by preparative HPLC on a XBridge™ C18 OBD column (5 μm, 250×19 mm ID) using a gradient of MeCN in $H_2O$/$NH_4HCO_3$ (10 mM) as mobile phase; PrepMethod N: The compound was purified by preparative HPLC on a XBridge™ C18 column (10 μm, 250×19 mm ID) using a gradient of MeCN in $H_2O$/MeCN/$NH_3$ (95/5/0.2) as mobile phase; PrepMethod O: The compound was purified by preparative HPLC on a XBridge™ C18 column (5 μm, 250×19 mm ID) using a gradient of MeOH in $H_2O$/$NH_4HCO_3$ (10 mM) as mobile phase; PrepMethod P: The compound was purified by preparative HPLC on a XBridge™ Shield C18 column (5 μm, 150×30 mm ID) using a gradient of MeCN in $H_2O$/FA (0.1%) as mobile phase; PrepMethod Q: The compound was purified by preparative HPLC on a Xbridge™ C18 ODB column (5 μm, 150×19 mm ID) using a gradient of MeCN in a $H_2O$/$NH_3$ (0.2%, pH 10) buffer system as mobile phase; PrepMethod R: The compound was purified by preparative HPLC on a XBridge™ C18 OBD column (5 μm, 150×30 mm ID) using a gradient of MeCN in $H_2O$//$NH_4HCO_3$ (10 mM) as mobile phase; PrepMethod T: The compound was purified by preparative HPLC on a XBridge™ Shield C18 column (5 μm, 150×30 mm ID) using a gradient of MeCN in a $H_2O$/$NH_4CO_3$ (10 mM)/$NH_3$ (0.1%, aq) buffer system as mobile phase; PrepMethod U: The compound was purified by preparative HPLC on a Xselect CSH F-Phenyl OBD column, (5 μm, 250×19 mm ID) using a gradient of MeCN in $H_2O$/FA (0.1%) as mobile phase; PrepMethod V: The compound was purified by preparative HPLC on a Waters™ Sunfire™ C18 OBD column (5 μm, 150×30 mm ID) using a gradient of MeCN in $H_2O$/FA (0.1 M) as mobile phase; PrepMethod X: The compound was purified by preparative HPLC on a Xselect CSH OBD column, (5 μm, 150×30 mm ID) using a gradient of MeCN in $H_2O$/FA (0.1%) as mobile phase;

SFC Prep Methods: PrepMethod SFC-A: The compound was purified by preparative SFC on a Phenomenex Luna® HILIC column (5 μm, 250×30 mm ID) using EtOH/FA (20 mM) in $CO_2$ as mobile phase; PrepMethod SFC-B: The compound was purified by preparative SFC on a DAICEL DCpak® P4VP, (5 μm, 250×20 mm ID) using MeOH/2M $NH_3$ in MeOH (99.5/0.5) in $CO_2$ as mobile phase; PrepMethod SFC-C: The compound was purified by preparative SFC on a Waters™ BEH, (5 μm, 250×30 mm ID) using MeOH/$H_2O$ ($NH_3$ 50 mM) (97/3) in $CO_2$ as mobile phase; PrepMethod SFC-D: The compound was purified by preparative SFC on a Waters™ BEH (5 μm, 30×250 mm ID) using EtOH/FA (20 mM) in $CO_2$ as mobile phase; PrepMethod SFC-E: The compound was purified by preparative SFC on a Waters™ BEH, (5 μm, 250×30 mm ID) using MeOH/$NH_3$ (20 mM) in $CO_2$ as mobile phase; PrepMethod SFC-G: The compound was purified by preparative SFC on a Waters™ BEH, (3.5 μm, 100×3 mm ID) using MeOH/$NH_3$ (20 mM) in $CO_2$ as mobile phase; PrepMethod SFC-H: The compound was purified by preparative SFC on a Phenomenex Luna® HILIC column (5 μm, 250×30 mm ID) using MeOH/$NH_3$ (20 mM) in $CO_2$ as mobile phase.

Relevant fractions were collected, combined and freeze-dried to give the purified compound or relevant fractions were collected, combined and concentrated at reduced pressure, extracted with DCM or EtOAc, and the organic phase was dried either over $Na_2SO_4$ or by using a phase-separator, and then concentrated at reduced pressure to give the purified compound;

(viii) chiral preparative chromatography was carried out using HPLC or SFC on a standard HPLC or SFC instruments, respectively, and using either isocratic or gradient run with mobile phase as described in the experimental section;

(x) yields, where present, are not necessarily the maximum attainable, and when necessary, reactions were repeated if a larger amount of the reaction product was required;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) in general, the structures of the end-products of the Formula (I) were confirmed by nuclear magnetic resonance (NMR) and/or mass spectral techniques; proton NMR chemical shift values were measured on the delta scale using Bruker Avance III 300, 400, 500 and 600 spectrometers, operating at $^1H$ frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g., dd, doublet of doublets, etc.): s, singlet; d, doublet; t, triplet; q, quartet; m, multiplet; br, broad; qn, quintet; p, pentet. In some cases, the structures of the end-products of the Formula (I) might appear as rotamers in the NMR-spectrum, in which instances only peaks of the major rotamer are reported. Electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported (xiii) intermediates were not necessarily fully purified but their structures and purity were assessed by TLC, analytical HPLC/UPLC, and/or NMR analysis and/or mass spectrometry;

(xiv) unless stated otherwise compounds containing an asymmetric carbon and/or sulfur atom were not resolved;

(xv) in general Examples and Intermediate compounds are named using ChemDraw Professional version 19.0.0.22 from PerkinElmer. ChemDraw Professional version 19.0.0.22 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure. In general chemical structures of Examples and Intermediates containing the label '&' at a stereocenter, means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

In general Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

In general, the descriptors (r) and (s) are used to describe the absolute configuration of any pseudoasymmetric centers in the structures of Examples and Intermediates.

In general, the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration;

(xvi) where reactions refer to being degassed or purged, this can be performed for example by purging the reaction solvent with a constant flow of nitrogen for a suitable period of time (for example 5 to 10 min)

(xvii) in addition to the ones mentioned above, the following abbreviations have been used:

| | | | |
|---|---|---|---|
| α2AP | α2-antiplasmin | MeI | iodomethane |
| Ala | alanine | MeOH | methanol |
| AMC | 7-amino-4-methylcoumarin | min | minute(s) |
| aq | aqueous | mL | milliliter |
| atm | atmosphere | MS | mass spectrometry |
| BMI | body mass index | MTBE | tert-butyl methyl ether |
| $Boc_2O$ | di-tert-butyl dicarbonate | MW | molecular weight |
| BSA | bovine serum albumin | m/z | mass spectrometry peak(s) |
| n-BuLi | n-butyllithium | NAFLD | nonalcoholic fatty liver disease |
| tert-BuOH | 2-methylpropan-2-ol | NASH | non-alcoholic steatohepatitis |
| C | Celcius | NBS | N-bromosuccinimide |
| Chaps | (3-((3-cholamidopropyl) dimethylammonio)-1-propanesulfonate) | NCS | N-chlorosuccinimide |
| $CL_{int}$ | intrinsic clearance | NHS | N-hydroxysuccinimide |
| conc | concentration | Ni | nickel |
| m-CPBA | 3-chlorobenzoperoxoic acid | $NiBr_2$ $O(CH_2CH_2OCH_3)_2$ | nickel(II) bromide 2-methoxyethyl ether complex |
| CPhos | 2'-(dicyclohexylphosphaneyl)-N2,N2,N6,N6-tetramethyl-[1,1'-biphenyl]-2,6-diamine | NMP | N-methyl-2-pyrrolidone |
| CPME | cyclopentyl methyl ether | NMR | nuclear magnetic resonance |
| CR | concentration response | NV | not valid |
| DA | dalton | OTf | trifluoromethanesulfonate |
| DAST | diethylaminosulfur trifluoride | $P_{app}$ | apparent permeability coefficient |
| DavePhos | 2'-(dicyclohexylphosphaneyl)-N,N-dimethyl-[1,1'-biphenyl]-2-amine | PBS | phosphate buffered saline |
| DCM | dichloromethane | PCR | polymeras chain reaction |
| DEA | diethylamine | Pd Catalyst [CAS: 1810068-35-9] | methanesulfonato(2-bis(3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium(II) |
| DIPEA | N-ethyl-N-isopropyl-propan-2-amine | $Pd(dba)_2$ | bis(dibenzylideneacetone)palladium |
| DMAP | 4-dimethylaminopyridine | $Pd_2(dba)_3$ | (tris(dibenzylideneacetone)-dipalladium(0) |
| DMF | N,N-dimethylformamide | $Pd(dppf)Cl_2$•DCM | [1,1'-bis(diphenylphosphino)-ferrocene]-dichloropalladium(II) complex with dichloromethane (1:1) |

-continued

| | | | |
|---|---|---|---|
| DMPU | N,N'-dimethylpropyleneurea | $Pd(dtbpf)Cl_2$ | 1,1'-bis(di-tert-butylphosphino)-ferrocene palladium dichloride |
| DMSO | dimethyl sulfoxide | $Pd(OAc)_2$ | palladium(II)acetate |
| DPP4 | dipeptidyl peptidase 4 | PK | pharmacokinetics |
| dppf | 1,1'-bis(diphenylphosphino)ferrocene | PPAR | peroxisome proliferator-activated receptor |
| EDC | 3-(ethyliminomethyleneamino)-N,N-dimethyl-propan-1-amine;hydrochloride | PREP | prolyl endopeptidase |
| EDTA | ethylenediaminetetraacetic acid | Pro | proline |
| % ee | enantiomeric excess | rHep | rat hepatocytes |
| EPhos Pd G4 | CAS No 2132978-44-8 | rpm | revolution per minute |
| ESI | electrospray ionization | rt | room temperature |
| EtOAc | ethyl acetate | RU | response unit |
| EtOH | ethanol | RuPhos | dicyclohexyl(2',6'-diisopropoxy-[1,1'-biphenyl]-2-yl)phosphane |
| $Et_2Zn$ | diethyl zink | RuPhos Pd G2 | chloro(2-dicyclohexylphosphino-2',6'-diisopropoxy-1,1'-biphenyl)[2-(2'-amino-1,1'-biphenyl)]palladium(II) [CAS Number 1375325-68-0] |
| FA | formic acid | RuPhos Pd G3 | dicyclohexyl(2',6'-diisopropoxy-[1,1'-biphenyl]-2-yl)phosphane (2'-amino-[1,1'-biphenyl]-2-yl)((methylsulfonyl)oxy)palladium [CAS No1445085-77-7] |
| FAC | final assay concentration | RuPhos Pd G4 | dicyclohexyl(2',6'-diisopropoxy-[1,1'-biphenyl]-2-yl)phosphane (2'-(methylamino)-[1,1'-biphenyl]-2-yl)((methylsulfonyl)oxy)palladium [CAS Number 1599466-85-9] |
| FAP | prolyl endopeptidase fibroblast activation protein | sat | saturated |
| FGF21 | fibroblast growth factor 21 | SD | standard deviation |
| g | gram | SFC | supercritical fluid chromatography |
| GLP1 | glucagon-like peptide-1 receptor | SGLT2 | sodium-glucose transport protein 2 |
| gly | glycine | SPhos | dicyclohexyl(2',6'-dimethoxy-[1,1'-biphenyl]-2-yl)phosphane |
| h | hour(s) | SPhos Pd G3 | (2-dicyclohexylphosphino-2',6'-dimethoxybiphenyl) [2-(2'-amino-1,1'-biphenyl)]palladium(II) methanesulfonate [CAS No 1445085-82-4] |
| HATU | (1-[bis(dimethylamino)-methylene]-1H-1,2,3-triazolo[4,5-b]pyridinium 3-oxide hexafluorophosphate | TBTU | 2-(1H-benzotriazole-1-yl)-1,1,3,3-tetramethylaminium tetrafluoro-borate |
| hDPP7 | human dipeptidylpeptidase VII | TCEP | tris(2-carboxyethyl)phosphine hydrochloride |
| hDPP8 | human dipeptidylpeptidase VIII | TEA | triethylamine |
| hDPP9 | human dipeptidylpeptidase IX | TFA | trifluoro acetic acid |
| HEPES | (4-(2-hydroxyethyl)-1-piperazineethanesulfonic acid) | TFAA | trifluoro acetic acid anhydride |
| hFAP | human prolyl endopeptidase fibroblast activation protein | THF | tetrahydrofuran |
| HFIP | 1,1,1,3,3,3-hexafluoropropan-2-ol | TLC | thin layer chromatography |
| HIS | histidine | T3P | propanephosphonic acid anhydride |
| HLM | human liver microsomes | Triphosgene | bis(trichloromethyl) carbonate |
| HOBt | 1-hydroxybenzotriazole; hydrate | Tris HCl | tris(hydroxymethyl)aminomethane hydrochloride |
| HOMA-IR | homeostatic model assessment of insulin resistance | Triton X-100 | t-octylphenoxypolyethoxyethanol |
| HPLC | high performance liquid chromatography | TsOH | p-toluenesulfonic acid |
| HRMS | high resolution mass spectrometry | μL | microliter |
| $IC_{50}$ | half-maximum inhibitory concentration | UPLC | ultra performance liquid chromatography |
| ID | inner diameter | UV | ultraviolet |
| IPA | propan-2-ol | v/v | volume by volume |
| KOtBu | potassium: tert-butoxide | XantPhos | (9,9-dimethyl-9H-xanthene-4,5-diyl)bis(diphenylphosphane) |
| LC | liquid chromatography | XantPhos Pd G4 | [CAS No 1621274-19-8] |
| M | Molar | XPhos | dicyclohexyl(2',4',6'-triisopropyl-[1,1'-biphenyl]-2-yl)phosphane |
| MeCN | acetonitrile | XPhos-Pd-G2 | chloro(2-dicyclohexylphosphino-2',4',6'-triisopropyl-1,1'-biphenyl)[2- |

-continued

| | |
|---|---|
| | (2'-amino-1,1'-biphenyl)-]palladium(II), X-Phos aminobiphenyl palladium chloride precatalyst [CAS No 1310584-14-5] |
| XPhos Pd G3 | (2-dicyclohexylphosphino-2',4',6'-triisopropyl-1,1'-biphenyl)[2-(2'-amino-1,1'-biphenyl)]palladium(II) methanesulfonate [CAS Number 1445085-55-1] |

B. Intermediate Compounds

Intermediate 1: tert-Butyl (R)-4-cyanothiazolidine-3-carboxylate

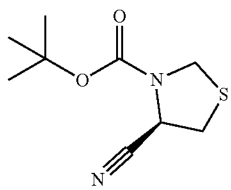

Step a) tert-Butyl (R)-4-carbamoylthiazolidine-3-carboxylate

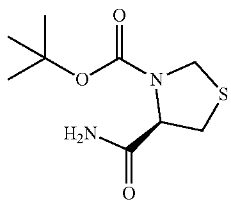

$Boc_2O$ (18.6 mL, 80.2 mmol) was added to a stirred solution of (R)-3-(tert-butoxycarbonyl)thiazolidine-4-carboxylic acid (17.0 g, 72.9 mmol) and pyridine (7.07 mL, 87.5 mmol) in EtOAc (170 mL) and the reaction mixture was stirred at rt for 3 h. Then, a solution of $NH_3$ (aq, 25%, 6 mL) was added dropwise and the mixture was stirred at rt overnight. The reaction mixture was diluted with EtOAc, the phases were separated and the organic phase was washed with sat NaCl, dried, filtered through a pad of silica gel, washed with EtOAc and evaporated to give the crude title compound (16.9 g, 100%) as a colorless oil, which was used directly in the next step.

Step b) tert-Butyl (R)-4-cyanothiazolidine-3-carboxylate

TFAA (12.4 mL, 87.5 mmol) as a solution in EtOAc (20 mL) was added to a solution of crude tert-butyl (R)-4-carbamoylthiazolidine-3-carboxylate (16.9 g, 72.9 mmol) and pyridine (14.7 mL, 182 mmol) in EtOAc (150 mL) at rt. The mixture was stirred at rt for 4 h and then diluted with EtOAc, washed with aq, HCl (1 M), and sat $NaHCO_3$. The organic phase was dried, filtered through a pad of silica gel, washed with EtOAc, and evaporated to give a light yellow oil which solidified on standing. The crude solid material was suspended in heptane:EtOAc (4:1, 50 mL) and stirred at rt overnight. The solids were filtered off, washed with heptane:EtOAc (4:1), and dried to give the title compound (12.0 g, 83%) as a colorless solid; $^1H$ NMR (400 MHz, $CDCl_3$) δ 5.20-4.79 (m, 1H), 4.60-4.53 (m, 1H), 4.53-4.36 (m, 1H), 3.40-3.18 (m, 2H), 1.51 (s, 9H).

Intermediate 2: (R)-Thiazolidine-4-carbonitrile hydrochloride

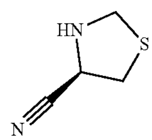

A solution of aq HCl (12 M, 11 mL) in MeOH (140 mL) was added slowly to a solution of tert-butyl (R)-4-cyanothiazolidine-3-carboxylate Intermediate 1 (6.0 g, 28 mmol) in MeOH (140 mL) at rt. The clear colorless solution was stirred at rt for 2 h. Solvents were evaporated to give the title compound (4.22 g, 100%) as a colorless solid; $^1H$ NMR (400 MHz, CD3OD) δ 4.90 (dd, 1H), 4.35-4.24 (m, 2H), 3.37-3.24 (m, 2H).

Intermediate 3: tert-Butyl (R)-(2-(4-cyanothiazolidin-3-yl)-2-oxoethyl)carbamate

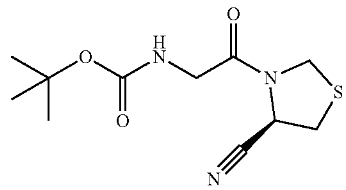 [SMILES: CC(C)(C)OC(=O)NCC(=O)N1CSC[C@H]1C#N]

DIPEA (19.6 mL, 112 mmol) was added to a suspension of (R)-thiazolidine-4-carbonitrile hydrochloride Intermediate 2 (4.22 g, 28 mmol), (tert-butoxycarbonyl)glycine (6.13 g, 35.0 mmol) and T3P (41.6 mL, 70.0 mmol, 50% solution in EtOAc) in EtOAc (120 mL). The mixture was heated at 60° C. for 4 h. The mixture was diluted with EtOAc, and sequentially washed with water, aq HCl (1 M) and sat $NaHCO_3$. The organic phase was dried, filtered and evaporated. The residue was filtered through a pad of silica gel, washed with heptane:EtOAc (1:1) and evaporated to give an oil which was triturated with heptane:DCM to give the title compound (7.60 g, 100%) as an almost colorless solid; $^1H$ NMR (400 MHz, $CDCl_3$) δ 5.36-5.25 (m, 2H), 4.59-4.52 (m, 2H), 4.14-3.90 (m, 2H), 3.29 (d, 2H), 1.45 (s, 9H).

Intermediate 4: (R)-3-Glycylthiazolidine-4-carbonitrile hydrochloride

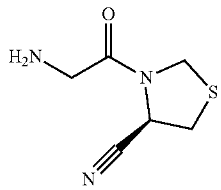 [SMILES: N#C[C@@H]1CSCN1C(=O)CN]

A solution of aq HCl (12 M, 5.6 mL) in MeOH (140 mL) was added slowly to a solution of tert-butyl (R)-(2-(4-cyanothiazolidin-3-yl)-2-oxoethyl)carbamate Intermediate 3 (7.60 g, 28.0 mmol) in MeOH (140 mL), then the solution was stirred at rt overnight. The solvents were evaporated to give the title compound (5.80 g, 100%) as a colorless solid; $^1H$ NMR (400 MHz, $CD_3OD$) δ 5.34 (t, 1H), 4.72 (d, 1H), 4.62 (d, 1H), 4.11-3.94 (m, 2H), 3.41-3.36 (m, 2H).

Intermediate 5: Ethyl 6-(1,2-oxazinan-2-yl)quinoline-4-carboxylate

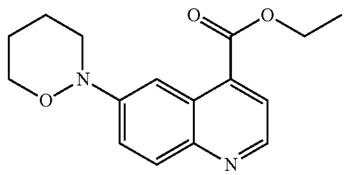 [SMILES: CCOC(=O)c1ccnc2ccc(N3CCCCO3)cc12]

1,2-Oxazinane hydrochloride (37 mg, 0.30 mmol) was added to a mixture of ethyl 6-bromoquinoline-4-carboxylate (56 mg, 0.20 mmol), $Cs_2CO_3$ (195 mg, 0.60 mmol), $Pd_2dba_3$ (9.0 mg, 10 μmol) and XPhos (9.5 mg, 0.02 mmol) in dioxane (1 mL). The flask was sealed, purged with $N_2$ (g) and the mixture was heated at 90° C. overnight. The mixture was diluted with EtOAc and washed with water. The organic phase was dried, filtered and evaporated. The residue was purified by straight phase flash chromatography on silica (gradient: 20-50% EtOAc in heptane) to give the title compound (50 mg, 87%) as a yellow oil which solidified on standing; MS m/z (ESI) $[M+H]^+$ 287.2.

Intermediate 6: 6-(1,2-Oxazinan-2-yl)quinoline-4-carboxylic acid

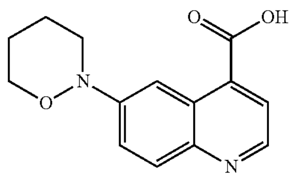

Aq NaOH (1 M, 0.52 mL) was added to a solution of ethyl 6-(1,2-oxazinan-2-yl)quinoline-4-carboxylate Intermediate 5 (50 mg, 0.17 mmol) in MeOH (2 mL) and water (1 mL). The mixture was stirred at rt for 3 h, then neutralized with aq HCl (1 M), and evaporated to give the title compound (45 mg, 100%) as a yellow-red semisolid; MS m/z (ESI), $[M+H]^+$ 259.1.

Intermediate 7: Ethyl 3-fluoro-6-morpholinoquinoline-4-carboxylate

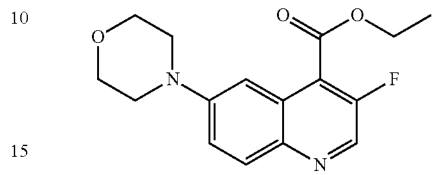

Morpholine (70 mg, 0.80 mmol) was added to a mixture of ethyl 6-chloro-3-fluoroquinoline-4-carboxylate (101 mg, 0.4 mmol), $Cs_2CO_3$ (0.391 g, 1.20 mmol), $Pd_2dba_3$ (18 mg, 0.02 mmol) and XPhos (19 mg, 0.04 mmol) in dioxane (2 mL). The flask was sealed, purged with $N_2$ (g) and the mixture was heated at 90° C. for 1 h. The mixture was diluted with EtOAc and washed with water. The organic phase was dried, filtered and evaporated to give the title compound (122 mg, 100%) as a yellow semisolid; MS m/z (ESI) $[M+H]^+$ 305.2.

Intermediate 8: 3-Fluoro-6-morpholinoquinoline-4-carboxylic acid

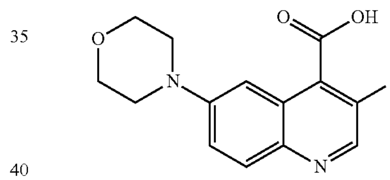

Aq NaOH (1 M, 1.25 mL) was added to a solution of ethyl 3-fluoro-6-morpholinoquinoline-4-carboxylate Intermediate 7 (190 mg, 0.62 mmol) in MeOH (6 mL) and water (3 mL). The mixture was stirred at rt for 3 h. The mixture was neutralized with aq HCl (1 M), and evaporated to give the title compound (172 mg, 100%) as a red-yellow semisolid; MS m/z (ESI) $[M+H]^+$ 277.3.

Intermediate 9: Ethyl 6-thiomorpholinoquinoline-4-carboxylate

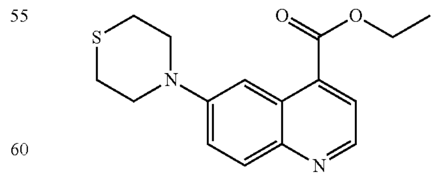

Thiomorpholine (41 mg, 0.40 mmol) was added to a mixture ethyl 6-bromoquinoline-4-carboxylate (56 mg, 0.2 mmol), $Cs_2CO_3$ (0.130 g, 0.40 mmol), $Pd_2dba_3$ (9.2 mg, 0.01 mmol) and XPhos (9.5 mg, 0.02 mmol) in dioxane (1 mL). The flask was sealed, purged with $N_2$ (g) and the mixture was heated at 90° C. overnight. The mixture was diluted with EtOAc, washed with water (3×). The organic phase was dried, filtered and evaporated. The residue was purified by straight phase flash chromatography on silica (gradient: 20-50% EtOAc in heptane) to give the title compound (55 mg, 91%) as a yellow oil; MS m/z (ESI) $[M+H]^+$ 303.2.

Intermediate 10: 6-Thiomorpholinoquinoline-4-carboxylic acid

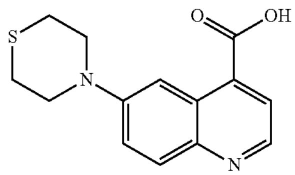 [SMILES: O=C(O)c1ccnc2ccc(N3CCSCC3)cc12]

LiOH (22 mg, 0.91 mmol) was added to a solution of ethyl 6-thiomorpholinoquinoline-4-carboxylate Intermediate 9 (55 mg, 0.18 mmol) in MeOH (1 mL) and water (1 mL). The mixture was stirred at rt overnight, and then neutralized with aq HCl (1 M). The solvents were evaporated under reduced pressure to give the title compound (50 mg, 100%) as a yellow-red semisolid; MS m/z (ESI) $[M+H]^+$ 275.1.

Intermediate 11: Ethyl 6-(2,2-difluoromorpholino)quinoline-4-carboxylate

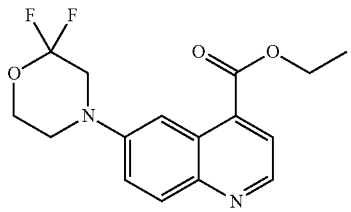 [SMILES: CCOC(=O)c1ccnc2ccc(N3CCOC(F)(F)C3)cc12]

2,2-Difluoromorpholine hydrochloride (72 mg, 0.45 mmol) was added to a mixture of ethyl 6-bromoquinoline-4-carboxylate (84 mg, 0.30 mmol), $Cs_2CO_3$ (0.293 g, 0.90 mmol), $Pd_2dba_3$ (14 mg, 0.02 mmol) and XPhos (14 mg, 0.03 mmol) in dioxane (1.5 mL). The flask was sealed, purged with $N_2$ (g) and the mixture was heated at 90° C. overnight. The mixture was diluted with EtOAc and washed with water. The organic phase was dried, filtered and evaporated. The residue was purified by straight phase flash chromatography on silica (heptane:EtOAc 1:1) to give the title compound (85 mg, 88%) as a yellow solid; MS m/z (ESI) $[M+H]^+$ 323.4.

Intermediate 12: 6-(2,2-Difluoromorpholino)quinoline-4-carboxylic acid

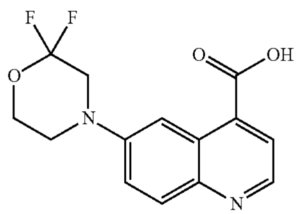 [SMILES: O=C(O)c1ccnc2ccc(N3CCOC(F)(F)C3)cc12]

Aq NaOH (1 M, 0.5 mL) was added to a solution of ethyl 6-(2,2-difluoromorpholino)quinoline-4-carboxylate Intermediate 11 (80 mg, 0.25 mmol) in MeOH (2.5 mL) and water (1 mL). The mixture was stirred at rt overnight, and then neutralized with aq HCl (1 M). The solvents were evaporated under reduced pressure to give the title compound (73 mg, 100%) as a yellow solid; MS m/z (ESI) $[M+H]^+$ 295.3.

Intermediate 13: Ethyl 6-(2,2,6,6-tetrafluoromorpholino)quinoline-4-carboxylate

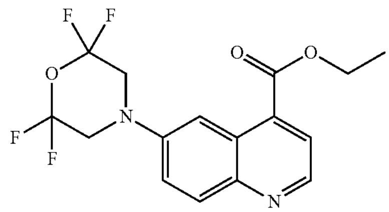 [SMILES: CCOC(=O)c1ccnc2ccc(N3CC(F)(F)OC(F)(F)C3)cc12]

2,2,6,6-Tetrafluoromorpholine (64 mg, 0.40 mmol) was added to a mixture of ethyl 6-bromoquinoline-4-carboxylate (56 mg, 0.2 mmol), $Cs_2CO_3$ (0.195 g, 0.60 mmol), $Pd_2dba_3$ (9.2 mg, 0.01 mmol) and XPhos (9.5 mg, 0.02 mmol) in dioxane (1 mL). The flask was sealed, purged with $N_2$ (g) and the mixture was heated at 90° C. overnight. The mixture was diluted with EtOAc and washed with water. The organic phase was dried, filtered and evaporated. The residue was purified by straight phase flash chromatography on silica (gradient: 20-50% EtOAc in heptane) to give the title compound (60 mg, 84%) as an almost colorless solid; MS m/z (ESI) $[M+H]^+$ 359.2.

Intermediate 14: 6-(2,2,6,6-Tetrafluoromorpholino)quinoline-4-carboxylic acid

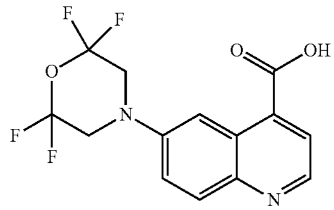 [SMILES: O=C(O)c1ccnc2ccc(N3CC(F)(F)OC(F)(F)C3)cc12]

Aq NaOH (1 M, 0.5 mL, 0.50 mmol) was added a solution of ethyl 6-(2,2,6,6-tetrafluoromorpholino)quinoline-4-carboxylate Intermediate 13 (60 mg, 0.17 mmol) in MeOH (2 mL) and water (1 mL). The mixture was stirred at rt for 3 h, and then neutralized with aq HCl (1 M). The solvents were evaporated under reduced pressure to give the title compound (55 mg, 99%) as a light yellow solid; MS m/z (ESI) $[M+H]^+$ 331.1.

Intermediate 15: Ethyl 6-(2,3-dihydro-4H-benzo[b][1,4]oxazin-4-yl)quinoline-4-carboxylate

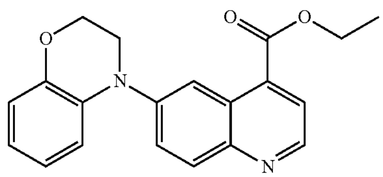 [SMILES: CCOC(=O)c1ccnc2ccc(N3CCOc4ccccc43)cc12]

3,4-Dihydro-2H-benzo[b][1,4]oxazine (54 mg, 0.40 mmol) was added to a mixture of ethyl 6-bromoquinoline-4-carboxylate (56 mg, 0.2 mmol), $Cs_2CO_3$ (0.130 g, 0.40 mmol) and RuPhos Pd G2 (16 mg, 0.02 mmol) in dioxane (1 mL). The flask was sealed, purged with $N_2$ (g) and the mixture was heated at 90° C. overnight. The mixture was diluted with EtOAc and washed with water. The organic phase was dried, filtered and evaporated. The residue was purified by straight phase flash chromatography on silica (gradient: 20-50% EtOAc in heptane) to give the title compound (53 mg, 79%) as a yellow semisolid; MS m/z (ESI) $[M+H]^+$ 335.2.

Intermediate 16: 6-(2,3-Dihydro-4H-benzo[b][1,4]oxazin-4-yl)quinoline-4-carboxylic acid

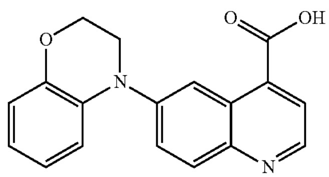 [SMILES: O=C(O)c1ccnc2ccc(N3CCOc4ccccc43)cc12]

Aq NaOH (1 M, 0.5 mL) was added a solution of ethyl 6-(2,3-dihydro-4H-benzo[b][1,4]oxazin-4-yl)quinoline-4-carboxylate Intermediate 15 (53 mg, 0.16 mmol) in MeOH (1 mL) and water (0.5 mL). The mixture was stirred at rt overnight, and then neutralized with aq HCl (1 M). The solvents were evaporated under reduced pressure to give the title compound (49 mg, 100%) as a yellow-red semisolid; MS m/z (ESI) $[M+H]^+$ 307.2.

Intermediate 17: Ethyl 6-((3S,4s,5R)-4-hydroxy-3,5-dimethylpiperidin-1-yl)quinoline-4-carboxylate

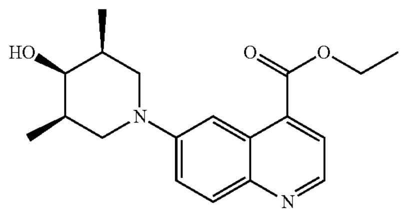 [SMILES: CCOC(=O)c1ccnc2ccc(N3C[C@@H](C)[C@@H](O)[C@@H](C)C3)cc12]

(3R,4s,5S)-3,5-Dimethylpiperidin-4-ol hydrochloride (50 mg, 0.30 mmol) was added to a mixture of ethyl 6-bromoquinoline-4-carboxylate (56 mg, 0.2 mmol), $Cs_2CO_3$ (0.195 g, 0.60 mmol), $Pd_2(dba)_3$ (9 mg, 0.01 mmol) and XPhos (9.5 mg, 0.02 mmol) in 1,4-dioxane (1 mL). The flask was sealed, purged with $N_2$ (g), and heated at 90° C. overnight. The mixture was diluted with EtOAc and washed with water. The organic phase was dried, filtered and evaporated. The residue was purified by straight phase flash chromatography on silica (gradient: 20-50% EtOAc in heptane) to give the title compound (20 mg, 30%) as a yellow semisolid; MS m/z (ESI) $[M+H]^+$ 329.2.

Intermediate 18: 6-((3S,4s,5R)-4-Hydroxy-3,5-dimethylpiperidin-1-yl)quinoline-4-carboxylic acid

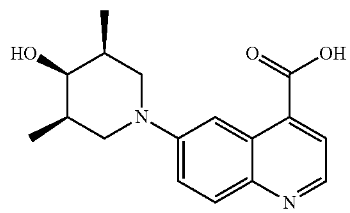 [SMILES: C[C@@H]1CN(c2ccc3nccc(C(=O)O)c3c2)C[C@H](C)[C@@H]1O]

Aq NaOH (1 M, 0.18 mL) was added to a solution of ethyl 6-((3S,4s,5R)-4-hydroxy-3,5-dimethylpiperidin-1-yl)quinoline-4-carboxylate Intermediate 17 (20 mg, 0.06 mmol) in MeOH (1 mL) and water (0.5 mL). The mixture was stirred at rt overnight. The mixture was neutralized with aq HCl (1 M,), and evaporated to give the title compound (18 mg, 98%) as a yellow-red semisolid; MS m/z (ESI) $[M+H]^+$ 301.2.

Intermediate 19: tert-Butyl 6-(4-methoxypiperidin-1-yl)quinoline-4-carboxylate

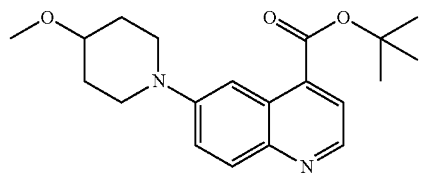 [SMILES: COC1CCN(c2ccc3nccc(C(=O)OC(C)(C)C)c3c2)CC1]

4-Methoxypiperidine (179 mg, 1.56 mmol) was added to tert-butyl 6-bromoquinoline-4-carboxylate (WO2019/154886) (400 mg, 1.30 mmol), $Cs_2CO_3$ (846 mg, 2.60 mmol), XPhos (124 mg, 0.26 mmol) and $Pd_2(dba)_3$ (119 mg, 0.13 mmol) in 1,4-dioxane (15 mL) at 15° C. under $N_2$ (g). The resulting mixture was stirred at 100° C. for 3 h. The reaction mixture was concentrated and the residue was dissolved in EtOAc (125 mL), and washed sequentially with water (75 mL) and sat brine (75 mL). The organic layer was dried over $Na_2SO_4$, filtered and evaporated. The residue was purified by preparative TLC (petroleum ether:EtOAc, 3:1) to afford the title compound (300 mg, 68%) as a yellow solid; MS m/z (ESI) $[M+H]^+$ 343.1.

Intermediate 20: 6-(4-Methoxypiperidin-1-yl)quinoline-4-carboxylic acid

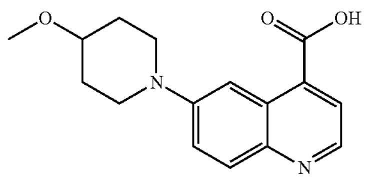 [SMILES: COC1CCN(c2ccc3nccc(C(=O)O)c3c2)CC1]

HCl (0.025 mL, 4 M in 1,4-dioxane) was added to tert-butyl 6-(4-methoxypiperidin-1-yl)quinoline-4-carboxylate Intermediate 19 (280 mg, 0.82 mmol) in 1,4-dioxane (15 mL) at 20° C. under air. The resulting mixture was stirred at 20° C. for 20 h. The precipitate was collected by filtration, washed with 1,4-dioxane (100 mL) and dried under vacuum to afford the title compound (200 mg, 85%) as a yellow solid; MS m/z (ESI) $[M+H]^+$ 287.1.

Intermediate 21: 6-Bromo-8-methylquinoline-2,4-dicarboxylic acid

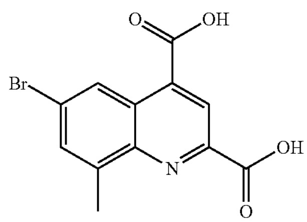 [SMILES: Cc1cc(Br)cc2c(C(=O)O)cc(C(=O)O)nc12]

5-Bromo-7-methylindoline-2,3-dione (500 mg, 2.08 mmol) was added to a solution of sodium 2-oxopropanoate (275 mg, 2.50 mmol) in aq NaOH (20%, 10 mL) in a microwave tube. The tube was sealed and heated at 110° C. for 1 h in a microwave reactor and then cooled to rt. The reaction mixture was acidified to pH 2 with aq HCl (2 M). The precipitate was collected by filtration, washed with water (100 mL) and dried under vacuum to give the title compound (550 mg, 85%) as a yellow solid; MS m/z (ESI) $[M+H]^+$ 309.9.

Intermediate 22: 6-Bromo-8-methylquinoline-4-carboxylic acid

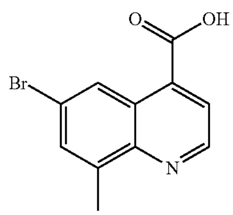

6-Bromo-8-methylquinoline-2,4-dicarboxylic acid Intermediate 21 (430 mg, 1.39 mmol) was dissolved in water (15 mL) in a steel reactor. The reactor was sealed, and heated at 190° C. for 6 h in an oil bath, and then cooled to rt. The precipitate was collected by filtration, washed with water (100 mL), and dried under vacuum to afford the title compound (233 mg, 63%) as a yellow solid; MS m/z (ESI) $[M+H]^+$ 265.9.

Intermediate 23: Methyl 6-bromo-8-methylquinoline-4-carboxylate

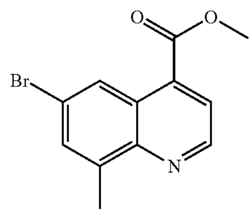 [SMILES: COC(=O)c1ccnc2c(C)cc(Br)cc12]

$SOCl_2$ (0.082 mL, 1.13 mmol) was added slowly to 6-bromo-8-methylquinoline-4-carboxylic acid Intermediate 22 (300 mg, 1.13 mmol) in MeOH (10 mL) at 15° C. under air. The resulting mixture was stirred at 60° C. for 16 h. The reaction mixture was concentrated, the residue was dissolved in DCM (100 mL), and washed sequentially with water (50 mL) and sat brine (50 mL). The organic layer was dried over $Na_2SO_4$, filtered, and evaporated. The crude product was purified by preparative TLC (DCM:MeOH, 40:1) to afford the title compound (250 mg, 79%) as a yellow solid; MS m/z (ESI) $[M+H]^+$ 279.9.

Intermediate 24: Methyl 8-methyl-6-morpholinoquinoline-4-carboxylate

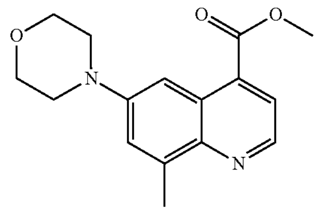 [SMILES: COC(=O)c1ccnc2c(C)cc(N3CCOCC3)cc12]

Morpholine (311 mg, 3.57 mmol) was added to a mixture of methyl 6-bromo-8-methylquinoline-4-carboxylate Intermediate 23 (200 mg, 0.71 mmol), $Cs_2CO_3$ (465 mg, 1.43 mmol), Pd Catalyst [CAS: 1810068-35-9] (82 mg, 0.07 mmol) in 1,4-dioxane (15 mL) at 20° C. under $N_2$ (g). The resulting mixture was heated at 100° C. for 5 h. The reaction mixture was concentrated and diluted with EtOAc (100 mL), and washed sequentially with water (50 mL) and sat brine (50 mL). The organic layer was dried over $Na_2SO_4$, filtered, and evaporated. The residue was purified by preparative TLC (petroleum ether:EtOAc, 5:1) to afford the title compound (190 mg, 93%) as a yellow solid; MS m/z (ESI) $[M+H]^+$ 287.0.

Intermediate 25: 8-Methyl-6-morpholinoquinoline-4-carboxylic acid

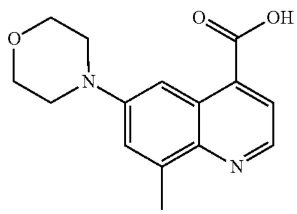 [SMILES: Cc1cc(N2CCOCC2)cc2c(C(=O)O)ccnc12]

A solution of NaOH (126 mg, 3.14 mmol) in water (3 mL) was added to a stirred solution of methyl 8-methyl-6-morpholinoquinoline-4-carboxylate Intermediate 24 (180 mg, 0.63 mmol) in MeOH (9 mL) at 20° C. The resulting mixture was stirred at 20° C. for 2 h. The reaction mixture was acidified to pH 5 with aq HCl (2 M). The reaction mixture was concentrated and diluted with EtOAc (125 mL), and washed sequentially with water (50 mL) and sat brine (50 mL). The organic layer was dried over $Na_2SO_4$, filtered and evaporated to afford the title compound (150 mg, 88%) as a red solid; MS m/z (ESI) $[M+H]^+$ 273.0.

Intermediate 26: 6-Bromo-7-methylquinoline-2,4-dicarboxylic acid

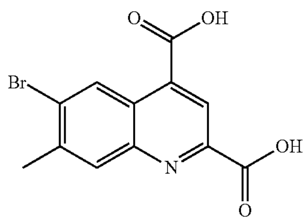 [SMILES: Cc1cc2nc(C(=O)O)cc(C(=O)O)c2cc1Br]

5-Bromo-7-methylindoline-2,3-dione (800 mg, 3.33 mmol) was added to sodium 2-oxopropanoate (440 mg, 4.00 mmol) in aq NaOH (20%, 15 mL) in a microwave reactor tube. The tube was sealed and heated at 110° C. for 1 h in a microwave reactor and then cooled to rt. The reaction mixture was acidified to pH 2 with aq HCl (2 M). The precipitate was collected by filtration, washed with water (50 mL), and dried under vacuum to afford the title compound (540 mg, 52%) as a brown solid; MS m/z (ESI) $[M+H]^+$ 309.9.

Intermediate 27: 6-Bromo-7-methylquinoline-4-carboxylic acid

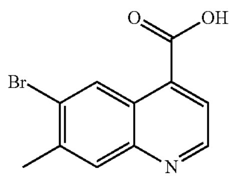

6-Bromo-7-methylquinoline-2,4-dicarboxylic acid Intermediate 26 (400 mg, 1.29 mmol) was dissolved in water (10 mL) in a steel reactor. The reactor was sealed, and heated at 190° C. for 6 h in an oil bath, and then cooled to rt. The precipitate was collected by filtration, washed with water (125 mL), and dried under vacuum to afford the title compound (200 mg, 58%) as a dark solid; MS m/z (ESI) $[M+H]^+$ 265.9.

Intermediate 28: Methyl 6-bromo-7-methylquinoline-4-carboxylate

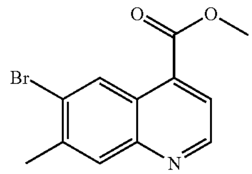 [SMILES: COC(=O)c1ccnc2cc(C)c(Br)cc12]

$SOCl_2$ (0.34 mL, 4.7 mmol) was added slowly to 6-bromo-7-methylquinoline-4-carboxylic acid Intermediate 27 (250 mg, 0.94 mmol) in MeOH (10 mL) at 15° C. under air. The resulting mixture was heated at 60° C. for 2 h. The reaction mixture was concentrated, the residue was diluted with DCM (75 mL), and washed sequentially with water (20 mL) and sat brine (20 mL). The organic layer was dried over $Na_2SO_4$, filtered, and evaporated. The residue was purified by preparative TLC (DCM:MeOH, 40:1) to afford the title compound (215 mg, 82%) as a yellow solid; MS m/z (ESI) $[M+H]^+$ 279.9.

Intermediate 29: Methyl 7-methyl-6-morpholinoquinoline-4-carboxylate

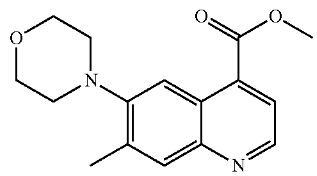 [SMILES: COC(=O)c1ccnc2cc(C)c(N3CCOCC3)cc12]

Morpholine (112 mg, 1.29 mmol) was added to methyl 6-bromo-7-methylquinoline-4-carboxylate Intermediate 28 (180 mg, 0.64 mmol), Pd Catalyst [CAS: 1810068-35-9] (73 mg, 0.06 mmol) and $Cs_2CO_3$ (419 mg, 1.29 mmol) in 1,4-dioxane (10 mL) at 15° C. under $N_2$ (g). The resulting mixture was heated at 100° C. for 16 h. The reaction mixture was filtered through filter paper and the filtrate was concentrated. The residue was diluted with EtOAc (100 mL), and washed sequentially with sat brine (25 mL) and water (25 mL). The organic layer was dried over $Na_2SO_4$, filtered, and evaporated. The residue was purified by preparative TLC (petroleum ether:EtOAc, 5:1) to afford the title compound (138 mg, 75%) as a yellow solid; MS m/z (ESI) $[M+H]^+$ 287.0.

Intermediate 30

7-Methyl-6-morpholinoquinoline-4-carboxylic acid

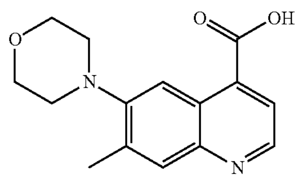 [SMILES: Cc1cc2nccc(C(=O)O)c2cc1N1CCOCC1]

NaOH (112 mg, 2.79 mmol) in water (3 mL) was added to a stirred solution of methyl 7-methyl-6-morpholinoquinoline-4-carboxylate Intermediate 29 (160 mg, 0.56 mmol) in MeOH (9 mL) at 16° C. under $N_2$ (g). The resulting mixture was stirred at 20° C. for 2 h. The reaction mixture was adjusted to pH 5 with aq HCl (2 M). The reaction mixture was concentrated, and the residue was dissolved in EtOAc (50 mL), and washed sequentially with sat brine (25 mL) and water (25 mL). The organic layer was dried over $Na_2SO_4$, filtered, and evaporated to afford the title compound (120 mg, 79%) as a yellow solid; MS m/z (ESI) $[M+H]^+$ 273.0.

Intermediate 31: tert-Butyl 6-(2-oxopyrrolidin-1-yl)quinoline-4-carboxylate

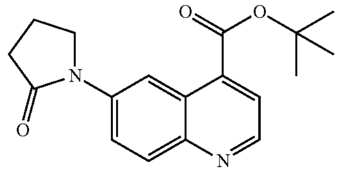 [SMILES: CC(C)(C)OC(=O)c1ccnc2ccc(N3CCCC3=O)cc12]

Pyrrolidin-2-one (57 mg, 0.67 mmol) was added to tert-butyl 6-bromoquinoline-4-carboxylate (160 mg, 0.52 mmol), $Cs_2CO_3$ (254 mg, 0.78 mmol) and XPhos Pd G3 (44 mg, 0.05 mmol) in 1,4-dioxane (5 mL) at 15° C. The resulting suspension was stirred at 100° C. for 2 h under $N_2$ (g). The reaction mixture was filtered through Celite®. The filtrate was concentrated under reduced pressure and the residue was purified by preparative TLC (EtOAc:petroleum ether, 2:1), to afford the title compound (160 mg, 99%) as a beige oil which solidified on standing; MS m/z (ESI) $[M+H]^+$ 313.15.

Intermediate 32: 6-(2-Oxopyrrolidin-1-yl)quinoline-4-carboxylic acid

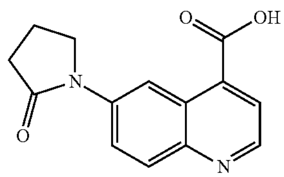 [SMILES: O=C(O)c1ccnc2ccc(N3CCCC3=O)cc12]

TFA (5 mL, 65 mmol) was added to a stirred solution of tert-butyl 6-(2-oxopyrrolidin-1-yl)quinoline-4-carboxylate Intermediate 31 (140 mg, 0.45 mmol) in DCM (5 mL) at 27° C. The resulting solution was stirred at 27° C. for 7 h. The solvent was removed under reduced pressure to afford the title compound (115 mg, 100%) as a yellow solid; MS m/z (ESI) $[M+H]^+$ 257.0.

Intermediate 33: tert-Butyl 6-(3,3-dimethyl-2-oxopyrrolidin-1-yl)quinoline-4-carboxylate

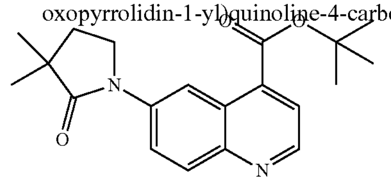

3,3-Dimethylpyrrolidin-2-one (132 mg, 1.17 mmol) was added to a mixture of tert-butyl 6-bromoquinoline-4-carboxylate (300 mg, 0.97 mmol), $Cs_2CO_3$ (634 mg, 1.95 mmol), $Pd_2(dba)_3$ (89 mg, 0.10 mmol) and XPhos (93 mg, 0.19 mmol) in 1,4-dioxane (15 mL) at 20° C. under $N_2$ (g). The resulting mixture was heated at 100° C. for 3 h. The reaction mixture was concentrated, diluted with EtOAc (100 mL), and washed sequentially with water (25 mL) and sat brine (25 mL). The organic layer was dried over $Na_2SO_4$, filtered, and evaporated. The residue was purified by preparative TLC (petroleum ether:EtOAc, 5:1) to afford the title compound (220 mg, 66%) as a yellow solid; MS m/z (ESI) $[M+H]^+$ 341.0.

Intermediate 34: 6-(3,3-Dimethyl-2-oxopyrrolidin-1-yl)quinoline-4-carboxylic acid

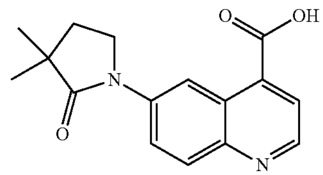 [SMILES: CC1(C)CCN(c2ccc3nccc(C(=O)O)c3c2)C1=O]

TFA (2 mL, 26 mmol) was added to tert-butyl 6-(3,3-dimethyl-2-oxopyrrolidin-1-yl)quinoline-4-carboxylate Intermediate 33 (200 mg, 0.59 mmol) in DCM (10 mL) at 20° C. under air. The resulting mixture was stirred at 20° C. for 3 h. The reaction mixture was concentrated, redissolved in DCM (50 mL), and washed with water (15 mL). The organic layer was dried over $Na_2SO_4$, filtered, and evaporated to afford crude product. The residue was purified by preparative TLC (DCM:MeOH, 10:1) to afford the title compound (120 mg, 72%) as a yellow solid; MS m/z (ESI) $[M+H]^+$ 285.0.

Intermediate 35: tert-Butyl 6-(5,5-dimethyl-2-oxooxazolidin-3-yl)quinoline-4-carboxylate

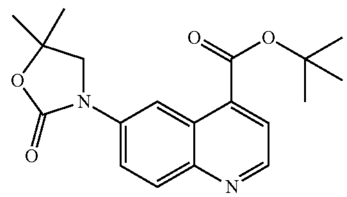 [SMILES: CC(C)(C)OC(=O)c1ccnc2ccc(N3CC(C)(C)OC3=O)cc12]

5,5-Dimethyloxazolidin-2-one (134 mg, 1.17 mmol) was added to a mixture of tert-butyl 6-bromoquinoline-4-carboxylate (300 mg, 0.97 mmol), $Cs_2CO_3$ (634 mg, 1.95 mmol), $Pd_2(dba)_3$ (89 mg, 0.10 mmol) and XPhos (93 mg, 0.19 mmol) in 1,4-dioxane (10 mL) at 20° C. under $N_2$ (g). The resulting mixture was stirred at 100° C. for 3 h. The reaction mixture was concentrated, and redissolved in EtOAc (100 mL), and washed sequentially with water (20 mL) and sat brine (20 mL). The organic layer was dried over $Na_2SO_4$, filtered and evaporated to afford crude product. The residue was purified by preparative TLC (EtOAc: petroleum ether, 1:5) to afford the title compound (240 mg, 72%) as a yellow solid; MS m/z (ESI) $[M+H]^+$ 343.1.

Intermediate 36: 6-(5,5-Dimethyl-2-oxooxazolidin-3-yl)quinoline-4-carboxylic acid

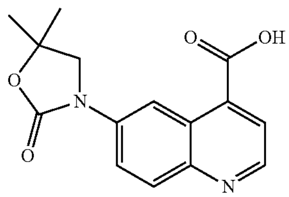 [SMILES: CC1(C)CN(c2ccc3nccc(C(=O)O)c3c2)C(=O)O1]

HCl (4 M in 1,4-dioxane) (10 mL) was added to tert-butyl 6-(5,5-dimethyl-2-oxooxazolidin-3-yl)quinoline-4-carboxylate Intermediate 35 (220 mg, 0.64 mmol) at 20° C. under air. The resulting mixture was stirred at 40° C. for 6 h. The reaction mixture was concentrated, the residue was dissolved in EtOAc (50 mL), and washed with water (20 mL). The organic layer was dried over $Na_2SO_4$, filtered, and evaporated to afford the title compound (150 mg, 82%) as a yellow solid; MS m/z (ESI) $[M+H]^+$ 287.0.

Intermediate 37: tert-Butyl 6-(2-oxopiperidin-1-yl)quinoline-4-carboxylate

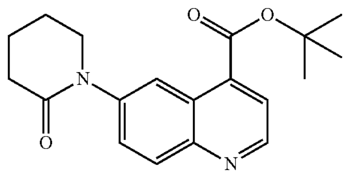 [SMILES: CC(C)(C)OC(=O)c1ccnc2ccc(N3CCCCC3=O)cc12]

Piperidin-2-one (575 mg, 5.80 mmol) was added to tert-butyl 6-bromoquinoline-4-carboxylate (500 mg, 1.45 mmol), $Cs_2CO_3$ (945 mg, 2.90 mmol), $Pd_2(dba)_3$ (13 mg, 0.01 mmol) and XPhos (14 mg, 0.03 mmol) in 1,4-dioxane (20 mL) at 15° C. The resulting suspension was stirred at 100° C. for 15 h under $N_2$ (g). The reaction mixture was filtered through Celite®. The solvent was removed under reduced pressure. The residue was purified by preparative TLC (petroleum ether:EtOAc, 4:1) to afford the title compound (132 mg, 28%) as a brown solid; MS m/z (ESI) $[M+H]^+$ 327.2.

Intermediate 38: 6-(2-Oxopiperidin-1-yl)quinoline-4-carboxylic acid

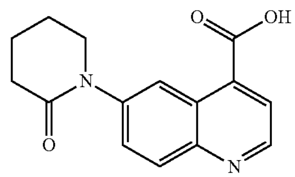 [SMILES: O=C(O)c1ccnc2ccc(N3CCCCC3=O)cc12]

TFA (0.11 mL, 1.5 mmol) was added to a solution of tert-butyl 6-(2-oxopiperidin-1-yl)quinoline-4-carboxylate Intermediate 37 (120 mg, 0.37 mmol) in DCM (2 mL). The resulting solution was stirred at 25° C. for 6 h. The solvent was removed under reduced pressure afford the title compound (130 mg) as a brown solid; MS m/z (ESI) $[M+H]^+$ 271.15.

Intermediate 39: tert-Butyl 6-(3,3-dimethyl-2-oxopiperidin-1-yl)quinoline-4-carboxylate

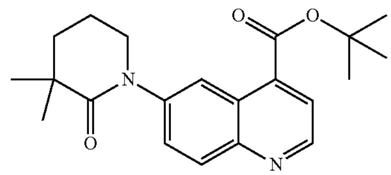

3,3-Dimethylpiperidin-2-one (825 mg, 6.49 mmol) was added to a mixture of tert-butyl 6-bromoquinoline-4-carboxylate (500 mg, 1.62 mmol), $Cs_2CO_3$ (793 mg, 2.43 mmol), $Pd_2(dba)_3$ (15 mg, 0.02 mmol), and XPhos (15 mg, 0.03 mmol) in 1,4-dioxane (15 mL) under $N_2$ (g). The resulting suspension was stirred at 100° C. for 24 h. The reaction mixture was filtered through silica. The solvent was removed under reduced pressure. The residue was purified by preparative TLC (petroleum ether:EtOAc, 2:1) to afford the title compound (80 mg, 14%) as a brown solid. MS m/z (ESI) $[M+H]^+$ 355.2.

Intermediate 40: 6-(3,3-Dimethyl-2-oxopiperidin-1-yl)quinoline-4-carboxylic acid

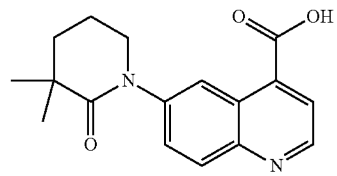 [SMILES: CC1(C)CCCN(c2ccc3nccc(C(=O)O)c3c2)C1=O]

TFA (0.061 mL, 0.79 mmol) was added to a solution of tert-butyl 6-(3,3-dimethyl-2-oxopiperidin-1-yl)quinoline-4-carboxylate Intermediate 39 (70 mg, 0.20 mmol) in DCM (2 mL). The resulting solution was stirred at 25° C. for 6 h. The solvent was removed under reduced pressure to afford the title compound (60 mg, 100%) as a brown solid; MS m/z (ESI) $[M+H]^+$ 299.15.

Intermediate 41: tert-Butyl 6-(2,2-dimethyl-3-oxo-morpholino)quinoline-4-carboxylate

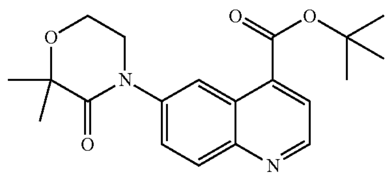 [SMILES: CC(C)(C)OC(=O)c1ccnc2ccc(N3CCOC(C)(C)C3=O)cc12]

2,2-Dimethylmorpholin-3-one (122 mg, 0.94 mmol) was added to a mixture of tert-butyl 6-bromoquinoline-4-carboxylate (291 mg, 0.94 mmol), $Cs_2CO_3$ (616 mg, 1.89 mmol), $Pd_2(dba)_3$ (86 mg, 0.09 mmol) and CPhos (82 mg, 0.19 mmol) in 1,4-dioxane (1 mL) at 25° C. The resulting suspension was stirred at 100° C. for 2 h. The reaction mixture was extracted with DCM (3×100 mL). The organic phases were combined and washed with sat brine (2×60 mL). The organic layer was dried over $Na_2SO_4$, filtered and concentrated under reduced pressure. The residue was purified by preparative TLC (petroleum ether:EtOAc, 1:2) to afford the title compound (299 mg, 89%) as a yellow solid; MS m/z (ESI) $[M+H]^+$ 357.2.

Intermediate 42: 6-(2,2-Dimethyl-3-oxomorpholino)quinoline-4-carboxylic acid

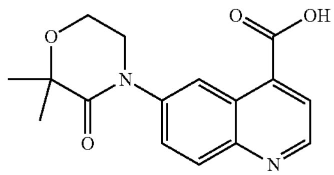 [SMILES: CC1(C)OCCN(c2ccc3nccc(C(=O)O)c3c2)C1=O]

HCl (4 M in 1,4-dioxane, 10 mL) was added to tert-butyl 6-(5,5-dimethyl-2-oxooxazolidin-3-yl)quinoline-4-carboxylate Intermediate 41 (289 mg, 0.84 mmol) at 20° C. under air. The resulting mixture was stirred at 40° C. for 12 h. The solvent was removed under reduced pressure to afford the title compound (315 mg) as a tan solid; MS m/z (ESI) $[M+H]^+$ 301.1.

Intermediate 43: tert-Butyl 6-(2-azaspiro[3.3]heptan-2-yl)quinoline-4-carboxylate

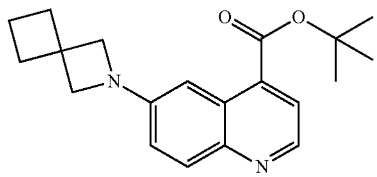 [SMILES: CC(C)(C)OC(=O)c1ccnc2ccc(N3CC4(CCC4)C3)cc12]

2-Azaspiro[3.3]heptane hydrochloride (347 mg, 2.60 mmol) was added to tert-butyl 6-bromoquinoline-4-carboxylate (400 mg, 1.30 mmol), $Cs_2CO_3$ (1.69 g, 5.19 mmol), $Pd_2(dba)_3$ (119 mg, 0.13 mmol), and XPhos (124 mg, 0.26 mmol) in 1,4-dioxane (10 mL) at 10° C. The resulting suspension was stirred at 100° C. for 3 h under $N_2$ (g). The solvent was removed under reduced pressure. The residue was purified by preparative TLC (petroleum ether:EtOAc, 2:1) to afford the title compound (150 mg, 36%) as a yellow solid. MS m/z (ESI) $[M+H]^+$ 325.3.

Intermediate 44: 6-(2-Azaspiro[3.3]heptan-2-yl)quinoline-4-carboxylic acid

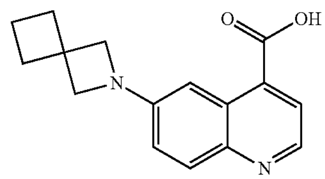 [SMILES: O=C(O)c1ccnc2ccc(N3CC4(CCC4)C3)cc12]

TFA (53 mg, 0.46 mmol) was added to a solution of tert-butyl 6-(2-azaspiro[3.3]heptan-2-yl)quinoline-4-carboxylate Intermediate 43 (150 mg, 0.46 mmol) in 1,4-dioxane (3 mL), and stirred at 25° C. overnight. The solvent was removed under reduced pressure to give the title compound; MS m/z (ESI) $[M+H]^+$ 269.1.

Intermediate 45: tert-Butyl 6-(3,3-dimethyl-1-oxa-6-azaspiro[3.3]heptan-6-yl)quinoline-4-carboxylate

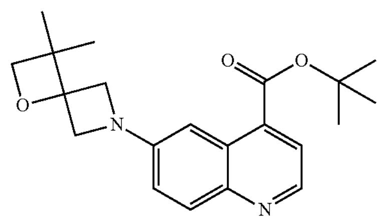 [SMILES: CC(C)(C)OC(=O)c1ccnc2ccc(N3CC4(C3)OCC4(C)C)cc12]

3,3-Dimethyl-1-oxa-6-azaspiro[3.3]heptane hydrochloride (223 mg, 1.36 mmol) was added to tert-butyl 6-bromoquinoline-4-carboxylate (280 mg, 0.91 mmol), $Cs_2CO_3$ (888 mg, 2.73 mmol) and Pd Catalyst [CAS: 1810068-35-9] (52 mg, 0.05 mmol) in 1,4-dioxane (15 mL) at 25° C. The resulting suspension was stirred at 100° C. for 4 h under $N_2$ (g). The solid was filtered off. The filtrate was concentrated under reduced pressure. The residue was purified by preparative TLC (petroleum ether:EtOAc, 2:1) to afford the title compound (200 mg, 62%) as a yellow solid; MS m/z (ESI) $[M+H]^+$ 355.2.

Intermediate 46: 6-(3,3-Dimethyl-1-oxa-6-azaspiro[3.3]heptan-6-yl)quinoline-4-carboxylic acid

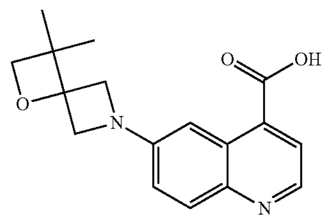 [SMILES: CC1(C)COC12CN(c1ccc3nccc(C(=O)O)c3c1)C2]

TFA (3 mL) was added to a solution of tert-butyl 6-(3,3-dimethyl-1-oxa-6-azaspiro[3.3]heptan-6-yl)quinoline-4-carboxylate Intermediate 45 (200 mg, 0.56 mmol) in DCM (6 mL). The reaction was stirred at rt for 15 h. The solvent was removed under reduced pressure, and the residue was dried under vacuum to give the title compound (168 mg, 100%) as a yellow solid; MS m/z (ESI) $[M+H]^+$ 299.2.

Intermediate 47: Methyl 6-(1-azaspiro[3.3]heptan-1-yl)quinoline-4-carboxylate

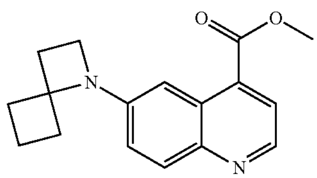 [SMILES: COC(=O)c1ccnc2ccc(N3CCC34CCC4)cc12]

1-Azaspiro[3.3]heptane hydrochloride (301 mg, 2.25 mmol) was added to a mixture of methyl 6-bromoquinoline-4-carboxylate (300 mg, 1.13 mmol), $Pd_2(dba)_3$ (103 mg, 0.11 mmol), XPhos (161 mg, 0.34 mmol) and $Cs_2CO_3$ (1.10 g, 3.38 mmol) in 1,4-dioxane (15 mL) under $N_2$ (g). The reaction was stirred at 100° C. for 15 h. The solid was filtered off. The filtrate was concentrated under reduced pressure. The residue was purified by preparative TLC (petroleum ether:EtOAc, 1:1) to afford the title compound (250 mg, 79%) as a yellow solid; MS m/z (ESI) $[M+H]^+$ 283.2.

Intermediate 48: 6-(1-Azaspiro[3.3]heptan-1-yl) quinoline-4-carboxylic acid

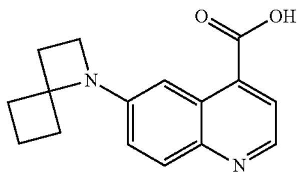 [SMILES: O=C(O)c1ccnc2ccc(N3CCC34CCC4)cc12]

LiOH (106 mg, 4.43 mmol) was added to a solution of methyl 6-(1-azaspiro[3.3]heptan-1-yl)quinoline-4-carboxylate Intermediate 47 (250 mg, 0.89 mmol) in MeOH (10 mL) and water (2 mL). The reaction was stirred at rt for 5 h. The solvent was removed under reduced pressure. The residue was diluted with water and adjusted to pH 6 with citric acid. The reaction mixture was extracted with EtOAc, and the organic phases were washed with water. The organic layer was dried over $Na_2SO_4$, filtered and evaporated to afford the title compound (215 mg, 90%) as an orange solid; MS m/z (ESI) $[M+H]^+$ 269.2.

Intermediate 49: Methyl 6-(2,2-dimethylazetidin-1-yl)quinoline-4-carboxylate

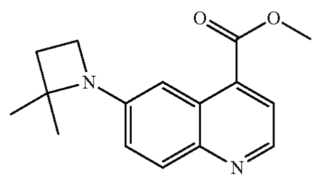

2,2-Dimethylazetidine hydrochloride (147 mg, 1.21 mmol) was added to a mixture of methyl 6-bromoquinoline-4-carboxylate (215 mg, 0.81 mmol), $Cs_2CO_3$ (1.05 g, 3.23 mmol) and RuPhos Pd G3 (68 mg, 0.08 mmol) in 1,4-dioxane (5 mL) at 5° C. The resulting suspension was stirred at 100° C. for 2 h under $N_2$ (g). The reaction mixture was diluted with EtOAc (10 mL) and filtered through Celite®. The filter pad was washed with EtOAc, and the filtrate was concentrated under reduced pressure. The residue was purified by preparative TLC (petroleum ether:EtOAc, 1:1) to afford the title compound (196 mg, 90%) as a brown gum; MS m/z (ESI) $[M+H]^+$ 271.2.

Intermediate 50: 6-(2,2-Dimethylazetidin-1-yl)quinoline-4-carboxylic acid

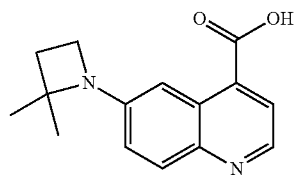 [SMILES: CC1(C)CCN1c1ccc2nccc(C(=O)O)c2c1]

NaOH (96 mg, 2.4 mmol) in water (2 mL) was added slowly to a stirred solution of methyl 6-(2,2-dimethylazetidin-1-yl)quinoline-4-carboxylate Intermediate 49 (130 mg, 0.48 mmol) in MeOH (6 mL) cooled to 0° C. The resulting solution was stirred at 10° C. for 2 h. The reaction mixture was diluted with water (20 mL) and acidified with aq HCl (1 M). The mixture was extracted with EtOAc (5×75 mL). The organic layers were combined and washed with water (4×25 mL). The aqueous layers were combined and extracted with EtOAc (4×25 mL). All organic layers were combined, dried over $Na_2SO_4$, filtered and evaporated to afford the title compound (120 mg, 97%) as a yellow solid; MS m/z (ESI) $[M+H]^+$ 257.2.

Intermediate 51: Methyl 6-(3-fluoroazetidin-1-yl)quinoline-4-carboxylate

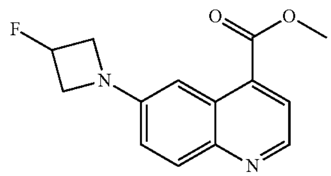 [SMILES: COC(=O)c1ccnc2ccc(N3CC(F)C3)cc12]

3-Fluoroazetidine hydrochloride (252 mg, 2.25 mmol) was added to a mixture of methyl 6-bromoquinoline-4-carboxylate (300 mg, 1.13 mmol), $Cs_2CO_3$ (1.10 mg, 3.38 mmol), $Pd_2(dba)_3$ (103 mg, 0.11 mmol) and XPhos (161 mg, 0.34 mmol) in 1,4-dioxane (20 mL) was stirred at 100° C. for 2 h. The precipitate was collected by filtration, washed with MeOH, and dried under vacuum. The residue was purified by preparative TLC (petroleum ether:EtOAc, 1:1) to afford the title compound (180 mg, 61%) as a yellow solid; MS m/z (ESI) $[M+H]^+$ 261.0.

Intermediate 52: 6-(3-Fluoroazetidin-1-yl)quinoline-4-carboxylic acid

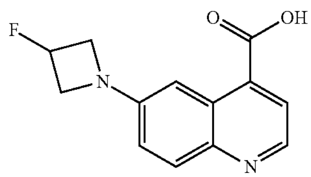 [SMILES: O=C(O)c1ccnc2ccc(N3CC(F)C3)cc12]

LiOH (83 mg, 3.5 mmol) was added to a solution of methyl 6-(3-fluoroazetidin-1-yl)quinoline-4-carboxylate Intermediate 51 (180 mg, 0.69 mmol) in MeOH (10 mL) and water (2 mL). The reaction was stirred at rt for 2 h. The reaction mixture was adjusted to pH 5 with aq HCl (1 M). The reaction mixture was diluted with water, and extracted with EtOAc. The organic layer was dried over $Na_2SO_4$, filtered and evaporated to give the title compound (150 mg, 88%) as a yellow solid; MS m/z (ESI) $[M+H]^+$ 247.1.

Intermediate 53: Methyl 6-(3,3-dimethylazetidin-1-yl)quinoline-4-carboxylate

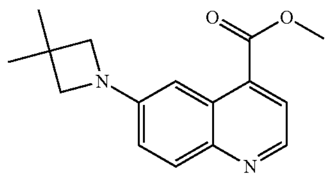

3,3-Dimethylazetidine hydrochloride (274 mg, 2.25 mmol) was added to a mixture of methyl 6-bromoquinoline-4-carboxylate (300 mg, 1.13 mmol), $Cs_2CO_3$ (1.10 mg, 3.38 mmol), $Pd_2(dba)_3$ (103 mg, 0.11 mmol) and XPhos (161 mg, 0.34 mmol) in 1,4-dioxane (20 mL). The mixture was stirred at 100° C. for 4 h under $N_2$ (g). The precipitate was collected by filtration, washed with MeOH and dried under vacuum to afford the crude product, which was purified by preparative TLC (petroleum ether:EtOAc, 1:1) to afford the title compound (200 mg, 66%) as a yellow solid; MS m/z (ESI) $[M+H]^+$ 271.10.

Intermediate 54: 6-(3,3-Dimethylazetidin-1-yl)quinoline-4-carboxylic acid

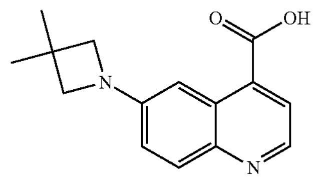 [SMILES: CC1(C)CN(c2ccc3nccc(C(=O)O)c3c2)C1]

LiOH (89 mg, 3.7 mmol) was added to a solution of methyl 6-(3,3-dimethylazetidin-1-yl)quinoline-4-carboxylate Intermediate 53 (200 mg, 0.74 mmol) MeOH (10 mL) and water (2 mL). The reaction was stirred at rt for 2 h, and then adjusted to pH 5 with aq HCl (1 M). The reaction mixture was diluted with EtOAc, and washed with water. The organic layer was dried over $Na_2SO_4$, filtered and evaporated to afford the title compound (180 mg, 95%) as a yellow solid; MS m/z (ESI) $[M+H]^+$ 257.2.

Intermediate 55: Methyl 6-(3,3-difluoroazetidin-1-yl)quinoline-4-carboxylate

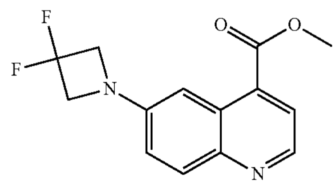 [SMILES: COC(=O)c1ccnc2ccc(N3CC(F)(F)C3)cc12]

3,3-Difluoroazetidine hydrochloride (294 mg, 2.27 mmol) was added to a mixture of methyl 6-bromoquinoline-4-carboxylate (302 mg, 1.13 mmol), $Cs_2CO_3$ (1.11 g, 3.40 mmol), $Pd_2(dba)_3$ (104 mg, 0.11 mmol) and XPhos (108 mg, 0.23 mmol) in 1,4-dioxane (3 mL) at 10° C. The resulting suspension was stirred at 100° C. for 2 h under $N_2$ (g). The reaction mixture was diluted with water (50 mL), and extracted with EtOAc (3×50 mL). The organic phases were combined and washed with sat brine (150 mL). The organic layer was dried over $Na_2SO_4$, filtered and evaporated. The residue was purified by preparative TLC (petroleum ether: EtOAc, 1:1) to afford the title compound (313 mg, 99%) as a brown solid; MS m/z (ESI) $[M+H]^+$ 279.2.

Intermediate 56: 6-(3,3-Difluoroazetidin-1-yl)quinoline-4-carboxylic acid

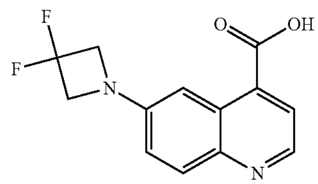 [SMILES: O=C(O)c1ccnc2ccc(N3CC(F)(F)C3)cc12]

NaOH (224 mg, 5.61 mmol) was added to methyl 6-(3,3-difluoroazetidin-1-yl)quinoline-4-carboxylate Intermediate 55 (312 mg, 1.12 mmol) in MeOH (3 mL) and water (1 mL) at 10° C. The resulting solution was stirred at 10° C. for 1 h under $N_2$ (g). The solvent was removed under reduced pressure. The reaction mixture was diluted with water (50 mL), adjusted to pH 5 with aq HCl (1 M), and extracted with EtOAc (6×50 mL). The combined organic phases were dried over $Na_2SO_4$, filtered and evaporated. The crude product was purified by preparative HPLC PrepMethod F (gradient: 0-50%) to afford the title compound (127 mg, 43%) as a yellow solid; MS m/z (ESI) $[M+H]^+$ 265.2.

Intermediate 57: Methyl 6-(3-fluoro-3-methylazetidin-1-yl)quinoline-4-carboxylate

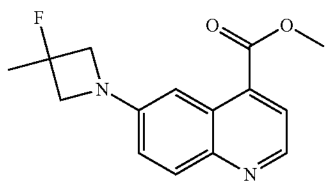

3-Fluoro-3-methylazetidine hydrochloride (176 mg, 1.40 mmol) was added to a mixture of methyl 6-bromoquinoline-4-carboxylate (212 mg, 0.70 mmol), $Cs_2CO_3$ (685 mg, 2.10 mmol), $Pd_2(dba)_3$ (64 mg, 0.07 mmol) and XPhos (67 mg, 0.14 mmol) in 1,4-dioxane (3 mL) at 10° C. The resulting suspension was stirred at 100° C. for 2 h under $N_2$ (g). The reaction mixture was diluted with DCM. The solvents were removed under reduced pressure. The residue was suspended in water (5 mL), and extracted with EtOAc (3×20 mL). The organic layers were combined and was washed with brine (20 mL), the organic phase was dried over $Na_2SO_4$, filtered and evaporated. The residue was purified by preparative TLC (petroleum ether:EtOAc, 1:1) to afford the title compound (153 mg, 80%) as a brown gum; MS m/z (ESI) $[M+H]^+$ 275.0.

Intermediate 58: 6-(3-Fluoro-3-methylazetidin-1-yl)quinoline-4-carboxylic acid

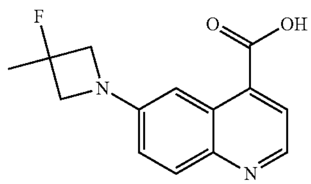 [SMILES: CC1(F)CN(c2ccc3nccc(C(=O)O)c3c2)C1]

NaOH (112 mg, 2.79 mmol) was added to methyl 6-(3-fluoro-3-methylazetidin-1-yl)quinoline-4-carboxylate Intermediate 57 (153 mg, 0.56 mmol) in MeOH (3 mL) and water (1 mL) at 5° C. The resulting solution was stirred at 5° C. for 1 h under $N_2$ (g). The solvent was removed under reduced pressure. The reaction mixture was diluted with water and adjusted to pH 5 with aq HCl (1 M). The mixture was diluted with water (10 mL) and extracted with EtOAc (25 mL). The combined organic layers were dried over $Na_2SO_4$, filtered and evaporated. The crude product was purified by preparative HPLC PrepMethod F (gradient: 0-50%) to afford the title compound (88 mg, 61%) as an orange solid; MS m/z (ESI) $[M+H]^+$ 261.2.

Intermediate 59: tert-Butyl 6-(3-methylazetidin-1-yl)quinoline-4-carboxylate

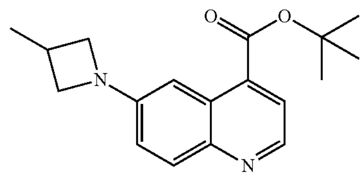 [SMILES: CC1CN(c2ccc3nccc(C(=O)OC(C)(C)C)c3c2)C1]

3-Methylazetidine (102 mg, 1.43 mmol) was added to a mixture of tert-butyl 6-bromoquinoline-4-carboxylate (400 mg, 1.30 mmol), $Cs_2CO_3$ (1.06 g, 3.24 mmol), $Pd_2(dba)_3$ (119 mg, 0.13 mmol) and DavePhos (102 mg, 0.26 mmol) in 1,4-dioxane (2 mL). The resulting mixture was heated at 100° C. for 3 h under $N_2$ (g). The reaction mixture was filtered through Celite®, and the filtrate was concentrated under reduced pressure. The residue was purified by preparative TLC (petroleum ether:EtOAc, 3:1) to afford the title compound (350 mg, 90%) as a yellow solid; MS m/z (ESI) $[M+H]^+$ 299.3.

Intermediate 60: 6-(3-Methylazetidin-1-yl)quinoline-4-carboxylic acid

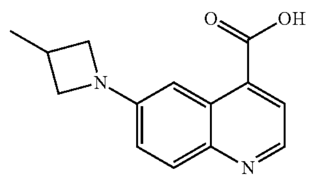 [SMILES: CC1CN(c2ccc3nccc(C(=O)O)c3c2)C1]

TFA (4.5 mL) was added to tert-butyl 6-(3-methylazetidin-1-yl)quinoline-4-carboxylate Intermediate 59 (300 mg, 1.01 mmol) in DCM (9 mL). The resulting mixture was stirred at 40° C. for 3 h. The solvents were removed under reduced pressure to give the title compound (200 mg, 82%) as a violet solid; MS m/z (ESI) $[M+H]^+$ 243.2.

Intermediate 61: tert-Butyl 6-(3-(trifluoromethyl)azetidin-1-yl)quinoline-4-carboxylate

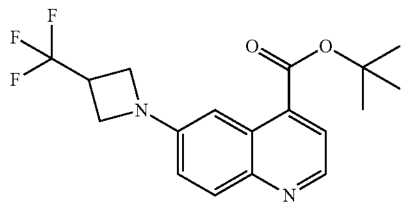 [SMILES: CC(C)(C)OC(=O)c1ccnc2ccc(N3CC(C(F)(F)F)C3)cc12]

3-(Trifluoromethyl)azetidine (112 mg, 0.89 mmol) was added to a mixture of tert-butyl 6-bromoquinoline-4-carboxylate (250 mg, 0.81 mmol), $Cs_2CO_3$ (661 mg, 2.03 mmol), XPhos (77 mg, 0.16 mmol) and $Pd_2(dba)_3$ (74 mg, 0.08 mmol) in 1,4-dioxane (2 mL). The resulting mixture was heated at 100° C. for 3 h under $N_2$ (g). The reaction mixture was filtered through Celite®, and the filtrate was concentrated under reduced pressure. The residue was purified by preparative TLC (petroleum ether:EtOAc, 1:1) to afford the title compound (180 mg, 63%) as a yellow oil; MS m/z (ESI) $[M+H]^+$ 253.2.

Intermediate 62: 6-(3-(Trifluoromethyl)azetidin-1-yl)quinoline-4-carboxylic acid

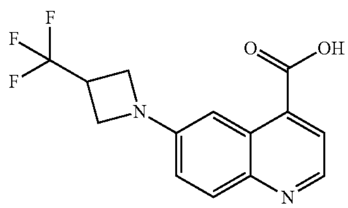 [SMILES: O=C(O)c1ccnc2ccc(N3CC(C(F)(F)F)C3)cc12]

TFA (42 mg, 0.37 mmol) was added to tert-butyl 6-(3-(trifluoromethyl)azetidin-1-yl)quinoline-4-carboxylate Intermediate 61 (130 mg, 0.37 mmol) in DCM (1.5 mL). The resulting mixture was heated at 60° C. for 5 h. The solvent was removed under reduced pressure to give the title compound (100 mg, 91%) as a violet solid; MS m/z (ESI) $[M+H]^+$ 297.1.

Intermediate 63: tert-Butyl 6-(3-(fluoromethyl)-3-methylazetidin-1-yl)quinoline-4-carboxylate

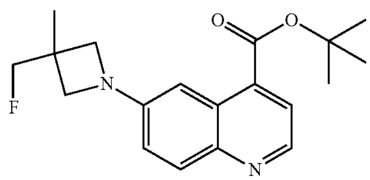 [SMILES: CC1(CF)CN(c2ccc3nccc(C(=O)OC(C)(C)C)c3c2)C1]

KOtBu (336 mg, 3.00 mmol) was added to tert-butyl 6-bromoquinoline-4-carboxylate (308 mg, 1.00 mmol), 3-(fluoromethyl)-3-methylazetidine (206 mg, 2.00 mmol), $Pd(OAc)_2$ (150 mg, 0.67 mmol), and XantPhos (300 mg, 0.52 mmol) in 1,4-dioxane (3 mL) at 10° C. The resulting suspension was stirred at 100° C. for 2 h under $N_2$ (g). The reaction mixture was diluted with DCM. The solvent was removed under reduced pressure. The residue was purified by preparative TLC (petroleum ether: EtOAc, 1:1) to afford the title compound (147 mg, 44%) as a brown gum; MS m/z (ESI) $[M+H]^+$ 331.3.

Intermediate 64: 6-(3-(Fluoromethyl)-3-methylazetidin-1-yl)quinoline-4-carboxylic acid

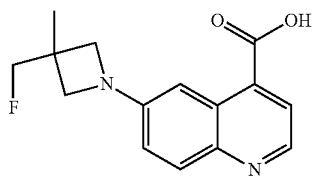 [SMILES: CC1(CF)CN(c2ccc3nccc(C(=O)O)c3c2)C1]

TFA (3 mL) was added to tert-butyl 6-(3-(fluoromethyl)-3-methylazetidin-1-yl)quinoline-4-carboxylate Intermediate 63 (147 mg, 0.44 mmol) in DCM (3 mL) at 10° C. The resulting solution was stirred at 10° C. overnight under $N_2$ (g). The solvent was removed under reduced pressure to afford the title compound (298 mg) as a red gum; MS m/z (ESI) $[M+H]^+$ 275.05.

Intermediate 65: tert-Butyl 6-3-(difluoromethyl)azetidin-1-yl)quinoline-4-carboxylate

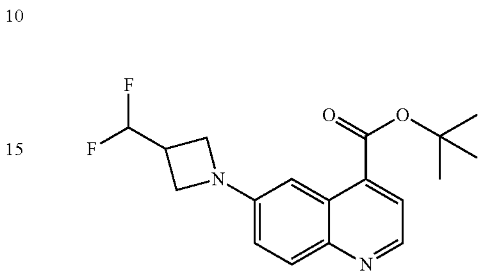

$Pd_2(dba)_3$ (149 mg, 0.16 mmol) was added to 3-(difluoromethyl)azetidine (191 mg, 1.78 mmol), tert-butyl 6-bromoquinoline-4-carboxylate (500 mg, 1.62 mmol), $Cs_2CO_3$ (1.06 g 3.24 mmol) and XPhos (155 mg, 0.32 mmol) in 1,4-dioxane (10 mL) at 25° C. under $N_2$ (g). The resulting mixture was stirred at 100° C. for 5 h. The reaction mixture was concentrated, and the residue was dissolved in EtOAc (125 mL), and washed sequentially with sat brine (75 mL) and water (75 mL). The organic layer was dried over $Na_2SO_4$, filtered and evaporated. The residue was purified by preparative TLC (petroleum ether:EtOAc, 3:1) to afford the title compound (380 mg, 70%) as a yellow solid; MS m/z (ESI) $[M+H]^+$ 335.05.

Intermediate 66: 6-(3-(Difluoromethyl)azetidin-1-yl)quinoline-4-carboxylic acid

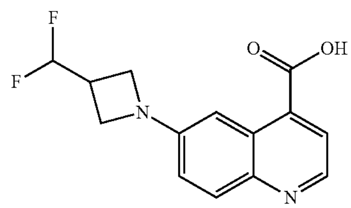 [SMILES: O=C(O)c1ccnc2ccc(N3CC(C(F)F)C3)cc12]

TFA (0.17 mL, 2.2 mmol) was added to tert-butyl 6-(3-(difluoromethyl)azetidin-1-yl)quinoline-4-carboxylate Intermediate 65 (250 mg, 0.75 mmol) in DCM (5 mL) at 20° C. under air. The resulting mixture was stirred at 25° C. for 16 h. The reaction mixture was concentrated and diluted with DCM (100 mL), and washed sequentially with sat $NaHCO_3$ (25 mL), sat brine (25 mL), and water (25 mL). The organic layer was dried over $Na_2SO_4$, filtered and evaporated. The residue was purified by preparative TLC (DCM:MeOH, 5:1) to afford the title compound (150 mg, 72%) as a yellow solid. MS m/z (ESI) $[M+H]^+$ 279.2.

Intermediate 67: Ethyl 6-(3-(methoxymethyl)-3-methylazetidin-1-yl)quinoline-4-carboxylate

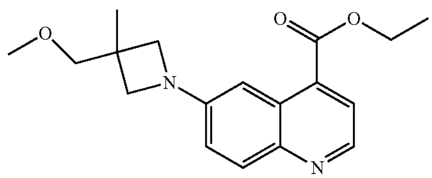 [SMILES: CCOC(=O)c1ccnc2ccc(N3CC(C)(COC)C3)cc12]

3-(Methoxymethyl)-3-methylazetidine hydrochloride (108 mg, 0.71 mmol) was added to a mixture of ethyl 6-bromoquinoline-4-carboxylate (100 mg, 0.36 mmol), $Cs_2CO_3$ (465 mg, 1.43 mmol), XPhos (34 mg, 0.07 mmol) and $Pd_2(dba)_3$ (33 mg, 0.04 mmol) in 1,4-dioxane (2 mL). The vial was sealed, purged with $N_2$ (g), and the reaction was heated at 100° C. for 2 h. After cooling to rt, water (10 mL) and DCM (10 mL) were added, the mixture was stirred, filtered through a phase separator. The phase separator was rinsed with more DCM and evaporated. The residue was purified by straight phase flash chromatography on silica (gradient: 5-50% EtOAc in heptane) to give the title compound (87 mg, 78%); MS m/z (ESI) $[M+H]^+$ 315.3.

Intermediate 68: 6-(3-(Methoxymethyl)-3-methylazetidin-1-yl)quinoline-4-carboxylic acid

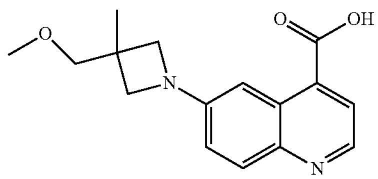 [SMILES: COCC1(C)CN(c2ccc3nccc(C(=O)O)c3c2)C1]

Aq NaOH (1 M, 0.51 mL) was added to ethyl 6-(3-(methoxymethyl)-3-methylazetidin-1-yl)quinoline-4-carboxylate Intermediate 67 (80 mg, 0.25 mmol) in MeOH (2 mL). The reaction was stirred at 50° C. for 20 min, then cooled to rt. Aq HCl (3.8 M, mL) was added, the mixture stirred, then evaporated to give the title compound (73 mg, 100%); MS m/z (ESI) $[M+H]^+$ 287.3.

Intermediate 69: tert-Butyl 6-((2S,3R)-3-methoxy-2-methylazetidin-1-yl)quinoline-4-carboxylate

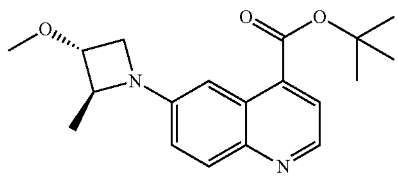 [SMILES: CO[C@@H]1CN(c2ccc3nccc(C(=O)OC(C)(C)C)c3c2)[C@H]1C]

(2S,3R)-3-Methoxy-2-methylazetidine oxalate (285 mg, 1.95 mmol) was added to a mixture of tert-butyl 6-bromoquinoline-4-carboxylate (300 mg, 0.97 mmol), $Cs_2CO_3$ (1.27 mg, 3.89 mmol) and Pd Catalyst [CAS: 1810068-35-9] (55 mg, 0.05 mmol) in 1,4-dioxane (20 mL) at 25° C. The resulting suspension was heated at 100° C. for 48 h under $N_2$ (g). The solid was filtered off, and the filtrate was concentrated under reduced pressure. The residue was purified by preparative TLC (petroleum ether:EtOAc, 2:1) to afford the title compound (200 mg, 63%) as a yellow solid; MS m/z (ESI) $[M+H]^+$ 329.2.

Intermediate 70: 6-((2S,3R)-3-Methoxy-2-methylazetidin-1-yl)quinoline-4-carboxylic acid

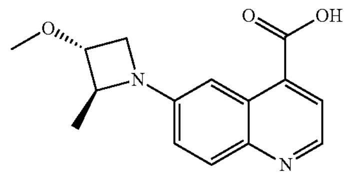 [SMILES: CO[C@@H]1CN(c2ccc3nccc(C(=O)O)c3c2)[C@H]1C]

TFA (3 mL) was added to a solution of tert-butyl 6-((2S,3R)-3-methoxy-2-methylazetidin-1-yl)quinoline-4-carboxylate Intermediate 69 (200 mg, 0.61 mmol) in DCM (6 mL). The solution was stirred at rt for 4 h. The solvent was removed under reduced pressure to give the crude title compound (166 mg, 100%); MS m/z (ESI) $[M+H]^+$ 273.2.

Intermediate 71: Methyl 6-(3-cyclopropyl-3-fluoroazetidin-1-yl)quinoline-4-carboxylate

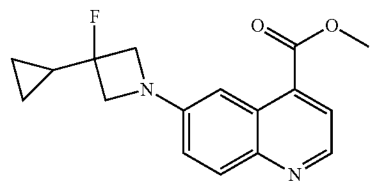 [SMILES: COC(=O)c1ccnc2ccc(N3CC(F)(C4CC4)C3)cc12]

3-Cyclopropyl-3-fluoroazetidine (143 mg, 1.24 mmol) was added to a mixture of methyl 6-bromoquinoline-4-carboxylate (300 mg, 1.13 mmol), $Cs_2CO_3$ (21 mg, 0.06 mmol), $Pd_2(dba)_3$ (103 mg, 0.11 mmol) and XPhos (107 mg, 0.23 mmol) in 1,4-dioxane (2 mL) at 20° C. under $N_2$ (g). The mixture was heated at 100° C. for 5 h. The reaction mixture was concentrated and the residue was diluted with EtOAc (75 mL), and washed sequentially with sat $NH_4C_1$ (25 mL), brine (25 mL), and water (25 mL). The organic layer was dried over $Na_2SO_4$, filtered and evaporated. The residue was purified by preparative TLC (petroleum ether: EtOAc, 3:1) to afford the title compound (180 mg, 53%) as a yellow solid; MS m/z (ESI) $[M+H]^+$ 301.1.

Intermediate 72: 6-(3-Cyclopropyl-3-fluoroazetidin-1-yl)quinoline-4-carboxylic acid

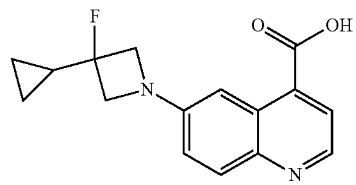 [SMILES: O=C(O)c1ccnc2ccc(N3CC(F)(C4CC4)C3)cc12]

A solution of NaOH (113 mg, 2.83 mmol) in water (4 mL) was added to a stirred solution of methyl 6-(3-cyclopropyl-3-fluoroazetidin-1-yl)quinoline-4-carboxylate Intermediate 71 (170 mg, 0.57 mmol) in MeOH (12 mL) at 20° C. The resulting mixture was stirred at 25° C. for 2 h. The reaction mixture was adjusted to pH 5 with aq HCl (2 M). The reaction mixture was concentrated, and the residue was redissolved in DCM (50 mL), and washed sequentially with brine (25 mL) and water (25 mL). The organic layer was dried over $Na_2SO_4$, filtered and evaporated to afford the title compound (130 mg, 80%) as a red solid; MS m/z (ESI) $[M+H]^+$ 287.0.

Intermediate 73: Methyl 6-(piperidin-1-yl)quinoline-4-carboxylate

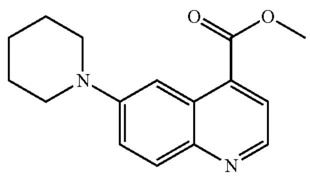 [SMILES: COC(=O)c1ccnc2ccc(N3CCCCC3)cc12]

Piperidine (0.061 mL, 0.62 mmol) was added to a mixture of methyl 6-bromoquinoline-4-carboxylate (150 mg, 0.56 mmol), $Cs_2CO_3$ (367 mg, 1.13 mmol), DavePhos (44 mg, 0.11 mmol) and $Pd_2(dba)_3$ (52 mg, 0.06 mmol) in 1,4-dioxane (2 mL) at 16° C. The resulting suspension was heated at 100° C. for 2 h under $N_2$ (g). The reaction mixture was diluted with DCM (5 mL). The organic layer was filtered and the solvents were evaporated under reduced pressure. The crude product was purified by preparative TLC (DCM:MeOH, 30:1) to afford the title compound (109 mg, 71%) as a yellow oil; MS m/z (ESI) $[M+H]^+$ 271.2.

Intermediate 74: 6-(Piperidin-1-yl)quinoline-4-carboxylic acid

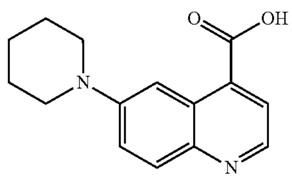 [SMILES: O=C(O)c1ccnc2ccc(N3CCCCC3)cc12]

A solution of NaOH (81 mg, 2.0 mmol) in water (1 mL) was added slowly to a stirred solution of methyl 6-(piperidin-1-yl)quinoline-4-carboxylate Intermediate 73 (109 mg, 0.40 mmol) in MeOH (4 mL) cooled to 0° C. The resulting solution was stirred at 16° C. for 1 h. The reaction mixture was diluted with water (20 mL), adjusted to pH 5 with aq HCl (2 M), and extracted with EtOAc (4×50 mL). The organic layers were combined and washed with water (4×25 mL), dried over $Na_2SO_4$, filtered and evaporated to afford the title compound (90 mg, 87%) as a yellow oil; MS m/z (ESI) $[M+H]^+$ 257.1.

Intermediate 75: Methyl 6-(4,4-dimethylpiperidin-1-yl)quinoline-4-carboxylate

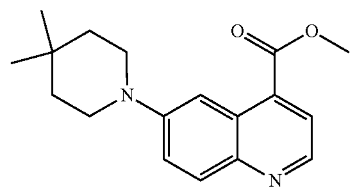

4,4-Dimethylpiperidine hydrochloride (93 mg, 0.62 mmol) was added to a mixture of methyl 6-bromoquinoline-4-carboxylate (150 mg, 0.56 mmol), $Cs_2CO_3$ (551 mg, 1.69 mmol), $Pd_2(dba)_3$ (52 mg, 0.06 mmol) and XPhos (54 mg, 0.11 mmol) in 1,4-dioxane (3 mL) at 15° C. The resulting suspension was heated at 100° C. for 4 h under $N_2$ (g). The reaction mixture was diluted with DCM (5 mL) and filtered. The filtrate was dried over $Na_2SO_4$, filtered and evaporated to afford crude product. The residue was purified by preparative TLC (DCM:MeOH, 20:1) to afford the title compound (140 mg, 83%) as a yellow oil; MS m/z (ESI) $[M+H]^+$ 299.1.

Intermediate 76: 6-(4,4-Dimethylpiperidin-1-yl) quinoline-4-carboxylic acid

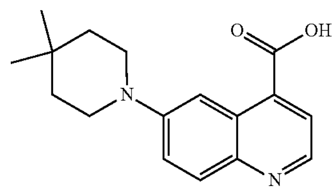 [SMILES: CC1(C)CCN(c2ccc3nccc(C(=O)O)c3c2)CC1]

A solution of NaOH (94 mg, 2.4 mmol) in water (1 mL) was added slowly to a stirred solution of methyl 6-(4,4-dimethylpiperidin-1-yl)quinoline-4-carboxylate Intermediate 75 (140 mg, 0.47 mmol) in MeOH (4 mL) cooled to 0° C. The resulting solution was stirred at 15° C. for 1 h. The reaction mixture was diluted with water (20 mL), adjusted to pH 5 with aq HCl (2 M), and extracted with EtOAc (4×50 mL). The organic layers were combined and washed with water (4×30 mL). The organic layer was dried over $Na_2SO_4$, filtered and evaporated to afford the title compound (101 mg, 76%) as a yellow solid; MS m/z (ESI) $[M+H]^+$ 285.3.

Intermediate 77: Methyl 6-(4-fluoro-4-methylpiperidin-1-yl)quinoline-4-carboxylate

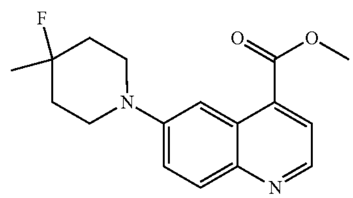

4-Fluoro-4-methylpiperidine hydrochloride (76 mg, 0.50 mmol) was added to a mixture of methyl 6-bromoquinoline- 4-carboxylate (120 mg, 0.45 mmol), $Cs_2CO_3$ (441 mg, 1.35 mmol), $Pd_2(dba)_3$ (41 mg, 0.05 mmol) and DavePhos (36 mg, 0.09 mmol) in 1,4-dioxane (2 mL) at 15° C. The resulting suspension was heated at 100° C. for 2 h under $N_2$ (g). The reaction mixture was diluted with DCM (2 mL), filtered, and evaporated under reduced pressure. The residue was purified by preparative TLC (DCM:MeOH, 20:1) to afford the title compound (102 mg, 75%) as a yellow oil; MS m/z (ESI) $[M+H]^+$ 303.1.

Intermediate 78: 6-(4-Fluoro-4-methylpiperidin-1-yl)quinoline-4-carboxylic acid

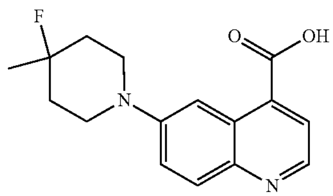 [SMILES: CC1(F)CCN(c2ccc3nccc(C(=O)O)c3c2)CC1]

A solution of NaOH (67 mg, 1.7 mmol) in water (1 mL) was added to a stirred solution of methyl 6-(4-fluoro-4-methylpiperidin-1-yl)quinoline-4-carboxylate Intermediate 77 (101 mg, 0.33 mmol) in MeOH (4 mL) at 18° C. The resulting solution was stirred at 18° C. for 1 h. The reaction mixture was diluted with water (20 mL), and adjusted to pH 4 with aq HCl (2 M). The mixture was extracted with EtOAc (4×50 mL). The organic layers were combined and washed with water (4×25 mL). The organic layer was dried over $Na_2SO_4$, filtered and evaporated to afford the title compound (65 mg, 68%) as a yellow solid; MS m/z (ESI) $[M+H]^+$ 289.2.

Intermediate 79: Methyl 6-(4,4-difluoropiperidin-1-yl)quinoline-4-carboxylate

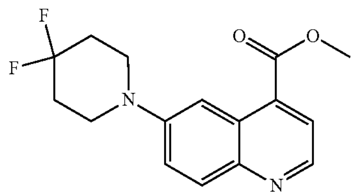 [SMILES: COC(=O)c1ccnc2ccc(N3CCC(F)(F)CC3)cc12]

4,4-Difluoropiperidine (89 mg, 0.73 mmol) was added to a mixture of methyl 6-bromoquinoline-4-carboxylate (150 mg, 0.56 mmol), $Cs_2CO_3$ (551 mg, 1.69 mmol), $Pd_2(dba)_3$ (52 mg, 0.06 mmol) and XPhos (54 mg, 0.11 mmol) in 1,4-dioxane (15 mL) at 20° C. The resulting mixture was stirred at 100° C. for 15 h under $N_2$ (g). The solvents were evaporated under reduced pressure and the residue was purified by preparative TLC (petroleum ether:EtOAc, 5:1) to afford the title compound (160 mg, 93%) as a pale yellow oil; MS m/z (ESI) $[M+H]^+$ 307.2.

Intermediate 80: 6-(4,4-Difluoropiperidin-1-yl)quinoline-4-carboxylic acid

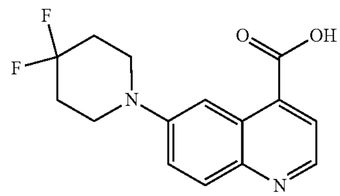 [SMILES: O=C(O)c1ccnc2ccc(N3CCC(F)(F)CC3)cc12]

Aq NaOH (1 M, 3 mL) was added to methyl 6-(4,4-difluoropiperidin-1-yl)quinoline-4-carboxylate Intermediate 79 (150 mg, 0.49 mmol) in MeOH (10 mL) at 20° C. The resulting mixture was stirred at 20° C. for 3 h. The reaction mixture was adjusted to pH 5 with aq HCl (1 M). Solvents were evaporated to afford the title compound (140 mg, 98%) as a yellow solid; MS m/z (ESI) $[M+H]^+$ 293.2.

Intermediate 81: Methyl 6-(3,3-difluoropiperidin-1-yl)quinoline-4-carboxylate

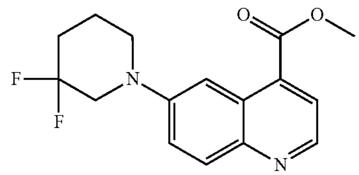 [SMILES: COC(=O)c1ccnc2ccc(N3CCCC(F)(F)C3)cc12]

3,3-Difluoropiperidine hydrochloride (98 mg, 0.62 mmol) was added to a mixture of methyl 6-bromoquinoline-4-carboxylate (150 mg, 0.56 mmol), $Cs_2CO_3$ (551 mg, 1.69 mmol), $Pd_2(dba)_3$ (52 mg, 0.06 mmol) and XPhos (54 mg, 0.11 mmol) in 1,4-dioxane (3 mL) at 15° C. The resulting suspension was heated at 100° C. for 2 h under $N_2$ (g). The reaction mixture was diluted with DCM (5 mL) and filtered. The filtrate was dried over $Na_2SO_4$, filtered and evaporated. The crude product was purified by preparative TLC (DCM:MeOH, 20:1) to afford the title compound (162 mg, 94%) as a yellow gum; MS m/z (ESI) $[M+H]^+$ 307.1.

Intermediate 82: 6-(3,3-Difluoropiperidin-1-yl)quinoline-4-carboxylic acid

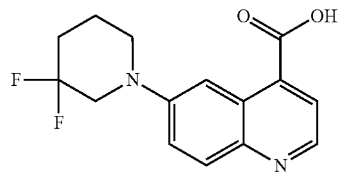 [SMILES: O=C(O)c1ccnc2ccc(N3CCCC(F)(F)C3)cc12]

A solution of NaOH (104 mg, 2.61 mmol) in water (1 mL) was added dropwise to a stirred solution of methyl 6-(3,3-difluoropiperidin-1-yl)quinoline-4-carboxylate Intermediate 81 (160 mg, 0.52 mmol) in MeOH (4 mL) cooled to 0° C. The resulting solution was stirred at 15° C. for 1 h. The reaction mixture was diluted with water (20 mL), and adjusted to pH 4 with aq HCl (2 M). The mixture was extracted with EtOAc (4×50 mL). The organic layers were combined and washed with water (4×25 mL). The organic layer was dried over $Na_2SO_4$, filtered and evaporated to afford the title compound (143 mg, 94%) as a yellow solid; MS m/z (ESI) $[M+H]^+$ 293.1.

Intermediate 83: Methyl 6-(4-(fluoromethyl)-4-methylpiperidin-1-yl)quinoline-4-carboxylate

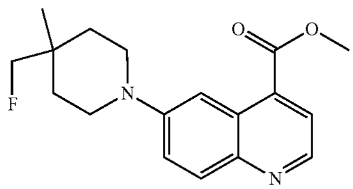 [SMILES: COC(=O)c1ccnc2ccc(N3CCC(C)(CF)CC3)cc12]

4-(Fluoromethyl)-4-methylpiperidine hydrochloride (162 mg, 0.97 mmol) was added to a mixture of methyl 6-bromoquinoline-4-carboxylate (266 mg, 0.88 mmol), $Cs_2CO_3$ (859 mg, 2.64 mmol), $Pd_2(dba)_3$ (81 mg, 0.09 mmol) and DavePhos (69 mg, 0.18 mmol) in 1,4-dioxane (5 mL) at 11° C. The resulting suspension was heated at 100° C. for 2 h under $N_2$ (g). The reaction mixture was diluted with DCM (3 mL) and filtered. The filtrate was concentrated under reduced pressure, and the residue was purified by preparative TLC (petroleum ether:EtOAc, 1:1) to afford the title compound (170 mg, 61%) as a yellow oil; MS m/z (ESI) $[M+H]^+$ 317.3.

Intermediate 84: 6-(4-(Fluoromethyl)-4-methylpiperidin-1-yl)quinoline-4-carboxylic acid

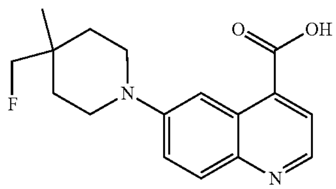 [SMILES: CC1(CF)CCN(c2ccc3nccc(C(=O)O)c3c2)CC1]

A solution of NaOH (107 mg, 2.69 mmol) in water (1 mL) was added slowly to a stirred solution of methyl 6-(4-(fluoromethyl)-4-methylpiperidin-1-yl)quinoline-4-carboxylate Intermediate 83 (170 mg, 0.54 mmol) in MeOH (3 mL) cooled to 0° C. The resulting solution was stirred at 10° C. for 1 h. The reaction mixture was diluted with water (20 mL), adjusted to pH 5 with aq HCl (2 M), and extracted with EtOAc (4×50 mL). The organic layers were combined and washed with water (4×25 mL). The organic layer was dried over $Na_2SO_4$, filtered and evaporated to afford the title compound (129 mg, 79%) as a yellow solid; MS m/z (ESI) $[M+H]^+$ 303.2.

Intermediate 85: Methyl 6-(4,4-difluoro-3,3-dimethylpiperidin-1-yl)quinoline-4-carboxylate

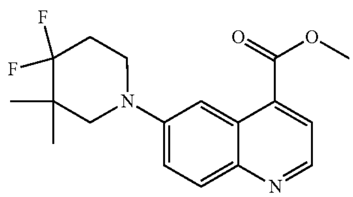

4,4-Difluoro-3,3-dimethylpiperidine hydrochloride (230 mg, 1.24 mmol) was added to a mixture of methyl 6-bromoquinoline-4-carboxylate (300 mg, 1.13 mmol), $Cs_2CO_3$ (1.10 g, 3.38 mmol), XPhos (107 mg, 0.23 mmol) and $Pd_2(dba)_3$ (103 mg, 0.11 mmol) in 1,4-dioxane (10 mL) at 11° C. The resulting suspension was heated at 100° C. for 5 h under $N_2$ (g). The reaction mixture was filtered. The filtrate was concentrated and redissolved in EtOAc (75 mL), and washed sequentially with brine (25 mL) and water (20 mL). The organic layer was dried over $Na_2SO_4$, filtered and evaporated. The residue was purified by preparative TLC (EtOAc:petroleum ether, 1:1) to afford the title compound (310 mg, 82%) as a yellow oil; MS m/z (ESI) $[M+H]^+$ 335.1.

Intermediate 86: 6-(4,4-Difluoro-3,3-dimethylpiperidin-1-yl)quinoline-4-carboxylic acid

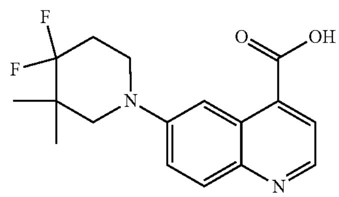 [SMILES: CC1(C)CN(c2ccc3nccc(C(=O)O)c3c2)CCC1(F)F]

A solution of NaOH (179 mg, 4.49 mmol) in water (4 mL) was added to a stirred solution of methyl-(4,4-difluoro-3,3-dimethylpiperidin-1-yl)quinoline-4-carboxylate Intermediate 85 (300 mg, 0.90 mmol) in MeOH (12 mL) at 20° C. The resulting mixture was stirred at 20° C. for 3 h. The reaction mixture adjusted to pH 5 with aq HCl (2 M). Solvents were evaporated under reduced pressure, the residue was dissolved in EtOAc (100 mL) and washed with brine (25 mL). The organic layer was dried over $Na_2SO_4$, filtered, and evaporated to afford the title compound (250 mg, 87%) as a yellow solid; MS m/z (ESI) $[M+H]^+$ 321.1.

Intermediate 87: Methyl 6-(4-(trifluoromethyl)piperidin-1-yl)quinoline-4-carboxylate

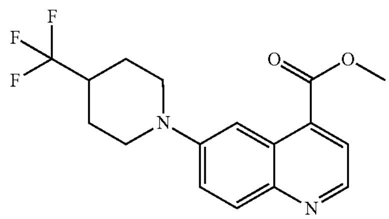 [SMILES: COC(=O)c1ccnc2ccc(N3CCC(C(F)(F)F)CC3)cc12]

4-(Trifluoromethyl)piperidine (169 mg, 1.10 mmol) was added to a mixture of methyl 6-bromoquinoline-4-carboxylate (303 mg, 1.00 mmol), $Cs_2CO_3$ (0.98 g, 3.00 mmol) $Pd_2(dba)_3$ (92 mg, 0.10 mmol) and DavePhos (79 mg, 0.20 mmol) in 1,4-dioxane (1 mL) at 10° C. The resulting suspension was heated at 100° C. for 2 h under $N_2$ (g). The reaction mixture was diluted with DCM (3 mL) and filtered. The filtrate was concentrated under reduced pressure. The residue was purified by preparative TLC (EtOAc:petroleum ether, 1:1) to afford the title compound (243 mg, 72%) as a yellow oil which solidified on standing; MS m/z (ESI) $[M+H]^+$ 339.1.

Intermediate 88: 6-(4-(Trifluoromethyl)piperidin-1-yl)quinoline-4-carboxylic acid

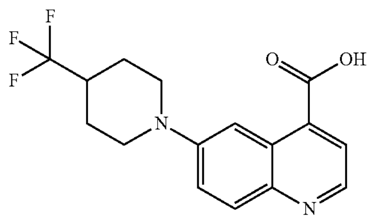 [SMILES: O=C(O)c1ccnc2ccc(N3CCC(C(F)(F)F)CC3)cc12]

A solution of NaOH (142 mg, 3.55 mmol) in water (1 mL) was added slowly to a stirred solution of methyl 6-(4-(trifluoromethyl)piperidin-1-yl)quinoline-4-carboxylate Intermediate 87 (240 mg, 0.71 mmol) in MeOH (4 mL) cooled to 0° C. The resulting solution was stirred at 12° C. for 1 h. The reaction mixture was diluted with water (20 mL), and adjusted to pH 5 with aq HCl (2 M). The aqueous layer was extracted with EtOAc (4×50 mL). The organic layers were combined and washed with water (4×25 mL). The organic layer was dried over $Na_2SO_4$, filtered and evaporated to afford the title compound (190 mg, 83%) as a brown solid; MS m/z (ESI) $[M+H]^+$ 325.0.

Intermediate 89: rac-Methyl (R)-6-(3-fluoropiperidin-1-yl)quinoline-4-carboxylate

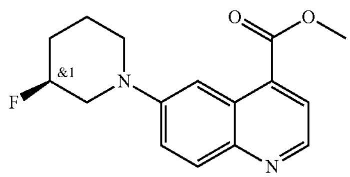 [SMILES: COC(=O)c1ccnc2ccc(N3CCC[C@H](F)C3)cc12]

3-Fluoropiperidine (64 mg, 0.62 mmol) was added to a solution of methyl 6-bromoquinoline-4-carboxylate (150 mg, 0.56 mmol), $Cs_2CO_3$ (367 mg, 1.13 mmol), DavePhos (44 mg, 0.11 mmol) and $Pd_2(dba)_3$ (52 mg, 0.06 mmol) in 1,4-dioxane (20 mL) at 16° C. The resulting suspension was stirred at 100° C. for 2 h under $N_2$ (g). The solvent was removed under reduced pressure. The residue was purified by preparative TLC (petroleum ether:EtOAc, 1:1), to afford the title compound (140 mg, 86%) as a yellow gum; MS m/z (ESI) $[M+H]^+$ 289.0.

Intermediate 90: rac-(R)-6-(3-Fluoropiperidin-1-yl)quinoline-4-carboxylic acid

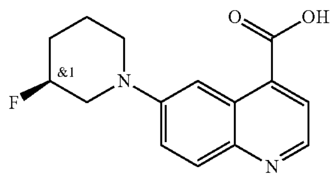

NaOH (78 mg, 1.9 mmol) in water (3.5 mL) was added to a stirred solution of methyl 6-(3-fluoropiperidin-1-yl)quinoline-4-carboxylate Intermediate 89 (140 mg, 0.49 mmol) in MeOH (14 mL) at 0° C., and then stirred for 1 h at rt. The reaction mixture was diluted with water (15 mL), adjusted to pH 5 with aq HCl (2 M), and extracted with EtOAc (3×25 mL). The combined organic phases were washed with brine (15 mL), the organic layer was dried over $Na_2SO_4$, filtered and evaporated to afford the title compound (120 mg, 90%) as an orange solid; MS m/z (ESI) $[M+H]^+$ 275.2.

Intermediate 91: rac-Methyl (R)-6-(3-methoxypiperidin-1-yl)quinoline-4-carboxylate

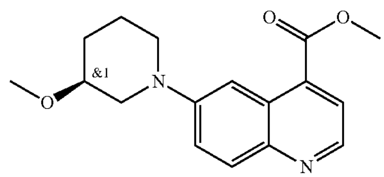

3-Methoxypiperidine (71 mg, 0.62 mmol) was added to a mixture of methyl 6-bromoquinoline-4-carboxylate (150 mg, 0.56 mmol), $Cs_2CO_3$ (367 mg, 1.13 mmol), DavePhos (44 mg, 0.11 mmol) and $Pd_2(dba)_3$ (52 mg, 0.06 mmol) in 1,4-dioxane (20 mL) at 16° C. The resulting suspension was heated at 100° C. for 2 h under $N_2$ (g). The solvent was removed under reduced pressure. The residue was purified by preparative TLC (petroleum ether:EtOAc, 1:2) to afford the title compound (150 mg, 89%) as a yellow gum; MS m/z (ESI) $[M+H]^+$ 301.1.

Intermediate 92: rac-(R)-6-(3-Methoxypiperidin-1-yl)quinoline-4-carboxylic acid

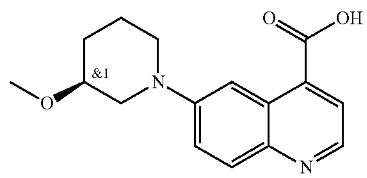 [SMILES: CO[C@H]1CCCN(c2ccc3nccc(C(=O)O)c3c2)C1]

A solution of NaOH (104 mg, 2.59 mmol) in water (3 mL) was added slowly to a stirred solution of methyl 6-(piperidin-1-yl)quinoline-4-carboxylate Intermediate 91 (140 mg, 0.52 mmol) in MeOH (12 mL) cooled to 0° C. The resulting solution was stirred at 16° C. for 1 h. The reaction mixture was diluted with water (20 mL), and adjusted to pH 5 with aq HCl (2 M), and extracted with EtOAc (4×50 mL). The combined organic layers were dried over $Na_2SO_4$, filtered and evaporated. The crude product was purified by reversed phase flash chromatography on a C18 column (gradient: 0-50% MeCN in water) to give the title compound (133 mg, 100%) as a yellow gum.

Intermediate 93: tert-Butyl 6-(4-methoxy-4-methylpiperidin-1-yl)quinoline-4-carboxylate

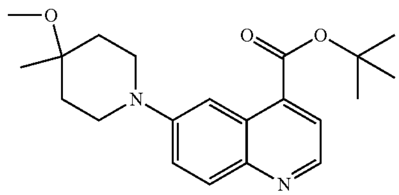 [SMILES: COC1(C)CCN(c2ccc3nccc(C(=O)OC(C)(C)C)c3c2)CC1]

4-Methoxy-4-methylpiperidine hydrochloride (105 mg, 0.63 mmol) was added to a mixture of tert-butyl 6-bromoquinoline-4-carboxylate (150 mg, 0.49 mmol), $Cs_2CO_3$ (206 mg, 0.63 mmol), XPhos (46 mg, 0.10 mmol) and $Pd_2(dba)_3$ (45 mg, 0.05 mmol) in 1,4-dioxane (5 mL) at 25° C. The resulting suspension was heated at 100° C. for 2 h under $N_2$ (g). The reaction mixture was filtered, the filtrated was concentrated under reduced pressure, and purified by preparative TLC (EtOAc:petroleum ether, 3:2) to afford the title compound (140 mg, 81%) as a yellow oil which solidified on standing; MS m/z (ESI) $[M+H]^+$ 357.2.

Intermediate 94: 6-(4-Methoxy-4-methylpiperidin-1-yl)quinoline-4-carboxylic acid

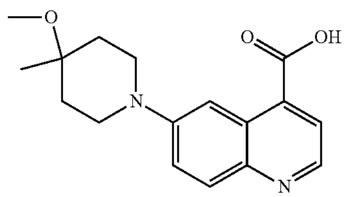 [SMILES: COC1(C)CCN(c2ccc3nccc(C(=O)O)c3c2)CC1]

HCl in 1,4-dioxane (4 M, 5 mL) was added slowly to a stirred solution of tert-butyl 6-(4-methoxy-4-methylpiperidin-1-yl)quinoline-4-carboxylate Intermediate 93 (110 mg, 0.31 mmol) in 1,4-dioxane (5 mL) at 25° C. The resulting solution was stirred at 50° C. for 15 h. The solvent was removed under reduced pressure to afford the title compound (90 mg, 97%) as a red solid; MS m/z (ESI) $[M+H]^+$ 301.2.

Intermediate 95: tert-Butyl 6-(4-isopropoxypiperidin-1-yl)quinoline-4-carboxylate

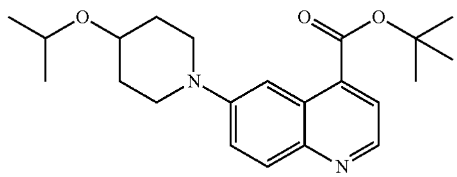 [SMILES: CC(C)OC1CCN(c2ccc3nccc(C(=O)OC(C)(C)C)c3c2)CC1]

4-Isopropoxypiperidine hydrochloride (117 mg, 0.65 mmol) was added to a mixture of tert-butyl 6-bromoquinoline-4-carboxylate (200 mg, 0.65 mmol), $Cs_2CO_3$ (634 mg, 1.95 mmol), $Pd_2(dba)_3$ (59 mg, 0.06 mmol) and XPhos (91 mg, 0.19 mmol) in 1,4-dioxane (10 mL) under $N_2$ (g). The reaction was heated at 80° C. for 20 h. The solvent was removed under reduced pressure. The residue was diluted with EtOAc, and washed with water. The organic layer was dried over $Na_2SO_4$, filtered and evaporated. The residue was purified by preparative TLC (petroleum ether:EtOAc, 5:1) to afford the title compound (180 mg, 75%) as a yellow solid; MS m/z (ESI) $[M+H]^+$ 371.1.

Intermediate 96: 6-(4-Isopropoxypiperidin-1-yl)quinoline-4-carboxylic acid

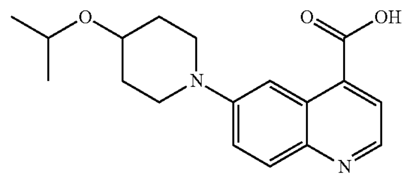 [SMILES: CC(C)OC1CCN(c2ccc3nccc(C(=O)O)c3c2)CC1]

TFA (3 mL) was added to a solution of tert-butyl 6-(4-isopropoxypiperidin-1-yl)quinoline-4-carboxylate Intermediate 95 (120 mg, 0.32 mmol) in DCM (6 mL). The reaction was stirred at rt for 2 h. The solvent was removed under reduced pressure to give the title compound (100 mg, 98%) as a yellow solid; MS m/z (ESI) $[M+H]^+$ 315.05.

Intermediate 97: rac-Methyl (R)-6-(4,4-difluoro-2-methylpiperidin-1-yl)quinoline-4-carboxylate

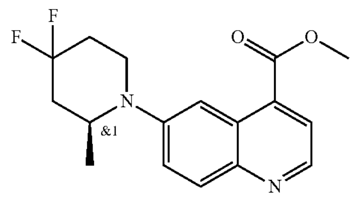 [SMILES: COC(=O)c1ccnc2ccc(N3CCC(F)(F)C[C@@H]3C)cc12]

4,4-Difluoro-2-methylpiperidine hydrochloride (387 mg, 2.25 mmol) was added to a mixture of methyl 6-bromoquinoline-4-carboxylate (300 mg, 1.13 mmol), $Cs_2CO_3$ (1.10 g, 3.38 mmol) and Pd Catalyst [CAS: 1810068-35-9] (64 mg, 0.06 mmol) in 1,4-dioxane (20 mL) at 25° C. The resulting suspension was heated at 85° C. for 18 h under $N_2$ (g). The reaction mixture was filtered, and the filtrate was concentrated under reduced pressure. The residue was purified by preparative TLC (petroleum ether:EtOAc, 1:1) to afford the title compound (170 mg, 47%) as a yellow solid; MS m/z (ESI) $[M+H]^+$ 321.2.

Intermediate 98: rac-(R)-6-(4,4-Difluoro-2-methylpiperidin-1-yl)quinoline-4-carboxylic acid

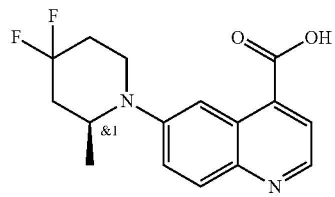 [SMILES: C[C@H]1CC(F)(F)CCN1c1ccc2nccc(C(=O)O)c2c1]

LiOH (64 mg, 2.65 mmol) was added to a solution of methyl 6-(4,4-difluoro-2-methylpiperidin-1-yl)quinoline-4-carboxylate Intermediate 97 (170 mg, 0.53 mmol) in MeOH (10 mL) and water (2 mL). The reaction was stirred at rt for 2 h. The solvent was removed under reduced pressure. The reaction mixture was diluted with water, the pH was adjusted to 6 with aq HCl (2 M), and evaporated under reduced pressure. The residue was dissolved in EtOAc, and washed with water. The organic layer was dried over $Na_2SO_4$, filtered and evaporated to afford the title compound (150 mg, 92%) as a yellow solid; MS m/z (ESI) $[M+H]^+$ 307.1.

Intermediate 99: Methyl (S)-6-(2-(fluoromethyl)piperidin-1-yl)quinoline-4-carboxylate

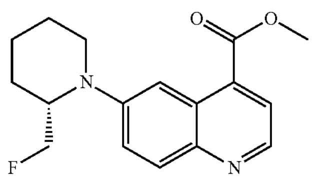 [SMILES: COC(=O)c1ccnc2ccc(N3CCCC[C@H]3CF)cc12]

(S)-2-(Fluoromethyl)piperidine hydrobromide (447 mg, 2.25 mmol) was added to a mixture of methyl 6-bromoquinoline-4-carboxylate (300 mg, 1.13 mmol), $Cs_2CO_3$ (1.10 g, 3.38 mmol) and Pd Catalyst [CAS: 1810068-35-9] (64 mg, 0.06 mmol) in 1,4-dioxane (20 mL) at 25° C. The resulting suspension was heated at 100° C. for 18 h under $N_2$ (g). The reaction mixture was filtered, and the filtrate was concentrated under reduced pressure. The residue was purified by preparative TLC (petroleum ether:EtOAc, 1:1) to afford the title compound (110 mg, 32%) as a yellow solid; MS m/z (ESI) $[M+H]^+$ 303.2.

Intermediate 100: (S)-6-(2-(Fluoromethyl)piperidin-1-yl)quinoline-4-carboxylic acid

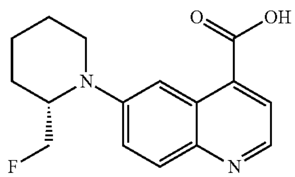 [SMILES: O=C(O)c1ccnc2ccc(N3CCCC[C@H]3CF)cc12]

LiOH (44 mg, 1.82 mmol) was added to a solution of methyl (S)-6-(2-(fluoromethyl)piperidin-1-yl)quinoline-4-carboxylate Intermediate 99 (110 mg, 0.36 mmol) in MeOH (5 mL) and water (1 mL). The reaction was stirred at rt for 2 h. The solvent was removed under reduced pressure. The residue was diluted with water and adjusted to pH 6 with aq HCl (2 M), and evaporated under reduced pressure. The residue was dissolved in EtOAc, and washed with water. The organic layer was dried over $Na_2SO_4$, filtered and evaporated to afford the title compound (90 mg, 86%); MS m/z (ESI) $[M+H]^+$ 289.2.

Intermediate 101: Methyl 6-(5-azaspiro[2.5]octan-5-yl)quinoline-4-carboxylate

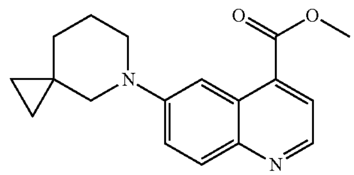 [SMILES: COC(=O)c1ccnc2ccc(N3CCCC4(CC4)C3)cc12]

5-Azaspiro[2.5]octane hydrochloride (325 mg, 2.20 mmol) was added to a mixture of methyl 6-bromoquinoline-4-carboxylate (605 mg, 2.00 mmol), $Cs_2CO_3$ (2.60 g, 8.00 mmol), $Pd_2(dba)_3$ (183 mg, 0.20 mmol) and DavePhos (157 mg, 0.40 mmol) in 1,4-dioxane (5 mL) at 10° C. The resulting suspension was heated at 100° C. overnight under $N_2$ (g). The reaction mixture was diluted with DCM (3 mL) and filtered. The solvent was removed under reduced pressure. The residue was purified by preparative TLC (petroleum ether:EtOAc, 1:1) to afford the title compound (273 mg, 46%) as a yellow oil which solidified on standing; MS m/z (ESI) $[M+H]^+$ 297.05.

Intermediate 102: 6-(5-Azaspiro[2.5]octan-5-yl)quinoline-4-carboxylic acid

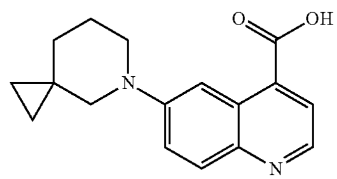 [SMILES: O=C(O)c1ccnc2ccc(N3CCCC4(CC4)C3)cc12]

A solution of NaOH (151 mg, 3.78 mmol) in water (2 mL) was added slowly to a stirred solution of methyl 6-(5-azaspiro[2.5]octan-5-yl)quinoline-4-carboxylate Intermediate 101 (270 mg, 0.76 mmol) in MeOH (6 mL) cooled to 0° C. The resulting solution was stirred at 10° C. for 1 h. The solvent was removed under reduced pressure. The residue was dissolved with water (5 mL) and adjusted to pH 4 with aq HCl (2 M). The solvent was removed under reduced pressure. The crude product was purified by preparative HPLC PrepMethod P (gradient: 0-50%) to afford the title compound (115 mg, 54%) as an orange solid; MS m/z (ESI) $[M+H]^+$ 283.1.

Intermediate 103: Methyl 6-(3,3-difluoropyrrolidin-1-yl)quinoline-4-carboxylate

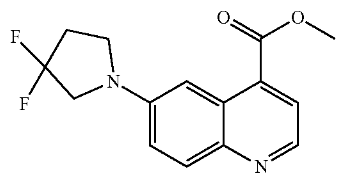 [SMILES: COC(=O)c1ccnc2ccc(N3CCC(F)(F)C3)cc12]

3,3-Difluoropyrrolidine hydrochloride (324 mg, 2.25 mmol) was added to a mixture of methyl 6-bromoquinoline- 4-carboxylate (300 mg, 1.13 mmol), $Cs_2CO_3$ (1.10 g, 3.38 mmol), $Pd_2(dba)_3$ (52 mg, 0.06 mmol) and XPhos (161 mg, 0.34 mmol) in 1,4-dioxane (20 mL). The reaction was heated at 100° C. for 4 h. The precipitate was collected by filtration, washed with MeOH and dried under vacuum to afford crude product, which was purified by preparative TLC (petroleum ether:EtOAc, 1:1) to afford the title compound (180 mg, 55%) as a yellow solid; MS m/z (ESI) $[M+H]^+$ 293.0.

Intermediate 104: 6-(3,3-Difluoropyrrolidin-1-yl) quinoline-4-carboxylic acid

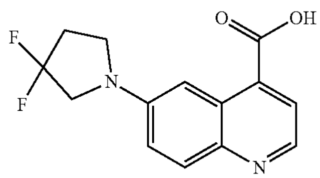 [SMILES: O=C(O)c1ccnc2ccc(N3CCC(F)(F)C3)cc12]

LiOH (74 mg, 3.1 mmol) was added to a solution of methyl 6-(3,3-difluoropyrrolidin-1-yl)quinoline-4-carboxylate Intermediate 103 (180 mg, 0.62 mmol) in MeOH (10 mL) and water (2 mL). The mixture was stirred at rt for 2 h. The reaction mixture was adjusted to pH 5 with aq HCl (2 M). The reaction mixture was diluted with EtOAc, and washed with water. The organic layer was dried over $Na_2SO_4$, filtered and evaporated to afford the title compound (150 mg, 88%) as a yellow solid; MS m/z (ESI) $[M+H]^+$ 279.1.

Intermediate 105: tert-Butyl 6-(3,3-dimethylpyrrolidin-1-yl)quinoline-4-carboxylate

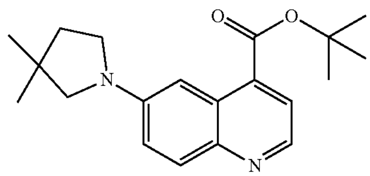 [SMILES: CC1(C)CCN(c2ccc3nccc(C(=O)OC(C)(C)C)c3c2)C1]

3,3-Dimethylpyrrolidine hydrochloride (149 mg, 1.10 mmol) was added to a mixture of tert-butyl 6-bromoquinoline-4-carboxylate (308 mg, 1.00 mmol), $Cs_2CO_3$ (977 mg, 3.00 mmol), $Pd_2(dba)_3$ (92 mg, 0.10 mmol), and XPhos (95 mg, 0.20 mmol) in 1,4-dioxane (5 mL) at 8° C. The resulting suspension was heated at 100° C. for 2 h under $N_2$ (g). The reaction mixture was diluted with DCM (3 mL). The reaction mixture was filtered, and the filtrate was concentrated under reduced pressure. The residue was purified preparative TLC (EtOAc:petroleum ether, 1:1) to afford the title compound (285 mg, 87%) as a brown solid; MS m/z (ESI) $[M+H]^+$ 327.3.

Intermediate 106: 6-(3,3-Dimethylpyrrolidin-1-yl) quinoline-4-carboxylic acid

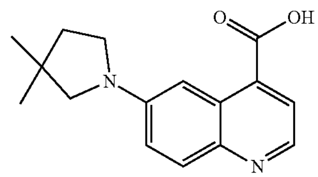 [SMILES: CC1(C)CCN(c2ccc3nccc(C(=O)O)c3c2)C1]

TFA (2.5 mL, 32 mmol) was added to a stirred solution of tert-butyl 6-(3,3-dimethylpyrrolidin-1-yl)quinoline-4-carboxylate Intermediate 105 (265 mg, 0.81 mmol) in DCM (5 mL) at 8° C. The resulting solution was stirred at 8° C. overnight. The solvent was removed under reduced pressure to afford the title compound (343 mg) as a dark red gum; MS m/z (ESI) $[M+H]^+$ 271.1.

Intermediate 107: tert-Butyl 6-(5-azaspiro[2.4]heptan-5-yl)quinoline-4-carboxylate

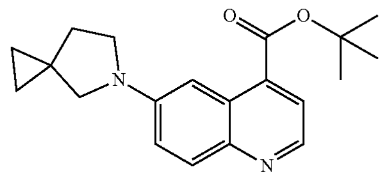 [SMILES: CC(C)(C)OC(=O)c1ccnc2ccc(N3CCC4(CC4)C3)cc12]

5-Azaspiro[2.4]heptane hydrochloride (147 mg, 1.10 mmol) was added to a mixture of tert-butyl 6-bromoquinoline-4-carboxylate (308 mg, 1.00 mmol), $Cs_2CO_3$ (977 mg, 3.00 mmol), $Pd_2(dba)_3$ (92 mg, 0.10 mmol), and XPhos (95 mg, 0.20 mmol) in 1,4-dioxane (5 mL) at 8° C. The resulting suspension was heated at 100° C. for 2 h under $N_2$ (g). The reaction mixture was diluted with DCM (3 mL) and filtered, and the filtrate was concentrated under reduced pressure. The residue was purified by preparative TLC (EtOAc: petroleum ether, 1:1) to afford the title compound (243 mg, 75%) as a brown oil which solidified on standing; MS m/z (ESI) $[M+H]^+$ 325.2.

Intermediate 108: 6-(5-Azaspiro[2.4]heptan-5-yl) quinoline-4-carboxylic acid

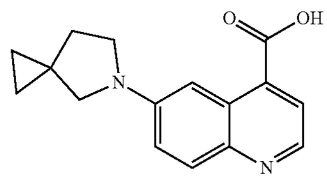 [SMILES: O=C(O)c1ccnc2ccc(N3CCC4(CC4)C3)cc12]

TFA (5.0 mL, 65 mmol) was added to a stirred solution of tert-butyl 6-(5-azaspiro[2.4]heptan-5-yl)quinoline-4-carboxylate Intermediate 107 (240 mg, 0.74 mmol) in DCM (5 mL) at 8° C. The resulting solution was stirred at 8° C. overnight. The solvent was removed under reduced pressure to afford the title compound (423 mg) as a dark red solid; MS m/z (ESI) $[M+H]^+$ 269.1.

Intermediate 109: tert-Butyl 6-((3R,4S)-3,4-difluoropyrrolidin-1-yl)quinoline-4-carboxylate

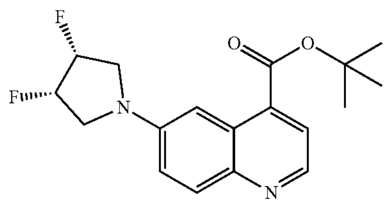 [SMILES: CC(C)(C)OC(=O)c1ccnc2ccc(N3C[C@@H](F)[C@@H](F)C3)cc12]

(3R,4S)-3,4-Difluoropyrrolidine hydrochloride (158 mg, 1.10 mmol) was added to a mixture of tert-butyl 6-bromoquinoline-4-carboxylate (308 mg, 1.00 mmol), $Cs_2CO_3$ (977 mg, 3.00 mmol), $Pd_2(dba)_3$ (92 mg, 0.10 mmol), and XPhos (95 mg, 0.20 mmol) in 1,4-dioxane (1 mL) at 5° C. The resulting suspension was heated at 100° C. for 2 h under $N_2$ (g). The reaction mixture was diluted with DCM (3 mL). The reaction mixture was filtered, and the filtrate was concentrated under reduced pressure. The residue was purified by preparative TLC (EtOAc: petroleum ether, 2:1) to afford the title compound (263 mg, 79%) as a brown solid; MS m/z (ESI) $[M+H]^+$ 335.2.

Intermediate 110: 6-((3R,4S)-3,4-Difluoropyrrolidin-1-yl)quinoline-4-carboxylic acid

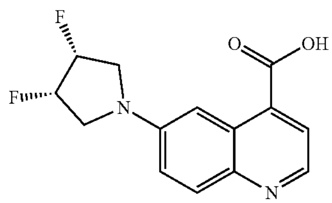 [SMILES: O=C(O)c1ccnc2ccc(N3C[C@@H](F)[C@@H](F)C3)cc12]

TFA (2.5 mL, 32 mmol) was added to a stirred solution of tert-butyl 6-((3S,4R)-3,4-difluoropyrrolidin-1-yl)quinoline-4-carboxylate Intermediate 109 (233 mg, 0.70 mmol) in DCM (5 mL) at 9° C. The resulting solution was stirred at 9° C. overnight. The solvent was removed under reduced pressure to afford the title compound (350 mg) as a red dark solid; MS m/z (ESI) $[M+H]^+$ 279.0.

Intermediate 111: tert-Butyl (S)-6-(3-fluoropyrrolidin-1-yl)quinoline-4-carboxylate

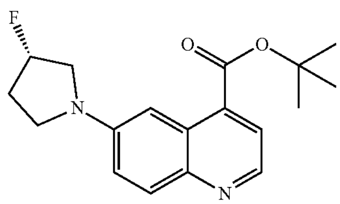 [SMILES: CC(C)(C)OC(=O)c1ccnc2ccc(N3CC[C@H](F)C3)cc12]

(S)-3-Fluoropyrrolidine hydrochloride (138 mg, 1.10 mmol) was added to a mixture of tert-butyl 6-bromoquinoline-4-carboxylate (308 mg, 1.00 mmol), $Cs_2CO_3$ (977 mg, 3.00 mmol), $Pd_2(dba)_3$ (92 mg, 0.10 mmol), and XPhos (95 mg, 0.20 mmol) in 1,4-dioxane (5 mL) at 9° C. The resulting suspension was heated at 100° C. for 2 h under $N_2$ (g). The reaction mixture was diluted with DCM (3 mL) and filtered, and the filtrate was concentrated under reduced pressure. The residue was purified by preparative TLC (EtOAc: petroleum ether, 1:1) to afford the title compound (246 mg, 78%) as a brown oil which solidified on standing; MS m/z (ESI) $[M+H]^+$ 317.3.

Intermediate 112: (S)-6-(3-Fluoropyrrolidin-1-yl)quinoline-4-carboxylic acid

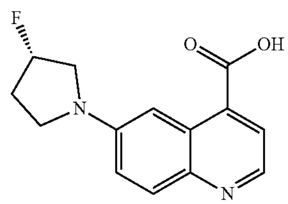 [SMILES: O=C(O)c1ccnc2ccc(N3CC[C@H](F)C3)cc12]

TFA (4 mL, 52 mmol) was added to a stirred solution of tert-butyl (S)-6-(3-fluoropyrrolidin-1-yl)quinoline-4-carboxylate Intermediate 111 (217 mg, 0.69 mmol) in DCM (5 mL) at 9° C. The resulting solution was stirred at 9° C. overnight. The solvent was removed under reduced pressure to afford the title compound (305 mg) as a dark red oil which solidified on standing; MS m/z (ESI) $[M+H]^+$ 261.2.

Intermediate 113: tert-Butyl (R)-6-(3-fluoropyrrolidin-1-yl)quinoline-4-carboxylate

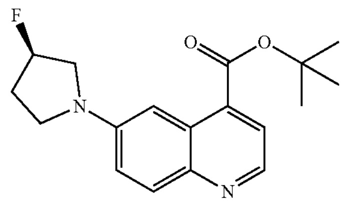 [SMILES: CC(C)(C)OC(=O)c1ccnc2ccc(N3CC[C@@H](F)C3)cc12]

(R)-3-Fluoropyrrolidine hydrochloride (138 mg, 1.10 mmol) was added to a mixture of tert-butyl 6-bromoquinoline-4-carboxylate (308 mg, 1.00 mmol), $Cs_2CO_3$ (977 mg, 3.00 mmol), $Pd_2(dba)_3$ (92 mg, 0.10 mmol), and XPhos (95 mg, 0.20 mmol) in 1,4-dioxane (5 mL) at 8° C. The resulting suspension was stirred at 100° C. for 2 h under $N_2$ (g). The reaction mixture was diluted with DCM (3 mL) and filtered, and the filtrate was concentrated under reduced pressure. The residue was purified by preparative TLC (EtOAc: petroleum ether, 1:1) to afford the title compound (245 mg, 77%) as a brown oil which solidified on standing; MS m/z (ESI) $[M+H]^+$ 317.3.

Intermediate 114: (R)-6-(3-Fluoropyrrolidin-1-yl) quinoline-4-carboxylic acid

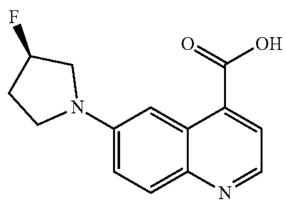 [SMILES: O=C(O)c1ccnc2ccc(N3CC[C@@H](F)C3)cc12]

TFA (4 mL, 52 mmol) was added to a stirred solution of tert-butyl (R)-6-(3-fluoropyrrolidin-1-yl)quinoline-4-carboxylate Intermediate 113 (230 mg, 0.73 mmol) in DCM (5 mL) at 9° C. The resulting solution was stirred at 9° C. overnight. The solvent was removed under reduced pressure to afford the title compound (447 mg) as a dark red oil which solidified on standing; MS m/z (ESI) $[M+H]^+$ 261.2.

Intermediate 115: Methyl 6-(hexahydrocyclopenta[c]pyrrol-2(1H)-yl)quinoline-4-carboxylate

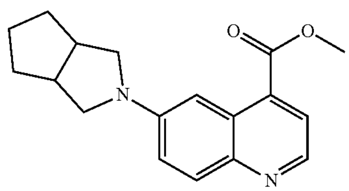 [SMILES: COC(=O)c1ccnc2ccc(N3CC4CCCC4C3)cc12]

Octahydrocyclopenta[c]pyrrole hydrochloride (333 mg, 2.25 mmol) was added to a mixture of methyl 6-bromoquinoline-4-carboxylate (300 mg, 1.13 mmol), $Cs_2CO_3$ (1.10 g, 3.38 mmol), $Pd_2(dba)_3$ (103 mg, 0.11 mmol) and XPhos (161 mg, 0.34 mmol) in 1,4-dioxane (20 mL). The mixture was heated 100° C. for 4 h under $N_2$ (g). The precipitate was collected by filtration, washed with MeOH, and dried under vacuum to afford crude product, which was purified by preparative TLC (petroleum ether:EtOAc, 1:1) to afford the title compound (200 mg, 60%) as a yellow solid; MS m/z (ESI) $[M+H]^+$ 297.1.

Intermediate 116: 6-(Hexahydrocyclopenta[c]pyrrol-2(1H)-yl)quinoline-4-carboxylic acid

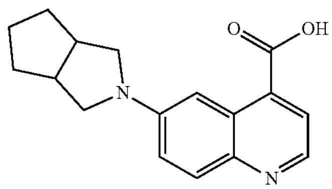 [SMILES: O=C(O)c1ccnc2ccc(N3CC4CCCC4C3)cc12]

LiOH (40 mg, 1.69 mmol) was added to a solution of methyl 6-(hexahydrocyclopenta[c]pyrrol-2(1H)-yl)quinoline-4-carboxylate Intermediate 115 (100 mg, 0.34 mmol) in MeOH (10 mL) and water (2 mL). The reaction was stirred at rt for 2 h. The reaction mixture was adjusted to pH 5 with aq HCl (2 M). The reaction mixture was diluted with EtOAc, and washed with water. The organic layer was dried over $Na_2SO_4$, filtered and evaporated to afford the title compound (85 mg, 89%) as a yellow solid; MS m/z (ESI) $[M+H]^+$ 283.2.

Intermediate 117: tert-Butyl (S)-6-(3-methylpyrrolidin-1-yl)quinoline-4-carboxylate

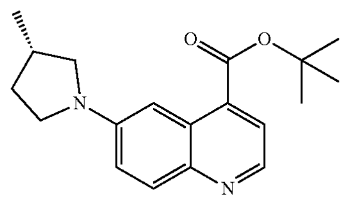 [SMILES: C[C@H]1CCN(c2ccc3nccc(C(=O)OC(C)(C)C)c3c2)C1]

(S)-3-Methyl-pyrrolidine hydrochloride (87 mg, 0.71 mmol) was added to a mixture of tert-butyl 6-bromoquinoline-4-carboxylate (200 mg, 0.65 mmol), $Cs_2CO_3$ (634 mg, 1.95 mmol), $Pd_2(dba)_3$ (59 mg, 0.06 mmol), and XantPhos (75 mg, 0.13 mmol) in 1,4-dioxane (5 mL) at 20° C. The resulting suspension was then heated at 100° C. for 2 h under $N_2$ (g). The reaction mixture was filtered through Celite®. The solvent was removed under reduced pressure. The residue was purified by preparative TLC (petroleum ether: EtOAc, 2:1) to afford the title compound (125 mg, 61%) as a brown solid; MS m/z (ESI) $[M+H]^+$ 313.3.

Intermediate 118: (S)-6-(3-Methylpyrrolidin-1-yl) quinoline-4-carboxylic acid

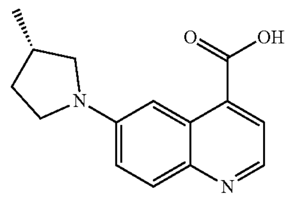 [SMILES: C[C@H]1CCN(c2ccc3nccc(C(=O)O)c3c2)C1]

HCl (4 M in 1,4-dioxane, 0.3 mL) was added to tert-butyl (S)-6-(3-methylpyrrolidin-1-yl)quinoline-4-carboxylate Intermediate 117 (240 mg, 0.77 mmol) in 1,4-dioxane (5 mL) at 0° C. The reaction was stirred at 25° C. for 19 h. The solvent was removed under reduced pressure to give the title compound (197 mg); MS m/z (ESI) $[M+H]^+$ 257.3.

Intermediate 119: tert-Butyl (R)-6-(3-methylpyrrolidin-1-yl)quinoline-4-carboxylate

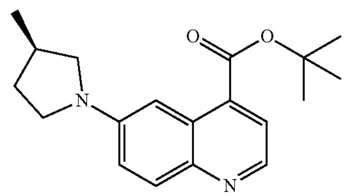 [SMILES: C[C@@H]1CCN(c2ccc3nccc(C(=O)OC(C)(C)C)c3c2)C1]

(R)-3-Methyl-pyrrolidine hydrochloride (118 mg, 0.97 mmol) was added to a mixture of tert-butyl 6-bromoquinoline-4-carboxylate (200 mg, 0.65 mmol), $Cs_2CO_3$ (423 mg, 1.30 mmol), $Pd_2(dba)_3$ (30 mg, 0.03 mmol), and XantPhos (38 mg, 0.06 mmol) in 1,4-dioxane (5 mL) at 20° C. The resulting suspension was then heated at 100° C. for 2 h under $N_2$ (g). The reaction mixture was filtered through Celite®. The solvent was removed under reduced pressure. The residue was purified by preparative TLC (petroleum ether: EtOAc, 2:1), to afford the title compound (135 mg, 66%) as a brown solid; MS m/z (ESI) $[M+H]^+$ 313.4.

Intermediate 120: (R)-6-(3-Methylpyrrolidin-1-yl)quinoline-4-carboxylic acid

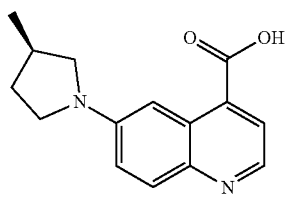 [SMILES: C[C@@H]1CCN(c2ccc3nccc(C(=O)O)c3c2)C1]

HCl (4 M in 1,4-dioxane, 0.65 mL) was added to tert-butyl (R)-6-(3-methylpyrrolidin-1-yl)quinoline-4-carboxylate Intermediate 119 (270 mg, 0.86 mmol) in 1,4-dioxane (5 mL) at 0° C. The reaction was stirred at 25° C. for 19 h. The solvent was removed under reduced pressure to give the title compound (222 mg); MS m/z (ESI) $[M+H]^+$ 257.2.

Intermediate 121: Methyl (S)-6-(2-(trifluoromethyl)pyrrolidin-1-yl)quinoline-4-carboxylate

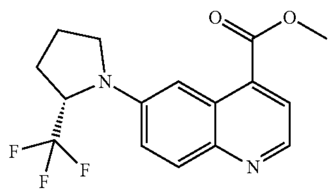 [SMILES: COC(=O)c1ccnc2ccc(N3CCC[C@H]3C(F)(F)F)cc12]

(S)-2-(Trifluoromethyl)pyrrolidine (314 mg, 2.25 mmol) was added to a mixture of methyl 6-bromoquinoline-4-carboxylate (300 mg, 1.13 mmol), $Cs_2CO_3$ (1.10 g, 3.38 mmol) and Pd Catalyst [CAS: 1810068-35-9] (129 mg, 0.11 mmol) in 1,4-dioxane (15 mL) at 25° C. The resulting suspension was heated at 100° C. for 18 h under $N_2$ (g). The solid was filtered off and the filtrate was concentrated under reduced pressure. The residue was purified by preparative TLC (petroleum ether:EtOAc, 1:1) to afford the title compound (150 mg, 41%) as a yellow solid; MS m/z (ESI) $[M+H]^+$ 325.1.

Intermediate 122: (S)-6-(2-(Trifluoromethyl)pyrrolidin-1-yl)quinoline-4-carboxylic acid

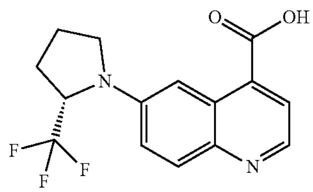 [SMILES: O=C(O)c1ccnc2ccc(N3CCC[C@H]3C(F)(F)F)cc12]

LiOH (55 mg, 2.31 mmol) was added to a solution of methyl (S)-6-(2-(trifluoromethyl)pyrrolidin-1-yl)quinoline-4-carboxylate Intermediate 121 (150 mg, 0.46 mmol) in MeOH (5 mL) and water (1 mL). The reaction was stirred at rt for 2 h. The solvent was removed under reduced pressure. The residue was diluted with water, adjusted to pH 6 with aq HCl (1 M), and extracted with EtOAc. The combined organic phases were washed with water. The organic layer was dried over $Na_2SO_4$, filtered and evaporated to afford the title compound (130 mg, 91%) as a yellow solid; MS m/z (ESI) $[M+H]^+$ 311.05.

Intermediate 123: tert-Butyl 6-(2,2-dimethylpyrrolidin-1-yl)quinoline-4-carboxylate

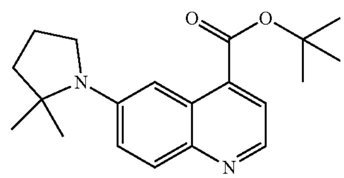 [SMILES: CC(C)(C)OC(=O)c1ccnc2ccc(N3CCCC3(C)C)cc12]

2,2-Dimethylpyrrolidine (193 mg, 1.95 mmol) was added to a mixture of tert-butyl 6-bromoquinoline-4-carboxylate (300 mg, 0.97 mmol), $Cs_2CO_3$ (952 mg, 2.92 mmol) and Pd Catalyst [CAS: 1810068-35-9] (55 mg, 0.05 mmol) in 1,4-dioxane (15 mL) at 25° C. The resulting suspension was stirred at 100° C. for 18 h under $N_2$ (g). The solid was filtered off and the filtrate was concentrated under vacuum. The residue was purified by preparative TLC (petroleum ether: EtOAc, 2:1) to afford the title compound (160 mg, 50%) as a yellow solid; MS m/z (ESI) $[M+H]^+$ 327.3.

Intermediate 124: 6-(2,2-Dimethylpyrrolidin-1-yl)quinoline-4-carboxylic acid

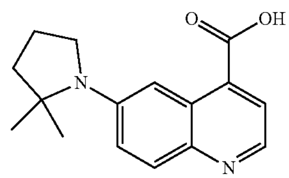 [SMILES: CC1(C)CCCN1c1ccc2nccc(C(=O)O)c2c1]

TFA (3 mL) was added to a solution of tert-butyl 6-(2,2-dimethylpyrrolidin-1-yl)quinoline-4-carboxylate Intermediate 123 (150 mg, 0.46 mmol) in DCM (6 mL). The reaction was stirred at rt for 4 h. The solvent was removed under reduced pressure to give the title compound (300 mg); MS m/z (ESI) $[M+H]^+$ 271.2.

Intermediate 125: tert-Butyl (R)-6-(6-(fluoromethyl)-5-azaspiro[2.4]heptan-5-yl)quinoline-4-carboxylate

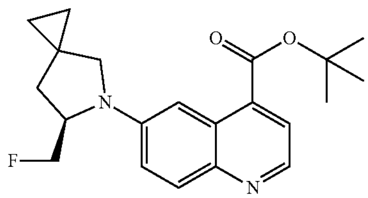 [SMILES: CC(C)(C)OC(=O)c1ccnc2ccc(N3CC4(CC4)C[C@@H]3CF)cc12]

(R)-6-(Fluoromethyl)-5-azaspiro[2.4]heptane hydrochloride (202 mg, 1.22 mmol) was added to a mixture of tert-butyl 6-bromoquinoline-4-carboxylate (250 mg, 0.81 mmol), $Cs_2CO_3$ (793 mg, 2.43 mmol) and Pd Catalyst [CAS: 1810068-35-9] (46 mg, 0.04 mmol) in 1,4-dioxane (15 mL) at 25° C. The resulting suspension was stirred at 100° C. for 4 h under $N_2$ (g). The reaction mixture was filtered, and the filtrate was concentrated under vacuum. The residue was purified by preparative TLC (petroleum ether:EtOAc, 2:1) to afford the title compound (180 mg, 62%) as a yellow solid; MS m/z (ESI) $[M+H]^+$ 357.3.

Intermediate 126: (R)-6-(6-(Fluoromethyl)-5-azaspiro[2.4]heptan-5-yl)quinoline-4-carboxylic acid

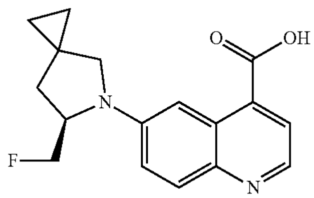 [SMILES: O=C(O)c1ccnc2ccc(N3CC4(CC4)C[C@@H]3CF)cc12]

TFA (3 mL) was added to a solution of tert-butyl (R)-6-(6-(fluoromethyl)-5-azaspiro[2.4]heptan-5-yl)quinoline-4-carboxylate Intermediate 125 (180 mg, 0.50 mmol) in DCM (6 mL). The reaction was stirred at rt for 5 h. The solvent was removed under reduced pressure to give the title compound (152 mg, 100%); MS m/z (ESI) $[M+H]^+$ 301.2.

Intermediate 127: tert-Butyl (S)-6-(2-methylpyrrolidin-1-yl)quinoline-4-carboxylate

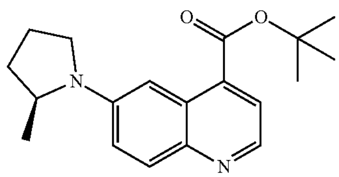 [SMILES: C[C@H]1CCCN1c1ccc2nccc(C(=O)OC(C)(C)C)c2c1]

(S)-2-Methylpyrrolidine (111 mg, 1.30 mmol) was added to a mixture of tert-butyl 6-bromoquinoline-4-carboxylate (200 mg, 0.65 mmol), $Cs_2CO_3$ (634 mg, 1.95 mmol) and Pd Catalyst [CAS: 1810068-35-9] (37 mg, 0.03 mmol) in 1,4-dioxane (5 mL). The mixture was stirred under an atmosphere of $N_2$ (g) at 100° C. overnight. The solvent was removed under reduced pressure. The residue was purified by preparative TLC (petroleum ether:EtOAc, 3:1) to afford the title compound (120 mg, 59%) as a yellow solid; MS m/z (ESI) $[M+H]^+$ 313.3.

Intermediate 128: (S)-6-(2-Methylpyrrolidin-1-yl)quinoline-4-carboxylic acid

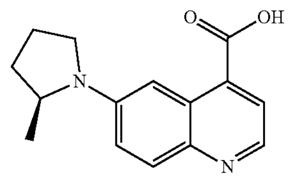 [SMILES: C[C@H]1CCCN1c1ccc2nccc(C(=O)O)c2c1]

TFA (44 mg, 0.38 mmol) was added to a solution of tert-butyl (S)-6-(2-methylpyrrolidin-1-yl)quinoline-4-carboxylate Intermediate 127 (120 mg, 0.38 mmol) in DCM (3 mL). The reaction was stirred at 25° C. overnight. The solvent was removed under reduced pressure to give the title compound; MS m/z (ESI) $[M+H]^+$ 257.15.

Intermediate 129: Methyl (R)-6-(3-fluoroazepan-1-yl)quinoline-4-carboxylate

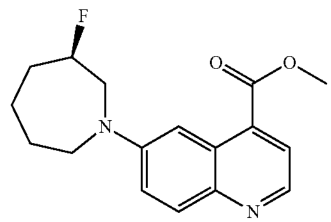 [SMILES: COC(=O)c1ccnc2ccc(N3CCCC[C@@H](F)C3)cc12]

(R)-3-Fluoroazepane hydrobromide (395 mg, 2.00 mmol) was added to a mixture of methyl 6-bromoquinoline-4-carboxylate hydrochloride Intermediate 422 (302 mg, 1.00 mmol), $Cs_2CO_3$ (976 mg, 2.99 mmol), $Pd_2(dba)_3$ (150 mg, 0.16 mmol) and XPhos (150 mg, 0.31 mmol) in 1,4-dioxane (20 mL) at 10° C. The resulting suspension was stirred at 100° C. for 2 h under $N_2$ (g). The reaction mixture was diluted with DCM (2 mL) and filtered. The filtrate was concentrated under reduced pressure. The residue was purified by preparative TLC (petroleum ether:EtOAc, 1:1) to afford the title compound (195 mg, 65%) as a yellow gum; MS m/z (ESI) $[M+H]^+$ 303.1.

Intermediate 130: (R)-6-(3-Fluoroazepan-1-yl)quinoline-4-carboxylic acid

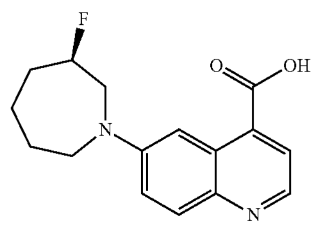 [SMILES: O=C(O)c1ccnc2ccc(N3CCCC[C@@H](F)C3)cc12]

NaOH (97 mg, 2.42 mmol) was added to methyl (R)-6-(3-fluoroazepan-1-yl)quinoline-4-carboxylate Intermediate 129 (195 mg, 0.48 mmol) in MeOH (3 mL) and water (1 mL) at 13° C. The resulting suspension was stirred at 13° C. for 1 h. The reaction mixture was acidified to pH 4 with aq HCl (1 M). The reaction mixture was diluted with water (20 mL), and extracted with EtOAc (3×50 mL). The organic layer was dried over $Na_2SO_4$, filtered and evaporated. The crude product was purified by preparative HPLC PrepMethod P to afford the title compound (20 mg, 14%); MS m/z (ESI) $[M+H]^+$ 289.2.

Intermediate 131: Methyl (S)-6-(3-fluoroazepan-1-yl)quinoline-4-carboxylate

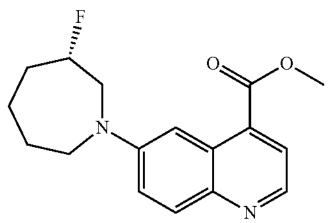 [SMILES: COC(=O)c1ccnc2ccc(N3CCCC[C@H](F)C3)cc12]

(S)-3-Fluoroazepane hydrobromide (395 mg, 2.00 mmol) was added to a mixture of methyl 6-bromoquinoline-4-carboxylate hydrochloride Intermediate 422 (302 mg, 1.00 mmol), $Cs_2CO_3$ (976 mg, 2.99 mmol), $Pd_2(dba)_3$ (91 mg, 0.10 mmol) and XPhos (95 mg, 0.20 mmol) in 1,4-dioxane (5 mL) at 13° C. The resulting suspension was stirred at 100° C. overnight under $N_2$ (g). The reaction mixture was diluted with DCM (20 mL) and filtered. The filtrate was concentrated under reduced pressure. The residue was purified by preparative TLC (petroleum ether:EtOAc, 1:1) to afford the title compound (173 mg, 57%) as a yellow gum; MS m/z (ESI) $[M+H]^+$ 303.1.

Intermediate 132: (S)-6-(3-Fluoroazepan-1-yl)quinoline-4-carboxylic acid

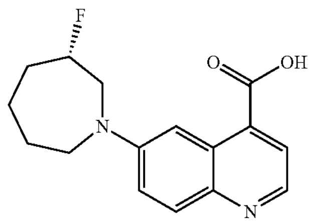 [SMILES: O=C(O)c1ccnc2ccc(N3CCCC[C@H](F)C3)cc12]

NaOH (80 mg, 2.00 mmol) was added to methyl (S)-6-(3-fluoroazepan-1-yl)quinoline-4-carboxylate Intermediate 131 (173 mg, 0.40 mmol) in MeOH (3 mL) and water (1 mL) 13° C. The resulting solution was stirred at 13° C. for 1 h. The reaction mixture was acidified to pH 4 with aq HCl (1 M). The reaction mixture was diluted with water (20 mL), and extracted with EtOAc (3×50 mL). The organic layer was dried over $Na_2SO_4$, filtered and evaporated. The crude product was purified by preparative HPLC PrepMethod P to afford the title compound (84 mg, 73%) as an orange solid; MS m/z (ESI) $[M+H]^+$ 289.2.

Intermediate 133: tert-Butyl (R)-6-(7-methyl-1,4-oxazepan-4-yl)quinoline-4-carboxylate

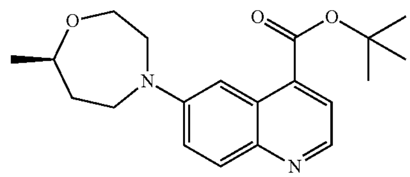 [SMILES: C[C@@H]1CCN(c2ccc3nccc(C(=O)OC(C)(C)C)c3c2)CCO1]

(R)-7-Methyl-1,4-oxazepane hydrochloride (100 mg, 0.66 mmol) was added to a mixture of tert-butyl 6-bromoquinoline-4-carboxylate (185 mg, 0.60 mmol), $Cs_2CO_3$ (587 mg, 1.80 mmol), and RuPhos Pd G3 (50 mg, 0.06 mmol) in 1,4-dioxane (3 mL) at 10° C. The resulting suspension was stirred at 100° C. for 2 h under $N_2$ (g). The reaction mixture was filtered, and the filtrate was washed with water (3 mL). The aqueous layer was extracted with EtOAc (3×15 mL). The organic layers were combined and washed with water (3×5 mL). The organic layer was dried over $Na_2SO_4$, filtered and evaporated. The residue was purified by preparative TLC (petroleum ether:EtOAc, 2:1) to afford the title compound (155 mg, 75%) as a brown gum; MS m/z (ESI) $[M+H]^+$ 343.15.

Intermediate 134: (R)-6-(7-Methyl-1,4-oxazepan-4-yl)quinoline-4-carboxylic acid

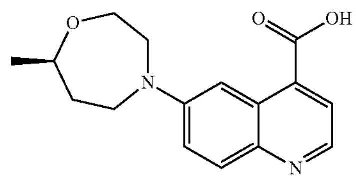 [SMILES: C[C@@H]1CCN(c2ccc3nccc(C(=O)O)c3c2)CCO1]

TFA (5 mL, 65 mmol) was added to a stirred solution of tert-butyl (R)-6-(7-methyl-1,4-oxazepan-4-yl)quinoline-4-carboxylate Intermediate 133 (136 mg, 0.40 mmol) in DCM (5 mL) at 3° C. The resulting solution was stirred at 3° C. overnight. The solvent was removed under reduced pressure to afford the title compound (265 mg) as a dark red gum. MS m/z (ESI) $[M+H]^+$ 287.1.

Intermediate 135: tert-Butyl (S)-6-(7-methyl-1,4-oxazepan-4-yl)quinoline-4-carboxylate

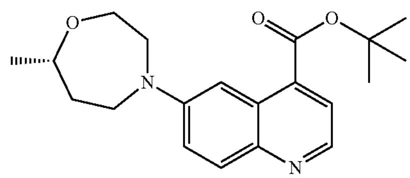 [SMILES: C[C@H]1CCN(c2ccc3nccc(C(=O)OC(C)(C)C)c3c2)CCO1]

(S)-7-Methyl-1,4-oxazepane hydrochloride (100 mg, 0.66 mmol) was added to a mixture of tert-butyl 6-bromoquinoline-4-carboxylate (185 mg, 0.60 mmol), $Cs_2CO_3$ (587 mg, 1.80 mmol) and RuPhos Pd G3 (50 mg, 0.06 mmol) in 1,4-dioxane (3 mL) at 10° C. The resulting suspension was stirred at 100° C. for 2 h under $N_2$ (g). The reaction mixture was filtered, the filtrate was washed with water (3 mL). The aqueous layer was extracted with EtOAc (3×15 mL). The organic layers were combined and washed with water (3×5 mL). The organic layer was dried over $Na_2SO_4$, filtered and evaporated. The residue was purified by preparative TLC (petroleum ether:EtOAc, 2:1) to afford the title compound (166 mg, 81%) as a brown gum; MS m/z (ESI) [M+H]+ 343.15.

Intermediate 136: (S)-6-(7-Methyl-1,4-oxazepan-4-yl)quinoline-4-carboxylic acid

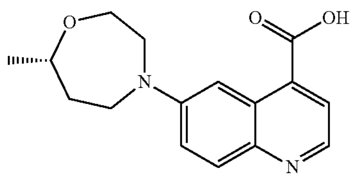 [SMILES: C[C@H]1CCN(c2ccc3nccc(C(=O)O)c3c2)CCO1]

TFA (5 mL, 65 mmol) added slowly to a stirred solution of tert-butyl (S)-6-(7-methyl-1,4-oxazepan-4-yl)quinoline-4-carboxylate Intermediate 135 (148 mg, 0.43 mmol) in DCM (5 mL) at 3° C. The resulting solution was stirred at 3° C. overnight. The solvent was removed under reduced pressure to afford the title compound (405 mg) as a dark red gum; MS m/z (ESI) [M+H]+ 287.1.

Intermediate 137: Methyl (S)-6-(3-methyl-1,4-oxazepan-4-yl)quinoline-4-carboxylate

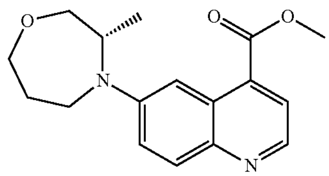 [SMILES: COC(=O)c1ccnc2ccc(N3CCCOC[C@@H]3C)cc12]

(S)-3-Methyl-1,4-oxazepane hydrochloride (228 mg, 1.50 mmol) was added to a mixture of methyl 6-bromoquinoline-4-carboxylate (200 mg, 0.75 mmol), $Cs_2CO_3$ (1.47 g, 4.51 mmol), and Pd Catalyst [CAS: 1810068-35-9] (43 mg, 0.04 mmol) in 1,4-dioxane (3 mL) at 5° C. The resulting suspension was stirred at 100° C. for 2 days under $N_2$ (g). The reaction mixture was diluted with EtOAc. The solvent was removed under reduced pressure. The residue was diluted with water (50 mL), and extracted with EtOAc (3×50 mL). The organic layers were combined and washed with brine (200 mL). The organic layer was dried over $Na_2SO_4$, filtered and evaporated. The residue was purified by preparative TLC (petroleum ether:EtOAc, 1:1) to afford the title compound (147 mg, 65%) as an orange solid; MS m/z (ESI) [M+H]+ 301.0.

Intermediate 138: (S)-6-(3-Methyl-1,4-oxazepan-4-yl)quinoline-4-carboxylic acid

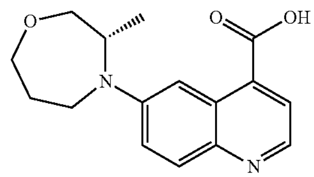 [SMILES: C[C@H]1COCCCN1c1ccc2nccc(C(=O)O)c2c1]

NaOH (91 mg, 2.3 mmol) was added to methyl (R)-6-(3-methyl-1,4-oxazepan-4-yl)quinoline-4-carboxylate Intermediate 137 (136 mg, 0.45 mmol) in MeOH (3 mL) and water (1 mL) at 10° C. The resulting solution was stirred at 10° C. for 1 h. The solvent was removed under reduced pressure. The residue was diluted with water (20 mL) and adjusted to pH 5 with aq aq HCl (1 M). The mixture was diluted with water (10 mL), and extracted with EtOAc (6×30 mL). The organic layers were combined, dried over $Na_2SO_4$, filtered and evaporated. The crude product was purified by preparative HPLC PrepMethod F to afford the title compound (80 mg, 62%) as an orange solid; MS m/z (ESI) [M+H]+ 287.0.

Intermediate 139: tert-Butyl (R)-6-(2-methyl-1,4-oxazepan-4-yl)quinoline-4-carboxylate

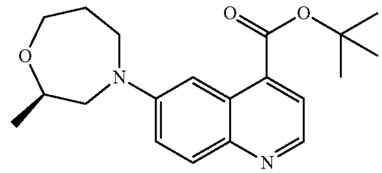 [SMILES: C[C@@H]1CN(c2ccc3nccc(C(=O)OC(C)(C)C)c3c2)CCCO1]

(R)-2-Methyl-1,4-oxazepane (168 mg, 1.46 mmol) was added to a mixture of tert-butyl 6-bromoquinoline-4-carboxylate (300 mg, 0.97 mmol), $Cs_2CO_3$ (952 mg, 2.92 mmol), $Pd_2(dba)_3$ (89 mg, 0.10 mmol) and XantPhos (113 mg, 0.19 mmol) in 1,4-dioxane (5 mL). The reaction was stirred under an atmosphere of $N_2$ (g) at 100° C. for 3 h. The solvent was removed under reduced pressure. The residue was purified by preparative TLC (petroleum ether:EtOAc, 2:1) to afford the title compound (150 mg, 45%) as a yellow solid; MS m/z (ESI) [M+H]+ 343.3.

Intermediate 140: (R)-6-(2-Methyl-1,4-oxazepan-4-yl)quinoline-4-carboxylic acid

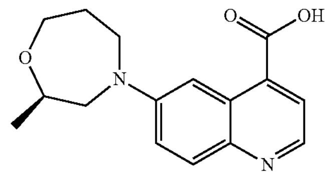 [SMILES: C[C@@H]1CN(c2ccc3nccc(C(=O)O)c3c2)CCCO1]

TFA (50 mg, 0.44 mmol) was added to tert-butyl (R)-6-(2-methyl-1,4-oxazepan-4-yl)quinoline-4-carboxylate Intermediate 139 (150 mg, 0.44 mmol) in DCM (3 mL). The reaction was stirred at 25° C. overnight. The solvent was removed by under reduced pressure to give the title compound; MS m/z (ESI) $[M+H]^+$ 287.3.

Intermediate 141: Ethyl 6-(3-methoxyazetidin-1-yl)quinoline-4-carboxylate

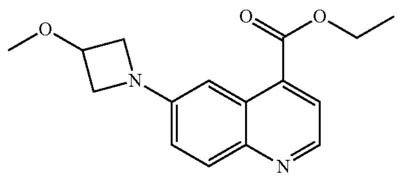 [SMILES: CCOC(=O)c1ccnc2ccc(N3CC(OC)C3)cc12]

A mixture of ethyl 6-bromoquinoline-4-carboxylate (140 mg, 0.50 mmol), $Cs_2CO_3$ (651 mg, 2.00 mmol), RuPhos Pd G4 (43 mg, 0.05 mmol), 3-methoxyazetidine hydrochloride (80 mg, 0.65 mmol) and dioxane (1.2 mL) under $N_2$ (g) was stirred at 90° C. for 5.5 h. The reaction mixture was diluted with EtOAc (5 mL), SiliaMetS® Thiol (150 mg; loading 1.4 mmol/g) was added and the mixture was stirred for 1 h. The mixture was filtered through a pad of Celite® 521, the filter pad was washed with EtOAc (12 mL) and the filtrate was concentrated. The residue was purified using preparative HPLC, PrepMethod H, (gradient: 30-70%) to give the title compound (104 mg, 0.36 mmol); MS (ESI) m/z $[M+H]^+$ 287.3.

Intermediate 142: 6-(3-Methoxyazetidin-1-yl)quinoline-4-carboxylic acid

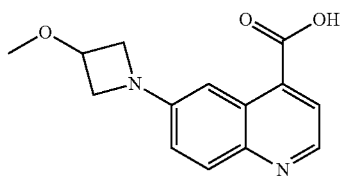 [SMILES: COC1CN(c2ccc3nccc(C(=O)O)c3c2)C1]

Aq NaOH (3.8 M, 184 μL, 0.70 mmol) was added to a solution of ethyl 6-(3-methoxyazetidin-1-yl)quinoline-4-carboxylate Intermediate 141 (100 mg, 0.35 mmol) in MeOH (2 mL) and the reaction mixture was stirred at rt overnight. Aq HCl (3.8 M, 230 μL, 0.87 mmol) was added dropwise and the resulting mixture was concentrated and freeze-dried from a mixture of $MeCN/H_2O$ to give the crude title compound (0.102 g); MS m/z (ESI) $[M+H]^+$ 259.1.

Intermediate 143: Ethyl 6-morpholinoquinoline-4-carboxylate

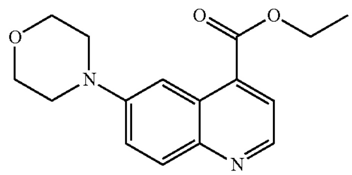

Morpholine (0.22 mL, 2.5 mmol) was added to a mixture of ethyl 6-bromoquinoline-4-carboxylate (0.355 g, 1.27 mmol), $Pd(dba)_2$ (36 mg, 0.06 mmol), RuPhos (59 mg, 0.13 mmol) and $K_3PO_4$ (0.538 g, 2.53 mmol) in tert-BuOH (2.3 mL). The flask was sealed, purged with $N_2$ (g), and heated at 90° C. overnight. The reaction mixture was diluted with EtOAc, washed sequentially with water and brine. The organic layer was dried by passing through a phase separator and concentrated under reduced pressure to give the title compound (110 mg, 30%); MS m/z (ESI), $[M+H]^+$ 287.2.

Intermediate 144: 6-Morpholinoquinoline-4-carboxylic acid

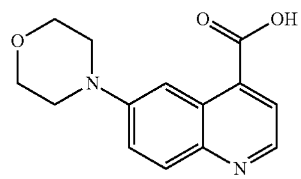 [SMILES: O=C(O)c1ccnc2ccc(N3CCOCC3)cc12]

NaOH (31 mg, 0.77 mmol) was added to a solution of ethyl 6-morpholinoquinoline-4-carboxylate Intermediate 143 (110 mg, 0.38 mmol) in MeOH (4 mL), and heated at 60° C. for 2 h. The reaction mixture was cooled to rt, and aq HCl (0.023 mL) was added. The reaction mixture was concentrated under reduced pressure to give the title compound (95 mg, 96%); MS m/z (ESI), $[M+H]^+$ 259.1.

Intermediate 145: tert-Butyl (R)-6-(2-(fluoromethyl) morpholino)quinoline-4-carboxylate

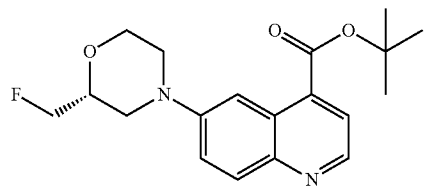 [SMILES: CC(C)(C)OC(=O)c1ccnc2ccc(N3CCO[C@@H](CF)C3)cc12]

A mixture of tert-butyl 6-bromoquinoline-4-carboxylate (0.616 g, 2 mmol), (R)-2-(fluoromethyl)morpholine hydrochloride (0.405 g, 2.60 mmol), RuPhos Pd G4 (0.170 g, 0.20 mmol), $Cs_2CO_3$ (1.955 g, 6.00 mmol) and dioxane (5 mL) under $N_2$ (g) was stirred vigorously at 85-90° C. for 19 h. After cooling to rt the reaction mixture was diluted with EtOAc (8 mL) and stirred with SiliaMetS® Thiol scavenger (0.7 g; 1.4 mmol/g) at rt overnight. The reaction mixture was filtered through Celite® 521. The filter pad was washed with EtOAc and the combined filtrates were concentrated under reduced pressure. The residue was purified by preparative HPLC, PrepMethod H, (gradient: 35-75%) to give the title compound (0.62 g, 89%) as a yellow syrup; MS (ESI) m/z $[M+H]^+$ 347.3.

Intermediate 146: (R)-6-(2-(Fluoromethyl)morpholino)quinoline-4-carboxylic acid

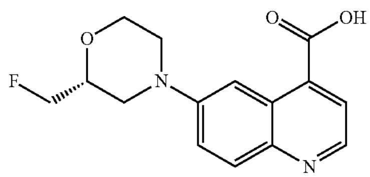 [SMILES: O=C(O)c1ccnc2ccc(N3CCO[C@@H](CF)C3)cc12]

A solution of tert-butyl (R)-6-(2-(fluoromethyl)morpholino)quinoline-4-carboxylate Intermediate 145 (0.554 g, 1.60 mmol) in 90% TFA (aq, 3 mL) was stirred at 50° C. for 70 min. The volatiles were removed under reduced pressure and the residue was concentrated from heptane twice to give the crude title compound (1.09 g); MS (ESI) m/z $[M+H]^+$ 291.1.

Intermediate 147: Ethyl 6-((2R,6R)-2,6-dimethylmorpholino)quinoline-4-carboxylate

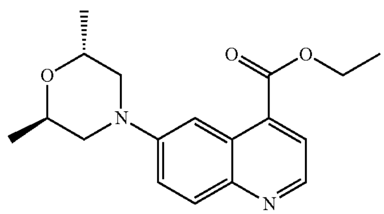 [SMILES: CCOC(=O)c1ccnc2ccc(N3C[C@@H](C)O[C@H](C)C3)cc12]

A mixture of ethyl 6-bromoquinoline-4-carboxylate (0.098 g, 0.35 mmol), $Cs_2CO_3$ (0.456 g, 1.40 mmol), RuPhos Pd G4 (0.030 g, 0.04 mmol), (2R,6R)-2,6-dimethylmorpholine hydrochloride (70 mg, 0.46 mmol) and dioxane (0.9 mL) under $N_2$ (g) was stirred at 90° C. for 4.5 h. After cooling to rt, SilaMetS® Thiol scavenger (150 mg; loading 1.4 mmol/g) was added and the mixture was stirred overnight, diluted with EtOAc (3 mL) and filtered through a pad of Celite® 521. The filter pad was washed with EtOAc (10 mL) and the filtrate was concentrated. The residue was purified by preparative HPLC, PrepMethod H, (gradient: 35-75%) to give the title compound (83 mg, 76%) as a yellow film; MS (ESI) m/z $[M+H]^+$ 315.2.

Intermediate 148: 6-((2R,6R)-2,6-Dimethylmorpholino)quinoline-4-carboxylic acid

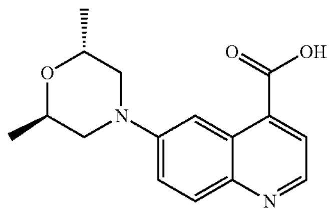 [SMILES: C[C@@H]1CN(c2ccc3nccc(C(=O)O)c3c2)C[C@@H](C)O1]

Aq NaOH (3.8 M. 158 μL, 0.60 mmol) was added to a solution of ethyl 6-((2R,6R)-2,6-dimethylmorpholino)quinoline-4-carboxylate Intermediate 147 (81 mg, 0.26 mmol) in MeOH (2 mL) and the reaction was stirred at rt for 2.5 h and then at 50° C. for 30 min after which the reaction was allowed to reach rt. Aq HCl (3.8 M, 0.12 mL, 0.45 mmol) was added dropwise and the resulting mixture was concentrated under reduced pressure at rt to give the crude title compound (99 mg) as a red solid; MS (ESI) m/z $[M+H]^+$ 287.3.

Intermediate 149: tert-Butyl 6-((2R,6S)-2,6-dimethylmorpholino)quinoline-4-carboxylate

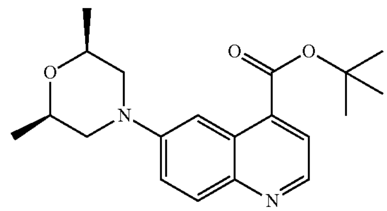 [SMILES: C[C@@H]1CN(c2ccc3nccc(C(=O)OC(C)(C)C)c3c2)C[C@H](C)O1]

A mixture of tert-butyl 6-bromoquinoline-4-carboxylate (149 mg, 0.48 mmol), $Cs_2CO_3$ (473 mg, 1.45 mmol), RuPhos Pd G3 (40 mg, 0.05 mmol), (2R,6S)-2,6-dimethylmorpholine (69 mg, 0.63 mmol) and dioxane (1.2 mL) under $N_2$ (g) was stirred at for 22 h. After cooling to rt the reaction mixture was diluted with EtOAc (2 mL). SiliaMetS® Thiol (ca 150 mg; loading 1.4 mmol/g) was added and the mixture was stirred for 2 h and filtered through a pad of Celite® 521. The filter pad was washed with EtOAc (9 mL) and the combined filtrate was concentrated. The residue was purified by preparative HPLC, PrepMethod H, (gradient: 35-75%) to give the title compound (141 mg, 85%); MS (ESI) m/z $[M+H]^+$ 343.4.

Intermediate 150: tert-Butyl (S)-6-(2-(fluoromethyl)morpholino)quinoline-4-carboxylate

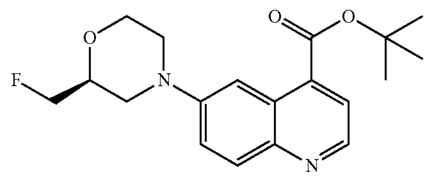 [SMILES: CC(C)(C)OC(=O)c1ccnc2ccc(N3CCO[C@H](CF)C3)cc12]

A mixture of tert-butyl 6-bromoquinoline-4-carboxylate (149 mg, 0.48 mmol), $Cs_2CO_3$ (473 mg, 1.45 mmol), RuPhos Pd G3 (40 mg, 0.05 mmol) (S)-2-(fluoromethyl)morpholine hydrochloride (98 mg, 0.63 mmol) and dioxane (1.2 mL) under $N_2$ (g) was stirred at 85° C. for 19 h. After cooling to rt, the reaction mixture was diluted with EtOAc (2 mL). SilaMetS® Thiol scavenger (ca 150 mg; loading 1.4 mmol/g) was added and the mixture was stirred for 2 h and filtered through a pad of Celite® 521. The filter pad was washed with EtOAc (9 mL) and the combined filtrates were concentrated. The residue was purified by preparative HPLC PrepMethod H, (gradient: 35-75%) to give the title compound (137 mg, 82%); MS m/z (ESI) $[M+H]^+$ 347.3.

Intermediate 151: Ethyl (R)-6-(2-methylmorpholino)quinoline-4-carboxylate

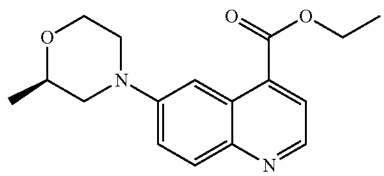 [SMILES: CCOC(=O)c1ccnc2ccc(N3CCO[C@H](C)C3)cc12]

A mixture of ethyl 6-bromoquinoline-4-carboxylate (0.280 g, 1.0 mmol), (R)-2-methylmorpholine hydrochloride (0.179 g, 1.30 mmol), RuPhos Pd G4 (0.085 g, 0.10 mmol), $Cs_2CO_3$ (0.977 g, 3.00 mmol) and dioxane (2.5 mL) under $N_2$ (g) was stirred vigorously at 85-90° C. for 1 h 45 min. After cooling to rt the reaction mixture was diluted with EtOAc (5 mL) and stirred with SilaMetS® Thiol scavenger (0.5 g; loading: 1.4 mmol/g) at rt for 1.5 h. The reaction mixture was filtered through Celite® 521. The filter was washed with EtOAc and the combined filtrates were concentrated. The residue was purified by preparative HPLC, PrepMethod H, (gradient: 30-70%) to give the title compound (0.248 g, 83%) as a yellow solid; MS (ESI) m/z $[M+H]^+$ 301.3.

Intermediate 152: (R)-6-(2-Methylmorpholino)quinoline-4-carboxylic acid

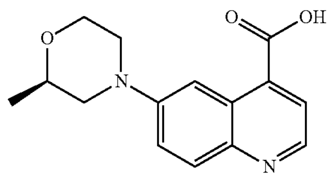 [SMILES: C[C@@H]1CN(c2ccc3nccc(C(=O)O)c3c2)CCO1]

Aq NaOH (3.8 M, 0.42 mL, 1.6 mmol) was added to a solution of ethyl (R)-6-(2-methylmorpholino)quinoline-4-carboxylate Intermediate 151 (241 mg, 0.80 mmol) in MeOH (5 mL) and the reaction was stirred at rt overnight and at 50° C. for 1 h. Additional aq NaOH (3.8 M, 106 μL, 0.40 mmol) was added and the heating was continued for 20 min. Aq HCl (3.8 M, 528 μL, 2.01 mmol) was added dropwise and the resulting mixture was concentrated under reduced pressure. The residue was concentrated from MeCN to give the crude (R)-6-(2-methylmorpholino)quinoline-4-carboxylic acid (0.309 g) as a red solid; MS (ESI) m/z $[M+H]^+$ 273.1.

Intermediate 153: Ethyl (R)-6-(2-(trifluoromethyl) morpholino)quinoline-4-carboxylate

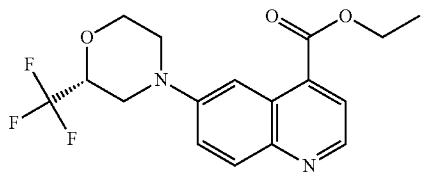 [SMILES: CCOC(=O)c1ccnc2ccc(N3CCO[C@@H](C(F)(F)F)C3)cc12]

A mixture of ethyl 6-bromoquinoline-4-carboxylate (0.098 g, 0.35 mmol), $Cs_2CO_3$ (0.456 g, 1.40 mmol), RuPhos Pd G4 (0.030 g, 0.04 mmol) and (R)-2-(trifluoromethyl)-morpholine hydrochloride (0.088 g, 0.46 mmol) in dioxane (0.9 mL) under $N_2$ (g) was stirred at 90° C. for 4.5 h. After cooling to rt SilaMetS® Thiol scavenger (0.150 g; loading 1.4 mmol/g) was added and the mixture was stirred overnight at rt. The mixture was diluted with EtOAc (3 mL) and filtered through a pad of Celite® 521. The filter pad was washed with EtOAc (10 mL) and the combined filtrates were concentrated. The residue was purified by preparative HPLC, PrepMethod H, (gradient: 35-75%) to give the title compound (0.113 g, 91%) as a yellow film; MS (ESI) m/z $[M+H]^+$ 355.2.

Intermediate 154: (R)-6-(2-(Trifluoromethyl)morpholino)quinoline-4-carboxylic acid

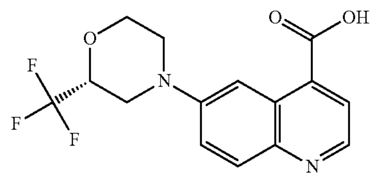 [SMILES: O=C(O)c1ccnc2ccc(N3CCO[C@@H](C(F)(F)F)C3)cc12]

Aq NaOH (3.8 M, 0.16 mL, 0.60 mmol) was added to a solution of ethyl (R)-6-(2-(trifluoromethyl)morpholino)quinoline-4-carboxylate Intermediate 153 (0.106 g, 0.30 mmol) in MeOH (2 mL) and the reaction was stirred at rt for 2.5 h and then at 50° C. for 30 min. The reaction was allowed to reach rt, aq HCl (3.8 M, 0.118 mL, 0.45 mmol) was added dropwise and the resulting mixture was concentrated to give the crude title compound (0.121 g) as a red solid; MS (ESI) m/z $[M+H]^+$ 327.1.

Intermediate 155: Ethyl (S)-6-(2-(trifluoromethyl) morpholino)quinoline-4-carboxylate

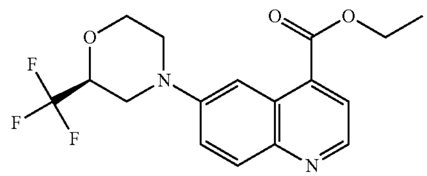 [SMILES: CCOC(=O)c1ccnc2ccc(N3CCO[C@H](C(F)(F)F)C3)cc12]

A mixture of ethyl 6-bromoquinoline-4-carboxylate (0.098 g, 0.35 mmol), $Cs_2CO_3$ (0.456 g, 1.40 mmol), RuPhos Pd G4 (0.030 g, 0.04 mmol) and (S)-2-(trifluoromethyl)-morpholine hydrochloride (0.088 g, 0.46 mmol) in dioxane (0.9 mL) under $N_2$ (g) was stirred at 90° C. for 4.5 h. After cooling to rt SilaMetS® Thiol scavenger (0.150 g; loading 1.4 mmol/g) was added and the mixture was stirred overnight at rt. The mixture was diluted with EtOAc (3 mL) and filtered through a pad of Celite® 521. The filter pad was washed with EtOAc (10 mL) and the combined filtrates were concentrated. The residue was purified by preparative HPLC, PrepMethod H, (gradient: 35-75%) to give the title compound (0.114 g, 92%) as a yellow film; MS (ESI) m/z $[M+H]^+$ 355.2.

Intermediate 156: (S)-6-(2-(Trifluoromethyl)morpholino)quinoline-4-carboxylic acid

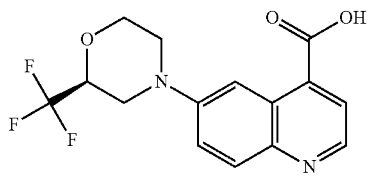 [SMILES: O=C(O)c1ccnc2ccc(N3CCO[C@H](C(F)(F)F)C3)cc12]

Aq NaOH (3.8 M, 159 μL, 0.60 mmol) was added to a solution of ethyl (S)-6-(2-(trifluoromethyl)morpholino)quinoline-4-carboxylate Intermediate 155 (0.107 g, 0.30 mmol) in MeOH (2 mL) and the reaction was stirred at rt for 2.5 h and then at 50° C. for 30 min. The reaction was allowed to reach rt, aq HCl (3.8 M, 119 μL, 0.45 mmol) was added and the resulting mixture was concentrated to give the crude title compound (0.120 g) as a red solid; MS (ESI) m/z $[M+H]^+$ 327.17.

Intermediate 157: Ethyl 6-((1S,4S)-2-oxa-5-azabicyclo[2.2.1]heptan-5-yl)quinoline-4-carboxylate

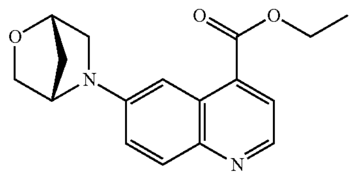 [SMILES: CCOC(=O)c1ccnc2ccc(N3C[C@@H]4C[C@H]3CO4)cc12]

A mixture of ethyl 6-bromoquinoline-4-carboxylate (0.098 g, 0.35 mmol), (1S,4S)-2-oxa-5-azabicyclo[2.2.1] heptane (0.045 g, 0.46 mmol), RuPhos Pd G4 (0.030 g, 0.04 mmol), $Cs_2CO_3$ (0.342 g, 1.05 mmol) and dioxane (0.9 mL) under $N_2$ (g) was stirred vigorously at 85-90° C. for 1 h 50 min. After cooling to rt the reaction mixture was diluted with EtOAc (3 mL) and stirred with SilaMetS® Thiol scavenger (0.15 g; 1.4 mmol/g) at rt overnight. The reaction mixture was filtered through Celite® 521. The filter pad was washed with EtOAc and the combined filtrates were concentrated. The residue was purified by preparative HPLC, PrepMethod H, (gradient: 25-65%) to give the title compound (0.097 g, 93%) as a yellow solid; MS (ESI) m/z $[M+H]^+$ 299.2.

Intermediate 158: 6-((1S,4S)-2-Oxa-5-azabicyclo[2.2.1]heptan-5-yl)quinoline-4-carboxylic acid

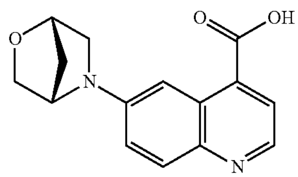 [SMILES: O=C(O)c1ccnc2ccc(N3C[C@@H]4C[C@H]3CO4)cc12]

Aq NaOH (3.8 M, 0.16 mL, 0.62 mmol) was added to a solution of ethyl 6-((1S,4S)-2-oxa-5-azabicyclo[2.2.1]heptan-5-yl)quinoline-4-carboxylate Intermediate 157 (0.092 g, 0.31 mmol) in MeOH (2 mL) and the reaction mixture was stirred at 50° C. for 90 min and then at rt overnight. Aq HCl (3.8 M, 0.122 mL, 0.46 mmol) was added dropwise and the resulting mixture was concentrated at rt to give the crude title compound (0.110 g) as a red solid; MS (ESI) m/z $[M+H]^+$ 271.1.

Intermediate 159: Ethyl 6-α1R,4R)-2-oxa-5-azabicyclo[2.2.1]heptan-5-yl)quinoline-4-carboxylate

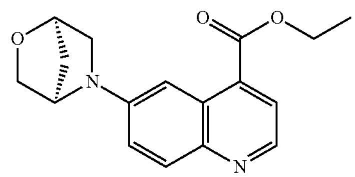 [SMILES: CCOC(=O)c1ccnc2ccc(N3C[C@H]4C[C@@H]3CO4)cc12]

A mixture of ethyl 6-bromoquinoline-4-carboxylate (0.098 g, 0.35 mmol), (1R,4R)-2-oxa-5-azabicyclo[2.2.1] heptane hydrochloride (0.062 g, 0.46 mmol), RuPhos Pd G4 (0.030 g, 0.04 mmol), $Cs_2CO_3$ (0.342 g, 1.05 mmol) and dioxane (0.9 mL) under $N_2$ (g) was stirred vigorously at 85-90° C. for 85 min. After cooling to rt the reaction mixture was diluted with EtOAc (3 mL) and stirred with SilaMetS® Thiol scavenger (0.15 g; 1.4 mmol/g) at rt overnight. The mixture was filtered through Celite® 521. The filter pad was washed with EtOAc and the combined filtrates were concentrated. The residue was purified by preparative HPLC, PrepMethod H, (gradient: 15-55%) to give the title compound (0.087 g, 83%) as a solid; MS (ESI) m/z $[M+H]^+$ 299.3.

Intermediate 160: 6-α1R,4R)-2-Oxa-5-azabicyclo[2.2.1]heptan-5-yl)quinoline-4-carboxylic acid

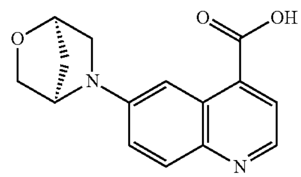 [SMILES: O=C(O)c1ccnc2ccc(N3C[C@H]4C[C@@H]3CO4)cc12]

Aq NaOH (3.8 M, 0.15 mL, 0.56 mmol) was added to a solution of ethyl 6-((1R,4R)-2-oxa-5-azabicyclo[2.2.1]heptan-5-yl)quinoline-4-carboxylate Intermediate 159 (0.084 g, 0.28 mmol) in MeOH (2 mL) and the reaction was stirred at 50° C. for 1 h 30 min and then at rt overnight. Aq HCl (3.8 M, 0.11 mL, 0.42 mmol) was added dropwise and the resulting mixture was concentrated at rt to give the crude title compound (0.099 g) as a red solid; MS (ESI) m/z $[M+H]^+$ 271.2.

Intermediate 161: Ethyl 6-(6-oxa-3-azabicyclo[3.1.1]heptan-3-yl)quinoline-4-carboxylate

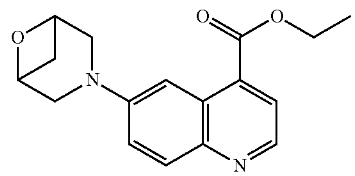 [SMILES: CCOC(=O)c1ccnc2ccc(N3CC4CC(C3)O4)cc12]

A mixture of ethyl 6-bromoquinoline-4-carboxylate (0.098 g, 0.35 mmol), $Cs_2CO_3$ (0.456 g, 1.40 mmol), RuPhos Pd G4 (0.030 g, 0.04 mmol), 6-oxa-3-azabicyclo[3.1.1]heptane 4-methylbenzenesulfonate (0.125 g, 0.46 mmol) and dioxane (0.9 mL) was stirred at 90° C. for 4.5 h under $N_2$ (g). After cooling to rt SilaMetS® Thiol scavenger (0.15 g; loading 1.4 mmol/g) was added and the mixture was stirred overnight at rt, diluted with EtOAc (3 mL) and filtered through a pad of Celite® 521. The filter pad was washed with EtOAc (10 mL) and the combined filtrate was concentrated. The residue was purified by preparative HPLC, PrepMethod H, (gradient: 20-60%) to give the compound as a yellow film; MS (ESI) m/z $[M+H]^+$ 299.3.

Intermediate 162: 6-(6-Oxa-3-azabicyclo[3.1.1]heptan-3-yl)quinoline-4-carboxylic acid

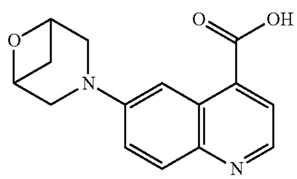 [SMILES: O=C(O)c1ccnc2ccc(N3CC4CC(C3)O4)cc12]

Aq NaOH 3.8 M, 0.16 mL, 0.60 mmol) was added to a solution of ethyl 6-(6-oxa-3-azabicyclo[3.1.1]heptan-3-yl) quinoline-4-carboxylate Intermediate 161 (89 mg, 0.30 mmol) in MeOH (2 mL) and the reaction was stirred at rt overnight. 1 M TFA in MeOH (299 μL, 0.30 mmol) was added dropwise and the resulting mixture was concentrated at rt. The residue was slurried in MeCN and concentrated to give the crude title compound (0.123 g) as a red solid; MS (ESI) m/z $[M+H]^+$ 271.2.

Intermediate 163: Ethyl 6-((2S,6S)-2,6-dimethylmorpholino)quinoline-4-carboxylate

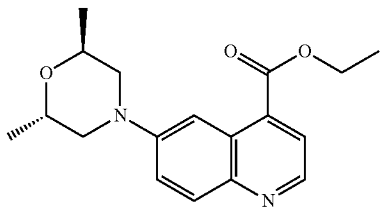 [SMILES: CCOC(=O)c1ccnc2ccc(N3C[C@H](C)O[C@@H](C)C3)cc12]

A mixture of ethyl 6-bromoquinoline-4-carboxylate (0.098 g, 0.35 mmol), (2S,6S)-2,6-dimethylmorpholine (0.052 g, 0.46 mmol), RuPhos Pd G4 (0.030 g, 0.04 mmol), $Cs_2CO_3$ (0.342 g, 1.05 mmol) and dioxane (0.9 mL) under $N_2$ (g) was stirred vigorously at 85-90° C. for 1.5 h. After cooling to rt the reaction mixture was diluted with EtOAc (3 mL), stirred with SilaMetS® Thiol scavenger (0.15 g; 1.4 mmol/g) at rt overnight and filtered through Celite® 521. The filter pad was washed with EtOAc and the combined filtrates were concentrated. The residue was purified by preparative HPLC, PrepMethod H (gradient: 35-75%) to give the title compound (0.109 g, 99%) as a yellow syrup; MS (ESI) m/z $[M+H]^+$ 315.3.

Intermediate 164: 6-((2S,6S)-2,6-Dimethylmorpholino)quinoline-4-carboxylic acid

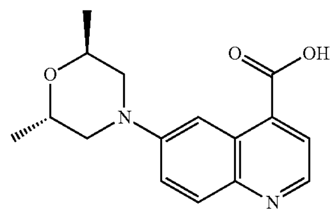 [SMILES: C[C@H]1CN(c2ccc3nccc(C(=O)O)c3c2)C[C@H](C)O1]

Aq NaOH (3.8 M, 149 μL, 0.57 mmol) was added to a solution of ethyl 6-((2S,6S)-2,6-dimethylmorpholino)quinoline-4-carboxylate Intermediate 163 (89 mg, 0.28 mmol) in MeOH (2 mL) and the reaction was stirred at rt overnight. Additional aq NaOH (3.8 M, 37 μL, 0.14 mmol) was added and the reaction mixture was stirred at 50° C. for 45 min. The reaction was allowed to reach rt, Aq HCl (3.8 M, 149 μL, 0.57 mmol) was added dropwise and the resulting mixture was concentrated and freeze-dried from MeCN/$H_2O$ to give the crude title compound (0.116 g) as a red solid; m/z (ESI) $[M+H]^+$ 287.2.

Intermediate 165: Ethyl 6-(8-oxa-3-azabicyclo[3.2.1]octan-3-yl)quinoline-4-carboxylate

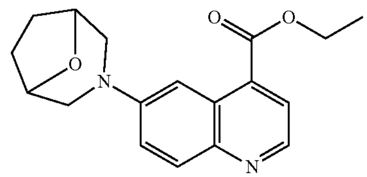 [SMILES: CCOC(=O)c1ccnc2ccc(N3CC4CCC(C3)O4)cc12]

A mixture of ethyl 6-bromoquinoline-4-carboxylate (0.098 g, 0.35 mmol), 8-oxa-3-azabicyclo[3.2.1]octane (0.051 g, 0.46 mmol), RuPhos Pd G4 (0.030 g, 0.04 mmol), $Cs_2CO_3$ (0.342 g, 1.05 mmol) and dioxane (0.9 mL) under $N_2$ (g) was stirred vigorously at 85-90° C. for 1 h 50 min After cooling to rt, the reaction mixture was diluted with EtOAc (3 mL) and stirred with SilaMetS® Thiol scavenger (0.15 g, 1.4 mmol/g) at rt overnight. The mixture was filtered through Celite® 521. The filter pad was washed with EtOAc and the combined filtrates were concentrated. The residue was purified by preparative HPLC, PrepMethod H, (gradient: 25-65%) to give the title compound (0.099 g, 91%) as a yellow solid; MS (ESI) m/z $[M+H]^+$ 313.2.

Intermediate 166: 6-(8-Oxa-3-azabicyclo[3.2.1]octan-3-yl)quinoline-4-carboxylic acid

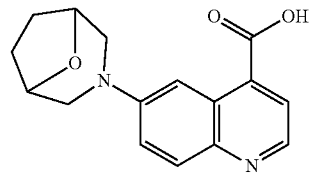 [SMILES: O=C(O)c1ccnc2ccc(N3CC4CCC(C3)O4)cc12]

Aq NaOH (3.8 M, 160 μL, 0.61 mmol) was added to a solution of ethyl 6-(8-oxa-3-azabicyclo[3.2.1]octan-3-yl) quinoline-4-carboxylate Intermediate 165 (95 mg, 0.30 mmol) in MeOH (2 mL) and the reaction was stirred at 50° C. for 1 h 30 min, and then at rt overnight. Aq HCl (3.8 M, 0.12 mL, 0.46 mmol) was added dropwise and the resulting mixture was concentrated at rt to give the crude title compound (0.108 g) as a red solid; MS (ESI) m/z $[M+H]^+$ 285.1.

Intermediate 167: Ethyl (S)-6-(2-methylmorpholino)quinoline-4-carboxylate

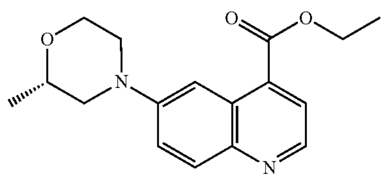 [SMILES: CCOC(=O)c1ccnc2ccc(N3CCO[C@@H](C)C3)cc12]

A mixture of ethyl 6-bromoquinoline-4-carboxylate (0.098 g, 0.35 mmol), (S)-2-methylmorpholine (0.046 g, 0.46 mmol), RuPhos Pd G4 (0.030 g, 0.04 mmol), $Cs_2CO_3$ (0.342 g, 1.05 mmol) and dioxane (0.9 mL) under $N_2$ (g) was stirred vigorously at 85-90° C. for 2 h. After cooling to rt, the reaction mixture was diluted with EtOAc (3 mL) and stirred with SilaMetS® Thiol scavenger (0.15 g; 1.4 mmol/g) at rt overnight. The mixture was filtered through Celite® 521, the filter pad was washed with EtOAc and the combined filtrates were concentrated. The residue was purified by preparative HPLC, PrepMethod H (gradient: 20-60%) to give the title compound (0.096 g, 91%) as a yellow solid; MS (ESI) m/z $[M+H]^+$ 301.3.

Intermediate 168: (S)-6-(2-Methylmorpholino)quinoline-4-carboxylic acid

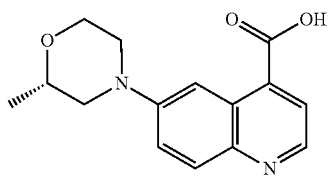 [SMILES: C[C@H]1CN(c2ccc3nccc(C(=O)O)c3c2)CCO1]

Aq NaOH (3.8 M, 0.16 mL, 0.61 mmol) was added to a solution of ethyl (S)-6-(2-methylmorpholino)quinoline-4-carboxylate Intermediate 167 (91 mg, 0.30 mmol) in MeOH (2 mL) and stirred at 50° C. for 1 h 30 min and then at rt overnight. Aq HCl (3.8 M, 120 μL, 0.45 mmol) was added dropwise and the resulting mixture was concentrated to give the crude title compound (0.108 g) as a red solid; MS (ESI) m/z $[M+H]^+$ 273.1.

Intermediate 169: Ethyl 6-((2R,3S)-2,3-dimethylmorpholino)quinoline-4-carboxylate

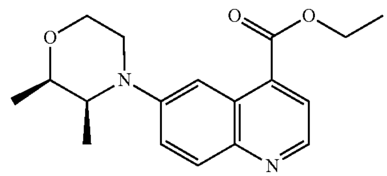 [SMILES: CCOC(=O)c1ccnc2ccc(N3CCO[C@H](C)[C@@H]3C)cc12]

A mixture of ethyl 6-bromoquinoline-4-carboxylate (0.140 g, 0.5 mmol), (2R,3S)-2,3-dimethylmorpholine hydrochloride (0.099 g, 0.65 mmol), Pd Catalyst [CAS: 1810068-35-9] (0.057 g, 0.05 mmol), $Cs_2CO_3$ (0.489 g, 1.50 mmol) and anhydrous dioxane (1.3 mL) under $N_2$ (g) was stirred vigorously at 80-85° C. overnight. The reaction mixture was allowed to reach rt and was stirred with SilaMetS® Thiol scavenger (0.2 g; 1.4 mmol/g) overnight. The mixture was filtered (Celite® 521) and the filter pad was washed with EtOAc (10 mL). The combined filtrates were concentrated and the residue was purified by preparative HPLC, PrepMethod H, (gradient: 35-75%). The compound was dissolved in DCM, washed with $H_2O$ and the organic layer was concentrated to give the title compound (0.111 g, 71%) as a yellow solid; MS (ESI) m/z $[M+H]^+$ 315.3.

Intermediate 170: 6-((2R,3S)-2,3-Dimethylmorpholino)quinoline-4-carboxylic acid

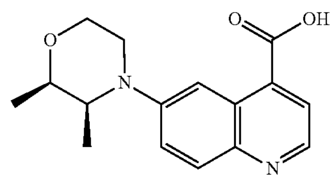 [SMILES: C[C@H]1OCCN(c2ccc3nccc(C(=O)O)c3c2)[C@H]1C]

Aq NaOH (3.8 M, 228 μL, 0.87 mmol) was added to a solution of ethyl 6-((2R,3S)-2,3-dimethylmorpholino)quinoline-4-carboxylate Intermediate 169 (109 mg, 0.35 mmol) in MeOH (3 mL) and the reaction mixture was stirred at 50° C. for 70 min. The reaction mixture was allowed to cool to rt, aq HCl (3.8 M, 0.18 mL, 0.69 mmol) was added dropwise and the resulting mixture was concentrated and freeze-dried from $MeCN/H_2O$ to give the crude title compound (0.137 g) as a red solid; MS (ESI) m/z $[M+H]^+$ 287.2.

Intermediate 171: Ethyl 6-((2S,3S)-2,3-dimethylmorpholino)quinoline-4-carboxylate

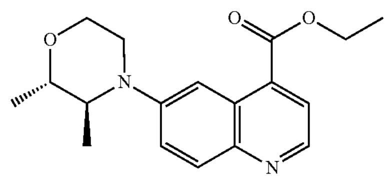 [SMILES: CCOC(=O)c1ccnc2ccc(N3CCO[C@@H](C)[C@@H]3C)cc12]

A mixture of ethyl 6-bromoquinoline-4-carboxylate (98 mg, 0.35 mmol), (2S,3S)-2,3-dimethylmorpholine hydrobromide (WO2014/016849) (95 mg, 0.48 mmol), Pd Catalyst [CAS: 1810068-35-9] (44 mg, 0.04 mmol), $Cs_2CO_3$ (342 mg, 1.05 mmol) and anhydrous dioxane (0.9 mL) under $N_2$ (g) was stirred vigorously at 80-85° C. overnight. The reaction mixture was allowed to reach rt, diluted with EtOAc (2 mL) and stirred with SilaMetS® Thiol scavenger (0.15 g; 1.4 mmol/g) at rt overnight. The mixture was filtered, and the filter cake was washed with EtOAc. The combined filtrates were concentrated and the residue was purified by preparative HPLC, PrepMethod H, (gradient: 35-65%) to give the title compound (0.088 g, 80%) as a yellow film; m/z (ESI) $[M+H]^+$ 315.3.

Intermediate 172: 6-((2S,3S)-2,3-Dimethylmorpholino)quinoline-4-carboxylic acid

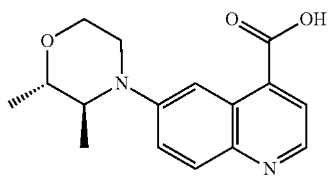 [SMILES: C[C@@H]1OCCN(c2ccc3nccc(C(=O)O)c3c2)[C@H]1C]

Aq NaOH (3.8 M, 182 μL, 0.69 mmol) was added to a solution of ethyl 6-((2S,3S)-2,3-dimethylmorpholino)quinoline-4-carboxylate Intermediate 171 (87 mg, 0.28 mmol) in MeOH (2.3 mL) and stirred at 50° C. for 50 min. The reaction was allowed to cool to rt, aq HCl (3.8 M, 0.146 mL, 0.55 mmol) was added dropwise and the resulting mixture was concentrated and freeze-dried from $MeCN/H_2O$ give the crude title compound (0.107 g) as a dark orange solid; MS (ESI) m/z $[M+H]^+$ 287.2.

Intermediate 173: Ethyl 6-((2R,3R)-2,3-dimethylmorpholino)quinoline-4-carboxylate

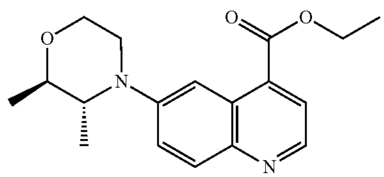 [SMILES: CCOC(=O)c1ccnc2ccc(N3CCO[C@H](C)[C@H]3C)cc12]

A mixture of ethyl 6-bromoquinoline-4-carboxylate (98 mg, 0.35 mmol), (2R,3R)-2,3-dimethylmorpholine hydrobromide (89 mg, 0.45 mmol), Pd Catalyst [CAS: 1810068-35-9] (45 mg, 0.04 mmol), $Cs_2CO_3$ (342 mg, 1.05 mmol) and dioxane (0.9 mL) under $N_2$ (g) was stirred vigorously at 80-85° C. for 17.5 h. The reaction was allowed to reach rt, diluted with EtOAc (2 mL), and was stirred with SilaMetS® Thiol scavenger (0.15 g, 1.4 mmol/g) at rt overnight. The mixture was filtered, and the filter cake was washed with EtOAc (10 mL). The combined filtrates were concentrated and the residue was purified by preparative HPLC, PrepMethod H, (gradient: 35-70%) to give the title compound (0.088 g, 80%) as a yellow film; MS (ESI) m/z $[M+H]^+$ 315.27.

Intermediate 174: 6-((2R,3R)-2,3-Dimethylmorpholino)quinoline-4-carboxylic acid

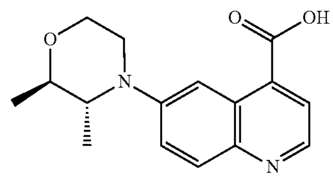 [SMILES: C[C@@H]1[C@@H](C)OCCN1c1ccc2nccc(C(=O)O)c2c1]

Aq NaOH (3.8 M, 178 μL, 0.68 mmol) was added to a solution of ethyl 6-((2R,3R)-2,3-dimethylmorpholino)quinoline-4-carboxylate Intermediate 173 (85 mg, 0.27 mmol) in MeOH (2.3 mL) and the reaction mixture was stirred at 50° C. for 45 min. The reaction was allowed to reach rt, aq HCl (3.8 M, 142 μL, 0.54 mmol) was added dropwise and the resulting mixture was concentrated and freeze-dried from $MeCN/H_2O$ to give the crude title compound (0.111 g) as a dark orange solid; MS (ESI) m/z $[M+H]^+$ 287.3.

Intermediate 175: rac-tert-Butyl (R)-6-(3-(trifluoromethyl)morpholino)quinoline-4-carboxylate

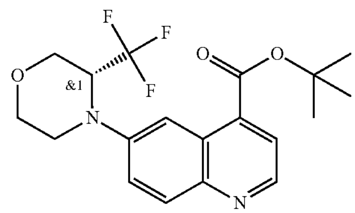 [SMILES: CC(C)(C)OC(=O)c1ccnc2ccc(N3CCOC[C@@H]3C(F)(F)F)cc12]

A mixture of tert-butyl 6-bromoquinoline-4-carboxylate (298 mg, 0.97 mmol), Pd Catalyst [CAS: 1810068-35-9] (110 mg, 0.10 mmol), rac-(R)-3-(trifluoromethyl)morpholine hydrochloride (241 mg, 1.26 mmol), $Cs_2CO_3$ (945 mg, 2.90 mmol) and dioxane (2.4 mL) under $N_2$ (g) was stirred vigorously at 80-85° C. overnight. The reaction mixture was cooled to rt, SilaMetS® Thiol scavenger (360 mg, loading 1.4 mmol/g) was added, and the mixture was stirred overnight, diluted with EtOAc and filtered (Celite® 521). The filter cake was washed with EtOAc, and the combined filtrates were concentrated. The residue was purified by preparative HPLC, PrepMethod H, (gradient: 35-75%) to give the title compound (0.26 g, 70%); MS (ESI) m/z $[M+H]^+$ 383.29.

Intermediate 176: rel-tert-Butyl (R)-6-(3-(trifluoromethyl)morpholino)quinoline-4-carboxylate Isomer 1

Intermediate 177: rel-tert-butyl (R)-6-(3-(trifluoromethyl)morpholino)quinoline-4-carboxylate Isomer 2

Isomer 1

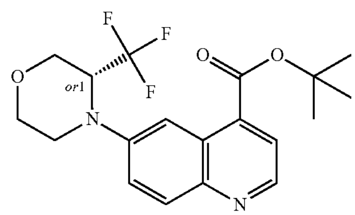

-continued

Isomer 2

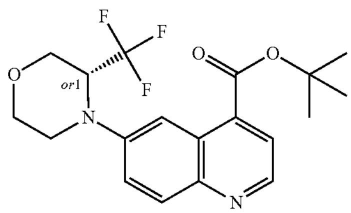

The isomers of rac-tert-butyl (R)-6-(3-(trifluoromethyl) morpholino)quinoline-4-carboxylate Intermediate 175 (259 mg, 0.68 mmol) were separated by preparative chiral SFC on a Chiralpak IC (5 μm, 250×30 mm ID) using 20% IPA/DEA 100/20 mM in $CO_2$, 120 bar as mobile phase, to give the first eluting compound rel-tert-butyl (R)-6-(3-(trifluoromethyl)-morpholino)quinoline-4-carboxylate Isomer 1 Intermediate 176 (0.114 g, 44%) and the second eluting compound rel-tert-butyl (R)-6-(3-(trifluoromethyl)morpholino)quinoline-4-carboxylate Isomer 2 Intermediate 177 (0.122 g, 47%).

Intermediate 178: rel-(R)-6-(3-(Trifluoromethyl) morpholino)quinoline-4-carboxylic acid Isomer 1

Isomer 1

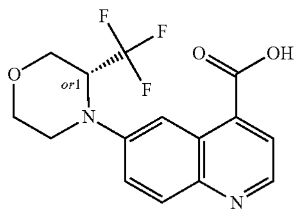

A solution of rel-tert-butyl (R)-6-(3-(trifluoromethyl)morpholino)quinoline-4-carboxylate Isomer 1 Intermediate 176 (101 mg, 0.26 mmol) in 90% TFA (aq, 0.5 mL) was heated at 50° C. for 1 h. The reaction solution was concentrated and the residue was freeze-dried from $MeCN/H_2O$ to give the crude title compound (0.150 g) as a red viscous oil; MS (ESI) m/z $[M+H]^+$ 327.1.

Intermediate 179: rel-(R)-6-(3-(Trifluoromethyl) morpholino)quinoline-4-carboxylic acid Isomer 2

Isomer 2

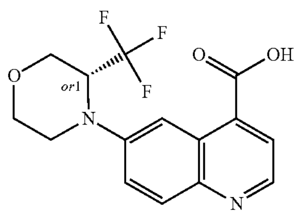

A solution of Intermediate 177 rel-tert-butyl (R)-6-(3-(trifluoromethyl)morpholino)-quinoline-4-carboxylate Isomer 2 (108 mg, 0.28 mmol) in 90% TFA (aq, 0.5 mL) was heated at 50° C. for 1 h. The reaction solution was concentrated and the residue was freeze-dried from $MeCN/H_2O$ to give the crude title compound (0.152 g) as a red oil; MS (ESI) m/z $[M+H]^+$ 327.1.

Intermediate 180: tert-Butyl 6-(3-oxa-9-azabicyclo [3.3.1]nonan-9-yl)quinoline-4-carboxylate

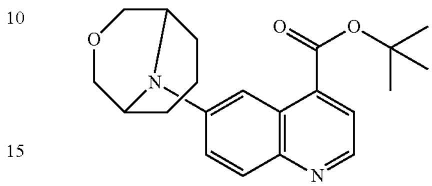

A mixture of tert-butyl 6-bromoquinoline-4-carboxylate (82 mg, 0.27 mmol), Pd Catalyst [CAS: 1810068-35-9] (30 mg, 0.03 mmol), 3-oxa-9-azabicyclo[3.3.1]nonane hydrochloride (56 mg, 0.34 mmol), $Cs_2CO_3$ (260 mg, 0.80 mmol) and dioxane (0.65 mL) under $N_2$ (g) was stirred vigorously at 80-85° C. overnight. The reaction mixture was allowed to reach rt, diluted with EtOAc (3 mL) and the mixture was stirred with SilaMetS® Thiol scavenger (140 mg; 1.4 mmol/g) at rt for 2 h. The mixture was filtered through Celite® 521 and the filtrate was concentrated. The residue was purified by preparative HPLC, PrepMethod H, (gradient: 35-80%) to give the title compound (0.065 g, 69%); MS (ESI) m/z $[M+H]^+$ 355.4.

Intermediate 181: 6-(3-Oxa-9-azabicyclo[3.3.1] nonan-9-yl)quinoline-4-carboxylic acid

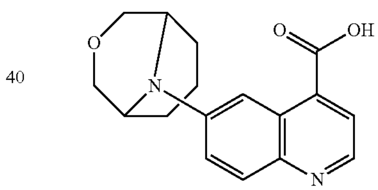

A solution of tert-butyl 6-(3-oxa-9-azabicyclo[3.3.1] nonan-9-yl)quinoline-4-carboxylate Intermediate 180 (56 mg, 0.15 mmol) in 90% TFA (aq, 0.5 mL) was stirred at 50° C. for 1.5 h. The reaction solution was concentrated and freeze-dried from $MeCN/H_2O$ to give the crude title compound (0.070 g); MS (ESI) m/z $[M+H]^+$ 299.3.

Intermediate 182: tert-Butyl 6-((2R,5R)-2,5-dimethylmorpholino)quinoline-4-carboxylate

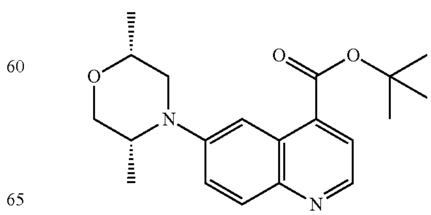

A mixture of tert-butyl 6-bromoquinoline-4-carboxylate (149 mg, 0.48 mmol), $Cs_2CO_3$ (473 mg, 1.45 mmol), Pd Catalyst [CAS: 1810068-35-9] (55 mg, 0.05 mmol), (2R, 5R)-2,5-dimethylmorpholine hydrochloride (96 mg, 0.63 mmol) and dioxane (1.2 mL) under $N_2$ (g) was stirred at 85° C. for 19 h. After cooling to rt the reaction mixture was diluted with EtOAc (2 mL) and stirred with SilaMetS® Thiol scavenger (150 mg; loading 1.4 mmol/g) for 2 h. The mixture was filtered through a pad of Celite® 521, the filter pad was washed with EtOAc (9 mL) and the combined filtrates were concentrated. The residue was purified by preparative HPLC, PrepMethod H, (gradient: 35-75%) to give the title compound (0.147 g, 89%); MS (ESI) m/z $[M+H]^+$ 343.3.

Intermediate 183: 6-((2R,5R)-2,5-Dimethylmorpholino)quinoline-4-carboxylic acid

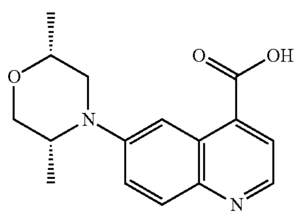 [SMILES: C[C@@H]1CN(c2ccc3nccc(C(=O)O)c3c2)[C@H](C)CO1]

A vial was charged with tert-butyl 6-((2R,5R)-2,5-dimethylmorpholino)quinoline-4-carboxylate Intermediate 182 (0.12 g, 0.35 mmol) and 90% TFA (aq, 0.5 mL) and heated at for 1 h 40 min. The reaction mixture was concentrated. A mixture of $H_2O$ and MeCN was added to the residue and the resulting mixture was concentrated to give the crude title compound (0.158 g); MS (ESI) m/z $[M+H]^+$ 287.2.

Intermediate 184: tert-Butyl 6-(2,2-dimethylmorpholino)quinoline-4-carboxylate

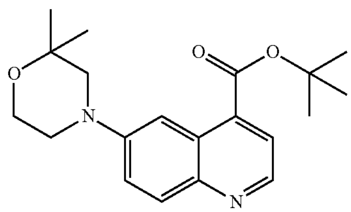 [SMILES: CC(C)(C)OC(=O)c1ccnc2ccc(N3CCOC(C)(C)C3)cc12]

A mixture of tert-butyl 6-bromoquinoline-4-carboxylate (149 mg, 0.48 mmol), $Cs_2CO_3$ (473 mg, 1.45 mmol), RuPhos Pd G3 (40 mg, 0.05 mmol), 2,2-dimethylmorpholine (0.069 g, 0.63 mmol) and dioxane (1.2 mL) under $N_2$ (g) was stirred at 85° C. for 22 h. After cooling to rt the reaction mixture was diluted with EtOAc (2 mL), SilaMetS® Thiol scavenger (0.150 g; loading 1.4 mmol/g) was added and the mixture was stirred for 2 h. The mixture was filtered through a pad of Celite® 521, the filter pad was washed with EtOAc (9 mL) and the combined filtrates were concentrated. The residue was purified by preparative HPLC, PrepMethod H, (gradient: 35-75%) to give the title compound (0.136 mg, 82%); MS (ESI) m/z $[M+H]^+$ 343.4.

Intermediate 185: 6-(2,2-Dimethylmorpholino)quinoline-4-carboxylic acid

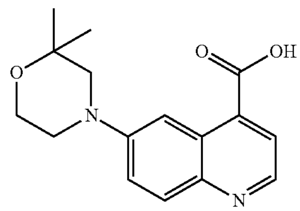 [SMILES: CC1(C)CN(c2ccc3nccc(C(=O)O)c3c2)CCO1]

A vial was charged with crude tert-butyl 6-(2,2-dimethylmorpholino)quinoline-4-carboxylate Intermediate 184 (0.120 g, 0.35 mmol) and 90% TFA (aq, 0.5 mL). The vial was heated at 50° C. for 1 h 40 min. The reaction mixture was concentrated. A mixture of $H_2O$ and MeCN was added to the residue and the mixture was concentrated to give the crude title compound (0.145 g); MS (ESI) m/z $[M+H]^+$ 287.2.

Intermediate 186: tert-Butyl (S)-6-(3-(methoxymethyl)morpholino)quinoline-4-carboxylate

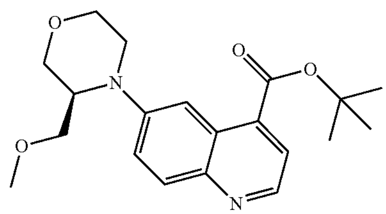 [SMILES: COC[C@H]1COCCN1c1ccc2nccc(C(=O)OC(C)(C)C)c2c1]

A mixture of tert-butyl 6-bromoquinoline-4-carboxylate (150 mg, 0.49 mmol), (S)-3-(methoxymethyl)morpholine hydrochloride (106 mg, 0.63 mmol), Pd Catalyst [CAS: 1810068-35-9] (56 mg, 0.05 mmol), $Cs_2CO_3$ (476 mg, 1.46 mmol) and dioxane (1.2 mL) was stirred vigorously at 80-85° C. for 15 h. The reaction mixture was diluted with EtOAc and filtered through Celite®. The filter pad was washed with EtOAc and the combined filtrates were concentrated. The residue was purified by straight phase flash chromatography on silica (gradient: 0-75% EtOAc in heptane) to give the title compound (0.146 g, 84%) as a yellow solid; MS (ESI) m/z $[M+H]^+$ 359.3.

Intermediate 187: tert-Butyl 6-((3S,5R)-3,5-dimethylmorpholino)quinoline-4-carboxylate

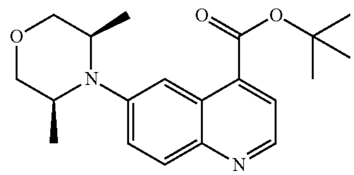 [SMILES: C[C@@H]1COC[C@H](C)N1c1ccc2nccc(C(=O)OC(C)(C)C)c2c1]

A mixture of tert-butyl 6-bromoquinoline-4-carboxylate (149 mg, 0.48 mmol), $Cs_2CO_3$ (473 mg, 1.45 mmol), Pd Catalyst [CAS: 1810068-35-9] (55 mg, 0.05 mmol), (3S, 5R)-3,5-dimethylmorpholine hydrochloride (96 mg, 0.63 mmol) and dioxane (1.2 mL) under $N_2$ (g) was stirred at 85° C. for 60 h. After cooling to rt the reaction mixture was diluted to 3.5 mL with EtOAc and was filtered through a pad of Celite® 521. The filter pad was washed with EtOAc and the combined filtrates were concentrated. The residue was purified by straight phase flash chromatography on silica (gradient: 0-75% EtOAc in heptane) to afford the title compound (73 mg, 41%) as a yellow oil; MS (ESI) m/z $[M+H]^+$ 343.3.

Intermediate 188: 6-((3S,5R)-3,5-Dimethylmorpholino)quinoline-4-carboxylic acid

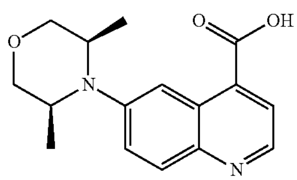 [SMILES: C[C@@H]1COC[C@H](C)N1c1ccc2nccc(C(=O)O)c2c1]

A solution of tert-butyl 6-((3S,5R)-3,5-dimethylmorpholino)quinoline-4-carboxylate Intermediate 187 (67 mg, 0.20 mmol) in 90% TFA (aq, 1 mL) was stirred at 50° C. for 3 h. The reaction was concentrated and the residue was concentrated from a mixture of DCM and heptane and dried under vacuum to give the crude title compound (0.127 g); MS (ESI) m/z $[M+H]^+$ 287.2.

Intermediate 189: tert-Butyl 6-(1,4-oxazepan-4-yl)quinoline-4-carboxylate

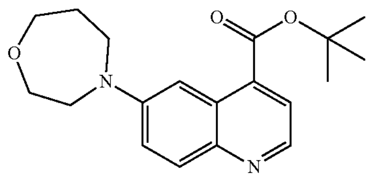 [SMILES: CC(C)(C)OC(=O)c1ccnc2ccc(N3CCCOCC3)cc12]

A mixture of tert-butyl 6-bromoquinoline-4-carboxylate (149 mg, 0.48 mmol), $Cs_2CO_3$ (473 mg, 1.45 mmol), RuPhos Pd G3 (40 mg, 0.05 mmol), 1,4-oxazepane hydrochloride (83 mg, 0.6 mmol) and dioxane (1.2 mL) under $N_2$ (g) was stirred at 85° C. for 22 h. After cooling to rt the reaction mixture was diluted with EtOAc (2 mL). SilaMetS® Thiol scavenger (ca 150 mg; loading 1.4 mmol/g) was added and the mixture were stirred for 2 h and filtered through a pad of Celite® 521. The filter pad was washed with EtOAc (9 mL) and the filtrate was concentrated. The residue was purified by preparative HPLC, PrepMethod G (gradient: 25-100%). The relevant fractions were partially concentrated to remove the MeCN and the aqueous mixture was basified with 8% $NaHCO_3$ (aq) and extracted with DCM. The organic layer was concentrated to give the title compound (0.117 g, 74%); MS (ESI) m/z $[M+H]^+$ 329.3.

Intermediate 190: (R)-4-Benzyl-2-((methylthio)methyl)morpholine

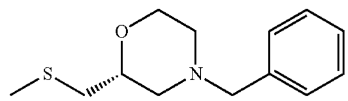 [SMILES: CSC[C@H]1CN(Cc2ccccc2)CCO1]

KI (7.3 g, 44.5 mmol) was added to a solution of (R)-4-benzyl-2-(chloromethyl)morpholine (200 g, 0.89 mol) in DMF (2.0 L) followed by 18% $NaSCH_3$ (aq, 690 g, 1.78 mol) at 0° C. The mixture was stirred at rt for 12 h. The reaction mixture was poured into ice-water and extracted with EtOAc (3×500 mL). The combined organic layers were washed with water (500 mL) and brine (500 mL), dried over $Na_2SO_4$, filtered and evaporated to dryness to give the title compound (192 g, 91%) as a colorless oil; MS m/z (ESI) $[M+H]^+$ 238.0.

Intermediate 191: (R)-4-Benzyl-2-((methylsulfonyl)methyl)morpholine

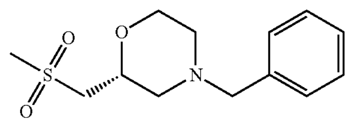 [SMILES: CS(=O)(=O)C[C@H]1CN(Cc2ccccc2)CCO1]

m-CPBA (494 g, 2.435 mol) was added portion wise at 10° C. to a solution of (R)-4-benzyl-2-((methylthio)methyl) morpholine Intermediate 190 (192 g, 0.812 mol) in anhydrous DCM (2 L). After addition, the mixture was stirred at rt for 16 h. The mixture was filtered and the filtrate was washed with sat $NaHSO_3$ (2×1 L), sat $NaHCO_3$ (3×1 L), and brine (800 mL), dried over $Na_2SO_4$, filtered and concentrated under vacuum. The residue was triturated by MTBE/petroleum ether (100 mL/500 mL) and the solids were collected by filtration to afford of the title compound (130 g, 60%) as a white solid; MS m/z (ESI) $[M+H]^+$ 269.9.

Intermediate 192: (R)-2-((Methylsulfonyl)methyl)morpholine

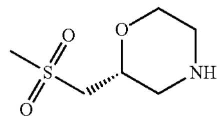

A mixture of (R)-4-benzyl-2-((methylsulfonyl)methyl) morpholine Intermediate 191 (120 g, 0.44 mol) and $Pd(OH)_2/C$ (12 g) in MeOH (1000 mL) was hydrogenated (50 Psi $H_2$) at for 24 h. The resulting mixture was filtered to remove $Pd(OH)_2/C$ and the filtrate was concentrated to give the title compound (68 g, 86%) as a white solid; MS m/z (ESI) $[M+H]^+$ 180.2.

Intermediate 193: tert-Butyl (R)-6-(2-((methylsulfonyl)methyl)morpholino)quinoline-4-carboxylate

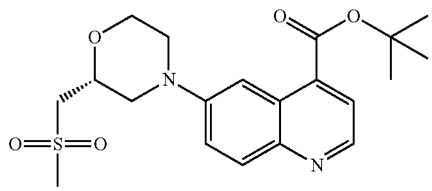 [SMILES: CC(C)(C)OC(=O)c1ccnc2ccc(N3CCO[C@@H](CS(C)(=O)=O)C3)cc12]

The title compound was synthesized analogous to the procedure of Intermediate 189 starting from tert-butyl 6-bromoquinoline-4-carboxylate (149 mg, 0.48 mmol) and (R)-2-((methylsulfonyl)methyl)morpholine Intermediate 192 (0.108 g, 0.6 mmol) to give the title compound (147 mg, 75%); MS (ESI) m/z $[M+H]^+$ 407.2.

Intermediate 194: tert-Butyl (S)-6-(2-(methoxymethyl)morpholino)quinoline-4-carboxylate

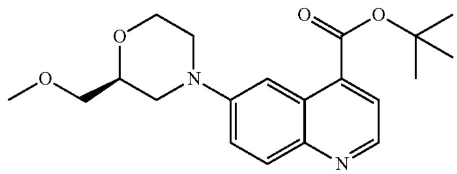 [SMILES: COC[C@@H]1CN(c2ccc3nccc(C(=O)OC(C)(C)C)c3c2)CCO1]

The title compound was synthesized and purified analogous to the procedure of Intermediate 187 starting from tert-butyl 6-bromoquinoline-4-carboxylate (149 mg, 0.48 mmol) and (S)-2-(methoxymethyl)morpholine hydrochloride (0.106 g, 0.63 mmol) with a reaction time of 20 h to give the title compound (0.16 g, 88%); MS (ESI) m/z $[M+H]^+$ 359.3.

Intermediate 195: (S)-4-Benzyl-2-((methylthio)methyl)morpholine

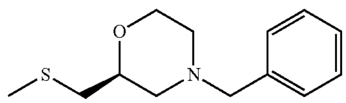 [SMILES: CSC[C@@H]1CN(Cc2ccccc2)CCO1]

KI (7.3 g, 0.045 mol) was added to a solution of (S)-4-benzyl-2-(chloromethyl)morpholine (200 g, 0.89 mol) in DMF (2.0 L) followed by 18% $NaSCH_3$ (aq, 690 g, 1.78 mol) at 0° C. and the mixture was stirred at rt for 12 h. The reaction mixture was poured into ice-water and extracted with EtOAc (3×0.5 L). The combined organic layers were washed with water (0.5 L) and brine (0.5 L), dried over $Na_2SO_4$ and evaporated to dryness to give the title compound (200 g, 95%) as a colorless oil; MS m/z (ESI) $[M+H]^+$ 238.0.

Intermediate 196: (S)-4-Benzyl-2-((methylsulfonyl)methyl)morpholine

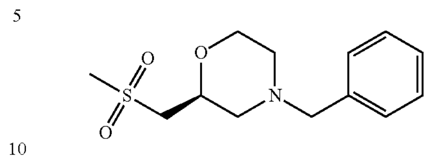

m-CPBA (494 g, 2.44 mol) was added portion wise below 10° C. to a solution of (S)-4-benzyl-2-((methylthio)methyl) morpholine Intermediate 195 (192 g, 0.812 mol) in anhydrous DCM (2 L), and the mixture was stirred at rt for 16 h. The mixture was filtered and the filtrate was washed with sat $NaHSO_3$ (2×1 L), sat $NaHCO_3$ (3×1 L) and brine (0.8 L), dried over $Na_2SO_4$, filtered and concentrated under reduced pressure. The residue was triturated by a mixture of MTBE (100 mL) and petroleum ether (500 mL). The solids were collected by filtration to give the title compound (150 g. 68%) as a white solid; MS m/z (ESI) $[M+H]^+$ 270.0.

Intermediate 197: (S)-2-((Methylsulfonyl)methyl)morpholine

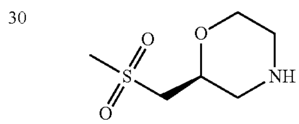

A mixture of (S)-4-benzyl-2-((methylsulfonyl)methyl) morpholine Intermediate 196 (120 g, 0.44 mol) and $Pd(OH)_2/C$ (12 g) in MeOH (1 L) was hydrogenated (50 Psi $H_2$) at for 24 h. The resulting mixture was filtered to remove $Pd(OH)_2/C$ and the filtrate was concentrated to give the title compound (49 g, 62%) as white solid; MS m/z (ESI) $[M+H]^+$ 180.2.

Intermediate 198: tert-Butyl (S)-6-(2-((methylsulfonyl)methyl)morpholino)quinoline-4-carboxylate

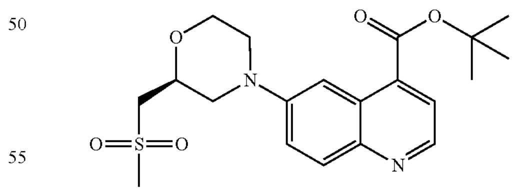

The title compound was synthesized and purified analogous to the procedure of Intermediate 187 starting from tert-butyl 6-bromoquinoline-4-carboxylate (149 mg, 0.48 mmol) and (S)-2-((methylsulfonyl)methyl)morpholine Intermediate 197 (0.113 g, 0.63 mmol) with a reaction time of 20 h to give the title compound (0.111 g, 50%); MS (ESI) m/z $[M+H]^+$ 407.2.

Intermediate 199: (R)-4-Benzyl-3-(2-methoxyethyl)morpholine

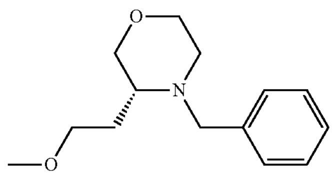 [SMILES: COCC[C@@H]1COCCN1Cc1ccccc1]

NaH (24.4 g, 0.61 mol) was added at to a solution of (R)-2-(4-benzylmorpholin-3-yl)ethan-1-ol WO 2011111875 (90 g, 0.41 mol) in THF (1.30 L) at 0° C. and the reaction was stirred for 1 h. MeI (63.6 g, 448 mmol) was added at 0° C. and stirred for 6 h. The reaction was quenched with $H_2O$ (0.80 L), extracted with EtOAc (2×1.50 L). The organic phase was dried over $Na_2SO_4$, filtered and concentrated to give the title compound (100 g, 100%); MS m/z (ESI) $[M+H]^+$ 236.1.

Intermediate 200: (R)-3-(2-Methoxyethyl)morpholine hydrochloride

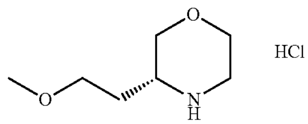

Pd(OH)$_2$/C (25 g) was added to a solution of (R)-4-benzyl-3-(2-methoxyethyl)morpholine Intermediate 199 (100 g, 0.425 mol) in MeOH (1.0 L). The mixture was hydrogenated at 50° C. for 16 h. The reaction mixture was filtered and HCl/EtOAc was added to the filtrate. The filtrate was concentrated and the residue was triturated with EtOAc to give the title compound (52 g, 68%); MS m/z (ESI) $[M+H]^+$ 145.9.

Intermediate 201: tert-Butyl (R)-6-(3-(2-methoxyethyl)morpholino)quinoline-4-carboxylate

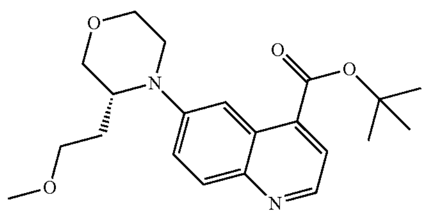 [SMILES: COCC[C@@H]1COCCN1c1ccc2nccc(C(=O)OC(C)(C)C)c2c1]

The title compound was synthesized and purified analogous to the procedure of Intermediate 187 starting from tert-butyl 6-bromoquinoline-4-carboxylate (149 mg, 0.48 mmol) and (R)-3-(2-methoxyethyl)morpholine hydrochloride Intermediate 200 (0.114 g, 0.63 mmol) with a reaction time of 20 h to give the title compound (0.151 g, 79%); MS (ESI) m/z $[M+H]^+$ 373.3.

Intermediate 202: (2S,3S)-4-Benzyl-3-(methoxymethyl)-2-methylmorpholine

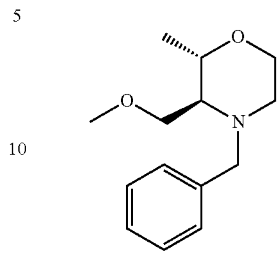

NaH (19.5 g, 814 mmol) was added to a solution of ((2S,3S)-4-benzyl-2-methylmorpholin-3-yl)methanol (WO2015/144093) (90 g, 407 mmol) in THF (1.2 L) at 0° C., and the suspension was stirred at 5° C. for 1 h. MeI (63.6 g, 448 mmol) was added at 0° C. and the reaction was stirred for 2 h. The temperature was increased to rt and the reaction was stirred overnight. The reaction was quenched by addition of $H_2O$ at 0° C. and extracted with DCM (2×2 L). The combined organic layers were concentrated to give the title compound (100 g) as an oil; MS m/z (ESI) $[M+H]^+$ 235.9.

Intermediate 203: (2S,3S)-3-(Methoxymethyl)-2-methylmorpholine hydrochloride

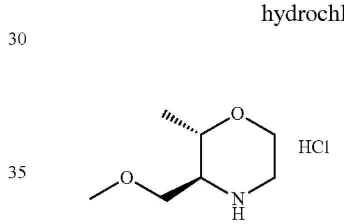

Pd(OH)$_2$/C (20 g) was added to a solution of (2S,3S)-4-benzyl-3-(methoxymethyl)-2-methylmorpholine Intermediate 202 (100 g, 407 mmol) in MeOH (1 L) under $N_2$ (g). The system was evacuated and backfilled with $N_2$ (g) (3×) and hydrogenated (50 psi) at 50° C. for 18 h. The reaction was filtered and the filtrate was concentrated. HCl in EtOAc was added to the residue and the mixture was stirred for 30 min. The solid was collected by filtration, washed with EtOAc and dried to give the title compound (57 g, 79%) as a solid; MS m/z (ESI) $[M+H]^+$ 146.1.

Intermediate 204: tert-Butyl 6-((2S,3S)-3-(methoxymethyl)-2-methylmorpholino)-quinoline-4-carboxylate

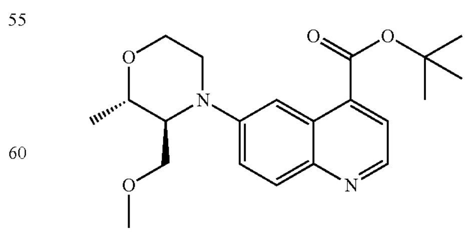

The title compound was synthesized and purified analogous to the procedure of Intermediate 187 starting from tert-butyl 6-bromoquinoline-4-carboxylate (149 mg, 0.48 mmol) and (2S,3S)-3-(methoxymethyl)-2-methylmorpholine hydrochloride Intermediate 203 (0.114 g, 0.63 mmol) with a reaction time of 20 h to give the title compound (0.155 g, 71%); MS (ESI) m/z $[M+H]^+$ 373.4.

Intermediate 205: (2R,3R)-4-Benzyl-3-(methoxymethyl)-2-methylmorpholine

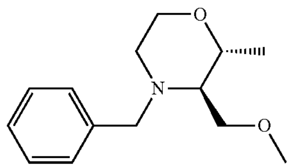 [SMILES: COC[C@@H]1[C@@H](C)OCCN1Cc1ccccc1]

NaH (23.4 g, 584 mmol, 60%) was added to a solution of ((2R,3R)-4-benzyl-2-methylmorpholin-3-yl)methanol (86 g, 0.39 mol) in THF (1.5 L) at −5-0° C. and the mixture was stirred at 0° C. for 2 h. MeI (60.7 g, 428 mmol) was added dropwise and the mixture was stirred at rt overnight. The mixture was quenched with $H_2O$ and extracted with DCM (3×1 L). The combined organic layers were dried over anhydrous $MgSO_4$, filtered and concentrated under reduced pressure to give the title compound (88 g, 86%); MS m/z (ESI) $[M+H]^+$ 236.1.

Intermediate 206: (2R,3R)-3-(Methoxymethyl)-2-methylmorpholine hydrochloride

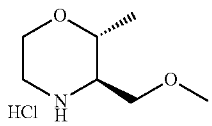

$Pd(OH)_2$ (20 g) was added to a solution of (2R,3R)-4-benzyl-3-(methoxymethyl)-2-methylmorpholine Intermediate 205 (86 g, 370 mmol) in MeOH (1 L). The mixture was stirred at 50° C. under $H_2$ (g) (50 Psi) overnight. The mixture was filtered, 4 M HCl in EtOAc (200 mL) was added to the filtrate and the solvent was evaporated to give the title compound (55 g, 82%) as a light yellow solid; MS m/z (ESI) $[M+H]^+$ 146.0.

Intermediate 207: tert-Butyl 6-((2R,3R)-3-(methoxymethyl)-2-methylmorpholino)-quinoline-4-carboxylate

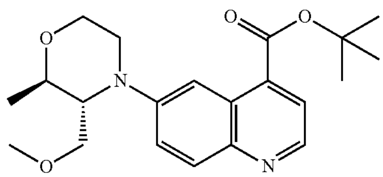 [SMILES: COC[C@@H]1[C@@H](C)OCCN1c1ccc2nccc(C(=O)OC(C)(C)C)c2c1]

The title compound was synthesized analogous to the procedure of Intermediate 187 starting from tert-butyl 6-bromoquinoline-4-carboxylate (0.149 g, 0.48 mmol) and (2R,3R)-3-(methoxymethyl)-2-methylmorpholine hydrochloride Intermediate 206 (0.110 g, 0.61 mmol) with a reaction time of 14.5 h. The compound was purified by straight phase flash chromatography on silica (0-40% EtOAc in heptane) to give the title compound (0.128 g, 71%); MS (ESI) m/z $[M+H]^+$ 373.4.

Intermediate 208: tert-Butyl 6-(3-oxa-8-azabicyclo[3.2.1]octan-8-yl)quinoline-4-carboxylate

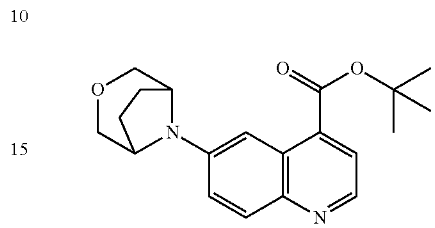

A mixture of tert-butyl 6-bromoquinoline-4-carboxylate (200 mg, 0.65 mmol), 3-oxa-8-azabicyclo[3.2.1]octane hydrochloride (126 mg, 0.84 mmol), Pd Catalyst [CAS: 1810068-35-9] (74 mg, 0.06 mmol), $Cs_2CO_3$ (634 mg, 1.95 mmol) and dioxane (1.6 mL) under $N_2$ (g) was stirred vigorously at 80-85° C. for 27 h. After cooling to rt the reaction mixture was diluted with EtOAc and filtered through Celite® 521. The filter pad was washed with EtOAc and the combined filtrates were concentrated. The compound was purified by straight phase flash chromatography on silica (0-75% EtOAc in heptane) to give the title compound (0.20 g, 90%) as a yellow solid; MS (ESI) m/z $[M+H]^+$ 341.3.

Intermediate 209: tert-Butyl 6-(1,9-dioxa-4-azaspiro[5.5]undecan-4-yl)quinoline-4-carboxylate

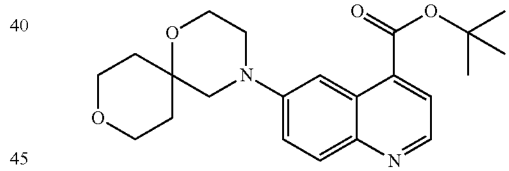

The title compound was synthesized analogous to the procedure of Intermediate 189 starting from tert-butyl 6-bromoquinoline-4-carboxylate (149 mg, 0.48 mmol) and 1,9-dioxa-4-azaspiro[5.5]undecane hydrochloride (0.116 g, 0.6 mmol) to give the title compound (147 mg, 75%); MS (ESI) m/z $[M+H]^+$ 385.3.

Intermediate 210: Ethyl 6-((3S,5R)-3,5-dimethylmorpholino)quinoline-4-carboxylate

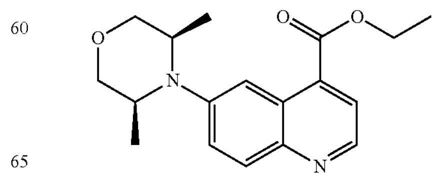

A mixture of ethyl 6-bromoquinoline-4-carboxylate (160 mg, 0.57 mmol) and (3R,5S)-3,5-dimethylmorpholine hydrochloride (106 mg, 0.70 mmol), Pd Catalyst [CAS: 1810068-35-9] (49 mg, 0.04 mmol), $Cs_2CO_3$ (558 mg, 1.71 mmol) and dioxane (1 mL) under $N_2$ (g) was stirred vigorously at 90° C. for 13 h. Another batch of Pd Catalyst [CAS: 1810068-35-9] (20 mg, 0.02 mmol) was added and the reaction was stirred vigorously at 90° C. overnight. After cooling to rt the reaction mixture was diluted with EtOAc and filtered through Celite® 521. The filter pad was washed with EtOAc and the combined filtrates were concentrated. The residue was purified by straight phase flash chromatography on silica (gradient: 0-65% EtOAc in heptane) to give the title compound (0.070 g, 39%) as a yellow film; MS (ESI) m/z $[M+H]^+$ 315.2.

Intermediate 211: Ethyl 7-bromo-6-((3S,5R)-3,5-dimethylmorpholino)quinoline-4-carboxylate

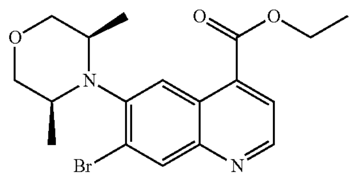 [SMILES: CCOC(=O)c1ccnc2cc(Br)c(N3[C@H](C)COC[C@@H]3C)cc12]

NBS (39 mg, 0.21 mmol) was added to a solution of ethyl 6-((3S,5R)-3,5-dimethylmorpholino)quinoline-4-carboxylate Intermediate 210 (65 mg, 0.21 mmol) in HFIP (2 mL) at 0° C. and the reaction was stirred for 1 h at 0° C. NBS (8 mg, 0.04 mmol) was added and the reaction was stirred for 10 min at 0° C. The reaction mixture was concentrated and the compound was purified by straight phase flash chromatography on silica (gradient: 0-65% EtOAc in heptane) to give the title compound (0.012 g, 15%); MS (ESI) m/z $[M+H]^+$ 393.1, 395.1.

Intermediate 212: 7-Bromo-6-((3S,5R)-3,5-dimethylmorpholino)quinoline-4-carboxylic acid

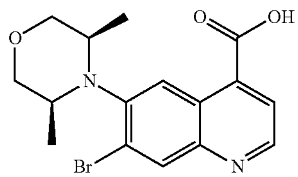 [SMILES: C[C@@H]1COC[C@H](C)N1c1cc2c(C(=O)O)ccnc2cc1Br]

2 M NaOH (aq, 75 μL, 0.15 mmol) was added to a suspension of ethyl 7-bromo-6-((3S,5R)-3,5-dimethylmorpholino)quinoline-4-carboxylate Intermediate 211 (12 mg, 0.03 mmol in MeOH (200 μL). The reaction was heated at 50° C. for 25 min. The solution was cooled to rt, aq HCl (3.8 M, 39.5 μL, 0.15 mmol) was added and the resulting mixture was concentrated under a stream of $N_2$ (g). The residue was slurried in EtOAc and concentrated (3×) to give the crude title compound (0.020 g) as an orange solid; MS (ESI) m/z $[M+H]^+$ 365.1, 367.1.

Intermediate 213: Ethyl 5-chloro-6-morpholinoquinoline-4-carboxylate hydrochloride

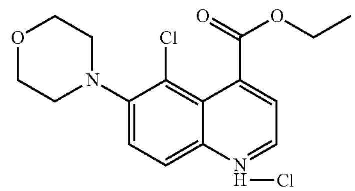

NCS (56 mg, 0.42 mmol) was added to a solution of ethyl 6-morpholinoquinoline-4-carboxylate Intermediate 143 (100 mg, 0.35 mmol) in MeCN (1.5 mL) at rt and the reaction mixture was stirred at rt overnight. The reaction mixture was concentrated and the residue was dissolved in EtOAc (2 mL). 4 M HCl in dioxane (87 μL, 0.35 mmol) was added and the mixture was stirred until precipitation appeared complete. The solids were collected by filtration, washed with EtOAc and dried under vacuum to give the title compound (0.103 g, 83%) as a yellow solid; MS (ESI) m/z $[M+H]^+$ 321.2.

Intermediate 214: tert-Butyl (S)-6-(3-methylmorpholino)quinoline-4-carboxylate

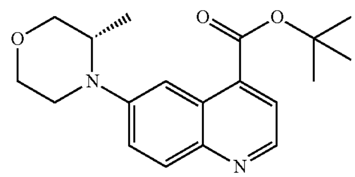 [SMILES: C[C@H]1COCCN1c1ccc2nccc(C(=O)OC(C)(C)C)c2c1]

A mixture of tert-butyl 6-bromoquinoline-4-carboxylate (104 mg, 0.34 mmol), 2'-(bis(3,5-bis(trifluoromethyl)phenyl)phosphaneyl)-3',6'-dimethoxy-$N^2$,$N^2$,$N^6$,$N^6$-tetramethyl-[1,1'-biphenyl]-2,6-diamine (26 mg, 0.03 mmol), $Pd_2(dba)_3$ (9 mg, 10 μmol), sodium 2-methylbutan-2-olate (48 mg, 0.44 mmol) and (S)-3-methylmorpholine (41 mg, 0.40 mmol) in CPME (0.7 mL) under argon was heated at 80-85° C. for 3 h. The mixture was diluted with EtOAc and washed with $H_2O$. The aqueous layer was extracted with EtOAc and the combined organic layers were dried over $Na_2SO_4$, filtered and concentrated. The residue was purified by straight phase flash chromatography on silica (gradient: 0-75% EtOAc in heptane) to give the title compound (0.052 g, 47%) as a yellow film; MS (ESI) m/z $[M+H]^+$ 329.4.

Intermediate 215: tert-Butyl 6-((3S,5S)-3,5-dimethylmorpholino)quinoline-4-carboxylate

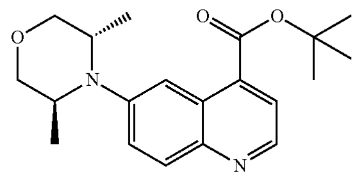 [SMILES: C[C@H]1COC[C@H](C)N1c1ccc2nccc(C(=O)OC(C)(C)C)c2c1]

A mixture of tert-butyl 6-bromoquinoline-4-carboxylate (100 mg, 0.32 mmol), 2'-(bis(3,5-bis(trifluoromethyl)phenyl)phosphaneyl)-3',6'-dimethoxy-$N^2$,$N^2$,$N^6$,$N^6$-tetramethyl-[1,1'-biphenyl]-2,6-diamine (25 mg, 0.03 mmol), $Pd_2(dba)_3$ (9 mg, 9.7 μmol), sodium 2-methylbutan-2-olate (39 mg, 0.36 mmol), (3S,5S)-3,5-dimethylmorpholine (59 mg, 0.51 mmol) and CPME (0.7 mL) under argon was stirred at 80° C. for 4 h. After cooling to rt the reaction mixture was diluted with EtOAc and washed with $H_2O$. The aqueous layer was extracted with EtOAc and the combined organic layers were dried over $Na_2SO_4$, filtered and concentrated. The residue was purified by straight phase flash chromatography on silica (gradient: 0-75% EtOAc in heptane) to give the title compound (0.054 g, 48%) as a yellow film; MS (ESI) m/z $[M+H]^+$ 343.4.

Intermediate 216: tert-Butyl 6-(8-oxa-5-azaspiro[3.5]nonan-5-yl)quinoline-4-carboxylate

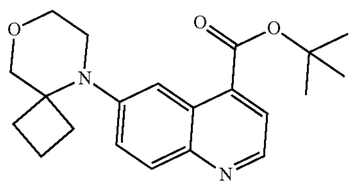 [SMILES: CC(C)(C)OC(=O)c1ccnc2ccc(N3CCOCC34CCC4)cc12]

A mixture of tert-butyl 6-bromoquinoline-4-carboxylate (150 mg, 0.49 mmol), 8-oxa-hydrochloride (104 mg, 0.63 mmol), Pd Catalyst [CAS: 1810068-35-9] (56 mg, 0.05 mmol), $Cs_2CO_3$ (476 mg, 1.46 mmol) and dioxane (1.2 mL) under $N_2$ (g) was stirred vigorously at 80-85° C. for 18 h. After cooling to rt the reaction mixture was diluted with EtOAc and filtered through Celite® 521. The filter pad was washed with EtOAc and the combined filtrates were concentrated. The residue was purified on straight phase flash chromatography on silica (gradient: 0-65% EtOAc in heptane) to give the title compound (0.103 g, 60%) as a yellow film; MS (ESI) m/z $[M+H]^+$ 355.4.

Intermediate 217: tert-Butyl 6-((3R,5R)-3,5-dimethylmorpholino)quinoline-4-carboxylate

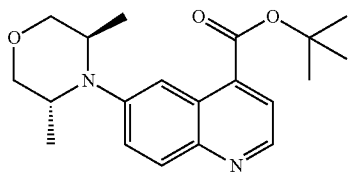 [SMILES: C[C@@H]1COC[C@@H](C)N1c1ccc2nccc(C(=O)OC(C)(C)C)c2c1]

Under $N_2$ (g) a vial was charged with a stirring bar, tert-butyl 6-bromoquinoline-4-carboxylate (40 mg, 0.13 mmol), (3R,5R)-3,5-dimethylmorpholine hydrochloride (30 mg, 0.19 mmol), Pd Catalyst [CAS: 1810068-35-9] (18 mg, 15 μmol, $Cs_2CO_3$ (127 mg, 0.39 mmol) and dioxane (0.6 mL). The vial was stirred vigorously at 80-85° C. for 18 h and was then allowed to cool to rt. The reaction was repeated but using (26 mg, 23 μmol) of the Pd Catalyst [CAS: 1810068-35-9]. The reaction mixtures were diluted with EtOAc and the combined mixtures were filtered through a pad of Celite® 521. The filter pad was washed with EtOAc and the combined filtrates were concentrated. The residue was purified by straight phase flash chromatography on silica (gradient: 0-65% EtOAc in heptane) to give the title compound (48 mg, 54%) as a yellow oil; MS (ESI) m/z $[M+H]^+$ 343.4.

Intermediate 218: tert-Butyl (S)-6-(3-ethylmorpholino)quinoline-4-carboxylate

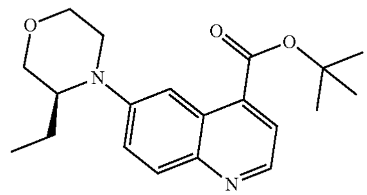 [SMILES: CC[C@H]1COCCN1c1ccc2nccc(C(=O)OC(C)(C)C)c2c1]

A mixture of tert-butyl 6-bromoquinoline-4-carboxylate (87 mg, 0.28 mmol), Pd Catalyst [CAS: 1810068-35-9] (9 mg, 7.72 μmol), (S)-3-ethylmorpholine hydrochloride (86 mg, 0.56 mmol), $Cs_2CO_3$ (276 mg, 0.85 mmol) and CPME (1.5 mL) under argon was stirred at 80° C. overnight. Pd Catalyst [CAS: 1810068-35-9] (17 mg, 0.01 mmol) was added and the stirring was continued at 80° C. to a reaction time of 2 days. The reaction mixture was diluted with EtOAc and washed with $H_2O$. The aqueous layer was extracted with EtOAc and the combined organic layer was dried over $Na_2SO_4$, filtered and concentrated. The residue was purified by straight phase flash chromatography on silica (gradient: 0-75% EtOAc in heptane) to give the title compound (0.050 g, 51%) as a yellow film; MS (ESI) m/z $[M+H]^+$ 343.4.

Intermediate 219: (S)-6-(3-Ethylmorpholino)quinoline-4-carboxylic acid

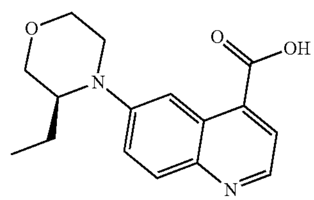 [SMILES: CC[C@H]1COCCN1c1ccc2nccc(C(=O)O)c2c1]

A solution of tert-butyl (S)-6-(3-ethylmorpholino)quinoline-4-carboxylate Intermediate 218 (32 mg, 0.09 mmol) in 90% TFA (aq, 0.5 mL) was stirred at 25-30° C. for 4 h. The solution was concentrated under reduced pressure and the residue was concentrated from heptane (2×) to give the crude title compound (0.048 g, 99%); MS (ESI) m/z $[M+H]^+$ 287.3.

Intermediate 220: tert-Butyl 6-(3,3-dimethylmorpholino)quinoline-4-carboxylate

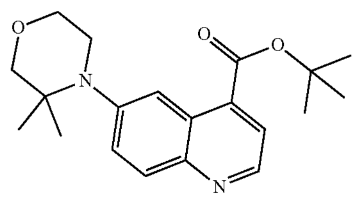 [SMILES: CC(C)(C)OC(=O)c1ccnc2ccc(N3CCOCC3(C)C)cc12]

A mixture of tert-butyl 6-bromoquinoline-4-carboxylate (100 mg, 0.32 mmol), Pd Catalyst [CAS: 1810068-35-9] (50 mg, 0.04 mmol), 3,3-dimethylmorpholine (75 mg, 0.65 mmol), $Cs_2CO_3$ (211 mg, 0.65 mmol) and CPME (1.5 mL) was stirred at 80° C. under argon for 2 days. The reaction mixture was diluted with EtOAc and washed with $H_2O$. The aqueous layer was extracted with EtOAc and the combined organic layer was dried over $Na_2SO_4$, filtered and concentrated. The residue was purified by straight phase flash chromatography on silica (gradient: 0-75% EtOAc in heptane) to give the title compound (0.053 g, 48%) as a yellow film; MS (ESI) m/z $[M+H]^+$ 343.3.

Intermediate 221: tert-Butyl (R)-6-(3-methylmorpholino)quinoline-4-carboxylate

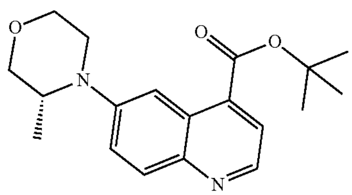 [SMILES: C[C@@H]1COCCN1c1ccc2nccc(C(=O)OC(C)(C)C)c2c1]

A mixture of tert-butyl 6-bromoquinoline-4-carboxylate (83 mg, 0.27 mmol), 2'-(bis(3,5-bis(trifluoromethyl)phenyl)phosphaneyl)-3',6'-dimethoxy-$N^2$,$N^2$,$N^6$,$N^6$-tetramethyl-[1,1'-biphenyl]-2,6-diamine (31 mg, 0.04 mmol), Pd 2 (dba) 3 (12 mg, 0.01 mmol), sodium 2-methylbutan-2-olate (39 mg, 0.35 mmol), (R)-3-methylmorpholine (33 mg, 0.32 mmol) and CPME (0.6 mL) under argon was stirred at 80-85° C. for 3 h. After cooling to rt, the reaction mixture was partitioned between EtOAc and $H_2O$. The mixture was filtered and the layers were allowed to separate. The aqueous layer was extracted with EtOAc (2×) and the combined organic layer was passed through a phase separator and concentrated. The residue was purified by straight phase flash chromatography on silica (gradient: 0-75% EtOAc in heptane) to give the title compound (0.067 g, 76%) as a yellow film; MS (ESI) m/z $[M+H]^+$ 329.3.

Intermediate 222: Ethyl 2-methyl-6-morpholinoquinoline-4-carboxylate

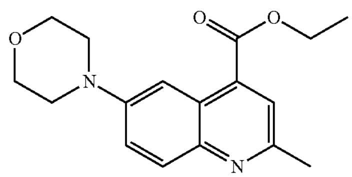 [SMILES: CCOC(=O)c1cc(C)nc2ccc(N3CCOCC3)cc12]

$Pd(dba)_2$ (16 mg, 0.03 mmol), RuPhos (25 mg, 0.05 mmol) and $K_3PO_4$ (231 mg, 1.09 mmol) was added to ethyl 6-bromo-2-methylquinoline-4-carboxylate (160 mg, 0.54 mmol), in tert-BuOH (3 mL). Morpholine (47 mg, 0.54 mmol) was added, and the reaction flask was fitted with a rubber septum, purged with $N_2$ (g) and heated at 90° C. overnight. The reaction mixture was diluted with EtOAc and washed with $H_2O$ and brine. The organic layer was evaporated and the residue was purified by preparative HPLC, PrepMethod E, (gradient: 15-55%) to give the title compound (89 mg, 55%); MS (ESI) m/z (M+H)+301.3.

Intermediate 223: tert-Butyl 6-(2-oxo-1-oxa-3-azaspiro[5.5]undecan-3-yl)quinoline-4-carboxylate

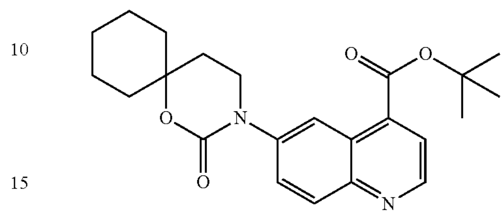

Step a) tert-Butyl 6-((2-(1-hydroxycyclohexyl)ethyl)amino)quinoline-4-carboxylate A mixture of tert-butyl 6-bromoquinoline-4-carboxylate (0.200 g, 0.65 mmol), XantPhos Pd G4 (0.062 g, 0.06 mmol), $Cs_2CO_3$ (0.634 g, 1.95 mmol), 1-(2-aminoethyl)-cyclohexan-1-ol hydrochloride (0.152 g, 0.84 mmol) and anhydrous dioxane (3.25 mL) under $N_2$ (g) was stirred vigorously at 85° C. for 3 h. The vial was allowed to reach rt, SilaMetS® Thiol scavenger (300 mg; loading: 1.4 mmol/g) was added and the mixture was stirred overnight. The mixture was diluted with EtOAc and $H_2O$ and the resulting mixture was filtered. The layers of the filtrate were separated and the organic layer was dried over $Na_2SO_4$, filtered and concentrated to give crude tert-butyl 6-((2-(1-hydroxycyclohexyl)ethyl)amino)-quinoline-4-carboxylate.

Step b) tert-Butyl 6-(2-oxo-1-oxa-3-azaspiro[5.5]undecan-3-yl)quinoline-4-carboxylate Triphosgene (0.148 g, 0.5 mmol) was added to a stirred mixture of the crude tert-butyl 6-((2-(1-hydroxycyclohexyl)ethyl)amino)quinoline-4-carboxylate from Step a) and DIPEA (0.453 mL, 2.60 mmol) in EtOAc (12 mL) at rt. The reaction mixture was stirred at rt for min and was then heated at 120° C. for 20 min. DIPEA (0.113 mL, 0.65 mmol) was added and the reaction was heated at 120° C. for 5 min. The reaction mixture was diluted with EtOAc and washed with $H_2O$ and 8% $NaHCO_3$ (aq), passed through a phase separator and concentrated. The residue was purified by preparative HPLC, PrepMethod H, (gradient: 35-75%). The purified product was dissolved in DCM, washed with $H_2O$ and concentrated to give the title compound (0.12 g, 47%) as a pale yellow solid; MS (ESI) m/z $[M+H]^+$ 397.5.

Intermediate 224: tert-Butyl 6-((2-(1-hydroxycyclopentyl)ethyl)amino)quinoline-4-carboxylate

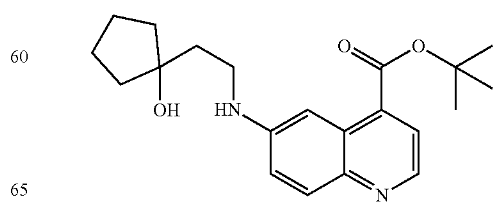

A mixture of tert-butyl 6-bromoquinoline-4-carboxylate (0.200 g, 0.65 mmol), XantPhos Pd G4 (0.062 g, 0.06 mmol), $Cs_2CO_3$ (0.634 g, 1.95 mmol), 1-(2-aminoethyl)-cyclopentan-1-ol (170 mg, 1.32 mmol) and anhydrous dioxane (3.25 mL) under $N_2$ (g) was stirred vigorously at 80-85° C. for 75 min and was then allowed to reach rt. SilaMetS® Thiol scavenger (300 mg; loading 1.4 mmol/g) was added and the mixture was stirred for 1.5 h, diluted with EtOAc and filtered (Celite® 521). The filter pad was washed with EtOAc and the combined filtrates were concentrated. The residue was purified by preparative HPLC, PrepMethod H, (gradient: 35-75%). Pure fractions were partially concentrated to remove most of the MeCN and the resulting aqueous mixture was extracted with DCM and the phases were separated using a phase separator. The organic layer was concentrated to give the title compound (0.163 g, 71%) as a yellow viscous oil; MS (ESI) m/z $[M+H]^+$ 357.4.

Intermediate 225: tert-Butyl 6-(7-oxo-6-oxa-8-azaspiro[4.5]decan-8-yl)quinoline-4-carboxylate

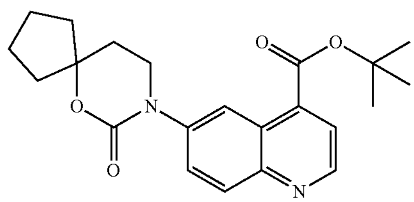 [SMILES: CC(C)(C)OC(=O)c1ccnc2ccc(N3CCC4(CCCC4)OC3=O)cc12]

Triphosgene (74 mg, 0.25 mmol) was added to a stirred mixture of tert-butyl 6-((2-(1-hydroxycyclopentyl)ethyl) amino)quinoline-4-carboxylate Intermediate 224 (159 mg, 0.41 mmol) and DIPEA (289 μL, 1.66 mmol) in anhydrous DCM (4.5 mL) at rt. The reaction mixture was stirred at rt for 1.5 h and was then heated at 120° C. for 15 min. The solution was concentrated and the residue was purified by preparative HPLC, PrepMethod H, (gradient: 30-70%). The purified product was dissolved in DCM and washed with $H_2O$. The aqueous layer was extracted with DCM (×4) and the combined organic layers were concentrated to give the title compound (0.106 g, 67%) as a pale yellow foam; MS (ESI) m/z $[M+H]^+$ 383.4.

Intermediate 226: tert-Butyl 6-(6,6-dimethyl-2-oxo-1,3-oxazinan-3-yl)quinoline-4-carboxylate

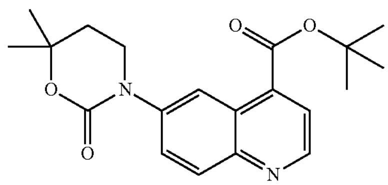 [SMILES: CC(C)(C)OC(=O)c1ccnc2ccc(N3CCC(C)(C)OC3=O)cc12]

A mixture of tert-butyl 6-bromoquinoline-4-carboxylate (280 mg, 0.91 mmol), 6,6-dimethyl-1,3-oxazinan-2-one (WO2013/050454) (176 mg, 1.36 mmol), $Pd_2(dba)_3$ (25 mg, 0.03 mmol), XPhos (26 mg, 0.05 mmol) and $Cs_2CO_3$ (592 mg, 1.82 mmol) in 1,4-dioxane (5 mL) under $N_2$ (g) was stirred at 100° C. for 24 h. The solvent was removed under reduced pressure and the residue was purified by preparative TLC (eluent: petroleum ether, EtOAc 1:1), to afford the title compound (0.040 g, 12%) as a white solid; MS m/z (ESI) $[M+H]^+$ 357.25.

Intermediate 227: tert-Butyl 6-(3-(fluoromethyl) azetidin-1-yl)quinoline-4-carboxylate

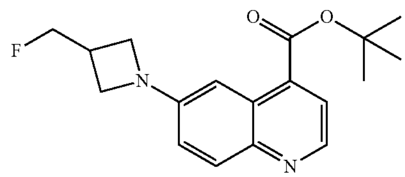 [SMILES: CC(C)(C)OC(=O)c1ccnc2ccc(N3CC(CF)C3)cc12]

$Cs_2CO_3$ (977 mg, 3.00 mmol) was added to tert-butyl 6-bromoquinoline-4-carboxylate (308 mg, 1.00 mmol), 3-(fluoromethyl)azetidine hydrochloride (251 mg, 2.00 mmol), $Pd_2(dba)_3$ (92 mg, 0.10 mmol) and DavePhos (79 mg, 0.20 mmol) in 1,4-dioxane (3 mL) at 13° C. The resulting suspension was stirred at 100° C. for 2 h under $N_2$ (g). The reaction mixture was diluted with DCM. The solvent was removed under reduced pressure and the residue was purified by preparative TLC (petroleum ether:EtOAc, 1:1) to give the title compound (0.282 g, 89%) as a brown gum; MS m/z (ESI) $[M+H]^+$ 317.

Intermediate 228: 6-(3-(Fluoromethyl)azetidin-1-yl) quinoline-4-carboxylic acid

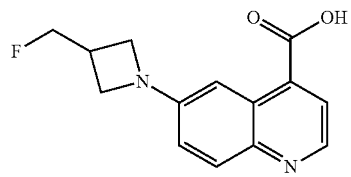 [SMILES: O=C(O)c1ccnc2ccc(N3CC(CF)C3)cc12]

TFA (5 mL) was added to tert-butyl 6-(3-(fluoromethyl) azetidin-1-yl)quinoline-4-carboxylate Intermediate 227 (274 mg, 0.87 mmol) in DCM (5 mL) at 10° C. The resulting solution was stirred at 10° C. overnight. The solvent was removed under reduced pressure to afford the crude title compound (0.466 g); MS m/z (ESI) $[M+H]^+$ 261.

Intermediate 229: tert-Butyl 6-(4,5,6,7-tetrahydro-1H-indazol-1-yl)quinoline-4-carboxylate Intermediate 230: tert-Butyl 6-(4,5,6,7-tetrahydro-2H-indazol-2-yl)quinoline-4-carboxylate

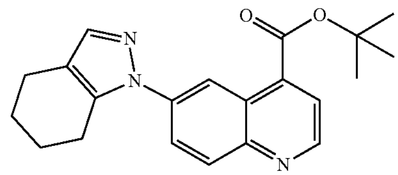

-continued

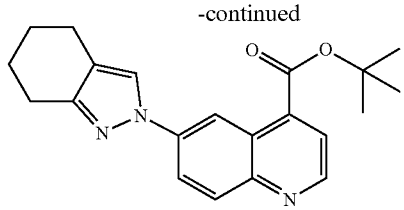

$Cs_2CO_3$ (1057 mg, 3.24 mmol) was added to tert-butyl 6-bromoquinoline-4-carboxylate (500 mg, 1.62 mmol), 4,5,6,7-tetrahydro-1H-indazole (297 mg, 2.43 mmol) and EPhos Pd G4 (149 mg, 0.16 mmol) in 1,4-dioxane (10 mL) at 15° C. The resulting suspension was stirred at 100° C. for 16 h under $N_2$ (g). The mixture was filtered through a pad of Celite® and the filtrate was concentrated under reduced pressure. The residue was purified by preparative TLC (EtOAc:petroleum ether, 2:1) followed by preparative HPLC, PrepMethod F, (gradient: 70-90%), to give the first eluting compound tert-butyl 6-(4,5,6,7-tetrahydro-1H-indazol-1-yl)quinoline-4-carboxylate Intermediate 229 (0.040 g, 7%) as a pale yellow solid; MS m/z (ESI) $[M+H]^+$ 350; $^1H$ NMR (300 MHz, $CDCl_3$) δ 9.01 (d, 1H), 8.92 (d, 1H), 8.25 (d, 1H), 8.12 (dd, 1H), 7.91 (d, 1H), 7.57 (s, 1H), 2.92 (t, 2H), 2.65 (t, 2H), 1.89 (t, 4H), 1.70 (s, 9H).

and the second eluting compound tert-butyl 6-(4,5,6,7-tetrahydro-2H-indazol-2-yl)quinoline-4-carboxylate Intermediate 230 (0.245 g, 43%) as a white solid; MS m/z (ESI) $[M+H]^+$ 350; $^1H$ NMR (300 MHz, $CDCl_3$) δ 9.01 (d, 1H), 8.92 (d, 1H), 8.25 (d, 1H), 8.12 (dd, 1H), 7.91 (d, 1H), 7.57 (s, 1H), 2.92 (t, 2H), 2.65 (t, 2H), 1.89 (t, 4H), 1.70 (s, 9H).

The configuration of the regioisomers were assigned by NOESY NMR

Intermediate 231: tert-Butyl 6-(5-methyl-3-(trifluoromethyl)-1H-pyrazol-1-yl)quinoline-4-carboxylate

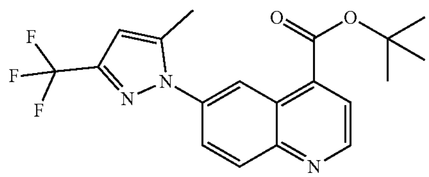 [SMILES: Cc1cc(C(F)(F)F)nn1-c1ccc2nccc(C(=O)OC(C)(C)C)c2c1]

$Cs_2CO_3$ (529 mg, 1.62 mmol) was added to tert-butyl 6-bromoquinoline-4-carboxylate (250 mg, 0.81 mmol), 5-methyl-3-(trifluoromethyl)-1H-pyrazole (183 mg, 1.22 mmol) and EPhos Pd G4 (75 mg, 0.08 mmol) in 1,4-dioxane (5 mL) at 10° C. under $N_2$ (g). The resulting suspension was stirred at 100° C. for 15 h. The reaction mixture was filtered through Celite® and the filtrate was concentrated under reduced pressure. The residue was purified by preparative TLC (EtOAc:petroleum ether, 2:1) followed by preparative HPLC, PrepMethod F, (gradient: 60-85%), to give the title compound (0.133 g, 43%) as a white solid; MS m/z (ESI) $[M+H]^+$ 378.

Intermediate 232: 6,6-Dimethyl-2,4,5,6-tetrahydrocyclopenta[c]pyrazole hydrochloride

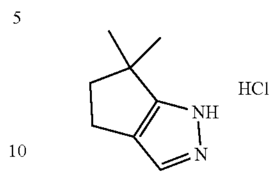

Hydrazine hydrate (5.3 g, 106 mmol) was added dropwise with stirring at 25° C. over 10 min to stirred (5E)-5-[(dimethylamino)methylidene]-2,2-dimethylcyclopentan-1-one (18 g, 108 mmol) in a 500-mL 3-necked round-bottom flask purged and maintained with an inert atmosphere of $N_2$ (g). EtOH (180 mL, 3.10 mol) was added and the resulting solution was heated at reflux overnight in an oil bath. The reaction mixture was cooled to 25° C. The resulting mixture was concentrated under vacuum. The residue was dissolved in 200 mL of ether and the HCl salt of the title compound was precipitated (12.6 g, 68%) as an off-white solid; MS m/z (ESI) $[M+H]^+$ 137.1.

Intermediate 233: tert-Butyl 6-(6,6-dimethyl-5,6-dihydrocyclopenta[c]pyrazol-2(4H)-yl)quinoline-4-carboxylate

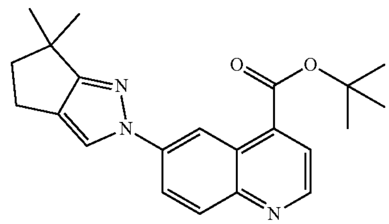 [SMILES: CC(C)(C)OC(=O)c1ccnc2ccc(-n3cc4c(n3)C(C)(C)CC4)cc12]

$Cs_2CO_3$ (793 mg, 2.43 mmol) was added to tert-butyl 6-bromoquinoline-4-carboxylate (250 mg, 0.81 mmol), 6,6-dimethyl-2,4,5,6-tetrahydrocyclopenta[c]pyrazole hydrochloride Intermediate 232 (210 mg, 1.22 mmol) and EPhos Pd G4 (75 mg, 0.08 mmol) in 1,4-dioxane (1 mL) at 15° C. The resulting suspension was stirred at 100° C. for 16 h under $N_2$ (g). The reaction mixture was filtered through Celite® and the filter cake was washed with DCM (10 mL). The filtrate was concentrated under reduced pressure and the residue was purified by preparative TLC (EtOAc:petroleum ether, 2:1), to give the title compound (0.268 g, 91%) as a yellow solid; MS m/z (ESI) $[M+H]^+$ 364.

Intermediate 234: 6-(3-(Trifluoromethyl)-1H-pyrazol-1-yl)quinoline-4-carboxylic acid

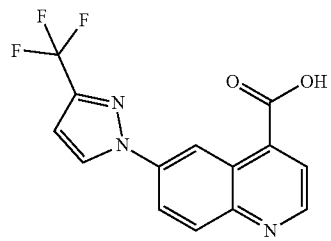 [SMILES: O=C(O)c1ccnc2ccc(-n3ccc(C(F)(F)F)n3)cc12]

$Cs_2CO_3$ (776 mg, 2.38 mmol) was added to 6-bromoquinoline-4-carboxylic acid (200 mg, 0.79 mmol), 3-(trifluoromethyl)-1H-pyrazole (162 mg, 1.19 mmol) and $Cu_2O$ (11 mg, 0.08 mmol) in DMF (5 mL) at 10° C. The resulting suspension was stirred at 120° C. for 20 h under $N_2$ (g). The reaction mixture was filtered through Celite®. The reaction mixture was adjusted to pH 6 with aq HCl (2 M) and the mixture was filtered through Celite® again. The filtrate was purified by preparative HPLC, PrepMethod C, (gradient: 40-60%) to give the title compound (0.088 g, 36%) as a white solid; MS m/z (ESI) $[M+H]^+$ 308.

Intermediate 235: 6-(4,6-Difluoro-1H-indol-1-371) quinoline-4-carboxylic acid

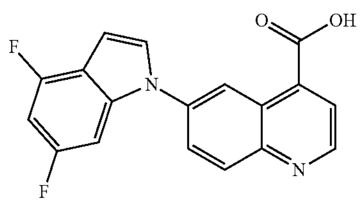 [SMILES: O=C(O)c1ccnc2ccc(-n3ccc4c(F)cc(F)cc43)cc12]

CuI (15 mg, 0.08 mmol) was added to a solution of 6-bromoquinoline-4-carboxylic acid (200 mg, 0.79 mmol), 4,6-difluoro-1H-indole (243 mg, 1.59 mmol) and $K_2CO_3$ (219 mg, 1.59 mmol) in DMF (10 mL) under $N_2$ (g). The reaction was stirred at 150° C. for 15 h. The solvent was removed under reduced pressure. The reaction mixture was diluted with $H_2O$ (15 mL) and the reaction mixture was adjusted to pH 6 with aq HCl (1 M). The precipitate was collected by filtration and washed with $H_2O$ (30 mL) to provide a brown solid. The solid was dissolved in DMF (15 mL) and filtered. The filtrate was concentrated under vacuum to give the crude title compound (0.20 g, 78%) as a brown solid; MS m/z (ESI) $[M+H]^+$ 325.

Intermediate 236: 6-(5-Fluoro-1H-indol-1-yl)quinoline-4-carboxylic acid

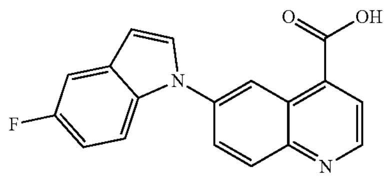 [SMILES: O=C(O)c1ccnc2ccc(-n3ccc4cc(F)ccc43)cc12]

$Cs_2CO_3$ (238 mg, 0.73 mmol) was added to tert-butyl 6-bromoquinoline-4-carboxylate (150 mg, 0.49 mmol), 5-fluoro-/H-indole (99 mg, 0.73 mmol) and $Cu_2O$ (7 mg, 0.05 mmol) in dry DMF (5 mL) at 10° C. The resulting suspension was stirred at 120° C. for 19 h under $N_2$ (g). The reaction mixture was adjusted to pH 6 with aq HCl (1 M), and filtered through a Celite® pad. The filtrate was purified by preparative HPLC, PrepMethod F, (gradient: 45-70%) to give the title compound (0.035 g, 23%) as a pale yellow solid; MS m/z (ESI) $[M+H]^+$ 307.

Intermediate 237: 6-(3-Methyl-1H-pyrrol-1-yl)quinoline-4-carboxylic acid

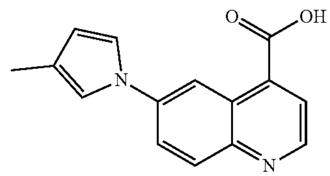 [SMILES: Cc1ccn(-c2ccc3nccc(C(=O)O)c3c2)c1]

$K_2CO_3$ (123 mg, 0.89 mmol) was added to 6-bromoquinoline-4-carboxylic acid (150 mg, 0.60 mmol), 3-methyl-/H-pyrrole (78 μL, 0.89 mmol) and CuI (11 mg, 0.06 mmol) in dry DMF (3 mL) at 10° C. The resulting suspension was stirred at 150° C. for 15 h under $N_2$ (g). The reaction mixture was adjusted to pH 6 with aq HCl (1 M). The mixture was filtered through a Celite® pad. The filtrate was purified by preparative HPLC, PrepMethod D, (gradient: 50-65%), to give the title compound (0.050 g, 33%) as a grey solid; MS m/z (ESI) $[M+H]^+$ 253.

Intermediate 238: Ethyl 6-(3-morpholinoazetidin-1-yl)quinoline-4-carboxylate

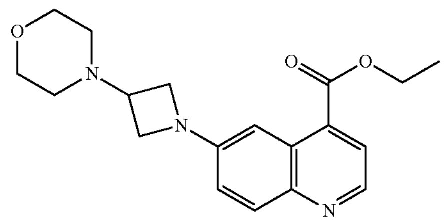 [SMILES: CCOC(=O)c1ccnc2ccc(N3CC(N4CCOCC4)C3)cc12]

A mixture of ethyl 6-bromoquinoline-4-carboxylate (140 mg, 0.50 mmol), $Cs_2CO_3$ (651 mg, 2.00 mmol), RuPhos Pd G4 (43 mg, 0.05 mmol) and 4-(azetidin-3-yl)morpholine hydrochloride (116 mg, 0.65 mmol) and dioxane (1.2 mL) under $N_2$ (g) was stirred at 90° C. for 5.5 h. The reaction mixture was diluted with EtOAc (5 mL). SilaMetS® Thiol scavenger (150 mg; loading 1.4 mmol/g) was added and the mixture was stirred for 1 h and then filtered through a pad of Celite® 521. The filter pad was washed with EtOAc (12 mL) and the combined filtrates were concentrated. The residue was purified by preparative reversed phase HPLC, PrepMethod H, (gradient: 15-65%) to give the title compound (0.141 g, 83%) as a yellow solid; MS (ESI) m/z $[M+H]^+$ 342.3.

Intermediate 239: 6-(3-Morpholinoazetidin-1-yl) quinoline-4-carboxylic acid

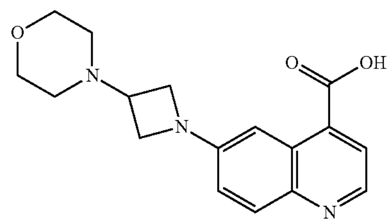 [SMILES: O=C(O)c1ccnc2ccc(N3CC(N4CCOCC4)C3)cc12]

Aq NaOH (3.8 M, 0.220 mL, 0.84 mmol) was added to a solution of ethyl 6-(3-morpholinoazetidin-1-yl)quinoline-4-carboxylate Intermediate 238 (143 mg, 0.42 mmol) in MeOH (2 mL) and the reaction was stirred at rt overnight. Aq HCl (3.8 M, 0.220 mL, 0.84 mmol) was added dropwise and the resulting mixture was concentrated under reduced pressure at rt. The residue was concentrated under reduced pressure from MeCN to give the crude title compound (0.176 g); MS (ESI) m/z $[M+H]^+$ 314.3.

Intermediate 240: 6-(4,5,6,7-Tetrahydro-1H-indazol-1-yl)quinoline-4-carboxylic acid

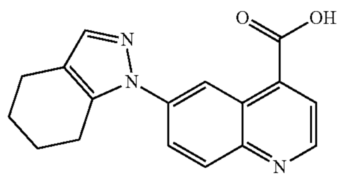 [SMILES: O=C(O)c1ccnc2ccc(-n3ncc4c3CCCC4)cc12]

TFA (4 mL) was added slowly to a stirred solution of tert-butyl 6-(4,5,6,7-tetrahydro-1H-indazol-1-yl)quinoline-4-carboxylate Intermediate 229 (36 mg, 0.10 mmol) in DCM (4 mL) at 15° C. The resulting solution was stirred at 15° C. for 15 h. The solvent was removed under reduced pressure to afford the crude title compound (0.063 g) as a beige solid; MS m/z (ESI) $[M+H]^+$ 294.

Intermediate 241: 6-(4,5,6,7-Tetrahydro-2H-indazol-2-yl)quinoline-4-carboxylic acid

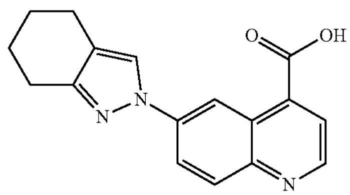 [SMILES: O=C(O)c1ccnc2ccc(-n3cc4c(n3)CCCC4)cc12]

TFA (5 mL) was added slowly to a stirred solution of tert-butyl 6-(4,5,6,7-tetrahydro-2H-indazol-2-yl)quinoline-4-carboxylate Intermediate 230 (239 mg, 0.68 mmol) in DCM (5 mL) at 15° C. The resulting solution was stirred at 15° C. for 15 h. The solvent was removed under reduced pressure to afford the crude title compound (0.527 g) as a yellow oil which solidified on standing; MS m/z (ESI) $[M+H]^+$ 294.

Intermediate 242: 6-(5-Methyl-3-(trifluoromethyl)-1H-pyrazol-1-371)quinoline-4-carboxylic acid

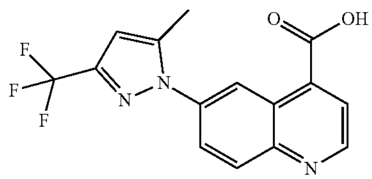 [SMILES: Cc1cc(C(F)(F)F)nn1-c1ccc2nccc(C(=O)O)c2c1]

TFA (5 mL) was added to a stirred solution of tert-butyl 6-(5-methyl-3-(trifluoromethyl)-1H-pyrazol-1-yl)quinoline-4-carboxylate Intermediate 231 (130 mg, 0.34 mmol) in DCM (5 mL) at 15° C. The resulting solution was stirred at 15° C. for 18 h. The solvent was removed under reduced pressure to afford the crude title compound (0.230 g) as a brown gum; MS m/z (ESI) $[M+H]^+$ 322.

Intermediate 243: 6-(6,6-Dimethyl-5,6-dihydrocyclopenta[c]pyrazol-2(4H)-yl)quinoline-4-carboxylic acid

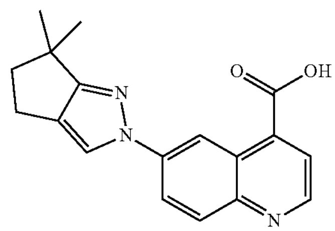 [SMILES: CC1(C)CCc2cn(-c3ccc4nccc(C(=O)O)c4c3)nc21]

TFA (5 mL) was added to a stirred solution of tert-butyl 6-(6,6-dimethyl-5,6-dihydrocyclopenta[c]pyrazol-2(4H)-yl) quinoline-4-carboxylate Intermediate 233 (260 mg, 0.72 mmol) in DCM (5 mL) at 15° C. The resulting solution was stirred at 15° C. for 15 h. The solvent was removed under reduced pressure to give the crude title compound (0.552 g) as a yellow oil; MS m/z (ESI) $[M+H]^+$ 308.

Intermediate 244: 6-(5,5-Dimethyl-5,6-dihydro-4H-pyrrolo[1,2-b]pyrazol-3-yl)quinoline-4-carboxylic acid

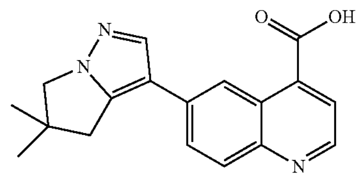 [SMILES: CC1(C)Cc2c(-c3ccc4nccc(C(=O)O)c4c3)cnn2C1]

1,4-Dioxane (3 mL) and water (0.75 mL) were added to a mixture of 6-bromoquinoline-4-carboxylic acid (100 mg, 0.40 mmol), 5,5-dimethyl-3-(4,4,5,5-tetramethyl-1,3,2-dioxaborolan-2-yl)-5,6-dihydro-4H-pyrrolo[1,2-b]pyrazole (114 mg, 0.44 mmol), $Cs_2CO_3$ (323 mg, 0.99 mmol) and Pd(dtbpf)$Cl_2$ (26 mg, 0.04 mmol). The reaction mixture was purged with $N_2$(g) and then stirred at rt overnight. DMSO (3 mL) was added to the reaction mixture and it was concentrated under reduced pressure. The residue was purified by preparative HPLC, PrepMethod E, (gradient: 5-45%) to give the title compound (74 mg, 61%) as a light yellow solid; MS (ESI) m/z $[M+H]^+$ 308.3.

Intermediate 245: 6-(2-Fluoropyridin-4-yl)quinoline-4-carboxylic acid

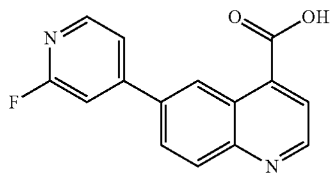 [SMILES: O=C(O)c1ccnc2ccc(-c3ccnc(F)c3)cc12]

The title compound was prepared as described for Intermediate 244 using 6-bromoquinoline-4-carboxylic acid (100 mg, 0.40 mmol) and (2-fluoropyridin-4-yl)boronic acid (61 mg, 0.44 mmol). The crude product was purified by preparative HPLC, PrepMethod E, (gradient: 0-40%) to give the title compound (5 mg, 5%) as white solid; MS (ESI) m/z $[M+H]^+$ 269.2.

Intermediate 246: 6-(5-Fluoropyridin-2-yl)quinoline-4-carboxylic acid

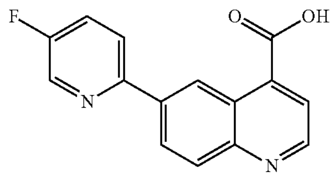 [SMILES: O=C(O)c1ccnc2ccc(-c3ccc(F)cn3)cc12]

1,4-Dioxane (3 mL) and water (0.75 mL) were added to a mixture of 6-bromoquinoline-4-carboxylic acid (100 mg, 0.40 mmol), (5-fluoropyridin-2-yl)boronic acid (67 mg, 0.48 mmol), $Cs_2CO_3$ (323 mg, 0.99 mmol) and Pd(dtbpf)$Cl_2$ (26 mg, 0.04 mmol). The reaction mixture was purged with $N_2$ (g) and then stirred at rt overnight. (5-Fluoropyridin-2-yl) boronic acid (67 mg, 0.48 mmol), Pd(dtbpf)$Cl_2$ (26 mg, 0.04 mmol) and $Cs_2CO_3$ (323 mg, 0.99 mmol) were added to the reaction mixture and it was purged with $N_2$ (g), and heated at 100° C. overnight in a microwave reactor. DMSO was added to the reaction mixture (2 mL) and it was concentrated under reduced pressure. The residue was purified by preparative HPLC, PrepMethod E, (gradient: 0-40%) to give the title compound (6 mg, 6%) as white solid; MS (ESI) m/z $[M+H]^+$ 269.2.

Intermediate 247: Methyl 6-(3-((trifluoromethoxy) methyl)azetidin-1-yl)quinoline-4-carboxylate

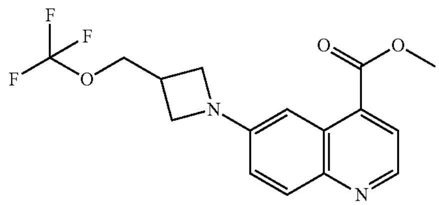 [SMILES: COC(=O)c1ccnc2ccc(N3CC(COC(F)(F)F)C3)cc12]

$Cs_2CO_3$ (255 mg, 0.78 mmol) was added to a mixture of methyl 6-bromoquinoline-4-carboxylate (160 mg, 0.60 mmol), 3-((trifluoromethoxy)methyl)azetidine hydrochloride (150 mg, 0.78 mmol), $Pd_2(dba)_3$ (55 mg, 0.06 mmol) and XPhos (57 mg, 0.12 mmol) in 1,4-dioxane (1 mL) at 30° C., and the reaction mixture was stirred at 100° C. for 2 h. The reaction mixture was filtered through Celite®, and the filtrate was concentrated under reduced pressure. The residue was purified by preparative TLC (EtOAc:petroleum ether, 3:2), to give the title compound (0.20 g, 98%) as a brown oil which solidified on standing; MS (ESI) m/z $[M+H]^+$ 431.

Intermediate 248: 6-(34(Trifluoromethoxy)methyl) azetidin-1-yl)quinoline-4-carboxylic acid

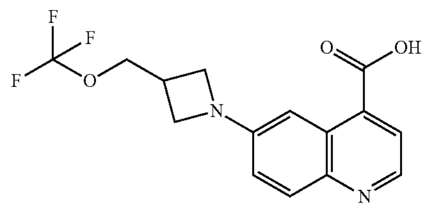 [SMILES: O=C(O)c1ccnc2ccc(N3CC(COC(F)(F)F)C3)cc12]

A solution of NaOH (109 mg, 2.72 mmol) in water (2 mL) was added slowly to a stirred solution of methyl 6-(3-((trifluoromethoxy)methyl)azetidin-1-yl)quinoline-4-carboxylate Intermediate 247 (185 mg, 0.54 mmol) in MeOH (6 mL), cooled to 0° C., and the resulting mixture was stirred at 30° C. for 1 h. The reaction mixture was diluted with water (20 mL), pH was adjusted to 6 with aq HCl (2 M,), and extracted with EtOAc (8×75 mL). The combined organic layer was dried over $Na_2SO_4$, filtered and evaporated at reduced pressure, to give the title compound (0.175 g, 99%) as an orange solid; MS (ESI) m/z $[M+H]^+$ 327.

Intermediate 249: Methyl 6-(3-methyl-3-(2,2,2-trifluoroethyl)azetidin-1-yl)quinoline-4-carboxylate

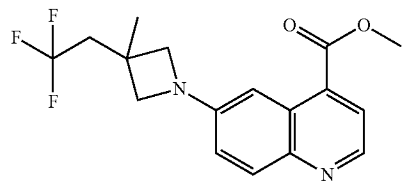 [SMILES: COC(=O)c1ccnc2ccc(N3CC(C)(CC(F)(F)F)C3)cc12]

$Cs_2CO_3$ (255 mg, 0.78 mmol) was added to a mixture of methyl 6-bromoquinoline-4-carboxylate (160 mg, 0.60 mmol), 3-methyl-3-(2,2,2-trifluoroethyl)azetidine hydrochloride (148 mg, 0.78 mmol), $Pd_2(dba)_3$ (55 mg, 0.06 mmol) and XPhos (57 mg, 0.12 mmol) in 1,4-dioxane (1 mL) at 30° C., and the reaction mixture was stirred at 100° C. for 2 h. The reaction mixture was filtered through Celite®, and the filtrate was concentrated under reduced pressure. The crude product was purified by preparative TLC (EtOAc:petroleum ether, 3:2), to give the title compound (0.199 g, 98%) as a brown oil which solidified on standing; MS (ESI) m/z $[M+H]^+$ 339.

Intermediate 250: 6-(3-Methyl-3-(2,2,2-trifluoroethyl)azetidin-1-yl)quinoline-4-carboxylic acid

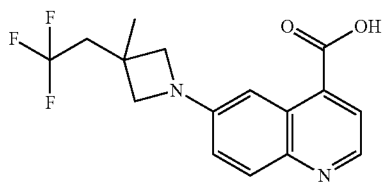 [SMILES: CC1(CC(F)(F)F)CN(c2ccc3nccc(C(=O)O)c3c2)C1]

A solution of NaOH (109 mg, 2.73 mmol) in water (2 mL) was added slowly to a stirred solution of methyl 6-(3-methyl-3-(2,2,2-trifluoroethyl)azetidin-1-yl)quinoline-4-carboxylate Intermediate 249 (185 mg, 0.55 mmol) in MeOH (6 mL) cooled to 0° C. and the reaction mixture was stirred at 30° C. for 1 h. The reaction mixture was diluted with water (20 mL), pH was adjusted to 6 with aq HCl (2 M), and extracted with EtOAc (8×75 mL). The combined organic layer was dried over $Na_2SO_4$, filtered and evaporated at reduced pressure to give the title compound (0.173 g, 98%) as a yellow solid; MS (ESI) m/z $[M+H]^+$ 325.

Intermediate 251: Methyl 6-(3-(trifluoromethoxy)azetidin-1-yl)quinoline-4-carboxylate

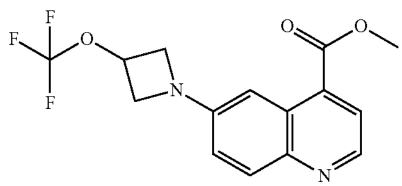 [SMILES: COC(=O)c1ccnc2ccc(N3CC(OC(F)(F)F)C3)cc12]

$Cs_2CO_3$ (478 mg, 1.47 mmol) was added to a mixture of methyl 6-bromoquinoline-4-carboxylate (300 mg, 1.13 mmol), 3-(trifluoromethoxy)azetidine hydrochloride (260 mg, 1.47 mmol), $Pd_2(dba)_3$ (103 mg, 0.11 mmol) and XPhos (107 mg, 0.23 mmol) in 1,4-dioxane (10 mL) at 35° C., and the reaction mixture was stirred at 100° C. for 2 h. The reaction mixture was filtered through Celite®, and the filtrate was concentrated under reduced pressure. The crude product was purified by preparative TLC (EtOAc:petroleum ether, 2:1) to give the title compound (0.354 g, 96%) as a brown oil which solidified on standing; MS (ESI) m/z $[M+H]^+$ 327.

Intermediate 252: 6-(3-(Trifluoromethoxy)azetidin-1-yl)quinoline-4-carboxylic acid

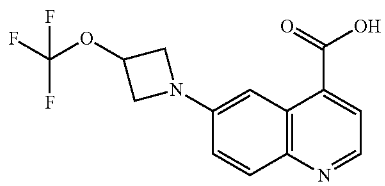 [SMILES: O=C(O)c1ccnc2ccc(N3CC(OC(F)(F)F)C3)cc12]

A solution of NaOH (201 mg, 5.03 mmol) in water (2 mL) was added to a stirred solution of methyl 6-(3-(trifluoromethoxy)azetidin-1-yl)quinoline-4-carboxylate Intermediate 251 (328 mg, 1.01 mmol) in MeOH (6 mL) cooled to 0° C., and the reaction mixture was stirred at 37° C. for 1 h. The reaction mixture was diluted with water (20 mL), the pH was adjusted to 6 with aq HCl (2 M), and extracted with EtOAc (6×75 mL). The combined organic layer was dried over $Na_2SO_4$, filtered and evaporated at reduced pressure to give the title compound (0.30 g, 96%) as a yellow solid; MS (ESI) m/z $[M+H]^+$ 313.

Intermediate 253: Methyl 6-(3-(2,2-difluoroethyl)-3-methylazetidin-1-yl)quinoline-4-carboxylate

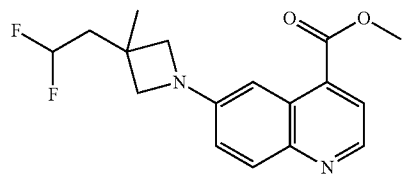

I $Cs_2CO_3$ (302 mg, 0.93 mmol) was added to a mixture of methyl 6-bromoquinoline-4-carboxylate (190 mg, 0.71 mmol), 3-(2,2-difluoroethyl)-3-methylazetidine hydrochloride (159 mg, 0.93 mmol), $Pd_2(dba)_3$ (65 mg, 0.07 mmol) and XPhos (68 mg, 0.14 mmol) in 1,4-dioxane (10 mL) at 28° C., and the reaction mixture was stirred at 100° C. for 2 h. The reaction mixture was filtered through Celite®, and the filtrate was concentrated under reduced pressure. The crude product was purified by preparative TLC (EtOAc: petroleum ether, 3:2) followed by purification on reversed phase flash chromatography on a C18 column, (gradient: MeCN in water) to give the title compound (0.203 g) as a tan gum; MS (ESI) m/z $[M+H]^+$ 321.

Intermediate 254: 6-(3-(2,2-Difluoroethyl)-3-methylazetidin-1-yl)quinoline-4-carboxylic acid

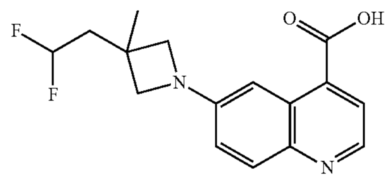 [SMILES: CC1(CC(F)F)CN(c2ccc3nccc(C(=O)O)c3c2)C1]

A solution of NaOH (97 mg, 2.4 mmol) in water (2 mL) was added slowly to a stirred solution of methyl 6-(3-(2,2-difluoroethyl)-3-methylazetidin-1-yl)quinoline-4-carboxylate Intermediate 253 (173 mg) in MeOH (6 mL), cooled to 0° C., and the reaction mixture was stirred at 28° C. for 1 h. The reaction mixture was diluted with water (20 mL), pH was adjusted to 6 with aq HCl (2 M), and extracted with EtOAc (4×100 mL). The combined organic layer was dried over $Na_2SO_4$, filtered and evaporated at reduced pressure give the title compound (0.14 g, 94%) as an orange solid; MS (ESI) m/z $[M+H]^+$ 307.

Intermediate 255: Methyl 6-(3-cyclopropyl-3-methylazetidin-1-yl)quinoline-4-carboxylate

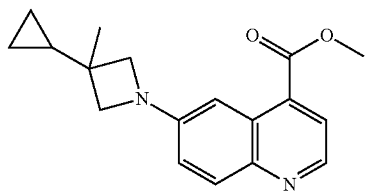

$Cs_2CO_3$ (207 mg, 0.64 mmol) was added to a mixture of methyl 6-bromoquinoline-4-carboxylate (130 mg, 0.49 mmol), 3-cyclopropyl-3-methylazetidine (71 mg, 0.64 mmol), $Pd_2(dba)_3$ (45 mg, 0.05 mmol) and XPhos (47 mg, 0.10 mmol) in 1,4-dioxane (10 mL) at 30° C., and the reaction mixture was stirred at 100° C. for 3 h. The reaction mixture was filtered, and the filtrate was concentrated under reduced pressure. The crude product was purified by preparative TLC (EtOAc:petroleum ether, 3:2), to give the title compound (0.14 g, 97%) as a brown gum; MS (ESI) m/z $[M+H]^+$ 297.

Intermediate 256: 6-(3-Cyclopropyl-3-methylazetidin-1-yl)quinoline-4-carboxylic acid

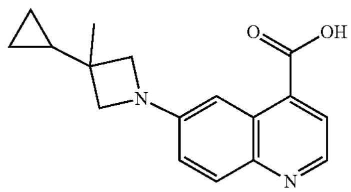 [SMILES: CC1(C2CC2)CN(c2ccc3nccc(C(=O)O)c3c2)C1]

A solution of NaOH (74 mg, 1.9 mmol) in water (2 mL) was added to a stirred suspension of methyl 6-(3-cyclopropyl-3-methylazetidin-1-yl)quinoline-4-carboxylate Intermediate 255 (110 mg, 0.37 mmol) in MeOH (6 mL) cooled to 0° C., and the reaction mixture was stirred at 23° C. for 1 h. The reaction mixture was diluted with water (15 mL), pH was adjusted to 6 with aq HCl (2 M), and extracted with EtOAc (4×75 mL). The combined organic layer was dried over $Na_2SO_4$, filtered and evaporated at reduced pressure to give the title compound (0.10 g, 95%) as a yellow solid; MS (ESI) m/z $[M+H]^+$ 283.

Intermediate 257: Methyl 6-(3-(difluoromethyl)-3-methylazetidin-1-yl)quinoline-4-carboxylate

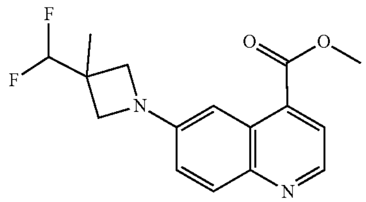 [SMILES: COC(=O)c1ccnc2ccc(N3CC(C)(C(F)F)C3)cc12]

$Cs_2CO_3$ (207 mg, 0.64 mmol) was added to a mixture of methyl 6-bromoquinoline-4-carboxylate (130 mg, 0.49 mmol), 3-(difluoromethyl)-3-methylazetidine hydrochloride (100 mg, 0.64 mmol), $Pd_2(dba)_3$ (45 mg, 0.05 mmol) and XPhos (47 mg, 0.10 mmol) in 1,4-dioxane (10 mL) at 30° C., and the reaction mixture was stirred at 100° C. for 4 h. The reaction mixture was filtered through Celite®, and the filtrate was concentrated under reduced pressure. The crude product was purified by preparative TLC (EtOAc:petroleum ether, 6:5), to give the title compound (0.145 g, 97%) as a brown gum; MS (ESI) m/z $[M+H]^+$ 307.

Intermediate 258: 6-(3-(Difluoromethyl)-3-methylazetidin-1-yl)quinoline-4-carboxylic acid

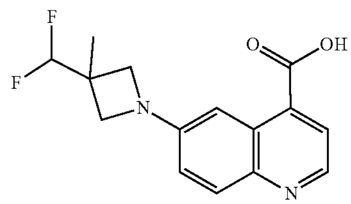 [SMILES: CC1(C(F)F)CN(c2ccc3nccc(C(=O)O)c3c2)C1]

NaOH (78 mg, 2.0 mmol) was added to a stirred solution of methyl 6-(3-(difluoromethyl)-3-methylazetidin-1-yl)quinoline-4-carboxylate Intermediate 257 (120 mg, 0.39 mmol) in MeOH (8 mL) and water (2 mL) at 0° C., and the reaction mixture was stirred at 23° C. for 1 h. The reaction mixture was diluted with water (15 mL), and pH was adjusted to 6 with aq HCl (2 M), and extracted with EtOAc (6×75 mL). The combined organic layer was, dried over $Na_2SO_4$, filtered and evaporated at reduced pressure, to give the title compound (0.11 g, 96%) as a yellow solid; MS (ESI) m/z $[M+H]^+$ 293.

Intermediate 259: Methyl 6-(3-(difluoromethoxy)azetidin-1-yl)quinoline-4-carboxylate

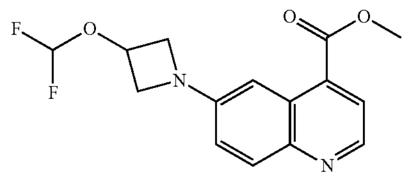 [SMILES: COC(=O)c1ccnc2ccc(N3CC(OC(F)F)C3)cc12]

$Cs_2CO_3$ (398 mg, 1.22 mmol) was added to a mixture of methyl 6-bromoquinoline-4-carboxylate (250 mg, 0.94 mmol), 3-(difluoromethoxy)azetidine hydrochloride (195 mg, 1.22 mmol), $Pd_2(dba)_3$ (86 mg, 0.09 mmol) and XPhos (90 mg, 0.19 mmol) in 1,4-dioxane (10 mL) at 28° C., and the reaction mixture was stirred at 100° C. for 2 h. The reaction mixture was filtered through Celite®, and the filtrate was concentrated under reduced pressure. The crude product was purified by preparative TLC (EtOAc:petroleum ether, 3:2) followed by reversed phase flash chromatography on a C18 column (gradient: 0-4% MeCN in water) to give the title compound (0.281 g) as a brown gum; MS (ESI) m/z $[M+H]^+$ 309.

Intermediate 260: 6-(3-(Difluoromethoxy)azetidin-1-yl)quinoline-4-carboxylic acid

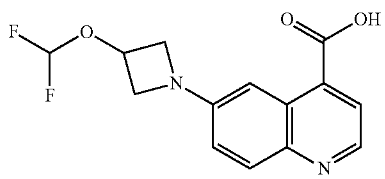

A solution of NaOH (154 mg, 3.85 mmol) in water (3 mL) was added slowly to a stirred solution of crude methyl 6-(3-(difluoromethoxy)azetidin-1-yl)quinoline-4-carboxylate Intermediate 259 (260 mg) in MeOH (9 mL) cooled to 0° C., and the reaction mixture was stirred at 28° C. for 1 h. The reaction mixture was diluted with water (20 mL), pH was adjusted to 6 with aq HCl (2 M), and extracted with EtOAc (8×100 mL). The combined organic layer was dried over $Na_2SO_4$, filtered and evaporated at reduced pressure to give the title compound (0.207 g, 91%) as an orange solid; MS (ESI) m/z $[M+H]^+$ 295.

Intermediate 261: Methyl 6-(3-ethyl-3-methylazetidin-1-yl)quinoline-4-carboxylate

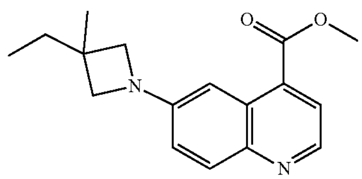 [SMILES: CCC1(C)CN(c2ccc3nccc(C(=O)OC)c3c2)C1]

$Cs_2CO_3$ (276 mg, 0.85 mmol) was added to a mixture of methyl 6-bromoquinoline-4-carboxylate (150 mg, 0.56 mmol), 3-ethyl-3-methylazetidine hydrochloride (115 mg, 0.85 mmol), $Pd_2(dba)_3$ (52 mg, 0.06 mmol) and XPhos (54 mg, 0.11 mmol) in 1,4-dioxane (10 mL) at 25° C., and the reaction mixture was stirred at 100° C. for 6 h. The reaction mixture was filtered through Celite®, and the filtrate was concentrated under reduced pressure. The crude product was purified by preparative TLC (EtOAc:petroleum ether, 1:1), to give the title compound (0.157 g, 98%) as a brown oil which solidified on standing; MS (ESI) m/z $[M+H]^+$ 285.

Intermediate 262: 6-(3-Ethyl-3-methylazetidin-1-yl)quinoline-4-carboxylic acid

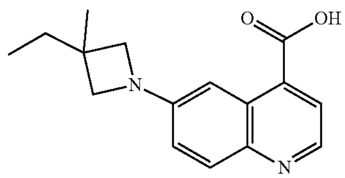 [SMILES: CCC1(C)CN(c2ccc3nccc(C(=O)O)c3c2)C1]

A solution of NaOH (98 mg, 2.5 mmol) in water (2 mL) was added slowly to a stirred suspension of methyl 6-(3-ethyl-3-methylazetidin-1-yl)quinoline-4-carboxylate Intermediate 261 (140 mg, 0.49 mmol) in MeOH (6 mL) cooled to 0° C., and the reaction mixture was stirred at 30° C. for 1 h. The reaction mixture was diluted with water (15 mL), pH was adjusted to 6 with aq HCl (2 M), and extracted with EtOAc (6×75 mL). The combined organic layer was, dried over $Na_2SO_4$, filtered and evaporated at reduced pressure, to give the title compound (0.13 g, 98%) as an orange solid; MS (ESI) m/z $[M+H]^+$ 271.

Intermediate 263: Methyl 6-(3-ethyl-3-fluoroazetidin-1-yl)quinoline-4-carboxylate

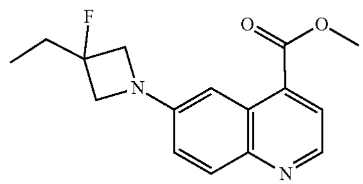 [SMILES: CCC1(F)CN(c2ccc3nccc(C(=O)OC)c3c2)C1]

$Pd_2(dba)_3$ (138 mg, 0.15 mmol) was added to a mixture of methyl 6-bromoquinoline-4-carboxylate (400 mg, 1.50 mmol), 3-ethyl-3-fluoroazetidine (186 mg, 1.80 mmol), $Cs_2C_{03}$ (980 mg, 3.01 mmol) and XPhos (143 mg, 0.30 mmol) in 1,4-dioxane (15 mL) at 25° C., and the reaction mixture was stirred at 100° C. for 3 h. The reaction mixture was concentrated and diluted with EtOAc (125 mL), and washed sequentially with sat brine (75 mL) and water (75 mL). The organic layer was dried over $Na_2SO_4$, filtered and evaporated at reduced pressure. The crude product was purified by preparative TLC (MeOH:DCM, 1:5), to give the title compound (0.20 g, 46%) as a yellow solid; MS (ESI) m/z $[M+H]^+$ 289.

Intermediate 264: 6-(3-Ethyl-3-fluoroazetidin-1-yl)quinoline-4-carboxylic acid

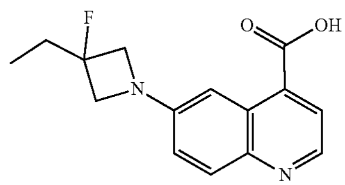 [SMILES: CCC1(F)CN(c2ccc3nccc(C(=O)O)c3c2)C1]

A solution of NaOH (104 mg, 2.60 mmol) in water (4 mL) was added to a stirred solution of methyl 6-(3-ethyl-3-fluoroazetidin-1-yl)quinoline-4-carboxylate Intermediate 263 (150 mg, 0.52 mmol) in MeOH (12 mL) at 20° C., and the reaction mixture was stirred at 25° C. for 2 h. The pH of the reaction mixture was adjusted to 4 using aq HCl (2 M, 7 mL). The reaction mixture was concentrated under reduced pressure, diluted with EtOAc (100 mL), and washed sequentially with sat brine (50 mL) and water (50 mL). The organic layer was dried over $Na_2SO_4$, filtered and evaporated at reduced pressure to give the title compound (0.12 g, 84%) as a red solid; MS (ESI) m/z $[M+H]^+$ 275.0.

Intermediate 265: Methyl 6-(2-azaspiro[3.4]octan-2-yl)quinoline-4-carboxylate

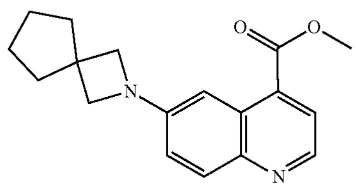 [SMILES: COC(=O)c1ccnc2ccc(N3CC4(CCCC4)C3)cc12]

$Pd_2(dba)_3$ (103 mg, 0.11 mmol) was added to a mixture of methyl 6-bromoquinoline-4-carboxylate (300 mg, 1.13 mmol), 2-azaspiro[3.4]octane (150 mg, 1.35 mmol), $Cs_2CO_3$ (735 mg, 2.25 mmol) and XPhos (107 mg, 0.23 mmol) in 1,4-dioxane (15 mL) at 20° C., and the reaction mixture was stirred at 100° C. for 5 h. The reaction mixture was concentrated under reduced pressure, diluted with EtOAc (125 mL), and washed sequentially with water (75 mL) and sat brine (75 mL). The organic layer was dried over $Na_2SO_4$, filtered and concentrated under reduced pressure. The crude product was purified by preparative TLC (EtOAc: petroleum ether, 1:2), to give the title compound (0.20 g, 60%) as a yellow solid; MS (ESI) m/z $[M+H]^+$ 397.0.

Intermediate 266: 6-(2-Azaspiro[3.4]octan-2-yl)quinoline-4-carboxylic acid

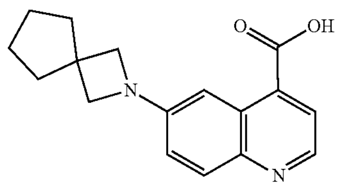 [SMILES: O=C(O)c1ccnc2ccc(N3CC4(CCCC4)C3)cc12]

A solution of NaOH (135 mg, 3.37 mmol) in water (3 mL) was added to a stirred solution of methyl 6-(2-azaspiro[3.4]octan-2-yl)quinoline-4-carboxylate Intermediate 265 (200 mg, 0.67 mmol) in MeOH (9 mL) at 20° C., and the reaction mixture was stirred at 25° C. for 2 h. The pH of the reaction mixture was adjusted to 4 using aq HCl (2 M, 25 mL). The reaction mixture was concentrated under reduced pressure, diluted with EtOAc (100 mL), and washed sequentially with water (25 mL) and sat brine (25 mL). The organic layer was dried over $Na_2SO_4$, filtered and evaporated at reduced pressure to give the title compound (0.15 g, 79%) as a red solid; MS (ESI) m/z $[M+H]^+$ 283.3.

Intermediate 267: Methyl 6-(3-(2,2-difluoropropyl)azetidin-1-yl)quinoline-4-carboxylate

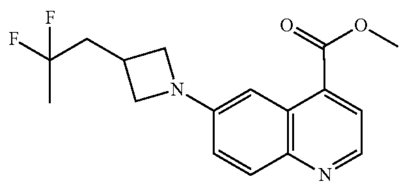 [SMILES: COC(=O)c1ccnc2ccc(N3CC(CC(C)(F)F)C3)cc12]

XPhos (107 mg, 0.23 mmol) was added to a mixture of methyl 6-bromoquinoline-4-carboxylate (300 mg, 1.13 mmol), 3-(2,2-difluoropropyl)azetidine (183 mg, 1.35 mmol), $Pd_2(dba)_3$ (103 mg, 0.11 mmol) and $Cs_2CO_3$ (735 mg, 2.25 mmol) in 1,4-dioxane (15 mL) at 20° C., and the reaction mixture was stirred at 100° C. for 3 h. The reaction mixture was concentrated under reduced pressure, diluted with EtOAc (100 mL), and washed sequentially with water (25 mL) and sat brine (25 mL). The organic layer was dried over $Na_2SO_4$, filtered and evaporated at reduced pressure. The crude product was purified by preparative TLC (EtOAc: petroleum ether, 1:3), to give the title compound (0.25 g, 69%) as a yellow oil; MS (ESI) m/z $[M+H]^+$ 321.0.

Intermediate 268: 6-(3-(2,2-Difluoropropyl)azetidin-1-yl)quinoline-4-carboxylic acid

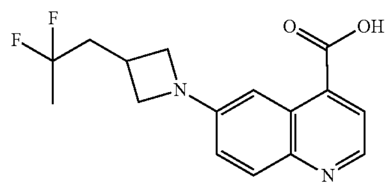 [SMILES: CC(F)(F)CC1CN(c2ccc3nccc(C(=O)O)c3c2)C1]

A solution of NaOH (181 mg, 4.53 mmol) in water (3 mL) was added to a stirred solution of methyl 6-(3-(2,2-difluoropropyl)azetidin-1-yl)quinoline-4-carboxylate Intermediate 267 (290 mg, 0.91 mmol) in MeOH (9 mL) at 20° C., and the reaction mixture was stirred at 25° C. for 2 h. The pH was adjusted to 5 with aq HCl (2 M). The reaction mixture was concentrated under reduced pressure, diluted with EtOAc (125 mL), and washed sequentially with sat brine (75 mL) and water (75 mL). The organic layer was dried over $Na_2SO_4$, filtered and evaporated at reduced pressure to give the title compound (0.20 g, 72%) as a yellow solid; MS (ESI) m/z $[M+H]^+$ 307.0.

Intermediate 269: Methyl 6-(5,5-difluoro-2-azaspiro[3.4]octan-2-yl)quinoline-4-carboxylate

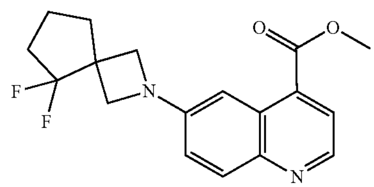 [SMILES: COC(=O)c1ccnc2ccc(N3CC4(CCCC4(F)F)C3)cc12]

$Pd_2(dba)_3$ (55 mg, 0.06 mmol) was added to a mixture of methyl 6-bromoquinoline-4-carboxylate (160 mg, 0.60 mmol), 5,5-difluoro-2-azaspiro[3.4]octane (106 mg, 0.72 mmol), $Cs_2CO_3$ (24 mg, 0.08 mmol) and XPhos (57 mg, 0.12 mmol) in 1,4-dioxane (15 mL) at 25° C., and the reaction mixture was stirred at 100° C. for 3 h. The reaction mixture was concentrated under reduced pressure, diluted with EtOAc (125 mL), and washed sequentially with sat brine (75 mL) and water (75 mL). The organic layer was dried over $Na_2SO_4$, filtered and evaporated at reduced pressure. The crude product was purified by preparative TLC (EtOAc:petroleum ether, 1:3), to give the title compound (0.15 g, 75%) as a yellow solid; MS (ESI) m/z $[M+H]^+$ 333.0.

Intermediate 270: 6-(5,5-Difluoro-2-azaspiro[3.4]octan-2-yl)quinoline-4-carboxylic acid

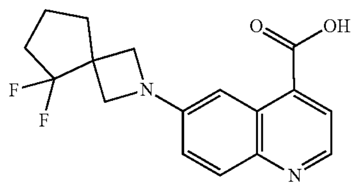 [SMILES: O=C(O)c1ccnc2ccc(N3CC4(CCCC4(F)F)C3)cc12]

A solution of NaOH (120 mg, 3.01 mmol) in water (3 mL) was added to a stirred solution of methyl 6-(5,5-difluoro-2-azaspiro[3.4]octan-2-yl)quinoline-4-carboxylate Intermediate 269 (200 mg, 0.60 mmol) in MeOH (9 mL) at 20° C. and the reaction mixture was stirred at 25° C. for 3 h. The pH of the reaction mixture was adjusted to 5 with aq HCl (2 M). The reaction mixture was concentrated under reduced pressure, diluted with EtOAc (100 mL), and washed sequentially with sat brine (20 mL) and water (20 mL). The organic layer was dried over $Na_2SO_4$, filtered and evaporated at reduced pressure to give the title compound (0.15 g, 78%) as a red solid; MS (ESI) m/z $[M+H]^+$ 319.0.

Intermediate 271: Methyl 6-(3-(3,3,3-trifluoropropyl)azetidin-1-yl)quinoline-4-carboxylate

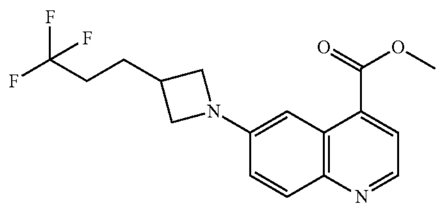

$Pd_2(dba)_3$ (43 mg, 0.05 mmol) was added to a mixture of methyl 6-bromoquinoline-4-carboxylate (250 mg, 0.94 mmol), 3-(3,3,3-trifluoropropyl)azetidine hydrochloride (267 mg, 1.41 mmol), XPhos (67 mg, 0.14 mmol) and $Cs_2CO_3$ (918 mg, 2.82 mmol) in 1,4-dioxane (10 mL) and the reaction mixture was stirred at 100° C. for 2 h. The solid was filtered off, and the filtrate was concentrated under reduced pressure. The residue was diluted with EtOAc, and washed with water. The organic layer was dried over $Na_2SO_4$, filtered and evaporated at reduced pressure. The crude product was purified by preparative TLC (petroleum ether:EtOAc, 2:1), to give the title compound (0.25 g, 79%) as an orange gum; MS (ESI) m/z $[M+H]^+$ 339.

Intermediate 272: 6-(3-(3,3,3-Trifluoropropyl)azetidin-1-yl)quinoline-4-carboxylic acid

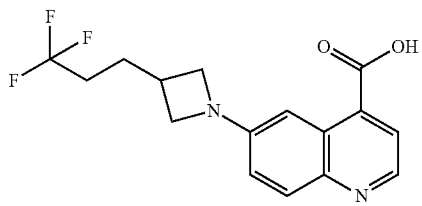 [SMILES: O=C(O)c1ccnc2ccc(N3CC(CCC(F)(F)F)C3)cc12]

A solution of methyl 6-(3-(3,3,3-trifluoropropyl)azetidin-1-yl)quinoline-4-carboxylate Intermediate 271 (230 mg, 0.68 mmol) and LiOH (49 mg, 2.0 mmol) in MeOH (10 mL) and water (2 mL) was stirred at rt for 2 h. The solvent was removed under reduced pressure, and the reaction mixture was diluted with water. The pH of the reaction mixture was adjusted to 6 with aq HCl (0.1M). The precipitate was collected by filtration, washed with water and dried under vacuum to give the title compound (0.20 g, 91%) as an orange solid; MS (ESI) m/z $[M+H]^+$ 325.

Intermediate 273: Methyl 6-(3-fluoro-3-(trifluoromethyl)azetidin-1-yl)quinoline-4-carboxylate

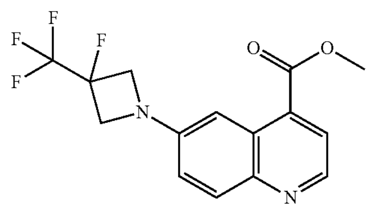 [SMILES: COC(=O)c1ccnc2ccc(N3CC(F)(C(F)(F)F)C3)cc12]

$Pd_2(dba)_3$ (34 mg, 0.04 mmol) was added to a mixture of methyl 6-bromoquinoline-4-carboxylate (200 mg, 0.75 mmol), 3-fluoro-3-(trifluoromethyl)azetidine hydrochloride (202 mg, 1.13 mmol), XPhos (54 mg, 0.11 mmol) and $Cs_2CO_3$ (735 mg, 2.25 mmol) in 1,4-dioxane (10 mL) and the reaction mixture was stirred at 100° C. for 2 h. The solid was filtered off and the filtrate was concentrated under reduced pressure. The residue was diluted with EtOAc, and washed with water. The organic layer was dried over $Na_2SO_4$, filtered and evaporated at reduced pressure. The crude product was purified by preparative TLC (petroleum ether:EtOAc, 2:1), to give the title compound (0.20 g, 81%) as a yellow solid; MS (ESI) m/z $[M+H]^+$ 329.

Intermediate 274: 6-(3-Fluoro-3-(trifluoromethyl)azetidin-1-yl)quinoline-4-carboxylic acid

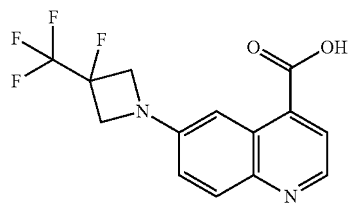 [SMILES: O=C(O)c1ccnc2ccc(N3CC(F)(C(F)(F)F)C3)cc12]

A solution of methyl 6-(3-fluoro-3-(trifluoromethyl)azetidin-1-yl)quinoline-4-carboxylate Intermediate 273 (200 mg, 0.61 mmol) and LiOH (44 mg, 1.83 mmol) in MeOH (8 mL) and water (2 mL) was stirred at rt for 2 h. The solvent was removed under reduced pressure and the reaction mixture was diluted with water. The pH of the reaction mixture was set to 6 with aq HCl (1 M). The precipitate was collected by filtration, washed with water and dried under vacuum to give the title compound (0.17 g, 89%) as a yellow solid; MS (ESI) m/z $[M+H]^+$ 315.

Intermediate 275: Methyl 6-(3-(2,2-difluoroethyl)azetidin-1-yl)quinoline-4-carboxylate

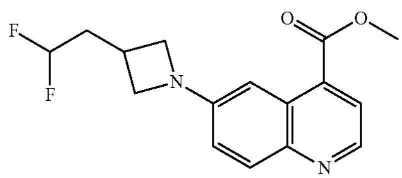 [SMILES: COC(=O)c1ccnc2ccc(N3CC(CC(F)F)C3)cc12]

$Pd_2(dba)_3$ (43 mg, 0.05 mmol) was added to a mixture of methyl 6-bromoquinoline-4-carboxylate (250 mg, 0.94 mmol), 3-(2,2-difluoroethyl)azetidine 2,2,2,-trifluoroacetate (247 mg, 1.13 mmol), XPhos (67 mg, 0.14 mmol) and $Cs_2CO_3$ (918 mg, 2.82 mmol) in 1,4-dioxane (10 mL) and the reaction mixture was stirred at 100° C. for 2 h. The solid was filtered off, and the filtrate was concentrated under reduced pressure. The residue was diluted with EtOAc, and washed sequentially with water. The organic layer was dried over $Na_2SO_4$, filtered and evaporated at reduced pressure. The crude product was purified by preparative TLC (petroleum ether:EtOAc, 2:1), to give the title compound (0.23 g, 80%) as an orange gum; MS (ESI) m/z $[M+H]^+$ 307.

Intermediate 276: 6-(3-(2,2-Difluoroethyl)azetidin-1-yl)quinoline-4-carboxylic acid

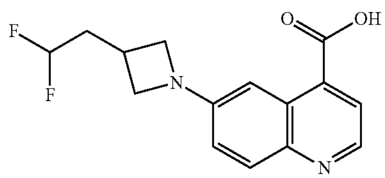 [SMILES: O=C(O)c1ccnc2ccc(N3CC(CC(F)F)C3)cc12]

A solution of methyl 6-(3-(2,2-difluoroethyl)azetidin-1-yl)quinoline-4-carboxylate Intermediate 275 (230 mg, 0.75 mmol) and LiOH (54 mg, 2.3 mmol) in MeOH (10 mL) and water (2 mL) was stirred at rt for 2 h. The solvent was removed under reduced pressure and the reaction mixture was diluted with water. The pH of the reaction mixture was adjusted to 6 with aq HCl (1 M). The precipitate was collected by filtration, washed with water and dried under vacuum to give the title compound (0.19 g, 87%) as an orange solid; MS (ESI) m/z $[M+H]^+$ 293.

Intermediate 277: Methyl 6-(3-cyclopropylazetidin-1-yl)quinoline-4-carboxylate

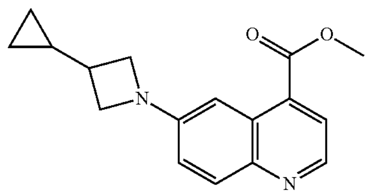 [SMILES: COC(=O)c1ccnc2ccc(N3CC(C4CC4)C3)cc12]

$Pd_2(dba)_3$ (43 mg, 0.05 mmol) was added to a mixture of methyl 6-bromoquinoline-4-carboxylate (250 mg, 0.94 mmol), 3-cyclopropylazetidine hydrochloride (151 mg, 1.13 mmol), XPhos (67 mg, 0.14 mmol) and $Cs_2CO_3$ (918 mg, 2.82 mmol) in 1,4-dioxane (10 mL) and the reaction mixture was stirred at 100° C. for 2 h. The solid was filtered off, and the filtrate was concentrated under reduced pressure. The residue was diluted with EtOAc, and washed sequentially with water. The organic layer was dried over $Na_2SO_4$, filtered and evaporated at reduced pressure. The crude product was purified by preparative TLC (petroleum ether: EtOAc, 2:1), to give the title compound (0.20 g, 75%) as an orange solid; MS (ESI) m/z $[M+H]^+$ 283.

Intermediate 278: 6-(3-Cyclopropylazetidin-1-yl)quinoline-4-carboxylic acid

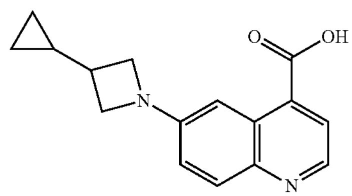 [SMILES: O=C(O)c1ccnc2ccc(N3CC(C4CC4)C3)cc12]

A solution of methyl 6-(3-cyclopropylazetidin-1-yl)quinoline-4-carboxylate Intermediate 277 (200 mg, 0.71 mmol) and LiOH (51 mg, 2.1 mmol) in MeOH (10 mL) and water (2 mL) was stirred at rt for 2 h. The solvent was removed under reduced pressure and the reaction mixture was diluted with water. The pH of the reaction mixture was adjusted to 6 with aq HCl (1 M). The precipitate was collected by filtration, washed with water and dried under vacuum to give the title compound (0.17 g, 89%) as an orange solid; MS (ESI) m/z $[M+H]^+$ 269.

Intermediate 279: Methyl 6-(3-(2-fluoroethyl)azetidin-1-yl)quinoline-4-carboxylate

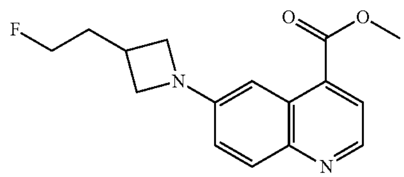 [SMILES: COC(=O)c1ccnc2ccc(N3CC(CCF)C3)cc12]

$Pd_2(dba)_3$ (34 mg, 0.04 mmol) was added to a mixture of methyl 6-bromoquinoline-4-carboxylate (200 mg, 0.75 mmol), 3-(2-fluoroethyl)azetidine 2,2,2-trifluoroacetate (197 mg, 0.98 mmol), XPhos (54 mg, 0.11 mmol) and $Cs_2CO_3$ (735 mg, 2.25 mmol) in 1,4-dioxane (12 mL) and the reaction mixture was stirred at 100° C. for 2 h. The solid was filtered off and the filtrate was concentrated under reduced pressure. The residue was diluted with EtOAc, and washed sequentially with water. The organic layer was dried over $Na_2SO_4$, filtered and evaporated at reduced pressure. The crude product was purified by preparative TLC (petroleum ether:EtOAc, 2:1), to give the title compound (0.17 g, 78%) as a yellow solid; MS (ESI) m/z $[M+H]^+$ 289.

Intermediate 280: 6-(3-(2-Fluoroethyl)azetidin-1-yl) quinoline-4-carboxylic acid

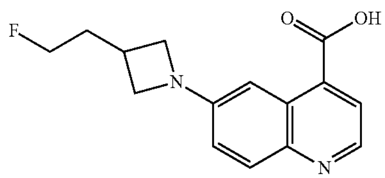 [SMILES: O=C(O)c1ccnc2ccc(N3CC(CCF)C3)cc12]

A solution of methyl 6-(3-(2-fluoroethyl)azetidin-1-yl) quinoline-4-carboxylate Intermediate 279 (170 mg, 0.59 mmol) and LiOH (42 mg, 1.77 mmol) in MeOH (8 mL) and water (2 mL) was stirred at rt for 2 h. The solvent was removed under reduced pressure and the reaction mixture was diluted with water. The pH of the reaction mixture was adjusted to 6 with aq HCl (1 M). The precipitate was collected by filtration, washed with water and dried under vacuum to give the title compound (0.145 g, 90%) as a yellow solid; MS (ESI) m/z $[M+H]^+$ 275.

Intermediate 281: Methyl 6-(3-(1,1-difluoroethyl) azetidin-1-yl)quinoline-4-carboxylate

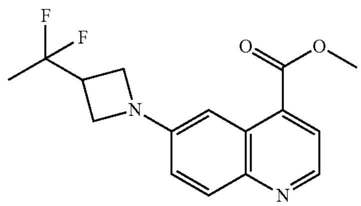 [SMILES: COC(=O)c1ccnc2ccc(N3CC(C(C)(F)F)C3)cc12]

$Pd_2(dba)_3$ (34 mg, 0.04 mmol) was added to a mixture of methyl 6-bromoquinoline-4-carboxylate (200 mg, 0.75 mmol), 3-(1,1-difluoroethyl)azetidine hydrochloride (142 mg, 0.90 mmol), XPhos (54 mg, 0.11 mmol) and $Cs_2CO_3$ (735 mg, 2.3 mmol) in 1,4-dioxane (10 mL) and the reaction mixture was stirred at 100° C. for 2 h. The solid was filtered off and the filtrate was concentrated under reduced pressure. The residue was diluted with EtOAc, and washed with water. The organic layer was dried over $Na_2SO_4$, filtered and evaporated at reduced pressure. The crude product was purified by preparative TLC (petroleum ether:EtOAc, 2:1), to give the title compound (0.18 g, 78%) as a yellow solid; MS (ESI) m/z $[M+H]^+$ 307.

Intermediate 282: 6-(3-(1,1-Difluoroethyl)azetidin-1-371)quinoline-4-carboxylic acid

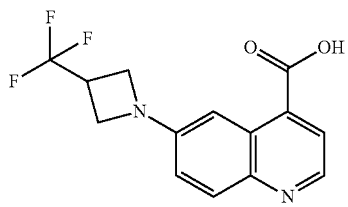 [SMILES: O=C(O)c1ccnc2ccc(N3CC(C(F)(F)F)C3)cc12]

A solution of methyl 6-(3-(1,1-difluoroethyl)azetidin-1-yl)quinoline-4-carboxylate Intermediate 281 (180 mg, 0.59 mmol) and LiOH (42 mg, 1.8 mmol) in MeOH (8 mL) and water (2 mL) was stirred at rt for 3 h. The solvent was removed under reduced pressure, and the reaction mixture was diluted with water. The pH of the reaction mixture was adjusted to 6 with aq HCl (1 M). The precipitate was collected by filtration, washed with water and dried under vacuum to give the title compound (0.155 g, 90%) as a yellow solid; MS (ESI) m/z $[M+H]^+$ 293.

Intermediate 283: Meth-(3-isopropylazetidin-1-yl) quinoline-4-carboxylate

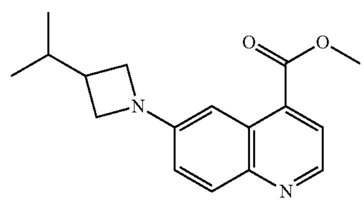 [SMILES: COC(=O)c1ccnc2ccc(N3CC(C(C)C)C3)cc12]

$Cs_2CO_3$ (765 mg, 2.35 mmol) was added to a mixture of methyl 6-bromoquinoline-4-carboxylate (250 mg, 0.94 mmol), 3-isopropylazetidine hydrochloride (255 mg, 1.88 mmol), $Pd_2(dba)_3$ (86 mg, 0.09 mmol) and CPhos (410 mg, 0.94 mmol) in 1,4-dioxane (5.0 mL) at 25° C. and the reaction mixture was stirred at 100° C. for 2 h. The reaction mixture was diluted with DCM (10 mL) and the solvent was removed under reduced pressure. The crude product was purified by preparative TLC (EtOAc:petroleum ether, 1:1), to give the title compound (0.262 g, 98%) as an orange gum; MS (ESI) m/z $[M+H]^+$ 285.

Intermediate 284: 6-(3-Isopropylazetidin-1-yl)quinoline-4-carboxylic acid

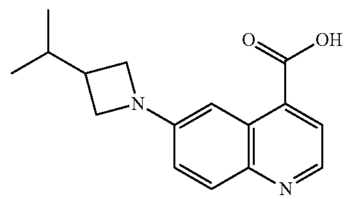 [SMILES: CC(C)C1CN(c2ccc3nccc(C(=O)O)c3c2)C1]

NaOH (181 mg, 4.52 mmol) was added to methyl 6-(3-isopropylazetidin-1-yl)quinoline-4-carboxylate Intermediate 283 (257 mg, 0.90 mmol) in MeOH (9 mL) and water (3 mL) at 25° C. and the reaction mixture was stirred at 25° C. for 1 h. The solvent was removed under reduced pressure and the residue was diluted with water (50 mL). The pH of the reaction mixture was adjusted to 3 with aq HCl (1 M) and extracted with EtOAc (3×50 mL), The combined organic layer was dried over $Na_2SO_4$, filtered and evaporated at reduced pressure to give the title compound (0.242 g, 99%) as an orange solid; MS (ESI) m/z $[M+H]^+$ 271.

Intermediate 285: Methyl 6-(6-methyl-2-azaspiro[3.3]heptan-2-yl)quinoline-4-carboxylate

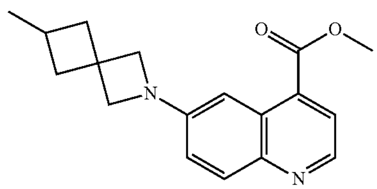

$Cs_2CO_3$ (612 mg, 1.88 mmol) was added to methyl 6-bromoquinoline-4-carboxylate (200 mg, 0.75 mmol), 6-methyl-2-azaspiro[3.3]heptane hydrochloride (222 mg, 1.50 mmol), $Pd_2(dba)_3$ (69 mg, 0.08 mmol) and SPhos (62 mg, 0.15 mmol) in 1,4-dioxane (5 mL) at 25° C., and the reaction mixture was stirred at 100° C. for 2 h. The reaction mixture was diluted with DCM (10 mL) and the solvent was removed under reduced pressure. The crude product was purified by preparative TLC (EtOAc:petroleum ether, 1:1), to give the title compound (0.22 g, 99%) as an orange solid; MS (ESI) m/z $[M+H]^+$ 297.

Intermediate 286: 6-(6-Methyl-2-azaspiro[3.3]heptan-2-yl)quinoline-4-carboxylic acid

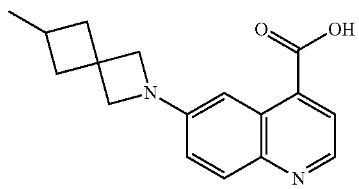 [SMILES: CC1CC2(C1)CN(c1ccc3nccc(C(=O)O)c3c1)C2]

NaOH (145 mg, 3.63 mmol) was added to a solution of methyl 6-(6-methyl-2-azaspiro[3.3]heptan-2-yl)quinoline-4-carboxylate Intermediate 285 (215 mg, 0.73 mmol) in MeOH (6 mL) and water (2 mL) at 25° C. and the reaction solution was stirred at 25° C. for 1 h. The solvent was removed under reduced pressure, the residue was diluted with water (50 mL) and pH was adjusted to 3 with aq HCl (1 M). The aqueous phase was extracted with EtOAc (3×50 mL), the combined organic layer was dried over $Na_2SO_4$, filtered and evaporated at reduced pressure to give the title compound (0.20 g, 98%) as an orange solid; MS (ESI) m/z $[M+H]^+$ 283.

Intermediate 287: Methyl 6-(6-(trifluoromethyl)-2-azaspiro[3.3]heptan-2-yl)quinoline-4-carboxylate

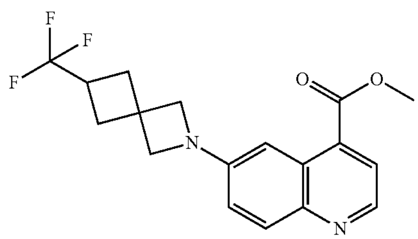 [SMILES: COC(=O)c1ccnc2ccc(N3CC4(CC(C(F)(F)F)C4)C3)cc12]

$Cs_2CO_3$ (612 mg, 1.88 mmol) was added to a mixture of methyl 6-bromoquinoline-4-carboxylate (200 mg, 0.75 mmol), 6-(trifluoromethyl)-2-azaspiro[3.3]heptane hydrochloride (303 mg, 1.50 mmol), $Pd_2(dba)_3$ (69 mg, 0.08 mmol) and SPhos (62 mg, 0.15 mmol) in 1,4-dioxane (5 mL) at 25° C., and the reaction mixture was stirred at 100° C. for 2 h. The reaction mixture was diluted with DCM (10 mL), and the solvent was removed under reduced pressure. The crude product was purified by preparative TLC (EtOAc: petroleum ether, 1:1), to give the title compound (0.26 g, 99%) as a yellow solid; MS (ESI) m/z $[M+H]^+$ 351.

Intermediate 288: 6-(6-(Trifluoromethyl)-2-azaspiro[3.3]heptan-2-yl)quinoline-4-carboxylic acid

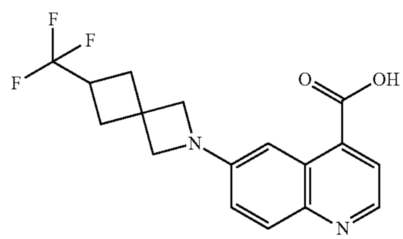 [SMILES: O=C(O)c1ccnc2ccc(N3CC4(CC(C(F)(F)F)C4)C3)cc12]

NaOH (148 mg, 3.70 mmol) was added to a solution of methyl 6-(6-(trifluoromethyl)-2-azaspiro[3.3]heptan-2-yl)quinoline-4-carboxylate Intermediate 287 (259 mg, 0.74 mmol) in MeOH (9 mL) and water (3 mL) at 25° C. and the reaction mixture was stirred at 25° C. for 1 h. The solvent was removed under reduced pressure and the reaction mixture was diluted with water (50 mL) and pH was adjusted to 3 with aq HCl (1 M). The aqueous phase was extracted with EtOAc (3×50 mL), the combined organic layer was dried over $Na_2SO_4$, filtered and evaporated at reduced pressure to give the title compound (0.24 g, 97%) as an orange solid; MS (ESI) m/z $[M+H]^+$ 337.

Intermediate 289: Methyl 6-(3-methoxy-3-methylazetidin-1-yl)quinoline-4-carboxylate

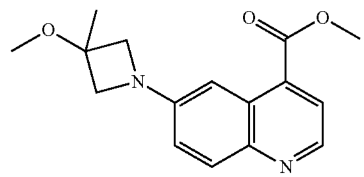

$Cs_2CO_3$ (918 mg, 2.82 mmol) was added to a mixture of methyl 6-bromoquinoline-4-carboxylate (300 mg, 1.13 mmol), 3-methoxy-3-methylazetidine hydrochloride (310 mg, 2.25 mmol), $Pd_2(dba)_3$ (103 mg, 0.11 mmol) and RuPhos (105 mg, 0.23 mmol) in 1,4-dioxane (5 mL) at 25° C., and the reaction mixture was stirred at 100° C. for 2 h under $N_2$ (g). The reaction mixture was diluted with DCM (10 mL), and the solvent was removed under reduced pressure. The crude product was purified by preparative TLC (EtOAc:petroleum ether, 1:1), to give the title compound (0.321 g, 99%) as a brown gum; MS (ESI) m/z $[M+H]^+$ 287.

Intermediate 290: 6-(3-Methoxy-3-methylazetidin-1-yl)quinoline-4-carboxylic acid

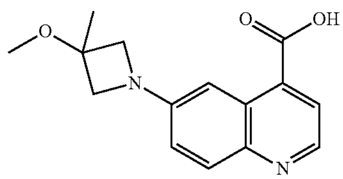 [SMILES: COC1(C)CN(c2ccc3nccc(C(=O)O)c3c2)C1]

NaOH (223 mg, 5.59 mmol) was added to a solution of methyl 6-(3-methoxy-3-methylazetidin-1-yl)quinoline-4-carboxylate Intermediate 289 (320 mg, 1.12 mmol) in MeOH (6 mL) and water (2 mL) at 25° C., and the reaction mixture was stirred at 25° C. for 1 h. The solvent was removed under reduced pressure, the reaction mixture was diluted with water (50 mL) and pH was adjusted to 3 with aq HCl (1 M). The aqueous phase was extracted with EtOAc (3×50 mL), the combined organic layer was dried over $Na_2SO_4$, filtered and evaporated at reduced pressure to give the title compound (0.296 g, 97%) as an orange solid; MS (ESI) m/z $[M+H]^+$ 273.

Intermediate 291: Methyl 6-(3-ethoxy-3-methylazetidin-1-yl)quinoline-4-carboxylate

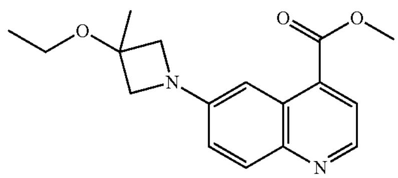 [SMILES: CCOC1(C)CN(c2ccc3nccc(C(=O)OC)c3c2)C1]

$Cs_2CO_3$ (918 mg, 2.82 mmol) was added to a mixture of methyl 6-bromoquinoline-4-carboxylate (300 mg, 1.13 mmol), 3-ethoxy-3-methylazetidine hydrochloride (342 mg, 2.25 mmol), $Pd_2(dba)_3$ (103 mg, 0.11 mmol) and RuPhos (105 mg, 0.23 mmol) in 1,4-dioxane (5 mL) at 25° C., and the reaction mixture was stirred at 100° C. for 2 h. The reaction mixture was diluted with DCM (10 mL), and the solvent was removed under reduced pressure. The crude product was purified by preparative TLC (petroleum ether: EtOAc, 1:1), to give the title compound (0.33 g, 97%) as a red gum; MS (ESI) m/z $[M+H]^+$ 301.

Intermediate 292: 6-(3-Ethoxy-3-methylazetidin-1-yl)quinoline-4-carboxylic acid

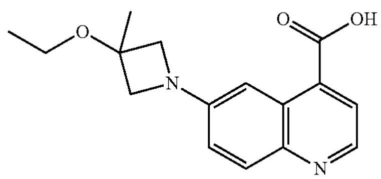 [SMILES: CCOC1(C)CN(c2ccc3nccc(C(=O)O)c3c2)C1]

NaOH (216 mg, 5.41 mmol) was added to a solution of methyl 6-(3-ethoxy-3-methylazetidin-1-yl)quinoline-4-carboxylate Intermediate 291 (325 mg, 1.08 mmol) in MeOH (9 mL) and water (3 mL) at 25° C., and the reaction was stirred at 25° C. for 1 h. The solvent was removed under reduced pressure, the reaction mixture was diluted with water (50 mL) and pH was adjusted to 3 with aq HCl (1 M). The aqueous phase was extracted with EtOAc (3×50 mL), and the combined organic layer was dried over $Na_2SO_4$, filtered and evaporated at reduced pressure to give the title compound (0.305 g, 98%) as an orange solid; MS (ESI) m/z $[M+H]^+$ 287.

Intermediate 293: Methyl 6-(1-oxa-6-azaspiro[3.3]heptan-6-yl)quinoline-4-carboxylate

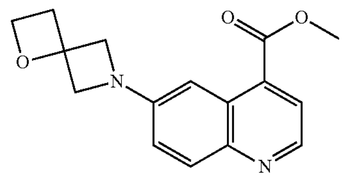 [SMILES: COC(=O)c1ccnc2ccc(N3CC4(CCO4)C3)cc12]

$Cs_2CO_3$ (430 mg, 1.32 mmol) was added to a mixture of methyl 6-bromoquinoline-4-carboxylate (270 mg, 1.01 mmol), 1-oxa-6-azaspiro[3.3]heptane oxalate (250 mg, 1.32 mmol) and RuPhos Pd G3 (85 mg, 0.10 mmol) in 1,4-dioxane (5 mL) at 35° C., and the reaction mixture was stirred at 100° C. for 2 h. The reaction mixture was filtered through Celite®, and the filtrate was concentrated under reduced pressure. The crude product was purified by preparative TLC (MeOH: DCM, 1:10), to give the title compound (0.283 g, 98%) as a yellow solid; MS (ESI) m/z $[M+H]^+$ 285.

Intermediate 294: 6-(1-Oxa-6-azaspiro[3.3]heptan-6-yl)quinoline-4-carboxylic acid

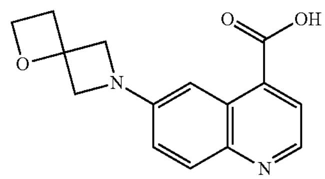 [SMILES: O=C(O)c1ccnc2ccc(N3CC4(CCO4)C3)cc12]

A solution of NaOH (177 mg, 4.43 mmol) in water (2 mL) was added to a stirred solution of methyl 6-(1-oxa-6-azaspiro[3.3]heptan-6-yl)quinoline-4-carboxylate Intermediate 293 (252 mg, 0.89 mmol) in MeOH (6 mL) at 0° C., and the reaction mixture was stirred at 37° C. for 1 h. The reaction mixture was diluted with water (20 mL), and the pH was adjusted to 6 with aq HCl (2 M). The reaction mixture was extracted with EtOAc (8×75 mL), the combined organic layer was dried over $Na_2SO_4$, filtered and evaporated at reduced pressure, to give the title compound (0.214 g, 89%) as an orange solid; MS (ESI) m/z $[M+H]^+$ 271.

Intermediate 295: Methyl 6-(3-ethyl-3-hydroxyazetidin-1-yl)quinoline-4-carboxylate

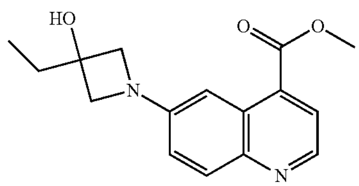 [SMILES: CCC1(O)CN(c2ccc3nccc(C(=O)OC)c3c2)C1]

$Pd_2(dba)_3$ (103 mg, 0.11 mmol) was added to a mixture of methyl 6-bromoquinoline-4-carboxylate (300 mg, 1.13 mmol), 3-ethylazetidin-3-ol (137 mg, 1.35 mmol), $Cs_2CO_3$ (735 mg, 2.25 mmol) and DavePhos (89 mg, 0.23 mmol) in 1,4-dioxane (15 mL) at 20° C. and the reaction mixture was stirred at 100° C. for 3 h. The reaction mixture was concentrated under reduced pressure and the residue was diluted with EtOAc (75 mL). The mixture was washed sequentially with water (20 mL) and sat brine (20 mL), and the organic layer was dried over $Na_2SO_4$, filtered, and evaporated at reduced pressure. The crude product was purified by preparative TLC (EtOAc:petroleum ether, 1:5) to give the title compound (0.20 g, 62%) as a yellow solid; MS (ESI) m/z $[M+H]^+$ 287.0.

Intermediate 296: 6-(3-Ethyl-3-hydroxyazetidin-1-yl)quinoline-4-carboxylic acid

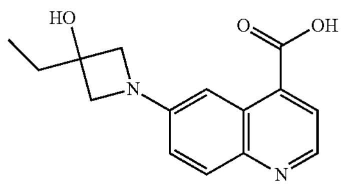 [SMILES: CCC1(O)CN(c2ccc3nccc(C(=O)O)c3c2)C1]

A solution of NaOH (140 mg, 3.49 mmol) in water (3 mL) was added to a stirred solution of methyl 6-(3-ethyl-3-hydroxyazetidin-1-yl)quinoline-4-carboxylate Intermediate 295 (200 mg, 0.70 mmol) in MeOH (9 mL) at 25° C., and the reaction mixture was stirred at 25° C. for 3 h. The pH of the reaction mixture was adjusted to 4 with aq HCl (2 M), and the reaction mixture was concentrated under reduced pressure. The residue was diluted with EtOAc (75 mL), and the organic layer was washed sequentially with water (25 mL) and sat brine (25 mL), dried over $Na_2SO_4$, filtered and evaporated at reduced pressure to give the title compound (0.15 g, 79%) as a red solid; MS (ESI) m/z $[M+H]^+$ 273.0.

Intermediate 297: Methyl 6-(6-fluoro-2-azaspiro[3.3]heptan-2-yl)quinoline-4-carboxylate

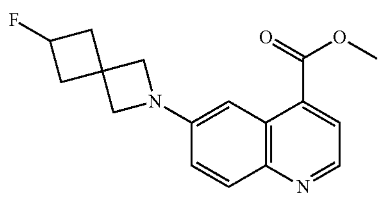 [SMILES: COC(=O)c1ccnc2ccc(N3CC4(CC(F)C4)C3)cc12]

$Cs_2CO_3$ (612 mg, 1.88 mmol) was added to a mixture of methyl 6-bromoquinoline-4-carboxylate (200 mg, 0.75 mmol), 6-fluoro-2-azaspiro[3.3]heptane trifluoroacetate (344 mg, 1.50 mmol), $Pd_2(dba)_3$ (69 mg, 0.08 mmol) and DavePhos (59 mg, 0.15 mmol) in 1,4-dioxane (5 mL) at 25° C., and the reaction mixture was stirred at 100° C. for 2 h. The reaction mixture was diluted with DCM (10 mL) and the solvent was removed under reduced pressure. The crude product was purified by preparative TLC (EtOAc:petroleum ether, 1:1), to give the title compound (0.22 g, 97%) as an orange gum; MS (ESI) m/z $[M+H]^+$ 301.

Intermediate 298: 6-(6-Fluoro-2-azaspiro[3.3]heptan-2-yl)quinoline-4-carboxylic acid

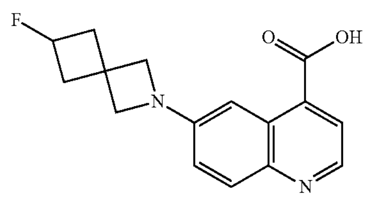 [SMILES: O=C(O)c1ccnc2ccc(N3CC4(CC(F)C4)C3)cc12]

NaOH (146 mg, 3.65 mmol) was added to a solution of methyl 6-(6-fluoro-2-azaspiro[3.3]heptan-2-yl)quinoline-4-carboxylate Intermediate 297 (219 mg, 0.73 mmol) in MeOH (6 mL) and water (2 mL) at 25° C., and the reaction was stirred at 25° C. for 1 h. The solvent was removed under reduced pressure and the residue was diluted with water (50 mL), and pH was adjusted to 3 with aq HCl (1 M). The aqueous phase was extracted with EtOAc (3×50 mL), the combined organic layer was dried over $Na_2SO_4$, filtered and evaporated at reduced pressure to give the title compound (0.205 g, 98%) as an orange solid; MS (ESI) m/z $[M+H]^+$ 287.

Intermediate 299: rac-Methyl 6-((1R,5R)-6-azabicyclo[3.2.0]heptan-6-yl)quinoline-4-carboxylate

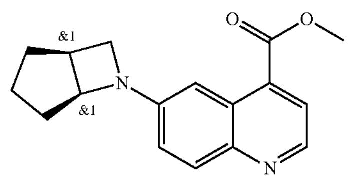 [SMILES: COC(=O)c1ccnc2ccc(N3C[C@@H]4CCC[C@@H]43)cc12]

A solution of methyl 6-bromoquinoline-4-carboxylate (400 mg, 1.50 mmol) in 1,4-dioxane (10 mL) was added to a mixture of 6-azabicyclo[3.2.0]heptane (146 mg, 1.50 mmol), $Pd_2(dba)_3$ (14 mg, 0.02 mmol) XPhos (14 mg, 0.03 mmol) and $Cs_2CO_3$ (980 mg, 3.01 mmol), and the reaction mixture was stirred at 100° C. for 3 h. The reaction mixture was filtered through silica, and the filtrate was concentrated under reduced pressure. The crude product was purified by preparative TLC (petroleum ether:EtOAc, 2:1), to give the title compound (0.17 g, 40%) as a yellow solid; MS (ESI) m/z $[M+H]^+$ 382.2.

Intermediate 300: rac-6-((1R,5R)-6-Azabicyclo[3.2.0]heptan-6-yl)quinoline-4-carboxylic acid

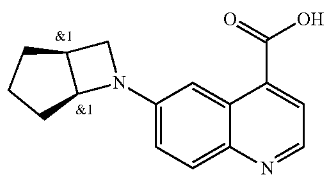 [SMILES: O=C(O)c1ccnc2ccc(N3C[C@@H]4CCC[C@@H]43)cc12]

LiOH (25 mg, 1.1 mmol) was added to a stirred solution of methyl 6-(6-azabicyclo[3.2.0]heptan-6-yl)quinoline-4-carboxylate Intermediate 299 (150 mg, 0.53 mmol) in THF (3 mL) and water (3 mL), and the reaction mixture was stirred at 25° C. for 4 h. The pH of the reaction mixture was adjusted to 5 with aq HCl (2 M), and the reaction mixture was concentrated under reduced pressure to give the title compound (0.13 g, 91%) as a red solid; MS (ESI) m/z $[M+H]^+$ 269.2.

Intermediate 301: Methyl 6-(3-hydroxy-3-(hydroxymethyl)azetidin-1-yl)quinoline-4-carboxylate

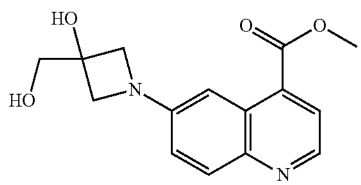 [SMILES: COC(=O)c1ccnc2ccc(N3CC(O)(CO)C3)cc12]

$Cs_2CO_3$ (814 mg, 2.50 mmol) was added to methyl 6-bromoquinoline-4-carboxylate (266 mg, 1.00 mmol), 3-(hydroxymethyl)azetidin-3-ol oxalate (193 mg, 1.30 mmol), $Pd_2(dba)_3$ (92 mg, 0.10 mmol) and XPhos (95 mg, 0.20 mmol) in 1,4-dioxane (5 mL) at 12° C., and the reaction mixture was stirred at 100° C. for 15 h. The reaction mixture was filtered through Celite®, and the filtrated was concentrated under reduced pressure. The crude product was purified by preparative TLC (DCM:MeOH, 10:1), to give the title compound (0.134 g, 46%) as a brown solid; MS (ESI) m/z $[M+H]^+$ 289.

Intermediate 302: Methyl 6-(3-fluoro-3-(fluoromethyl)azetidin-1-yl)quinoline-4-carboxylate

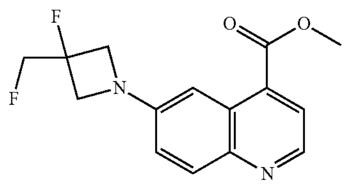 [SMILES: COC(=O)c1ccnc2ccc(N3CC(F)(CF)C3)cc12]

A solution of DAST (972 μL, 7.35 mmol) in anhydrous DCM (5 mL) was added dropwise to a stirred solution of methyl 6-(3-hydroxy-3-(hydroxymethyl)azetidin-1-yl)quinoline-4-carboxylate Intermediate 301 (212 mg, 0.74 mmol) in anhydrous DCM (25 mL), cooled to −60° C., over a period of 10 min. The reaction mixture was warmed to 25° C. and stirred for 8 h. The reaction mixture was poured into sat $NaHCO_3$(25 mL, aq), and extracted with DCM (5×75 mL). The combined organic layer was washed with water (3×50 mL), dried over $Na_2SO_4$, filtered and evaporated under reduced pressure. The crude product was purified by preparative TLC (DCM:MeOH, 10:1), to give the title compound (0.12 g, 56%) as a brown oil; MS (ESI) m/z $[M+H]^+$ 293.

Intermediate 303: 6-(3-Fluoro-3-(fluoromethyl)azetidin-1-yl)quinoline-4-carboxylic acid

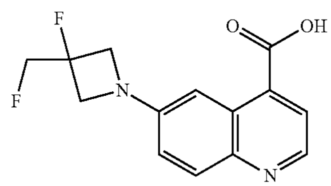 [SMILES: O=C(O)c1ccnc2ccc(N3CC(F)(CF)C3)cc12]

A solution of NaOH (45 mg, 1.13 mmol) in water (1 mL) was added slowly to a stirred solution of methyl 6-(3-fluoro-3-(fluoromethyl)azetidin-1-yl)quinoline-4-carboxylate Intermediate 302 (110 mg, 0.38 mmol) in MeOH (3 mL), cooled to 0° C., and the reaction mixture was stirred at 28° C. for 1.5 h. The reaction mixture was acidified with aq HCl (2 M), and extracted with EtOAc (5×100 mL). The combined organic layer was dried over $Na_2SO_4$, filtered and evaporated under reduced pressure to give the title compound (0.10 g, 95%) as a beige solid; MS (ESI) m/z $[M+H]^+$ 279.

Intermediate 304: Methyl 6-(3-(2,2,2-trifluoroethyl)azetidin-1-yl)quinoline-4-carboxylate

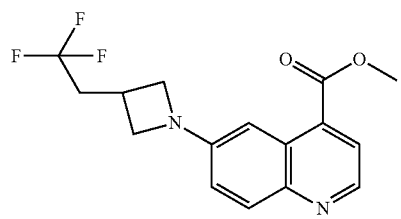 [SMILES: COC(=O)c1ccnc2ccc(N3CC(CC(F)(F)F)C3)cc12]

$Cs_2CO_3$ (563 mg, 1.73 mmol) was added to methyl 6-bromoquinoline-4-carboxylate (200 mg, 0.75 mmol), 3-(2,2,2-trifluoroethyl)azetidine hydrochloride (172 mg, 0.98 mmol), $Pd_2(dba)_3$ (69 mg, 0.08 mmol) and XPhos (72 mg, 0.15 mmol) in 1,4-dioxane (20 mL) at 28° C., and the reaction mixture was stirred at 100° C. for 2 h. The reaction mixture was filtered through Celite®, and the filtrate was concentrated under reduced pressure. The crude product was purified by preparative TLC (DCM:MeOH, 10:1), to give the title compound (0.415 g) as a crude; MS (ESI) m/z $[M+H]^+$ 325.

Intermediate 305: 6-(3-(2,2,2-Trifluoroethyl)azetidin-1-yl)quinoline-4-carboxylic acid

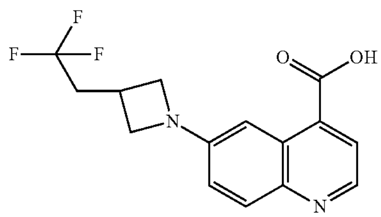 [SMILES: O=C(O)c1ccnc2ccc(N3CC(CC(F)(F)F)C3)cc12]

A solution of NaOH (134 mg, 3.36 mmol) in water (2 mL) was added to a stirred solution of methyl 6-(3-(2,2,2-trifluoroethyl)azetidin-1-yl)quinoline-4-carboxylate Intermediate 304 (363 mg, 1.12 mmol) in MeOH (6 mL), cooled to 0° C., and the reaction mixture was stirred at 20° C. for 2 h. The reaction mixture was acidified to pH 6 with aq HCl (2 M, aq), and extracted with EtOAc (10×100 mL). The combined organic layer was dried over $Na_2SO_4$, filtered and evaporated under reduced pressure, to give the title compound (0.333 g, 96%) as an orange solid; MS (ESI) m/z $[M+H]^+$ 311.

Intermediate 306: rac-Methyl (R)-6-(3,3-difluoro-2-methylazetidin-1-yl)quinoline-4-carboxylate

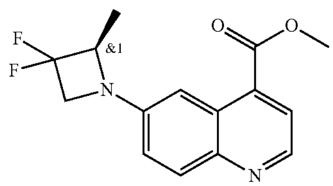 [SMILES: COC(=O)c1ccnc2ccc(N3CC(F)(F)[C@H]3C)cc12]

$Cs_2CO_3$ (735 mg, 2.25 mmol) was added to a mixture of methyl 6-bromoquinoline-4-carboxylate (200 mg, 0.75 mmol), 3,3-difluoro-2-methylazetidine hydrochloride (216 mg, 1.50 mmol) and RuPhos Pd G3 (63 mg, 0.08 mmol) in 1,4-dioxane (4 mL) at 20° C., and the reaction mixture was stirred at 100° C. for 4 h. The reaction mixture was diluted with DCM, and filtered through silica, and the filter cake was washed with DCM. The filtrate was concentrated under reduced pressure, and the crude product was purified by preparative TLC (petroleum ether:EtOAc, 1:1), to give the title compound (0.215 g, 98%) as a brown gum; MS (ESI) m/z $[M+H]^+$ 293.

Intermediate 307: rac-(R)-6-(3,3-Difluoro-2-methylazetidin-1-yl)quinoline-4-carboxylic acid

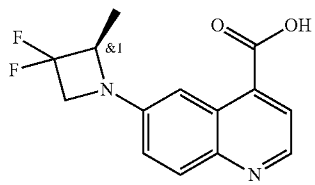 [SMILES: C[C@H]1N(c2ccc3nccc(C(=O)O)c3c2)CC1(F)F]

NaOH (146 mg, 3.66 mmol) was added to a solution of methyl 6-(3,3-difluoro-2-methylazetidin-1-yl)quinoline-4-carboxylate Intermediate 306 (214 mg, 0.73 mmol) in MeOH (1.5 mL) and water (0.5 mL) at 20° C., and the reaction mixture was stirred at 20° C. for 1 h. The reaction mixture was concentrated under reduced pressure, diluted with water, and the pH was adjusted to 3 with aq HCl (1 M). The reaction mixture was diluted with water (50 mL), and washed with EtOAc (5×50 mL). The combined organic layer was dried over $Na_2SO_4$, filtered and evaporated under reduced pressure to give the title compound (0.198 g, 97%) as a yellow solid; MS (ESI) m/z $[M+H]^+$ 279.

Intermediate 308: tert-Butyl 6-(6,6-difluoro-3-azabicyclo[3.1.0]hexan-3-yl)quinoline-4-carboxylate

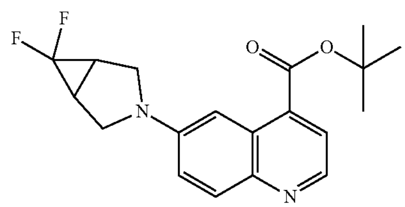 [SMILES: CC(C)(C)OC(=O)c1ccnc2ccc(N3CC4C(C3)C4(F)F)cc12]

$Cs_2CO_3$ (132 mg, 0.41 mmol) was added to a mixture of tert-butyl 6-bromoquinoline-4-carboxylate (50 mg, 0.16 mmol), 6,6-difluoro-3-azabicyclo[3.1.0]hexane hydrochloride (28 mg, 0.18 mmol), $Pd_2(dba)_3$ (15 mg, 0.02 mmol) and XPhos (15 mg, 0.03 mmol) in 1,4-dioxane (5 mL) at 20° C., and the reaction mixture was stirred at 100° C. for 5 h. The reaction mixture was filtered through Celite®, and the filtrate was concentrated under reduced pressure. The crude product was purified by preparative TLC (EtOAc:petroleum ether, 2:1), followed by reversed phase flash chromatography on a C18 column (gradient: 0-75% MeCN in water) to give the title compound (0.137 g) as a crude yellow solid; MS (ESI) m/z $[M+H]^+$ 347.

Intermediate 309: 6-(6,6-Difluoro-3-azabicyclo[3.1.0]hexan-3-yl)quinoline-4-carboxylic acid

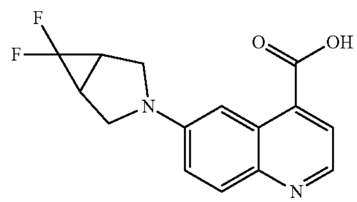 [SMILES: O=C(O)c1ccnc2ccc(N3CC4C(C3)C4(F)F)cc12]

TFA (5 mL) was added to a stirred solution of tert-butyl 6-(6,6-difluoro-3-azabicyclo[3.1.0]hexan-3-yl)quinoline-4-carboxylate Intermediate 308 (123 mg, 0.36 mmol) in DCM (5 mL) at 15° C., and the reaction mixture was stirred at 15° C. for 15 h. The solvent was removed under reduced pressure, to give the title compound (0.198 g, 97%) as a crude, dark red solid; MS (ESI) m/z $[M+H]^+$ 291.

Intermediate 310: Methyl (R)-6-(3-methoxypyrrolidin-1-yl)quinoline-4-carboxylate

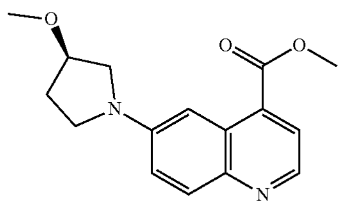

$Cs_2CO_3$ (735 mg, 2.25 mmol), $Pd_2(dba)_3$ (10 mg, 0.01 mmol) and XPhos (11 mg, 0.02 mmol) was added to a solution of methyl 6-bromoquinoline-4-carboxylate (300 mg, 1.13 mmol) and (R)-3-methoxypyrrolidine (228 mg, 2.25 mmol) in 1,4-dioxane (10 mL), and the reaction mixture was stirred at 100° C. for 2 h. The solvent was removed under reduced pressure and the crude product was purified by preparative TLC (petroleum ether:EtOAc, 2:1), to give the title compound (0.30 g, 93%) as a red oil which solidified on standing; MS (ESI) m/z $[M+H]^+$ 287.1.

Intermediate 311: (R)-6-(3-Methoxypyrrolidin-1-yl)quinoline-4-carboxylic acid

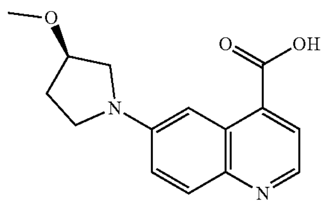 [SMILES: CO[C@@H]1CCN(c2ccc3nccc(C(=O)O)c3c2)C1]

LiOH (90 mg, 3.8 mmol) was add to a solution of methyl (R)-6-(3-methoxypyrrolidin-1-yl)quinoline-4-carboxylate Intermediate 310 (270 mg, 0.94 mmol) in THF (0.5 mL) and water (0.5 mL), and the reaction mixture was stirred at 25° C. for 3 h. The pH of the reaction mixture was adjusted to 5 with aq HCl (2 M), and the reaction mixture was concentrated under reduced pressure to give the title compound (0.20 g, 78%) as a red solid; MS (ESI) m/z $[M+H]^+$ 273.

Intermediate 312: Methyl 6-(3-oxa-9-azaspiro[5.5]undecan-9-yl)quinoline-4-carboxylate

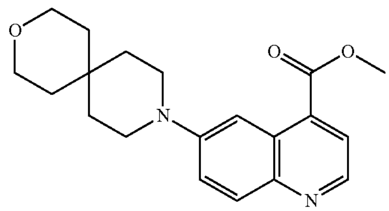 [SMILES: COC(=O)c1ccnc2ccc(N3CCC4(CCOCC4)CC3)cc12]

$Pd_2(dba)_3$ (52 mg, 0.06 mmol) was added to a mixture of methyl 6-bromoquinoline-4-carboxylate (300 mg, 1.13 mmol), 3-oxa-9-azaspiro[5.5]undecane (263 mg, 1.69 mmol), $Cs_2CO_3$ (735 mg, 2.25 mmol) and XantPhos (98 mg, 0.17 mmol) in 1,4-dioxane (15 mL) and the reaction mixture was stirred at 80° C. for 2 h. The reaction mixture was concentrated under reduced pressure, diluted with EtOAc, and washed with water. The organic layer was dried over $Na_2SO_4$, filtered and evaporated under reduced pressure. The crude product was purified by preparative TLC (petroleum ether:EtOAc, 2:1), to give the title compound (0.24 g, 62%) as a yellow gum; MS (ESI) m/z $[M+H]^+$ 341.

Intermediate 313: 6-(3-Oxa-9-azaspiro[5.5]undecan-9-yl)quinoline-4-carboxylic acid

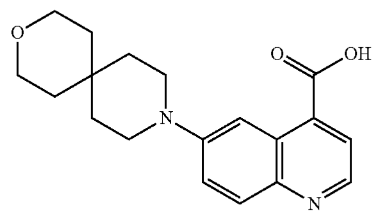 [SMILES: O=C(O)c1ccnc2ccc(N3CCC4(CCOCC4)CC3)cc12]

A solution of methyl 6-(3-oxa-9-azaspiro[5.5]undecan-9-yl)quinoline-4-carboxylate Intermediate 312 (230 mg, 0.68 mmol) and LiOH (81 mg, 3.4 mmol) in MeOH (10 mL) and water (2 mL) was stirred at rt for 3 h. The solvent was removed under reduced pressure and the reaction mixture was diluted with water, and the pH was adjusted to 6 with aq HCl (1 M). The precipitate was collected by filtration, washed with water and dried under vacuum to give the title compound (0.20 g, 91%) as a yellow solid; MS (ESI) m/z $[M+H]^+$ 327.

Intermediate 314: Methyl 6-(5,8-dioxa-2-azaspiro[3.4]octan-2-yl)quinoline-4-carboxylate

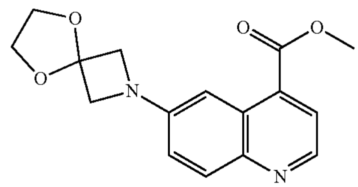 [SMILES: COC(=O)c1ccnc2ccc(N3CC4(C3)OCCO4)cc12]

A solution of methyl 6-bromoquinoline-4-carboxylate (400 mg, 1.50 mmol) in 1,4-dioxane (15 mL) was added to a mixture of 5,8-dioxa-2-azaspiro[3.4]octane (260 mg, 2.25 mmol), $Pd_2(dba)_3$ (14 mg, 0.02 mmol) XPhos (14 mg, 0.03 mmol) and $Cs_2CO_3$ (980 mg, 3.01 mmol), and the reaction mixture was stirred at 100° C. for 3 h. The reaction mixture was filtered through silica, and the filtrate was concentrated under reduced pressure. The crude product was purified by preparative TLC (petroleum ether:EtOAc, 2:1), to give the title compound (0.35 g, 78%) as a yellow solid; MS (ESI) m/z $[M+H]^+$ 301.1.

Intermediate 315: 6-(5,8-Dioxa-2-azaspiro[3.4]octan-2-yl)quinoline-4-carboxylic acid

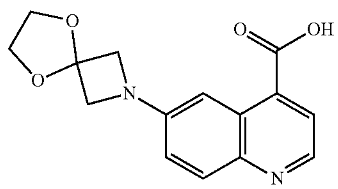 [SMILES: O=C(O)c1ccnc2ccc(N3CC4(C3)OCCO4)cc12]

LiOH (115 mg, 4.79 mmol) was added to a stirred solution of methyl 6-(5,8-dioxa-2-azaspiro[3.4]octan-2-yl) quinoline-4-carboxylate Intermediate 314 (360 mg, 1.20 mmol) in THF (5 mL) and water (5 mL), and the reaction mixture was stirred at 25° C. for 4 h. The pH of the reaction mixture was adjusted to 5 with aq HCl (2 M) and the reaction mixture was concentrated under reduced pressure to give the title compound (0.30 g, 87%) as a red solid; MS (ESI) m/z $[M+H]^+$ 287.1.

Intermediate 316: Methyl 6-(5-azaspiro[2.3]hexan-5-yl)quinoline-4-carboxylate

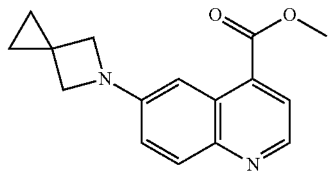 [SMILES: COC(=O)c1ccnc2ccc(N3CC4(CC4)C3)cc12]

$Cs_2CO_3$ (612 mg, 1.88 mmol) was added to a mixture of methyl 6-bromoquinoline-4-carboxylate (200 mg, 0.75 mmol), 5-azaspiro[2.3]hexane hydrochloride (135 mg, 1.13 mmol), $Pd_2(dba)_3$ (69 mg, 0.08 mmol) and XPhos (72 mg, 0.15 mmol) in 1,4-dioxane (4 mL) at 15° C., and the reaction mixture was stirred at 100° C. for 2 h. The reaction mixture was diluted with DCM, and the solvent was removed under reduced pressure. The crude product was purified by preparative TLC (petroleum ether:EtOAc, 1:1), to give the title compound (0.189 g, 94%) as a yellow solid; MS (ESI) m/z $[M+H]^+$ 269.

Intermediate 317: 6-(5-Azaspiro[2.3]hexan-5-yl) quinoline-4-carboxylic acid

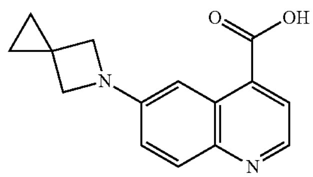 [SMILES: O=C(O)c1ccnc2ccc(N3CC4(CC4)C3)cc12]

NaOH (140 mg, 3.50 mmol) was added to a solution of methyl 6-(5-azaspiro[2.3]hexan-5-yl)quinoline-4-carboxylate Intermediate 316 (188 mg, 0.70 mmol) in MeOH (1.5 mL) and water (0.5 mL) at 15° C., and the reaction mixture was stirred at 15° C. for 1 h. The reaction mixture was concentrated under reduced pressure, diluted with water, and the pH was adjusted to 3 with aq HCl (1 M). The reaction mixture was diluted with EtOAc (50 mL), and washed with water (10×50 mL). The organic layer was dried over $Na_2SO_4$, filtered and evaporated under reduced pressure to give the title compound (0.327 g) as an orange solid; MS (ESI) m/z $[M+H]^+$ 255.

Intermediate 318: Methyl 6-(3-hydroxy-3-methylazetidin-1-yl)quinoline-4-carboxylate

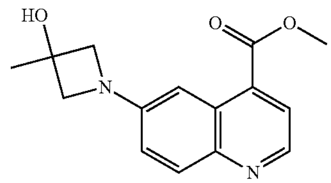

$Cs_2CO_3$ (1.30 g, 4.01 mmol) was added to a mixture of methyl 6-bromoquinoline-4-carboxylate hydrochloride Intermediate 422 (303 mg, 1.00 mmol), 3-methylazetidin-3-ol hydrochloride (155 mg, 1.25 mmol), $Pd_2(dba)_3$ (92 mg, 0.10 mmol) and XPhos (95 mg, 0.20 mmol) in 1,4-dioxane (7 mL) at 20° C., and the reaction mixture was stirred at 100° C. for 2 h. The reaction mixture was filtered, and the filtrate was concentrated under reduced pressure. The crude product was purified by preparative TLC (EtOAc:petroleum ether, 10:1), to give the title compound (0.193 g, 71%) as a yellow solid; MS (ESI) m/z $[M+H]^+$ 273.

Intermediate 319: 6-(3-Hydroxy-3-methylazetidin-1-yl)quinoline-4-carboxylic acid

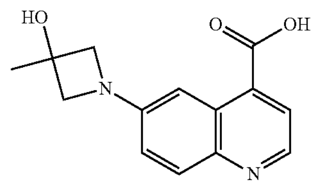 [SMILES: CC1(O)CN(c2ccc3nccc(C(=O)O)c3c2)C1]

A solution of NaOH (110 mg, 2.75 mmol) in water (4 mL) was added slowly to a stirred solution of methyl 6-(3-hydroxy-3-methylazetidin-1-yl)quinoline-4-carboxylate Intermediate 318 (150 mg, 0.55 mmol) in MeOH (12 mL), cooled to 0° C., and the reaction mixture was stirred at 20° C. for 1 h. The pH of the reaction mixture was adjusted to 6 with aq HCl (2 M), and the mixture was extracted with EtOAc (5×75 mL). The combined organic layer was washed with water (3×50 mL), dried over $Na_2SO_4$, filtered and evaporated under reduced pressure to give the title compound (0.095 g, 67%) as a yellow oil which solidified on standing; MS (ESI) m/z $[M+H]^+$ 259.

Intermediate 320: Methyl 6-(2-oxa-6-azaspiro[3.3]heptan-6-yl)quinoline-4-carboxylate

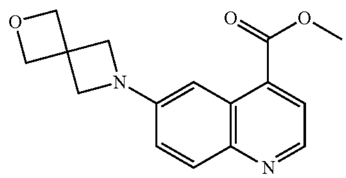 [SMILES: COC(=O)c1ccnc2ccc(N3CC4(COC4)C3)cc12]

$Cs_2CO_3$ (1.53 g, 4.70 mmol) was added to a mixture of methyl 6-bromoquinoline-4-carboxylate (500 mg, 1.88 mmol), 2-oxa-6-azaspiro[3.3]heptane oxalate (462 mg, 2.44 mmol) and RuPhos Pd G3 (157 mg, 0.19 mmol) in 1,4-dioxane (15 mL) at 28° C., and the reaction mixture was stirred at 100° C. for 4 h. The reaction mixture was filtered through Celite®, and the filtrate was concentrated under reduced pressure. The crude product was purified by preparative TLC (DCM:MeOH, 10:1), to give the title compound (0.254 g, 48%) as a yellow solid; MS (ESI) m/z $[M+H]^+$ 285.

Intermediate 321: 6-(2-Oxa-6-azaspiro[3.3]heptan-6-yl)quinoline-4-carboxylic acid

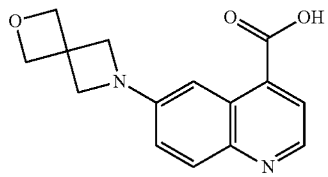 [SMILES: O=C(O)c1ccnc2ccc(N3CC4(COC4)C3)cc12]

A solution of NaOH (196 mg, 4.90 mmol) in water (3 mL) was added slowly to a stirred suspension of methyl 6-(2-oxa-6-azaspiro[3.3]heptan-6-yl)quinoline-4-carboxylate Intermediate 320 (232 mg, 0.82 mmol) in MeOH (12 mL) cooled to 0° C., and the reaction mixture was stirred at 25° C. for 1 h. The reaction mixture was diluted with water (20 mL), the pH was adjusted to 6 with aq HCl (2 M), and the reaction mixture was extracted with EtOAc (6×100 mL). The combined organic layer was dried over $Na_2SO_4$, filtered and evaporated under reduced pressure to give the title compound (0.19 g, 86%) as a red solid; MS (ESI) m/z $[M+H]^+$ 271.

Intermediate 322: Methyl (R)-6-(3-hydroxy-3-methylpyrrolidin-1-yl)quinoline-4-carboxylate

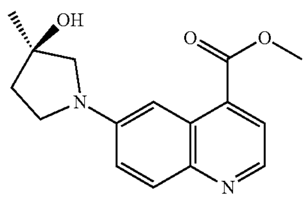 [SMILES: COC(=O)c1ccnc2ccc(N3CC[C@@](C)(O)C3)cc12]

$Pd_2(dba)_3$ (52 mg, 0.06 mmol) was added to a mixture of methyl 6-bromoquinoline-4-carboxylate (300 mg, 1.13 mmol), (R)-3-methylpyrrolidin-3-ol (228 mg, 2.25 mmol), XPhos (81 mg, 0.17 mmol) and $Cs_2CO_3$ (735 mg, 2.25 mmol) in 1,4-dioxane (15 mL) and the reaction mixture was stirred at 100° C. for 3 h. The reaction mixture was filtered, and the filtrate was concentrated under vacuum. The residue was diluted with EtOAc, and washed with water. The organic layer was dried over $Na_2SO_4$, filtered and evaporated under reduced pressure. The crude product was purified by preparative TLC (petroleum ether:EtOAc, 1:3), to give the title compound (0.28 g, 87%) as a yellow solid; MS (ESI) m/z $[M+H]^+$ 287.

Intermediate 323: (R)-6-(3-Hydroxy-3-methylpyrrolidin-1-yl)quinoline-4-carboxylic acid

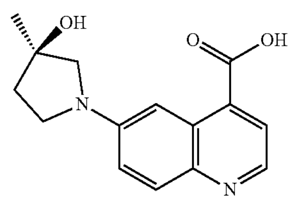 [SMILES: C[C@@]1(O)CCN(c2ccc3nccc(C(=O)O)c3c2)C1]

A solution of methyl (R)-6-(3-hydroxy-3-methylpyrrolidin-1-yl)quinoline-4-carboxylate Intermediate 322 (280 mg, 0.98 mmol) and LiOH (94 mg, 3.91 mmol) in MeOH (10 mL) and water (2 mL) was stirred at rt for 1 h. The solvent was removed under reduced pressure. The residue was diluted with water, and the pH was adjusted to 6 with aq HCl (1 M). The precipitate was collected by filtration, washed with water and dried under vacuum to give the title compound (0.22 g, 83%) as an orange solid; MS (ESI) m/z $[M+H]^+$ 273.

Intermediate 324: Methyl (S)-6-(3-hydroxy-3-methylpyrrolidin-1-yl)quinoline-4-carboxylate

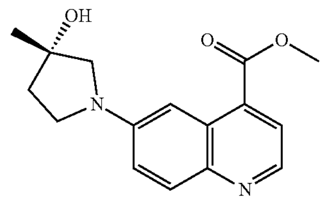

$Pd_2(dba)_3$ (52 mg, 0.06 mmol) was added to a mixture of methyl 6-bromoquinoline-4-carboxylate (300 mg, 1.13 mmol), (S)-3-methylpyrrolidin-3-ol hydrochloride (233 mg, 1.69 mmol), XPhos (81 mg, 0.17 mmol) and $Cs_2CO_3$ (1.10 g, 3.38 mmol) in 1,4-dioxane (10 mL), and the reaction mixture was stirred at 100° C. for 2 h. The reaction mixture was filtered, and the filtrate was concentrated under reduced pressure. The reaction mixture was diluted with EtOAc, and washed with water. The organic layer was dried over $Na_2SO_4$, filtered and evaporated under reduced pressure. The crude product was purified by preparative TLC (petroleum ether:EtOAc, 1:3), to give the title compound (0.26 g, 81%) as a yellow solid; MS (ESI) m/z $[M+H]^+$ 287.

Intermediate 325: (S)-6-(3-Hydroxy-3-methylpyrrolidin-1-yl)quinoline-4-carboxylic acid

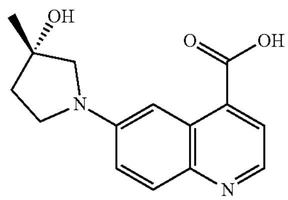 [SMILES: C[C@]1(O)CCN(c2ccc3nccc(C(=O)O)c3c2)C1]

A solution of methyl (S)-6-(3-hydroxy-3-methylpyrrolidin-1-yl)quinoline-4-carboxylate Intermediate 324 (250 mg, 0.87 mmol) and LiOH (63 mg, 2.6 mmol) in MeOH (10 mL) and water (2 mL) was stirred at rt for 2 h. The solvent was removed under reduced pressure. The reaction mixture was diluted with water, and the pH was adjusted to 6 with aq HCl (1 M). The precipitate was collected by filtration, washed with water and dried under vacuum to give the title compound (0.21 g, 88%) as an orange solid; MS (ESI) m/z $[M+H]^+$ 273.

Intermediate 326: 6-(6-(Difluoromethyl)pyridin-3-371)quinoline-4-carboxylic acid

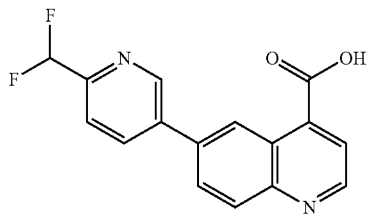 [SMILES: O=C(O)c1ccnc2ccc(-c3ccc(C(F)F)nc3)cc12]

A mixture of (6-(difluoromethyl)pyridin-3-yl)boronic acid (103 mg, 0.60 mmol), 6-bromoquinoline-4-carboxylic acid (150 mg, 0.60 mmol), $Cs_2CO_3$ (388 mg, 1.19 mmol) and Pd(dtbpf)$Cl_2$ (58 mg, 0.09 mmol) in 1,4-dioxane (4.8 mL) and water (1.2 mL) was stirred at rt for 2 h. The reaction mixture was concentrated under reduced pressure, diluted with water and the pH was adjusted to 2 with aq HCl (1 M). The precipitate was filtered off, washed with diethyl ether and dried under vacuum to give the title compound (143 mg, 80%); MS (ESI) m/z $[M+H]^+$ 301.1.

Intermediate 327: 6-(1-Cyclopropyl-1H-pyrazol-4-yl)quinoline-4-carbolic acid

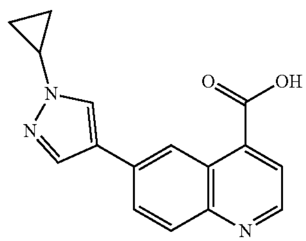 [SMILES: O=C(O)c1ccnc2ccc(-c3cnn(C4CC4)c3)cc12]

A mixture of 6-bromoquinoline-4-carboxylic acid (150 mg, 0.60 mmol), (1-cyclopropyl-1H-pyrazol-4-yl)boronic acid (136 mg, 0.89 mmol), $Cs_2CO_3$ (388 mg, 1.19 mmol) and Pd(dtbpf)$Cl_2$ (58 mg, 0.09 mmol) in 1,4-dioxane (4.8 mL) and water (1.2 mL) was stirred at rt for 2 h. The reaction mixture was concentrated under reduced pressure, diluted with water and the pH was adjusted to 2 with aq HCl (1 M). The precipitate was filtered off, washed with diethyl ether and dried under vacuum to give the title compound (0.124 g, 75%); MS (ESI) m/z $[M+H]^+$ 280.1.

Intermediate 328: 6-(1,3-Dimethyl-1H-pyrazol-4-yl)quinoline-4-carboxylic acid

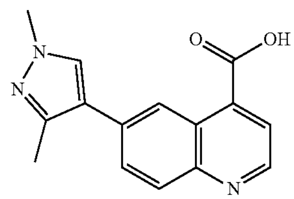 [SMILES: Cc1nn(C)cc1-c1ccc2nccc(C(=O)O)c2c1]

A mixture of 1,3-dimethyl-4-(4,4,5,5-tetramethyl-1,3,2-dioxaborolan-2-yl)-1H-pyrazole (0.448 g, 2.02 mmol), 6-bromoquinoline-4-carboxylic acid (0.508 g, 2.02 mmol), $Cs_2CO_3$ (1.31 g, 4.03 mmol) and Pd(dtbpf)$Cl_2$ (0.131 g, 0.20 mmol) in 1,4-dioxane (10 mL) and water (2.5 mL) was stirred overnight. Pd(dtbpf)$Cl_2$ (25 mg, 0.04 mmol) was added and the reaction was stirred for 6 h. Pd(dtbpf)$Cl_2$ (25 mg, 0.04 mmol) was added and the reaction was stirred for 4 days. The reaction mixture was diluted with a few mL of DMSO and evaporated under reduced pressure, and the crude product was purified by preparative HPLC, PrepMethod E, (gradient: 0-30%) to give the title compound (0.314 g, 58%); MS (ESI) m/z $[M+H]^+$ 268.

Intermediate 329: 6-(3,5-Dimethyl-1-(tetrahydro-2H-pyran-4-yl)-1H-pyrazol-4-yl)quinoline-4-carboxylic acid

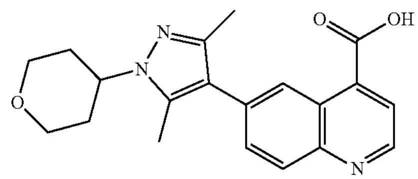 [SMILES: Cc1nn(C2CCOCC2)c(C)c1-c1ccc2nccc(C(=O)O)c2c1]

A mixture of 3,5-dimethyl-1-(tetrahydro-2H-pyran-4-yl)-4-(4,4,5,5-tetramethyl-1,3,2-dioxaborolan-2-yl)-1H-pyrazole (68 mg, 0.22 mmol), 6-bromoquinoline-4-carboxylic acid (56 mg, 0.22 mmol), $Cs_2CO_3$ (145 mg, 0.44 mmol) and Pd(dtbpf)$Cl_2$ (14 mg, 0.02 mmol) in 1,4-dioxane (1 mL) and water (0.25 mL) was stirred overnight. The reaction mixture was diluted with a few mL of DMSO and evaporated under reduced pressure, and the crude product was purified by preparative HPLC, PrepMethod E, (gradient: 5-45%) to give the title compound (40 mg, 51%); MS (ESI) m/z $[M+H]^+$ 352.

Intermediate 330: 6-(1-(Tetrahydro-2H-pyran-4-O-1H-pyrazol-4-yl)quinoline-4-carboxylic acid

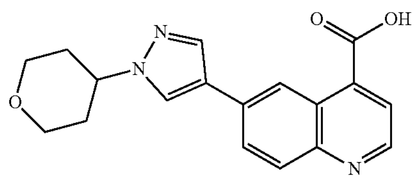 [SMILES: O=C(O)c1ccnc2ccc(-c3cnn(C4CCOCC4)c3)cc12]

A mixture of (1-(tetrahydro-2H-pyran-4-yl)-1H-pyrazol-4-yl)boronic acid (40 mg, 0.21 mmol), 6-bromoquinoline-4-carboxylic acid (52 mg, 0.21 mmol), $Cs_2CO_3$ (134 mg, 0.41 mmol) and Pd(dtbpf)$Cl_2$ (13 mg, 0.02 mmol) in 1,4-dioxane (1 mL) and water (0.25 mL) was stirred overnight. The reaction mixture was diluted with a few mL of DMSO and evaporated under reduced pressure, and the crude product was purified by preparative HPLC, PrepMethod E, (gradient: 5-45%) to give the title compound (26 mg, 39%); MS (ESI) m/z $[M+H]^+$ 324.

Intermediate 331: 6-(1-Methyl-1H-pyrazol-5-yl)quinoline-4-carboxylic acid

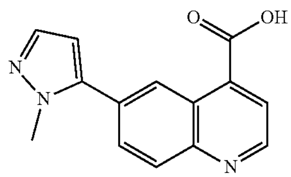 [SMILES: Cn1nccc1-c1ccc2nccc(C(=O)O)c2c1]

A mixture of 1-methyl-5-(4,4,5,5-tetramethyl-1,3,2-dioxaborolan-2-yl)-1H-pyrazole (41 mg, 0.20 mmol), 6-bromoquinoline-4-carboxylic acid (50 mg, 0.20 mmol), $Cs_2CO_3$ (194 mg, 0.60 mmol) and Pd(dtbpf)$Cl_2$ (22 mg, 0.03 mmol) in 1,4-dioxane (1 mL) and water (0.25 mL) was stirred overnight. The reaction mixture was diluted with a few mL of DMSO and evaporated under reduced pressure, and the crude product was purified by preparative HPLC, PrepMethod E, (gradient: 0-30%) to give the title compound (29 mg, 58%); MS (ESI) m/z $[M+H]^+$ 254.

Intermediate 332: (5,6,7,8-Tetrahydroimidazo[1,2-a]pyridin-3-yl)boronic acid

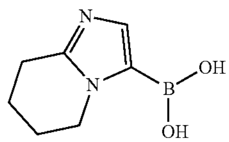 [SMILES: OB(O)c1cnc2n1CCCC2]

A solution of n-BuLi (280 mL, 0.69 mol, 2.5 M in hexane) was cannulated into a solution of 5,6,7,8-tetrahydroimidazo[1,2-a]pyridine in THF at −60° C. and over 20 min. The reaction mixture was stirred at rt for 30 min, and then cooled to −60° C., and added dropwise to a solution of B $(C_3H_7O)_3$ (150 g, 0.7 mol). The reaction mixture was stirred at rt for 6 h, and then quenched by the addition of aq HCl (1 M). The reaction mixture was concentrated under reduced pressure and the pH was adjusted to 2 with aq HCl (1 M). The reaction mixture was filtered, and the filter cake was washed with EtOAc, and dried in vacuo to give the title compound (54 g, 57%); MS (ESI) m/z $[M+H]^+$ 167.1.

Intermediate 333: 6-(5,6,7,8-Tetrahydroimidazo[1,2-a]pyridin-3-yl)quinoline-4-carboxylic acid

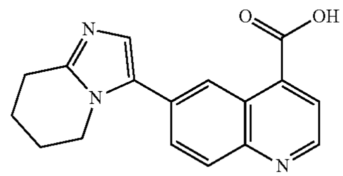 [SMILES: O=C(O)c1ccnc2ccc(-c3cnc4n3CCCC4)cc12]

A mixture of (5,6,7,8-tetrahydroimidazo[1,2-c]pyridin-3-yl)boronic acid Intermediate 332 (37 mg, 0.22 mmol), 6-bromoquinoline-4-carboxylic acid (56 mg, 0.22 mmol), $Cs_2CO_3$ (145 mg, 0.44 mmol) and Pd(dtbpf)$Cl_2$ (14 mg, 0.02 mmol) in 1,4-dioxane (1 mL) and water (0.25 mL) was stirred overnight. The reaction mixture was diluted with a few mL of DMSO and evaporated under reduced pressure, and the crude compound was purified by preparative HPLC, PrepMethod E, (gradient: 0-45%) to give the title compound (25 mg, 38%); MS (ESI) m/z $[M+H]^+$ 294.

Intermediate 334: Methyl 6-bromo-7-chloroquinoline-4-carboxylate

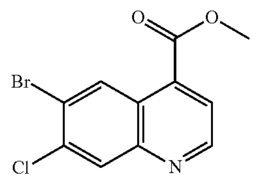 [SMILES: COC(=O)c1ccnc2cc(Cl)c(Br)cc12]

$SOCl_2$ (410 μL, 5.62 mmol) was added slowly to a solution of 6-bromo-7-chloroquinoline-4-carboxylic acid (322 mg, 1.12 mmol) in MeOH (10 mL) at 20° C., and the reaction mixture was stirred at 60° C. for 4 h. The reaction mixture was diluted with DCM (75 mL), and washed sequentially with water (20 mL) and sat brine (20 mL, aq). The organic layer was dried over $Na_2SO_4$, filtered and evaporated under reduced pressure. The crude product was purified by preparative TLC (DCM:MeOH, 40:1), to give the title compound (0.188 g, 56%) as a yellow solid; MS (ESI) m/z $[M+H]^+$ 301.9.

Intermediate 335: Methyl 7-chloro-6-morpholinoquinoline-4-carboxylate

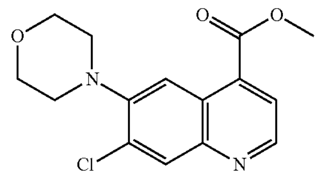 [SMILES: COC(=O)c1ccnc2cc(Cl)c(N3CCOCC3)cc12]

$Pd_2(dba)_3$ (46 mg, 0.05 mmol) was added to a suspension of methyl 6-bromo-7-chloroquinoline-4-carboxylate Intermediate 334 (150 mg, 0.50 mmol), morpholine (217 mg, 2.50 mmol), $Cs_2CO_3$ (22 mg, 0.07 mmol) and XantPhos (58 mg, 0.10 mmol) in 1,4-dioxane (15 mL) at 20° C., and the reaction mixture was stirred at 100° C. for 5 h. The reaction mixture was concentrated under reduced pressure, diluted with EtOAc (75 mL), and washed sequentially with water (15 mL) and sat brine (15 mL, aq). The organic layer was dried over $Na_2SO_4$, filtered and evaporated under reduced pressure. The crude product was purified by preparative TLC (DCM:MeOH, 40:1), to give the title compound (0.074 g, 48%) as a yellow solid; MS (ESI) m/z $[M+H]^+$ 307.0.

Intermediate 336: 7-Chloro-6-morpholinoquinoline-4-carboxylic acid

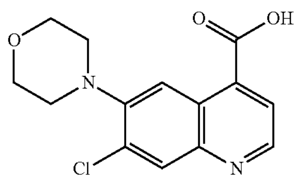 [SMILES: O=C(O)c1ccnc2cc(Cl)c(N3CCOCC3)cc12]

NaOH (46 mg, 1.1 mmol) was added to a solution of methyl 7-chloro-6-morpholinoquinoline-4-carboxylate Intermediate 335 (70 mg, 0.23 mmol) in MeOH (9 mL) and water (1 mL) at 20° C., and the reaction mixture was stirred at 25° C. for 3 h. The pH of the reaction mixture was adjusted to 3 using aq HCl (2 M, 15 mL). The reaction mixture was concentrated under reduced pressure, diluted with EtOAc (20 mL), and washed with water (10 mL). The organic layer was dried over $Na_2SO_4$, filtered and evaporated under reduced pressure to give the title compound (0.060 g, 90%) as a yellow solid; MS (ESI) m/z $[M+H]^+$ 292.9.

Intermediate 337: Methyl 6-bromo-8-chloroquinoline-4-carboxylate

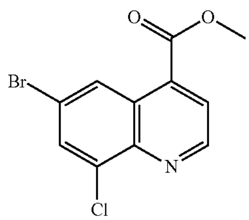 [SMILES: COC(=O)c1ccnc2c(Cl)cc(Br)cc12]

$SOCl_2$ (159 μL, 2.18 mmol) was added slowly to a solution of 6-bromo-8-chloroquinoline-4-carboxylic acid (125 mg, 0.44 mmol) in MeOH (10 mL) at 20° C., and the reaction mixture was stirred at 60° C. for 3 h. The reaction mixture was concentrated under reduced pressure, diluted with EtOAc (50 mL), and washed sequentially with water (15 mL) and sat brine (15 mL). The organic layer was dried over $Na_2SO_4$, filtered and evaporated under reduced pressure. The crude product was purified by preparative TLC (EtOAc:petroleum ether, 1:5), to give the title compound (0.10 g, 76%) as a yellow solid; MS (ESI) m/z $[M+H]^+$ 301.9.

Intermediate 338: Methyl 8-chloro-6-morpholinoquinoline-4-carboxylate

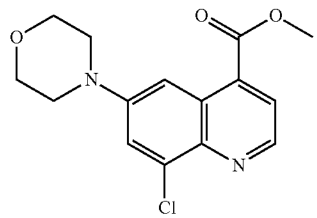 [SMILES: COC(=O)c1ccnc2c(Cl)cc(N3CCOCC3)cc12]

$Pd_2(dba)_3$ (30 mg, 0.03 mmol) was added to a suspension of methyl 6-bromo-8-chloroquinoline-4-carboxylate Intermediate 337 (100 mg, 0.33 mmol), morpholine (145 mg, 1.66 mmol), XantPhos (38 mg, 0.07 mmol) and $Cs_2CO_3$ (217 mg, 0.67 mmol) in 1,4-dioxane (15 mL) at 20° C., and the reaction mixture was stirred at 100° C. for 2 h. The reaction mixture was concentrated under reduced pressure, diluted with EtOAc (50 mL), and washed sequentially with sat brine (15 mL) and water (15 mL). The organic layer was dried over $Na_2SO_4$, filtered and evaporated under reduced pressure. The crude product was purified by preparative TLC (EtOAc:petroleum ether, 1:5), to give the title compound (0.082 g, 80%) as a yellow solid; MS (ESI) m/z $[M+H]^+$ 307.

Intermediate 339: 8-Chloro-6-morpholinoquinoline-4-carboxylic acid

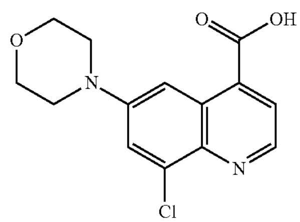 [SMILES: O=C(O)c1ccnc2c(Cl)cc(N3CCOCC3)cc12]

A solution of NaOH (52 mg, 1.3 mmol) in water (3 mL) was added to a stirred solution of methyl 8-chloro-6-morpholinoquinoline-4-carboxylate Intermediate 338 (80 mg, 0.26 mmol) in MeOH (9 mL) at 20° C., and the reaction mixture was stirred at 25° C. for 2 h. The pH of the reaction mixture was adjusted to 4 with aq HCl (2 M). The reaction mixture was concentrated under reduced pressure, diluted with EtOAc (50 mL), and washed sequentially with sat brine (20 mL) and water (15 mL). The organic layer was dried over $Na_2SO_4$, filtered and evaporated under reduced pressure to give the title compound (0.070 g, 92%) as a red solid; MS (ESI) m/z $[M+H]^+$ 293.0.

Intermediate 340: Ethyl 6-(3-(acetamidomethyl)-3-methylazetidin-1-yl)quinoline-4-carboxylate

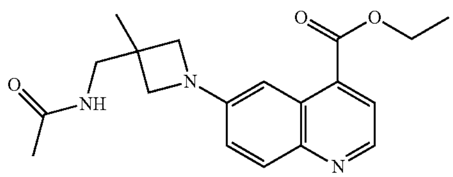 [SMILES: CCOC(=O)c1ccnc2ccc(N3CC(C)(CNC(C)=O)C3)cc12]

Ethyl 6-bromoquinoline-4-carboxylate (100 mg, 0.36 mmol), N-((3-methylazetidin-3-yl)methyl)acetamide hydrochloride, (128 mg, 0.71 mmol), $Cs_2CO_3$ (465 mg, 1.43 mmol), XPhos (34 mg, 0.07 mmol) and $Pd_2(dba)_3$ (33 mg, 0.04 mmol) were weighed into a 5 mL vial. Dioxane (2 mL) was added and the reaction mixture was purged with $N_2$ (g) for 10 min. The vial was sealed and the reaction mixture was stirred at 100° C. for 2 h. After cooling to rt, water (10 mL) and DCM (10 mL) were added and the reaction mixture was stirred and filtered through a phase separator and evaporated. The residue was purified by straight phase flash chromatography on silica (gradient: 20-100% of EtOAc (containing 5% 2 M $NH_3$ in MeOH) in heptane) to give the title compound (47 mg, 39%); MS (ESI) m/z $[M+H]^+$ 342.3.

Intermediate 341: 6-(3-(Acetamidomethyl)-3-methylazetidin-1-yl)quinoline-4-carboxylic acid

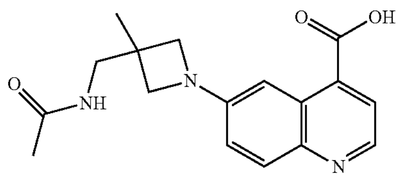 [SMILES: CC(=O)NCC1(C)CN(c2ccc3nccc(C(=O)O)c3c2)C1]

Aq NaOH (1 M, 264 μL, 0.26 mmol, 1 M) was added to a solution of ethyl 6-(3-(acetamidomethyl)-3-methylazetidin-1-yl)quinoline-4-carboxylate Intermediate 340 (45 mg, 0.13 mmol) in MeOH (1.5 mL). The reaction mixture was stirred at 50° C. for 20 min, then cooled to rt. Aq HCl (3.8 M, 87 μL, 0.33 mmol, 3.8 M) was added, and the reaction mixture was evaporated under reduced pressure and co-evaporated under reduced pressure with EtOH (2×) and MeCN (1×), to give the crude title compound; MS (ESI) m/z $[M+H]^+$ 314.2.

Intermediate 342: Ethyl 6-(3-fluoro-3-phenylazetidin-1-yl)quinoline-4-carboxylate

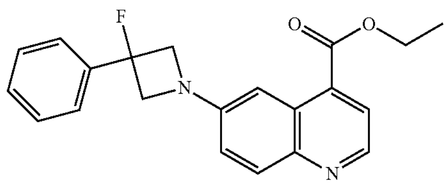 [SMILES: CCOC(=O)c1ccnc2ccc(N3CC(F)(c4ccccc4)C3)cc12]

Ethyl 6-bromoquinoline-4-carboxylate (120 mg, 0.43 mmol), 3-fluoro-3-phenylazetidine hydrochloride (161 mg, 0.86 mmol), $Cs_2CO_3$ (558 mg, 1.71 mmol), XPhos (41 mg, 0.09 mmol) and $Pd_2(dba)$ 3 (39 mg, 0.04 mmol) were weighed into a 5 mL vial. Dioxane (2 mL) was added and the reaction mixture was purged with $N_2$ (g) for 10 min. The vial was sealed and the reaction mixture was stirred at 100° C. for 2 h. After cooling to rt, water (10 mL) and DCM (10 mL) were added and the reaction mixture was stirred, filtered through a phase separator and evaporated under reduced pressure. The residue was purified by straight phase flash chromatography on silica (gradient: 5-50% of EtOAc in heptane) to give the title compound (26 mg, 17%); MS (ESI) m/z $[M+H]^+$ 351.3.

Intermediate 343: 6-(3-Fluoro-3-phenylazetidin-1-yl)quinoline-4-carboxylic acid

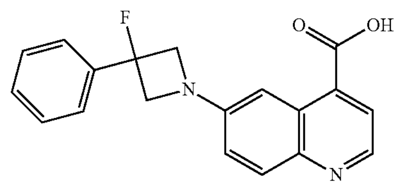 [SMILES: O=C(O)c1ccnc2ccc(N3CC(F)(c4ccccc4)C3)cc12]

Aq NaOH (1 M, 143 μL, 0.14 mmol) was added to a solution of ethyl 6-(3-fluoro-3-phenylazetidin-1-yl)quinoline-4-carboxylate Intermediate 342 (25 mg, 0.07 mmol) in MeOH (1 mL), and the reaction mixture was stirred at 50° C. for 20 min, and then cooled to rt. Aq HCl (3.8 M, 47 μL, 0.18 mmol) was added, and the reaction mixture was evaporated under reduced pressure and co-evaporated under reduced pressure with EtOH (2×), and MeCN (1×), to give the crude title compound; MS (ESI) m/z $[M+H]^+$: 323.2.

Intermediate 344: Ethyl 6-(3-(p-tolyl)azetidin-1-yl)quinoline-4-carboxylate

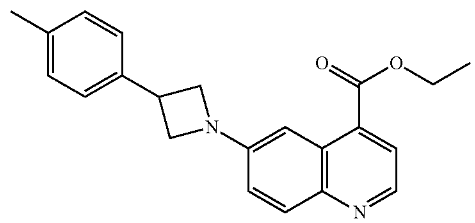 [SMILES: CCOC(=O)c1ccnc2ccc(N3CC(c4ccc(C)cc4)C3)cc12]

Ethyl 6-bromoquinoline-4-carboxylate (150 mg, 0.54 mmol), 3-(p-tolyl)azetidine hydrochloride, (148 mg, 0.80 mmol), $Cs_2CO_3$ (698 mg, 2.14 mmol), XPhos (51 mg, 0.11 mmol) and $Pd_2(dba)_3$ (49 mg, 0.05 mmol) were weighed into a 5 mL vial. Dioxane (2 mL) was added and the reaction mixture was purged with $N_2$ (g) for 10 min. The vial was sealed and the reaction mixture was stirred at 100° C. for 3 h. After cooling to rt, water (10 mL) and DCM (15 mL) were added and the reaction mixture was stirred, filtered through a phase separator and evaporated under reduced pressure. The residue was purified by straight phase flash chromatography on silica (gradient: 5-50% of EtOAc in heptane) to give the title compound (22 mg, 12%); MS (ESI) m/z $[M+H]^+$ 347.3.

Intermediate 345: 6-(3-(p-Tolyl)azetidin-1-yl)quinoline-4-carboxylic acid

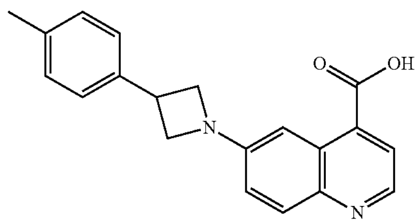 [SMILES: Cc1ccc(C2CN(c3ccc4nccc(C(=O)O)c4c3)C2)cc1]

Aq NaOH (1M, 115 μL, 0.12 mmol) was added to a solution of ethyl 6-(3-(p-tolyl)azetidin-1-yl)quinoline-4-carboxylate Intermediate 344 (20 mg, 0.06 mmol) in MeOH (1 mL). The reaction mixture was stirred at 50° C. for 20 min, then cooled to rt. Aq HCl (1 M, 144 μL, 0.14 mmol) was added and the reaction mixture was stirred, evaporated under reduced pressure, and co-evaporated under reduced pressure with EtOH (2×), and MeCN (1×), to give the crude title compound; MS (ESI) m/z $[M+H]^+$ 319.2.

Intermediate 346: Ethyl 6-(6-acetyl-2,6-diazaspiro[3.3]heptan-2-yl)quinoline-4-carboxylate

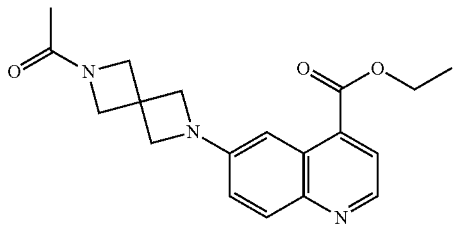 [SMILES: CCOC(=O)c1ccnc2ccc(N3CC4(CN(C(C)=O)C4)C3)cc12]

Ethyl 6-bromoquinoline-4-carboxylate (120 mg, 0.43 mmol), 1-(2,6-diazaspiro[3.3]-heptan-2-yl)ethan-1-one oxalate, (148 mg, 0.64 mmol), $Cs_2CO_3$ (558 mg, 1.71 mmol), XPhos (41 mg, 0.09 mmol) and $Pd_2(dba)_3$ (39 mg, 0.04 mmol) were weighed into a 5 mL vial. Dioxane (2.5 mL) was added and the reaction mixture was purged with $N_2$ (g) for 10 min. The vial was sealed and the reaction mixture was stirred at 100° C. for 3 h. After cooling to rt, water (10 mL) and DCM (15 mL) were added, and the reaction mixture was stirred, filtered through a phase separator and evaporated under reduced pressure. The residue was purified by straight phase flash chromatography on silica (gradient: 25-100% of EtOAc (containing 5% 2 M $NH_3$ in MeOH) in heptane) to give the title compound (120 mg, 83%); MS (ESI) m/z $[M+H]^+$ 340.29.

Intermediate 347: 6-(6-Acetyl-2,6-diazaspiro[3.3]heptan-2-yl)quinoline-4-carboxylic acid

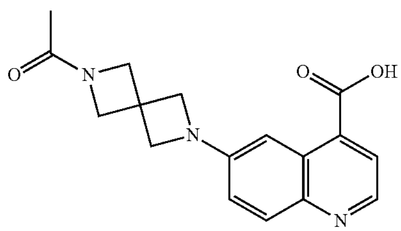 [SMILES: CC(=O)N1CC2(C1)CN(c1ccc3nccc(C(=O)O)c3c1)C2]

Aq NaOH (1 M, 707 μL, 0.71 mmol) was added to a solution of ethyl 6-(6-acetyl-2,6-diazaspiro[3.3]heptan-2-yl)quinoline-4-carboxylate Intermediate 346 (120 mg, 0.35 mmol) in MeOH (4 mL). The reaction mixture was stirred at 50° C. for 20 min, and then cooled to rt. Aq HCl (1 M, 884 μL, 0.88 mmol) was added, and the reaction mixture was stirred, evaporated under reduced pressure, and co-evaporated under reduced pressure with EtOH (2×), and MeCN (1×), to give the crude title compound; MS (ESI) m/z $[M+H]^+$ 312.2.

Intermediate 348: Ethyl 6-(3-(4-fluorophenyl)azetidin-1-yl)quinoline-4-carboxylate

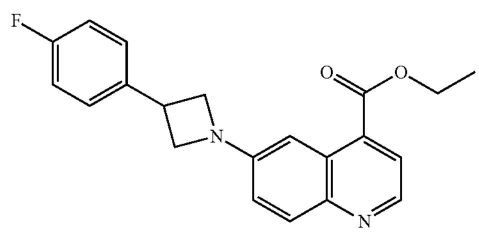 [SMILES: CCOC(=O)c1ccnc2ccc(N3CC(c4ccc(F)cc4)C3)cc12]

Ethyl 6-bromoquinoline-4-carboxylate (120 mg, 0.43 mmol), 3-(4-fluorophenyl)-azetidine hydrochloride (121 mg, 0.64 mmol), $Cs_2CO_3$ (558 mg, 1.71 mmol), XPhos (41 mg, 0.09 mmol) and $Pd_2(dba)_3$ (39 mg, 0.04 mmol) were weighed into a 5 mL vial. Toluene (2.5 mL) was added and the reaction mixture was purged with $N_2$ (g) for 10 min. The vial was sealed and the reaction mixture was stirred at 110° C. for 2 h. After cooling to rt, water (10 mL) and DCM (15 mL) were added, and the reaction mixture was stirred, filtered through a phase separator and evaporated under reduced pressure. The residue was purified by straight phase flash chromatography on silica (gradient: 5-50% of EtOAc in heptane) to give the title compound (130 mg, 87%); MS (ESI) m/z $[M+H]^+$ 351.2.

Intermediate 349: 6-(3-(4-Fluorophenyl)azetidin-1-yl)quinoline-4-carboxylic acid

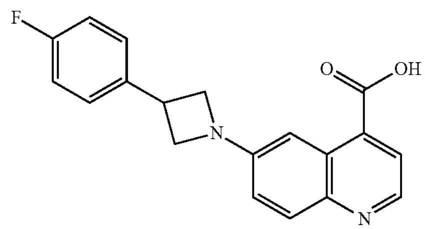 [SMILES: O=C(O)c1ccnc2ccc(N3CC(c4ccc(F)cc4)C3)cc12]

Aq NaOH (1 M, 685 μL, 0.68 mmol) was added to a solution of ethyl 6-(3-(4-fluorophenyl)azetidin-1-yl)quinoline-4-carboxylate Intermediate 348 (120 mg, 0.34 mmol) in MeOH (4 mL). The reaction mixture was stirred at 50° C. for 20 min, then cooled to rt. Aq HCl (1 M, 856 μL, 0.86 mmol) was added, and the reaction mixture was stirred, evaporated under reduced pressure and co-evaporated under reduced pressure with EtOH (2×), and MeCN (1×), to give the crude title compound; MS (ESI) m/z $[M+H]^+$ 323.19.

Intermediate 350: Ethyl 6-(3-(m-tolyl)azetidin-1-yl) quinoline-4-carboxylate

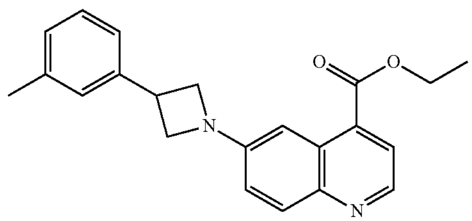 [SMILES: CCOC(=O)c1ccnc2ccc(N3CC(c4cccc(C)c4)C3)cc12]

Ethyl 6-bromoquinoline-4-carboxylate (120 mg, 0.43 mmol), 3-(m-tolyl)azetidine hydrochloride (118 mg, 0.64 mmol), $Cs_2CO_3$ (558 mg, 1.71 mmol), XPhos (41 mg, 0.09 mmol) and $Pd_2(dba)_3$ (39 mg, 0.04 mmol) were weighed into a 5 mL vial. Toluene (2.5 mL) was added and the reaction mixture was purged with $N_2$ (g) for 10 min. The vial was sealed and the reaction mixture was stirred at 100° C. for 3 h. After cooling to rt, water (10 mL) and DCM (15 mL) were added and the reaction mixture was stirred, filtered through a phase separator and evaporated under reduced pressure. The residue was purified by straight phase flash chromatography on silica (gradient: 5-50% of EtOAc in heptane) to give the title compound (128 mg, 86%); MS (ESI) m/z $[M+H]^+$ 347.36.

Intermediate 351: 6-(3-(m-Tolyl)azetidin-1-yl)quinoline-4-carboxylic acid

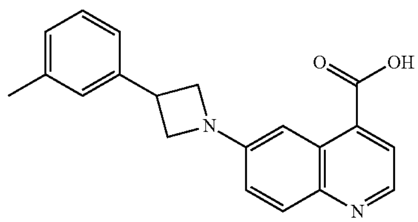 [SMILES: Cc1cccc(C2CN(c3ccc4nccc(C(=O)O)c4c3)C2)c1]

Aq NaOH (1 M, 687 μL, 0.69 mmol) was added to a solution of ethyl 6-(3-(m-tolyl)azetidin-1-yl)quinoline-4-carboxylate Intermediate 350 (119 mg, 0.34 mmol) in MeOH (4 mL). The reaction mixture was stirred at 50° C. for 20 min, then cooled to rt. Aq HCl (1 M, 859 μL, 0.86 mmol) was added, and the reaction mixture was stirred, evaporated under reduced pressure and co-evaporated under reduced pressure with EtOH (2×), MeCN (1×), to give the crude title compound; MS (ESI) m/z $[M+H]^+$ 319.2.

Intermediate 352: Ethyl 6-(3-(4-chlorobenzyl)azetidin-1-yl)quinoline-4-carboxylate

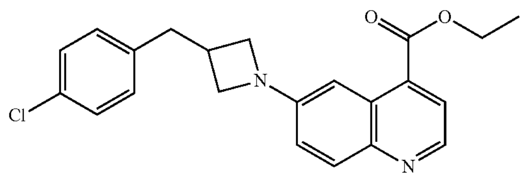 [SMILES: CCOC(=O)c1ccnc2ccc(N3CC(Cc4ccc(Cl)cc4)C3)cc12]

Ethyl 6-bromoquinoline-4-carboxylate (100 mg, 0.36 mmol), 3-(4-chlorobenzyl)azetidine hydrochloride (117 mg, 0.54 mmol), $Cs_2CO_3$ (465 mg, 1.43 mmol), XPhos (34 mg, 0.07 mmol) and $Pd_2(dba)_3$ (33 mg, 0.04 mmol) were weighed into a 5 mL vial. Toluene (2 mL) was added and the reaction mixture was purged with $N_2$ (g) for 10 min. The vial was sealed and the reaction mixture was stirred at 110° C. for 1 h. After cooling to rt, water (10 mL) and DCM (15 mL) were added and the reaction mixture was stirred, filtered through a phase separator and evaporated under reduced pressure. The residue was purified by straight phase flash chromatography on silica (gradient: 5-50% of EtOAc in heptane) to give the title compound (110 mg, 81%); MS (ESI) m/z $[M+H]^+$ 381.22.

Intermediate 353: 6-(3-(4-Chlorobenzyl)azetidin-1-yl)quinoline-4-carboxylic acid

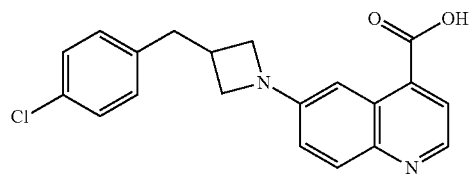 [SMILES: O=C(O)c1ccnc2ccc(N3CC(Cc4ccc(Cl)cc4)C3)cc12]

Aq NaOH (1 M, 525 μL, 0.53 mmol) was added to a solution of ethyl 6-(3-(4-chlorobenzyl)azetidin-1-yl)quinoline-4-carboxylate Intermediate 352 (100 mg, 0.26 mmol) in MeOH (3 mL). The reaction mixture was stirred at 50° C. for 20 min, then cooled to rt. Aq HCl (1 M, 656 μL, 0.66 mmol) was added, and the reaction mixture was stirred, evaporated under reduced pressure, and co-evaporated under reduced pressure with EtOH (2×), and MeCN (1×), to give the crude title compound; MS (ESI) m/z $[M+H]^+$ 353.2.

Intermediate 354: Ethyl 6-(3-methyl-3-((methylsulfonyl)methyl)azetidin-1-yl)quinoline-4-carboxylate

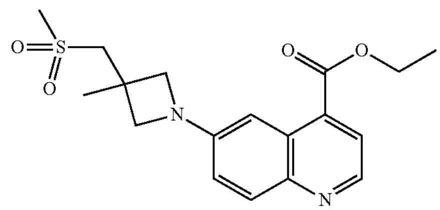 [SMILES: CCOC(=O)c1ccnc2ccc(N3CC(C)(CS(C)(=O)=O)C3)cc12]

Ethyl 6-bromoquinoline-4-carboxylate (100 mg, 0.36 mmol), 3-methyl-3-((methylsulfonyl)methyl)azetidine hydrochloride (143 mg, 0.71 mmol), $Cs_2CO_3$ (465 mg, 1.43 mmol), XPhos (34 mg, 0.07 mmol) and $Pd_2(dba)_3$ (33 mg, 0.04 mmol) were weighed into a 5 mL vial. Dioxane (2 mL) was added, and the reaction mixture was purged with $N_2$ (g) for 10 min. The vial was sealed and the reaction mixture was stirred at 100° C. for 2 h. After cooling to rt, water (10 mL) and DCM (10 mL) were added, and the reaction mixture was stirred, filtered through a phase separator and evaporated under reduced pressure. The residue was purified by straight phase flash chromatography on silica (gradient: 10-100% of EtOAc in heptane) to give the title compound (77 mg, 60%); MS (ESI) m/z $[M+H]^+$ 363.21.

Intermediate 355: 6-(3-Methyl-3-((methylsulfonyl) methyl)azetidin-1-yl)quinoline-4-carboxylic acid

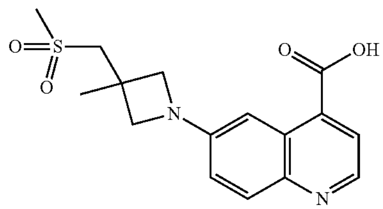 [SMILES: CC1(CS(C)(=O)=O)CN(c2ccc3nccc(C(=O)O)c3c2)C1]

Aq NaOH (1 M, 386 μL, 0.39 mmol) was added to a solution of ethyl 6-(3-methyl-3-((methylsulfonyl)methyl) azetidin-1-yl)quinoline-4-carboxylate Intermediate 354 (70 mg, 0.19 mmol) in MeOH (2 mL). The reaction mixture was stirred at 50° C. for 20 min, then cooled to rt. Aq HCl (3.8 M, 127 μL, 0.48 mmol) was added, and the reaction mixture was stirred, evaporated under reduced pressure, and co-evaporated under reduced pressure with EtOH (2×), and MeCN (1×), to give the crude title compound MS (ESI) m/z $[M+H]^+$ 335.1.

Intermediate 356: tert-Butyl 6-(4-ethyl-4-hydroxypiperidin-1-yl)quinoline-4-carboxylate

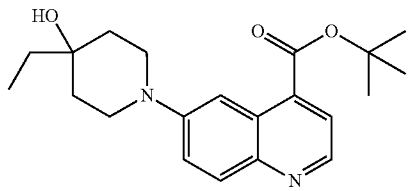 [SMILES: CCC1(O)CCN(c2ccc3nccc(C(=O)OC(C)(C)C)c3c2)CC1]

$Cs_2CO_3$ (206 mg, 0.63 mmol) was added to a mixture of tert-butyl 6-bromoquinoline-4-carboxylate (150 mg, 0.49 mmol), 4-ethylpiperidin-4-ol hydrochloride (105 mg, 0.63 mmol), XPhos (46 mg, 0.10 mmol) and $Pd_2(dba)_3$ (45 mg, 0.05 mmol) in 1,4-dioxane (10 mL) and the reaction mixture was stirred at 100° C. for 15 h. 4-Ethylpiperidin-4-ol hydrochloride (105 mg, 0.63 mmol), $Cs_2CO_3$ (206 mg, 0.63 mmol), XPhos (46 mg, 0.10 mmol) and $Pd_2(dba)_3$ (45 mg, 0.05 mmol) were added and the reaction mixture was stirred at 100° C. for an additional 24 h. The reaction mixture was filtered and the filtrate concentrated under reduced pressure. The residue was purified by preparative TLC (EtOAc: petroleum ether; 3:2), to give the title compound (0.147 g, 85%) as a brown gum; MS (ESI) m/z $[M+H]^+$ 357.

Intermediate 357: 6-(4-Ethyl-4-hydroxypiperidin-1-yl)quinoline-4-carboxylic acid

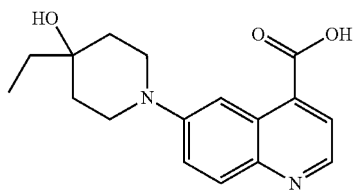 [SMILES: CCC1(O)CCN(c2ccc3nccc(C(=O)O)c3c2)CC1]

HCl in 1,4-dioxane (4 M, 5 mL) was added to a stirred solution of tert-butyl 6-(4-ethyl-4-hydroxypiperidin-1-yl) quinoline-4-carboxylate Intermediate 356 (130 mg, 0.36 mmol) in 1,4-dioxane (5 mL) and the reaction mixture was stirred at 50° C. for 15 h. Volatiles were removed under reduced pressure, to give the title compound (0.105 g, 96%) as a red solid; MS (ESI) m/z $[M+H]^+$ 301.

Intermediate 358: tert-Butyl 6-(4-hydroxy-4-methylpiperidin-1-yl)quinoline-4-carboxylate

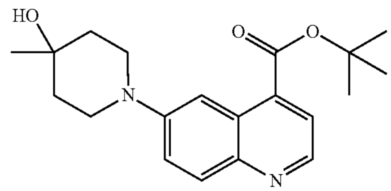 [SMILES: CC1(O)CCN(c2ccc3nccc(C(=O)OC(C)(C)C)c3c2)CC1]

$Cs_2CO_3$ (793 mg, 2.43 mmol) was added to a stirred solution of tert-butyl 6-bromoquinoline-4-carboxylate (250 mg, 0.81 mmol), 4-methylpiperidin-4-ol (140 mg, 1.22 mmol), XPhos (58 mg, 0.12 mmol) and $Pd_2(dba)_3$ (74 mg, 0.08 mmol) in 1,4-dioxane (10 mL) and stirred at 80° C. for 2 h. Volatiles were removed under reduced pressure, diluted with EtOAc, and washed with $H_2O$. The organic layer was dried over $Na_2SO_4$, filtered and evaporated. The residue was purified by preparative TLC (EtOAc: petroleum ether; 1:1), to give the title compound (0.20 g, 72%) as a yellow solid; MS (ESI) m/z $[M+H]^+$ 343.

Intermediate 359: 6-(4-Hydroxy-4-methylpiperidin-1-yl)quinoline-4-carboxylic acid

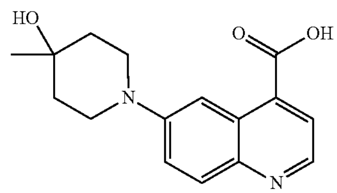 [SMILES: CC1(O)CCN(c2ccc3nccc(C(=O)O)c3c2)CC1]

A solution of DCM (6 mL) and TFA (3 mL) was added to tert-butyl 6-(4-hydroxy-4-methylpiperidin-1-yl)quinoline-4-carboxylate Intermediate 358 (100 mg, 0.29 mmol) and stirred at rt for 2 h. Volatiles were removed under reduced pressure to give the title compound (0.084 g, 100%) as a yellow solid; MS (ESI) m/z $[M+H]^+$ 287.

Intermediate 360: tert-Butyl 6-(4-ethyl-4-methoxypiperidin-1-yl)quinoline-4-carboxylate

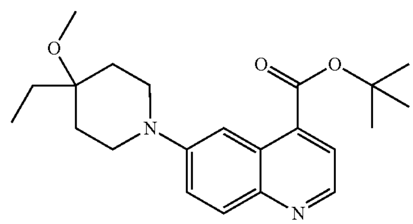 [SMILES: CCC1(OC)CCN(c2ccc3nccc(C(=O)OC(C)(C)C)c3c2)CC1]

$Cs_2CO_3$ (634 mg, 1.95 mmol) was added to a mixture of tert-butyl 6-bromoquinoline-4-carboxylate (200 mg, 0.65 mmol), 4-ethyl-4-methoxypiperidine hydrochloride (128 mg, 0.71 mmol), XPhos (93 mg, 0.19 mmol) and $Pd_2(dba)_3$ (59 mg, 0.06 mmol) in 1,4-dioxane (10 mL) and stirred at 80° C. for 20 h. Volatiles were removed under reduced pressure, diluted with EtOAc (20 mL), and washed with $H_2O$ (20 mL). The organic layer was dried over $Na_2SO_4$, filtered and evaporated. The residue was purified by preparative TLC (EtOAc: petroleum ether; 1:1), to give the title compound (0.20 g, 83%) as a yellow solid; MS (ESI) m/z $[M+H]^+$ 371.

Intermediate 361: 6-(4-Ethyl-4-methoxypiperidin-1-yl)quinoline-4-carboxylic acid

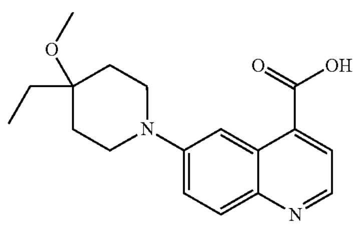 [SMILES: CCC1(OC)CCN(c2ccc3nccc(C(=O)O)c3c2)CC1]

A solution of DCM (10 mL) and TFA (3 mL) was added to tert-butyl 6-(4-ethyl-4-methoxypiperidin-1-yl)quinoline-4-carboxylate Intermediate 360 (100 mg, 0.29 mmol) and stirred at rt for 5 h. The solvent was removed under reduced pressure and the solid was further dried under vacuum to give the title compound (0.085 g, 100%) as a solid; MS (ESI) m/z $[M+H]^+$ 315.

Intermediate 362: tert-Butyl 6-(4-hydroxy-4-isopropylpiperidin-1-yl)quinoline-4-carboxylate

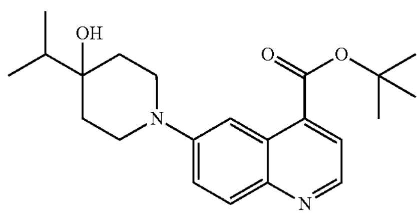 [SMILES: CC(C)C1(O)CCN(c2ccc3nccc(C(=O)OC(C)(C)C)c3c2)CC1]

$Cs_2CO_3$ (275 mg, 0.84 mmol) was added to a mixture of tert-butyl 6-bromoquinoline-4-carboxylate (200 mg, 0.65 mmol), 4-isopropylpiperidin-4-ol (121 mg, 0.84 mmol), XPhos (62 mg, 0.13 mmol) and $Pd_2(dba)_3$ (59 mg, 0.06 mmol) in 1,4-dioxane (10 mL) and stirred at 100° C. for 15 h. The reaction mixture was filtered, the filtrate was concentrated under reduced pressure. The residue was purified by preparative TLC (EtOAc: petroleum ether; 3:2), to give the title compound (0.209 g, 87%) as a brown gum; MS (ESI) m/z $[M+H]^+$ 371.

Intermediate 363: 6-(4-Hydroxy-4-isopropylpiperidin-1-yl)quinoline-4-carboxylic acid

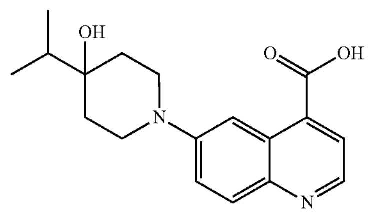 [SMILES: CC(C)C1(O)CCN(c2ccc3nccc(C(=O)O)c3c2)CC1]

HCl in 1,4-dioxane (4 M, 5 mL) was added slowly to a stirred solution of tert-butyl 6-(4-hydroxy-4-isopropylpiperidin-1-yl)quinoline-4-carboxylate Intermediate 362 (185 mg, 0.50 mmol) in 1,4-dioxane (5 mL) at 28° C. and the reaction mixture was stirred at 50° C. for h. Volatiles were removed under reduced pressure, to give the title compound (0.155 g, 91%) as a red solid; MS (ESI) m/z $[M+H]^+$ 315.

Intermediate 364: tert-Butyl (3R,4s,5S)-4-hydroxy-3,4,5-trimethylpiperidine-1-carboxylate

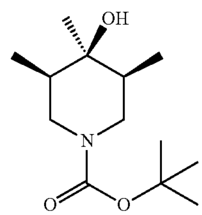 [SMILES: C[C@@H]1CN(C(=O)OC(C)(C)C)C[C@H](C)[C@]1(C)O]

MeMgBr (120 mL, 360 mmol) was slowly added to a stirred solution of tert-butyl (3R,5S)-3,5-dimethyl-4-oxopiperidine-1-carboxylate (30.8 g, 136 mmol) in THF (500 mL) at 0° C. The reaction mixture was allowed to return to rt and was stirred overnight. The reaction was quenched with a sat $NH_4C_1$ (aq) and extracted with EtOAc (3×400 mL). The combined organic layers were concentrated to give the title compound (33 g, 100%) as a white solid; $^1H$ NMR (300 MHz, $CDCl_3$) δ 3.95-3.55 (m, 2H), 2.80-2.55 (m, 2H), 1.58-1.50 (m, 2H), 1.50 (s, 9H), 1.18 (s, 3H), 0.92-0.90 (m, 6H).

Intermediate 365: (3R,4s,5S)-3,4,5-Trimethylpiperidin-4-ol

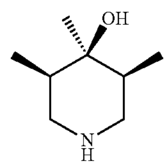

Methanolic HCl (400 mL) was added to a solution of tert-butyl (3R,4s,5S)-4-hydroxy-3,4,5-trimethylpiperidine-1-carboxylate Intermediate 364 (33 g, 0.0.23 mol) in MeOH (100 mL). The reaction mixture was stirred at rt for 5 h and then concentrated to give the title compound (24.5 g, 100%) as a white solid; MS (ESI) m/z $[M+H]^+$ 144.1.

Intermediate 366: tert-Butyl 6-((3R,4s,5S)-4-hydroxy-3,4,5-trimethylpiperidin-1-yl)quinoline-4-carboxylate

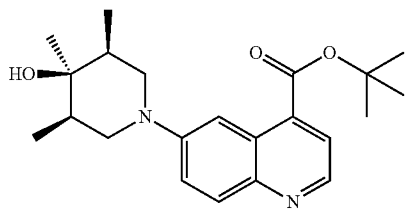 [SMILES: C[C@@H]1CN(c2ccc3nccc(C(=O)OC(C)(C)C)c3c2)C[C@H](C)[C@]1(C)O]

$Cs_2CO_3$ (137 mg, 0.42 mmol) was added to a mixture of tert-butyl 6-bromoquinoline-4-carboxylate (100 mg, 0.32 mmol), (3R,4s,5S)-3,4,5-trimethylpiperidin-4-ol Intermediate 365 (76 mg, 0.42 mmol), XPhos (30 mg, 0.06 mmol) and $Pd_2(dba)_3$ (30 mg, 0.03 mmol) in 1,4-dioxane (5 mL) at 25° C. The resulting suspension was stirred at 100° C. for 23 h. The reaction mixture was filtered and the filtrate was concentrated under reduced pressure. The residue was purified by preparative TLC (EtOAc:petroleum ether; 1:1), to give the title compound (0.118 g, 98%) as an orange solid; MS (ESI) m/z $[M+H]^+$ 371.

Intermediate 367: 6-((3R,4s,5S)-4-Hydroxy-3,4,5-trimethylpiperidin-1-yl)quinoline-4-carboxylic acid

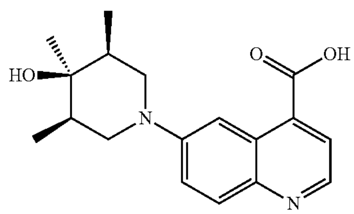 [SMILES: C[C@@H]1CN(c2ccc3nccc(C(=O)O)c3c2)C[C@H](C)[C@]1(C)O]

HCl in dioxane (4 M, 5 mL) was added slowly to a stirred solution of tert-butyl 6-((3R,4s,5S)-4-hydroxy-3,4,5-trimethylpiperidin-1-yl)quinoline-4-carboxylate Intermediate 366 (105 mg, 0.28 mmol) in 1,4-dioxane (5 mL) at 20° C. and the reaction mixture was stirred at 50° C. for 3 h. Volatiles were removed under reduced pressure, to give the title compound (0.85 g, 95%) as a dark red solid; MS (ESI) m/z $[M+H]^+$ 315.

Intermediate 368: Ethyl 6-((1R,5S)-9-oxa-3-azabicyclo[3.3.1]nonan-3-yl)quinoline-4-carboxylate

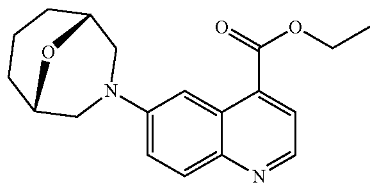 [SMILES: CCOC(=O)c1ccnc2ccc(N3C[C@H]4CCC[C@@H](C3)O4)cc12]

A mixture of ethyl 6-bromoquinoline-4-carboxylate (0.098 g, 0.35 mmol), 9-oxa-3-azabicyclo[3.3.1]nonane hydrochloride (0.074 g, 0.46 mmol), RuPhos Pd G4 (30 mg, 0.04 mmol), $Cs_2CO_3$ (0.342 g, 1.05 mmol) and dioxane (0.9 mL) was degassed by cycles and stirred vigorously at 90° C. for 17 h. The reaction mixture was allowed to return to rt and was diluted with EtOAc (3 mL) and stirred with SilaMet S-thiol scavenger (0.15 g; 1.4 mmol/g) at rt for 7 h. The mixture was filtered through Celite® 521. The filter was washed with EtOAc and the combined filtrates were concentrated. The residue was purified by preparative HPLC, PrepMethod G (gradient: 35-75%) to give the title compound (0.085 g, 75%) as a yellow syrup; MS (ESI) m/z $[M+H]^+$ 327.3.

Intermediate 369: 6-((1R,5S)-9-Oxa-3-azabicyclo[3.3.1]nonan-3-yl)quinoline-4-carboxylic acid

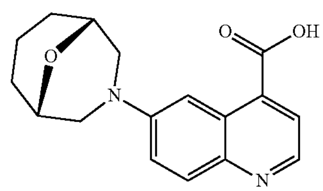 [SMILES: O=C(O)c1ccnc2ccc(N3C[C@H]4CCC[C@@H](C3)O4)cc12]

NaOH (3.8 M, 156 µL, aq) was added to a solution of ethyl 6-((1R,5S)-9-oxa-3-azabicyclo[3.3.1]nonan-3-yl)quinoline-4-carboxylate Intermediate 368 (77 mg, 0.24 mmol) in MeOH (2 mL) and the reaction mixture was stirred at 50° C. for 1 h. Aq HCl (3 M, 125 µL) was added dropwise and the resulting mixture was concentrated and lyophilized from $MeCN/H_2O$ give the title compound (0.097 g) as a red solid; MS (ESI) m/z $[M+H]^+$ 299.22.

Intermediate 370: 4-(4-Chloroquinolin-6-yl)-1-methylpiperidin-4-ol

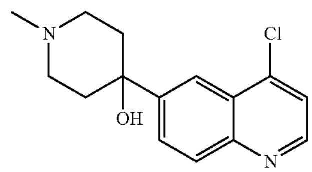 [SMILES: CN1CCC(O)(c2ccc3nccc(Cl)c3c2)CC1]

6-Bromo-4-chloroquinoline (1 g, 4 mmol) was dissolved in THF (25 mL) in a dried two necked flask under argon, cooled to −70° C., and n-BuLi (2.47 mL, 6.19 mmol) was slowly added dropwise so that the internal temperature did not exceed −65° C. The reaction mixture was stirred for 1 h at −70° C. 1-Methylpiperidin-4-one (0.70 g, 6.2 mmol) in THF (3 mL) was slowly added dropwise so that the internal temperature did not exceed −65° C. The reaction mixture was stirred for 1 h at −70° C. and then allowed to return to rt and stirred for 3 h. The reaction mixture was diluted with EtOAc, and washed with $H_2O$. The organic layer was dried over $Na_2SO_4$, filtered and concentrated. The residue was purified by preparative TLC (DCM:MeOH; 10:1), to give the title compound (0.30 g, 26%) as a pale yellow solid; MS (ESI) m/z $[M+H]^+$ 277.

Intermediate 371: Methyl 6-(4-hydroxy-1-methylpiperidin-4-yl)quinoline-4-carboxylate

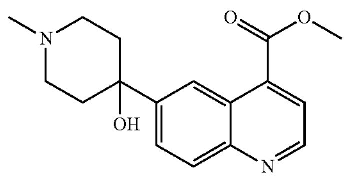

TEA (0.45 mL, 3.3 mmol) was added to a stirred solution of 4-(4-chloroquinolin-6-yl)-1-methylpiperidin-4-ol Intermediate 370 (300 mg, 1.08 mmol), $Pd(OAc)_2$ (24 mg, 0.11 mmol), $PdCl_2$(dppf) (40 mg, 0.05 mmol) and dppf (90 mg, 0.16 mmol) in MeOH (15 mL). The resulting mixture was stirred under an atmosphere of CO (g) at 10 atm of pressure and 100° C. for 12 h. The reaction mixture was filtered and the filtrate was concentrated under vacuum. The residue was purified by preparative TLC (DCM:MeOH; 10:1), to give the title compound (0.25 g, 77%) as a pale yellow solid; MS (ESI) m/z $[M+H]^+$ 301.

Intermediate 372: Methyl 6-(4-fluoro-1-methylpiperidin-4-yl)quinoline-4-carboxylate

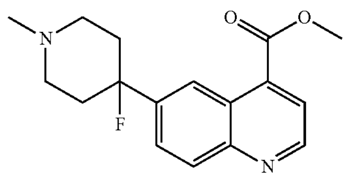

DAST (0.22 mL, 1.7 mmol) in DCM (2 mL) was added dropwise to a solution of methyl 6-(4-hydroxy-1-methylpiperidin-4-yl)quinoline-4-carboxylate Intermediate 371 (250 mg, 0.83 mmol) in DCM (10 mL) at 0° C. The reaction mixture was allowed to return to rt and stirred for 2 h. The solvent was removed under reduced pressure and the reaction mixture was diluted with EtOAc, and washed with $H_2O$. The organic layer was dried over $Na_2SO_4$, filtered and evaporated. The residue was purified by preparative TLC (DCM:MeOH; 10:1), to give the title compound (0.25 g, 53%) as a white solid; MS (ESI) m/z $[M+H]^+$ 303.

Intermediate 373: 6-(4-Fluoro-1-methylpiperidin-4-yl)quinoline-4-carboxylic acid

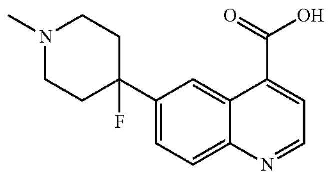 [SMILES: CN1CCC(F)(c2ccc3nccc(C(=O)O)c3c2)CC1]

Methyl 6-(4-fluoro-1-methylpiperidin-4-yl)quinoline-4-carboxylate Intermediate 372 (230 mg, 0.55 mmol) and LiOH (132 mg, 5.52 mmol) was dissolved in a mixture of MeOH (8 mL) and $H_2O$ (2 mL). The reaction mixture was stirred at rt for 2 h and volatiles were removed under reduced pressure. The reaction mixture was diluted with $H_2O$ and pH 6 was set with aq HCl (0.1 M). EtOAc was added, and the mixture was washed with $H_2O$. The organic layer was dried over $Na_2SO_4$, filtered and evaporated to give the title compound (0.145 g, 91%) as a white solid; MS (ESI) m/z $[M+H]^+$ 289.

Intermediate 374: 6-(1H-Pyrazol-5-yl)quinoline-4-carboxylic acid

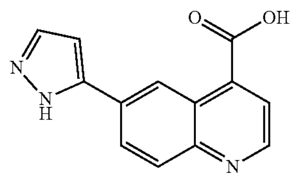 [SMILES: O=C(O)c1ccnc2ccc(-c3ccn[nH]3)cc12]

A mixture of 1-(tetrahydro-2H-pyran-2-yl)-5-(4,4,5,5-tetramethyl-1,3,2-dioxaborolan-2-yl)-1H-pyrazole (59 mg, 0.21 mmol), 6-bromoquinoline-4-carboxylic acid (53 mg, 0.21 mmol), $Cs_2CO_3$ (137 mg, 0.42 mmol) and Pd(dtbpf)$Cl_2$ (14 mg, 0.02 mmol) in 1,4-dioxane (1 mL) and $H_2O$ (0.250 mL) was stirred at rt overnight. The reaction mixture was diluted with DMSO and concentrated under reduced pressure. The compound was purified by preparative HPLC, PrepMethod E (gradient: 5-45%) to give the title compound (32 mg, 64%); MS (ESI) m/z $[M+H]^+$ 240.2.

Intermediate 375: 6-(1-Isopropyl-1H-pyrazol-5-yl)quinoline-4-carboxylic acid

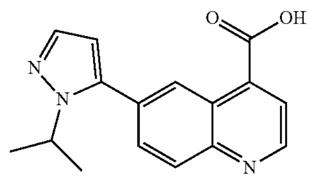 [SMILES: CC(C)n1nccc1-c1ccc2nccc(C(=O)O)c2c1]

A mixture of 1-isopropyl-5-(4,4,5,5-tetramethyl-1,3,2-dioxaborolan-2-yl)-1H-pyrazole (48 mg, 0.20 mmol), 6-bromoquinoline-4-carboxylic acid (51 mg, 0.20 mmol), $Cs_2CO_3$ (198 mg, 0.61 mmol) and Pd(dtbpf)$Cl_2$ (13 mg, 0.02 mmol in 1,4-dioxane (1 mL) and $H_2O$ (0.25 mL) was stirred at rt overnight. The reaction mixture concentrated under reduced pressure to give the title compound (56 mg); MS (ESI) m/z $[M+H]^+$ 282.2.

Intermediate 376: rac-tert-Butyl (R)-6-(3-fluoro-3-methylpyrrolidin-1-yl)quinoline-4-carboxylate

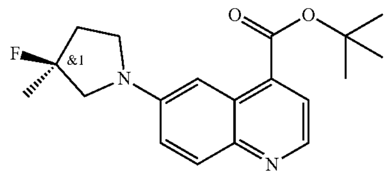 [SMILES: CC(C)(C)OC(=O)c1ccnc2ccc(N3CC[C@](C)(F)C3)cc12]

$Cs_2CO_3$ (587 mg, 1.80 mmol) was added to a mixture of tert-butyl 6-bromoquinoline-4-carboxylate (185 mg, 0.60 mmol), 3-fluoro-3-methylpyrrolidine hydrochloride (168 mg, 1.20 mmol) and $Pd_2(dba)_3$ (55 mg, 0.06 mmol), XPhos (57 mg, 0.12 mmol) in 1,4-dioxane (4 mL). The resulting suspension was stirred at 100° C. for 2 h. The reaction mixture was diluted with EtOAc and $H_2O$ (50 mL) and extracted with EtOAc (3×50 mL). The organic layers were combined and washed with brine (150 mL). The organic layer was dried over $Na_2SO_4$, filtered and evaporated. The residue was purified by preparative TLC (EtOAc:petroleum ether; 1:1), to give the title compound (0.188 g, 95%) as a brown gum; MS (ESI) m/z $[M+H]^+$ 331.

Intermediate 377: rac-(R)-6-(3-Fluoro-3-methylpyrrolidin-1-yl)quinoline-4-carboxylic acid

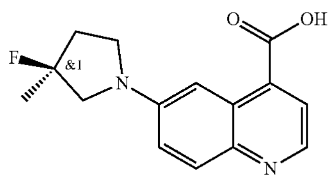 [SMILES: C[C@]1(F)CCN(c2ccc3nccc(C(=O)O)c3c2)C1]

TFA (2 mL) was added to rac-tert-butyl (R)-6-(3-fluoro-3-methylpyrrolidin-1-yl)quinoline-4-carboxylate Intermediate 376 (187 mg, 0.57 mmol) in DCM (2 mL) at 10° C. and stirred overnight. Volatiles were removed under reduced pressure to give the title compound (0.494 g) as a red gum; MS (ESI) m/z $[M+H]^+$ 275.

Intermediate 378: rac-(R)-6-(3-Methyl-2-oxopyrrolidin-1-yl)quinoline-4-carboxylate

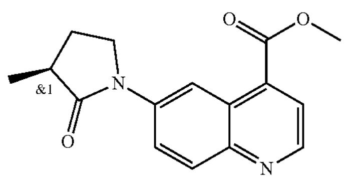

$Cs_2CO_3$ (244 mg, 0.75 mmol) was added to a mixture of methyl 6-bromoquinoline-4-carboxylate (133 mg, 0.50 mmol), 3-methylpyrrolidin-2-one (64 mg, 0.65 mmol) and XPhos Pd G3 (42 mg, 0.05 mmol) in 1,4-dioxane (7 mL) at 20° C. The resulting suspension was stirred at 100° C. for 2 h and filtered through a Celite® pad. The filtrate was concentrated under reduced pressure and the resulting residue was purified by preparative TLC (EtOAc:petroleum ether; 3:1) to give the title compound (0.55 g) as a beige solid; MS (ESI) m/z $[M+H]^+$ 285.

Intermediate 379: rac-(R)-6-(3-Methyl-2-oxopyrrolidin-1-yl)quinoline-4-carboxylic acid

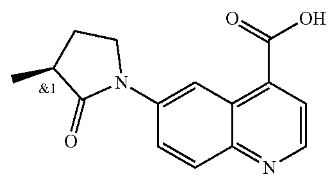 [SMILES: C[C@H]1CCN(c2ccc3nccc(C(=O)O)c3c2)C1=O]

NaOH (366 mg, 9.14 mmol) was added to a stirred solution of rac-(R)-6-(3-methyl-2-oxopyrrolidin-1-yl)quinoline-4-carboxylate Intermediate 378 (520 mg, 1.83 mmol) in MeOH (9 mL) and $H_2O$ (3 mL) at 20° C. and stirred for 1 h. The reaction mixture was acidified with aq HCl (2 M). The aq layer was extracted with EtOAc (6×50 mL), the combined organic layers were washed with $H_2O$ (3×25 mL) and the organic layer was dried over $Na_2SO_4$, filtered and evaporated to give the title compound (0.31 g, 63%) as a beige oil; MS (ESI) m/z $[M+H]^+$ 271.

Intermediate 380: rac-tert-Butyl (R)-6-(3-methyl-2-oxopiperidin-1-yl)quinoline-4-carboxylate

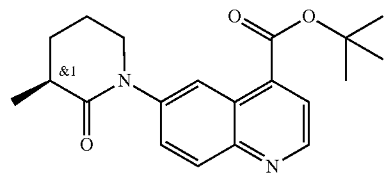 [SMILES: C[C@H]1CCCN(c2ccc3nccc(C(=O)OC(C)(C)C)c3c2)C1=O]

$Cs_2CO_3$ (634 mg, 1.95 mmol) was added a mixture of tert-butyl 6-bromoquinoline-4-carboxylate (400 mg, 1.30 mmol), 3-methylpiperidin-2-one (588 mg, 5.19 mmol) and $Pd_2(dba)_3$ (12 mg, 0.01 mmol), XPhos (12 mg, 0.03 mmol) in 1,4-dioxane (20 mL). The resulting suspension was stirred at 100° C. for 24 h. The reaction mixture was filtered through silica and volatiles were removed under reduced pressure. The residue was purified by preparative TLC (EtOAc:petroleum ether; 4:1), to give the title compound (0.33 g, 75%) as a brown solid; MS (ESI) m/z $[M+H]^+$ 341.20.

Intermediate 381: rac-(R)-6-(3-Methyl-2-oxopiperidin-1-yl)quinoline-4-carboxylic acid

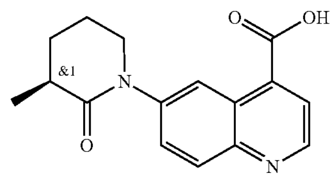 [SMILES: C[C@H]1CCCN(c2ccc3nccc(C(=O)O)c3c2)C1=O]

TFA (0.27 mL, 3.5 mmol) was added to a solution of rac-tert-butyl (R)-6-(3-methyl-2-oxopiperidin-1-yl)quinoline-4-carboxylate Intermediate 380 (300 mg, 0.88 mmol) in DCM (5 mL) and stirred at 25° C. for 6 h. Volatiles were removed under reduced pressure and the solid was further dried under vacuum to give the title compound (0.33 g) as a brown solid; MS (ESI) m/z $[M+H]^+$ 285.1.

Intermediate 382: tert-Butyl 6-(4-fluoropiperidin-1-yl)quinoline-4-carboxylate

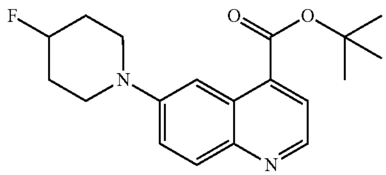 [SMILES: CC(C)(C)OC(=O)c1ccnc2ccc(N3CCC(F)CC3)cc12]

$Cs_2CO_3$ (977 mg, 3.00 mmol) was added a mixture of tert-butyl 6-bromoquinoline-4-carboxylate (308 mg, 1.00 mmol), 4-fluoropiperidine hydrochloride (153 mg, 1.10 mmol), and $Pd_2(dba)_3$ (92 mg, 0.10 mmol), XPhos (95 mg, 0.20 mmol) in 1,4-dioxane (1 mL). The resulting suspension was stirred at 100° C. for 2 h and filtered through Celite®. The solvent was removed under reduced pressure and the residue was purified by preparative TLC (EtOAc:petroleum ether; 2:1), to give the title compound (0.33 g, 100%) as a yellow gum; MS (ESI) m/z $[M+H]^+$ 331.

Intermediate 383: 6-(4-Fluoropiperidin-1-yl)quinoline-4-carboxylic acid

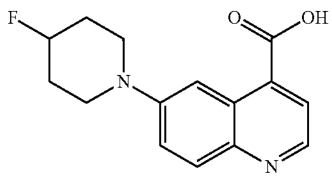 [SMILES: O=C(O)c1ccnc2ccc(N3CCC(F)CC3)cc12]

tert-Butyl 6-(4-fluoropiperidin-1-yl)quinoline-4-carboxylate Intermediate 382 (320 mg, 0.97 mmol) was added to a mixture of TFA (4.5 mL) in DCM (4.5 mL) and stirred at 20° C. for 15 h. Volatiles were removed under reduced pressure and the solid was further dried under vacuum to give the title compound (0.674 g) as a dark red gum; MS (ESI) m/z $[M+H]^+$ 275.

Intermediate 384: tert-Butyl 6-(3-azabicyclo[3.1.0]hexan-3-yl)quinoline-4-carboxylate

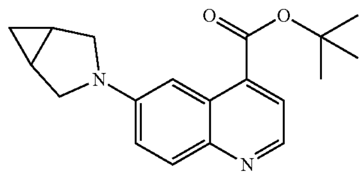 [SMILES: CC(C)(C)OC(=O)c1ccnc2ccc(N3CC4CC4C3)cc12]

$Cs_2CO_3$ (977 mg, 3.00 mmol) was added a mixture of tert-butyl 6-bromoquinoline-4-carboxylate (308 mg, 1.00 mmol), 3-azabicyclo[3.1.0]hexane hydrochloride (239 mg, 2.00 mmol) and $Pd_2(dba)_3$ (92 mg, 0.10 mmol), XPhos (95 mg, 0.20 mmol) in 1,4-dioxane (3 mL). The resulting suspension was stirred at 100° C. for 2 h. The reaction mixture was diluted with DCM and concentrated under reduced pressure. The reaction mixture was partitioned between $H_2O$ and EtOAc, extracted with EtOAc (3×20 mL) and the organic phases washed with brine (20 mL). The organic phases were dried over $Na_2SO_4$, filtered and concentrated. The residue was purified by preparative TLC (EtOAc:petroleum ether; 1:1), to give the title compound (0.281 g, 91%) as a yellow solid; MS (ESI) m/z $[M+H]^+$ 311.

Intermediate 385: 6-(3-Azabicyclo[3.1.0]hexan-3-yl)quinoline-4-carboxylic acid

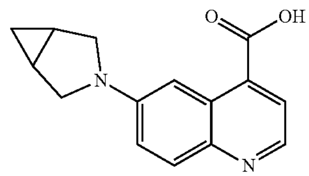 [SMILES: O=C(O)c1ccnc2ccc(N3CC4CC4C3)cc12]

tert-Butyl 6-(3-azabicyclo[3.1.0]hexan-3-yl)quinoline-4-carboxylate Intermediate 384 (320 mg, 0.97 mmol) was added to a mixture of TFA (3 mL) in DCM (3 mL) and stirred at 10° C. overnight. The solvent was removed under reduced pressure and the solid was further dried under vacuum to give the title compound (0.435 g) as a red gum; MS (ESI) m/z $[M+H]^+$ 255.

Intermediate 386: Methyl (S)-6-(3-methoxypyrrolidin-1-yl)quinoline-4-carboxylate

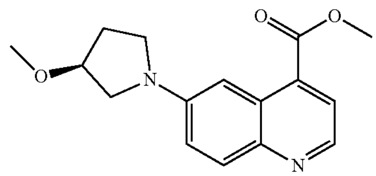

$Cs_2CO_3$ (735 mg, 2.25 mmol) was added a mixture of methyl 6-bromoquinoline-4-carboxylate (300 mg, 1.13 mmol), (S)-3-methoxypyrrolidine (171 mg, 1.69 mmol) and $Pd_2(dba)_3$ (10 mg, 0.01 mmol), XPhos (11 mg, 0.02 mmol) in 1,4-dioxane (10 mL). The resulting suspension was stirred at 100° C. for 2 h. The reaction mixture was concentrated under reduced pressure. The residue was purified by preparative TLC (EtOAc:petroleum ether; 1:1), to give the title compound (0.298 g, 92%) as a yellow solid; MS (ESI) m/z $[M+H]^+$ 287.

Intermediate 387: (S)-6-(3-Methoxypyrrolidin-1-yl)quinoline-4-carboxylic acid

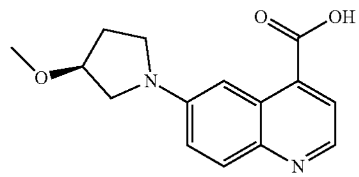 [SMILES: CO[C@H]1CCN(c2ccc3nccc(C(=O)O)c3c2)C1]

Methyl (S)-6-(3-methoxypyrrolidin-1-yl)quinoline-4-carboxylate Intermediate 386 (270 mg, 0.94 mmol) and LiOH (132 mg, 5.52 mmol) was dissolved in a mixture of THF (5 mL) and $H_2O$ (5 mL) under air. The reaction mixture was stirred at 25° C. for 3 h. The solvent was removed under reduced pressure and the reaction mixture was diluted with $H_2O$ and pH 5 was set with aq HCl (2 M). The reaction mixture was concentrated under vacuum to give the title compound (0.20 g, 78%) as a red solid; MS (ESI) m/z $[M+H]^+$ 273.1.

Intermediate 388: tert-Butyl 6-((1R,5S,6r)-6-(trifluoromethyl)-3-azabicyclo[3.1.0]hexan-3-yl)quinoline-4-carboxylate

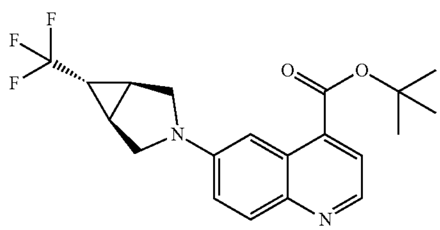 [SMILES: CC(C)(C)OC(=O)c1ccnc2ccc(N3C[C@@H]4[C@H](C3)[C@H]4C(F)(F)F)cc12]

$Cs_2CO_3$ (977 mg, 3.00 mmol) was added a stirred suspension of tert-butyl 6-bromoquinoline-4-carboxylate (308 mg, 1.00 mmol), (1R,5S,60-6-(trifluoromethyl)-3-azabicyclo[3.1.0]hexane hydrochloride (375 mg, 2.00 mmol) and $Pd_2(dba)_3$ (92 mg, 0.10 mmol), XPhos (95 mg, 0.20 mmol) in 1,4-dioxane (3 mL). The resulting suspension was stirred at 100° C. for 2 h. The reaction mixture was diluted with DCM and concentrated under reduced pressure. The reaction mixture was diluted with EtOAc (50 mL) and washed with $H_2O$ (3×50 mL), the organic layer dried over $Na_2SO_4$, filtered and evaporated. The residue was purified by preparative TLC (EtOAc:petroleum ether; 1:1), to give the title compound (0.455 g, 92%) as a brown solid; MS (ESI) m/z $[M+H]^+$ 379.

Intermediate 389: 6-((1R,5S,6r)-6-(Trifluoromethyl)-3-azabicyclo[3.1.0]hexan-3-yl)quinoline-4-carboxylic acid

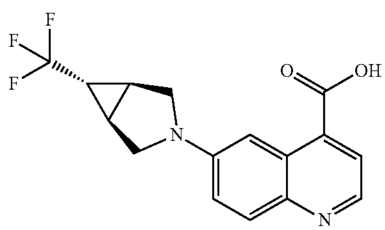 [SMILES: O=C(O)c1ccnc2ccc(N3C[C@@H]4[C@H](C3)[C@H]4C(F)(F)F)cc12]

tert-Butyl 6-((1R,5S,60-6-(trifluoromethyl)-3-azabicyclo[3.1.0]hexan-3-yl)quinoline-4-carboxylate Intermediate 388 (454 mg, 1.20 mmol) was added to a mixture of TFA (5 mL) in DCM (5 mL) and stirred at 13° C. overnight under air. The solvent was removed under reduced pressure and the solid was further dried under vacuum to give the title compound (0.728 g) as a red gum; MS (ESI) m/z $[M+H]^+$ 323.

Intermediate 390: Methyl 6-(7-azabicyclo[2.2.1]heptan-7-yl)quinoline-4-carboxylate

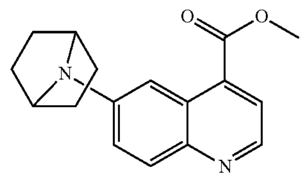 [SMILES: COC(=O)c1ccnc2ccc(N3C4CCC3CC4)cc12]

$Cs_2CO_3$ (1.47 g, 4.51 mmol) was added to a mixture of methyl 6-bromoquinoline-4-carboxylate (200 mg, 0.75 mmol), 7-azabicyclo[2.2.1]heptane hydrochloride (201 mg, 1.50 mmol) and Pd Catalyst [CAS: 1810068-35-9] (43 mg, 0.04 mmol) in 1,4-dioxane (3 mL). The resulting suspension was stirred at 100° C. for 2 days. The reaction mixture was diluted with $H_2O$ (50 mL), extracted with EtOAc (3×50 mL), the organic layers were washed with brine (200 mL), dried over $Na_2SO_4$, filtered and concentrated under reduced pressure. The residue was purified by preparative TLC (EtOAc:petroleum ether; 1:1), to give the title compound (0.039 g, 18%) as a yellow solid; MS (ESI) m/z $[M+H]^+$ 283.

Intermediate 391: 6-(7-Azabicyclo[2.2.1]heptan-7-yl)quinoline-4-carboxylic acid

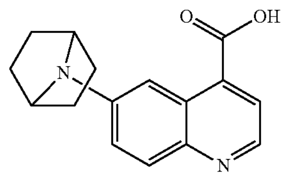 [SMILES: O=C(O)c1ccnc2ccc(N3C4CCC3CC4)cc12]

Methyl 6-(7-azabicyclo[2.2.1]heptan-7-yl)quinoline-4-carboxylate Intermediate 390 (36 mg, 0.13 mmol) and NaOH (25 mg, 0.63 mmol) was dissolved in a mixture of MeOH (3 mL) and $H_2O$ (1 mL) under air. The reaction mixture was stirred at 10° C. for 1 h. The solvent was removed under reduced pressure. The reaction mixture was diluted with $H_2O$ (20 mL) and pH 3 was set with aq HCl (1 M). The reaction mixture was diluted with $H_2O$ (10 mL) and extracted with EtOAc (6×30 mL), dried over $Na_2SO_4$, filtered and concentrated under vacuum. The material was purified by preparative HPLC, PrepMethod P (gradient: 5-17%) to give the title compound (0.030 g, 89%) as a yellow solid; MS (ESI) m/z $[M+H]^+$ 269.

Intermediate 392: rac-tert-Butyl 6-((1R,4S)-2-azabicyclo[2.2.1]heptan-2-yl)quinoline-4-carboxylate

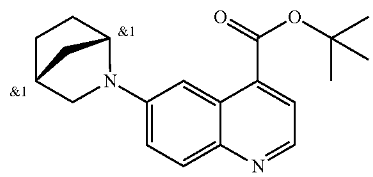 [SMILES: CC(C)(C)OC(=O)c1ccnc2ccc(N3C[C@@H]4CC[C@H]3C4)cc12]

$Cs_2CO_3$ (651 mg, 2.00 mmol) was added a mixture of tert-butyl 6-bromoquinoline-4-carboxylate (154 mg, 0.50 mmol), 2-azabicyclo[2.2.1]heptane (97 mg, 1.0 mmol) and Pd Catalyst [CAS: 1810068-35-9] (29 mg, 0.02 mmol) in 1,4-dioxane (5 mL). The resulting suspension was stirred at 100° C. for 24 h. 2-Azabicyclo[2.2.1]heptane (97 mg, 1.00 mmol) and $Cs_2CO_3$ (651 mg, 2.00 mmol) was added and the suspension was stirred at 100° C. for an additional 18 h. The reaction mixture was diluted with EtOAc (10 mL) and filtered through Celite®, the filter pad was washed with EtOAc (3×2 mL) and the combined filtrate was concentrated under vacuum. The residue was purified by preparative TLC (EtOAc:petroleum ether; 2:1), to give the title compound (0.059 g, 36%) as a yellow gum; MS (ESI) m/z $[M+H]^+$ 325.

Intermediate 393: rac-6-((1R,4S)-2-Azabicyclo[2.2.1]heptan-2-yl)quinoline-4-carboxylic acid

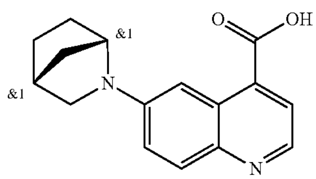 [SMILES: O=C(O)c1ccnc2ccc(N3C[C@@H]4CC[C@H]3C4)cc12]

tert-Butyl 6-(2-azabicyclo[2.2.1]heptan-2-yl)quinoline-4-carboxylate Intermediate 392 (50 mg, 0.15 mmol) was added to a mixture of TFA (3 mL) in DCM (5 mL) and stirred at 10° C. overnight under air. Volatiles were removed under reduced pressure and the solid was further dried under vacuum to give the title compound (0.11 g) as a dark purple gum; MS (ESI) m/z $[M+H]^+$ 269.

Intermediate 394: tert-Butyl (R)-6-(2-methylpyrrolidin-1-yl)quinoline-4-carboxylate

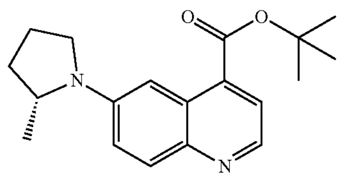 [SMILES: C[C@@H]1CCCN1c1ccc2nccc(C(=O)OC(C)(C)C)c2c1]

$Cs_2CO_3$ (634 mg, 1.95 mmol) was added a mixture of tert-butyl 6-bromoquinoline-4-carboxylate (200 mg, 0.65 mmol), (R)-2-methylpyrrolidine (111 mg, 1.30 mmol) and Pd Catalyst [CAS: 1810068-35-9] (37 mg, 0.03 mmol) in 1,4-dioxane (5 mL). The resulting suspension was stirred at 100° C. overnight. The solvent was removed under reduced pressure. The residue was purified by preparative TLC (EtOAc:petroleum ether; 3:1), to give the title compound (0.19 g, 94%) as a yellow gum; MS (ESI) m/z $[M+H]^+$ 313.3.

Intermediate 395: (R)-6-(2-Methylpyrrolidin-1-yl)quinoline-4-carboxylic acid

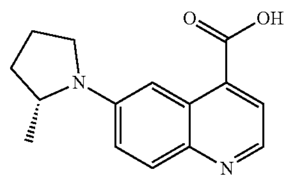 [SMILES: C[C@@H]1CCCN1c1ccc2nccc(C(=O)O)c2c1]

tert-Butyl (R)-6-(2-methylpyrrolidin-1-yl)quinoline-4-carboxylate Intermediate 394 (190 mg, 0.61 mmol) was added to a mixture of TFA (69 mg, 0.61 mmol) in DCM (5 mL) and stirred at 25° C. overnight under air. The solvent was removed under reduced pressure and the solid was further dried under vacuum to give the title compound (0.18 g) as a brown solid; MS (ESI) m/z $[M+H]^+$ 257.

Intermediate 396: tert-Butyl (S)-6-(2-(methoxymethyl)pyrrolidin-1-yl)quinoline-4-carboxylate

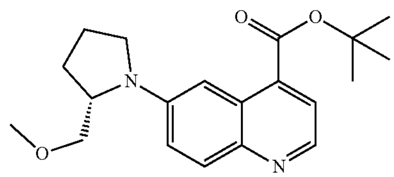 [SMILES: COC[C@@H]1CCCN1c1ccc2nccc(C(=O)OC(C)(C)C)c2c1]

$Cs_2CO_3$ (952 mg, 2.92 mmol) was added a mixture of tert-butyl 6-bromoquinoline-4-carboxylate (300 mg, 0.97 mmol), (S)-2-(methoxymethyl)pyrrolidine (224 mg, 1.95 mmol) and Pd Catalyst [CAS: 1810068-35-9] (56 mg, 0.05 mmol) in 1,4-dioxane (15 mL). The resulting suspension was stirred at 100° C. for 8 h. The reaction mixture was filtered and the filtrate was concentrated under reduced pressure. The residue was purified by preparative TLC (EtOAc:petroleum ether; 2:1), to give the title compound (0.18 g, 54%) as a yellow solid; MS (ESI) m/z $[M+H]^+$ 343.

Intermediate 397: (S)-6-(2-(Methoxymethyl)pyrrolidin-1-yl)quinoline-4-carboxylic acid

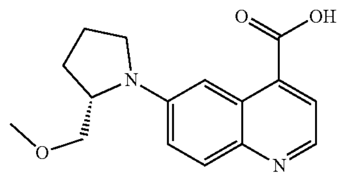 [SMILES: COC[C@@H]1CCCN1c1ccc2nccc(C(=O)O)c2c1]

tert-Butyl (S)-6-(2-(methoxymethyl)pyrrolidin-1-yl)quinoline-4-carboxylate Intermediate 396 (180 mg, 0.53 mmol) was added to a mixture of TFA (5 mL) in DCM (10 mL) and stirred at rt for 6 h under air. The solvent was removed under reduced pressure and the solid was further dried under vacuum to give the title compound (0.15 g, 100%) as a dark yellow; MS (ESI) m/z $[M+H]^+$ 287.

Intermediate 398: tert-Butyl 6-((3S,4S)-3,4-Difluoropyrrolidin-1-yl)quinoline-4-carboxylate

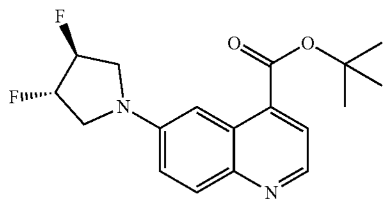 [SMILES: CC(C)(C)OC(=O)c1ccnc2ccc(N3C[C@H](F)[C@@H](F)C3)cc12]

$Cs_2CO_3$ (952 mg, 2.92 mmol) was added a mixture of tert-butyl 6-bromoquinoline-4-carboxylate (300 mg, 0.97 mmol), (3S,4S)-3,4-difluoropyrrolidine (115 mg, 1.07 mmol) and $Pd_2(dba)_3$ (89 mg, 0.10 mmol), XantPhos (113 mg, 0.19 mmol) in 1,4-dioxane (6 mL). The resulting suspension was stirred at 100° C. for 2 h. The reaction mixture was concentrated under reduced pressure. The residue was purified by preparative TLC (EtOAc:petroleum ether; 1:1), to give the title compound (0.30 g, 92%) as a red solid; MS (ESI) m/z $[M+H]^+$ 335.3.

Intermediate 399: 6-((3S,4S)-3,4-Difluoropyrrolidin-1-yl)quinoline-4-carboxylic acid

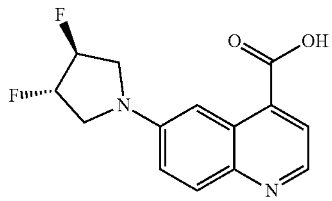 [SMILES: O=C(O)c1ccnc2ccc(N3C[C@H](F)[C@@H](F)C3)cc12]

tert-Butyl 6-((3S,4S)-3,4-Difluoropyrrolidin-1-yl)quinoline-4-carboxylate Intermediate 398 (300 mg, 0.90 mmol) was added to a mixture of TFA (512 mg, 4.49 mmol) in DCM (5 mL) and stirred at 25° C. overnight under air. The solvent was removed under reduced pressure and the solid was further dried under vacuum to give the title compound (0.3 g) as a solid; MS (ESI) m/z $[M+H]^+$ 279.2.

Intermediate 400: rac-tert-Butyl 6-((3R,4R)-3,4-difluoropyrrolidin-1-yl)quinoline-4-carboxylate

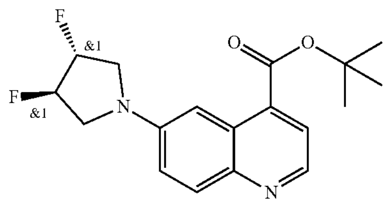 [SMILES: CC(C)(C)OC(=O)c1ccnc2ccc(N3C[C@@H](F)[C@H](F)C3)cc12]

$Cs_2CO_3$ (952 mg, 2.92 mmol) was added a mixture of tert-butyl 6-bromoquinoline-4-carboxylate (300 mg, 0.97 mmol), rac-(3R,4R)-3,4-difluoropyrrolidine (115 mg, 1.07 mmol) and $Pd_2(dba)_3$ (89 mg, 0.10 mmol), XantPhos (113 mg, 0.19 mmol) in 1,4-dioxane (8 mL). The resulting suspension was stirred at 100° C. for 2 h. The reaction mixture was concentrated under reduced pressure. The residue was purified by preparative TLC (EtOAc:petroleum ether; 2:1), to give the title compound (0.27 g, 83%) as a yellow solid; MS (ESI) m/z $[M+H]^+$ 335.3.

Intermediate 401: rac-6-α3R,4R)-3,4-Difluoropyrrolidin-1-yl)quinoline-4-carboxylic acid

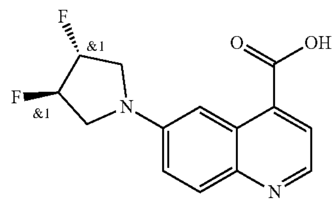 [SMILES: O=C(O)c1ccnc2ccc(N3C[C@@H](F)[C@H](F)C3)cc12]

rac-tert-Butyl 6-((3R,4R)-3,4-difluoropyrrolidin-1-yl)quinoline-4-carboxylate Intermediate 400 (260 mg, 0.78 mmol) was added to a mixture of TFA (443 mg, 3.89 mmol) in DCM (5 mL) and stirred at 25° C. for 5 h under air. The solvent was removed under reduced pressure and the solid was further dried under vacuum to give the title compound (0.23 g, 100%) as a solid; MS (ESI) m/z $[M+H]^+$ 279.2.

Intermediate 402: 6-(2,4-Dimethyloxazol-5-yl)quinoline-4-carboxylic acid

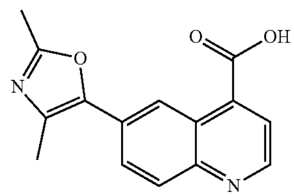 [SMILES: Cc1nc(C)c(-c2ccc3nccc(C(=O)O)c3c2)o1]

A mixture of 2,4-dimethyl-5-(4,4,5,5-tetramethyl-1,3,2-dioxaborolan-2-yl)oxazole (54 mg, 0.24 mmol), 6-bromoquinoline-4-carboxylic acid (61 mg, 0.24 mmol), $Cs_2CO_3$ (237 mg, 0.73 mmol) and $Pd(dtbpf)Cl_2$ (13 mg, 0.02 mmol) in 1,4-dioxane (2 mL) and $H_2O$ (0.5 mL) was stirred at rt overnight. The reaction mixture concentrated under reduced pressure and purified by preparative HPLC, PrepMethod E (gradient: 5-45%) to give the title compound (18 mg, 28%); MS (ESI) m/z $[M+H]^+$ 269.

Intermediate 403: 6-(3,5-Dimethylisoxazol-4-yl)quinoline-4-carboxylic acid

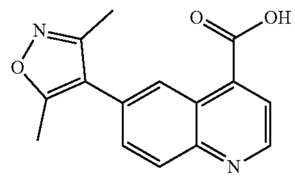 [SMILES: Cc1noc(C)c1-c1ccc2nccc(C(=O)O)c2c1]

A mixture of (3,5-dimethylisoxazol-4-yl)boronic acid (37 mg, 0.26 mmol), 6-bromoquinoline-4-carboxylic acid (60 mg, 0.24 mmol), $Cs_2CO_3$ (194 mg, 0.60 mmol) and $Pd(dtbpf)Cl_2$ (16 mg, 0.02 mmol) in 1,4-dioxane (2 mL) and $H_2O$ (0.5 mL) was stirred under argon at rt overnight. $H_2O$ was added to the reaction mixture and the aq layer was extracted with EtOAc. The aq layer was acidified with aq HCl (2 M) to pH 3 and concentrated under reduced pressure to give the title compound that was used in the next step without further purification; MS (ESI) m/z $[M+H]^+$ 269.2.

Intermediate 404: 6-(2-Phenyl-1H-imidazol-1-yl) quinoline-4-carboxylic acid

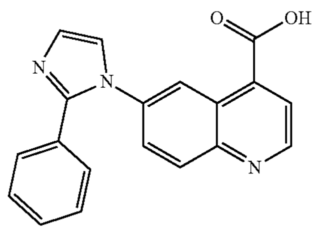 [SMILES: O=C(O)c1ccnc2ccc(-n3ccnc3-c3ccccc3)cc12]

A mixture of 2-phenyl-1H-imidazole (86 mg, 0.60 mmol), 6-bromoquinoline-4-carboxylic acid (100 mg, 0.40 mmol), $Cs_2CO_3$ (194 mg, 0.60 mmol) and $Cu_2O$ (6 mg, 0.04 mmol) in DMF (3 mL) was stirred at 150° C. for 14 h. The pH of the reaction mixture was adjusted to pH 6 with aq HCl (1 M) and filtered through a Celite® pad. The reaction mixture was concentrated under reduced pressure and purified by preparative HPLC, PrepMethod B (gradient: 2-30%) to give the title compound (0.033 g, 26%) as a yellow solid; MS (ESI) m/z $[M+H]^+$ 316.

Intermediate 405: 6-(3-Phenyl-1H-pyrrol-1-yl)quinoline-4-carboxylic acid

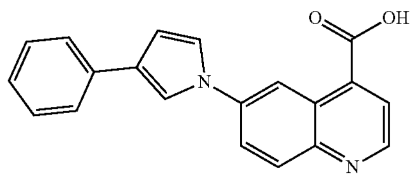 [SMILES: O=C(O)c1ccnc2ccc(-n3ccc(-c4ccccc4)c3)cc12]

$K_2CO_3$ (208 mg, 1.50 mmol) was added a mixture of methyl 6-bromoquinoline-4-carboxylate (200 mg, 0.75 mmol), 3-phenyl-1H-pyrrole (161 mg, 1.13 mmol) and CuI (14 mg, 0.08 mmol) in DMF (10 mL). The resulting suspension was stirred at 150° C. for 15 h. The reaction mixture was concentrated under reduced pressure and diluted with $H_2O$, and pH 6 was set with aq HCl (1 M). The formed precipitate was collected by filtration, washed with $H_2O$ (30 mL) and the collected brown solid was dissolved in DMF (15 mL), solids were filtered off and the filtrate was concentrated under reduced pressure to give the title compound (0.15 g, 64%) as a brown solid; MS (ESI) m/z $[M+H]^+$ 315.

Intermediate 406: 6-(4,5,6,7-Tetrahydro-1H-indol-1-yl)quinoline-4-carboxylic acid

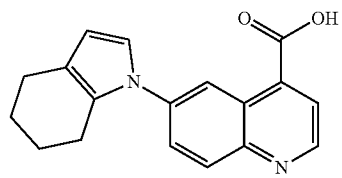

A mixture of 4,5,6,7-tetrahydro-1H-indole (216 mg, 1.79 mmol), 6-bromoquinoline-4-carboxylic acid (300 mg, 1.19 mmol), $Cs_2CO_3$ (1.16 g, 3.57 mmol) and EPhos Pd G4 (109 mg, 0.12 mmol) in 1,4-dioxane (4 mL) was stirred at 100° C. overnight. A second reaction batch was set up. A mixture of 4,5,6,7-tetrahydro-1H-indole (144 mg, 1.19 mmol), 6-bromoquinoline-4-carboxylic acid (200 mg, 0.79 mmol), $Cs_2CO_3$ (776 mg, 2.38 mmol) and EPhos Pd G4 (73 mg, 0.08 mmol) in 1,4-dioxane (3 mL) was stirred at 100° C. overnight. The reaction mixture of the two batches were combined and filtered through Celite®, pH 6 was set with aq HCl (2 M) and the filtrate was filtered through Celite® and concentrated. The residue was purified by preparative TLC (DCM:MeOH; 5:1), to give the title compound (0.055 g, 14%) as a yellow solid; MS (ESI) m/z $[M+H]^+$ 293.

Intermediate 407: tert-Butyl (R)-6-(3-(hydroxymethyl)pyrrolidin-1-yl)quinoline-4-carboxylate

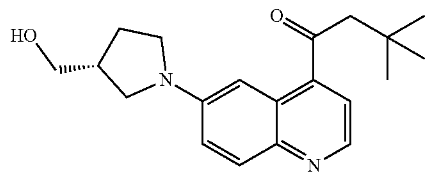 [SMILES: CC(C)(C)CC(=O)c1ccnc2ccc(N3CC[C@@H](CO)C3)cc12]

$Cs_2CO_3$ (634 mg, 1.95 mmol) was added a mixture of tert-butyl 6-bromoquinoline-4-carboxylate (300 mg, 0.97 mmol), (R)-pyrrolidin-3-ylmethanol (118 mg, 1.17 mmol) and $Pd_2(dba)_3$ (89 mg, 0.10 mmol), XantPhos (77 mg, 0.19 mmol) in 1,4-dioxane (15 mL). The resulting suspension was stirred at 100° C. for 5 h. The reaction mixture was concentrated under reduced pressure and diluted with EtOAc (125 mL). The organic layer was washed with $H_2O$ (2×75 mL), sat $NH_4C_1$ (75 mL, aq), dried over $Na_2SO_4$, filtered and concentrated under reduced pressure. The residue was purified by preparative TLC (DCM:MeOH; 10:1), to give the title compound (0.28 g, 88%) as a yellow oil; MS (ESI) m/z $[M+H]^+$ 329.1.

Intermediate 408: (R)-6-(3-(Hydroxymethyl)pyrrolidin-1-yl)quinoline-4-carboxylic acid

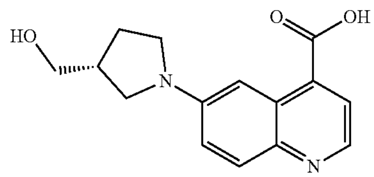 [SMILES: O=C(O)c1ccnc2ccc(N3CC[C@@H](CO)C3)cc12]

HCl in 1,4-dioxane (4 M, 8 mL) was added slowly to tert-butyl (R)-6-(3-(hydroxymethyl)pyrrolidin-1-yl)quinoline-4-carboxylate Intermediate 407 (200 mg, 0.61 mmol) and the reaction mixture was stirred at 20° C. for 12 h. Volatiles were removed under reduced pressure, and the reaction mixture was diluted with EtOAc (75 mL). The organic layer was washed with $H_2O$ (15 mL), brine (20 mL), dried over $Na_2SO_4$, filtered and concentrated to give the title compound (0.10 g, 60%) as a red solid; MS (ESI) m/z $[M+H]^+$ 273.

Intermediate 409: tert-Butyl (S)-6-(3-(hydroxymethyl)pyrrolidin-1-yl)quinoline-4-carboxylate

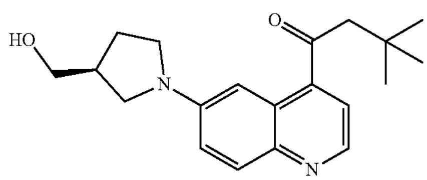 [SMILES: CC(C)(C)CC(=O)c1ccnc2ccc(N3CC[C@H](CO)C3)cc12]

$Cs_2CO_3$ (846 mg, 2.60 mmol) was added a mixture of tert-butyl 6-bromoquinoline-4-carboxylate (400 mg, 1.30 mmol), (S)-pyrrolidin-3-ylmethanol (158 mg, 1.56 mmol) and $Pd_2(dba)_3$ (119 mg, 0.13 mmol), XantPhos (102 mg, 0.26 mmol) in 1,4-dioxane (3 mL). The resulting suspension was stirred at 100° C. for 5 h. The reaction mixture was concentrated under reduced pressure and diluted with EtOAc (125 mL). The organic layer was washed with $H_2O$ (50 mL), brine (75 mL), dried over $Na_2SO_4$, filtered and concentrated under reduced pressure. The residue was purified by preparative TLC (DCM:MeOH; 10:1), to give the title compound (0.357 g, 84%) as a yellow solid; MS (ESI) m/z $[M+H]^+$ 329.1.

Intermediate 410: (S)-6-(3-(Hydroxymethyl)pyrrolidin-1-yl)quinoline-4-carboxylic acid

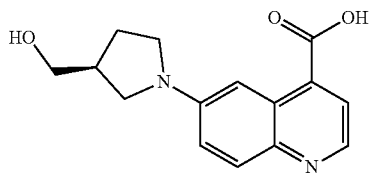 [SMILES: O=C(O)c1ccnc2ccc(N3CC[C@H](CO)C3)cc12]

HCl in 1,4-dioxane (4 M, 5 mL) was added slowly to tert-butyl (S)-6-(3-(hydroxymethyl)pyrrolidin-1-yl)quinoline-4-carboxylate Intermediate 409 (200 mg, 0.61 mmol) and the reaction mixture was stirred at 20° C. for 12 h. Volatiles were removed under reduced pressure, and the reaction mixture was diluted with EtOAc (75 mL). The organic layer was washed with $H_2O$ (25 mL), brine (25 mL), dried over $Na_2SO_4$, filtered and concentrated to give the title compound (0.12 g, 72%) as a red solid; MS (ESI) m/z $[M+H]^+$ 273.05.

Intermediate 411: Methyl 6-(1-thia-6-azaspiro[3.3]heptan-6-yl)quinoline-4-carboxylate

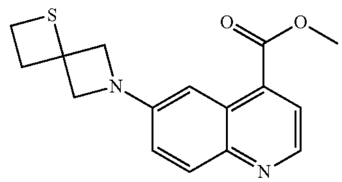 [SMILES: COC(=O)c1ccnc2ccc(N3CC4(CCS4)C3)cc12]

$Cs_2CO_3$ (367 mg, 1.13 mmol) was added to a mixture of methyl 6-bromoquinoline-4-carboxylate (150 mg, 0.56 mmol), 1-thia-6-azaspiro[3.3]heptane hydrochloride (171 mg, 1.13 mmol) and RuPhos Pd G3 (94 mg, 0.11 mmol) in 1,4-dioxane (10 mL) at 35° C. The resulting suspension was stirred at 100° C. for 15 h. $Cs_2CO_3$ (367 mg, 1.13 mmol), 1-thia-6-azaspiro[3.3]heptane hydrochloride (171 mg, 1.13 mmol) and RuPhos Pd G3 (94 mg, 0.11 mmol) was added and the reaction mixture stirred at 100° C. for 20 h. The reaction mixture was filtered and the filtrate concentrated under reduced pressure. The residue was purified by preparative TLC (EtOAc:petroleum ether; 6:5) to give the title compound (0.098 g, 58%) as a brown gum; MS (ESI) m/z $[M+H]^+$ 301.

Intermediate 412: 6-(1-Thia-6-azaspiro[3.3]heptan-6-yl)quinoline-4-carboxylic acid

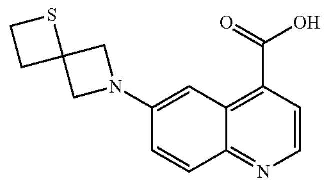 [SMILES: O=C(O)c1ccnc2ccc(N3CC4(CCS4)C3)cc12]

To a solution of methyl 6-(1-thia-6-azaspiro[3.3]heptan-6-yl)quinoline-4-carboxylate Intermediate 411 (84 mg, 0.28 mmol) dissolved in MeOH (6 mL) was added a solution of NaOH (56 mg, 1.4 mmol) in $H_2O$ (2 mL) under air at 0° C. The reaction mixture was stirred at 30° C. for 1 h. The reaction mixture was diluted with $H_2O$ (10 mL) and pH 6 was set with aq HCl (2 M). The reaction mixture was diluted with $H_2O$ (10 mL) and extracted with EtOAc (6×75 mL), dried over $Na_2SO_4$, filtered and concentrated under reduced pressure to give the title compound (0.075 g, 94%) as an orange solid; MS (ESI) m/z $[M+H]^+$ 287.

Intermediate 413: Methyl 6-(4-hydroxy-4-phenylpiperidin-1-yl)quinoline-4-carboxylate

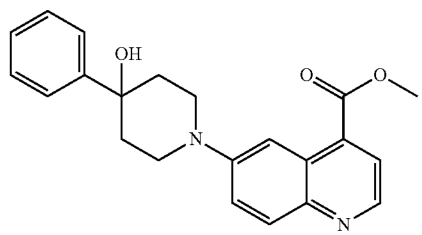 [SMILES: COC(=O)c1ccnc2ccc(N3CCC(O)(c4ccccc4)CC3)cc12]

$Cs_2CO_3$ (490 mg, 1.50 mmol) was added to a mixture of methyl 6-bromoquinoline-4-carboxylate (200 mg, 0.75 mmol), 4-phenylpiperidin-4-ol (266 mg, 1.50 mmol), XPhos (72 mg, 0.15 mmol) and $Pd_2(dba)_3$ (34 mg, 0.04 mmol) in 1,4-dioxane (8 mL). The resulting suspension was stirred at 90° C. for 2 h and filtered. The filtrate was concentrated under reduced pressure. EtOAc (25 mL) was added and the mixture was washed with water (2×15 mL), dried over $Na_2SO_4$, filtered and concentrated under reduced pressure. The residue was purified by preparative TLC (EtOAc: petroleum ether; 2:1), to give the title compound (0.20 g, 73%) as a yellow solid; MS (ESI) m/z $[M+H]^+$ 285.

Intermediate 414: Methyl 6-(4-fluoro-4-phenylpiperidin-1-yl)quinoline-4-carboxylate

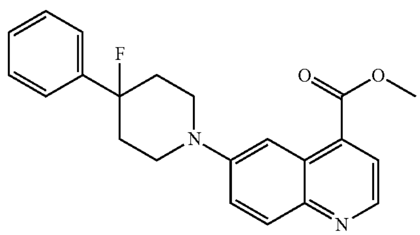 [SMILES: COC(=O)c1ccnc2ccc(N3CCC(F)(c4ccccc4)CC3)cc12]

DAST (146 μL, 1.10 mmol) was added dropwise to a solution of methyl 6-(4-hydroxy-4-phenylpiperidin-1-yl) quinoline-4-carboxylate Intermediate 413 (200 mg, 0.55 mmol) in DCM (10 mL) at −50° C. and stirred for 3 h. Volatiles were removed under reduced pressure. The residue was purified by preparative TLC (EtOAc:petroleum ether; 1:2), to give the title compound (0.15 g, 75%) as a yellow solid; MS (ESI) m/z $[M+H]^+$ 365.

Intermediate 415: 6-(4-Fluoro-4-phenylpiperidin-1-yl)quinoline-4-carboxylic acid

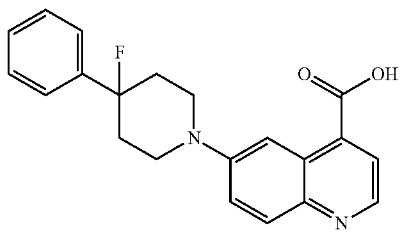 [SMILES: O=C(O)c1ccnc2ccc(N3CCC(F)(c4ccccc4)CC3)cc12]

Methyl 6-(4-fluoro-4-phenylpiperidin-1-yl)quinoline-4-carboxylate Intermediate 414 (140 mg, 0.38 mmol) and LiOH (18 mg, 0.77 mmol) was dissolved in a mixture of MeOH (10 mL) and $H_2O$ (1 mL). The reaction mixture was stirred at 30° C. for 2 h and volatiles were removed under reduced pressure. The reaction mixture was diluted with $H_2O$ (15 mL) and pH 6 was set with aq HCl (1 M). The precipitate was collected by filtration, washed with $H_2O$ and dried under vacuum to give the title compound (0.115 g, 85%) as a yellow solid; MS (ESI) m/z $[M+H]^+$ 351.

Intermediate 416: rac-tert-Butyl (R)-6-(3,3-difluoro-4-hydroxypyrrolidin-1-yl)quinoline-4-carboxylate

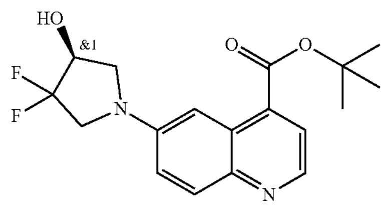 [SMILES: CC(C)(C)OC(=O)c1ccnc2ccc(N3C[C@H](O)C(F)(F)C3)cc12]

$Cs_2CO_3$ (634 mg, 1.95 mmol) was added to a mixture of tert-butyl 6-bromoquinoline-4-carboxylate (300 mg, 0.97 mmol), 4,4-difluoropyrrolidin-3-ol (144 mg, 1.17 mmol), DavePhos (77 mg, 0.19 mmol) and $Pd_2(dba)_3$ (89 mg, 0.10 mmol) in 1,4-dioxane (15 mL). The resulting suspension was stirred at 100° C. for 2 h and filtered. The reaction mixture was diluted with EtOAc (125 mL) and washed with water (75 mL), brine (75 mL), dried over $Na_2SO_4$, filtered and concentrated under reduced pressure. The residue was purified by preparative TLC (DCM:MeOH; 5:1), to give the title compound (0.28 g, 82%) as a yellow solid; MS (ESI) m/z $[M+H]^+$ 351.15.

Intermediate 417: rac-(R)-6-(3,3-Difluoro-4-hydroxypyrrolidin-1-yl)quinoline-4-carboxylic acid

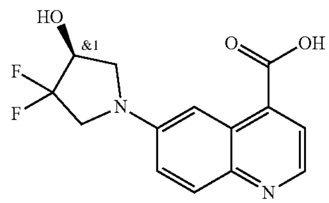 [SMILES: O=C(O)c1ccnc2ccc(N3C[C@H](O)C(F)(F)C3)cc12]

A solution of DCM (5 mL) and TFA (1.5 mL) was added to rac-tert-butyl (R)-6-(3,3-difluoro-4-hydroxypyrrolidin-1-yl)quinoline-4-carboxylate Intermediate 416 (160 mg, 0.46 mmol) and stirred at 20° C. for 16 h. Volatiles were removed under reduced pressure and the reaction mixture was diluted with DCM (75 mL), washed with $H_2O$ (25 mL), brine (25 mL), dried over $Na_2SO_4$, filtered and evaporated to give the title compound (0.12 g, 89%) as a red solid; MS (ESI) m/z $[M+H]^+$ 295.0.

Intermediate 418: rac-tert-Butyl 6-((3R,4R)-3,4-dimethylpyrrolidin-1-yl)quinoline-4-carboxylate

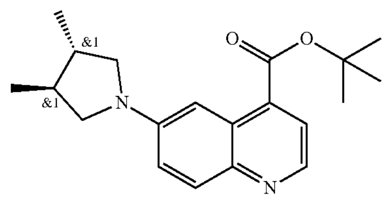 [SMILES: C[C@@H]1CN(c2ccc3nccc(C(=O)OC(C)(C)C)c3c2)C[C@H]1C]

$Cs_2CO_3$ (977 mg, 3.00 mmol) was added to a stirred solution of tert-butyl 6-bromoquinoline-4-carboxylate (308 mg, 1.00 mmol), rac-(3R,4R)-3,4-dimethylpyrrolidine hydrochloride (149 mg, 1.10 mmol), XPhos (95 mg, 0.20 mmol)) and $Pd_2(dba)_3$ (92 mg, 0.10 mmol) in 1,4-dioxane (5 mL) and stirred at 100° C. for 2 h. The reaction mixture was filtered, and the filtrate washed with $H_2O$ (3 mL). The aq layer was extracted with EtOAc (4×20 mL), the combined organic layers were washed with $H_2O$ (3×10 mL). The organic layers was dried over $Na_2SO_4$, filtered and concentrated under reduced pressure. The residue was purified by preparative TLC (EtOAc: petroleum ether; 1:1), to give the title compound (0.307 g, 94%) as a yellow solid; MS (ESI) m/z $[M+H]^+$ 327.

Intermediate 419: rac-6-((3R,4R)-3,4-Dimethylpyrrolidin-1-yl)quinoline-4-carboxylic acid

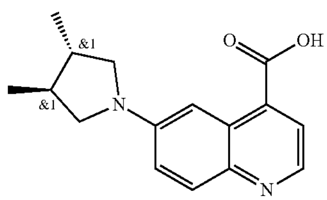 [SMILES: C[C@@H]1CN(c2ccc3nccc(C(=O)O)c3c2)C[C@H]1C]

TFA (5 mL) was added to a solution of rac-tert-butyl 6-((3R,4R)-3,4-dimethylpyrrolidin-1-yl)quinoline-4-carboxylate Intermediate 418 (270 mg, 0.83 mmol) in DCM (5 mL) and stirred at 6° C. for 15 h. Volatiles were removed under reduced pressure to give the title compound (0.493 g, 97%) as a dark red gum; MS (ESI) m/z $[M+H]^+$ 271.

Intermediate 420: rac-tert-Butyl (R)-6-(2-cyclopropylpyrrolidin-1-yl)quinoline-4-carboxylate

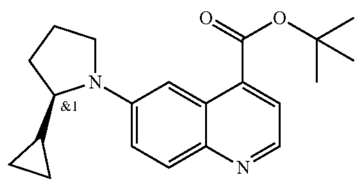 [SMILES: CC(C)(C)OC(=O)c1ccnc2ccc(N3CCC[C@@H]3C3CC3)cc12]

$Cs_2CO_3$ (977 mg, 3.00 mmol) was added a mixture of tert-butyl 6-bromoquinoline-4-carboxylate (308 mg, 1.00 mmol), rac-(R)-2-cyclopropylpyrrolidine hydrochloride (162 mg, 1.10 mmol) and Pd Catalyst [CAS: 1810068-35-9] (57 mg, 0.05 mmol) in 1,4-dioxane (5 mL). The resulting suspension was stirred at 100° C. for 48 h. The reaction mixture was diluted with EtOAc (10 mL) and filtered through Celite®, the filter pad was washed with EtOAc (3×2 mL) and the combined filtrates were concentrated under reduced pressure. The residue was purified by preparative TLC (EtOAc:petroleum ether; 1:1), to give the title compound (0.192 g, 57%) as a yellow solid; MS (ESI) m/z $[M+H]^+$ 339.

Intermediate 421: rac-(R)-6-(2-Cyclopropylpyrrolidin-1-yl)quinoline-4-carboxylic acid

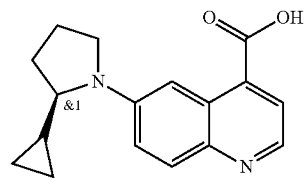 [SMILES: O=C(O)c1ccnc2ccc(N3CCC[C@@H]3C3CC3)cc12]

rac-tert-Butyl (R)-6-(2-cyclopropylpyrrolidin-1-yl)quinoline-4-carboxylate Intermediate 420 (180 mg, 0.53 mmol) was added to a mixture of TFA (5 mL) in DCM (5 mL) and stirred at 10° C. for 15 h. Volatiles were removed under reduced pressure and the solid was further dried under vacuum to give the title compound (0.37 g, 100%) as a red gum; MS (ESI) m/z $[M+H]^+$ 283.

Intermediate 422: Methyl 6-bromoquinoline-4-carboxylate hydrochloride

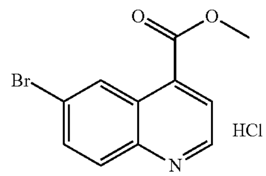

A solution of 6-bromoquinoline-4-carboxylic acid (3.0 g, 12 mmol) in MeOH (70 mL) was added dropwise to stirred $SOCl_2$ (7.08 g, 59.5 mmol) over a period of 25 min. The reaction mixture was heated at 60° C. for 13 h. The reaction mixture was concentrated at reduced pressure to give the title compound (3.50 g, 97%) as a yellow solid; MS (ESI) m/z $[M+H]^+$ 266.

Intermediate 423: Methyl 6-(1,5-dioxa-9-azaspiro[5.5]undecan-9-yl)quinoline-4-carboxylate

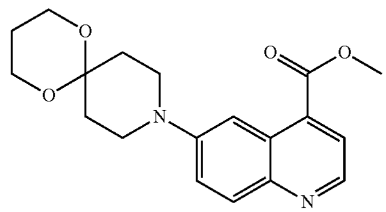 [SMILES: COC(=O)c1ccnc2ccc(N3CCC4(CC3)OCCCO4)cc12]

$Cs_2CO_3$ (490 mg, 1.50 mmol) was added to a mixture of methyl 6-bromoquinoline-4-carboxylate (200 mg, 0.75 mmol), 1,5-dioxa-9-azaspiro[5.5]undecane (236 mg, 1.50 mmol), $Pd_2(dba)_3$ (69 mg, 0.08 mmol) and SPhos (62 mg, 0.15 mmol) in 1,4-dioxane (4.0 mL) at 15° C. and the reaction mixture was stirred at 100° C. for 2 h under an atmosphere of $N_2$ (g). The solvent was removed under reduced pressure. The residue was diluted with water (30 mL), and the water phase was extracted with EtOAc (3×50 mL). The combined organic layer was dried over $Na_2SO_4$, filtered and evaporated at reduced pressure. The crude product was purified by preparative TLC (EtOAc:petroleum ether, 1:1), to give the title compound (0.25 g, 97%) as an orange gum; MS (ESI) m/z $[M+H]^+$ 343.1.

Intermediate 424: 6-(1,5-Dioxa-9-azaspiro[5.5]undecan-9-yl)quinoline-4-carboxylic acid

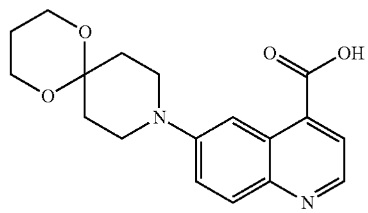 [SMILES: O=C(O)c1ccnc2ccc(N3CCC4(CC3)OCCCO4)cc12]

NaOH (146 mg, 3.65 mmol) was added to a solution of methyl 6-(1,5-dioxa-9-azaspiro[5.5]undecan-9-yl)quinoline-4-carboxylate Intermediate 423 (250 mg, 0.73 mmol) in MeOH (9.0 mL) and water (3.0 mL) at 15° C. and the reaction mixture was stirred at 15° C. for 1 h. The solvent was removed under reduced pressure. The residue was diluted with water (10 mL), and pH was adjusted to 3 with aq HCl (1 M). The aqueous phase was extracted with EtOAc (3×50 mL), and the combined organic layer was dried over $Na_2SO_4$, filtered and evaporated to give the title compound (0.221 g, 92%) as an orange solid; MS (ESI) m/z $[M+H]^+$ 329.0.

Intermediate 425: Methyl 6-(1,4-dioxa-8-azaspiro[4.5]decan-8-yl)quinoline-4-carboxylate

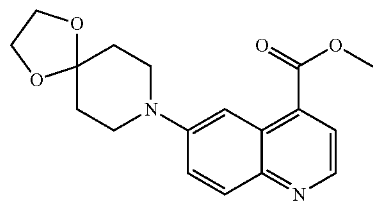 [SMILES: COC(=O)c1ccnc2ccc(N3CCC4(CC3)OCCO4)cc12]

$Cs_2CO_3$ (490 mg, 1.50 mmol) was added to a mixture of methyl 6-bromoquinoline-4-carboxylate (200 mg, 0.75 mmol), 1,4-dioxa-8-azaspiro[4.5]decane (215 mg, 1.50 mmol), $Pd_2(dba)_3$ (69 mg, 0.08 mmol) and SPhos (62 mg, 0.15 mmol) in 1,4-dioxane (5.0 mL) at 25° C., and the reaction mixture was stirred at 100° C. for 2 h under an atmosphere of $N_2$ (g). The solvent was removed under reduced pressure. The residue was diluted with water (50 mL), and the water phase was extracted with EtOAc (3×50 mL). The combined organic layer was dried over $Na_2SO_4$, filtered and evaporated at reduced pressure. The residue was purified by preparative TLC (EtOAc:petroleum ether, 1:1), to give the title compound (0.104 g, 42%) as a brown gum; MS (ESI) m/z $[M+H]^+$ 329.0.

Intermediate 426: 6-(1,4-Dioxa-8-azaspiro[4,5]decan-8-yl)quinoline-4-carboxylic acid

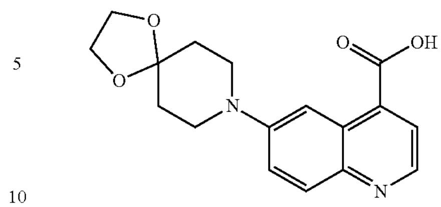

NaOH (60 mg, 1.50 mmol) was added to a solution of methyl 6-(1,4-dioxa-8-azaspiro[4.5]decan-8-yl)quinoline-4-carboxylate Intermediate 425 (99 mg, 0.30 mmol) in MeOH (9.0 mL) and water (3.0 mL) at 15° C., and the reaction mixture was stirred at 15° C. for 1 h. The solvent was removed under reduced pressure. The residue was diluted with water (20 mL) and the pH was adjusted to 3 with aq HCl (1 M). The aqueous phase was extracted with EtOAc (3×50 mL), and the combined organic layer was dried over $Na_2SO_4$, filtered and evaporated to give the crude title compound (0.137 g) as an orange solid; MS (ESI) m/z $[M+H]^+$ 315.

Intermediate 427: Methyl 6-(2-oxa-7-azaspiro[3.5]nonan-7-yl)quinoline-4-carboxylate

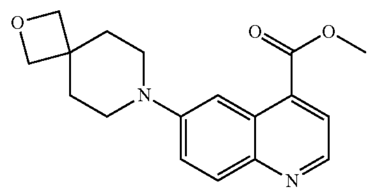 [SMILES: COC(=O)c1ccnc2ccc(N3CCC4(CC3)COC4)cc12]

$Cs_2CO_3$ (918 mg, 2.82 mmol) was added to methyl 6-bromoquinoline-4-carboxylate (300 mg, 1.13 mmol), 2-oxa-7-azaspiro[3.5]nonane oxalate (490 mg, 2.25 mmol) and SPhos Pd G3 (98 mg, 0.11 mmol) in 1,4-dioxane (5 mL) at 15° C., and the reaction mixture was stirred at 100° C. for 16 h under an atmosphere of $N_2$ (g). $Cs_2CO_3$ (367 mg, 1.13 mmol) and SPhos Pd G3 (98 mg, 0.11 mmol) were added and the reaction mixture was stirred at 100° C. for a further 5 h. The solvent was removed under reduced pressure. The residue was diluted with water (50 mL) and extracted with EtOAc (3×50 mL). The combined organic layer was dried over $Na_2SO_4$, filtered and evaporated. The residue was purified by preparative TLC (EtOAc:petroleum ether, 2:1), to give the title compound (0.142 g, 40%) as a brown gum; MS (ESI) m/z $[M+H]^+$ 313.1.

C. Final Compounds

Example 1: (R)—N-(2-(4-Cyanothiazolidin-3-yl)-2-oxoethyl)-6-(1,2-oxazinan-2-yl)-quinoline-4-carboxamide

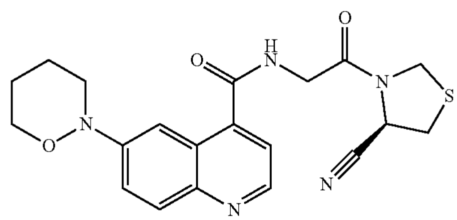 [SMILES: N#C[C@@H]1CSCN1C(=O)CNC(=O)c1ccnc2ccc(N3CCCCO3)cc12]

DIPEA (0.15 mL, 0.87 mmol) was added to a mixture of 6-(1,2-oxazinan-2-yl)quinoline-4-carboxylic acid Intermediate 6 (45 mg, 0.17 mmol), (R)-3-glycylthiazolidine-4-carbonitrile hydrochloride Intermediate 4 (54 mg, 0.26 mmol) and HATU (79 mg, 0.21 mmol) in EtOAc (1.5 mL) and MeCN (1.5 mL). The mixture was stirred at rt for 4 h. The mixture was diluted with EtOAc, washed sequentially with water and sat $NaHCO_3$. The organic phase was dried, filtered and evaporated. The residue was purified by straight phase flash chromatography on silica (gradient: 0-10% MeOH in EtOAc). Appropriate fractions were pooled and evaporated to give a yellow oil. The oil was dissolved in MeCN:water and freeze dried overnight to give the title compound (65 mg, 91%) as a fluffy yellow powder; HRMS (ESI) m/z $[M+H]^+$ calcd for $C_{20}H_{22}N_5O_3S$: 412.1438. found: 412.1438; $^1H$ NMR (500 MHz, DMSO-$d_6$) δ 9.02 (brs, 1H), 8.78 (d, 1H), 7.95 (d, 1H), 7.85 (d, 1H), 7.62 (dd, 1H), 7.48 (d, 1H), 5.34-5.31 (m, 1H), 4.88 (d, 1H), 4.71 (d, 1H), 4.31 (d, 2H), 4.09 (t, 2H), 3.55 (t, 2H), 3.46-3.35 (m, 2H), 1.91-1.83 (m, 2H), 1.72-1.65 (m, 2H).

Example 2: (R)—N-(2-(4-Cyanothiazolidin-3-yl)-2-oxoethyl)-3-fluoro-6-morpholino-quinoline-4-carboxamide

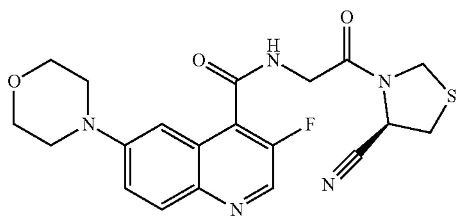 [SMILES: N#C[C@@H]1CSCN1C(=O)CNC(=O)c1c(F)cnc2ccc(N3CCOCC3)cc12]

DIPEA (0.33 mL, 1.9 mmol) was added to a mixture of 3-fluoro-6-morpholinoquinoline-4-carboxylic acid Intermediate 8 (172 mg, 0.62 mmol), (R)-3-glycylthiazolidine-4-carbonitrile hydrochloride Intermediate 4 (129 mg, 0.62 mmol) and HATU (308 mg, 0.81 mmol) in EtOAc (3 mL) and MeCN (3 mL). The mixture which was stirred at rt for 3 h. The mixture was diluted with EtOAc, washed sequentially with water and sat $NaHCO_3$. The organic phase was dried, filtered and evaporated. The residue was purified by straight phase flash chromatography on silica (gradient: 75-100% EtOAc in heptane), and then further purified using preparative HPLC, PrepMethod SFC-D, to give the title compound (60 mg, 22%); HRMS (ESI) m/z $[M+H]^+$ calcd for $C_{24}H_{21}FN_5O_3S$: 430.1344. found: 430.1318; $^1H$ NMR (600 MHz, DMSO-$d_6$) δ 9.28 (t, 1H), 8.70 (s, 1H), 7.93 (d, 1H), 7.65 (dd, 2H), 5.33 (dd, 1H), 4.90 (d, 1H), 4.71 (d, 1H), 4.41 (dd, 1H), 4.32 (dd, 1H), 3.80 (t, 4H), 3.44-3.36 (m, 6H).

Example 3: (R)—N-(2-(4-Cyanothiazolidin-3-yl)-2-oxoethyl)-6-thiomorpholinoquinoline-4-carboxamide

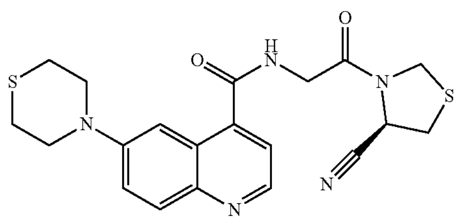 [SMILES: N#C[C@@H]1CSCN1C(=O)CNC(=O)c1ccnc2ccc(N3CCSCC3)cc12]

DIPEA (0.16 mL, 0.91 mmol) was added to a mixture of 6-thiomorpholinoquinoline-4-carboxylic acid Intermediate 10 (50 mg, 0.18 mmol), (R)-3-glycylthiazolidine-4-carbonitrile hydrochloride Intermediate 4 (38 mg, 0.18 mmol) and HATU (83 mg, 0.22 mmol) in EtOAc (1.5 mL) and MeCN (1.5 mL). The mixture was stirred at rt overnight. The mixture was diluted with EtOAc, washed sequentially with water and sat $NaHCO_3$. The organic phase was dried, filtered and evaporated. The residue was purified by straight phase flash chromatography on silica (gradient: 0-10% MeOH in EtOAc). Appropriate fractions were pooled and evaporated to give a yellow oil. The oil was dissolved in MeCN/water and freeze dried overnight to give the title compound (55 mg, 71%) as a fluffy yellow powder; HRMS (ESI) m/z $[M+H]^+$ calcd for $C_{20}H_{22}N_5O_2S_2$: 428.1210. found: 428.1210; $^1H$ NMR (500 MHz, DMSO-$d_6$) δ 9.01 (t, 1H), 8.67 (d, 1H), 7.89 (d, 1H), 7.73 (d, 1H), 7.64 (dd, 1H), 7.39 (d, 1H), 5.33 (dd, 1H), 4.89 (d, 1H), 4.71 (d, 1H), 4.37-4.25 (m, 2H), 3.79 (t, 4H), 3.44-3.35 (m, 2H), 2.71 (ddt, 4H).

Example 4: (R)—N-(2-(4-Cyanothiazolidin-3-yl)-2-oxoethyl)-6-(2,2-difluoromorpholino)-quinoline-4-carboxamide

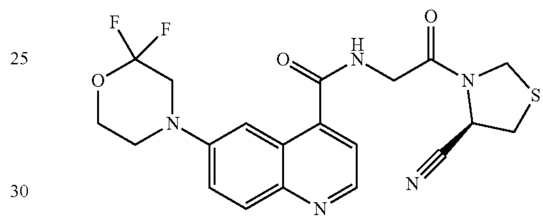

DIPEA (0.13 mL, 0.75 mmol) was added to a mixture of 6-(2,2-difluoromorpholino)quinoline-4-carboxylic acid Intermediate 12 (74 mg, 0.25 mmol), (R)-3-glycylthiazolidine-4-carbonitrile hydrochloride Intermediate 4 (52 mg, 0.25 mmol) and HATU (124 mg, 0.33 mmol) in EtOAc (2 mL) and MeCN (2 mL). The mixture was stirred at rt for 3 h. The mixture was diluted with EtOAc, washed sequentially with water and sat $NaHCO_3$. The organic phase was dried, filtered and evaporated. The residue was purified by straight phase flash chromatography on silica (gradient: 0-10% MeOH in EtOAc), and then further purified using preparative HPLC, PrepMethod SFC-D, to give the title compound (40 mg, 36%); HRMS (ESI) m/z $[M+H]^+$ calcd for $C_{20}H_{20}F_2N_5O_3S$: 448.1250. found: 448.1252; $^1H$ NMR (600 MHz, DMSO-$d_6$) δ 9.08 (t, 1H), 8.76 (d, 1H), 7.97 (d, 1H), 7.84 (d, 1H), 7.75 (dd, 1H), 7.47 (d, 1H), 5.32 (dd, 1H), 4.91 (d, 1H), 4.73 (d, 1H), 4.38-4.29 (m, 2H), 4.29-4.23 (m, 2H), 3.89-3.80 (m, 2H), 3.61-3.54 (m, 2H), 3.45-3.35 (m, 2H).

Example 5: (R)—N-(2-(4-Cyanothiazolidin-3-yl)-2-oxoethyl)-6-(2,2,6,6-tetrafluoromorpholino)quinoline-4-carboxamide

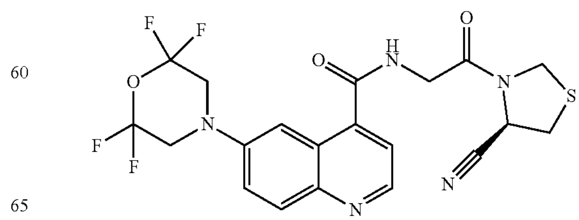

DIPEA (0.14 mL, 0.83 mmol) was added to a mixture of 6-(2,2,6,6-tetrafluoromorpholino)quinoline-4-carboxylic acid Intermediate 14 (55 mg, 0.17 mmol), (R)-3-glycylthiazolidine-4-carbonitrile hydrochloride Intermediate 4 (52 mg, 0.25 mmol) and HATU (76 mg, 0.20 mmol) in EtOAc (1.5 mL) and MeCN (1.5 mL). The mixture was stirred at rt overnight. The mixture was diluted with EtOAc, and washed sequentially with water and sat $NaHCO_3$. The organic phase was dried, filtered and evaporated. The residue was purified by straight phase flash chromatography on silica (gradient: 0-10% MeOH in EtOAc), and then further purified using preparative HPLC, PrepMethod SFC-D, to give the title compound (20 mg, 25%); HRMS (ESI) m/z $[M+H]^+$ calcd for $C_{20}H_{18}F_4N_5O_3S$: 484.1060. found: 484.1052; $^1H$ NMR (600 MHz, DMSO-$d_6$) δ 9.11 (t, 1H), 8.80 (d, 1H), 8.01 (d, 1H), 7.98 (d, 1H), 7.81 (dd, 1H), 7.48 (d, 1H), 5.28 (dd, 1H), 4.92 (d, 1H), 4.73 (d, 1H), 4.40-4.30 (m, 2H), 4.29-4.21 (m, 4H), 3.47-3.36 (m, 2H, overlapping with solvent).

Example 6: (R)—N-(2-(4-Cyanothiazolidin-3-yl)-2-oxoethyl)-6-(2,3-dihydro-4H-benzo[b][1,4]oxazin-4-yl)quinoline-4-carboxamide

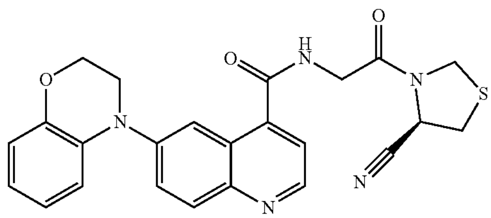 [SMILES: N#C[C@@H]1CSCN1C(=O)CNC(=O)c1ccnc2ccc(N3CCOc4ccccc43)cc12]

DIPEA (0.14 mL, 0.80 mmol) was added to a mixture of 6-(2,3-dihydro-4H-benzo[b.] [1,4]oxazin-4-yl)quinoline-4-carboxylic acid Intermediate 16 (49 mg, 0.16 mmol), (R)-3-glycylthiazolidine-4-carbonitrile hydrochloride Intermediate 4 (50 mg, 0.24 mmol) and HATU (73 mg, 0.19 mmol) in EtOAc (1.5 mL) and MeCN (1.5 mL). The mixture was stirred at rt overnight. The mixture was diluted with EtOAc and washed sequentially with water and sat $NaHCO_3$. The organic phase was dried, filtered and evaporated. The residue was purified by straight phase flash chromatography on silica (gradient: 0-10% MeOH in EtOAc). Appropriate fractions were pooled and evaporated to give a yellow oil. The oil was dissolved in MeCN/water and freeze dried overnight to give the title compound (59 mg, 80%) as a fluffy yellow powder; HRMS (ESI) m/z $[M+H]^+$ calcd for $C_{24}H_{22}N_5O_3S$: 460.1438. found: 460.1428; $^1H$ NMR (500 MHz, DMSO-$d_6$) δ 9.06 (t, 1H), 8.84 (d, 1H), 8.11 (d, 1H), 8.02 (d, 1H), 7.81 (dd, 1H), 7.53 (d, 1H), 7.05 (dd, 1H), 6.88 (dd, 1H), 6.85-6.72 (m, 2H), 5.32 (dd, 1H), 4.87 (d, 1H), 4.70 (d, 1H), 4.30 (t, 4H), 3.86 (q, 2H), 3.39 (dd, 2H).

Example 7: N-(2-((R)-4-Cyanothiazolidin-3-yl)-2-oxoethyl)-6-((3S,4S,5R)-4-hydroxy-3,5-dimethylpiperidin-1-yl)quinoline-4-carboxamide

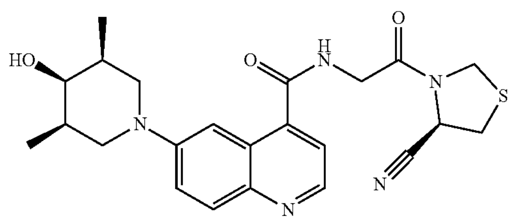 [SMILES: C[C@@H]1CN(c2ccc3nccc(C(=O)NCC(=O)N4CSC[C@H]4C#N)c3c2)C[C@H](C)[C@@H]1O]

DIPEA (0.052 mL, 0.30 mmol) was added to a mixture of 6-((3S,4s,5R)-4-hydroxy-3,5-dimethylpiperidin-1-yl)quinoline-4-carboxylic acid Intermediate 18 (18 mg, 0.06 mmol), (R)-3-glycylthiazolidine-4-carbonitrile hydrochloride Intermediate 4 (19 mg, 0.09 mmol) and HATU (27 mg, 0.07 mmol) in EtOAc (1.5 mL) and MeCN (1.5 mL). The mixture was stirred at rt overnight, and then diluted with EtOAc, washed sequentially with water and sat $NaHCO_3$. The organic phase was dried, filtered and evaporated. The residue was purified by straight phase flash chromatography on silica (gradient: 0-10% MeOH in EtOAc), and then further purified by preparative HPLC, PrepMethod SFC-A, to give the title compound (5 mg, 18%); HRMS (ESI) m/z $[M+H]^+$ calcd for $C_{23}H_{28}N_5O_3S$: 454.1908. found: 454.1886; $^1H$ NMR (600 MHz, DMSO-$d_6$) δ 8.98 (t, 1H), 8.63 (d, 1H), 7.86 (d, 1H), 7.70-7.60 (m, 2H), 7.37 (d, 1H), 5.30 (dd, 1H), 4.89 (d, 1H), 4.73 (d, 1H), 4.48 (brs, 1H), 4.35-4.25 (m, 2H), 3.60-3.50 (m, 3H), 2.74 (t, 4H), 1.85-1.75 (m, 2H), 0.98 (dd, 6H).

Example 8: (R)—N-(2-(4-Cyanothiazolidin-3-yl)-2-oxoethyl)-6-(4-methoxypiperidin-1-yl)quinoline-4-carboxamide

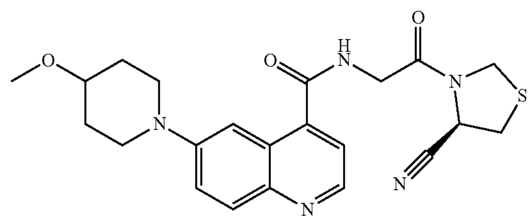 [SMILES: COC1CCN(c2ccc3nccc(C(=O)NCC(=O)N4CSC[C@H]4C#N)c3c2)CC1]

DIPEA (0.24 mL, 1.4 mmol) was added to 6-(4-methoxypiperidin-1-yl)quinoline-4-carboxylic acid Intermediate 20 (200 mg, 0.70 mmol), (R)-3-glycylthiazolidine-4-carbonitrile hydrochloride Intermediate 4 (179 mg, 1.05 mmol) and HATU (266 mg, 0.70 mmol) in MeCN (5 mL) and EtOAc (5 mL) at 20° C. under air. The resulting mixture was stirred at 20° C. for 4 h. The reaction mixture was concentrated, and the residue was dissolved in EtOAc (100 mL), and washed sequentially with sat $NaHCO_3$(25 mL), sat brine (50 mL), and water (25 mL). The organic layer was dried over $Na_2SO_4$, filtered and evaporated. The crude product was purified by preparative HPLC, PrepMethod F, (gradient: 12-37%) to give the title compound (70 mg, 23%) as a red solid; HRMS (ESI) m/z $[M+H]^+$ calcd for $C_{22}H_{26}N_5O_3S$: 440.1750. found: 440.1744; $^1H$ NMR (500 MHz, DMSO-$d_6$) δ 9.14 (t, 1H), 8.78 (d, 1H), 7.95 (d, 1H), 7.84-7.71 (m, 2H), 7.57 (d, 1H), 5.33 (dd, 1H), 4.91 (d, 1H), 4.72 (d, 1H), 4.40-4.27 (m, 2H), 3.79-3.71 (m, overlapping with solvent), 3.47-3.33 (m, 3H), 3.29 (s, 3H), 3.22-3.07 (m, 2H), 2.03-1.94 (m, 2H), 1.60-1.50 (m, 2H).

Example 9: (R)—N-(2-(4-Cyanothiazolidin-3-yl)-2-oxoethyl)-8-methyl-6-(4-methoxy-piperidin-1-yl) morpholinoquinoline-4-carboxamide

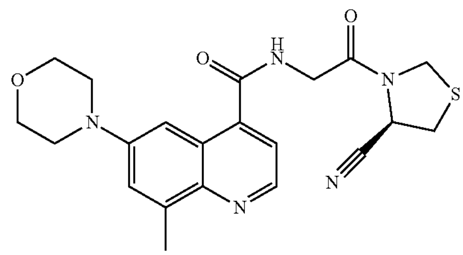 [SMILES: Cc1cc(N2CCOCC2)cc2c(C(=O)NCC(=O)N3CSC[C@H]3C#N)ccnc12]

DIPEA (0.205 mL, 1.18 mmol) was added to 8-methyl-6-morpholinoquinoline-4-carboxylic acid Intermediate 25 (160 mg, 0.59 mmol), (R)-3-glycylthiazolidine-4-carbonitrile hydrochloride Intermediate 4 (151 mg, 0.88 mmol) and HATU (223 mg, 0.59 mmol) in MeCN (5 mL) and EtOAc (5 mL) at 20° C. The resulting mixture was stirred at 20° C. for 3 h. The reaction mixture was concentrated and diluted with EtOAc (75 mL), and washed sequentially with sat $NaHCO_3$ (20 mL), water (15 mL), and sat brine (20 mL). The organic layer was dried over $Na_2SO_4$, filtered and evaporated to afford crude product. The crude product was purified by preparative HPLC, PrepMethod F, (gradient: 12-35%) to give the title compound (50 mg, 20%) as a red solid; HRMS (ESI) m/z $[M+H]^+$ calcd for $C_{21}H_{24}N_5O_3S$: 426.1594. found: 426.1600; $^1H$ NMR (400 MHz, DMSO-$d_6$) δ 9.17 (t, 1H), 8.81 (d, 1H), 7.77 (s, 1H), 7.68-7.62 (m, 2H), 5.32 (dd, 1H), 4.90 (d, 1H), 4.71 (d, 1H), 4.42-4.25 (m, 2H), 3.79 (t, 4H), 3.46-3.32 (m, overlapping with solvent), 2.73 (s, 3H).

Example 10: (R)—N-(2-(4-Cyanothiazolidin-3-yl)-2-oxoethyl)-7-methyl-6-morpholino-quinoline-4-carboxamide

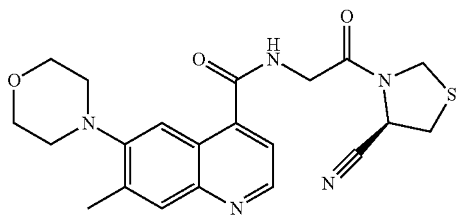 [SMILES: Cc1cc2nccc(C(=O)NCC(=O)N3CSC[C@H]3C#N)c2cc1N1CCOCC1]

DIPEA (0.31 mL, 1.8 mmol) was added to 7-methyl-6-morpholinoquinoline-4-carboxylic acid Intermediate 30 (160 mg, 0.59 mmol), (R)-3-glycylthiazolidine-4-carbonitrile hydrochloride Intermediate 4 (151 mg, 0.88 mmol) and T3P (50% solution in EtOAc, 712 mg, 2.24 mmol) in EtOAc (1 mL) and MeCN (1 mL) at 20° C. under $N_2$ (g). The resulting mixture was stirred at 20° C. for 4 h. The reaction mixture was concentrated, and the residue was dissolved in EtOAc (75 mL), and washed sequentially with sat brine (25 mL) and water (25 mL). The organic layer was dried over $Na_2SO_4$, filtered, and evaporated. The crude product was purified by preparative HPLC, PrepMethod F, (gradient: 12-35%) to give the title compound (50 mg, 20%) as a yellow solid; HRMS (ESI) m/z $[M+H]^+$ calcd for $C_{21}H_{24}N_5O_3S$: 426.1594. found: 426.1582; $^1H$ NMR (400 MHz, DMSO-$d_6$) δ 9.05 (t, 1H), 8.80 (d, 1H), 7.91 (s, 1H), 7.88 (s, 1H), 7.45 (d, 1H), 5.35 (dd, 1H), 4.90 (d, 1H), 4.72 (d, 1H), 4.32 (t, 2H), 3.79 (t, 4H), 3.45-3.35 (m, overlapping with solvent), 3.10-2.90 (m, 4H), 2.54-2.46 (m, overlapping with solvent).

Example 11: (R)—N-(2-(4-Cyanothiazolidin-3-yl)-2-oxoethyl)-6-(2-oxopyrrolidin-1-yl)-quinoline-4-carboxamide

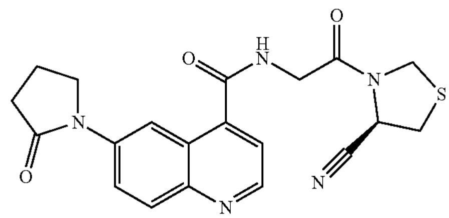 [SMILES: N#C[C@@H]1CSCN1C(=O)CNC(=O)c1ccnc2ccc(N3CCCC3=O)cc12]

DIPEA (1.8 mL, 10 mmol) was added to a stirred suspension of 6-(2-oxopyrrolidin-1-yl)quinoline-4-carboxylic acid Intermediate 32 (224 mg, 0.52 mmol), (R)-3-glycylthiazolidine-4-carbonitrile hydrochloride Intermediate 4 (214 mg, 1.03 mmol), HOBt (395 mg, 2.58 mmol) and EDC (494 mg, 2.58 mmol) in MeCN (5 mL) and EtOAc (5 mL) at 29° C. The resulting solution was stirred at 50° C. for 2 h. The solvent was removed under reduced pressure. The residue was dissolved in a mixture of $NaHCO_3$(aq, 40 mL) and EtOAc (80 mL). The phases were separated and the aqueous layer was extracted with EtOAc (5×75 mL). The organic layers were combined and washed with water (3×50 mL). The organic layer was dried over $Na_2SO_4$, filtered and evaporated to afford crude product. The crude product was purified by preparative HPLC, PrepMethod F, (gradient: 15-30%) to give the title compound (90 mg, 43%) as a white solid; HRMS (ESI) m/z $[M+H]^+$ calcd for $C_{24}H_{20}N_5O_3S$: 410.1282. found: 410.1288; $^1H$ NMR (300 MHz, DMSO-$d_6$) δ 9.10 (t, 1H), 8.90 (d, 1H), 8.55 (dd, 1H), 8.31-8.16 (m, 1H), 8.07 (d, 1H), 7.56 (d, 1H), 5.43-5.24 (m, 1H), 4.90 (m, 1H), 4.77 (d, 1H), 4.50-4.16 (m, 2H), 4.07-3.89 (m, 2H), 3.70-3.20 (m, overlapping with solvent) 2.57 (t, 2H), 2.22-2.02 (m, 2H).

Example 12: (R)—N-(2-(4-Cyanothiazolidin-3-yl)-2-oxoethyl)-6-(3,3-dimethyl-2-oxopyrrolidin-1-yl) quinoline-4-carboxamide

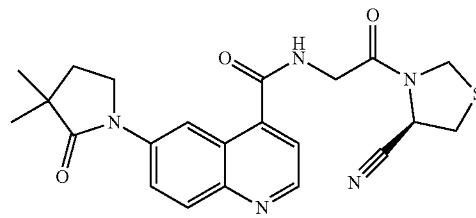

DIPEA (0.22 mL, 1.3 mmol) was added to a mixture of 6-(3,3-dimethyl-2-oxopyrrolidin-1-yl)quinoline-4-carboxylic acid Intermediate 34 (120 mg, 0.42 mmol), (R)-3-glycylthiazolidine-4-carbonitrile hydrochloride Intermediate 4 (108 mg, 0.63 mmol) and T3P (50% solution in EtOAc, 1.07 g, 1.69 mmol) in MeCN (5 mL) and EtOAc (5 mL) at 20° C. under $N_2$ (g). The resulting mixture was stirred at 20° C. for 3 h. The reaction mixture was concentrated and diluted with EtOAc (100 mL), and washed sequentially with water (20 mL) and sat brine (20 mL). The organic layer was dried over $Na_2SO_4$, filtered, and evaporated to afford crude product. The crude product was purified by preparative HPLC, PrepMethod F, (gradient: 25-40%) to afford the title compound (100 mg, 54%) as a yellow solid; HRMS (ESI) m/z $[M+H]^+$ calcd for $C_{22}H_{24}N_5O_3S$: 438.1594. found: 438.1616; $^1H$ NMR (400 MHz, $CD_3OD$) δ 8.93-8.85 (m, 1H), 8.66-8.59 (m, 1H), 8.45 (d, 1H), 8.10 (d, 1H), 7.68 (d, 1H), (dd, 1H), 4.95-4.83 (m, overlapping with solvent), 4.79 (d, 1H), 4.43 (s, 2H), 4.17-4.00 (m, 2H), 3.60-3.35 (m, 2H), 2.12 (t, 2H), 1.27 (s, 3H), 1.26 (s, 3H).

Example 13: (R)—N-(2-(4-Cyanothiazolidin-3-yl)-2-oxoethyl)-6-(5,5-dimethyl-2-oxooxazolidin-3-yl)quinoline-4-carboxamide

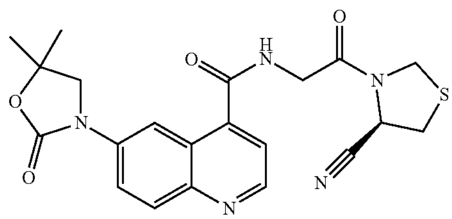 [SMILES: CC1(C)CN(c2ccc3nccc(C(=O)NCC(=O)N4CSC[C@H]4C#N)c3c2)C(=O)O1]

DIPEA (0.37 mL, 2.10 mmol) was added to a mixture of 6-(5,5-dimethyl-2-oxooxazolidin-3-yl)quinoline-4-carboxylic acid Intermediate 36 (200 mg, 0.70 mmol), (R)-3-glycylthiazolidine-4-carbonitrile hydrochloride Intermediate 4 (179 mg, 1.05 mmol) and T3P (50% solution in EtOAc, 1.78 g, 2.79 mmol) in EtOAc (8 mL) and MeCN (8 mL) at 20° C. under air. The resulting mixture was stirred at 25° C. for 3 h. The reaction mixture was concentrated and diluted with EtOAc (75 mL), and washed sequentially with water (20 mL) and sat brine (25 mL). The organic layer was dried over $Na_2SO_4$, filtered and evaporated to afford crude product. The crude product was purified by preparative HPLC, PrepMethod B, (gradient: 20-40%) to afford the title compound (70 mg, 23%) as a white solid; HRMS (ESI) m/z $[M+H]^+$ calcd for $C_{21}H_{22}N_5O_4S$: 440.1388. found: 440.1380; $^1H$ NMR (400 MHz, DMSO-$d_6$) δ 9.12 (t, 1H), 8.90 (d, 1H), 8.57 (dd, 1H), 8.21 (d, 1H), 8.10 (d, 1H), 7.55 (d, 1H), 5.33 (dd, 1H), 4.91 (d, 1H), 4.72 (d, 1H), 4.37-4.31 (m, 2H), 4.10-3.99 (m, 2H), 3.50-3.33 (m, overlapping with solvent), 1.55 (s, 3H), 1.52 (s, 3H).

Example 14: (R)—N-(2-(4-Cyanothiazolidin-3-yl)-2-oxoethyl)-6-(2-oxopiperidin-1-yl)-quinoline-4-carboxamide

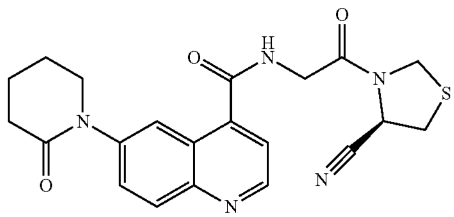 [SMILES: N#C[C@@H]1CSCN1C(=O)CNC(=O)c1ccnc2ccc(N3CCCCC3=O)cc12]

DIPEA (230 mg, 1.78 mmol) was added to a stirred mixture of 6-(2-oxopiperidin-1-yl)quinoline-4-carboxylic acid Intermediate 38 (120 mg, 0.44 mmol), (R)-3-glycylthiazolidine-4-carbonitrile hydrochloride Intermediate 4 (152 mg, 0.89 mmol) and T3P (1.13 mL, 50% in EtOAc) in DMF (5 mL). The resulting solution was stirred at 25° C. for 6 h. The solvent was removed under reduced pressure. The residue was purified by preparative TLC (DCM:MeOH, 19:1), followed by further purification by preparative HPLC, PrepMethod B, (gradient 13-33%) to give the title compound (48 mg, 26%) as a white solid; HRMS (ESI) m/z $[M+H]^+$ calcd for $C_{21}H_{22}N_5O_3S$: 424.1438. found: 424.1444; $^1H$ NMR (300 MHz, DMSO-$d_6$) δ 9.12 (t, 1H), 8.95 (d, 1H), 8.28 (d, 1H), 8.02 (d, 1H), 7.78 (dd, 1H), 7.56 (d, 1H), 5.33 (dd, 1H), 4.88 (d, 1H), 4.70 (d, 1H), 4.31 (d, 2H), 3.85-3.65 (m, 2H), 3.43-3.34 (m, overlapping with solvent), 2.46-2.35 (m, overlapping with solvent), 2.00-1.78 (m, 4H).

Example 15: (R)—N-(2-(4-Cyanothiazolidin-3-yl)-2-oxoethyl)-6-(3,3-dimethyl-2-oxopiperidin-1-yl)quinoline-4-carboxamide

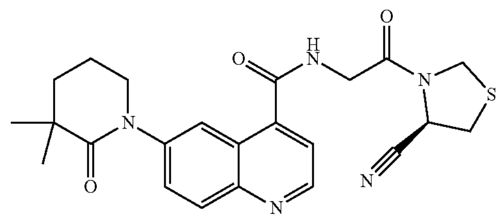 [SMILES: CC1(C)CCCN(c2ccc3nccc(C(=O)NCC(=O)N4CSC[C@H]4C#N)c3c2)C1=O]

DIPEA (104 mg, 0.80 mmol) was added to a mixture of 6-(3,3-dimethyl-2-oxopiperidin-1-yl)quinoline-4-carboxylic acid Intermediate 40 (60 mg, 0.20 mmol), (R)-3-glycylthiazolidine-4-carbonitrile hydrochloride Intermediate 4 (69 mg, 0.40 mmol) and T3P (0.51 mL, 50% in EtOAc) in DMF (2 mL). The resulting solution was stirred at 25° C. for 6 h. The solvent was removed under reduced pressure. The residue was purified by preparative TLC (DCM:MeOH, 18:1), followed by further purification by preparative HPLC, PrepMethod B, (gradient 22-42%) to give the title compound (25 mg, 28%) as a white solid; HRMS (ESI) m/z $[M+H]^+$ calcd for $C_{23}H_{26}N_5O_3S$: 452.1750. found: 452.1752; $^1H$ NMR (300 MHz, DMSO-$d_6$) δ 9.12 (t, 1H), 8.94 (d, 1H), 8.29 (d, 1H), 8.01 (d, 1H), 7.69 (dd, 1H), 7.55 (d, 1H), 5.32 (dd, 1H), 4.88 (d, 1H), 4.70 (d, 1H), 4.31 (d, 2H), 3.77 (t, 2H), 3.43-3.34 (m, overlapping with solvent), 2.04-1.91 (m, 2H), 1.88-1.75 (m, 2H), 1.24 (s, 3H), 1.24 (s, 3H).

Example 16: (R)—N-(2-(4-Cyanothiazolidin-3-yl)-2-oxoethyl)-6-(2,2-dimethyl-3-oxomorpholino)quinoline-4-carboxamide

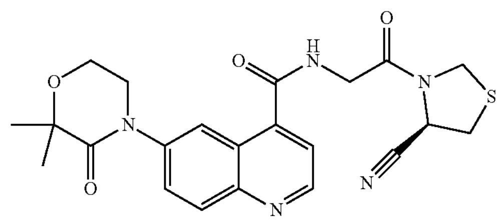 [SMILES: CC1(C)OCCN(c2ccc3nccc(C(=O)NCC(=O)N4CSC[C@H]4C#N)c3c2)C1=O]

DIPEA (0.88 mL, 5.1 mmol) was added to a mixture of 6-(2,2-dimethyl-3-oxomorpholino)quinoline-4-carboxylic acid Intermediate 42 (304 mg, 1.01 mmol), (R)-3-glycylthiazolidine-4-carbonitrile hydrochloride Intermediate 4 (260 mg, 1.52 mmol) and HATU (1.15 g, 3.04 mmol) in EtOAc (10 mL) and MeCN (10 mL) at 20° C. The resulting mixture was stirred at 25° C. for 6 h. The reaction mixture was diluted with sat $NaHCO_3$. The phases were separated and the aqueous layer was extracted with DCM (3×100 mL). The combined organic phases were dried over $Na_2SO_4$, filtered and evaporated. The residue was purified by preparative TLC (DCM:MeOH, 17:1), followed by further purification by preparative HPLC, PrepMethod C, (gradient 17-27%) to give the title compound (200 mg, 44%) as a white solid; HRMS (ESI) m/z $[M+H]^+$ calcd for $C_{22}H_{24}N_5O_4S$: 454.1544. found: 454.1542; $^1H$ NMR (300 MHz, DMSO-$d_6$) δ 9.16 (t, 1H), 8.99 (d, 1H), 8.42 (d, 1H), 8.08 (d 1H), 7.86 (dd, 1H), 7.60 (d, 1H), 5.45-5.25 (m, 1H), 4.90 (d, 1H), 4.71 (d, 1H), 4.34 (d, 2H), 4.11-3.96 (m, 2H), 3.94-3.80 (m, 2H), 3.59-3.35 (m, overlapping with solvent), 1.47 (s, 6H).

Example 17: (R)—N-(2-(4-Cyanothiazolidin-3-yl)-2-oxoethyl)-6-(2-azaspiro[3.3]heptan-2-yl)quinoline-4-carboxamide

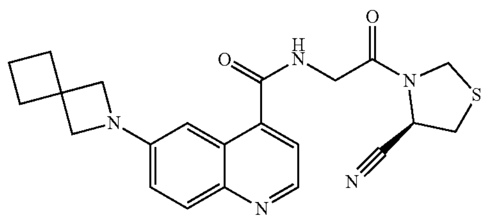 [SMILES: N#C[C@@H]1CSCN1C(=O)CNC(=O)c1ccnc2ccc(N3CC4(CCC4)C3)cc12]

DIPEA (289 mg, 2.24 mmol) was added to a mixture of 6-(2-azaspiro[3.3]heptan-2-yl)quinoline-4-carboxylic acid Intermediate 44 (100 mg, 0.37 mmol), (R)-3-glycylthiazolidine-4-carbonitrile hydrochloride Intermediate 4 (96 mg, 0.56 mmol) and HATU (283 mg, 0.75 mmol) in MeCN (5 mL) and EtOAc (5 mL). The reaction was stirred under an atmosphere of air at 25° C. for 3 h. The solvent was removed under reduced pressure. The crude product was purified by preparative HPLC, PrepMethod F, (gradient 20-40%) to give the title compound (44 mg, 28%) as a red solid; HRMS (ESI) m/z $[M+H]^+$ calcd for $C_{22}H_{24}N_5O_2S$: 422.1646. found: 422.1650; $^1H$ NMR (300 MHz, DMSO-$d_6$) δ 9.20-9.05 (m, 1H), 8.75 (d, 1H), 7.96 (d, 1H), 7.61 (d, 1H), 7.30-7.15 (m, 2H), 5.40-5.30 (m, 1H), 4.91 (d, 1H), 4.73 (d, 1H), 4.34 (d, 2H), 3.99 (s, 4H), 3.48-3.32 (m, 2H), 2.21 (t, 4H), 1.95-1.75 (m, 2H).

Example 18: (R)—N-(2-(4-Cyanothiazolidin-3-yl)-2-oxoethyl)-6-(3,3-dimethyl-1-oxa-6-azaspiro[3.3]heptan-6-yl)quinoline-4-carboxamide

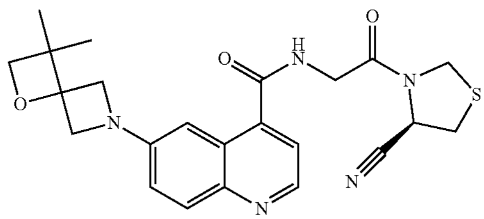 [SMILES: CC1(C)COC12CN(c1ccc3nccc(C(=O)NCC(=O)N4CSC[C@H]4C#N)c3c1)C2]

DIPEA (0.50 mL, 2.9 mmol) was added to a mixture of 6-(3,3-dimethyl-1-oxa-6-azaspiro[3.3]heptan-6-yl)quinoline-4-carboxylic acid Intermediate 46 (170 mg, 0.57 mmol), (R)-3-glycylthiazolidine-4-carbonitrile hydrochloride Intermediate 4 (178 mg, 0.85 mmol), EDC (218 mg, 1.14 mmol) and HOBt (175 mg, 1.14 mmol) in MeCN (5 mL) and EtOAc (5 mL). The reaction was stirred at 50° C. for 3 h. The solvent was removed under reduced pressure. The residue was diluted with EtOAc, and washed with water. The organic layer was dried over $Na_2SO_4$, filtered and evaporated. The crude product was purified by preparative HPLC, PrepMethod P, (gradient 15-25%) to give the title compound (160 mg, 62%) as a yellow solid; HRMS (ESI) m/z $[M+H]^+$ calcd for $C_{23}H_{26}N_5O_3S$: 452.1750. found: 452.1748; $^1H$ NMR (300 MHz, DMSO-$d_6$) δ 8.95 (t, 1H), 8.62 (d, 1H), 7.87 (d, 1H), 7.38 (d, 1H), 7.28 (d, 1H), 7.13 (dd, 1H), 5.35-5.25 (m, 1H), 4.88 (d, 1H), 4.70 (d, 1H), 4.35-4.20 (m, 4H), 4.16 (s, 2H), 3.94-3.83 (m, 2H), 3.42-3.34 (m, 2H), 1.22 (s, 6H).

Example 19: (R)—N-(2-(4-Cyanothiazolidin-3-yl)-2-oxoethyl)-6-(1-azaspiro[3.3]heptan-1-yl)quinoline-4-carboxamide

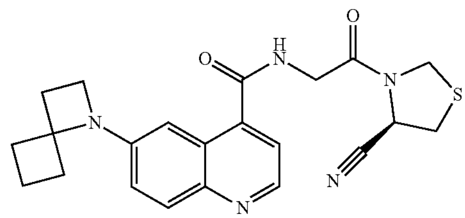 [SMILES: N#C[C@@H]1CSCN1C(=O)CNC(=O)c1ccnc2ccc(N3CCC34CCC4)cc12]

DIPEA (0.65 mL, 3.7 mmol) was added to a mixture of 6-(1-azaspiro[3.3]heptan-1-yl)quinoline-4-carboxylic acid Intermediate 48 (200 mg, 0.75 mmol), (R)-3-glycylthiazolidine-4-carbonitrile hydrochloride Intermediate 4 (232 mg, 1.12 mmol), EDC (286 mg, 1.49 mmol) and HOBt (228 mg, 1.49 mmol) in EtOAc (6 mL) and MeCN (6 mL). The mixture was stirred at 45° C. for 5 h. The solvent was removed under reduced pressure. The residue was dissolved in EtOAc, and washed with water. The organic layer was dried over $Na_2SO_4$, filtered and evaporated. The crude product was purified by preparative HPLC, PrepMethod B, (gradient: 28-48%) to afford the title compound (220 mg, 70%) as a yellow solid; HRMS (ESI) m/z $[M+H]^+$ calcd for $C_{22}H_{24}N_5O_2S$: 422.1646. found: 422.1626; $^1H$ NMR (300 MHz, $CD_3OD$) δ 8.55 (d, 1H), 7.89 (d, 1H), 7.49 (d, 1H), 7.37 (dd, 1H), 7.28 (d, 1H), 5.40-5.25 (m, 1H), 4.85-4.63 (m, 2H), 4.37 (d, 2H), 3.87 (t, 2H), 3.51-3.34 (m, 2H), 3.04-2.88 (m, 2H), 2.51 (t, 2H), 2.17-2.03 (m, 2H), 2.02-1.70 (m, 2H).

Example 20: (R)—N-(2-(4-Cyanothiazolidin-3-yl)-2-oxoethyl)-6-(2,2-dimethylazetidin-1-yl)quinoline-4-carboxamide

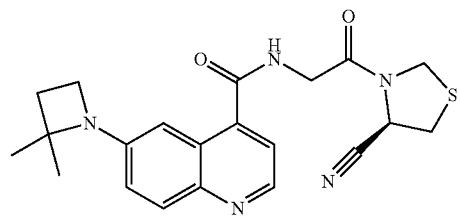 [SMILES: CC1(C)CCN1c1ccc2nccc(C(=O)NCC(=O)N3CSC[C@H]3C#N)c2c1]

TEA (0.62 mL, 4.5 mmol) was added to a stirred suspension of 6-(2,2-dimethylazetidin-1-yl)quinoline-4-carboxylic acid Intermediate 50 (114 mg, 0.44 mmol), (R)-3-glycylthiazolidine-4-carbonitrile hydrochloride Intermediate 4 (185 mg, 0.89 mmol), HOBt (341 mg, 2.22 mmol) and EDC (426 mg, 2.22 mmol) in EtOAc (13 mL) and MeCN (13 mL) at 10° C. The resulting suspension was stirred at 10° C. overnight. The solvent was removed under reduced pressure. The residue was dissolved with a mixture of a solution of $NaHCO_3$ (50 mL) and EtOAc (100 mL). The aqueous layer was extracted with EtOAc (4×100 mL). The organic layers were combined and washed with water (2×50 mL). The aqueous layers were combined and extracted with EtOAc (2×25 mL). The organic layers were combined, dried over $Na_2SO_4$, filtered and evaporated. The crude product was purified by preparative HPLC, PrepMethod B, (gradient: 34-48%) to afford the title compound (82 mg, 45%) as a yellow solid; HRMS (ESI) m/z $[M+H]^+$ calcd for $C_{21}H_{24}N_5O_2S$: 410.1646. found: 410.1640; $^1H$ NMR (300 MHz, DMSO-$d_6$) δ 9.00-8.89 (m, 1H), 8.58 (d, 1H), 7.83 (d, 1H), 7.37 (d, 1H), 7.14 (dd, 1H), 7.09 (d, 1H), 5.30 (dd, 1H), 4.88 (d, 1H), 4.71 (d, 1H), 4.28 (d, 2H), 3.75 (t, 2H), 3.35 (m, overlapping with solvent), 2.18-2.03 (m, 1H), 1.49 (s, 3H), 1.48 (s, 3H).

Example 21: (R)—N-(2-(4-Cyanothiazolidin-3-yl)-2-oxoethyl)-6-(3-fluoroazetidin-1-yl)quinoline-4-carboxamide

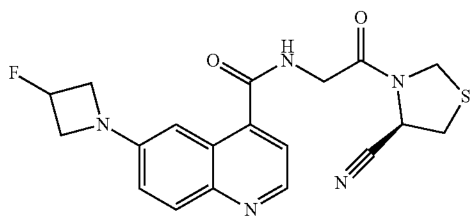 [SMILES: N#C[C@@H]1CSCN1C(=O)CNC(=O)c1ccnc2ccc(N3CC(F)C3)cc12]

DIPEA (0.53 mL, 3.1 mmol) was added to a mixture of 6-(3-fluoroazetidin-1-yl)quinoline-4-carboxylic acid Intermediate 52 (150 mg, 0.61 mmol), (R)-3-glycylthiazolidine-4-carbonitrile hydrochloride Intermediate 4 (253 mg, 1.22 mmol), EDC (234 mg, 1.22 mmol) and HOBt (187 mg, 1.22 mmol) in EtOAc (5 mL) and MeCN (5 mL). The mixture was stirred at rt for 10 h. The solvent was removed under reduced pressure. The residue was dissolved in EtOAc, and washed with water. The organic layer was dried over $Na_2SO_4$, filtered and evaporated. The crude product was purified by preparative HPLC, PrepMethod C, (gradient: 17-29%) to afford the title compound (110 mg, 45%) as a yellow solid; HRMS (ESI) m/z $[M+H]^+$ calcd for $C_{19}H_{19}FN_5O_2S$: 400.1238. found: 400.1246; $^1H$ NMR (300 MHz, $CD_3OD$) δ 8.60 (d, 1H), 7.91 (d, 1H), 7.50 (d, 1H), 7.32 (d, 1H), 7.18 (dd, 1H), 5.64-5.32 (m, 2H), 4.83-4.69 (m, overlapping with solvent), 4.50-4.25 (m, 4H), 4.20-4.00 (m, 2H), 3.52-3.34 (m, overlapping with solvent).

Example 22: (R)—N-(2-(4-Cyanothiazolidin-3-yl)-2-oxoethyl)-6-(3,3-dimethylazetidin-1-yl)quinoline-4-carboxamide

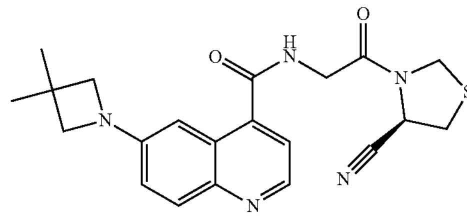 [SMILES: N#C[C@@H]1CSCN1C(=O)CNC(=O)c1ccnc2ccc(N3CC(F)(F)C3)cc12]

DIPEA (0.58 mL, 3.3 mmol) was added to a suspension of 6-(3,3-dimethylazetidin-1-yl)quinoline-4-carboxylic acid Intermediate 54 (170 mg, 0.66 mmol), (R)-3-glycylthiazolidine-4-carbonitrile hydrochloride Intermediate 4 (344 mg, 1.66 mmol), EDC (254 mg, 1.33 mmol) and HOBt (203 mg, 1.33 mmol) in MeCN (10 mL) and EtOAc (10 mL). The mixture was stirred at rt for 20 h. The solvent was removed under reduced pressure. The residue was dissolved in EtOAc, and washed with water. The organic layer was dried over $Na_2SO_4$, filtered and evaporated. The crude product was purified by preparative HPLC, PrepMethod C, (gradient: 19-30%) to afford the title compound (90 mg, 33%) as a yellow solid; HRMS (ESI) m/z $[M+H]^+$ calcd for $C_{21}H_{24}N_5O_2S$: 410.1646. found: 410.1642; $^1H$ NMR (300 MHz, $CD_3OD$) δ 8.54 (d, 1H), 7.87 (d, 1H), 7.48 (d, 1H), 7.21-7.07 (m, 2H), 5.40-5.28 (m, 1H), 4.82-4.59 (m, 2H), 4.38 (d, 2H), 3.74 (s, 4H), 3.53-3.35 (m, 2H), 1.35 (s, 6H).

Example 23: (R)—N-(2-(4-Cyanothiazolidin-3-yl)-2-oxoethyl)-6-(3,3-difluoroazetidin-1-yl)quinoline-4-carboxamide

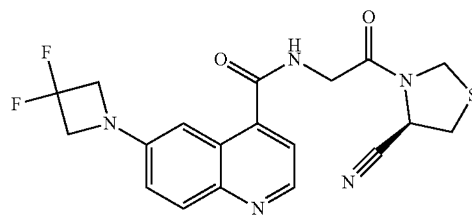

DIPEA (1.38 mL, 7.87 mmol) was added to 6-(3,3-difluoroazetidin-1-yl)quinoline-4-carboxylic acid Intermediate 56 (104 mg, 0.39 mmol), (R)-3-glycylthiazolidine-4-carbonitrile hydrochloride Intermediate 4 (123 mg, 0.59 mmol), HOBt (603 mg, 3.94 mmol) and EDC (755 mg, 3.94 mmol) in EtOAc (5 mL) and MeCN (5 mL) at 10° C. The resulting solution was stirred at 10° C. overnight under $N_2$ (g). The solvent was removed under reduced pressure. The residue was diluted with sat $NaHCO_3$ (50 mL), and extracted with EtOAc (6×50 mL). The organic layers were combined and washed with sat brine (5×200 mL). The organic layer was dried over $Na_2SO_4$, filtered and evaporated. The crude product was purified by preparative HPLC, PrepMethod P, (gradient: 18-45%) to afford the title compound (116 mg, 70%) as a yellow solid; HRMS (ESI) m/z $[M+H]^+$ calcd for $C_{19}H_{18}F_2N_5O_2S$: 418.1144. found: 418.1158; $^1H$ NMR (300 MHz, DMSO-$d_6$) δ 9.05-8.95 (m, 1H), 8.72 (d, 1H), 7.96 (d, 1H), 7.55 –7.38 (m, 2H), 7.25 (dd, 1H), 5.45-5.30 (m, 1H), 4.90 (d, 1H), 4.72 (d, 1H), 4.44 (t, 4H), 4.32 (d, 2H), 3.42-3.35 (m, overlapping with solvent).

Example 24: (R)—N-(2-(4-Cyanothiazolidin-3-yl)-2-oxoethyl)-6-(3-fluoro-3-methyl-azetidin-1-yl)quinoline-4-carboxamide

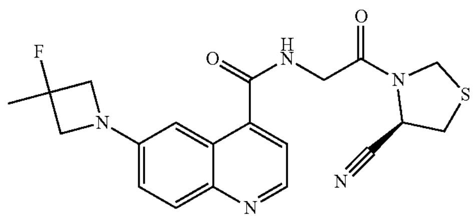 [SMILES: CC1(F)CN(c2ccc3nccc(C(=O)NCC(=O)N4CSC[C@H]4C#N)c3c2)C1]

DIPEA (0.43 mL, 2.5 mmol) was added to 6-(3-fluoro-3-methylazetidin-1-yl)quinoline-4-carboxylic acid Intermediate 58 (65 mg, 0.25 mmol), (R)-3-glycylthiazolidine-4-carbonitrile hydrochloride Intermediate 4 (103 mg, 0.50 mmol) and TBTU (282 mg, 0.74 mmol) in MeCN (6 mL) and EtOAc (6 mL) at 10° C. The resulting solution was stirred at 40° C. for 4 h under $N_2$ (g). The solvent was removed under reduced pressure. The reaction mixture was diluted with sat $NaHCO_3$ (50 mL), and extracted with EtOAc (6×50 mL). The organic layers were combined and washed with sat brine (5×50 mL). The organic layer was dried over $Na_2SO_4$, filtered and evaporated. The crude product was purified by preparative HPLC, PrepMethod D, (gradient: 20-45%) to afford the title compound (57 mg, 56%) as an orange solid; HRMS (ESI) m/z $[M+H]^+$ calcd for $C_{24}H_{21}FN_5O_2S$: 414.1394. found: 414.1394; $^1H$ NMR (300 MHz, DMSO-$d_6$) δ 9.05-8.96 (m, 1H), 8.66 (d, 1H), 7.91 (d, 1H), 7.42 (d, 1H), 7.31 (d, 1H), 7.17 (dd, 1H), 5.40-5.25 (m, 1H), 4.90 (d, 1H), 4.72 (d, 1H), 4.31 (d, 2H), 4.20-4.00 (m, 4H), 3.45-3.34 (m, overlapping with solvent), 1.66 (d, 3H).

Example 25: (R)—N-(2-(4-Cyanothiazolidin-3-yl)-2-oxoethyl)-6-(3-methylazetidin-1-yl)-quinoline-4-carboxamide

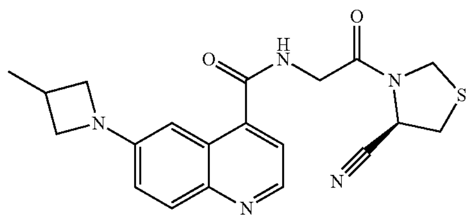 [SMILES: CC1CN(c2ccc3nccc(C(=O)NCC(=O)N4CSC[C@H]4C#N)c3c2)C1]

TEA (0.83 g, 8.3 mmol) was added to a mixture of 6-(3-methylazetidin-1-yl)quinoline-4-carboxylic acid Intermediate 60 (200 mg, 0.83 mmol), (R)-3-glycylthiazolidine-4-carbonitrile hydrochloride Intermediate 4 (141 mg, 0.83 mmol), EDC (317 mg, 1.65 mmol) and HOBt (253 mg, 1.65 mmol) in EtOAc (2.5 mL) and MeCN (2.5 mL). The resulting mixture was stirred at 25° C. for 3 h. The reaction mixture was diluted with EtOAc (20 mL), and washed with sat brine (3×50 mL). The organic layer was dried over $Na_2SO_4$, filtered and evaporated. The crude product was purified by preparative HPLC, PrepMethod F, (gradient: 15-30%) to afford the title compound (190 mg, 58%) as a red solid; HRMS (ESI) m/z $[M+H]^+$ calcd for $C_{20}H_{22}N_5O_2S$: 396.1488. found: 396.1490; $^1H$ NMR (300 MHz, $CD_3OD$) δ 8.69 (d, 1H), 7.99 (d, 1H), 7.80 (d, 1H), 7.37 (dd, 1H), 7.34-7.27 (m, 1H), 5.40-5.25 (m, 1H), 4.83-4.65 (m, overlapping with solvent), 4.44 (s, 2H), 4.35-4.18 (m, 3H), 3.77-3.67 (m, 2H), 3.36 (m, overlapping with solvent), 3.00-2.85 (m, 1H), 1.35 (d, 3H).

Example 26: (R)—N-(2-(4-Cyanothiazolidin-3-yl)-2-oxoethyl)-6-(3-(trifluoromethyl)-azetidin-1-yl)quinoline-4-carboxamide

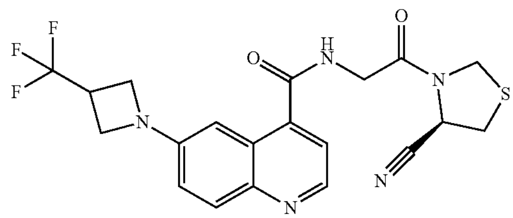 [SMILES: N#C[C@@H]1CSCN1C(=O)CNC(=O)c1ccnc2ccc(N3CC(C(F)(F)F)C3)cc12]

DIPEA (0.59 mL, 3.4 mmol) was added to a mixture of 6-(3-(trifluoromethyl)azetidin-1-yl)quinoline-4-carboxylic acid Intermediate 62 (100 mg, 0.34 mmol), (R)-3-glycylthiazolidine-4-carbonitrile hydrochloride Intermediate 4 (116 mg, 0.68 mmol) and HATU (261 mg, 0.68 mmol) in EtOAc (2 mL) and MeCN (2 mL). The resulting mixture was stirred at 25° C. for 4 h. The solvent was removed under reduced pressure. The crude product was purified by preparative HPLC, PrepMethod F, (gradient: 19-30%) to afford the title compound (60 mg, 40%) as a red solid; HRMS (ESI) m/z $[M+H]^+$ calcd for $C_{20}H_{19}F_3N_5O_2S$: 450.1206. found: 450.1194; $^1H$ NMR (400 MHz, $CD_3OD$) δ 8.79 (brs, 1H), 8.07 (d, 1H), 7.85 (d, 1H), 7.60-7.40 (m, 2H), 5.45-5.25 (m, 1H), 4.79 (d, overlapping with solvent), 4.52-4.35 (m, 4H), 4.28-4.15 (m, 2H), 3.80-3.60 (m, 1H), 3.45-3.34 (m, 2H).

Example 27: (R)—N-(2-(4-Cyanothiazolidin-3-yl)-2-oxoethyl)-6-(3-(fluoromethyl)-3-methylazetidin-1-yl)quinoline-4-carboxamide

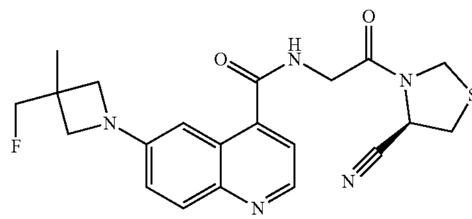

DIPEA (0.25 mL, 1.4 mmol) was added to a mixture of 6-(3-(fluoromethyl)-3-methylazetidin-1-yl)quinoline-4-carboxylic acid Intermediate 64 (268 mg, 0.28 mmol), (R)-3-glycylthiazolidine-4-carbonitrile hydrochloride Intermediate 4 (118 mg, 0.57 mmol), HOBt (192 mg, 1.42 mmol) and EDC (333 mg, 1.74 mmol) in MeCN (3 mL) and EtOAc (3 mL) at 13° C. The resulting solution was stirred at 13° C. overnight under $N_2$ (g). The solvent was removed under reduced pressure. The residue was diluted with sat $NaHCO_3$ (100 mL) and extracted with EtOAc (5×100 mL). The organic layers were combined and washed with brine (3×50 mL). The organic layer was dried over $Na_2SO_4$, filtered and evaporated. The crude product was purified by preparative HPLC, PrepMethod C, (gradient 17-30%) to afford the title compound (66 mg, 54%) as an orange solid; HRMS (ESI) m/z $[M+H]^+$ calcd for $C_{21}H_{23}FN_5O_2S$: 428.1550. found: 428.1538; $^1H$ NMR (400 MHz, DMSO-$d_6$) δ 8.94 (t, 1H), 8.63 (d, 1H), 7.89 (d, 1H), 7.41 (d, 1H), 7.23-7.16 (m, 1H), 7.12 (dd, 1H), 5.40-5.25 (m, 1H), 4.89 (d, 1H), 4.72 (d, 1H), 4.50 (d, 2H), 4.30 (d, 2H), 3.88 (d, 2H), 3.68 (dd, 2H), 3.44-3.34 (m, overlapping with solvent), 1.35 (s, 3H).

Example 28: (R)—N-(2-(4-Cyanothiazolidin-3-yl)-2-oxoethyl)-6-(3-(difluoromethyl)-azetidin-1-yl) quinoline-4-carboxamide

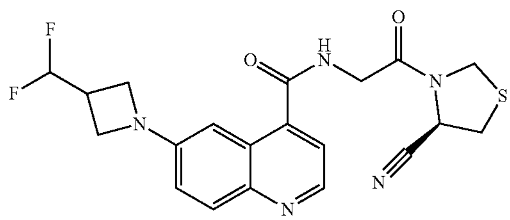 [SMILES: N#C[C@@H]1CSCN1C(=O)CNC(=O)c1ccnc2ccc(N3CC(C(F)F)C3)cc12]

DIPEA (0.19 mL, 1.1 mmol) was added to a mixture of 6-(3-(difluoromethyl)azetidin-1-yl)quinoline-4-carboxylic acid Intermediate 66 (120 mg, 0.43 mmol), (R)-3-glycylthiazolidine-4-carbonitrile hydrochloride Intermediate 4 (90 mg, 0.43 mmol), HOBt (99 mg, 0.65 mmol) and EDC (124 mg, 0.65 mmol) in MeCN (5 mL) and EtOAc (5 mL) at 20° C. under $N_2$ (g). The resulting mixture was stirred at 25° C. for 3 h. The reaction mixture was concentrated and diluted with DCM (100 mL), and washed sequentially with sat $NH_4C_1$ (50 mL), brine (50 mL), and water (50 mL). The organic layer was dried over $Na_2SO_4$, filtered and evaporated. The crude product was purified by preparative HPLC, PrepMethod C, (gradient 12-23%) to afford the title compound (71 mg, 38%) as a yellow solid; HRMS (ESI) m/z $[M+H]^+$ calcd for $C_{20}H_{20}F_2N_5O_2S$: 432.1300. found: 432.1292; $^1H$ NMR (400 MHz, DMSO-$d_6$) δ 8.97 (t, 1H), 8.64 (d, 1H), 7.90 (d, 1H), 7.41 (d, 1H), 7.22 (d, 1H), 7.15 (dd, 1H), 6.39 (td, 1H), 5.33 (dd, 1H), 4.89 (d, 1H), 4.71 (d, 1H), 4.29 (d, 2H), 4.15-4.05 (m, 2H), 3.95-3.85 (m, 2H), 3.44-3.30 (m, overlapping with solvent).

Example 29: (R)—N-(2-(4-Cyanothiazolidin-3-yl)-2-oxoethyl)-6-(3-(methoxymethyl)-3-methylazetidin-1-yl)quinoline-4-carboxamide

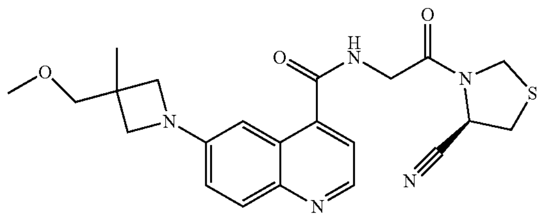 [SMILES: COCC1(C)CN(c2ccc3nccc(C(=O)NCC(=O)N4CSC[C@H]4C#N)c3c2)C1]

DIPEA (0.16 mL, 0.91 mmol) was added to a mixture of 6-(3-(methoxymethyl)-3-methylazetidin-1-yl)quinoline-4-carboxylic acid Intermediate 68 (65 mg, 0.23 mmol), (R)-3-glycylthiazolidine-4-carbonitrile hydrochloride Intermediate 4 (57 mg, 0.27 mmol) and HATU (129 mg, 0.34 mmol) in MeCN (2 mL) and EtOAc (2 mL). The mixture was stirred at rt overnight. DCM (10 mL) and sat $NaHCO_3$(aq, 7 mL) were added to the reaction mixture, and the mixture was stirred and filtered through a phase separator. The phase separator was washed with DCM, and the combined organic layer was evaporated. The crude product was purified by preparative HPLC, PrepMethod SFC-D, (gradient 2-94%) to give the title compound (38 mg, 38%); HRMS (ESI) m/z $[M+H]^+$ calcd for $C_{22}H_{26}N_5O_3S$: 440.1750. found: 440.1748; $^1H$ NMR (600 MHz, DMSO-$d_6$) δ 8.93 (t, 1H), 8.60 (d, 1H), 7.86 (d, 1H), 7.39 (d, 1H), 7.12 (d, 1H), 7.09 (dd, 1H), 5.32 (dd, 1H), 4.87 (d, 1H), 4.71 (d, 1H), 4.28 (d, 2H), 3.80 (dd, 2H), 3.60 (dd, 2H), 3.32-3.41 (m, overlapping with solvent), 3.31 (s, 3H), 1.30 (s, 3H).

Example 30: N-(2-((R)-4-Cyanothiazolidin-3-yl)-2-oxoethyl)-6-((2S,3R)-3-methoxy-2-methylazetidin-1-yl)quinoline-4-carboxamide

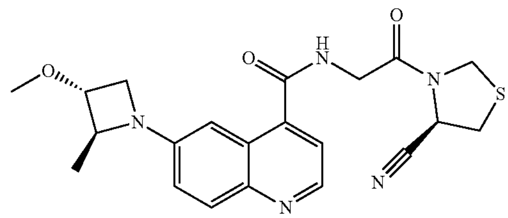 [SMILES: CO[C@@H]1CN(c2ccc3nccc(C(=O)NCC(=O)N4CSC[C@H]4C#N)c3c2)[C@H]1C]

DIPEA (0.51 mL, 2.9 mmol) was added to a mixture of 6-((2S,3R)-3-methoxy-2-methylazetidin-1-yl)quinoline-4-carboxylic acid Intermediate 70 (160 mg, 0.59 mmol), (R)-3-glycylthiazolidine-4-carbonitrile hydrochloride Intermediate 4 (183 mg, 0.88 mmol), EDC (225 mg, 1.18 mmol) and HOBt (180 mg, 1.18 mmol) in EtOAc (5 mL) and MeCN (5 mL). The mixture was stirred at 50° C. for 3 h. The solvent was removed under reduced pressure. The residue was diluted with EtOAc, and washed with water. The organic layer was dried over $Na_2SO_4$, filtered and evaporated. The crude product was purified by preparative HPLC, PrepMethod P, (gradient 13-23%) to give the title compound (220 mg, 88%) as a yellow solid; HRMS (ESI) m/z $[M+H]^+$ calcd for $C_{21}H_{24}N_5O_3S$: 426.1594. found: 426.1576; $^1H$ NMR (300 MHz, DMSO-$d_6$) δ 9.01-8.91 (m, 1H), 8.62 (d, 1H), 7.87 (d, 1H), 7.38 (d, 1H), 7.29 (d, 1H), 7.16 (dd, 1H), 5.31 (dd, 1H), 4.88 (d, 1H), 4.71 (d, 1H), 4.35-4.20 (m, 3H), 4.10-3.85 (m, 2H), 3.50-3.29 (m, overlapping with solvent), 3.27 (s, 3H), 1.50 (d, 3H).

Example 31: (R)—N-(2-(4-Cyanothiazolidin-3-yl)-2-oxoethyl)-6-(3-cyclopropyl-3-fluoroazetidin-1-yl) quinoline-4-carboxamide

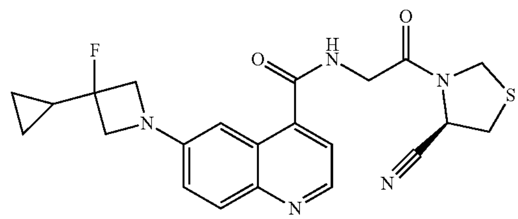 [SMILES: N#C[C@@H]1CSCN1C(=O)CNC(=O)c1ccnc2ccc(N3CC(F)(C4CC4)C3)cc12]

DIPEA (0.15 mL, 0.87 mmol) was added to a mixture of 6-(3-cyclopropyl-3-fluoroazetidin-1-yl)quinoline-4-carboxylic acid Intermediate 72 (100 mg, 0.35 mmol), (R)-3-glycylthiazolidine-4-carbonitrile hydrochloride Intermediate 4 (73 mg, 0.35 mmol), EDC (100 mg, 0.52 mmol) and HOBt (71 mg, 0.52 mmol) in EtOAc (8 mL) and MeCN (8 mL) at 20° C. under $N_2$ (g). The resulting mixture was stirred at 25° C. for 12 h. The reaction mixture was concentrated and diluted with EtOAc (100 mL), and washed sequentially with brine (50 mL) and water (50 mL). The organic layer was dried over $Na_2SO_4$, filtered and evaporated. The crude product was purified by preparative HPLC, PrepMethod C, (gradient 12-23%) to give the title compound (68 mg, 34%) as a yellow solid; HRMS (ESI) m/z $[M+H]^+$ calcd for $C_{22}H_{23}FN_5O_2S$: 440.1550. found: 440.1546; $^1H$ NMR (400 MHz, DMSO-$d_6$) δ 9.11 (t, 1H), 8.78 (d, 1H), 7.99 (d, 1H), 7.60 (d, 1H), 7.40 (d, 1H), 7.29 (dd, 1H), 5.34 (dd, 1H), 4.90 (d, 1H), 4.71 (d, 1H), 4.41-4.25 (m, 2H), 4.10-3.95 (m, 2H), 3.46-3.32 (m, 2H), 1.50-1.35 (m, 1H), 0.67-0.61 (2H, m), 0.49 (d, 2H), Example 32: (R)—N-(2-(4-Cyanothiazolidin-3-yl)-2-oxoethyl)-6-(piperidin-1-yl)quinoline-4-carboxamide

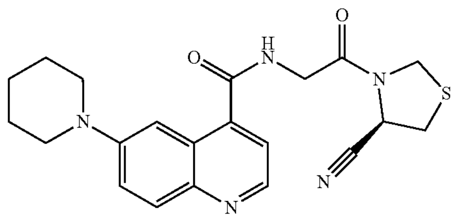

TEA (0.81 mL, 5.9 mmol) was added slowly to a mixture of 6-(piperidin-1-yl)quinoline-4-carboxylic acid Intermediate 74 (60 mg, 0.23 mmol), (R)-3-glycylthiazolidine-4-carbonitrile hydrochloride Intermediate 4 (194 mg, 0.94 mmol) and T3P (0.57 mL, 50% in EtOAc) in EtOAc (4 mL) at 15° C. under $N_2$ (g). The resulting mixture was stirred at 15° C. overnight under $N_2$ (g). The reaction mixture was filtered, the filtrate was washed sequentially with brine (3×10 mL) and water (2×10 mL). The organic layer was dried over $Na_2SO_4$, filtered and evaporated. The crude product was purified by preparative HPLC, PrepMethod F, (gradient: 15-30%) to give the title compound (12 mg, 12%) as a yellow solid; HRMS (ESI) m/z $[M+H]^+$ calcd for $C_{21}H_{24}N_5O_2S$: 410.1646. found: 410.1648; $^1H$ NMR (400 MHz, DMSO-$d_6$) δ 9.10-8.90 (m, 1H), 8.66 (d, 1H), 7.86 (d, 1H), 7.72-7.53 (m, 2H), 7.39 (d, 1H), 5.50-5.20 (m, 1H), 4.89 (d, 1H), 4.71 (d, 1H), 4.36-4.22 (m, 2H), 3.40-3.34 (m, overlapping with solvent), 1.75-1.50 (m, 6H).

Example 33: (R)—N-(2-(4-Cyanothiazolidin-3-yl)-2-oxoethyl)-6-(4,4-dimethylpiperidin-1-yl)(quinoline-4-carboxamide

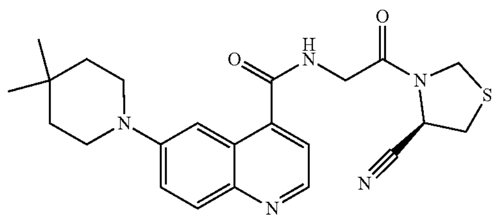 [SMILES: CC1(C)CCN(c2ccc3nccc(C(=O)NCC(=O)N4CSC[C@H]4C#N)c3c2)CC1]

TEA (0.34 mL, 2.5 mmol) was added slowly to a mixture of 6-(4,4-dimethylpiperidin-1-yl)quinoline-4-carboxylic acid Intermediate 76 (70 mg, 0.25 mmol), (R)-3-glycylthiazolidine-4-carbonitrile hydrochloride Intermediate 4 (102 mg, 0.49 mmol), EDC (142 mg, 0.74 mmol) and HOBt (113 mg, 0.74 mmol) in DMF (5 mL) at 10° C. under $N_2$ (g). The resulting suspension was stirred at 10° C. overnight. The reaction mixture was diluted with sat $NaHCO_3$(25 mL), and extracted with EtOAc (4×20 mL). The organic layers were combined and washed with brine (3×10 mL). The organic layer was dried over $Na_2SO_4$, filtered and evaporated. The crude product was purified by preparative HPLC, PrepMethod P, (gradient 10-25%) to give the title compound (12 mg, 11%) as a yellow solid; HRMS (ESI) m/z $[M+H]^+$ calcd for $C_{23}H_{28}N_5O_2S$: 438.1958. found: 438.1946; $^1H$ NMR (300 MHz, DMSO-$d_6$) δ 8.97 (t, 1H), 8.63 (d, 1H), 7.84 (d, 1H), 7.74-7.50 (m, 2H), 7.37 (d, 1H), 5.40-5.20 (m, 1H), 4.87 (d, 1H), 4.69 (d, 1H), 4.27 (d, 2H), 3.37-3.32 (m, overlapping with solvent), 1.65-1.35 (m, 4H), 0.96 (s, 6H).

Example 34: (R)—N-(2-(4-Cyanothiazolidin-3-yl)-2-oxoethyl)-6-(4-fluoro-4-methyl-piperidin-1-yl)quinoline-4-carboxamide

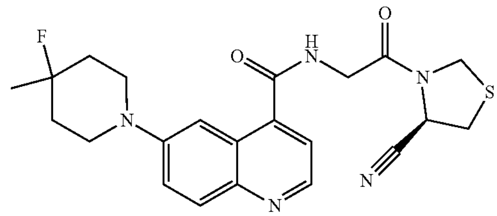 [SMILES: CC1(F)CCN(c2ccc3nccc(C(=O)NCC(=O)N4CSC[C@H]4C#N)c3c2)CC1]

DIPEA (0.30 mL, 1.7 mmol) was added slowly to a mixture of 6-(4-fluoro-4-methylpiperidin-1-yl)quinoline-4-carboxylic acid Intermediate 78 (50 mg, 0.17 mmol), (R)-3-glycylthiazolidine-4-carbonitrile hydrochloride Intermediate 4 (72 mg, 0.35 mmol) and HATU (198 mg, 0.52 mmol) in DMF (5 mL) at 10° C. under $N_2$ (g). The resulting mixture was stirred at 10° C. overnight. The reaction mixture was diluted with water (10 mL), and extracted with EtOAc (3×25 mL). The organic layers were combined and washed with brine (3×20 mL). The organic layer was dried over $Na_2SO_4$, filtered and evaporated. The crude product was purified by preparative HPLC, PrepMethod P, (gradient 10-25%) to give the title compound (13 mg, 17%) as a yellow solid; HRMS (ESI) m/z $[M+H]^+$ calcd for $C_{22}H_{25}FN_5O_2S$: 442.1708. found: 442.1726; $^1H$ NMR (300 MHz, DMSO-$d_6$) δ 9.05-8.91 (m, 1H), 8.65 (d, 1H), 7.87 (d, 1H), 7.74-7.62 (m, 2H), 7.37 (d, 1H), 5.40-5.20 (m, 1H), 4.87 (d, 1H), 4.69 (d, 1H), 4.32-4.24 (m, 2H), 3.82-3.60 (m, 2H), 3.55-3.07 (m, overlapping with solvent), 1.94-1.62 (m, 4H), 1.35 (d, 3H).

Example 35: (R)—N-(2-(4-Cyanothiazolidin-3-yl)-2-oxoethyl)-6-(4,4-difluoropiperidin-1-yl)quinoline-4-carboxamide

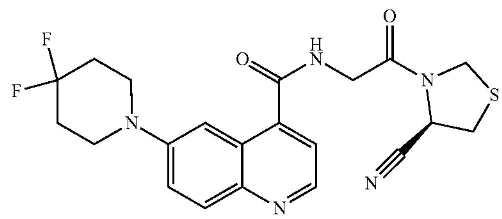 [SMILES: N#C[C@@H]1CSCN1C(=O)CNC(=O)c1ccnc2ccc(N3CCC(F)(F)CC3)cc12]

DIPEA (0.84 mL, 4.8 mmol) was added to 6-(4,4-difluoropiperidin-1-yl)quinoline-4-carboxylic acid Intermediate 80 (140 mg, 0.48 mmol), (R)-3-glycylthiazolidine-4-carbonitrile hydrochloride Intermediate 4 (98 mg, 0.57 mmol) and T3P (0.91 mL, 50% in EtOAc) in DMF (8 mL) at 20° C. The resulting mixture was stirred at 50° C. for 35 h. The reaction mixture was diluted with EtOAc (50 mL), and washed with water (3×50 mL), filtered and evaporated. The crude product was purified by preparative HPLC, PrepMethod C, (gradient 25-55%) to give the title compound (28 mg, 13%) as a pale yellow solid; HRMS (ESI) m/z $[M+H]^+$ calcd for $C_{21}H_{22}F_2N_5O_2S$: 446.1456. found: 446.1452; $^1H$ NMR (300 MHz, DMSO-$d_6$) δ 9.01 (t, 1H), 8.68 (d, 1H), 7.90 (d, 1H), 7.83 (d, 1H), 7.70 (dd, 1H), 7.39 (d, 1H), 5.37-5.20 (m, 1H), 4.88 (d, 1H), 4.69 (d, 1H), 4.40-4.20 (m, 2H), 3.65-3.45 (m, 4H), 3.42-3.33 (m, overlapping with solvent), 2.16-1.94 (m, 4H).

Example 36: (R)—N-(2-(4-Cyanothiazolidin-3-yl)-2-oxoethyl)-6-(3,3-difluoropiperidin-1-yl)quinoline-4-carboxamide

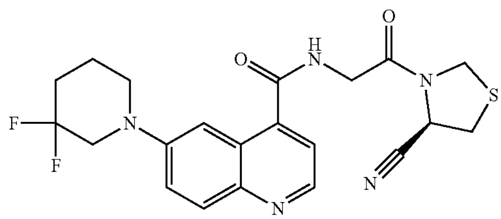 [SMILES: N#C[C@@H]1CSCN1C(=O)CNC(=O)c1ccnc2ccc(N3CCCC(F)(F)C3)cc12]

TEA (1.05 mL, 7.53 mmol) was added to 6-(3,3-difluoropiperidin-1-yl)quinoline-4-carboxylic acid Intermediate 82 (110 mg, 0.38 mmol), (R)-3-glycylthiazolidine-4-carbonitrile hydrochloride Intermediate 4 (782 mg, 3.78 mmol) and T3P (2.4 mL, 50% in EtOAc) in DMF (5 mL) at 10° C. under $N_2$ (g). The resulting mixture was stirred at 10° C. overnight under $N_2$ (g). The reaction mixture was diluted with sat $NaHCO_3$(25 mL), and extracted with EtOAc (4×25 mL). The organic layers were combined and washed with brine (5×20 mL). The organic layer was dried over $Na_2SO_4$, filtered and evaporated. The crude product was purified by preparative HPLC, PrepMethod P, (gradient 10-25%) to give the title compound (28 mg, 17%) as a yellow solid; HRMS (ESI) m/z $[M+H]^+$ calcd for $C_{21}H_{22}F_2N_5O_2S$: 446.1456. found: 446.1460; $^1H$ NMR (300 MHz, DMSO-$d_6$) δ 9.10-8.90 (m, 1H), 8.70 (d, 1H), 8.19-7.86 (m, 1H), 7.84-7.60 (m, 2H), 7.42 (d, 1H), 5.36-5.26 (m, 1H), 4.89 (d, 1H), 4.72 (d, 1H), 4.30 (d, 2H), 3.70 (t, 2H), 3.55-3.30 (m, overlapping with solvent), 2.18-1.99 (m, 2H), 1.98-1.80 (m, 2H).

Example 37: (R)—N-(2-(4-Cyanothiazolidin-3-yl)-2-oxoethyl)-6-(4-(fluoromethyl)-4-methylpiperidin-1-yl)quinoline-4-carboxamide

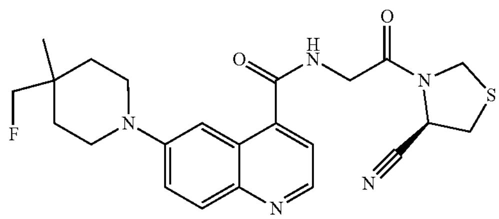 [SMILES: CC1(CF)CCN(c2ccc3nccc(C(=O)NCC(=O)N4CSC[C@H]4C#N)c3c2)CC1]

TEA (1.10 mL, 7.87 mmol) was added to 6-(4-(fluoromethyl)-4-methylpiperidin-1-yl)quinoline-4-carboxylic acid Intermediate 84 (119 mg, 0.39 mmol), (R)-3-glycylthiazolidine-4-carbonitrile hydrochloride Intermediate 4 (327 mg, 1.57 mmol), HOBt (532 mg, 3.94 mmol) and EDC (755 mg, 3.94 mmol) in DMF (5 mL) at 10° C. under $N_2$ (g). The resulting suspension was stirred at 10° C. overnight under $N_2$ (g). The reaction mixture was diluted with water (50 mL), and extracted with EtOAc (4×50 mL). The organic layers were combined and washed with brine (5×25 mL). The organic layer was dried over $Na_2SO_4$, filtered and evaporated. The crude product was purified by preparative HPLC, PrepMethod P, (gradient 10-25%) to give the title compound (16 mg, 9%) as a yellow solid; HRMS (ESI) m/z $[M+H]^+$ calcd for $C_{23}H_{27}FN_5O_2S$: 456.1864. found: 456.1850; $^1H$ NMR (300 MHz, DMSO-$d_6$) δ 8.97 (t, 1H), 8.64 (d, 1H), 7.93-7.80 (m, 1H), 7.65 (m, 2H), 7.38 (d, 1H), 5.82-5.23 (m, 1H), 4.89 (d, 1H), 4.71 (d, 1H), 4.35-4.07 (m, 4H), 3.70-3.00 (m, overlapping with solvent), 1.75-1.55 (m, 2H), 1.53-1.34 (m, 2H), 1.01 (d, 3H).

Example 38: (R)—N-(2-(4-Cyanothiazolidin-3-yl)-2-oxoethyl)-6-(4,4-difluoro-3,3-dimethylpiperidin-1-yl)quinoline-4-carboxamide

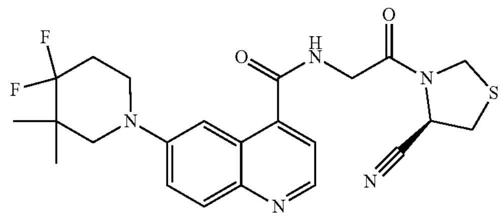 [SMILES: CC1(C)CN(c2ccc3nccc(C(=O)NCC(=O)N4CSC[C@H]4C#N)c3c2)CCC1(F)F]

DIPEA (0.22 mL, 1.3 mmol) was added to 6-(4,4-difluoro-3,3-dimethylpiperidin-1-yl)quinoline-4-carboxylic acid Intermediate 86 (200 mg, 0.62 mmol), (R)-3-glycylthiazolidine-4-carbonitrile hydrochloride Intermediate 4 (194 mg, 0.94 mmol) and HATU (237 mg, 0.62 mmol) in MeCN (10 mL) and EtOAc (10 mL) at 15° C. under $N_2$ (g). The resulting mixture was stirred at 20° C. for 3 h. The reaction mixture was filtered through silica. The filtrate was concentrated and redissolved in DCM (100 mL), and washed sequentially with brine (50 mL) and water (50 mL). The organic layer was dried over $Na_2SO_4$, filtered and evaporated. The crude product was purified by preparative HPLC, PrepMethod F, (gradient 30-40%) to give the title compound (75 mg, 25%) as a yellow solid; HRMS (ESI) m/z $[M+H]^+$ calcd for $C_{23}H_{26}F_2N_5O_2S$: 474.1770. found: 474.1760; $^1H$ NMR (300 MHz, DMSO-$d_6$) δ 9.03 (t, 1H), 8.68 (d, 1H), 7.90 (d, 1H), 7.80 (d, 1H), 7.71 (dd, 1H), 7.39 (d, 1H), 5.37-5.29 (m, 1H), 4.91 (d, 1H), 4.72 (d, 1H), 4.31 (d, 2H), 3.62-3.35 (m, overlapping with solvent), 2.28-2.12 (m, 2H), 1.12 (s, 6H).

Example 39: (R)—N-(2-(4-Cyanothiazolidin-3-yl)-2-oxoethyl)-6-(4-(trifluoromethyl)-piperidin-1-yl)quinoline-4-carboxamide

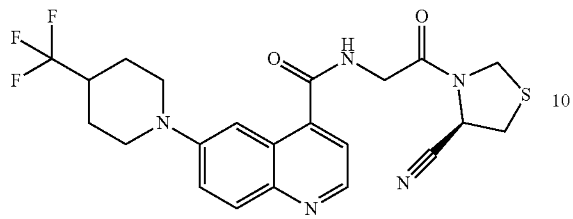

DIPEA (0.83 mL, 4.8 mmol) was added to 6-(4-(trifluoromethyl)piperidin-1-yl)quinoline-4-carboxylic acid Intermediate 88 (154 mg, 0.47 mmol), (R)-3-glycylthiazolidine-4-carbonitrile hydrochloride Intermediate 4 (197 mg, 0.95 mmol) and TBTU (540 mg, 1.42 mmol) in DMF (5 mL) at 10° C. under $N_2$ (g). The resulting solution was stirred at 10° C. overnight under $N_2$ (g). The reaction mixture was diluted with water (30 mL). The aqueous layer was extracted with EtOAc (4×50 mL). The organic layers were combined and washed with water (4×25 mL). The organic layer was dried over $Na_2SO_4$, filtered and evaporated. The residue was purified by preparative TLC (DCM:MeOH, 10:1), and further purified by preparative HPLC, PrepMethod D, (gradient 10-40%) to give the title compound (27 mg, 12%) as an orange solid; HRMS (ESI) m/z $[M+H]^+$ calcd for $C_{22}H_{23}F_3N_5O_2S$: 478.1518. found: 478.1514; $^1$H NMR (300 MHz, DMSO-$d_6$) δ 9.05 (t, 1H), 8.72 (d, 1H), 7.92 (d, 1H), 7.81-7.63 (m, 2H), 7.46 (d, 1H), 5.40-5.20 (m, 1H), 4.90 (d, 1H), 4.71 (m, 1H), 4.40-4.20 (m, 2H), 4.09 (d, 2H), 3.70-3.34 (m, overlapping with solvent), 2.91 (t, 2H), 1.94 (d, 2H), 1.70-1.45 (m, 2H).

Example 40: N-(2-((R)-4-Cyanothiazolidin-3-yl)-2-oxoethyl)-6-((RS)-3-fluoropiperidin-1-yl)quinoline-4-carboxamide

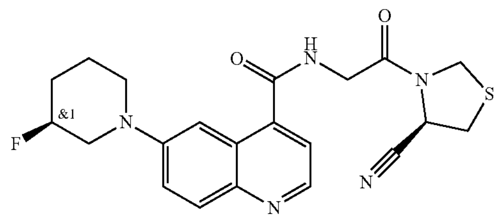 [SMILES: N#C[C@@H]1CSCN1C(=O)CNC(=O)c1ccnc2ccc(N3CCC[C@H](F)C3)cc12]

TEA (0.51 mL, 3.7 mmol) was added to a mixture of 6-(3-fluoropiperidin-1-yl)quinoline-4-carboxylic acid Intermediate 90 (100 mg, 0.36 mmol), (R)-3-glycylthiazolidine-4-carbonitrile hydrochloride Intermediate 4 (125 mg, 0.73 mmol), HOBt (279 mg, 1.82 mmol), and EDC (349 mg, 1.82 mmol) in DMF (15 mL) at rt. The mixture was stirred for 15 h at rt under $N_2$ (g). The reaction mixture was diluted with water (25 mL), and extracted with EtOAc (3×25 mL). The combined organic layers were dried over $Na_2SO_4$, filtered and evaporated. The residue was purified by preparative TLC (DCM:MeOH, 12:1), and further purified by preparative HPLC, PrepMethod C, (gradient 14-25%) to give the title compound (28 mg, 18%) as a yellow solid; HRMS (ESI) m/z $[M+H]^+$ calcd for $C_{21}H_{23}FN_5O_2S$: 428.1550. found: 428.1514; $^1$H NMR (300 MHz, DMSO-$d_6$) δ 8.99 (t, 1H), 8.66 (d, 1H), 7.87 (d, 1H), 7.75-7.55 (m, 2H,), 7.39 (d, 1H), 4.87 (d, 1H), 4.72 (d, 1H), 5.40-5.20 (m, 1H), 5.00-4.50 (m, 3H), 4.30 (d, 1H), 3.66-3.20 (m, overlapping with solvent), 2.06 –1.47 (4H, m).

Example 41: N-(2-((R)-4-Cyanothiazolidin-3-yl)-2-oxoethyl)-6-((RS)-3-methoxypiperidin-1-yl)quinoline-4-carboxamide

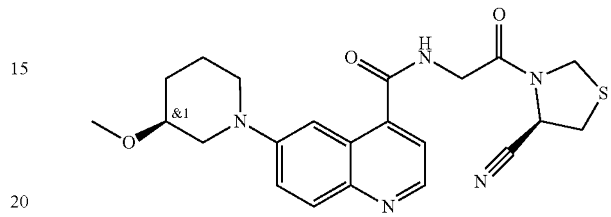

DIPEA (0.73 mL, 4.2 mmol) was added to a mixture of 6-(3-methoxypiperidin-1-yl)quinoline-4-carboxylic acid Intermediate 92 (120 mg, 0.42 mmol), (R)-3-glycylthiazolidine-4-carbonitrile hydrochloride Intermediate 4 (144 mg, 0.84 mmol) and HATU (478 mg, 1.26 mmol) in DMF (15 mL) at rt. The mixture was stirred for 15 h at rt under $N_2$ (g). The reaction mixture was diluted with water (20 mL) and extracted with EtOAc (3×25 mL). The combined organic phases were washed with brine (20 mL). The organic layer was dried over $Na_2SO_4$, filtered and evaporated to afford yellow oil, which was purified by preparative TLC (DCM:MeOH, 10:1), and then further purified by preparative HPLC, PrepMethod P, (gradient 57-67%) to give the title compound (11 mg, 6%) as a yellow solid; HRMS (ESI) m/z $[M+H]^+$ calcd for $C_{22}H_{26}N_5O_3S$: 440.1750. found: 440.1722; $^1$H NMR (300 MHz, DMSO-$d_6$) δ 9.10-8.90 (m, 1H), 8.64 (d, 1H), 7.86 (d, 1H), 7.77-7.56 (m, 2H), 7.38 (d, 1H), 5.40-5.20 (m, 1H), 4.87 (d, 1H), 4.70 (d, 1H), 4.28 (d, 2H), 3.85-3.70 (m, 1H), 3.66-3.33 (m, overlapping with solvent), 3.10-2.80 (m, 2H), 2.10-1.72 (2H, d), 1.65-1.30 (m, 2H).

Example 42: (R)—N-(2-(4-Cyanothiazolidin-3-yl)-2-oxoethyl)-6-(4-methoxy-4-methyl-piperidin-1-yl)quinoline-4-carboxamide

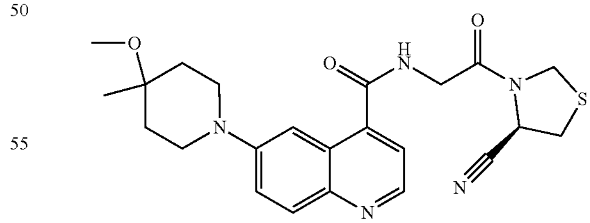

DIPEA (0.22 mL, 1.3 mmol) was added to a stirred suspension of 6-(4-methoxy-4-methylpiperidin-1-yl)quinoline-4-carboxylic acid Intermediate 94 (75 mg, 0.25 mmol), (R)-3-glycylthiazolidine-4-carbonitrile hydrochloride Intermediate 4 (104 mg, 0.50 mmol), HOBt (101 mg, 0.75 mmol) and EDC (144 mg, 0.75 mmol) in MeCN (5 mL) and EtOAc (5 mL) at 25° C. The resulting solution was stirred at 50° C. for 2 h. The solvent was removed under reduced pressure.

The residue was redissolved in a mixture of sat $NaHCO_3$(aq, 25 mL) and EtOAc (100 mL). The phases were separated, the aqueous layer was extracted with EtOAc (4×50 mL). The organic layers were combined and washed with water (3×25 mL). The organic layer was dried over $Na_2SO_4$, filtered and evaporated. The crude product was purified by preparative HPLC, PrepMethod C, (gradient 16-26%) to give the title compound (70 mg, 61%) as a yellow solid; HRMS (ESI) m/z $[M+H]^+$ calcd for $C_{23}H_{28}N_5O_3S$: 454.1908. found: 454.1918; $^1H$ NMR (300 MHz, DMSO-$d_6$) δ 8.99 (t, 1H), 8.64 (d, 1H), 7.85 (d, 1H), 7.75-7.55 (m, 2H), 7.38 (d, 1H), 5.40-5.20 (m, 1H), 4.88 (d, 1H), 4.69 (d, 1H), 4.32-4.22 (m, 2H), 3.55-3.33 (m, overlapping with solvent), 3.25-3.13 (m, overlapping with solvent), 1.90-1.68 (m, 2H), 1.66-1.49 (m, 2H), 1.12 (s, 3H).

Example 43: (R)—N-(2-(4-Cyanothiazolidin-3-yl)-2-oxoethyl)-6-(4-isopropoxypiperidin-1-yl)quinoline-4-carboxamide

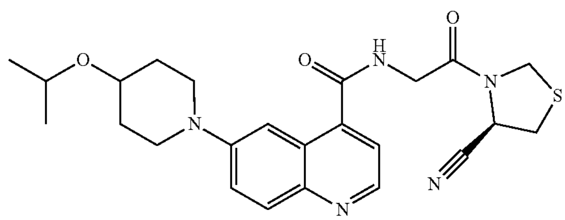 [SMILES: CC(C)OC1CCN(c2ccc3nccc(C(=O)NCC(=O)N4CSC[C@H]4C#N)c3c2)CC1]

DIPEA (0.17 mL, 0.95 mmol) was added to a mixture of 6-(4-isopropoxypiperidin-1-yl)quinoline-4-carboxylic acid Intermediate 96 (100 mg, 0.32 mmol), (R)-3-glycylthiazolidine-4-carbonitrile hydrochloride Intermediate 4 (99 mg, 0.48 mmol), EDC (91 mg, 0.48 mmol) and HOBt (73 mg, 0.48 mmol) in MeCN (5 mL) and EtOAc (5 mL). The reaction was stirred at 50° C. for 2 h. The solvent was removed under reduced pressure. The residue was diluted with EtOAc, and washed with water. The organic layer was dried over $Na_2SO_4$, filtered and evaporated. The crude product was purified by preparative HPLC, PrepMethod C, (gradient 20-30%) to give the title compound (105 mg, 71%) as a yellow solid; HRMS (ESI) m/z $[M+H]^+$ calcd for $C_{24}H_{30}N_5O_3S$: 468.2064. found: 468.2062; $^1H$ NMR (300 MHz, $CD_3OD$) δ 8.62 (d, 1H), 7.90 (d, 1H), 7.75 (s, 1H), 7.67 (dd, 1H), 7.49 (d, 1H), 5.43-5.23 (m, 1H), 4.90-4.65 (m, overlapping with solvent), 4.38 (s, 2H), 3.93-3.75 (m, 3H), 3.74-3.55 (m, 1H), 3.52-3.35 (m, 2H), 3.20-3.05 (m, 2H), 2.13-1.93 (m, 2H), 1.79-1.55 (m, 2H), 1.16 (d, 6H).

Example 44: N-(2-((R)-4-Cyanothiazolidin-3-yl)-2-oxoethyl)-6-((RS)-4,4-difluoro-2-methylpiperidin-1-yl)quinoline-4-carboxamide

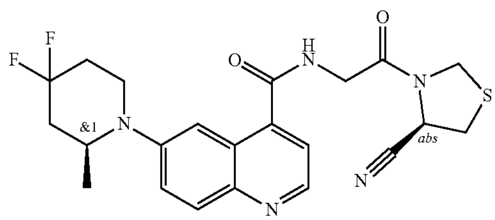 [SMILES: C[C@H]1CC(F)(F)CCN1c1ccc2nccc(C(=O)NCC(=O)N3CSC[C@H]3C#N)c2c1]

DIPEA (0.43 mL, 2.5 mmol) was added to mixture of 6-(4,4-difluoro-2-methylpiperidin-1-yl)quinoline-4-carboxylic acid Intermediate 98 (150 mg, 0.49 mmol), (R)-3-glycylthiazolidine-4-carbonitrile hydrochloride Intermediate 4 (153 mg, 0.73 mmol), EDC (141 mg, 0.73 mmol) and HOBt (112 mg, 0.73 mmol) in EtOAc (3 mL) and MeCN (3 mL). The reaction was stirred at 40° C. for 4 h. The solvent was removed under reduced pressure. The residue was redissolved in EtOAc, and washed with water. The organic layer was dried over $Na_2SO_4$, filtered and evaporated. The crude product was purified by preparative HPLC, PrepMethod P, (gradient 22-33%) to give the title compound (120 mg, 53%) as a yellow solid; HRMS (ESI) m/z $[M+H]^+$ calcd for $C_{22}H_{24}F_2N_5O_2S$: 460.1614. found: 460.1608; $^1H$ NMR (400 MHz, $CD_3OD$) δ 8.68 (d, 1H), 7.96 (d, 1H), 7.86 (dd, 1H), 7.71 (dd, 1H), 7.52 (dd, 1H), 5.38-5.32 (m, 1H), 4.83-4.73 (m, overlapping with solvent), 4.59-4.44 (m, 1H), 4.42-4.31 (m, 2H), 3.93-3.69 (m, 1H), 3.50-3.33 (m, overlapping with solvent), 2.38-1.96 (m, 4H), 1.23 (td, 3H).

Example 45: N-(2-((R)-4-Cyanothiazolidin-3-yl)-2-oxoethyl)-6-((S)-2-(fluoromethyl)-piperidin-1-yl)quinoline-4-carboxamide

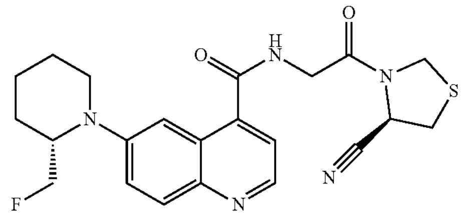 [SMILES: N#C[C@@H]1CSCN1C(=O)CNC(=O)c1ccnc2ccc(N3CCCC[C@H]3CF)cc12]

DIPEA (0.27 mL, 1.6 mmol) was added to a solution of (S)-6-(2-(fluoromethyl)piperidin-1-yl)quinoline-4-carboxylic acid Intermediate 100 (90 mg, 0.31 mmol), (R)-3-glycylthiazolidine-4-carbonitrile hydrochloride Intermediate 4 (97 mg, 0.47 mmol), EDC (90 mg, 0.47 mmol) and HOBt (72 mg, 0.47 mmol) in EtOAc (4 mL) and MeCN (4 mL). The reaction was stirred at 40° C. for 3 h. The solvent was removed under reduced pressure. The residue was diluted with EtOAc, and washed with water. The organic layer was dried over $Na_2SO_4$, filtered and evaporated. The crude product was purified by preparative HPLC, PrepMethod P, (gradient 17-27%) to give the title compound (45 mg, 33%) as a yellow solid; HRMS (ESI) m/z $[M+H]^+$ calcd for $C_{22}H_{25}FN_5O_2S$: 442.1708. found: 442.1708; $^1H$ NMR (300 MHz, $CD_3OD$) δ 8.59 (d, 1H), 7.89 (d, 1H), 7.75-7.55 (m, 2H), 7.47 (d, 1H), 5.40-5.27 (m, 1H), 4.87-4.65 (m, overlapping with solvent), 4.58-4.43 (m, 2H), 4.37 (s, 2H), 3.86-3.66 (m, 1H), 3.54-3.34 (m, overlapping with solvent), 3.25-3.13 (m, 1H), 2.03-1.60 (m, 6H).

Example 46: (R)—N-(2-(4-Cyanothiazolidin-3-yl)-2-oxoethyl)-6-(5-azaspiro[2.5]octan-5-yl)quinoline-4-carboxamide

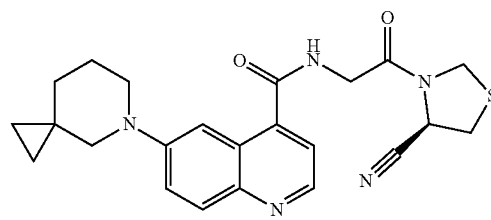

DIPEA (0.54 mL, 3.1 mmol) was added to a stirred suspension of 6-(5-azaspiro[2.5]octan-5-yl)quinoline-4-carboxylic acid Intermediate 102 (107 mg, 0.31 mmol), (R)-3-glycylthiazolidine-4-carbonitrile hydrochloride Intermediate 4 (129 mg, 0.62 mmol) and TBTU (354 mg, 0.93 mmol) in MeCN (5 mL) and EtOAc (5 mL) at 9° C. The resulting solution was stirred at 9° C. overnight. The solvent was removed under reduced pressure. The residue was dissolved in a mixture of sat $NaHCO_3$(aq, 60 mL) and EtOAc (80 mL). The aqueous layer was extracted with EtOAc (4×75 mL). The organic layers were combined and washed with water (4×50 mL). The aqueous layers were combined and extracted with EtOAc (3×25 mL). The organic layers were combined and dried over $Na_2SO_4$, filtered and evaporated. The crude product was purified by preparative HPLC, PrepMethod P, (gradient 16-26%) to afford the title compound (45 mg, 32%) as an orange solid; HRMS (ESI) m/z $[M+H]^+$ calcd for $C_{23}H_{26}N_5O_2S$: 436.1802. found: 436.1784; $^1H$ NMR (300 MHz, DMSO-$d_6$) δ 8.99 (t, 1H), 8.64 (d, 1H), 7.85 (d, 1H), 7.70-7.50 (m, 2H), 7.38 (d, 1H), 5.31 (dd, 1H), 4.89 (d, 1H), 4.71 (d, 1H), 4.37-4.20 (m, 2H), 3.50-3.20 (m, overlapping with solvent), 3.16 (s, 2H), 1.89-1.69 (m, 2H), 1.53-1.35 (m, 2H), 0.63-0.39 (m, 2H), 0.38-0.20 (m, 2H).

Example 47: (R)—N-(2-(4-Cyanothiazolidin-3-yl)-2-oxoethyl)-6-(3,3-difluoropyrrolidin-1-yl)quinoline-4-carboxamide

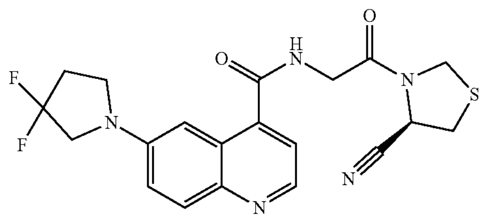 [SMILES: N#C[C@@H]1CSCN1C(=O)CNC(=O)c1ccnc2ccc(N3CCC(F)(F)C3)cc12]

DIPEA (0.63 mL, 3.6 mmol) was added to a mixture of 6-(3,3-difluoropyrrolidin-1-yl)quinoline-4-carboxylic acid Intermediate 104 (200 mg, 0.72 mmol), (R)-3-glycyl-thiazolidine-4-carbonitrile hydrochloride Intermediate 4 (299 mg, 1.44 mmol), EDC (276 mg, 1.44 mmol), HOBt (194 mg, 1.44 mmol) in EtOAc (6 mL) and MeCN (6 mL). The reaction at 25° C. for 10 h. The solvent was removed under reduced pressure. The reaction mixture was diluted with EtOAc (25 mL) and washed with water (3×10 mL). The organic layer was dried over $Na_2SO_4$, filtered and evaporated. The crude product was purified by preparative HPLC, PrepMethod C, (gradient 17-29%) to give the title compound (120 mg, 38%) as a yellow solid; HRMS (ESI) m/z $[M+H]^+$ calcd for $C_{20}H_{20}F_2N_5O_2S$: 432.1300. found: 432.1310; $^1H$ NMR (300 MHz, DMSO-$d_6$) δ 8.97 (t, 1H), 8.63 (d, 1H), 7.93 (d, 1H), 7.43-7.30 (m, 3H), 5.40-5.20 (m, 1H), 4.88 (d, 1H), 4.70 (d, 1H), 4.29 (d2H), 3.85 (t, 2H), 3.63 (t, 2H), 3.44-3.32 (m, overlapping with solvent), 2.70-2.50 (m, overlapping with solvent).

Example 48: (R)—N-(2-(4-Cyanothiazolidin-3-yl)-2-oxoethyl)-6-(3,3-dimethylpyrrolidin-1-yl)quinoline-4-carboxamide

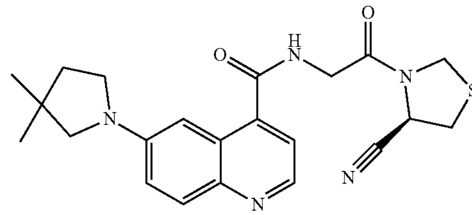

TEA (2.07 mL, 14.8 mmol) was added to a stirred suspension of 6-(3,3-dimethylpyrrolidin-1-yl)quinoline-4-carboxylic acid Intermediate 106 (347 mg, 0.74 mmol), (R)-3-glycylthiazolidine-4-carbonitrile hydrochloride Intermediate 4 (385 mg, 1.86 mmol), HOBt (568 mg, 3.71 mmol) and EDC (711 mg, 3.71 mmol) in MeCN (7 mL) and EtOAc (7 mL) at 7° C. The resulting suspension was stirred at 7° C. overnight. The solvent was removed under reduced pressure. The residue was suspended in EtOAc and washed with a solution of sat $NaHCO_3$ (50 mL). The aqueous layer was extracted with EtOAc (4×50 mL). The organic layers were combined and washed with water (4×20 mL) and concentrated under reduced pressure. The crude product was purified by preparative HPLC, PrepMethod P, to give the title compound (174 mg, 55%) as an orange solid; HRMS (ESI) m/z $[M+H]^+$ calcd for $C_{22}H_{26}N_5O_2S$: 424.1802. found: 424.1806; $^1H$ NMR (300 MHz, DMSO-$d_6$) δ 8.91 (t, 1H), 8.53 (d, 1H), 7.84 (d, 1H), 7.34 (d, 1H), 7.29-7.15 (m, 2H), 5.30 (dd, 1H), 4.89 (d, 1H), 4.71 (d, 1H), 4.27 (d, 2H), 3.51-3.33 (m, overlapping with solvent), 3.15 (s, 2H), 1.80 (t, 2H), 1.14 (s, 3H), 1.13 (s, H).

Example 49: (R)—N-(2-(4-Cyanothiazolidin-3-yl)-2-oxoethyl)-6-(5-azaspiro[2.4]heptan-5-yl)quinoline-4-carboxamide

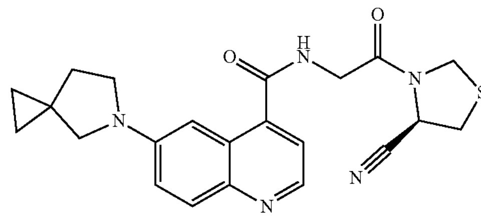

DIPEA (2.12 mL, 12.2 mmol) was added to a mixture of 6-(5-azaspiro[2.4]heptan-5-yl)quinoline-4-carboxylic acid Intermediate 108 (346 mg, 0.61 mmol), (R)-3-glycyl-thiazolidine-4-carbonitrile hydrochloride Intermediate 4 (253 mg, 1.22 mmol), HOBt (465 mg, 3.04 mmol) and EDC (583 mg, 3.04 mmol) in EtOAc (8 mL) and MeCN (8 mL) at 5° C. The resulting solution was stirred at 5° C. overnight. The solvent was removed under reduced pressure. The residue was dissolved in a mixture of a sat $NaHCO_3$(aq, 80 mL) and EtOAc (100 mL). The phases were separated, and the aqueous layer was extracted with EtOAc (4×100 mL). The organic layers were combined, and washed with water (4×25 mL). The aqueous layers were combined and extracted with EtOAc (3×20 mL). The organic layers were combined, dried over $Na_2SO_4$, filtered and evaporated. The crude product was purified by preparative HPLC, PrepMethod P, to give the title compound (120 mg, 47%) as an orange solid; HRMS (ESI) m/z $[M+H]^+$ calcd for $C_{22}H_{24}N_5O_2S$: 422.1646. found: 422.1654; $^1H$ NMR (300 MHz, DMSO-$d_6$) δ 8.91 (t, 1H), 8.54 (d, 1H), 7.85 (d, 1H), 7.34 (d, 1H), 7.30-7.14 (m, 2H), 5.29 (dd, 1H), 4.88 (d, 1H), 4.70 (d, 1H), 4.27 (d, 2H), 3.54 (t, 2H), 3.40-3.25 (m, overlapping with solvent), 1.94 (t, 2H), 0.75-0.57 (m, 4H).

Example 50: N-(2-((R)-4-Cyanothiazolidin-3-yl)-2-oxoethyl)-6-((3R,4S)-3,4-difluoropyrrolidin-1-yl) quinoline-4-carboxamide

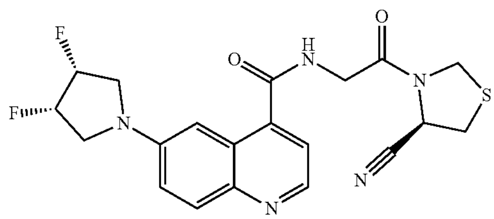 [SMILES: N#C[C@@H]1CSCN1C(=O)CNC(=O)c1ccnc2ccc(N3C[C@@H](F)[C@@H](F)C3)cc12]

TEA (1.86 mL, 13.4 mmol) was added to a stirred suspension of 6-((3S,4R)-3,4-difluoropyrrolidin-1-yl)quinoline-4-carboxylic acid Intermediate 110 (335 mg, 0.67 mmol), (R)-3-glycylthiazolidine-4-carbonitrile hydrochloride Intermediate 4 (347 mg, 1.67 mmol), HOBt (511 mg, 3.34 mmol) and EDC (640 mg, 3.34 mmol) in EtOAc (9 mL) and MeCN (9 mL) at 5° C. The resulting suspension was stirred at 5° C. overnight. The solvent was removed under reduced pressure. The residue was suspended in sat $NaHCO_3$ (50 mL), and extracted with EtOAc (4×50 mL). The organic layers were combined and washed with water (4×25 mL). The aqueous layers were combined and extracted with EtOAc (3×25 mL). The organic layers were combined and dried over $Na_2SO_4$, filtered and evaporated. The crude product was purified by preparative HPLC, PrepMethod P, to give the title compound (128 mg, 44%) as a yellow solid; HRMS (ESI) m/z $[M+H]^+$ calcd for $C_{20}H_{20}N_5O_2S$: 432.1300. found: 432.1294; $^1H$ NMR (300 MHz, DMSO-$d_6$) δ 9.06-8.89 (m, 1H), 8.62 (d, 1H), 7.93 (d, 1H), 7.40 (d, 1H), 7.38-7.30 (m, 2H), 5.65-5.25 (m, 3H), 4.89 (d, 1H), 4.72 (d, 1H), 4.34-4.15 (m, 2H), 3.92-3.75 (m, 2H), 3.71-3.53 (m, 2H), 3.41-3.34 (m, overlapping with solvent).

Example 51: N-(2-((R)-4-Cyanothiazolidin-3-yl)-2-oxoethyl)-6-((S)-3-fluoropyrrolidin-1-yl)quinoline-4-carboxamide

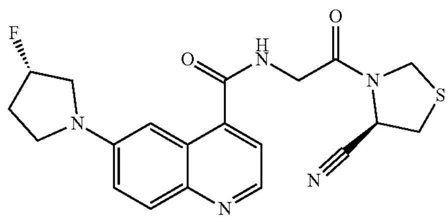 [SMILES: N#C[C@@H]1CSCN1C(=O)CNC(=O)c1ccnc2ccc(N3CC[C@H](F)C3)cc12]

DIPEA (2.64 mL, 15.1 mmol) was added to a stirred solution of (S)-6-(3-fluoropyrrolidin-1-yl)quinoline-4-carboxylic acid Intermediate 112 (282 mg, 0.76 mmol), (R)-3-glycylthiazolidine-4-carbonitrile hydrochloride Intermediate 4 (392 mg, 1.89 mmol) and TBTU (860 mg, 2.27 mmol) in EtOAc (7 mL) and MeCN (7 mL) at 6° C. The resulting solution was stirred at 5° C. overnight. The solvent was removed under reduced pressure. The residue was dissolved in a mixture of sat $NaHCO_3$(aq, 70 mL) and EtOAc (100 mL). The phases were separated, and the aqueous layer was extracted with EtOAc (4×100 mL). The organic layers were combined and washed with water (4×25 mL). The aqueous layers were combined and extracted with EtOAc (4×20 mL). The organic layers were combined, dried over $Na_2SO_4$, filtered and evaporated. The crude product was purified by preparative HPLC, PrepMethod P, to give the title compound (120 mg, 38%) as an orange solid; HRMS (ESI) m/z $[M+H]^+$ calcd for $C_{20}H_{21}FN_5O_2S$: 414.1394. found: 414.1384; $^1H$ NMR (300 MHz, DMSO-$d_6$) δ 8.95 (t, 1H), 8.60 (d, 1H), 7.90 (d, 1H), 7.45-7.30 (m, 3H), 5.49 (d, 1H), 5.36-5.25 (m, 1H), 4.89 (d, 1H), 4.72 (d, 1H), 4.30 (d, 2H), 3.80-3.34 (m, overlapping with solvent), 2.43-2.01 (m, 2H).

Example 52: N-(2-((R)-4-Cyanothiazolidin-3-yl)-2-oxoethyl)-6-((R)-3-fluoropyrrolidin-1-yl)quinoline-4-carboxamide

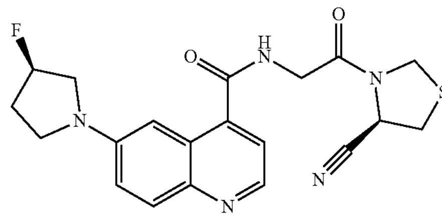

DIPEA (1.39 mL, 7.96 mmol) was added to a stirred solution of (R)-6-(3-fluoropyrrolidin-1-yl)quinoline-4-carboxylic acid Intermediate 114 (297 mg, 0.80 mmol), (R)-3-glycylthiazolidine-4-carbonitrile hydrochloride Intermediate 4 (248 mg, 1.19 mmol) and TBTU (905 mg, 2.39 mmol) in MeCN (7 mL) and EtOAc (7 mL) at 6° C. The resulting solution was stirred at 6° C. overnight. The solvent was removed under reduced pressure. The residue was dissolved with a mixture of sat $NaHCO_3$(70 mL) and EtOAc (100 mL). The phases were separated and the aqueous layer was extracted with EtOAc (4×100 mL). The organic layers were combined and washed with water (4×50 mL). The aqueous layers were combined and extracted with EtOAc (4×20 mL). The organic layers were combined and dried over $Na_2SO_4$, filtered and evaporated. The crude product was purified by preparative HPLC, PrepMethod P, to give the title compound (113 mg, 34%) as an orange solid; HRMS (ESI) m/z $[M+H]^+$ calcd for $C_{20}H_{21}FN_5O_2S$: 414.1394. found: 414.1406; $^1H$ NMR (300 MHz, DMSO-$d_6$) δ 8.93 (t, 1H), 8.59 (d, 1H), 7.90 (d, 1H), 7.48-7.22 (m, 3H), 5.49 (d, 1H), 5.32 (dd, 1H), 4.89 (d, 1H), 4.72 (d, 1H), 4.35-4.24 (m, 2H), 3.74-3.68 (m, 1H), 3.64-3.37 (m, overlapping with solvent), 2.38-2.17 (m, 2H).

Example 53: N-(2-((R)-4-Cyanothiazolidin-3-yl)-2-oxoethyl)-6-(hexahydrocyclopenta[c]pyrrol-2(1H)-yl)quinoline-4-carboxamide

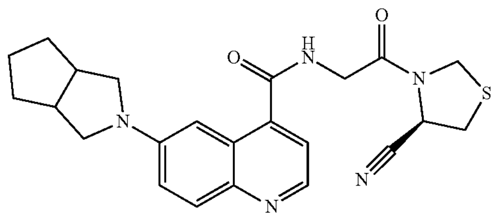 [SMILES: N#C[C@@H]1CSCN1C(=O)CNC(=O)c1ccnc2ccc(N3CC4CCCC4C3)cc12]

DIPEA (0.26 mL, 1.5 mmol) was added to a mixture of 6-(hexahydrocyclopenta[c]pyrrol-2(1H)-yl)quinoline-4-carboxylic acid Intermediate 116 (85 mg, 0.30 mmol), (R)-3-glycylthiazolidine-4-carbonitrile hydrochloride Intermediate 4 (94 mg, 0.45 mmol), EDC (87 mg, 0.45 mmol) and HOBt (69 mg, 0.45 mmol) in EtOAc (5 mL) and MeCN (5 mL). The reaction was stirred at 40° C. for 3 h. The solvent was removed under reduced pressure. The residue was diluted with EtOAc, and washed with water. The organic layer was dried over $Na_2SO_4$, filtered and evaporated. The crude product was purified by preparative HPLC, Prep-Method P, (gradient 23-33%) to give the title compound (40 mg, 30%) as a yellow solid; HRMS (ESI) m/z $[M+H]^+$ calcd for $C_{23}H_{26}N_5O_2S$: 436.1802. found: 436.1808; $^1H$ NMR (300 MHz, DMSO-$d_6$) δ 8.93 (t, 1H), 8.58 (d, 1H), 7.86 (d, 1H), 7.40-7.26 (m, 3H), 5.32 (dd, 1H), 4.89 (d, 1H), 4.71 (d, 1H), 4.29 (d, 2H), 3.62-3.50 (m, 2H), 3.45-3.33 (m, overlapping with solvent), 3.19-3.10 (m, 2H), 2.83-2.77 (m, 3H), 1.92-1.43 (m, 5H).

Example 54: N-(2-((R)-4-Cyanothiazolidin-3-yl)-2-oxoethyl)-6-((S)-3-methylpyrrolidin-1-yl)quinoline-4-carboxamide

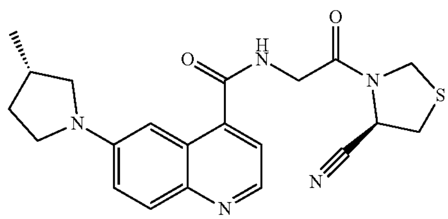 [SMILES: C[C@H]1CCN(c2ccc3nccc(C(=O)NCC(=O)N4CSC[C@H]4C#N)c3c2)C1]

DIPEA (0.20 mL, 1.2 mmol) was added to a mixture of (S)-6-(3-methylpyrrolidin-1-yl)quinoline-4-carboxylic acid Intermediate 118 (100 mg, 0.39 mmol) and (R)-3-glycylthiazolidine-4-carbonitrile hydrochloride Intermediate 4 (100 mg, 0.59 mmol) and HATU (297 mg, 0.78 mmol) in MeCN (10 mL) and EtOAc (10 mL). The reaction was stirred at 25° C. for 2 h. The solvent was removed under reduced pressure. The residue was purified by preparative TLC (DCM:MeOH, 8:1), and then further purified by preparative HPLC, Prep-Method F, (gradient 20-30%) to give the title compound (56 mg, 35%) as a red solid; HRMS (ESI) m/z $[M+H]^+$ calcd for $C_{21}H_{24}N_5O_2S$: 410.1646. found: 410.1634; $^1H$ NMR (400 MHz, DMSO-$d_6$) δ 9.12 (t, 1H), 8.71 (d, 1H), 7.97 (d, 1H), 7.60 (d, 1H), 7.47 (dd, 1H), 7.30 (d, 1H), 5.31 (dd, 1H), 4.90 (d, 1H), 4.72 (d, 1H), 4.49-4.17 (m, 2H), 3.66-3.30 (m, overlapping with solvent), 3.06-2.92 (m, 1H), 2.47-2.30 (m, 1H), 2.22-2.10 (m, 1H), 1.75-1.57 (m, 1H), 1.13 (d, 3H).

Example 55: N-(2-((R)-4-Cyanothiazolidin-3-yl)-2-oxoethyl)-6-((R)-3-methylpyrrolidin-1-yl)quinoline-4-carboxamide

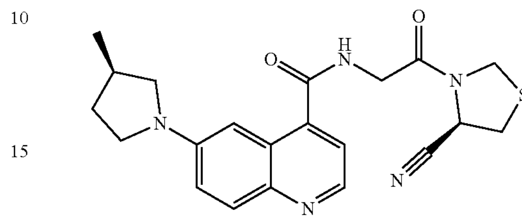

DIPEA (0.36 mL, 2.1 mmol) was added to a mixture of (R)-6-(3-methylpyrrolidin-1-yl)quinoline-4-carboxylic acid Intermediate 120 (175 mg, 0.68 mmol) and (R)-3-glycylthiazolidine-4-carbonitrile hydrochloride Intermediate 4 (175 mg, 1.02 mmol), and HATU (519 mg, 1.37 mmol) in MeCN (10 mL) and EtOAc (10 mL). The reaction was stirred at 25° C. for 2 h. The solvent was removed under reduced pressure. The residue was purified by preparative TLC (DCM:MeOH, 8:1), and then further purified by preparative HPLC, Prep-Method F, (gradient 17-36%) to give the title compound (80 mg, 29%) as a red solid; HRMS (ESI) m/z $[M+H]^+$ calcd for $C_{21}H_{24}N_5O_2S$: 410.1646. found: 410.1650; $^1H$ NMR (400 MHz, DMSO-$d_6$) δ 9.11 (t, 1H), 8.71 (d, 1H), 7.97 (d, 1H), 7.60 (d, 1H), 7.47 (dd, 1H), 7.30 (d, 1H), 5.32 (dd, 1H), 4.90 (d, 1H), 4.73 (d, 1H), 4.45-4.20 (m, 2H), 3.66-3.57 (m, 1H), 3.56-3.33 (m, overlapping with solvent), 3.04-2.93 (m, 1H), 2.47-2.30 (m, 1H), 2.25-2.05 (m, 1H), 1.76-1.56 (m, 1H), 1.13 (d, 3H).

Example 56: N-(2-((R)-4-Cyanothiazolidin-3-yl)-2-oxoethyl)-6-((S)-2-(trifluoromethyl)-pyrrolidin-1-yl)quinoline-4-carboxamide

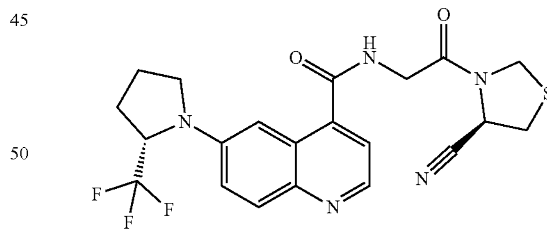

DIPEA (0.37 mL, 2.1 mmol) was added to a mixture of (S)-6-(2-(trifluoromethyl)pyrrolidin-1-yl)quinoline-4-carboxylic acid Intermediate 122 (130 mg, 0.42 mmol), (R)-3-glycylthiazolidine-4-carbonitrile hydrochloride Intermediate 4 (131 mg, 0.63 mmol), EDC (161 mg, 0.84 mmol) and HOBt (128 mg, 0.84 mmol) in EtOAc (5 mL) and MeCN (5 mL). The reaction was stirred at 50° C. for 4 h. The solvent was removed under reduced pressure. The residue was redissolved in EtOAc, and washed with water. The organic layer was dried over $Na_2SO_4$, filtered and evaporated. The crude product was purified by preparative HPLC, Prep-Method P, (gradient 25-35%) to give the title compound (110 mg, 57%) as a yellow solid; HRMS (ESI) m/z $[M+H]^+$ calcd for $C_{21}H_{21}F_3N_5O_2S$: 464.1362. found: 464.1366; $^1H$ NMR (400 MHz, $CD_3OD$) δ 8.61 (d, 1H), 7.94 (d, 1H), 7.75-7.61 (m, 1H), 7.60-7.40 (m, 2H), 5.32 (dd, 1H), 4.84-4.66 (m, overlapping with solvent), 4.47 (d, 1H), 4.31 (d, H), 3.91-3.74 (m, 1H), 3.50-3.34 (m, overlapping with solvent), 2.38-2.06 (m, 4H).

Example 57: (R)—N-(2-(4-Cyanothiazolidin-3-yl)-2-oxoethyl)-6-(2,2-dimethylpyrrolidin-1-yl)quinoline-4-carboxamide

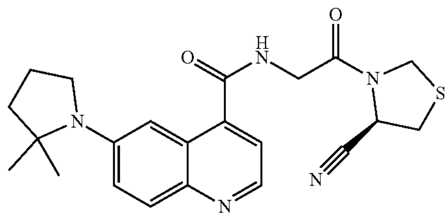 [SMILES: CC1(C)CCCN1c1ccc2nccc(C(=O)NCC(=O)N3CSC[C@H]3C#N)c2c1]

DIPEA (0.40 mL, 2.3 mmol) was added to a mixture of 6-(2,2-dimethylpyrrolidin-1-yl)quinoline-4-carboxylic acid Intermediate 124 (125 mg, 0.46 mmol), (R)-3-glycyl-thiazolidine-4-carbonitrile hydrochloride Intermediate 4 (144 mg, 0.69 mmol), EDC (133 mg, 0.69 mmol) and HOBt (106 mg, 0.69 mmol) in EtOAc (5 mL) and MeCN (5 mL). The reaction was stirred at 40° C. for 4 h. The solvent was removed under reduced pressure. The residue was dissolved in EtOAc and washed with water. The organic layer was dried over $Na_2SO_4$, filtered and evaporated. The crude product was purified by preparative HPLC, PrepMethod P, (gradient 15-25%) to give the title compound (110 mg, 56%) as a yellow solid; HRMS (ESI) m/z $[M+H]^+$ calcd for $C_{22}H_{26}N_5O_2S$: 424.1802. found: 424.1810; $^1H$ NMR (300 MHz, $CD_3OD$) δ 8.49 (d, 1H), 7.83 (d, 1H), 7.54 (dd, 1H), 7.46 (d, 1H), 7.36 (d, 1H), 5.40-5.20 (m, 1H), 4.84-4.65 (m, overlapping with solvent), 4.37 (s, 2H), 3.58-3.48 (m, 2H), 3.47-3.33 (m overlapping with solvent), 2.10-1.90 (m, 4H), 1.53 (s, 6H).

Example 58: N-(2-((R)-4-Cyanothiazolidin-3-yl)-2-oxoethyl)-6-((R)-6-(fluoromethyl)-5-azaspiro[2.4]heptan-5-yl)quinoline-4-carboxamide

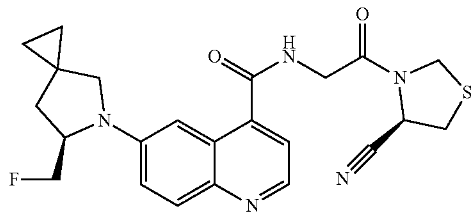 [SMILES: N#C[C@@H]1CSCN1C(=O)CNC(=O)c1ccnc2ccc(N3CC4(CC4)C[C@@H]3CF)cc12]

DIPEA (0.47 mL, 2.7 mmol) was added to a mixture of (R)-6-(6-(fluoromethyl)-5-azaspiro[2.4]heptan-5-yl)quinoline-4-carboxylic acid Intermediate 126 (160 mg, 0.53 mmol), (R)-3-glycylthiazolidine-4-carbonitrile hydrochloride Intermediate 4 (166 mg, 0.80 mmol), EDC (204 mg, 1.07 mmol) and HOBt (163 mg, 1.07 mmol) in EtOAc (6 mL) and MeCN (6 mL). The reaction was stirred at 50° C. for 5 h. The solvent was removed under reduced pressure. The residue was redissolved in EtOAc, and washed with water. The organic layer was dried over $Na_2SO_4$, filtered and evaporated. The crude product was purified by preparative HPLC, PrepMethod P, (gradient 18-28%) to give the title compound (145 mg, 60%) as a yellow solid; HRMS (ESI) m/z $[M+H]^+$ calcd for $C_{23}H_{25}FN_5O_2S$: 454.1708. found: 454.1712; $^1H$ NMR (300 MHz, DMSO-$d_6$) δ 8.94 (t, 1H), 8.57 (d, 1H), 7.87 (d, 1H), 7.44-7.31 (m, 3H), 5.27 (dd, 1H), 4.87 (d, 1H), 4.73-4.12 (m, 6H), 3.51-3.15 (m, overlapping with solvent), 2.35 (dd, 1H), 1.64 (d, 1H), 0.75-0.52 (m, 4H).

Example 59: N-(2-((R)-4-Cyanothiazolidin-3-yl)-2-oxoethyl)-6-((R)-3-fluoroazepan-1-yl)quinoline-4-carboxamide

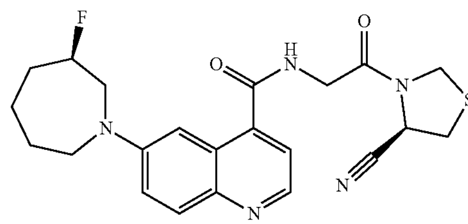

TEA (0.50 mL, 3.6 mmol) was added to (R)-6-(3-fluoroazepan-1-yl)quinoline-4-carboxylic acid Intermediate 130 (52 mg, 0.18 mmol), (R)-3-glycylthiazolidine-4-carbonitrile hydrochloride Intermediate 4 (150 mg, 0.72 mmol), HOBt (276 mg, 1.80 mmol) and EDC (346 mg, 1.80 mmol) in DMF (5 mL) at 15° C. The resulting solution was stirred at overnight under $N_2$ (g). The reaction mixture was diluted with sat $NaHCO_3$ (30 mL), and extracted with EtOAc (9×50 mL). The organic layers were combined and washed with brine (5×200 mL). The organic layer was dried over $Na_2SO_4$, filtered and evaporated to afford crude product. The crude product was purified by preparative HPLC, PrepMethod F, to give the title compound (39 mg, 49%) as an orange solid; HRMS (ESI) m/z $[M+H]^+$ calcd for $C_{22}H_{25}FN_5O_2S$: 442.1708. found: 442.1702; $^1H$ NMR (300 MHz, DMSO-$d_6$) δ 9.05-8.80 (m, 1H), 8.57 (d, 1H), 7.85 (d, 1H), 7.59-7.41 (m, 2H), 7.35 (d, 1H), 5.40-5.20 (m, 1H), 5.18-4.92 (m, 1H), 4.88 (d, 1H), 4.72 (d, 1H), 4.28 (d, 2H), 3.96-3.81 (m, 1H), 3.63-3.34 (m, overlapping with solvent), 2.00-1.58 (m, 5H), 1.52-1.28 (m, 1H).

Example 60: N-(2-((R)-4-Cyanothiazolidin-3-yl)-2-oxoethyl)-6-((S)-3-fluoroazepan-1-yl)quinoline-4-carboxamide

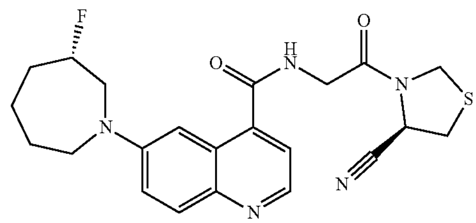 [SMILES: N#C[C@@H]1CSCN1C(=O)CNC(=O)c1ccnc2ccc(N3CCCC[C@H](F)C3)cc12]

TEA (0.68 mL, 4.9 mmol) was added to (S)-6-(3-fluoroazepan-1-yl)quinoline-4-carboxylic acid Intermediate 132 (70 mg, 0.24 mmol), (R)-3-glycylthiazolidine-4-carbonitrile hydrochloride Intermediate 4 (202 mg, 0.97 mmol), HOBt (372 mg, 2.43 mmol) and EDC (465 mg, 2.43 mmol) in DMF (10 mL) at 13° C. The resulting suspension was stirred at 30° C. for 5 h under $N_2$ (g). The reaction mixture was diluted with sat $NaHCO_3$ (50 mL), and extracted with EtOAc (9×50 mL). The organic layers were combined and washed with brine (5×200 mL). The organic layer was dried over $Na_2SO_4$, filtered and evaporated to afford crude product. The crude product was purified by preparative HPLC, PrepMethod P, to give the title compound (58 mg, 54%) as an orange solid; HRMS (ESI) m/z $[M+H]^+$ calcd for $C_{22}H_{25}FN_5O_2S$: 442.1708. found: 442.1698; 1H NMR (300 MHz, DMSO-$d_6$) δ 8.93 (t, 1H), 8.56 (d, 1H), 7.83 (d, 1H), 7.58-7.41 (m, 2H), 7.34 (d, 1H), 5.33-4.80 (m, 3H), 4.76-4.50 (m, 1H), 4.36-4.15 (m, 2H), 4.07-3.73 (m, 2H), 3.70-3.30 (m, overlapping with solvent), 1.89-1.32 (m, 6H).

Example 61: N-(2-((R)-4-Cyanothiazolidin-3-yl)-2-oxoethyl)-6-((R)-7-methyl-1,4-oxazepan-4-yl)quinoline-4-carboxamide

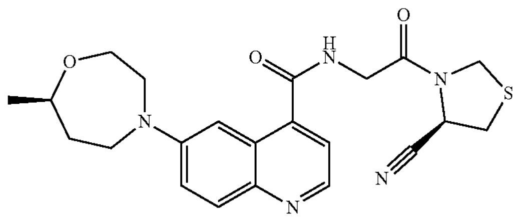 [SMILES: C[C@@H]1CCN(c2ccc3nccc(C(=O)NCC(=O)N4CSC[C@H]4C#N)c3c2)CCO1]

DIPEA (0.54 mL, 3.1 mmol) was added to a stirred suspension of (R)-6-(7-methyl-1,4-oxazepan-4-yl)quinoline-4-carboxylic acid Intermediate 134 (205 mg, 0.31 mmol), (R)-3-glycylthiazolidine-4-carbonitrile hydrochloride Intermediate 4 (96 mg, 0.46 mmol) and TBTU (350 mg, 0.92 mmol) in EtOAc (5 mL) and MeCN (5 mL) at 4° C. The resulting solution was stirred at 4° C. overnight. The solvent was removed under reduced pressure. The residue was dissolved in a mixture of sat $NaHCO_3$(70 mL) and EtOAc (100 mL). The phases were separated and the aqueous layer was extracted with EtOAc (3×100 mL). The organic layers were combined and washed with water (4×25 mL). The aqueous layers were combined and extracted with EtOAc (4×50 mL). All organic layers were combined, dried over $Na_2SO_4$, filtered and evaporated. The crude product was purified by preparative HPLC, PrepMethod F, to give the title compound (90 mg, 66%) as a yellow solid; HRMS (ESI) m/z $[M+H]^+$ calcd for $C_{22}H_{26}N_5O_3S$: 440.1750. found: 440.1746; $^1$H NMR (300 MHz, DMSO-$d_6$) δ 8.96 (t, 1H), 8.55 (d, 1H), 7.84 (d1H), 7.55-7.40 (m, 2H), 7.32 (d, 1H), 5.39-5.19 (m, 1H), 4.89 (d, 1H), 4.70 (d, 1H), 4.37-4.16 (m, 2H), 4.01-3.81 (m, 2H), 3.79-3.34 (m, overlapping with solvent), 2.16-1.95 (m, 1H), 1.74-1.51 (m, 1H), 1.05 (d, 3H).

Example 62: N-(2-((R)-4-Cyanothiazolidin-3-yl)-2-oxoethyl)-6-((S)-7-methyl-1,4-oxazepan-4-yl)quinoline-4-carboxamide

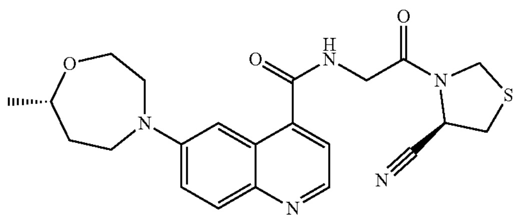 [SMILES: C[C@H]1CCN(c2ccc3nccc(C(=O)NCC(=O)N4CSC[C@H]4C#N)c3c2)CCO1]

DIPEA (1.14 mL, 6.51 mmol) was added to a stirred suspension of (S)-6-(7-methyl-1,4-oxazepan-4-yl)quinoline-4-carboxylic acid Intermediate 136 (305 mg, 0.33 mmol), (R)-3-glycylthiazolidine-4-carbonitrile hydrochloride Intermediate 4 (135 mg, 0.65 mmol), HOBt (249 mg, 1.63 mmol) and EDC (312 mg, 1.63 mmol) in EtOAc (5 mL) and MeCN (5 mL) at 6° C. The resulting solution was stirred at 4° C. overnight and then at 40° C. for a further 4 h. The solvent was removed under reduced pressure. The residue was dissolved in a mixture of sat $NaHCO_3$ (50 mL) and EtOAc (100 mL). The phases were separated and the aqueous layer was extracted with EtOAc (3×100 mL). The organic layers were combined and washed with water (4×25 mL). All organic layers were combined, dried over $Na_2SO_4$, filtered and evaporated. The crude product was purified by preparative HPLC, PrepMethod F, to give the title compound (100 mg, 70%) as a yellow solid; HRMS (ESI) m/z $[M+H]^+$ calcd for $C_{22}H_{26}N_5O_3S$: 440.1750. found: 440.1746; $^1$H NMR (300 MHz, DMSO-$d_6$) δ 8.95 (t, 1H), 8.56 (d, 1H), 7.85 (d, 1H), 7.59-7.43 (m, 2H), 7.33 (d, 1H), 5.40-5.20 (m, 1H), 4.89 (d, 1H), 4.71 (d, 1H), 4.33-4.19 (m, 2H), 4.05-3.80 (m, 2H), 3.78 −3.23 (m, overlapping with solvent), 2.17-1.98 (m, 1H), 1.75-1.50 (m, 1H), 1.07 (d, 3H).

Example 63: N-(2-((R)-4-Cyanothiazolidin-3-yl)-2-oxoethyl)-6-((S)-3-methyl-1,4-oxazepan-4-yl)quinoline-4-carboxamide

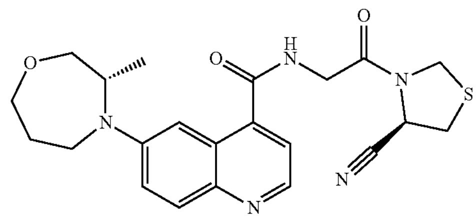 [SMILES: C[C@H]1COCCCN1c1ccc2nccc(C(=O)NCC(=O)N3CSC[C@H]3C#N)c2c1]

DIPEA (0.79 mL, 4.5 mmol) was added dropwise to a mixture of (R)-6-(3-methyl-1,4-oxazepan-4-yl)quinoline-4-carboxylic acid Intermediate 138 (65 mg, 0.23 mmol), (R)-3-glycylthiazolidine-4-carbonitrile hydrochloride Intermediate 4 (94 mg, 0.45 mmol), HOBt (348 mg, 2.27 mmol) and EDC (435 mg, 2.27 mmol) in MeCN (3 mL) and EtOAc (3 mL) at 10° C. The resulting solution was stirred at 10° C. for overnight under $N_2$ (g). The solvent was removed under reduced pressure. The residue was diluted with sat $NaHCO_3$ (100 mL), and extracted with EtOAc (6×100 mL). The organic layers were combined and washed with brine (5×200 mL). The organic layer was dried over $Na_2SO_4$, filtered and evaporated. The crude product was purified by preparative HPLC, PrepMethod C, to afford the title compound (45 mg, 45%) as an orange solid; HRMS (ESI) m/z $[M+H]^+$ calcd for $C_{22}H_{26}N_5O_3S$: 440.1750. found: 440.1742; $^1$H NMR (300 MHz, DMSO-$d_6$) δ 8.94 (brs, 0.5H), 8.52 (d, 1H), 8.32 (brs, 7.84 (d, 1H), 7.54-7.35 (m, 2H), 7.31 (d, 1H), 5.31 (dd, 1H), 4.87 (d, 1H), 4.68 (d, 1H), 4.37-4.10 (m, 3H), 4.00 (dd, 1H), 3.97-3.72 (m, 2H), 3.61 −3.30 (m, overlapping with solvent), 1.93-1.64 (m, 2H), 1.07 (d, 3H).

Example 64: N-(2-((R)-4-Cyanothiazolidin-3-yl)-2-oxoethyl)-6-((R)-2-methyl-1,4-oxazepan-4-yl)quinoline-4-carboxamide

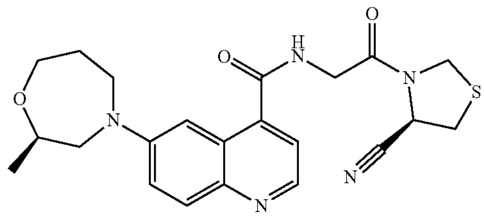 [SMILES: C[C@@H]1CN(c2ccc3nccc(C(=O)NCC(=O)N4CSC[C@H]4C#N)c3c2)CCCO1]

DIPEA (0.37 mL, 2.1 mmol) was added to a mixture of (R)-6-(2-methyl-1,4-oxazepan-4-yl)quinoline-4-carboxylic acid Intermediate 140 (100 mg, 0.35 mmol), (R)-3-glycylthiazolidine-4-carbonitrile hydrochloride Intermediate 4 (90 mg, 0.52 mmol) and HATU (266 mg, 0.70 mmol) in MeCN (5 mL) and EtOAc (5 mL). The mixture was stirred under an atmosphere of air at 25° C. for 3 h. The solvent was removed under reduced pressure. The residue was purified by preparative TLC (DCM:MeOH, 19:1), followed by preparative HPLC, PrepMethod F, (gradient 15-25%) to give the title compound (30 mg, 20%) as a red solid; HRMS (ESI) m/z $[M+H]^+$ calcd for $C_{22}H_{26}N_5O_3S$: 440.1750. found: 440.1724; $^1H$ NMR (400 MHz, DMSO-$d_6$) δ 9.18 (t, 1H), 8.74 (d, 1H), 7.98 (d, 1H), 7.74 (dd, 1H), 7.67-7.50 (m, 2H), 5.38-5.18 (m, 1H), 4.90 (d, 1H), 4.72 (d, 1H), 4.39-4.25 (m, 2H), 4.23-4.01 (m, 2H), 3.93-3.75 (m, 2H), 3.60-3.31 (m, overlapping with solvent), 3.29-3.06 (m, 2H), 2.19-1.98 (m, 1H), 1.95-1.80 (m, 1H), 1.20 (d, 3H).

Example 65: N-(2-((R)-4-Cyanothiazolidin-3-yl)-2-oxoethyl)-6-((S)-2-methylpyrrolidin-1-yl)quinoline-4-carboxamide

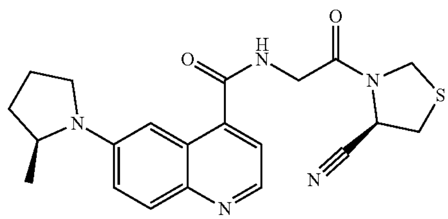 [SMILES: C[C@H]1CCCN1c1ccc2nccc(C(=O)NCC(=O)N3CSC[C@H]3C#N)c2c1]

DIPEA (0.41 mL, 2.3 mmol) was added to a mixture of (S)-6-(2-methylpyrrolidin-1-yl)quinoline-4-carboxylic acid Intermediate 128 (100 mg, 0.39 mmol), (R)-3-glycyl-thiazolidine-4-carbonitrile hydrochloride Intermediate 4 (122 mg, 0.59 mmol) and HATU (297 mg, 0.78 mmol) in MeCN (5 mL) and EtOAc (5 mL). The mixture was stirred at 25° C. for 3 h. The solvent was removed under reduced pressure. The residue was purified by preparative TLC (DCM:MeOH, 19:1), and further purified by preparative HPLC, PrepMethod F, (gradient 20-30%) to give the title compound (35 mg, 22%) as an orange solid; HRMS (ESI) m/z $[M+H]^+$ calcd for $C_{21}H_{24}N_5O_2S$: 410.1646. found: 410.1636; $^1H$ NMR (400 MHz, DMSO-$d_6$) δ 8.93 (t, 1H), 8.55 (d, 1H), 7.86 (d, 1H), 7.39-7.18 (m, 3H), 5.40-5.25 (m, 1H), 4.90 (d, 1H), 4.72 (d, 1H), 4.37-4.19 (m, 2H), 4.15-4.00 (m, 1H), 3.57-3.18 (m, overlapping with solvent), 2.16-1.94 (m, 3H), 1.80-1.60 (m, 1H), 1.17 (d, 3H).

Example 66: (R)—N-(2-(4-Cyanothiazolidin-3-yl)-2-oxoethyl)-6-(3-methoxyazetidin-1-yl)quinoline-4-carboxamide

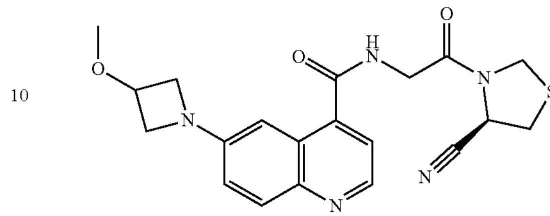

HATU (159 mg, 0.42 mmol) was added to a stirred mixture of crude 6-(3-methoxyazetidin-1-yl)quinoline-4-carboxylic acid Intermediate 142 (102 mg, 0.35 mmol) and DIPEA (0.303 mL, 1.74 mmol) in a mixture of MeCN (1.5 mL) and EtOAc (1.5 mL) at rt. The reaction was stirred for 1 min after which (R)-3-glycylthiazolidine-4-carbonitrile hydrochloride Intermediate 4 (87 mg, 0.42 mmol) was added and the reaction mixture was stirred for 1.5 h at rt. The reaction was diluted with EtOAc (8 mL) and washed with 8% $NaHCO_3$(aq, 6 mL). The aqueous layer was extracted with EtOAc and the combined organic layers was dried over $Na_2SO_4$, filtered and concentrated. The residue was purified by preparative HPLC, PrepMethod G, (gradient: 5-45%) to give the title compound (0.071 g, 49%) as an orange solid; HRMS (ESI) m/z $[M+H]^+$ calcd for $C_{20}H_{22}N_5O_3S$: 412.1438. found: 412.1442; $^1H$ NMR (500 MHz, DMSO-$d_6$) δ 9.14 (t, 1H). 8.79 (d, 1H), 7.98 (d, 1H), 7.65 (d, 1H), 7.33-7.27 (m, 2H), 5.34 (dd, 1H), 4.90 (d, 1H), 4.72 (d, 1H), 4.42-4.29 (m, 3H), 4.27-4.18 (m, 2H), 3.83 (dd, 2H), 3.41 (dd, 1H), 3.36 (dd, 1H), 3.27 (s, 3H).

Example 67: (R)—N-(2-(4-Cyanothiazolidin-3-yl)-2-oxoethyl)-6-morpholinoquinoline-4-carboxamide

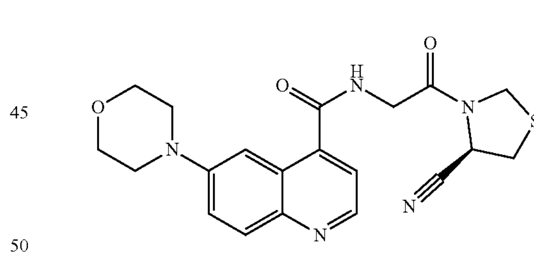

DIPEA (0.15 mL, 0.87 mmol) was added to a suspension of 6-morpholinoquinoline-4-carboxylic acid Intermediate 144 (75 mg, 0.29 mmol), (R)-3-glycylthiazolidine-4-carbonitrile hydrochloride Intermediate 4 (121 mg, 0.58 mmol), HOBt (53 mg, 0.35 mmol) and EDC (84 mg, 0.44 mmol) in EtOAc (1 mL) and MeCN (1 mL). Gives a clear yellow solution which was stirred at rt overnight. The mixture was diluted with EtOAc, washed with sat $NaHCO_3$ and brine. The organic phase was dried, filtered and evaporated. The residue was purified by preparative HPLC, PrepMethod E, (gradient 5-65%) to give the title compound (26 mg, 21%); HRMS (ESI) m/z $[M+H]^+$ calcd for $C_{20}H_{22}N_5O_3S$: 412.1438. found: 412.1437; $^1H$ NMR (400 MHz, $CD_3CN$) δ 8.71 (d, 1H), 8.05 (s, 1H), 7.96 (d, 1H), 7.69 (d, 1H), 7.60 (dd, 1H), 7.43 (d, 1H), 5.24 (dd, 1H), 4.79-4.60 (m, 2H), 4.30 (d, 2H), 3.88-3.79 (m, 4H), 3.35-3.28 (m, 6H).

Example 68: N-(2-((R)-4-Cyanothiazolidin-3-yl)-2-oxoethyl)-6-((2R,6S)-2,6-dimethyl-morpholino)quinoline-4-carboxamide

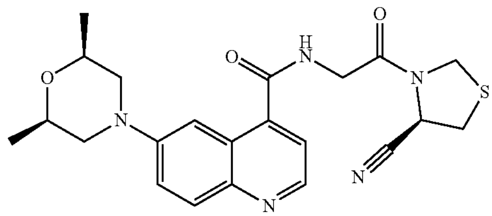 [SMILES: C[C@@H]1CN(c2ccc3nccc(C(=O)NCC(=O)N4CSC[C@H]4C#N)c3c2)C[C@H](C)O1]

A vial was charged with tert-butyl 6-((2R,6S)-2,6-dimethylmorpholino)quinoline-4-carboxylate Intermediate 149 (121 mg, 0.35 mmol) and 90% TFA (aq, 0.5 mL). The vial was heated at 50° C. for 1 h 40 min. The reaction mixture was concentrated and co-evaporated from a mixture of $H_2O$ and MeCN. MeCN (1.5 mL), EtOAc (1.5 mL) and DIPEA (0.305 mL, 1.75 mmol) were added to the residue followed by HATU (0.16 g, 0.42 mmol) and the mixture was stirred at for 1 min after which (R)-3-glycylthiazolidine-4-carbonitrile hydrochloride Intermediate 4 (0.087 g, 0.42 mmol) was added. The mixture was stirred at rt for 3 h. The reaction mixture was partitioned between EtOAc (25 mL) and 8% $NaHCO_3$(aq, 10 mL). The aqueous layer was extracted with EtOAc (10 mL) and the combined organic layers were concentrated. The residue was purified by preparative HPLC, PrepMethod G, (gradient of 5-45%) to give the title compound (85 mg, 55%) as an orange solid; HRMS (ESI) m/z $[M+H]^+$ calcd for $C_{22}H_{26}N_5O_3S$: 440.1750. found: 440.1756; $^1H$ NMR (500 MHz, DMSO-$d_6$) δ 9.08 (t, 1H), 8.72 (d, 1H), 7.93 (d, 1H), 7.77-7.71 (m, 2H), 7.45 (d, 1H), 5.31 (dd, 1H), 4.90 (d, 1H), 4.71 (d, 1H), 4.36-4.27 (m, 2H), 3.89 (dd, 2H), 3.79-3.69 (m, 2H), 3.42 (dd, 1H), 3.36 (dd, 1H), 2.42 (t, 2H), 1.25-1.17 (m, 6H).

Example 69: N-(2-((R)-4-Cyanothiazolidin-3-yl)-2-oxoethyl)-6-((R)-2-(fluoromethyl)-morpholino)quinoline-4-carboxamide

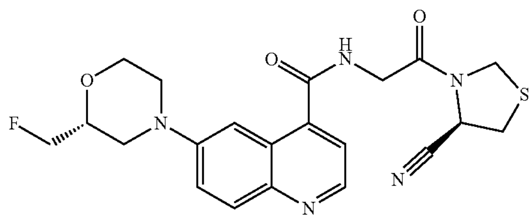 [SMILES: N#C[C@@H]1CSCN1C(=O)CNC(=O)c1ccnc2ccc(N3CCO[C@@H](CF)C3)cc12]

HATU (0.730 g, 1.92 mmol) was added to a stirred mixture of the crude (R)-6-(2-(fluoromethyl)morpholino) quinoline-4-carboxylic acid Intermediate 146 (1.60 mmol) and DIPEA (1.68 mL, 9.60 mmol) in a mixture of MeCN (7 mL) and EtOAc (7 mL) at rt. The reaction was stirred for 1 min after which (R)-3-glycylthiazolidine-4-carbonitrile hydrochloride Intermediate 4 (0.399 g, 1.92 mmol) was added and the reaction mixture was stirred for 1 h at rt. The reaction mixture was diluted with EtOAc (100 mL) and washed sequentially with 8% $NaHCO_3$(aq, 2×20) mL) and $H_2O$ (2×10 mL). The organic layer was dried over $Na_2SO_4$, filtered and concentrated. The residue was purified by straight phase flash chromatography on silica (EtOAc followed by EtOAc:MeOH 20:1). The product was further purified twice by preparative HPLC, PrepMethod G, (gradients: 0-30% and 5-35%). The product was further purified by straight phase flash chromatography on silica (EtOAc followed by EtOAc:MeOH, 20:1) to give the title compound (0.314 g, 44%) as a yellow solid; HRMS (ESI) m/z $[M+H]^+$ calcd for $C_{21}H_{23}FN_5O_3S$: 444.1500. found: 444.1506; $^1H$ NMR (500 MHz, DMSO-$d_6$) δ 9.05 (t, 1H), 8.71 (d, 1H), 7.93 (d, 1H), 7.76 (d, 1H), 7.70 (dd, 1H), 7.42 (d, 1H), 5.32 (dd, 1H), 4.90 (d, 1H), 4.71 (d, 1H), 4.68-4.48 (m, 2H), 4.37-4.25 (m, 2H), 4.08-4.01 (m, 1H), 3.95-3.82 (m, 2H), 3.82-3.68 (m, 2H), 3.43 (dd, 1H), 3.36 (dd, 1H), 2.82 (td, 1H), 2.68 (t, 1H).

Example 70: N-(2-((R)-4-Cyanothiazolidin-3-yl)-2-oxoethyl)-6-((2R,6R)-2,6-dimethyl-morpholino) quinoline-4-carboxamide

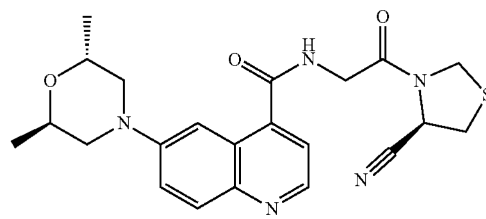

HATU (0.119 g, 0.31 mmol) was added to a stirred mixture of crude 6-((2R,6R)-2,6-dimethylmorpholino)quinoline-4-carboxylic acid Intermediate 148 (0.26 mmol) and DIPEA (0.227 mL, 1.30 mmol) in a mixture of MeCN (1.2 mL) and EtOAc (1.2 mL) at rt. The reaction was stirred for 1 min after which (R)-3-glycylthiazolidine-4-carbonitrile hydrochloride Intermediate 4 (0.065 g, 0.31 mmol) was added. The reaction was stirred for 4.5 h at rt. The reaction was diluted with EtOAc (5 mL) and washed with 8% $NaHCO_3$(aq, mL). The aqueous layer was extracted with EtOAc (3 mL) and the combined organic layers were dried over $Na_2SO_4$, filtered and concentrated. The residue was purified by preparative HPLC, PrepMethod G, (gradient: 15-55%). The compound was dissolved in EtOAc and the organic layer was washed twice with $H_2O$, concentrated and freeze-dried to give the title compound (0.042 g, 37%) as an orange solid; HRMS (ESI) m/z $[M+H]^+$ calcd for $C_{22}H_{26}N_5O_3S$: 440.1750. found: 440.1746; $^1H$ NMR (500 MHz, DMSO-$d_6$) δ 9.10 (t, 1H), 8.73 (d, 1H), 7.93 (d, 1H), 7.7-7.8 (m, 2H), 7.49 (d, 1H), 5.31 (dd, 1H), 4.90 (d, 1H), 4.71 (d, 1H), 4.25-4.39 (m, 2H), 4.07-4.16 (m, 2H), 3.43 (td, 3H), 3.36 (dd, 1H), 3.12 (dd, 2H), 1.24 (d, 6H).

Example 71: N-(2-((R)-4-Cyanothiazolidin-3-yl)-2-oxoethyl)-6-((S)-2-(fluoromethyl)-morpholino)quinoline-4-carboxamide

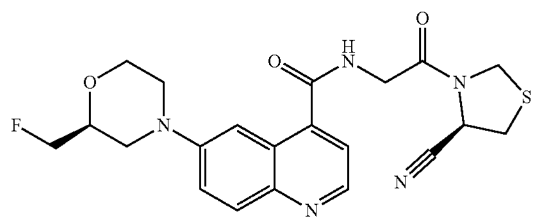 [SMILES: N#C[C@@H]1CSCN1C(=O)CNC(=O)c1ccnc2ccc(N3CCO[C@H](CF)C3)cc12]

A vial was charged with tert-butyl (S)-6-(2-(fluoromethyl) morpholino)quinoline-4-carboxylate Intermediate 150 (121 mg, 0.35 mmol) and 90% TFA (aq, 0.5 mL) and the reaction mixture was heated at 50° C. for 1 h 40 min. The reaction mixture was concentrated and the residue was co-evaporated from a mixture of $H_2O$ and MeCN. MeCN (1.5 mL), EtOAc (1.5 mL) and DIPEA (0.305 mL, 1.75 mmol) were added to the residue followed by HATU (0.160 g, 0.42 mmol). The mixture was stirred for 1 min after which (R)-3-glycylthiazolidine-4-carbonitrile hydrochloride Intermediate 4 (0.087 g, 0.42 mmol) was added. The mixture was stirred at rt for 3 h. The reaction mixture was partitioned between EtOAc (25 mL) and 8% $NaHCO_3$(aq, 10 mL). The aqueous layer was extracted with EtOAc (10 mL) and the combined organic layers were concentrated. The residue was purified by preparative HPLC, PrepMethod G, (gradient 5-45%) to give the title compound (65 mg, 42%) as an orange solid; HRMS (ESI) m/z $[M+H]^+$ calcd for $C_{21}H_{23}FN_5O_3S$: 444.1500. found: 444.1496; $^1H$ NMR (500 MHz, DMSO-$d_6$) δ 9.06 (t, 1H), 8.72 (d, 1H), 7.94 (d, 1H), 7.78 (d, 1H), 7.71 (dd, 1H), 7.44 (d, 1H), 5.34 (dd, 1H), 4.90 (d, 1H), 4.71 (d, 1H), 4.68-4.47 (m, 2H), 4.37-4.25 (m, 2H), 4.08-4.01 (m, 1H), 3.93-3.82 (m, 2H), 3.82-3.68 (m, 2H), 3.42 (dd, 1H), 3.36 (dd, 1H), 2.85 (td, 1H), 2.68 (t, 1H).

Example 72: N-(2-((R)-4-Cyanothiazolidin-3-yl)-2-oxoethyl)-6-((R)-2-methyl-morpholino)quinoline-4-carboxamide

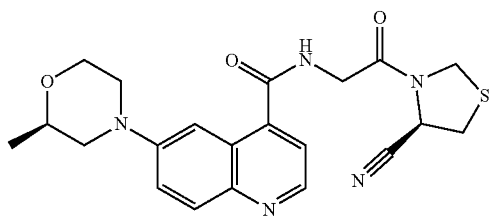 [SMILES: C[C@@H]1CN(c2ccc3nccc(C(=O)NCC(=O)N4CSC[C@H]4C#N)c3c2)CCO1]

HATU (0.160 g, 0.42 mmol) was added to a stirred mixture of crude (R)-6-(2-methylmorpholino)quinoline-4-carboxylic acid Intermediate 152 (0.134 g) and DIPEA (0.306 mL, 1.75 mmol) in a mixture of MeCN/EtOAc (3 mL, 1:1) at rt. The reaction was stirred for 1 min after which (R)-3-glycylthiazolidine-4-carbonitrile hydrochloride Intermediate 4 (0.087 g, 0.42 mmol) was added. The reaction was stirred for 45 min at rt. The reaction was diluted with EtOAc (6 mL) and washed with 8% $NaHCO_3$(aq, 6 mL). The aqueous layer was extracted with EtOAc (2×3 mL) and the combined organic layers were dried over $Na_2SO_4$, filtered and concentrated. The residue was purified by preparative HPLC, PrepMethod G, (gradient of 5-55%) to give the title compound (56 mg, 38%) as a red/orange solid; HRMS (ESI) m/z $[M+H]^+$ calcd for $C_2J$-$124N_5O_3S$: 426.1594. found: 426.1582; $^1H$ NMR (500 MHz, DMSO-$d_6$) δ 9.10 (t, 1H), 8.75 (d, 1H), 7.95 (d, 1H), 7.79-7.73 (m, 2H), 7.50 (d, 1H), 5.32 (dd, 1H), 4.90 (d, 1H), 4.71 (d, 1H), 4.39-4.25 (m, 2H), 4.01-3.94 (m, 1H), 3.88 (d, 1H), 3.78 (d, 1H), 3.74-3.62 (m, 3H), 3.42 (dd, 1H), 3.36 (dd, 1H), 2.83 (td, 1H), 1.22 (d, 3H).

Example 73: N-(2-((R)-4-Cyanothiazolidin-3-yl)-2-oxoethyl)-6-((R)-2-(trifluoromethyl)-morpholino) quinoline-4-carboxamide

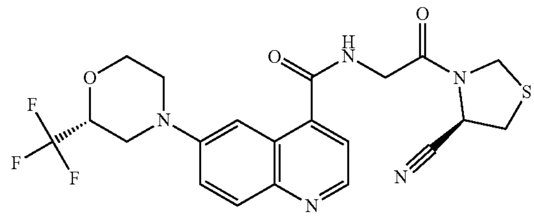 [SMILES: N#C[C@@H]1CSCN1C(=O)CNC(=O)c1ccnc2ccc(N3CCO[C@@H](C(F)(F)F)C3)cc12]

HATU (0.137 g, 0.36 mmol) was added to a stirred mixture of crude (R)-6-(2-(trifluoromethyl)morpholino)quinoline-4-carboxylic acid Intermediate 154 (0.30 mmol) and DIPEA (0.262 mL, 1.50 mmol) in a mixture of MeCN/EtOAc (2.8 mL, 1:1) at rt. The reaction was stirred for −1 min after which (R)-3-glycylthiazolidine-4-carbonitrile hydrochloride Intermediate 4 (0.075 g, 0.36 mmol) was added. The reaction mixture was stirred for 4.5 h at rt, diluted with EtOAc (5 mL) and washed with 8% $NaHCO_3$ (aq, 5 mL). The aqueous layer was extracted with EtOAc (3 mL) and the combined organic layers were dried over $Na_2SO_4$, filtered and concentrated. The residue was purified by preparative HPLC, PrepMethod G, (gradient: 5-55%). The purified compound was dissolved in EtOAc and washed sequentially with 8% $NaHCO_3$ (aq) and $H_2O$ (2×). The organic layer was concentrated and freeze-dried from MeCN/$H_2O$ to give the title compound (0.066 g, 46%) as a solid; HRMS (ESI) m/z $[M+H]^+$ calcd for $C_{211}H_{21}F_3N_5O_3S$: 480.1312. found: 480.1308; $^1H$ NMR (500 MHz, DMSO-$d_6$) δ 9.06 (t, 1H), 8.74 (d, 1H), 7.95 (d, 1H), 7.82 (d, 1H), 7.76 (dd, 1H), 7.44 (d, 1H), 5.26 (dd, 1H), 4.90 (d, 1H), 4.71 (d, 1H), 4.45-4.39 (m, 1H), 4.37-4.25 (m, 2H), 4.14 (d, 1H), 3.99 (d, 1H), 3.89-3.8 (m, 2H), 3.43 (dd, 1H), 3.37 (dd, 1H), 2.96-2.84 (m, 2H).

Example 74: N-(2-((R)-4-Cyanothiazolidin-3-yl)-2-oxoethyl)-6-((S)-2-(trifluoromethyl)-morpholino) quinoline-4-carboxamide

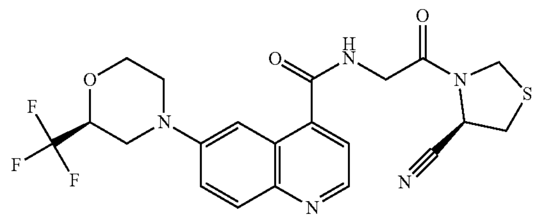 [SMILES: N#C[C@@H]1CSCN1C(=O)CNC(=O)c1ccnc2ccc(N3CCO[C@H](C(F)(F)F)C3)cc12]

HATU (0.137 g, 0.36 mmol) was added to a stirred mixture of crude (S)-6-(2-(trifluoromethyl)morpholino)quinoline-4-carboxylic acid Intermediate 156 (0.30 mmol) and DIPEA (0.262 mL, 1.50 mmol) in MeCN (1.4 mL) and EtOAc (1.4 mL) at rt. The reaction was stirred for 1 min after which (R)-3-glycylthiazolidine-4-carbonitrile hydrochloride Intermediate 4 (0.075 g, 0.36 mmol) was added and the mixture was stirred for 4.5 h at rt. The reaction mixture was diluted with EtOAc (5 mL) and washed with 8% $NaHCO_3$ (aq, 5 mL). The aqueous layer was extracted with EtOAc (3 mL) and the combined organic layers were dried over $Na_2SO_4$, filtered and concentrated. The residue was purified by preparative HPLC, PrepMethod G, (gradient: 5-55%). The product was partitioned between EtOAc and 8% $NaHCO_3$ (aq). The organic layer was washed with small portions of $H_2O$ (3×), concentrated and freeze-dried from $MeCN/H_2O$ to give the title compound (0.043 g, 30%); HRMS (ESI) m/z $[M+H]^+$ calcd for $C_{21}H_{21}F_3N_5O_3S$: 480.1312. found: 480.1302; $^1H$ NMR (500 MHz, DMSO-$d_6$) δ 9.04 (t, 1H), 8.74 (d, 1H), 7.95 (d, 1H), 7.84 (d, 1H), 7.76 (dd, 1H), 7.44 (d, 1H), 5.29-5.24 (m, 1H), 4.89 (d, 1H), 4.72 (d, 1H), 4.44-4.38 (m, 1H), 4.31 (dd, 2H), 4.15 (d, 1H), 3.96 (d, 1H), 3.89-3.79 (m, 2H), 3.43 (d, 1H), 3.37 (dd, 1H), 2.99-2.88 (m, 2H).

Example 75: 6-((1S,4S)-2-Oxa-5-azabicyclo[2.2.1]heptan-5-yl)-N-(2-((R)-4-cyano-thiazolidin-3-yl)-2-oxoethyl)quinoline-4-carboxamide

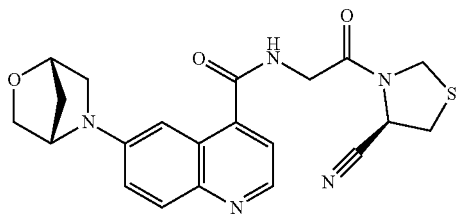 [SMILES: N#C[C@@H]1CSCN1C(=O)CNC(=O)c1ccnc2ccc(N3C[C@@H]4C[C@H]3CO4)cc12]

HATU (0.141 g, 0.37 mmol) was added to a stirred mixture of crude 6-((1S,4S)-2-oxa-5-azabicyclo[2.2.1]heptan-5-yl)quinoline-4-carboxylic acid Intermediate 158 (0.31 mmol) and DIPEA (0.271 mL, 1.55 mmol) in a mixture of MeCN/EtOAc (2.8 mL, 1:1) at rt and the reaction was stirred for 1 min. (R)-3-Glycylthiazolidine-4-carbonitrile hydrochloride Intermediate 4 (0.077 g, 0.37 mmol) was added and the reaction mixture was stirred for 45 min at rt. The reaction mixture was diluted with EtOAc (5 mL) and washed with 8% $NaHCO_3$(aq, 5 mL). The aqueous layer was extracted with EtOAc (3 mL) and the combined organic layers were dried over $Na_2SO_4$, filtered and concentrated. The residue was purified by preparative HPLC, PrepMethod G, (gradient of 5-45%) to give an orange solid which was dissolved in EtOAc. The organic layer was washed with 8% $NaHCO_3$(aq, 2×) and $H_2O$ (2×). The organic layer was concentrated and freeze-dried from a mixture of MeCN and $H_2O$ to give the title compound (0.035 g, 27%) as a yellow solid; HRMS (ESI) m/z $[M+H]^+$ calcd for $C_{21}H_{22}N_5O_3S$: 424.1438. found: 424.1442; $^1H$ NMR (500 MHz, DMSO-$d_6$) δ 8.96 (t, 1H), 8.59 (d, 1H), 7.87 (d, 1H), 7.45 (d, 1H), 7.36 (dd, 2H), 5.31 (dd, 1H), 4.89 (d, 1H), 4.77 (brs, 1H), 4.70 (d, 1H), 4.66 (brs, 1H), 4.36-4.23 (m, 2H), 3.84 (d, 1H), 3.74 (d, 1H), 3.62 (d, 1H), 3.42-3.34 (m, 2H), 3.14 (d, 1H), 1.98 (dd, 1H), 1.89 (d, 1H).

Example 76: 6-((1R,4R)-2-Oxa-5-azabicyclo[2.2.1]heptan-5-yl)-N-(2-((R)-4-cyano-thiazolidin-3-yl)-2-oxoethyl)quinoline-4-carboxamide

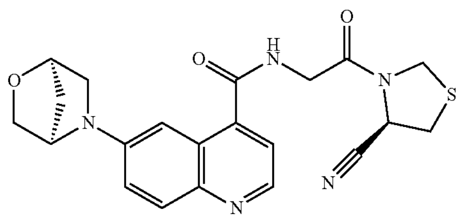 [SMILES: N#C[C@@H]1CSCN1C(=O)CNC(=O)c1ccnc2ccc(N3C[C@H]4C[C@@H]3CO4)cc12]

HATU (0.128 g, 0.34 mmol) was added to a stirred mixture of crude 6-((1R,4R)-2-oxa-5-azabicyclo[2.2.1]heptan-5-yl)quinoline-4-carboxylic acid Intermediate 160 (0.28 mmol) and DIPEA (0.245 mL, 1.40 mmol) in a mixture of MeCN/EtOAc (2.6 mL, 1:1) at rt. The reaction was stirred for 1 min after which (R)-3-glycylthiazolidine-4-carbonitrile hydrochloride Intermediate 4 (0.070 g, 0.34 mmol) was added. The reaction was stirred for 3 h at rt. The reaction mixture was diluted with EtOAc (5 mL) and washed with 8% $NaHCO_3$ (aq, 5 mL). The aqueous layer was extracted with EtOAc (3 mL) and the combined organic layers were dried over $Na_2SO_4$, filtered and concentrated. The residue was purified by straight phase flash chromatography on silica (EtOAc followed by EtOAc:MeOH, 6:1). The compound was further purified by preparative HPLC, PrepMethod G, (gradient of 5-45%). The compound was partitioned between EtOAc and 8% $NaHCO_3$ (aq). The organic layer was washed with 8% $NaHCO_3$ (aq) followed by $H_2O$ (2×). The organic layer was concentrated and the washing sequence was repeated. The crude compound was purified by straight phase flash chromatography (EtOAc:MeOH, 6:1) and freeze-dried from $MeCN/H_2O$ to give the title compound (0.026 g, 22%) as a yellow solid; HRMS (ESI) m/z $[M+H]^+$ calcd for $C_{21}H_{22}N_5O_3S$: 424.1438. found: 424.1430; $^1H$ NMR (500 MHz, DMSO-$d_6$) δ 8.97 (t, 1H), 8.59 (d, 1H), 7.87 (d, 1H), 7.47 (d, 1H), 7.38-7.32 (m, 2H), 5.32 (dd, 1H), 4.89 (d, 1H), 4.79 (brs, 1H), 4.70 (d, 1H), 4.68-4.64 (m, 1H), 4.29 (d, 2H), 3.82 (d, 1H), 3.75 (d, 1H), 3.62 (d, 1H), 3.41 (dd, 1H), 3.38-3.36 (m, 1H), 2.02-1.96 (m, 1H), 3.14 (d, 1H), 1.88 (m, 1H).

Example 77: 6-(6-Oxa-3-azabicyclo[3.1.1]heptan-3-yl)-N-(2-((R)-4-cyanothiazolidin-3-yl)-2-oxoethyl)quinoline-4-carboxamide

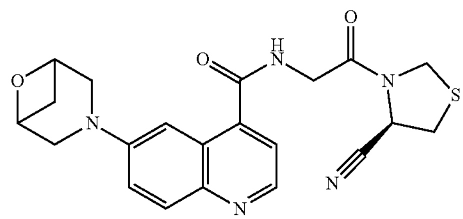 [SMILES: N#C[C@@H]1CSCN1C(=O)CNC(=O)c1ccnc2ccc(N3CC4CC(C3)O4)cc12]

HATU (0.137 g, 0.36 mmol) was added to a stirred mixture of the crude 6-(6-oxa-3-azabicyclo[3.1.1]heptan-3-yl)quinoline-4-carboxylic acid Intermediate 162 (0.30 mmol) and DIPEA (0.262 mL, 1.50 mmol) in a mixture of MeCN/EtOAc (2.8 mL, 1:1) at rt. The reaction mixture was stirred for 5 min after which (R)-3-glycylthiazolidine-4-carbonitrile hydrochloride Intermediate 4 (0.075 g, 0.36 mmol) was added. The reaction mixture was stirred for 4.5 h at rt, diluted with EtOAc (5 mL) and washed with 5 mL 8% $NaHCO_3$ (aq). The aqueous layer was extracted with EtOAc (3 mL) and the combined organic layers were dried over $Na_2SO_4$, filtered and concentrated. The residue was purified by preparative HPLC, PrepMethod G, (gradient: 5-45%) followed by straight phase flash chromatography on silica (EtOAc:MeOH, 9:1). The appropriate fractions were combined, concentrated, and the residue was partitioned between EtOAc and $NaHCO_3$ (aq). The organic layer was washed with $H_2O$ (3×), concentrated and freeze-dried from $MeCN/H_2O$ to give the title compound (0.028 g, 22%) as a solid; HRMS (ESI) m/z $[M+H]^+$ calcd for $C_{21}H_{22}N_5O_3S$:

424.1438. found: 424.1454; $^1H$ NMR (500 MHz, DMSO-$d_6$) δ 8.99 (t, 1H), 8.62 (d, 1H), 7.95 (d, 1H), 7.55-7.48 (m, 2H), 7.40 (d, 1H), 5.31 (dd, 1H), 4.89 (d, 1H), 4.76 (d, 2H), 4.71 (d, 1H), 4.37-4.23 (m, 2H), 3.71 (t, 2H), 3.56 (t, 2H), 3.43-3.34 (m, 2H), 3.16 (q, 1H), 1.94 (d, 1H).

Example 78: N-(2-((R)-4-Cyanothiazolidin-3-yl)-2-oxoethyl)-6-((2S,6S)-2,6-dimethyl-morpholino)quinoline-4-carboxamide

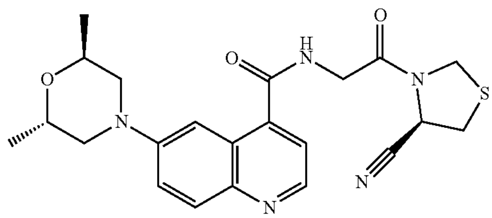 [SMILES: C[C@H]1CN(c2ccc3nccc(C(=O)NCC(=O)N4CSC[C@H]4C#N)c3c2)C[C@H](C)O1]

HATU (0.114 g, 0.30 mmol) was added to a stirred mixture of crude 6-((2S,6S)-2,6-dimethylmorpholino)quinoline-4-carboxylic acid Intermediate 164 (0.25 mmol) and DIPEA (0.218 mL, 1.25 mmol) in a mixture of MeCN/EtOAc (2.2 mL, 1:1) at rt. The reaction was stirred for 1 min after which (R)-3-glycylthiazolidine-4-carbonitrile hydrochloride Intermediate 4 (0.062 g, 0.30 mmol) was added and the reaction was stirred for 2 h 45 min at rt. The reaction mixture was diluted with EtOAc (5 mL) and washed twice with 8% $NaHCO_3$ (aq, 5+3 mL) followed by $H_2O$ (2×5 mL). The organic layer was dried over $Na_2SO_4$, filtered and concentrated. The residue was purified by normal phase flash chromatography on silica (EtOAc followed by EtOAc:MeOH, 10:1). The compound was further purified twice by preparative HPLC, PrepMethod G, (gradients: 15-55% and 5-45%) to give the title compound (0.041 g, 38%) as a yellow solid; HRMS (ESI) m/z $[M+H]^+$ calcd for $C_{22}H_{26}N_5O_3S$: 440.1750. found: 440.1754; $^1H$ NMR (500 MHz, DMSO-$d_6$) δ 9.03 (t, 1H), 8.67 (d, 1H), 7.90 (d, 1H), 7.70 (d, 1H), 7.65 (dd, 1H), 7.39 (d, 1H), 5.30 (dd, 1H), 4.90 (d, 1H), 4.71 (d, 1H), 4.31 (d, 2H), 4.15-4.06 (m, 2H), 3.44-3.37 (m, overlapping with solvent), 3.08 (dd, 2H), 1.25 (d, 6H).

Example 79: 6-(8-Oxa-3-azabicyclo[3.2.1]octan-3-yl)-N-(2-((R)-4-cyanothiazolidin-3-yl)-2-oxoethyl)quinoline-4-carboxamide

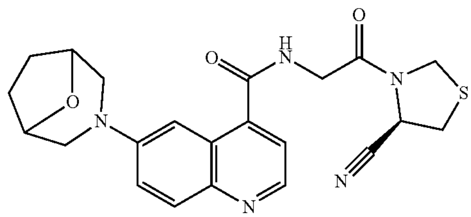 [SMILES: N#C[C@@H]1CSCN1C(=O)CNC(=O)c1ccnc2ccc(N3CC4CCC(C3)O4)cc12]

HATU (0.137 g, 0.36 mmol) was added to a stirred mixture of crude 6-(8-oxa-3-azabicyclo[3.2.1]octan-3-yl)quinoline-4-carboxylic acid Intermediate 166 (0.30 mmol) and DIPEA (0.262 mL, 1.50 mmol) in a mixture of MeCN/EtOAc (2.8 mL, 1:1) at rt. The reaction mixture was stirred for 1 min after which (R)-3-glycylthiazolidine-4-carbonitrile hydrochloride Intermediate 4 (0.075 g, 0.36 mmol) was added and the reaction was stirred for 3 h at rt. The reaction mixture was diluted with EtOAc (5 mL) and washed with 8% $NaHCO_3$(aq, 5 mL). The aqueous layer was extracted with EtOAc (3 mL) and the combined organic layers were dried over $Na_2SO_4$, filtered and concentrated. The crude compound was purified by straight phase flash chromatography on silica (EtOAc followed by EtOAc:MeOH, 6:1) and further purified by preparative HPLC, PrepMethod G, (gradient: 5-50%). The compound was dissolved in EtOAc and the organic layer was washed with 8% $NaHCO_3$(aq, 2×) and $H_2O$ (2×), concentrated and freeze-dried to give the title compound (0.051 g, 39%) a yellow solid; HRMS (ESI) m/z $[M+H]^+$ calcd for $C_{22}H_{24}N_5O_3S$: 438.1594. found: 438.1608; $^1H$ NMR (500 MHz, DMSO-$d_6$) δ 9.00 (t, 1H), 8.66 (d, 1H), 7.89 (d, 1H), 7.64-7.58 (m, 2H), 7.39 (d, 1H), 5.32 (dd, 1H), 4.90 (d, 1H), 4.71 (d, 1H), 4.48 (s, 2H), 4.36-4.23 (m, 2H), 3.61 (d, 2H), 3.41 (dd, 1H), 3.36 (dd, 1H), 2.95 (ddd, 2H), 1.86 (s, 4H).

Example 80: N-(2-((R)-4-Cyanothiazolidin-3-yl)-2-oxoethyl)-6-((S)-2-methyl-morpholino)quinoline-4-carboxamide

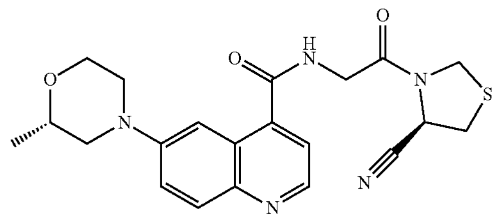 [SMILES: C[C@H]1CN(c2ccc3nccc(C(=O)NCC(=O)N4CSC[C@H]4C#N)c3c2)CCO1]

HATU (0.137 g, 0.36 mmol) was added to a stirred mixture of crude (S)-6-(2-methylmorpholino)quinoline-4-carboxylic acid Intermediate 168 (0.30 mmol) and DIPEA (0.262 mL, 1.50 mmol) in a mixture of MeCN/EtOAc (2.8 mL, 1:1) at rt. The reaction mixture was stirred for 1 min after which (R)-3-glycylthiazolidine-4-carbonitrile hydrochloride Intermediate 4 (0.075 g, 0.36 mmol) was added and the reaction was stirred for 45 min at rt. The reaction mixture was diluted with EtOAc (5 mL) and washed with 8% $NaHCO_3$(aq, 5 mL). The aqueous layer was extracted with EtOAc (3 mL) and the combined organic layers were dried over $Na_2SO_4$, filtered and concentrated. The residue was purified by preparative HPLC, PrepMethod G, (gradient of 5-45%). The compound was dissolved in EtOAc and the organic layer was washed with 8% $NaHCO_3$ (aq) and $H_2O$ (3×), concentrated and freeze-dried. The compound was further purified by normal phase flash chromatography on silica gel (EtOAc followed by EtOAc:MeOH, 20:1), and freeze-dried from MeCN/$H_2O$ to give the title compound (0.041 g, 32%) as a yellow solid; HRMS (ESI) m/z $[M+H]^+$ calcd for $C_{21}H_{24}N_5O_3S$: 426.1594. found: 426.1588; $^1H$ NMR (500 MHz, DMSO-$d_6$) δ 9.04 (t, 1H), 8.69 (d, 1H), 7.91 (d, 1H), 7.74-7.66 (m, 2H), 7.40 (d, 1H), 5.30 (dd, 1H), 4.90 (d, 1H), 4.71 (d, 1H), 4.31 (d, 2H), 3.96 (dd, 1H), 3.87 (d, 1H), 3.75 (d, 1H), 3.72-3.63 (m, 2H), 3.44-3.34 (m, 2H), 2.78 (td, 1H), 2.47 (d, 1H), 1.22 (d, 3H).

Example 81: N-(2-((R)-4-Cyanothiazolidin-3-yl)-2-oxoethyl)-6-((2R,3S)-2,3-dimethyl-morpholino)quinoline-4-carboxamide

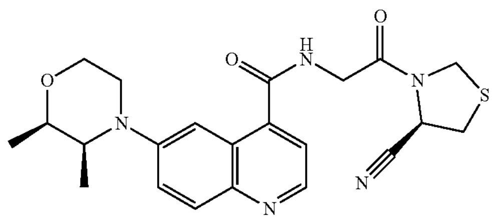 [SMILES: C[C@H]1OCCN(c2ccc3nccc(C(=O)NCC(=O)N4CSC[C@H]4C#N)c3c2)[C@H]1C]

HATU (0.160 g, 0.42 mmol) was added to a stirred mixture of crude 6-((2R,3S)-2,3-dimethylmorpholino)quinoline-4-carboxylic acid Intermediate 170 (0.35 mmol) and DIPEA (0.306 mL, 1.75 mmol) in a mixture of MeCN/EtOAc (3.2 mL, 1:1) at rt. The reaction was stirred for 1 min after which (R)-3-glycylthiazolidine-4-carbonitrile hydrochloride Intermediate 4 (0.087 g, 0.42 mmol) was added and the reaction was stirred for 2.5 h at rt. The reaction mixture was diluted with EtOAc (20 mL) and washed with 8% $NaHCO_3$(aq, mL) followed by $H_2O$ (2 mL). The organic layer was dried over $Na_2SO_4$, filtered and concentrated. The residue was purified by straight phase flash chromatography on silica (EtOAc followed by EtOAc:MeOH, 20:1). The compound was further purified by preparative HPLC, PrepMethod G, (gradient: 0-30% over 30 min) followed by straight phase flash chromatography on silica (EtOAc followed by EtOAc:MeOH, 20:1). The compound was freeze-dried from MeCN/$H_2O$ to give the title compound (0.073 g, 47%) as a yellow solid; HRMS (ESI) m/z $[M+H]^+$ calcd for $C_{22}H_{26}N_5O_3S$: 440.1750. found: 440.1752; $^1H$ NMR (500 MHz, DMSO-$d_6$) δ 9.01 (t, 1H), 8.65 (d, 1H), 7.90 (d, 1H), 7.68-7.60 (m, 2H), 7.38 (d, 1H), 5.32 (dd, 1H), 4.89 (d, 1H), 4.70 (d, 1H), 4.29 (d, 2H), 4.14-4.08 (dd, 1H), 3.98 (dd, 1H), 3.86-3.78 (m, 1H), 3.63 (td, 1H), 3.47-3.34 (m, 3H), 3.06 (td, 1H), 1.14 (d, 3H), 0.93 (d, 3H).

Example 82: N-(2-((R)-4-Cyanothiazolidin-3-yl)-2-oxoethyl)-6-((2S,3S)-2,3-dimethyl-morpholino)quinoline-4-carboxamide

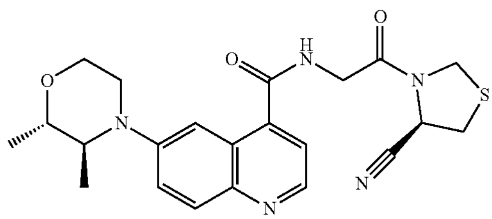 [SMILES: C[C@@H]1OCCN(c2ccc3nccc(C(=O)NCC(=O)N4CSC[C@H]4C#N)c3c2)[C@H]1C]

HATU (0.114 g, 0.30 mmol) was added to a stirred mixture of crude 6-((2S,3S)-2,3-dimethylmorpholino)quinoline-4-carboxylic acid Intermediate 172 (0.25 mmol) and DIPEA (0.218 mL, 1.25 mmol) in a mixture of MeCN/EtOAc (2.2 mL, 1:1) at rt. The reaction was stirred for 1 min after which (R)-3-glycylthiazolidine-4-carbonitrile hydrochloride Intermediate 4 (0.062 g, 0.30 mmol) was added and the reaction was stirred for 1.5 h at rt. The reaction mixture was diluted with EtOAc (15 mL) and washed with 8% $NaHCO_3$(aq, 6+3 mL) and $H_2O$ (2×2 mL). The organic layer was dried over $Na_2SO_4$, filtered and concentrated. The residue was purified by straight phase flash chromatography on silica (EtOAc followed by EtOAc/MeOH, 20:1). The compound was further purified by preparative HPLC, PrepMethod G, (gradient: 0-30% in 30 min) to give the title compound (0.056 g, 51%) as a yellow solid; HRMS (ESI) m/z $[M+H]^+$ calcd for $C_{22}H_{26}N_5O_3S$: 440.1750. found: 440.1750; $^1H$ NMR (500 MHz, DMSO-$d_6$) δ 9.03 (t, 1H), 8.71 (d, 1H), 7.92 (d, 1H), 7.77 (d, 1H), 7.63 (dd, 1H), 7.41 (d, 1H), 5.32 (dd, 1H), 4.89 (d, 1H), 4.71 (d, 1H), 4.30 (d, 2H), 3.92-3.84 (m, 1H), 3.75-3.64 (m, 3H), 3.45-3.35 (m, 2H), 3.27-3.18 (m, 2H), 1.34 (d, 3H), 1.06 (d, 3H).

Example 83: N-(2-((R)-4-Cyanothiazolidin-3-yl)-2-oxoethyl)-6-((2R,3R)-2,3-dimethyl-morpholino)quinoline-4-carboxamide

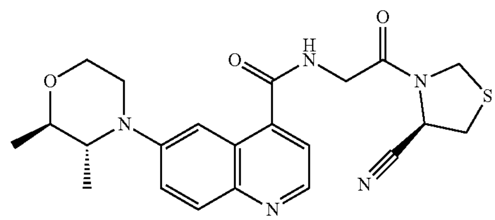 [SMILES: C[C@@H]1[C@@H](C)OCCN1c1ccc2nccc(C(=O)NCC(=O)N3CSC[C@H]3C#N)c2c1]

HATU (0.110 g, 0.29 mmol) was added to a stirred mixture of crude 6-((2R,3R)-2,3-dimethylmorpholino)quinoline-4-carboxylic acid Intermediate 174 (0.24 mmol) and DIPEA (0.210 mL, 1.20 mmol) in a mixture of MeCN/EtOAc (2.2 mL, 1:1) at rt. The reaction was stirred for 1 min after which (R)-3-glycylthiazolidine-4-carbonitrile hydrochloride Intermediate 4 (0.060 g, 0.29 mmol) was added and the reaction was stirred for 1.5 h at rt. The reaction mixture was diluted with EtOAc (15 mL) and washed with 8% $NaHCO_3$(aq, 6+3 mL) followed by $H_2O$ (2×2 mL). The organic layer was dried over $Na_2SO_4$, filtered and concentrated. The residue was purified by straight phase flash chromatography on silica (EtOAc followed by EtOAc:MeOH, 10:1). The compound was further purified by preparative HPLC, PrepMethod G, (gradient: 5-35%) to give the title compound (0.048 g, 46%) as an orange solid; HRMS (ESI) m/z $[M+H]^+$ calcd for $C_{22}H_{26}N_5O_3S$: 440.1750. found: 440.1756; $^1H$ NMR (500 MHz, DMSO-$d_6$) δ 9.03 (t, 1H); 8.71 (d, 1H), 7.92 (d, 1H), 7.73 (d, 1H), 7.63 (dd, 1H), 7.42 (d, 1H), 5.30 (dd, 1H), 4.90 (d, 1H), 4.70 (d, 1H), 4.34 (dd, 1H), 4.26 (dd, 1H), 3.93-3.84 (m, 1H), 3.75-3.65 (m, 3H), 3.43-3.34 (m, 2H), 3.30-3.17 (m, 2H), 1.34 (d, 3H), 1.07 (d, 3H).

Example 84: N-(2-((R)-4-Cyanothiazolidin-3-yl)-2-oxoethyl)-6-((R*)-3-(trifluoromethyl)-morpholino)quinoline-4-carboxamide Isomer 1

Isomer 1

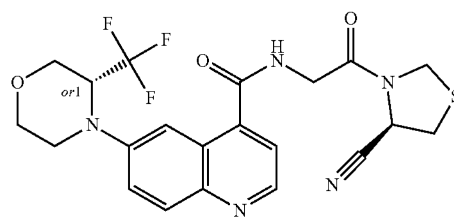

HATU (0.119 g, 0.31 mmol) was added to a stirred solution of crude rel-(R)-6-(3-(trifluoromethyl)morpholino) quinoline-4-carboxylic acid Isomer 1 Intermediate 178 (0.26 mmol) and DIPEA (0.227 mL, 1.30 mmol) in a mixture of MeCN/EtOAc (2.4 mL, 1:1) at rt. The reaction was stirred for 1 min after which (R)-3-glycylthiazolidine-4-carbonitrile hydrochloride Intermediate 4 (0.065 g, 0.31 mmol) was added and the reaction was stirred for 45 min at rt. The reaction was diluted with EtOAc (8 mL) and washed with 8% $NaHCO_3$ (aq, 5 mL). The aqueous layer was extracted with EtOAc and the combined organic layers were dried over $Na_2SO_4$, filtered and concentrated. The residue was purified by preparative HPLC, PrepMethod G, (gradient: 5-55%) to give the title compound (0.082 g, 66%) as an orange solid; HRMS (ESI) m/z $[M+H]^+$ calcd for $C_{21}H_{21}F_3N_5O_3S$: 480.1312. found: 480.1308; $^1H$ NMR (500 MHz, DMSO-$d_6$) δ 9.07 (t, 1H), 8.74 (d, 1H), 7.94 (d, 1H), 7.85-7.78 (m, 2H), 7.45 (d, 1H), 5.34 (dd, 1H), 5.11-5.01 (m, 1H), 4.89 (d, 1H), 4.71 (d, 1H), 4.38-4.27 (m, 2H), 4.24 (d, 1H), 4.06 (dd, 1H), 3.89-3.82 (m, 1H), 3.64 (td, 1H), 3.55-3.33 (m, overlapping with solvent).

Example 85: N-(2-((R)-4-Cyanothiazolidin-3-yl)-2-oxoethyl)-6-((R*)-3-(trifluoromethyl)-morpholino) quinoline-4-carboxamide Isomer 2

Isomer 2

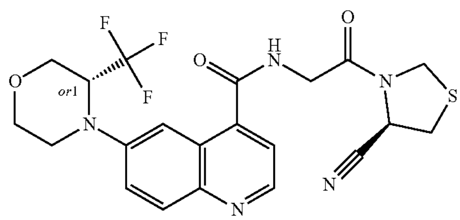

HATU (0.128 g, 0.34 mmol) was added to a stirred solution of crude rel-(R)-6-(3-(trifluoromethyl)morpholino) quinoline-4-carboxylic acid Isomer 2 Intermediate 179 (0.150 g, 0.28 mmol) and DIPEA (0.245 mL, 1.40 mmol) in a mixture of MeCN/EtOAc (2.4 mL, 1:1) at rt. The reaction was stirred for 1 min after which (R)-3-glycylthiazolidine-4-carbonitrile hydrochloride Intermediate 4 (0.070 g, 0.34 mmol) was added and the reaction was stirred for 1.5 h at rt. The reaction was diluted with EtOAc (8 mL) and washed with 8% $NaHCO_3$(aq, 5 mL). The aqueous layer was extracted with EtOAc and the combined organic layers were dried over $Na_2SO_4$, filtered and concentrated. The residue was purified by preparative HPLC, PrepMethod G, (gradient: 5-55%) to give the title compound (0.085 g, 63%) as a yellow solid; HRMS (ESI) m/z $[M+H]^+$ calcd for $C_{21}H_{21}F_3N_5O_3S$: 480.1312. found: 480.1308; $^1H$ NMR (500 MHz, DMSO-$d_6$) δ 9.07 (t, 1H), 8.73 (d, 1H), 7.94 (d, 1H), 7.83-7.76 (m, 2H), 7.45 (d, 1H), 5.29 (dd, 1H), 5.11-5.03 (dd, 1H), 4.90 (d, 1H), 4.70 (d, 1H), 4.37 (dd, 1H), 4.30-4.20 (m, 2H), 4.06 (dd, 1H), 3.89-3.81 (m, 1H), 3.64 (td, 1H), 3.56-3.32 (m, overlapping with solvent).

Example 86: 6-(3-Oxa-9-azabicyclo[3.3.1]nonan-9-yl)-N-(2-((R)-4-cyanothiazolidin-3-yl)-2-oxoethyl) quinoline-4-carboxamide

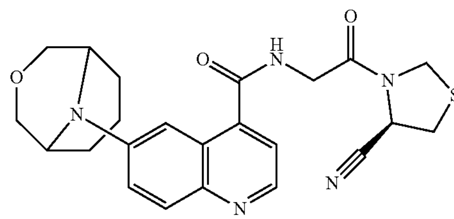

HATU (0.068 g, 0.18 mmol) was added to a stirred solution of the crude 6-(3-Oxa-9-azabicyclo[3.3.1]nonan-9-yl)quinoline-4-carboxylic acid Intermediate 181 (0.070 g, 0.15 mmol) and DIPEA (0.131 mL, 0.75 mmol) in a mixture of MeCN/EtOAc (1.2 mL, 1:1) at rt and the reaction was stirred for 1 min. (R)-3-glycylthiazolidine-4-carbonitrile hydrochloride Intermediate 4 (0.037 g, 0.18 mmol) was added and the reaction was stirred for 2 h at rt. The reaction mixture was diluted with EtOAc (8 mL) and washed with 8% $NaHCO_3$(aq, 5 mL). The aqueous layer was extracted with EtOAc and the combined organic layers were dried over $Na_2SO_4$, filtered and concentrated. The residue was purified by preparative HPLC, PrepMethod G, (gradient: 5-55%) to give the title compound (0.040 g, 60%) as an orange solid; HRMS (ESI) m/z $[M+H]^+$ calcd for $C_{23}H_{26}N_5O_3S$: 452.1750. found: 452.1756; $^1H$ NMR (500 MHz, DMSO-$d_6$) δ 9.01 (t, 1H), 8.62 (d, 1H), 7.89 (d, 1H), 7.73 (d, 1H), 7.61 (dd, 1H), 7.37 (d, 1H), 5.29 (dd, 1H), 4.89 (d, 1H), 4.69 (d, 1H), 4.35-4.22 (m, 2H), 4.11 (s, 2H), 3.99 (d, 2H), 3.85 (d, 2H), 3.44-3.35 (m, overlapping with solvent), 2.55-2.52 (m, overlapping with solvent), 1.98-1.83 (m, 2H), 1.83-1.70 (m, 2H), 1.58-1.48 (m, 1H).

Example 87: N-(2-((R)-4-Cyanothiazolidin-3-yl)-2-oxoethyl)-6-((2R,5R)-2,5-dimethyl-morpholino) quinoline-4-carboxamide

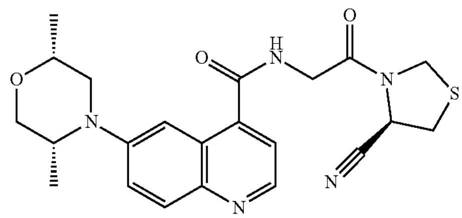 [SMILES: C[C@@H]1CN(c2ccc3nccc(C(=O)NCC(=O)N4CSC[C@H]4C#N)c3c2)[C@H](C)CO1]

HATU (0.160 g, 0.42 mmol) was added to a stirred mixture of the crude 6-((2R,5R)-2,5-dimethylmorpholino) quinoline-4-carboxylic acid Intermediate 183 (0.35 mmol) and DIPEA (0.305 mL, 1.75 mmol) in a mixture of MeCN/EtOAc (3 mL, 1:1) and the mixture was stirred for 1 min. (R)-3-Glycylthiazolidine-4-carbonitrile hydrochloride Intermediate 4 (0.087 g, 0.42 mmol) was added and the mixture was stirred at rt for 3 h. The reaction mixture was partitioned between EtOAc (25 mL) and 8% $NaHCO_3$(aq, 10 mL). The aqueous layer was extracted with EtOAc (10 mL) and the combined organic layers were concentrated. The residue was purified by preparative HPLC, PrepMethod G, (gradient: 5-45%) to give the title compound (0.072 g, 47%) as an orange solid; HRMS (ESI) m/z $[M+H]^+$ calcd for $C_{22}H_{26}N_5O_3S$: 440.1750. found: 440.1748; $^1H$ NMR (500 MHz, DMSO-$d_6$) δ 9.03 (t, 1H), 8.66 (d, 1H), 7.91 (d, 1H), 7.70-7.64 (m, 2H), 7.39 (d, 1H), 5.31 (dd, 1H), 4.89 (d, 1H), 4.71 (d, 1H), 4.34 (dd, 1H), 4.26 (dd, 1H), 4.20-4.14 (m, 1H), 3.85-3.73 (m, 2H), 3.69-3.53 (m, 2H), 3.45-3.33 (m, overlapping with solvent), 2.75 (dd, 1H), 1.27 (d, 3H), 1.05 (d, 3H).

Example 88: (R)—N-(2-(4-Cyanothiazolidin-3-yl)-2-oxoethyl)-6-(2,2-dimethyl-morpholino)quinoline-4-carboxamide

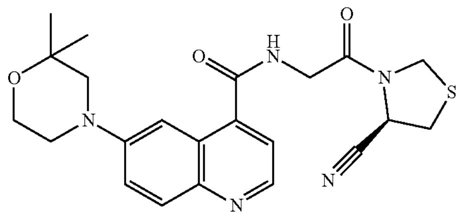 [SMILES: CC1(C)CN(c2ccc3nccc(C(=O)NCC(=O)N4CSC[C@H]4C#N)c3c2)CCO1]

HATU (0.160 g, 0.42 mmol) was added to a stirred mixture of the crude 6-(2,2-dimethylmorpholino)quinoline-4-carboxylic acid Intermediate 185 (0.35 mmol) and DIPEA (0.305 mL, 1.75 mmol) in a mixture of MeCN/EtOAc (3 mL, 1:1) and the mixture was stirred for 1 min. (R)-3-Glycylthiazolidine-4-carbonitrile hydrochloride Intermediate 4 (0.087 g, 0.42 mmol) was added and the mixture was stirred at rt for 3 h. The reaction mixture was partitioned between EtOAc (25 mL) and 8% $NaHCO_3$(aq, 10 mL). The aqueous layer was extracted with EtOAc (10 mL) and the combined organic layers were concentrated. The residue was purified by preparative HPLC, PrepMethod G, (gradient: 5-55%) to give the title compound (0.076 g, 49%) as an orange solid; HRMS (ESI) m/z $[M+H]^+$ calcd for $C_{22}H_{26}N_5O_3S$: 440.1750. found: 440.1768; $^1H$ NMR (500 MHz, DMSO-$d_6$) δ 9.05 (t, 1H), 8.69 (d, 1H), 7.91 (d, 1H), 7.74 (d, 1H), 7.68 (dd, 1H), 7.41 (d, 1H), 5.30 (dd, 1H), 4.90 (d, 1H), 4.71 (d, 1H), 4.36-4.26 (m, 2H), 3.81 (t, 2H), 3.47-3.15 (m, overlapping with solvent), 1.28 (s, 6H).

Example 89: N-(2-((R)-4-Cyanothiazolidin-3-yl)-2-oxoethyl)-6-((S)-3-(methoxymethyl)-morpholino) quinoline-4-carboxamide

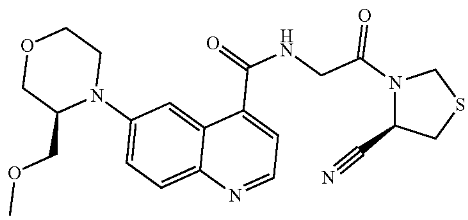 [SMILES: COC[C@H]1COCCN1c1ccc2nccc(C(=O)NCC(=O)N3CSC[C@H]3C#N)c2c1]

4 M HCl in dioxane (2 mL, 8 mmol) was added to a vial containing tert-butyl (S)-6-(3-(methoxymethyl)morpholino) quinoline-4-carboxylate Intermediate 186 (146 mg, 0.41 mmol). The reaction was heated at 60° C. for 1 h. The volatiles were removed under reduced pressure and the residue was suspended in EtOAc and concentrated (×2). A mixture of MeCN/EtOAc (4.8 mL, 1:1) was added to the residue at rt, followed by DIPEA (0.430 mL, 2.46 mmol) and HATU (0.187 g, 0.49 mmol). The mixture was stirred for 1 min after which (R)-3-glycylthiazolidine-4-carbonitrile hydrochloride Intermediate 4 (0.102 g, 0.49 mmol) was added and the reaction was stirred for 1.5 h at rt. The reaction mixture was diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-D, to give the title compound (0.062 g, 33%); HRMS (ESI) m/z $[M+H]^+$ calcd for $C_{22}H_{26}N_5O_4S$: 456.1700. found: 456.1698; $^1H$ NMR (500 MHz, DMSO-$d_6$) δ 9.00 (t, 1H), 8.67 (d, 1H), 7.91 (d, 1H), 7.69 (dd, 1H), 7.64 (d, 1H), 7.40 (d, 1H), 5.31 (dd, 1H), 4.88 (d, 1H), 4.70 (d, 1H), 4.35-4.23 (m, 2H), 4.12 (s, 1H), 4.02-3.95 (m, 2H), 3.70-3.64 (m, 2H), 3.58 (td, 1H), 3.45-3.42 (m, overlapping with solvent), 3.24-3.13 (m, overlapping with solvent).

Example 90: N-(2-((R)-4-Cyanothiazolidin-3-yl)-2-oxoethyl)-6-((3S,5R)-3,5-dimethyl-morpholino)quinoline-4-carboxamide

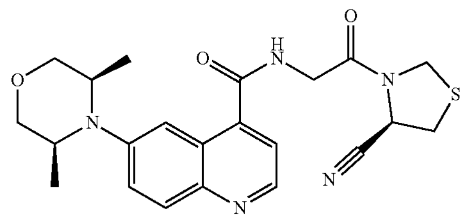 [SMILES: C[C@@H]1COC[C@H](C)N1c1ccc2nccc(C(=O)NCC(=O)N3CSC[C@H]3C#N)c2c1]

HATU (0.091 g, 0.24 mmol) was added to a stirred solution of the crude 6-((3S,5R)-3,5-dimethylmorpholino) quinoline-4-carboxylic acid Intermediate 188 (0.2 mmol) and DIPEA (0.210 mL, 1.20 mmol) in a mixture of MeCN/$H_2O$ (2.4 mL, 1:1) at rt. The reaction mixture was stirred for 1 min after which (R)-3-glycylthiazolidine-4-carbonitrile hydrochloride Intermediate 4 (0.050 g, 0.24 mmol) was added. The reaction mixture was stirred for 3 h at rt, diluted with EtOAc and washed with 0.4 M NaOH (aq, 4.5 mL). The aqueous layer was extracted with EtOAc and the combined organic layers were dried over $Na_2SO_4$, filtered and concentrated. The residue was purified by preparative SFC, PrepMethod SFC-D, to give the title compound (0.039 g, 44%); HRMS (ESI) m/z $[M+H]^+$ calcd for $C_{22}H_{26}N_5O_3S$: 440.1750. found: 440.1744; $^1H$ NMR (500 MHz, DMSO-$d_6$) δ 9.01 (t, 1H), 8.69 (d, 1H), 7.95 (d, 1H), 7.72 (d, 1H), 7.59 (dd, 1H), 7.41 (d, 1H), 5.31 (dd, 1H), 4.89 (d, 1H), 4.71 (d, 1H), 4.36-4.23 (m, 2H), 3.87-3.81 (m, 2H), 3.75-3.66 (m, 4H), 1.09 (d, 6H).

Example 91: (R)—N-(2-(4-Cyanothiazolidin-3-yl)-2-oxoethyl)-6-(1,4-oxazepan-4-yl)-quinoline-4-carboxamide

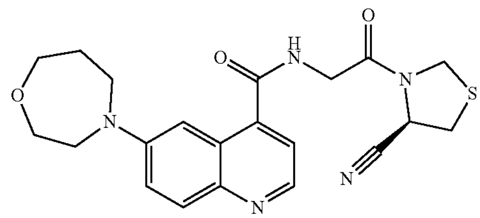 [SMILES: N#C[C@@H]1CSCN1C(=O)CNC(=O)c1ccnc2ccc(N3CCCOCC3)cc12]

A vial was charged with tert-butyl 6-(1,4-oxazepan-4-yl) quinoline-4-carboxylate Intermediate 189 (0.085 g, 0.25 mmol) and 90% TFA (aq, 0.5 mL) and the reaction mixture was heated at 50° C. for 3 h. The reaction mixture was concentrated, a mixture of heptane and DCM (3 mL, 2:1) was added to the residue and the mixture was concentrated. A mixture of MeCN/EtOAc (3 mL, 1:1) and DIPEA (0.261 mL, 1.50 mmol) was added to the residue followed by HATU (0.114 g, 0.30 mmol). The mixture was stirred for 1 min after which (R) −3-glycylthiazolidine-4-carbonitrile hydrochloride Intermediate 4 (0.062 g, 0.30 mmol) was added. The mixture was stirred at rt for 4 h and then partitioned between EtOAc (4 mL) and 8% $NaHCO_3$(aq, 5 mL). The aqueous layer was extracted with EtOAc (2×1 mL) and the combined organic layers were dried over $Na_2SO_4$, filtered and concentrated. The residue was purified by preparative SFC, PrepMethod SFC-A, followed by preparative HPLC, PrepMethod V, (gradient: 5-95%) to give the title compound (30 mg, 27%); HRMS (ESI) m/z $[M+H]^+$ calcd for $C_{21}H_{24}N_5O_3S$: 426.1594. found: 426.1576; $^1H$ NMR (600 MHz, DMSO-$d_6$) δ 8.93 (t, 1H), 8.53 (d, 1H), 7.82 (d, 1H), 7.50-7.45 (m, 2H), 7.30 (d, 1H), 5.26 (dd, 1H), 4.84 (d, 1H), 4.66 (d, 1H), 4.30-4.18 (m, 2H), 3.76-3.66 (m, overlapping with solvent), 3.57-3.51 (m, overlapping with solvent), 3.38-3.29 (m, overlapping with solvent), 1.95-1.88 (m, 2H).

Example 92: N-(2-((R)-4-Cyanothiazolidin-3-yl)-2-oxoethyl)-6-((R)-2-((methylsulfonyl)-methyl)morpholino)quinoline-4-carboxamide

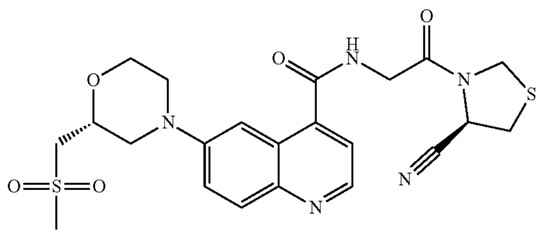 [SMILES: CS(=O)(=O)C[C@H]1CN(c2ccc3nccc(C(=O)NCC(=O)N4CSC[C@H]4C#N)c3c2)CCO1]

The compound was synthesized and purified analogous to the procedure of Example 91 starting from tert-butyl (R)-6-(2-((methylsulfonyl)methyl)morpholino)quinoline-4-carboxylate Intermediate 193 (0.102 g, 0.25 mmol) and (R)-3-glycylthiazolidine-4-carbonitrile hydrochloride Intermediate 4 (0.062 g, 0.30 mmol) to give the title compound (26 mg, 20%); HRMS (ESI) m/z $[M+H]^+$ calcd for $C_{22}H_{26}N_5O_5S_2$: 504.1370. found: 504.1372; $^1H$ NMR (600 MHz, DMSO-$d_6$) δ 9.00 (m, 1H), 8.68 (d, 1H), 7.91 (d, 1H), 7.68 (d, 1H), 7.62 (dd, 1H), 7.40 (d, 1H), 5.31-5.27 (m, 1H), 4.86 (d, 1H), 4.67 (d, 1H), 4.31 (dd, 1H), 4.23 (dd, 1H), 4.10-3.99 (m, 2H), 3.88-3.81 (m, 1H), 3.75-3.65 (m, 2H), 3.53 (dd, overlapping with solvent), 3.37-3.27 (m, overlapping with solvent), 3.01 (s, 3H), 2.91-2.82 (m, 1H), 2.73-2.68 (m, 1H).

Example 93: N-(2-((R)-4-Cyanothiazolidin-3-yl)-2-oxoethyl)-6-((S)-2-(methoxymethyl)-morpholino) quinoline-4-carboxamide

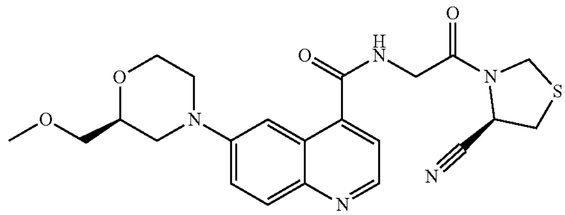 [SMILES: COC[C@@H]1CN(c2ccc3nccc(C(=O)NCC(=O)N4CSC[C@H]4C#N)c3c2)CCO1]

The compound was synthesized and purified analogous to the procedure of Example 91 starting from tert-butyl (S)-6-(2-(methoxymethyl)morpholino)quinoline-4-carboxylate Intermediate 194 (76 mg, 0.25 mmol) and (R)-3-glycylthiazolidine-4-carbonitrile hydrochloride Intermediate 4 (0.062 g, 0.30 mmol) to give the title compound (0.026 g, 22%); HRMS (ESI) m/z $[M+H]^+$ calcd for $C_{22}H_{26}N_5O_4S$: 456.1700. found: 456.1712; $^1H$ NMR (600 MHz, DMSO-$d_6$) δ 8.99 (t, 1H), 8.66 (d, 1H), 7.88 (d, 1H), 7.69 (d, 1H), 7.64 (dd, 1H), 7.38 (d, 1H), 5.29 (dd, 1H), 4.85 (d, 1H), 4.68 (d, 1H), 4.32-4.22 (m, 2H), 3.99-3.93 (m, 1H), 3.78-3.68 (m, 3H), 3.64 (td, 1H), 3.48-3.42 (m, overlapping with solvent), 3.35-3.31 (m, overlapping with solvent), 3.27 (s, 3H), 2.80 (td, 1H), 2.61-2.56 (m, overlapping with solvent).

Example 94: N-(2-((R)-4-Cyanothiazolidin-3-yl)-2-oxoethyl)-6-((S)-2-((methylsulfonyl)-methyl)morpholino)quinoline-4-carboxamide

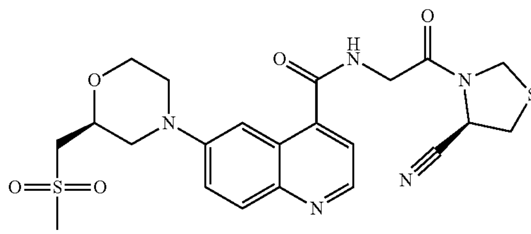

The compound was synthesized analogous to the procedure of Example 91 starting from tert-butyl (S)-6-(2-((methylsulfonyl)methyl)morpholino)quinoline-4-carboxylate Intermediate 198 (0.102 g, 0.25 mmol) and (R)-3-glycylthiazolidine-4-carbonitrile hydrochloride Intermediate 4 (0.062 g, 0.30 mmol). The compound was purified by preparative SFC, PrepMethod SFC-A, followed by PrepMethod SFC-D, to give the title compound (0.023 g, 18%); HRMS (ESI) m/z $[M+H]^+$ calcd for $C_{22}H_{26}N_5O_5S_2$: 504.1370. found: 504.1364; $^1H$ NMR (600 MHz, DMSO-$d_6$) δ 9.00 (t, 1H), 8.68 (d, 1H), 7.91 (d, 1H), 7.71 (d, 1H), 7.62 (dd, 1H), 7.39 (d, 1H), 5.31-5.26 (m, 1H), 4.85 (d, 1H), 4.67 (d, 1H), 4.32-4.22 (m, 2H), 4.09-3.98 (m, 2H), 3.86 (d, 1H), 3.70 (t, 2H), 3.52 (dd, overlapping with solvent), 3.34-3.27 (m, overlapping with solvent), 3.01 (s, 3H), 2.93-2.84 (m, 1H), 2.74-2.67 (m, 1H).

Example 95: N-(2-((R)-4-Cyanothiazolidin-3-yl)-2-oxoethyl)-6-((R)-3-(2-methoxyethyl)-morpholino)quinoline-4-carboxamide

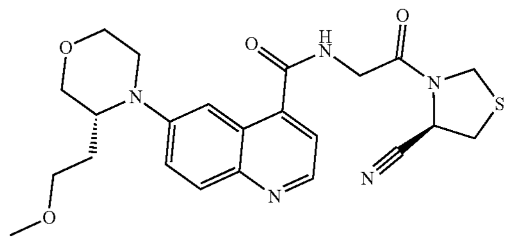 [SMILES: COCC[C@@H]1COCCN1c1ccc2nccc(C(=O)NCC(=O)N3CSC[C@H]3C#N)c2c1]

The compound was synthesized analogous to the procedure of Example 91 starting from tert-butyl (R)-6-(3-(2-methoxyethyl)morpholino)quinoline-4-carboxylate Intermediate 201 (0.093 g, 0.25 mmol) and (R)-3-glycylthiazolidine-4-carbonitrile hydrochloride Intermediate 4 (0.062 g, 0.30 mmol). The compound was purified by preparative SFC, PrepMethod SFC-A followed by preparative HPLC, PrepMethod F, to give the title compound (0.031 g, 25%); HRMS (ESI) m/z $[M+H]^+$ calcd for $C_{23}H_{28}N_5O_4S$: 470.1856. found: 470.1846; $^1H$ NMR (600 MHz, DMSO-d 6) δ 8.95 (t, 1H), 8.62 (d, 1H), 7.87 (d, 1H), 7.59-7.56 (m, 2H), 7.36 (d, 1H), 5.26 (dd, 1H), 4.85 (d, 1H), 4.67 (d, 1H), 4.30 (dd, 1H), 4.22 (dd, 1H), 4.05-4.00 (m, 1H), 3.93 (dd, 1H), 3.84 (d, 1H), 3.66-3.63 (m, 2H), 3.58-3.48 (m, overlapping with solvent), 3.46-3.42 (m, overlapping with solvent), 3.39-3.29 (m, overlapping with solvent), 3.28-3.21 (m, 1H), 3.17-3.10 (m, overlapping with solvent), 3.09 (s, 3H), 1.97-1.88 (m, 1H), 1.65-1.57 (m, 1H).

Example 96: N-(2-((R)-4-Cyanothiazolidin-3-yl)-2-oxoethyl)-6-((2S,3S)-3-(methoxymethyl)-2-methylmorpholino)quinoline-4-carboxamide

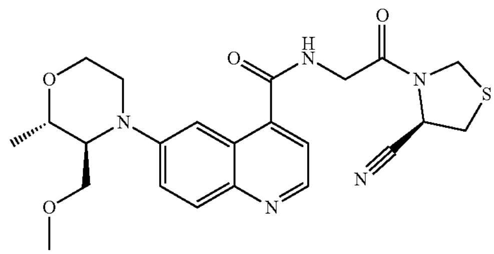 [SMILES: COC[C@H]1[C@H](C)OCCN1c1ccc2nccc(C(=O)NCC(=O)N3CSC[C@H]3C#N)c2c1]

The compound was synthesized and purified analogous to the procedure of Example 91 starting from tert-butyl 6-((2S,3S)-3-(methoxymethyl)-2-methylmorpholino)quinoline-4-carboxylate Intermediate 204 (0.093 g, 0.25 mmol) and (R)-3-glycylthiazolidine-4-carbonitrile hydrochloride Intermediate 4 (0.062 g, 0.30 mmol) to give the title compound (0.030 g, 25%); HRMS (ESI) m/z $[M+H]^+$ calcd for $C_{23}H_{28}N_5O_4S$: 470.1856. found: 470.1848; $^1H$ NMR (600 MHz, DMSO-$d_6$) δ 8.96 (t, 1H), 8.63 (d, 1H), 7.87 (d, 1H), 7.63-7.58 (m, 2H), 7.36 (d, 1H), 5.26 (dd, 1H), 4.85 (d, 1H), 4.67 (d, 1H), 4.29 (dd, 1H), 4.22 (dd, 1H), 4.05-3.98 (m, 1H), 3.88 (td, 1H), 3.83-3.80 (m, 1H), 3.67-3.61 (m, overlapping with solvent), 3.42-3.28 (m, overlapping with solvent), 3.17 (dd, 1H), 3.15-3.12 (m, 5H), 1.35 (d, 3H).

Example 97: N-(2-((R)-4-Cyanothiazolidin-3-yl)-2-oxoethyl)-6-42R,3R)-3-(methoxymethyl)-2-methylmorpholino)quinoline-4-carboxamide

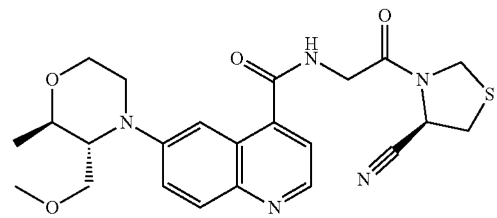 [SMILES: COC[C@@H]1[C@@H](C)OCCN1c1ccc2nccc(C(=O)NCC(=O)N3CSC[C@H]3C#N)c2c1]

The compound was synthesized analogous to the procedure of Example 91 starting from tert-butyl 6-((2R,3R)-3-(methoxymethyl)-2-methylmorpholino)quinoline-4-carboxylate Intermediate 207 (0.093 g, 0.25 mmol) and (R)-3-glycylthiazolidine-4-carbonitrile hydrochloride Intermediate 4 (0.062 g, 0.30 mmol). The compound was purified by preparative SFC, PrepMethod SFC-A, followed by PrepMethod SFC-D, to give the title compound (0.045 g, 36%); HRMS (ESI) m/z $[M+H]^+$ calcd for $C_{23}H_{28}N_5O_4S$: 470.1856. found: 470.1856; $^1H$ NMR (600 MHz, DMSO-$d_6$) δ 8.96 (t, 1H), 8.63 (d, 1H), 7.87 (d, 1H), 7.65 (d, 1H), 7.61 (dd, 1H), 7.37 (d, 1H), 5.27 (dd, 1H), 4.85 (d, 1H), 4.67 (d, 1H), 4.26 (d, 2H), 4.05-3.98 (m, 1H), 3.87 (td, 1H), 3.84-3.78 (m, 1H), 3.69-3.61 (m, 2H), 3.43-3.27 (m, overlapping with solvent), 3.19 (td, 1H), 3.15 (s, 3H), 1.35 (d, 3H).

Example 98: 6-(3-Oxa-8-azabicyclo[3.2.1]octan-8-yl)-N-(2-((R)-4-cyanothiazolidin-3-yl)-2-oxoethyl)quinoline-4-carboxamide

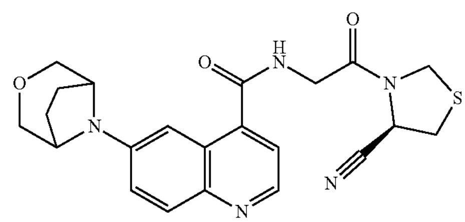 [SMILES: N#C[C@@H]1CSCN1C(=O)CNC(=O)c1ccnc2ccc(N3C4CCC3COC4)cc12]

The compound was synthesized and purified analogous to the procedure of Example 91 starting from tert-butyl 6-(3-oxa-8-azabicyclo[3.2.1]octan-8-yl)quinoline-4-carboxylate Intermediate 208 (0.085 g, 0.25 mmol) and (R)-3-glycylthiazolidine-4-carbonitrile hydrochloride Intermediate 4 (0.062 g, 0.30 mmol) to give the title compound (0.054 g, 49%); HRMS (ESI) m/z $[M+H]^+$ calcd for $C_{22}H_{24}N_5O_3S$: 438.1594. found: 438.1606; $^1H$ NMR (500 MHz, DMSO-$d_6$) δ 8.99 (t, 1H), 8.62 (d, 1H), 7.88 (d, 1H), 7.71 (d, 1H), 7.57 (dd, 1H), 7.35 (d, 1H), 5.29 (dd, 1H), 4.89 (d, 1H), 4.69 (d, 1H), 4.43-4.36 (m, 2H), 4.29 (d, 2H), 3.78 (dd, 2H), 3.50 (dd, 2H), 3.43-3.34 (m, overlapping with solvent), 2.04-1.93 (m, 4H).

Example 99: (R)—N-(2-(4-Cyanothiazolidin-3-yl)-2-oxoethyl)-6-(1,9-dioxa-4-azaspiro[5.5]undecan-4-yl)quinoline-4-carboxamide

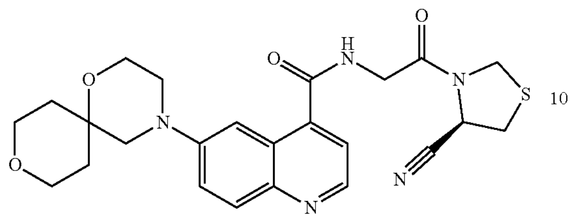

The compound was synthesized and purified analogous to the procedure of Example 91 starting from tert-butyl 6-(1,9-dioxa-4-azaspiro[5.5]undecan-4-yl)quinoline-4-carboxylat Intermediate 209 (0.096 g, 0.25 mmol) and (R)-3-glycylthiazolidine-4-carbonitrile hydrochloride Intermediate 4 (0.062 g, 0.30 mmol) to give the title compound (0.029 g, 24%); HRMS (ESI) m/z $[M+H]^+$ calcd for $C_{24}H_{28}N_5O_4S$: 482.1856. found: 482.1846; $^1H$ NMR (600 MHz, DMSO-$d_6$) δ 8.99 (t, 1H), 8.64 (d, 1H), 7.87 (d, 1H), 7.70 (d, 1H), 7.64 (dd, 1H), 7.36 (d, 1H), 5.26 (dd, 1H), 4.85 (d, 1H), 4.67 (d, 1H), 4.32-4.22 (m, 2H), 3.80 (t, overlapping with solvent), 3.62-3.54 (m, overlapping with solvent), 3.39-3.31 (m, overlapping with solvent), 3.28-3.18 (m, overlapping with solvent), 1.81-1.72 (m, 2H), 1.71-1.62 (m, 2H).

Example 100: 7-Bromo-N-(2-((R)-4-cyanothiazolidin-3-yl)-2-oxoethyl)-6-((3S,5R)-3,5-dimethylmorpholino)quinoline-4-carboxamide

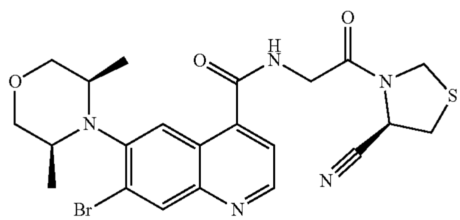 [SMILES: C[C@@H]1COC[C@H](C)N1c1cc2c(C(=O)NCC(=O)N3CSC[C@H]3C#N)ccnc2cc1Br]

HATU (13.5 mg, 0.04 mmol) was added to a solution of the crude 7-bromo-6-((3R,5S)-3,5-dimethylmorpholino)quinoline-4-carboxylic acid Intermediate 212 (0.020 g, 0.03 mmol) and DIPEA (25.9 μL, 0.15 mmol) in a mixture of MeCN/EtOAc (1 mL, 1:1) at rt. The reaction was stirred for 1.5 min after which (R)-3-glycylthiazolidine-4-carbonitrile hydrochloride Intermediate 4 (7 mg, 0.04 mmol) was added and the reaction was stirred for 2 h at rt. The reaction mixture was diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-A, to give the title compound (5.7 mg, 37%); HRMS (ESI) m/z $[M+H]^+$ calcd for $C_{22}H_{25}BrN_5O_3S$: 518.0856. found: 518.0858; $^1H$ NMR (600 MHz, DMSO-$d_6$) δ 9.14 (t, 1H), 8.96 (d, 1H), 8.41 (s, 1H), 8.38 (s, 1H), 7.59 (d, 1H), 5.30 (dd, 1H), 4.85 (d, 1H), 4.69 (d, 1H), 4.31 (d, 2H), 3.80 (d, overlapping with solvent), 3.37-3.31 (m, 2H), 3.17-3.08 (m, overlapping with solvent), 0.58 (d, 6H).

Example 101: (R)-5-Chloro-N-(2-(4-cyanothiazolidin-3-yl)-2-oxoethyl)-6-morpholino-quinoline-4-carboxamide

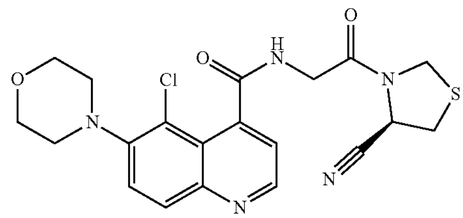

Step a) 2 M NaOH (aq, 1.025 mL, 2.05 mmol) was added to a suspension of ethyl 5-chloro-6-morpholinoquinoline-4-carboxylate hydrochloride Intermediate 213 (8 mg, 0.23 mmol) in MeOH (1.4 mL) and the reaction was heated at 80° C. for 20 min. Aq NaOH (3.8 M, 0.54 mL, 2.1 mmol) was added and the reaction was heated at 120° C. for 50 min. After cooling to rt, aq HCl (3.8 M, 1.2 mL, 4.6 mmol) was added dropwise and the resulting mixture was concentrated. The residue was co-evaporated once from $H_2O$ and twice from EtOAc to give crude 5-chloro-6-morpholinoquinoline-4-carboxylic acid as a solid; MS (ESI) m/z $[M+H]^+$ 293.1.

Step b) A mixture of MeCN/EtOAc (3 mL, 1:1) and DIPEA was added to the crude 5-chloro-6-morpholinoquinoline-4-carboxylic acid, followed by HATU (96 mg, 0.25 mmol). The reaction mixture was stirred for 2 min at rt after which (R)-3-glycylthiazolidine-4-carbonitrile hydrochloride Intermediate 4 (52 mg, 0.25 mmol) was added and the reaction mixture was stirred for 4.5 h at rt. The reaction mixture was diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-D, to give the title compound (0.042 g, 41%); HRMS (ESI) m/z $[M+H]^+$ calcd for $C_{20}H_{21}ClN_5O_3S$: 446.1048. found: 446.1044; $^1H$ NMR (600 MHz, DMSO-$d_6$) δ 8.91 (t, 1H), 8.85 (d, 1H), 8.03 (d, 1H), 7.73 (d, 1H), 7.46 (d, 1H), 5.30 (dd, 1H), 4.85 (d, 1H), 4.68 (d, 1H), 4.45-4.05 (m, 2H), 3.75 (t, 4H), 3.36 (dd, 1H), 3.30 (dd, 1H), 3.09 (brs, 4H).

Example 102: N-(2-((R)-4-Cyanothiazolidin-3-yl)-2-oxoethyl)-6-((S)-3-methyl-morpholino)quinoline-4-carboxamide

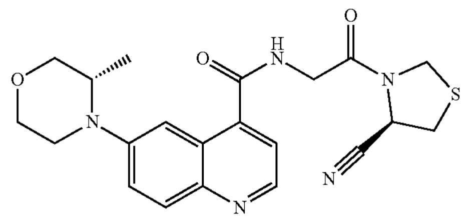 [SMILES: C[C@H]1COCCN1c1ccc2nccc(C(=O)NCC(=O)N3CSC[C@H]3C#N)c2c1]

A solution of tert-butyl (S)-6-(3-methylmorpholino)quinoline-4-carboxylate Intermediate 214 (48 mg, 0.15 mmol) in 90% TFA (aq, 0.5 mL) was stirred at rt for 5 h. The volatiles were removed under reduced pressure and the residue was suspended in a mixture of heptane/DCM, concentrated (2×) and dried under vacuum. HATU (0.068 g, 0.18 mmol) was added to a solution of the residue in a mixture of MeCN/EtOAc (2 mL, 1:1) and DIPEA (0.131 ml, 0.75 mmol). The reaction mixture was stirred for 1 min after which (R)-3-glycylthiazolidine-4-carbonitrile hydrochloride Intermediate 4 (0.037 g, 0.18 mmol) was added. The resulting solution was stirred for 1 h at rt, diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-C, to give the title compound (0.026 g, 41%); HRMS (ESI) m/z $[M+H]^+$ calcd for $C_{21}H_{24}N_5O_3S$: 426.1594. found: 426.1594; $^1H$ NMR (600 MHz, DMSO-$d_6$) δ 8.99 (t, 1H), 8.66 (d, 1H), 7.89 (d, 1H), 7.63 (dd, 2H), 7.40 (d, 1H), 5.28 (dd, 1H), 4.86 (d, 1H), 4.68 (d, 1H), 4.27 (d, 2H), 4.16-4.11 (m, 1H), 3.96 (dd, 1H), 3.72 (d, 2H), 3.54 (dd, 1H), 3.43-3.35 (m, overlapping with solvent), 3.33 (dd, 1H), 3.16-3.12 (m, 1H), 1.04 (d, 3H).

Example 103: N-(2-((R)-4-Cyanothiazolidin-3-yl)-2-oxoethyl)-6-((3S,5S)-3,5-dimethyl-morpholino)quinoline-4-carboxamide

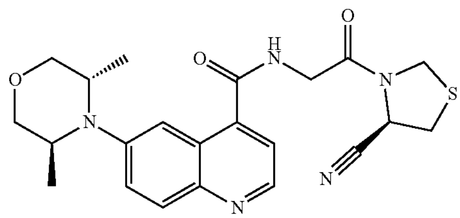 [SMILES: C[C@H]1COC[C@H](C)N1c1ccc2nccc(C(=O)NCC(=O)N3CSC[C@H]3C#N)c2c1]

A solution of tert-butyl 6-((3S,5S)-3,5-dimethylmorpholino)quinoline-4-carboxylate Intermediate 215 (54 mg, 0.16 mmol) in 90% TFA (aq, 0.5 mL) was stirred at rt for 5 h. The volatiles were removed under reduced pressure and the residue was suspended in a mixture of heptane/DCM, concentrated (2×) and dried under vacuum. HATU (0.073 g, 0.19 mmol) was added to a stirred solution of the residue in a mixture of MeCN/EtOAc (2 mL, 1:1) at rt. The reaction was stirred for 1 min, and (R)-3-glycylthiazolidine-4-carbonitrile hydrochloride Intermediate 4 (0.040 g, 0.19 mmol) was added. The resulting solution was stirred for 45 min at rt, diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-D, to give the title compound (0.029 g, 41%); HRMS (ESI) m/z $[M+H]^+$ calcd for $C_{22}H_{26}N_5O_3S$: 440.1750. found: 440.1738; $^1H$ NMR (600 MHz, DMSO-$d_6$) δ 9.02 (t, 1H), 8.76 (d, 1H), 7.91 (d, 1H), 7.79 (d, 1H), 7.58 (dd, 1H), 7.44 (d, 1H), 5.29 (dd, 1H), 4.85 (d, 1H), 4.68 (d, 1H), 4.31-4.24 (m, 2H), 3.84 (dd, overlapping with solvent), 3.72-3.67 (m, overlapping with solvent), 3.42 (dd, 2H), 3.38-3.31 (m, 2H), 0.87 (d, 6H).

Example 104: (R)—N-(2-(4-Cyanothiazolidin-3-yl)-2-oxoethyl)-6-(8-oxa-5-azaspiro[3.5]nonan-5-yl)quinoline-4-carboxamide

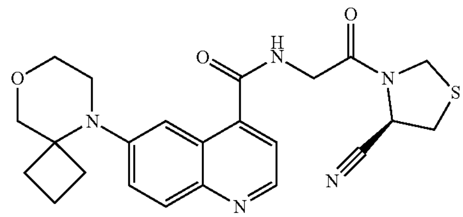 [SMILES: N#C[C@@H]1CSCN1C(=O)CNC(=O)c1ccnc2ccc(N3CCOCC34CCC4)cc12]

A solution of tert-butyl 6-(8-oxa-5-azaspiro[3.5]nonan-5-yl)quinoline-4-carboxylate Intermediate 216 (103 mg, 0.29 mmol) in 90% TFA (aq, 1 mL) was stirred at 50° C. for min. After cooling to rt the solution was concentrated under reduced pressure and the residue was suspended in a mixture of heptane/DCM and concentrated. This was repeated 3x and the residue was dried under vacuum overnight. HATU (0.132 g, 0.35 mmol) was added to a stirred solution of the residue (0.153 g, 0.29 mmol) and DIPEA (0.253 mL, 1.45 mmol) in a mixture of MeCN/EtOAc (3 mL, 1:1) at rt. The reaction was stirred for 1 min and (R)-3-glycylthiazolidine-4-carbonitrile hydrochloride Intermediate 4 (0.072 g, 0.35 mmol) was added. The resulting solution was stirred at rt for 80 min, diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-C, to give the title compound (0.042 g, 32%); HRMS (ESI) m/z $[M+H]^+$ calcd for $C_{23}H_{26}N_5O_3S$: 452.1750. found: 452.1754; $^1H$ NMR (600 MHz, DMSO-$d_6$) δ 9.00 (t, 1H), 8.73 (d, 1H), 7.88 (d, 1H), 7.56 (d, 1H), 7.48-7.41 (m, 2H), 5.28 (dd, 1H), 4.86 (d, 1H), 4.68 (d, 1H), 4.31 (dd, 1H), 4.21 (dd, 1H), 3.84-3.76 (m, 2H), 3.54-3.47 (m, overlapping with solvent), 3.37-3.29 (m, overlapping with solvent), 2.16-2.07 (m, 2H), 2.05-1.96 (m, 2H), 1.70-1.62 (m, 1H), 1.54-1.46 (m, 1H).

Example 105: N-(2-((R)-4-Cyanothiazolidin-3-yl)-2-oxoethyl)-6-((3R,5R)-3,5-dimethyl-morpholino)quinoline-4-carboxamide

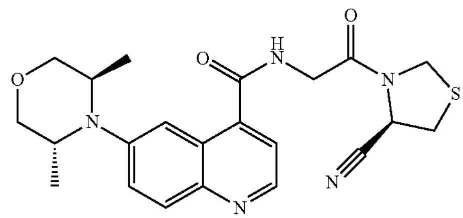 [SMILES: C[C@@H]1COC[C@@H](C)N1c1ccc2nccc(C(=O)NCC(=O)N3CSC[C@H]3C#N)c2c1]

A solution of tert-butyl 6-((3R,5R)-3,5-dimethylmorpholino)quinoline-4-carboxylate Intermediate 217 (84 mg, 0.25 mmol) in 90% TFA (aq, 2 mL) was stirred at rt for 5 h. After cooling to rt the solution was concentrated under reduced pressure and the residue was co-evaporated with a mixture of heptane/DCM (×2) and dried under vacuum overnight. HATU (132 mg, 0.35 mmol) was added to a stirred solution of the residue in a mixture of MeCN/EtOAc (3 mL, 1:1) and DIPEA (253 μL, 1.45 mmol) at rt. The reaction was stirred for 1 min after which (R)-3-glycylthiazolidine-4-carbonitrile hydrochloride Intermediate 4 (72 mg, 0.35 mmol) was added. The resulting solution was stirred for 1 h at rt, diluted with EtOAc and washed with 8% $NaHCO_3$ (aq). The aqueous layer was extracted with EtOAc and the combined organic layers were dried over $Na_2SO_4$, filtered and concentrated. The residue was purified by preparative SFC, PrepMethod SFC-D, to give the title compound (0.043 g, 39%); HRMS (ESI) m/z $[M+H]^+$ calcd for $C_{22}H_{26}N_5O_3S$: 440.1750. found: 440.1746; $^1H$ NMR (600 MHz, DMSO-$d_6$) δ 9.02 (t, 1H), 8.77 (d, 1H), 7.92 (d, 1H), 7.72 (d, 1H), 7.58 (dd, 1H), 7.46 (d, 1H), 5.29 (dd, 1H), 4.86 (d, 1H), 4.69 (d, 1H), 4.33 (dd, 1H), 4.23 (dd, 1H), 3.84 (dd, 2H), 3.70-3.62 (m, 2H), 3.43 (dd, 2H), 3.40-3.29 (m, 2H), 0.87 (d, 6H).

Example 106: N-(2-((R)-4-Cyanothiazolidin-3-yl)-2-oxoethyl)-6-((S)-3-ethyl-morpholino)quinoline-4-carboxamide

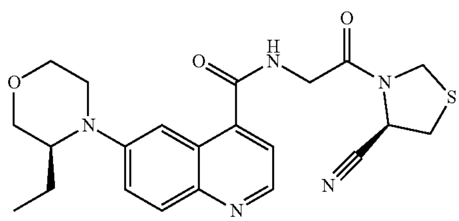 [SMILES: CC[C@H]1COCCN1c1ccc2nccc(C(=O)NCC(=O)N3CSC[C@H]3C#N)c2c1]

HATU (103 mg, 0.27 mmol) was added to a stirred solution of the crude (S)-6-(3-ethylmorpholino)quinoline-4-carboxylic acid Intermediate 219 (116 mg) and DIPEA (197 μL, 1.13 mmol) in DMF (2 mL) at rt. The reaction was stirred for −1 min after which (R)-3-glycylthiazolidine-4-carbonitrile hydrochloride Intermediate 4 (56.2 mg, 0.27 mmol) was added. The resulting solution was stirred for 2 h at rt. The reaction was diluted with DCM and washed with 8% $NaHCO_3$ (aq). The organic layer was concentrated and co-evaporated with heptane (×4) until most of the DMF was removed. The residue was purified by preparative SFC, PrepMethod SFC-D, to give the title compound (0.046 g, 47%); HRMS (ESI) m/z $[M+H]^+$ calcd for $C_{22}H_{26}N_5O_3S$: 440.1750. found: 440.1748; $^1H$ NMR (600 MHz, DMSO-$d_6$) δ 8.96 (t, 1H), 8.63 (d, 1H), 7.87 (d, 1H), 7.64-7.58 (m, 2H), 7.37 (d, 1H), 5.28 (dd, 1H), 4.85 (d, 1H), 4.67 (d, 1H), 4.26 (dd, 2H), 3.93 (dd, 1H), 3.87 (d, 1H), 3.85-3.79 (m, 1H), 3.61 (dd, 1H), 3.56-3.51 (m, 1H), 3.44 (d, overlapping with solvent), 3.38-3.30 (m, overlapping with solvent), 3.18-3.12 (m, 1H), 1.77 −1.66 (m, 1H), 1.36 (m, 1H), 0.82 (t, 3H).

Example 107: (R)—N-(2-(4-Cyanothiazolidin-3-yl)-2-oxoethyl)-6-(3,3-dimethyl-morpholino)quinoline-4-carboxamide

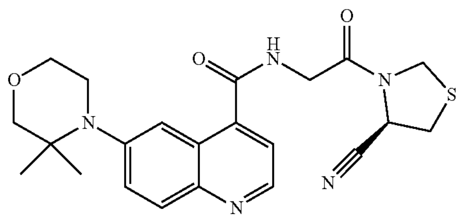 [SMILES: CC1(C)COCCN1c1ccc2nccc(C(=O)NCC(=O)N3CSC[C@H]3C#N)c2c1]

A solution of tert-butyl 6-(3,3-dimethylmorpholino)quinoline-4-carboxylate Intermediate 220 (51 mg, 0.15 mmol) in 90% TFA (aq, 1 mL) was stirred at rt for 5 h. The solution was concentrated under reduced pressure and the residue was suspended in a mixture of DCM/heptane and then concentrated (×2). The residue was dissolved in DMF (1 mL) and DIPEA (0.13 mL, 0.76 mmol), and HATU (69 mg, 0.18 mmol) was added at rt and the reaction mixture was stirred for 1 min, after which (R)-3-glycylthiazolidine-4-carbonitrile hydrochloride Intermediate 4 (38 mg, 0.18 mmol) was added. The resulting solution was stirred for 3 h at rt, diluted with DCM and washed with 8% $NaHCO_3$ (aq). The organic layer was concentrated and the residue was co-evaporated with heptane (×4) until most of the DMF was removed. The residue was purified by preparative SFC, PrepMethod SFC-A, to give the title compound (0.027 g, 41%); HRMS (ESI) m/z $[M+H]^+$ calcd for $C_{22}H_{26}N_5O_3S$: 440.1750. found: 440.1748; $^1H$ NMR (600 MHz, DMSO-$d_6$) δ 9.01 (t, 1H), 8.81 (d, 1H), 7.98 (d, 1H), 7.90 (d, 1H), 7.58 (dd, 1H), 7.47 (d, 1H), 5.30 (dd, 1H), 4.85 (d, 1H), 4.69 (d, 1H), 4.32-4.24 (m, 2H), 3.72 (t, 2H), 3.40 (s, 2H), 3.36 (dd, 1H), 3.32 (dd, 1H), 3.20-3.14 (m, 2H), 1.05 (s, 3H), 1.04 (s, 3H).

Example 108: N-(2-((R)-4-Cyanothiazolidin-3-yl)-2-oxoethyl)-6-((R)-3-methyl-morpholino)quinoline-4-carboxamide

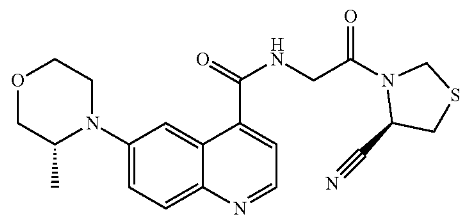 [SMILES: C[C@@H]1COCCN1c1ccc2nccc(C(=O)NCC(=O)N3CSC[C@H]3C#N)c2c1]

A solution of tert-butyl (R)-6-(3-methylmorpholino)quinoline-4-carboxylate Intermediate 221 (67 mg, 0.20 mmol) in 90% TFA (aq, 3 mL) was stirred at rt for 5 h. The solution was concentrated under reduced pressure and the residue was co-evaporated twice with heptane. The residue was dissolved in DMF (1 mL) and DIPEA (157 μL, 0.90 mmol), and HATU (82 mg, 0.22 mmol) was added at rt. The reaction was stirred for 1 min after which (R)-3-glycylthiazolidine-4-carbonitrile hydrochloride Intermediate 4 (45 mg, 0.22 mmol) was added. The resulting solution was stirred for 2 h at rt, diluted with DCM and washed with 8% $NaHCO_3$ (aq). The organic layer was concentrated and the residue was co-evaporated with heptane (4×) until most of the DMF had been removed. The residue was purified by preparative SFC, PrepMethod SFC-C, to give the title compound (0.028 g, 37%); HRMS (ESI) m/z $[M+H]^+$ calcd for $C_{21}H_{24}N_5O_3S$: 426.1594. found: 426.1602; $^1H$ NMR (600 MHz, DMSO-$d_6$) δ 8.96 (t, 1H), 8.63 (d, 1H), 7.88 (d, 1H), 7.63-7.58 (m, 2H), 7.36 (d, 1H), 5.27 (dd, 1H), 4.86 (d, 1H), 4.67 (d, 1H), 4.30 (dd, 1H), 4.22 (dd, 1H), 4.16-4.09 (m, 1H), 3.95 (dd, 1H), 3.71 (d, 2H), 3.55 (td, 1H), 3.42-3.30 (m, overlapping with solvent), 3.09 (td, 1H), 1.04 (d, 3H).

Example 109: (R)—N-(2-(4-Cyanothiazolidin-3-yl)-2-oxoethyl)-2-methyl-6-morpholino-quinoline-4-carboxamide

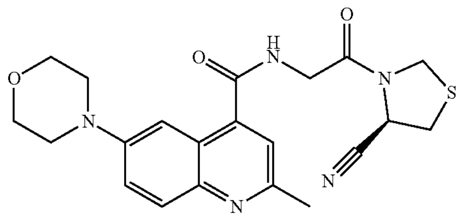 [SMILES: Cc1cc(C(=O)NCC(=O)N2CSC[C@H]2C#N)c2cc(N3CCOCC3)ccc2n1]

Ethyl 2-methyl-6-morpholinoquinoline-4-carboxylate Intermediate 222 (89 mg, 0.30 mmol) was dissolved in MeOH (1 mL). 2 M NaOH (aq, 0.148 mL, 0.30 mmol) was added and the reaction mixture was stirred at rt for 2 h and was then evaporated to dryness. HATU (141 mg, 0.37 mmol) and DIPEA (0.155 mL, 0.89 mmol) were added to a suspension of the residue and (R)-3-glycylthiazolidine-4-carbonitrile hydrochloride Intermediate 4 (61 mg, 0.30 mmol) in EtOAc (1 mL), MeCN (1.0 mL) and DMF (1.0 mL). The solution was stirred at rt overnight. The reaction mixture was evaporated and the residue was purified by preparative HPLC, PrepMethod Q, to give the title compound (0.6 mg, 0.5%); HRMS (ESI) m/z $[M+H]^+$ calcd for $C_{21}H_{24}N_5O_3S$: 426.1594. found: 426.1594.

Example 110: (R)—N-(2-(4-Cyanothiazolidin-3-yl)-2-oxoethyl)-6-(2-oxo-1-oxa-3-azaspiro[5.5]undecan-3-yl)quinoline-4-carboxamide

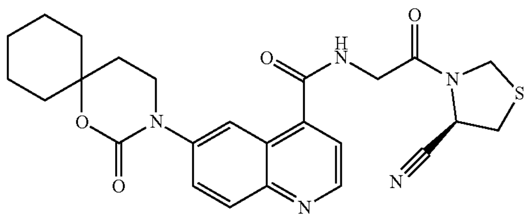 [SMILES: N#C[C@@H]1CSCN1C(=O)CNC(=O)c1ccnc2ccc(N3CCC4(CCCCC4)OC3=O)cc12]

A solution of tert-butyl 6-(2-oxo-1-oxa-3-azaspiro[5.5]undecan-3-yl)quinoline-4-carboxylate Intermediate 223 (115 mg, 0.29 mmol) in 90% TFA (2 mL) was stirred at 50° C. for 15 min. The reaction solution was concentrated and the residue was co-evaporated twice from water. A mixture of MeCN/EtOAc (2.6 mL, 1:1) and DIPEA (0.253 mL, 1.45 mmol) was added to the residue followed by HATU (0.132 g, 0.35 mmol). The reaction mixture was stirred for 1 min after which (R)-3-glycylthiazolidine-4-carbonitrile hydrochloride Intermediate 4 (0.072 g, 0.35 mmol) was added. The reaction mixture was stirred for 1 h min, diluted with EtOAc (20 mL) and washed with 8% $NaHCO_3$(aq, 10 mL) followed by $H_2O$ (2 mL). The organic layer was dried over $Na_2SO_4$, filtered and concentrated. The residue was purified by straight phase flash chromatography on silica (EtOAc followed by EtOAc:MeOH, 20:1). The compound was further purified by preparative HPLC, PrepMethod G, (gradient: 10-50%) and preparative SFC, PrepMethod SFC-D, to give the title compound (0.046 g, 32%); HRMS (ESI) m/z $[M+H]^+$ calcd for $C_{25}H_{28}N_5O_4S$: 494.1856. found: 494.1838; $^1H$ NMR (500 MHz, DMSO-$d_6$) δ 9.17 (t, 1H), 8.96 (d, 1H), 8.49 (d, 1H), 8.05 (d, 1H), 7.88 (dd, 1H), 7.56 (d, 1H), 5.32 (dd, 1H), 4.90 (d, 1H), 4.71 (d, 1H), 4.34 (d, 2H), 3.93-3.79 (m, 2H), 3.43 (dd, 1H), 3.36 (dd, 1H), 2.09 (t, 2H), 1.91-1.82 (m, 2H), 1.72-1.60 (m, 4H), 1.58-1.50 (m, 3H), 1.45-1.32 (m, 1H).

Example 111: (R)—N-(2-(4-Cyanothiazolidin-3-yl)-2-oxoethyl)-6-(7-oxo-6-oxa-8-azaspiro[4.5]decan-8-yl)quinoline-4-carboxamide

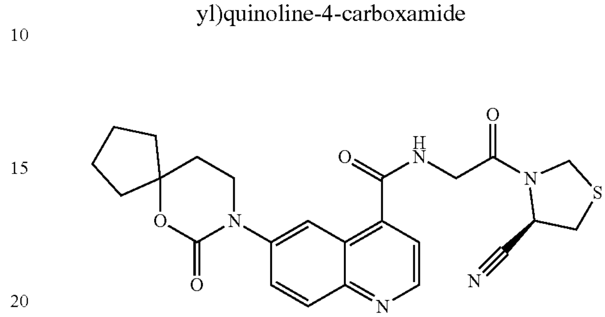

A solution of tert-butyl 6-(7-oxo-6-oxa-8-azaspiro[4.5]decan-8-yl)quinoline-4-carboxylate Intermediate 225 (105 mg, 0.27 mmol) in 90% TFA (aq, 1 mL) was stirred at for 15 min. The reaction solution was concentrated and the residue was dissolved in a mixture of water/MeCN and freeze-dried. A mixture of MeCN/EtOAc (2.4 mL, 1:1) was added to the residue followed by DIPEA (0.236 mL, 1.35 mmol) and HATU (0.123 g, 0.32 mmol). The reaction was stirred at rt for 1 min after which (R)-3-glycylthiazolidine-4-carbonitrile hydrochloride Intermediate 4 (0.067 g, 0.32 mmol) was added. The reaction mixture was stirred for 2 h, diluted with EtOAc (20 mL) and washed with of 8% $NaHCO_3$(aq, 10 mL) followed by water (2 mL). The organic layer was dried over $Na_2SO_4$, filtered and concentrated. The residue was purified by straight phase flash chromatography on silica (EtOAc followed by EtOAc/MeOH 10:1). The compound was further purified by preparative HPLC, PrepMethod G, (gradients: 0-30% and 0-45%) and preparative SFC to give the title compound (0.031 g, 24%) as a an off-white solid; HRMS (ESI) m/z $[M+H]^+$ calcd for $C_{24}H_{26}N_5O_4S$: 480.1700. found: 480.1718; $^1H$ NMR (500 MHz, DMSO-$d_6$) δ 9.17 (t, 1H), 8.96 (d, 1H), 8.49 (d, 1H), 8.05 (d, 1H), 7.89 (dd, 1H), 7.57 (d, 1H), 5.33 (dd, 1H), 4.90 (d, 1H), 4.71 (d, 1H), 4.34 (d, 2H), 3.93-3.82 (m, 2H), 3.46-3.36 (m, 2H), 2.18 (t, 2H), 2.03-1.95 (m, 2H), 1.87 −1.66 (m, 6H).

Example 112: (R)—N-(2-(4-Cyanothiazolidin-3-yl)-2-oxoethyl)-6-(6,6-dimethyl-2-oxo-1,3-oxazinan-3-yl)quinoline-4-carboxamide

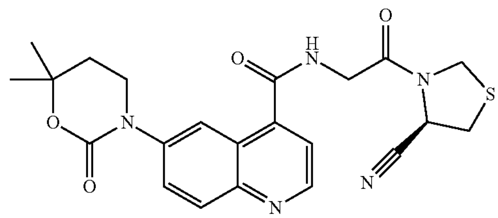 [SMILES: CC1(C)CCN(c2ccc3nccc(C(=O)NCC(=O)N4CSC[C@H]4C#N)c3c2)C(=O)O1]

TFA (35 μL, 0.45 mmol) was added to a solution of tert-butyl 6-(6,6-dimethyl-2-oxo-1,3-oxazinan-3-yl)quinoline-4-carboxylate Intermediate 226 (40 mg, 0.11 mmol) in DCM (2 mL). The resulting solution was stirred at 25° C. for 6 h. The solvent was removed by distillation under vacuum. The residue was dissolved in DMF (2 mL) and (R)-3-glycylthiazolidine-4-carbonitrile hydrochloride Intermediate 4 (55 mg, 0.27 mmol), T3P (170 mg, 0.53 mmol) and DIPEA (69 mg, 0.53 mmol) were added. The resulting solution was stirred at 25° C. for 6 h. The solvent was removed under reduced pressure and the residue was purified by preparative TLC (DCM:MeOH 18:1) followed by preparative HPLC, PrepMethod B, (gradient: 11-41%) to give the title compound (0.028 g, 46%) as a white solid; HRMS (ESI) m/z $[M+H]^+$ calcd for $C_{22}H_{24}N_5O_4S$: 454.1544. found: 454.1554; $^1H$ NMR (300 MHz, DMSO-$d_6$) δ 9.16 (t, 1H), 8.95 (d, 1H), 8.49 (d, 1H), 8.04 (d, 1H), 7.86 (dd, 1H), 7.55 (d, 1H), (dd, 1H), 4.88 (d, 1H), 4.69 (d, 1H), 4.33 (d, 2H), 3.86 (t, 2H), 3.46-3.32 (m, overlapping with solvent), 2.07 (t, 2H), 1.44 (s, 6H).

Example 113: (R)—N-(2-(4-Cyanothiazolidin-3-yl)-2-oxoethyl)-6-(3-(fluoromethyl)-azetidin-1-yl)quinoline-4-carboxamide

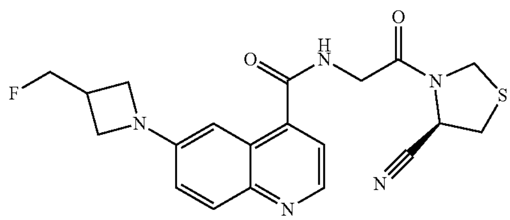 [SMILES: N#C[C@@H]1CSCN1C(=O)CNC(=O)c1ccnc2ccc(N3CC(CF)C3)cc12]

DIPEA (1.37 mL, 7.81 mmol) was added to a mixture crude 6-(3-(fluoromethyl)-azetidin-1-yl)quinoline-4-carboxylic acid Intermediate 228 (0.436 g, 0.724 mmol), (R)-3-glycylthiazolidine-4-carbonitrile hydrochloride Intermediate 4 (263 mg, 1.27 mmol), HOBt (428 mg, 3.16 mmol) and EDC (607 mg, 3.16 mmol) in EtOAc (5 mL) and MeCN (5 mL) at 13° C. The resulting solution was stirred at 13° C. overnight under $N_2$ (g). The solvent was removed under reduced pressure. The reaction mixture was diluted with sat $NaHCO_3$(aq, 100 mL), and extracted with EtOAc (5×100 mL). The organic layers were combined and washed with sat NaCl (aq, 3×50 mL), dried over $Na_2SO_4$, filtered and evaporated. The residue was purified by preparative HPLC, PrepMethod C, (gradient: 10-30%) and further purified by straight phase flash chromatography on silica (EtOAc: MeOH, 9:1) to give the title compound (0.103 g, 34%) as a yellow solid; HRMS (ESI) m/z $[M+H]^+$ calcd for $C_{24-121}FN_5O_2S$: 414.1394. found: 414.1412; $^1H$ NMR (500 MHz, DMSO-$d_6$) δ 8.97 (t, 1H), 8.63 (d, 1H), 7.89 (d, 1H), 7.41 (d, 1H), 7.19 (d, 1H), 7.13 (dd, 1H), 5.34 (dd, 1H), 4.89 (d, 1H), 4.72 (d, 1H), 4.70 (d, 1H), 4.60 (d, 1H), 4.30 (d, 2H), 4.07 (t, 2H), 3.78 (dd, 2H), 3.44-3.36 (m, 2H), 3.20-3.06 (m, 1H).

Example 114: (R)—N-(2-(4-Cyanothiazolidin-3-yl)-2-oxoethyl)-6-(4,5,6,7-tetrahydro-1H-indazol-1-yl)quinoline-4-carboxamide

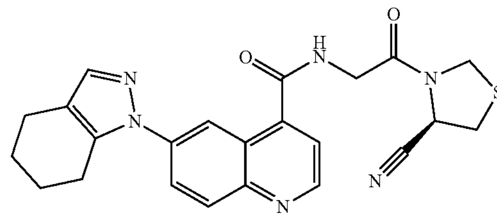

DIPEA (0.429 mL, 2.45 mmol) was added to a stirred suspension of crude 6-(4,5,6,7-tetrahydro-1H-indazol-1-yl)quinoline-4-carboxylic acid Intermediate 240 (50 mg, 0.08 mmol), (R)-3-glycylthiazolidine-4-carbonitrile hydrochloride Intermediate 4 (26 mg, 0.12 mmol), HOBt (55 mg, 0.41 mmol) and EDC (78 mg, 0.41 mmol) in MeCN (3 mL) and EtOAc (3 mL) at 18° C. The resulting solution was stirred at 50° C. for 2 h. The solvent was removed under reduced pressure. The residue was partitioned between sat $NaHCO_3$ (20 mL) and EtOAc (50 mL). The aqueous layer was extracted with EtOAc (5×50 mL). The organic layers were combined and washed with $H_2O$ (3×20 mL). The aqueous layers were combined and extracted with EtOAc (3×15 mL). All organic layers were combined and dried over $Na_2SO_4$, filtered and evaporated. The residue was purified by preparative HPLC, PrepMethod C, (gradient: 35-50%), to give the title compound (0.035 g, 96%) as a white solid; HRMS (ESI) m/z $[M+H]^+$ calcd for $C_{23}H_{23}N_6O_2S$: 447.1598. found: 447.1618; $^1H$ NMR (300 MHz, DMSO-$d_6$) δ 9.30-9.10 (m, 1H), 9.01 (d, 1H), 8.42 (d, 1H), 8.28-8.04 (m, 2H), 7.72-7.50 (m, 2H), 5.33 (dd, 1H), 4.91 (d, 1H), 4.72 (d, 1H), 4.48-4.23 (m, 2H), 3.48-3.34 (m, overlapping with solvent), 2.99-2.79 (m, 2H), 2.65-2.50 (m, overlapping with solvent), 1.89-1.63 (m, 4H).

Example 115: (R)—N-(2-(4-Cyanothiazolidin-3-yl)-2-oxoethyl)-6-(4,5,6,7-tetrahydro-2H-indazol-2-yl)quinoline-4-carboxamide

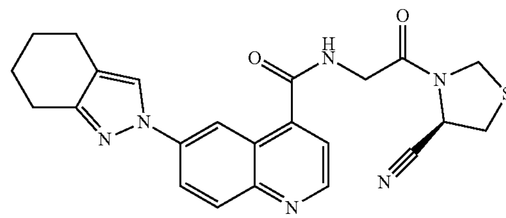

DIPEA (4.21 mL, 24.1 mmol) was added to a stirred suspension of the crude 6-(4,5,6,7-tetrahydro-2H-indazol-2-yl)quinoline-4-carboxylic acid Intermediate 241 (465 mg, 0.59 mmol), (R)-3-glycylthiazolidine-4-carbonitrile hydrochloride Intermediate 4 (185 mg, 0.89 mmol), HOBt (401 mg, 2.97 mmol) and EDC (569 mg, 2.97 mmol) in MeCN (5 mL) and EtOAc (5 mL) at 18° C. The resulting solution was stirred at 50° C. for 2 h. The solvent was removed under reduced pressure. The residue was partitioned between sat $NaHCO_3$(aq, 50 mL) and EtOAc (100 mL). The aqueous layer was extracted with EtOAc (5×100 mL). The organic layers were combined and washed with $H_2O$ (3×50 mL). The organic layer was dried over $Na_2SO_4$, filtered and evaporated. The residue was purified by preparative HPLC, PrepMethod C, (gradient: 35-45%), to give the title compound (0.122 g, 46%) as a white solid; HRMS (ESI) m/z $[M+H]^+$ calcd for $C_{23}H_{23}N_6O_2S$: 447.1598. found: 447.1594; $^1H$ NMR (300 MHz, DMSO-$d_6$) δ 9.28-9.08 (m, 1H), 8.94 (d, 1H), 8.77 (s, 1H), 8.43-8.30 (m, 2H), 8.16 (d, 1H), 7.60 (d, 1H), 5.45-5.28 (m, 1H), 4.93 (d, 1H), 4.74 (d, 1H), 4.39 (d, 2H), 3.50-3.34 (m, overlapping with solvent), 2.80-2.52 (m, overlapping with solvent), 1.77 (m, 4H).

Example 116: (R)—N-(2-(4-Cyanothiazolidin-3-yl)-2-oxoethyl)-6-(5-methyl-3-(trifluoromethyl)-1H-pyrazol-1-yl)quinoline-4-carboxamide

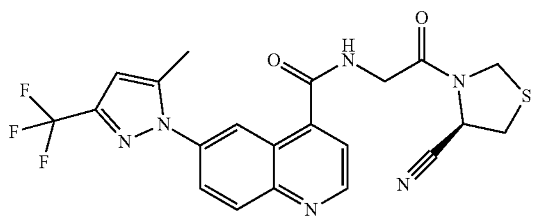 [SMILES: Cc1cc(C(F)(F)F)nn1-c1ccc2nccc(C(=O)NCC(=O)N3CSC[C@H]3C#N)c2c1]

DIPEA (1.56 mL, 8.92 mmol) was added to a stirred suspension of crude 6-(5-methyl-3-(trifluoromethyl)-1H-pyrazol-1-yl)quinoline-4-carboxylic acid Intermediate 242 (199 mg, 0.29 mmol), (R)-3-glycylthiazolidine-4-carbonitrile hydrochloride Intermediate 4 (90 mg, 0.44 mmol), HOBt (196 mg, 1.45 mmol) and EDC (278 mg, 1.45 mmol) in MeCN (5 mL) and EtOAc (5 mL) at 15° C. The resulting solution was stirred at 50° C. for 2 h. The solvent was removed under reduced pressure, and the residue was partitioned between sat $NaHCO_3$ (aq, 50 mL) and EtOAc (100 mL). The aqueous layer was extracted with EtOAc (4×100 mL). The organic layers were combined and washed with $H_2O$ (3×50 mL). The organic layer was dried over $Na_2SO_4$, filtered and evaporated. The residue was purified by preparative HPLC, PrepMethod C, (gradient: 40-52%) to give the title compound (0.090 g, 65%) as a white solid; HRMS (ESI) m/z $[M+H]^+$ calcd for $C_{21}H_{18}F_3N_6O_2S$: 475.1158. found: 475.1138; $^1H$ NMR (300 MHz, DMSO-$d_6$) δ 9.23 (t, 1H), 9.09 (d, 1H), 8.54 (d, 1H), 8.26 (d, 1H), 8.04 (dd, 1H), 7.71 (d, 1H), 6.83 (s, 1H), 5.40-5.20 (m, 1H), 4.87 (d, 1H), 4.69 (d, 1H), 4.36-4.28 (m, 2H), 3.42-3.32 (m, overlapping with solvent), 2.46 (s, overlapping with solvent).

Example 117: (R)—N-(2-(4-Cyanothiazolidin-3-yl)-2-oxoethyl)-6-(6,6-dimethyl-5,6-dihydrocyclopenta[c]pyrazol-2(4H)-yl)quinoline-4-carboxamide

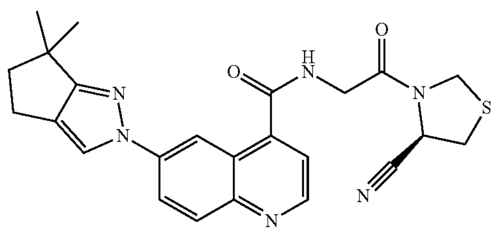 [SMILES: CC1(C)CCc2cn(-c3ccc4nccc(C(=O)NCC(=O)N5CSC[C@H]5C#N)c4c3)nc21]

DIPEA (3.29 mL, 18.8 mmol) was added to a stirred suspension of crude 6-(6,6-dimethyl-5,6-dihydrocyclopenta[c]pyrazol-2(4H)-yl)quinoline-4-carboxylic acid Intermediate 243 (482 mg, 0.62 mmol), (R)-3-glycylthiazolidine-4-carbonitrile hydrochloride Intermediate 4 (194 mg, 0.94 mmol), HOBt (420 mg, 3.14 mmol) and EDC (596 mg, 3.14 mmol) in MeCN (7 mL) and EtOAc (7 mL) at 15° C. The resulting solution was stirred at 50° C. for 2 h. The solvent was removed under reduced pressure and the residue was partitioned between sat $NaHCO_3$(aq, 60 mL) and EtOAc (100 mL). The aqueous layer was extracted with EtOAc (5×100 mL). The organic layers were combined and washed with $H_2O$ (3×50 mL). The organic layer was dried over $Na_2SO_4$, filtered and evaporated. The residue was purified by preparative HPLC, PrepMethod F, (gradient 42-52%) to give the title compound (0.14 g, 49%) as a white solid; HRMS (ESI) m/z $[M+H]^+$ calcd for $C_{24}H_{25}N_6O_2S$: 461.1754. found: 461.1742; $^1H$ NMR (300 MHz, DMSO-$d_6$) δ 9.14 (t, 1H), 8.92 (d, 1H), 8.70 (d, 1H), 8.31 (dd, 1H), 8.22 (s, 1H), 8.13 (d, 1H), 7.58 (d, 1H), 5.44-5.24 (m, 1H), 4.90 (d, 1H), 4.72 (d, 1H), 4.36 (d, 2H), 3.46-3.30 (m, overlapping with solvent), 2.66 (t, 2H), 2.19 (t, 2H), 1.30 (s, 6H).

Example 118: (R)—N-(2-(4-Cyanothiazolidin-3-yl)-2-oxoethyl)-6-(3-(trifluoromethyl)-1H-pyrazol-1-yl)quinoline-4-carboxamide

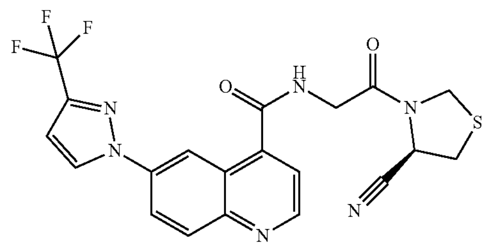 [SMILES: N#C[C@@H]1CSCN1C(=O)CNC(=O)c1ccnc2ccc(-n3ccc(C(F)(F)F)n3)cc12]

DIPEA (0.443 mL, 2.54 mmol) was added to a stirred suspension of 6-(3-(trifluoromethyl)-1H-pyrazol-1-yl)quinoline-4-carboxylic acid Intermediate 234 (78 mg, 0.25 mmol), (R)-3-glycylthiazolidine-4-carbonitrile hydrochloride Intermediate 4 (79 mg, 0.38 mmol), HOBt (172 mg, 1.27 mmol) and EDC (243 mg, 1.27 mmol) in MeCN (5 mL) and EtOAc (5 mL) at 10° C. The resulting suspension was stirred at 50° C. for 2 h. The solvent was removed under reduced pressure and the residue was partitioned between sat $NaHCO_3$ (30 mL) and EtOAc (60 mL). The aqueous layer was extracted with EtOAc (4×75 mL). The organic layers were combined and washed with $H_2O$ (3×20 mL). The organic layer was dried over $Na_2SO_4$, filtered and evaporated. The residue was purified by preparative HPLC, PrepMethod F, (gradient: 40-50%) to give the title compound (0.052 g, 43%) as a white solid; HRMS (ESI) m/z $[M+H]^+$ calcd for $C_{20}H_{16}F_3N_6O_2S$: 461.1002. found: 461.1018; $^1H$ NMR (300 MHz, DMSO-$d_6$) δ 9.22 (t, 1H), 9.04 (d, 1H), 8.94 (d, 1H), 8.88 (d, 1H), 8.38 (dd, 1H), 8.26 (d, 1H), 7.69 (d, 1H), 7.15-7.00 (m, 1H), 5.35 (dd, 1H), 4.91 (d, 1H) 4.73 (d, 1H), 4.44-4.25 (m, 2H), 3.70-3.34 (m, overlapping with solvent).

Example 119: (R)—N-(2-(4-Cyanothiazolidin-3-yl)-2-oxoethyl)-6-(4,6-difluoro-1H-indol-1-yl)quinoline-4-carboxamide

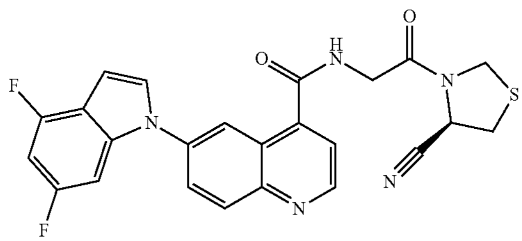 [SMILES: N#C[C@@H]1CSCN1C(=O)CNC(=O)c1ccnc2ccc(-n3ccc4c(F)cc(F)cc43)cc12]

A solution of 6-(4,6-difluoro-1H-indol-1-yl)quinoline-4-carboxylic acid Intermediate 235 (180 mg, 0.56 mmol), (R)-3-glycylthiazolidine-4-carbonitrile hydrochloride Intermediate 4 (173 mg, 0.83 mmol), EDC (213 mg, 1.11 mmol), HOBt (150 mg, 1.11 mmol) and DIPEA (485 μL, 2.78 mmol) in EtOAc (6 mL) and MeCN (6 mL) was stirred at 50° C. for 2 h. The solvent was removed under reduced pressure. The reaction mixture was diluted with EtOAc (25 mL) and washed with $H_2O$ (3×10 mL). The organic layer was dried over $Na_2SO_4$, filtered and evaporated. The residue was purified by preparative TLC (DCM:MeOH 10:1) followed by preparative HPLC, PrepMethod U, (gradient 40-50%) to give the title compound (0.105 g, 40%); HRMS (ESI) m/z $[M+H]^+$ calcd for $C_{24}H_{18}F_2N_5O_2S$: 478.1144. found: 478.1134; $^1H$ NMR (300 MHz, DMSO-$d_6$) δ 9.22 (t, 1H), 9.06 (d, 1H), 8.57 (d, 1H), 8.29 (d, 1H), 8.10 (dd, 1H), 7.86 (d, 1H), 7.71 (d, 1H), 7.42-7.32 (m, 1H), 7.03 (td, 1H), 6.85 (d, 1H), 5.81-5.20 (m, 1H), 4.86 (d, 1H), 4.69 (d, 1H), 4.55-4.26 (m, 2H), 3.36-3.25 (m, overlapping with solvent).

Example 120: (R)—N-(2-(4-Cyanothiazolidin-3-yl)-2-oxoethyl)-6-(5-fluoro-1H-indol-1-yl)quinoline-4-carboxamide

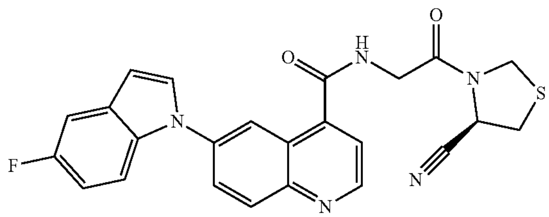 [SMILES: N#C[C@@H]1CSCN1C(=O)CNC(=O)c1ccnc2ccc(-n3ccc4cc(F)ccc43)cc12]

TEA (137 μL, 0.98 mmol) was added to a stirred suspension of 6-(5-fluoro-1H-indol-1-yl)quinoline-4-carboxylic acid Intermediate 236 (30 mg, 0.10 mmol), (R)-3-glycylthiazolidine-4-carbonitrile hydrochloride Intermediate 4 (31 mg, 0.15 mmol), HOBt (66 mg, 0.49 mmol) and EDC (94 mg, 0.49 mmol) in MeCN (3 mL) and EtOAc (3 mL) at 10° C. The resulting suspension was stirred at 50° C. for 2 h. The solvent was removed under reduced pressure. The residue was dissolved in a mixture of $NaHCO_3$(aq, 30 mL) and EtOAc (60 mL). The aqueous layer was extracted with EtOAc (4×75 mL). The organic layers were combined and washed with water (3×25 mL). The aqueous layers were combined and extracted with EtOAc (3×25 mL). All organic layers were combined, dried over $Na_2SO_4$, filtered and evaporated. The residue was purified by preparative HPLC, PrepMethod F, (gradient: 40-50%) to give the title compound (0.018 g, 40%) as a grey solid; HRMS (ESI) m/z $[M+H]^+$ calcd for $C_{24}H_{19}FN_5O_2S$: 460.1238. found: 460.1236; $^1H$ NMR (300 MHz, DMSO-$d_6$) δ 9.19 (t, 1H), 9.03 (d, 1H), 8.54 (d, 1H), 8.28 (d, 1H), 8.10 (dd, 1H), 7.89 (d, 1H), 7.75 (dd, 1H), 7.68 (d, 1H), 7.47 (dd, 1H), 7.16-7.05 (m, 1H), 6.77 (d, 1H), 5.39-5.19 (m, 1H), 4.88 (d, 1H), 4.71 (d, 1H), 4.32 (d, 2H), 3.38-3.34 (m, overlapping with solvent).

Example 121: (R)—N-(2-(4-Cyanothiazolidin-3-yl)-2-oxoethyl)-6-(3-methyl-1H-pyrrol-1-yl)quinoline-4-carboxamide

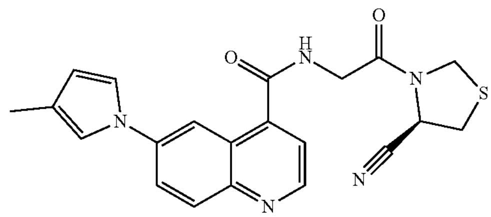 [SMILES: Cc1ccn(-c2ccc3nccc(C(=O)NCC(=O)N4CSC[C@H]4C#N)c3c2)c1]

TEA (249 μL, 1.78 mmol) was added to a stirred suspension of 6-(3-methyl-1H-pyrrol-1-yl)quinoline-4-carboxylic acid Intermediate 237 (45 mg, 0.18 mmol), (R)-3-glycylthiazolidine-4-carbonitrile hydrochloride Intermediate 4 (56 mg, 0.27 mmol), HOBt (121 mg, 0.89 mmol) and EDC (171 mg, 0.89 mmol) in MeCN (5 mL) and EtOAc (5 mL) at 10° C. The resulting suspension was stirred at 50° C. for 2 h. The solvent was removed under reduced pressure. The residue was partitioned between sat $NaHCO_3$ (30 mL) and EtOAc (60 mL). The aqueous layer was extracted with EtOAc (4×60 mL). The organic layers were combined and washed with water (3×30 mL). The aqueous layers were combined and extracted with EtOAc (2×20 mL). All the organic layers were combined, dried over $Na_2SO_4$, filtered and evaporated. The residue was purified by preparative HPLC, PrepMethod F, (gradient: 35-47%) to give the title compound (0.021 g, 29%) as a pale yellow solid; HRMS (ESI) m/z $[M+H]^+$ calcd for $C_{21}H_{20}N_5O_2S$: 406.1332. found: 406.1326; $^1H$ NMR (300 MHz, DMSO-$d_6$) δ 9.16 (t, 1H), 8.89 (d, 1H), 8.60-8.40 (m, 1H), 8.17-8.01 (m, 2H), 7.55 (d, 1H), 7.53-7.30 (m, 1H), 6.21-6.12 (m, 1H), 5.36 (dd, 1H), 4.90 (d, 1H), 4.72 (d, 1H), 4.35 (d, 2H), 3.41-3.37 (m, overlapping with solvent), 2.11 (s, 3H).

Example 122: (R)—N-(2-(4-Cyanothiazolidin-3-yl)-2-oxoethyl)-6-(3-morpholinoazetidin-1-yl)quinoline-4-carboxamide

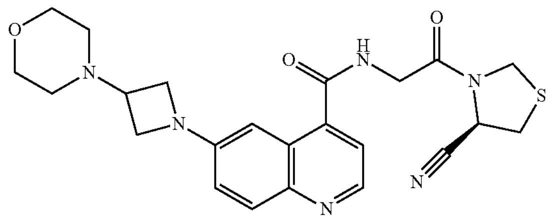 [SMILES: N#C[C@@H]1CSCN1C(=O)CNC(=O)c1ccnc2ccc(N3CC(N4CCOCC4)C3)cc12]

HATU (114 mg, 0.30 mmol) was added to a stirred mixture of crude 6-(3-morpholinoazetidin-1-yl)quinoline-4- carboxylic acid Intermediate 239 (104 mg) and DIPEA (0.217 mL, 1.24 mmol) in a mixture of MeCN/EtOAc (2.4 mL, 1:1) at rt. The reaction was stirred for 1 min after which (R)-3-glycylthiazolidine-4-carbonitrile hydrochloride Intermediate 4 (62 mg, 0.30 mmol) was added and the reaction mixture was stirred for 2 h at rt. The reaction mixture was diluted with EtOAc (8 mL) and washed with 8% $NaHCO_3$ (aq, 6 mL). The aqueous layer was extracted with EtOAc and the combined organic layers were dried over $Na_2SO_4$, filtered and concentrated. The residue was purified by preparative HPLC, PrepMethod G, (gradient 0-30%), followed by straight phase flash chromatography on silica (EtOAc: MeOH, 6:1) to give the title compound (0.037 g, 32%) as a yellow solid; HRMS (ESI) m/z $[M+H]^+$ calcd for $C_{23}H_{27}N_6O_3S$: 467.1860. found: 467.1860; $^1H$ NMR (500 MHz, DMSO-$d_6$) δ 8.96 (t, 1H), 8.62 (d, 1H), 7.88 (d, 1H), 7.39 (d, 1H), 7.23 (d, 1H), 7.12 (dd, 1H), (dd, 1H), 4.89 (d, 1H), 4.70 (d, 1H), 4.29 (d, 2H), 4.06 (t, 2H), 3.81-3.72 (m, 2H), 3.62-3.56 (m, 4H), 3.40 (dd, 1H), 3.36 (d, 1H), 3.32-3.26 (m, 1H), 2.41-2.30 (m, 4H).

Example 123: (R)—N-(2-(4-Cyanothiazolidin-3-yl)-2-oxoethyl)-6-(5,5-dimethyl-5,6-dihydro-4H-pyrrolo[1,2-b]pyrazol-3-yl)quinoline-4-carboxamide

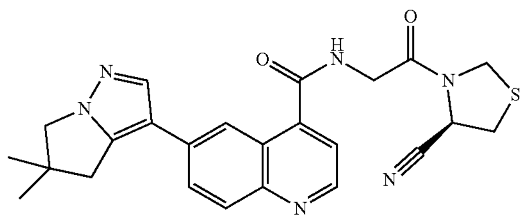 [SMILES: CC1(C)Cc2c(-c3ccc4nccc(C(=O)NCC(=O)N5CSC[C@H]5C#N)c4c3)cnn2C1]

(R)-3-Glycylthiazolidine-4-carbonitrile hydrochloride Intermediate 4 (57 mg, 0.27 mmol) was added to a mixture of 6-(5,5-dimethyl-5,6-dihydro-4H-pyrrolo[1,2-b]pyrazol-3-yl)quinoline-4-carboxylic acid Intermediate 244 (70 mg, 0.23 mmol), HATU (130 mg, 0.34 mmol) and DIPEA (119 μL, 0.68 mmol) in DMF (2 mL) and the reaction mixture was stirred at rt overnight. EtOAc (10 mL) and $NaHCO_3$ (5 mL, aq) were added and the reaction mixture was stirred, and the phases were separated. The organic layer was washed with water and brine, and the combined aqueous phase was extracted with EtOAc. The combined organic layer was dried over $MgSO_4$, filtered and evaporated at reduced pressure. The crude product was purified by preparative SFC, PrepMethod SFC-A, (gradient: 27-32%) to give the title compound (39 mg, 37%); HRMS (ESI) m/z $[M+H]^+$ calcd for $C_{24}H_{25}N_6O_2S$: 461.1754. found: 461.1748; $^1H$ NMR (600 MHz, DMSO-$d_6$) δ 9.09 (t, 1H), 8.84 (d, 1H), 8.37 (d, 1H), 8.19 (s, 1H), 8.03 (d, 1H), 7.96 (dd, 1H), 7.48 (d, 1H), 5.31 (d, 1H), 4.79 (dd, 2H), 4.30 (qd, 2H), 3.87 (s, 2H), 3.49-3.31 (m, 2H), 3.13 (s, 2H), 1.18-1.13 (m, 6H).

Example 124: (R)—N-(2-(4-Cyanothiazolidin-3-yl)-2-oxoethyl)-6-(2-fluoropyridin-4-yl)quinoline-4-carboxamide

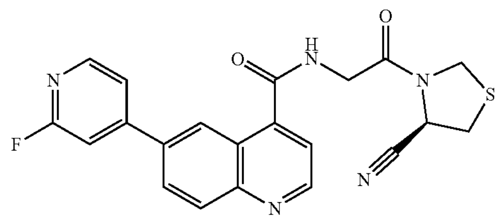 [SMILES: N#C[C@@H]1CSCN1C(=O)CNC(=O)c1ccnc2ccc(-c3ccnc(F)c3)cc12]

(R)-3-Glycylthiazolidine-4-carbonitrile hydrochloride Intermediate 4 (5 mg, 0.02 mmol) was added to a mixture of 6-(2-fluoropyridin-4-yl)quinoline-4-carboxylic acid Intermediate 245 (5 mg, 0.02 mmol), HATU (11 mg, 0.03 mmol) and DIPEA (9.8 μL, 0.06 mmol) in DMF (0.2 mL), and the reaction mixture was stirred at rt overnight. DCM (5 mL) and $NaHCO_3$ (aq) were added, and the reaction mixture was stirred, filtered through a phase separator, and the filtrate was evaporated at reduced pressure. The crude product was purified by preparative SFC, PrepMethod SFC-A, (gradient: 27-32%) to give the title compound (2 mg, 29%); HRMS (ESI) m/z $[M+H]^+$ calcd for $C_{21}H_{17}FN_5O_2S$: 422.1082. found: 422.1082.

Example 125: (R)—N-(2-(4-Cyanothiazolidin-3-yl)-2-oxoethyl)-6-(5-fluoropyridin-2-yl)quinoline-4-carboxamide

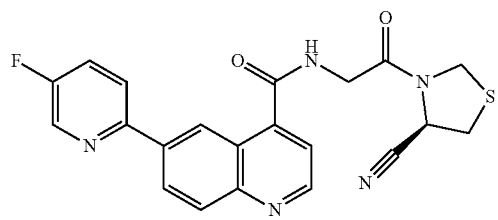 [SMILES: N#C[C@@H]1CSCN1C(=O)CNC(=O)c1ccnc2ccc(-c3ccc(F)cn3)cc12]

(R)-3-Glycylthiazolidine-4-carbonitrile hydrochloride Intermediate 4 (6 mg, 0.03 mmol) was added to a mixture of 6-(5-fluoropyridin-2-yl)quinoline-4-carboxylic acid Intermediate 246 (6 mg, 0.02 mmol), HATU (13 mg, 0.03 mmol) and DIPEA (12 μL, 0.07 mmol) in MeCN (0.2 mL) and EtOAc (0.2 mL) and the reaction mixture was stirred at rt overnight. EtOAc (3 mL) and $NaHCO_3$(3 mL, aq) were added, and the reaction mixture was stirred, and the phases were separated. The organic layer was filtered through a phase separator, and the filtrate was evaporated at reduced pressure. The crude product was purified by preparative SFC, PrepMethod SFC-A, (gradient: 27-32%) to give the title compound (2.5 mg, 26%); HRMS (ESI) m/z $[M+H]^+$ calcd for $C_{21}H_{17}FN_5O_2S$: 422.1082. found: 422.1092.

Example 126: (R)—N-(2-(4-Cyanothiazolidin-3-yl)-2-oxoethyl)-6-(pyridin-3-yl)quinoline-4-carboxamide

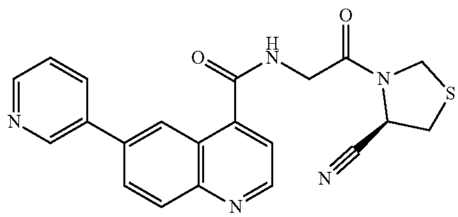 [SMILES: N#C[C@@H]1CSCN1C(=O)CNC(=O)c1ccnc2ccc(-c3cccnc3)cc12]

Step a) 6-(Pyridin-3-yl)quinoline-4-carboxylic acid

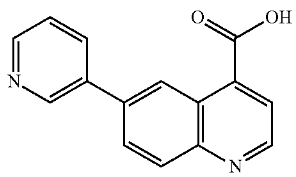 [SMILES: O=C(O)c1ccnc2ccc(-c3cccnc3)cc12]

A mixture of 6-bromoquinoline-4-carboxylic acid (60 mg, 0.24 mmol), pyridin-3-ylboronic acid (32 mg, 0.26 mmol), $Cs_2CO_3$ (194 mg, 0.60 mmol) and $Pd(dtbpf)Cl_2$ (16 mg, 0.02 mmol) in 1,4-dioxane (2 mL) and water (0.5 mL) was stirred at rt under an atmosphere of argon overnight. Water was added to the reaction mixture and the aqueous phase was washed with EtOAc. The water phase was concentrated under reduced pressure to give the title compound.

Step b) (R)—N-(2-(4-Cyanothiazolidin-3-yl)-2-oxoethyl)-6-(pyridin-3-yl)quinoline-4-carboxamide A mixture of crude 6-(pyridin-3-yl)quinoline-4-carboxylic acid, (R)-3-glycylthiazolidine-4-carbonitrile hydrochloride Intermediate 4 (60 mg, 0.29 mmol), HATU (109 mg, 0.29 mmol) and DIPEA (0.167 mL, 0.96 mmol) in DMF (2 mL) was stirred at rt overnight. The reaction mixture was diluted with DCM (15 mL) and washed with sat $NaHCO_3$(8 mL, aq). The organic phase was filtered through a phase separator and the filtrate was evaporated at reduced pressure. The crude product was purified by preparative HPLC, PrepMethod V, (gradient 0-50%), to give the title compound (28 mg, 29%); HRMS (ESI) m/z $[M+H]^+$ calcd for $C_{21}H_{18}N_5O_2S$: 404.1176. found: 404.1140; $^1H$ NMR (600 MHz, DMSO-$d_6$) δ 9.20 (t, 1H), 9.09 (d, 1H), 9.02 (d, 1H), 8.82 (d, 1H), 8.65 (dd, 1H), 8.36-8.19 (m, 3H), 7.62 (d, 1H), 7.57 (dd, 1H), 5.37 (dd, 1H), 4.82 (dd, 2H), 4.37 (d, 2H), 3.44-3.36 (m, overlapping with solvent).

Example 127: (R)—N-(2-(4-Cyanothiazolidin-3-yl)-2-oxoethyl)-6-(pyrimidin-5-yl)-quinoline-4-carboxamide

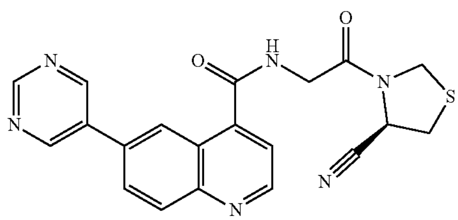 [SMILES: N#C[C@@H]1CSCN1C(=O)CNC(=O)c1ccnc2ccc(-c3cncnc3)cc12]

Step a) 6-(Pyrimidin-5-yl)quinoline-4-carboxylic acid

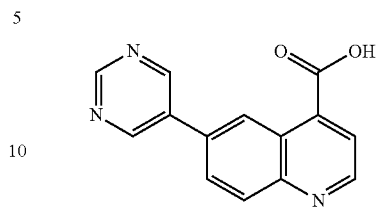

A mixture of 6-bromoquinoline-4-carboxylic acid (60 mg, 0.24 mmol), pyrimidin-5-ylboronic acid (32 mg, 0.26 mmol), $Cs_2CO_3$ (194 mg, 0.60 mmol) and $Pd(dtbpf)Cl_2$ (16 mg, 0.02 mmol) in 1,4-dioxane (2 mL) and water (0.5 mL) was stirred at rt under an atmosphere of argon overnight. Water was added to the reaction mixture and the aqueous phase was washed with EtOAc. The water phase was acidified to pH 3 with aq HCl (2 M), washed with DCM, and concentrated at reduced pressure to give the title compound.

Step b) (R)—N-(2-(4-Cyanothiazolidin-3-yl)-2-oxoethyl)-6-(pyrimidin-5-yl)-quinoline-4-carboxamide A mixture of crude 6-(pyrimidin-5-yl)quinoline-4-carboxylic acid, (R)-3-glycylthiazolidine-4-carbonitrile hydrochloride Intermediate 4 (60 mg, 0.29 mmol), HATU (109 mg, 0.29 mmol) and DIPEA (1.04 mL, 5.97 mmol) in DMF (2 mL) was stirred at rt overnight. The reaction mixture was diluted with DCM (15 mL) and washed with sat $NaHCO_3$(8 mL, aq). The organic phase was filtered through a phase separator, and the filtrate was evaporated at reduced pressure. The crude product was purified by preparative HPLC, PrepMethod V, (gradient: 0-50%) to give the title compound (40 mg, 42%); HRMS (ESI) m/z $[M+H]^+$ calcd for $C_{20}H_{17}N_6O_2S$: 405.1128. found: 405.1136; $^1H$ NMR (600 MHz, DMSO-$d_6$) δ 9.33 (s, 2H), 9.26 (s, 1H), 9.23 (t, 1H) 9.05 (d, 1H), 8.87 (d, 1H), 8.33-8.23 (m, 2H), 7.65 (d, 1H), 5.36 (dd, 1H), 4.82 (dd, 2H), 4.37 (dd, 2H), 3.44-3.36 (m, overlapping with solvent).

Example 128: (R)—N-(2-(4-Cyanothiazolidin-3-yl)-2-oxoethyl)-6-(2-methylpyridin-3-yl)-quinoline-4-carboxamide

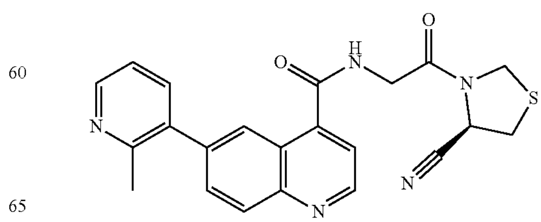

Step a) 6-(2-Methylpyridin-3-yl)quinoline-4-carboxylic acid

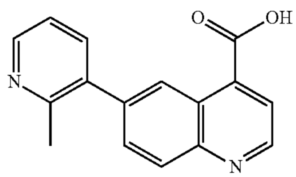 [SMILES: Cc1ncccc1-c1ccc2nccc(C(=O)O)c2c1]

The title compound was prepared as described in Example 127 Step a) from 6-bromoquinoline-4-carboxylic acid (60 mg, 0.24 mmol) and (2-methylpyridin-3-yl)boronic acid (36 mg, 0.26 mmol) to give the title compound as a crude product.

Step b) (R)—N-(2-(4-Cyanothiazolidin-3-yl)-2-oxo-ethyl)-6-(2-methylpyridin-3-yl)-quinoline-4-carboxamide The title compound was prepared as described for Example 127 Step b) from (R)-3-glycylthiazolidine-4-carbonitrile hydrochloride Intermediate 4 (57 mg, 0.27 mmol) and crude 6-(2-methylpyridin-3-yl)quinoline-4-carboxylic acid to give the title compound (38 mg, 40%); HRMS (ESI) m/z $[M+H]^+$ calcd for $C_{22}H_{20}N_5O_2S$: 418.1332. found: 418.1350; $^1H$ NMR (600 MHz, DMSO-$d_6$) δ 9.16 (t, 1H), 9.04 (d, 1H), 8.55 (dd, 1H), 8.37 (d, 1H), 8.19 (d, 1H), 7.90 (dd, 1H), 7.80 (d, 1H), 7.64 (d, 1H), 7.41 (dd, 1H), 5.31 (dd, 1H), 4.77 (dd, 2H), 4.31 (d, 2H), 3.40-3.35 (m, overlapping with solvent), 2.52 (s, 3H).

Example 129: (R)—N-(2-(4-Cyanothiazolidin-3-yl)-2-oxoethyl)-6-(1-methyl-1H-pyrazol-4-yl)quinoline-4-carboxamide

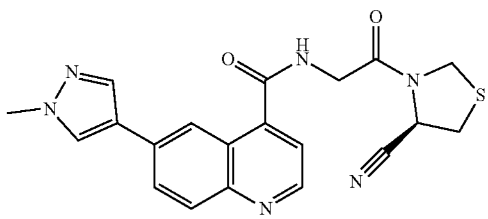 [SMILES: Cn1cc(-c2ccc3nccc(C(=O)NCC(=O)N4CSC[C@H]4C#N)c3c2)cn1]

Step a) 6-(1-Methyl-1H-pyrazol-4-yl)quinoline-4-carboxylic acid

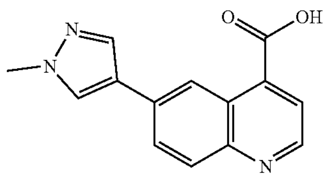 [SMILES: Cn1cc(-c2ccc3nccc(C(=O)O)c3c2)cn1]

The title compound was prepared as described in Example 127 step a) from 6-bromoquinoline-4-carboxylic acid (60 mg, 0.24 mmol) and (1-methyl-1H-pyrazol-4-yl)boronic acid (33 mg, 0.26 mmol) to give the title compound as a crude product.

Step b) (R)—N-(2-(4-Cyanothiazolidin-3-yl)-2-oxo-ethyl)-6-(1-methyl-1H-pyrazol-4-yl)quinoline-4-carboxamide The title compound was prepared as described for Example 127 Step b) from (R)-3-glycylthiazolidine-4-carbonitrile hydrochloride Intermediate 4 (59 mg, 0.28 mmol) and crude 6-(1-methyl-1H-pyrazol-4-yl)quinoline-4-carboxylic acid to give the title compound (39 mg, 41%); HRMS (ESI) m/z $[M+H]^+$ calcd for $C_{20}H_{19}N_6O_2S$: 407.1284. found: 407.1286; $^1H$ NMR (600 MHz, DMSO-$d_6$) δ 9.14 (t, 1H), 8.88 (d, 1H), 8.74 (d, 1H), 8.37 (s, 1H), 8.11-8.03 (m, 3H), 7.50 (d, 1H), 5.42 (dd, 1H), 4.83 (dd, 2H), 4.37 (d, 2H), 3.92 (s, 3H), 3.51-3.37 (m, 2H).

Example 130: (R)—N-(2-(4-Cyanothiazolidin-3-yl)-2-oxoethyl)-6-(3-((trifluoromethoxy)-methyl)azetidin-1-yl)quinoline-4-carboxamide

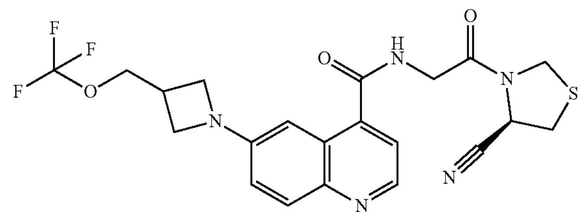 [SMILES: N#C[C@@H]1CSCN1C(=O)CNC(=O)c1ccnc2ccc(N3CC(COC(F)(F)F)C3)cc12]

DIPEA (415 μL, 2.38 mmol) was added to a stirred suspension of 6-(3-((trifluoromethoxy)methyl)azetidin-1-yl) quinoline-4-carboxylic acid Intermediate 248 (155 mg, 0.48 mmol), (R)-3-glycylthiazolidine-4-carbonitrile hydrochloride Intermediate 4 (197 mg, 0.95 mmol), HOBt (193 mg, 1.43 mmol) and EDC (273 mg, 1.43 mmol) in MeCN (10 mL) and EtOAc (10 mL) at 20° C., and the reaction mixture was stirred at 50° C. for 2 h. The solvent was removed under reduced pressure, and the residue was dissolved in $NaHCO_3$ (40 mL, aq) and EtOAc (100 mL). The phases were separated and the aqueous layer was extracted with EtOAc (4×75 mL). The combined organic layer was washed with water (3×50 mL), dried over $Na_2SO_4$, filtered and evaporated at reduced pressure. The crude product was purified by preparative HPLC, PrepMethod R, (gradient: 32-52%) to give the title compound (0.090 g, 39%) as a yellow solid; HRMS (ESI) m/z $[M+H]^+$ calcd for $C_{21}H_{21}F_3N_5O_3S$: 480.1312. found: 480.1292; $^1H$ NMR (300 MHz, DMSO-$d_6$) δ 8.95 (t, 1H), 8.62 (d, 1H), 7.87 (d, 1H), 7.40 (d, 1H), 7.18-7.07 (m, 2H), 5.35-5.26 (m, 1H), 4.87 (d, 1H), 4.69 (d, 1H), 4.34 (d, 2H), 4.29 (d, 2H), 4.06 (t, 2H), 3.79-3.69 (m, 2H), 3.39-3.35 (m, overlapping with solvent), 3.21-3.04 (m, 2H).

Example 131: (R)—N-(2-(4-Cyanothiazolidin-3-yl)-2-oxoethyl)-6-(3-methyl-3-(2,2,2-trifluoroethyl)azetidin-1-yl)quinoline-4-carboxamide

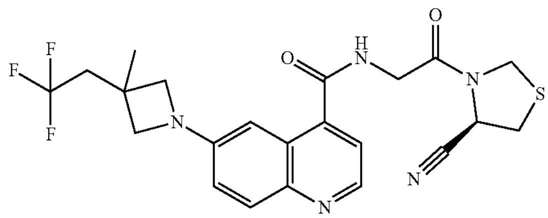 [SMILES: CC1(CC(F)(F)F)CN(c2ccc3nccc(C(=O)NCC(=O)N4CSC[C@H]4C#N)c3c2)C1]

DIPEA (404 μL, 2.31 mmol) was added to a stirred suspension of 6-(3-methyl-3-(2,2,2-trifluoroethyl)azetidin-1-yl)quinoline-4-carboxylic acid Intermediate 250 (150 mg, 0.46 mmol), (R)-3-glycylthiazolidine-4-carbonitrile hydrochloride Intermediate 4 (192 mg, 0.93 mmol), HOBt (187 mg, 1.39 mmol) and EDC (266 mg, 1.39 mmol) in MeCN (10 mL) and EtOAc (10 mL) at 20° C., and the reaction mixture was stirred at 50° C. for 2 h. The solvent was removed under reduced pressure and the residue was dissolved in $NaHCO_3$(40 mL, aq) and EtOAc (100 mL). The phases were separated and the aqueous layer was extracted with EtOAc (4×75 mL). The combined organic layer was washed with water (3×50 mL), dried over $Na_2SO_4$, filtered and evaporated at reduced pressure. The crude product was purified by preparative HPLC, PrepMethod R, (gradient: 33-55%) to give the title compound (0.080 g, 36%) as a yellow solid; HRMS (ESI) m/z $[M+H]^+$ calcd for $C_{22}H_{23}F_3N_5O_2S$: 478.1518. found: 478.1524 $^1H$ NMR (300 MHz, DMSO-$d_6$) δ 8.93 (t, 1H), 8.61 (d, 1H), 7.86 (d, 1H), 7.39 (d, 1H), 7.18-7.07 (m, 2H), 5.29 (dd, 1H), 4.87 (d, 1H), 4.69 (d, 1H), 4.28 (d, 2H), 3.84 (d, 2H), 3.72 (d, 2H), 3.45-3.34 (m, overlapping with solvent), 2.72 (q, 2H), 1.46 (s, 3H).

Example 132: (R)—N-(2-(4-Cyanothiazolidin-3-yl)-2-oxoethyl)-6-(3-(trifluoromethoxy)-azetidin-1-yl)quinoline-4-carboxamide

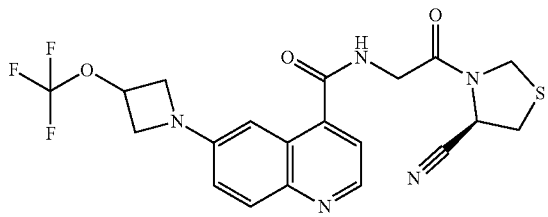 [SMILES: N#C[C@@H]1CSCN1C(=O)CNC(=O)c1ccnc2ccc(N3CC(OC(F)(F)F)C3)cc12]

DIPEA (783 μL, 4.48 mmol) was added to a stirred suspension of 6-(3-(trifluoromethoxy)azetidin-1-yl)quinoline-4-carboxylic acid Intermediate 252 (280 mg, 0.90 mmol), (R)-3-glycylthiazolidine-4-carbonitrile hydrochloride Intermediate 4 (372 mg, 1.79 mmol), HOBt (364 mg, 2.69 mmol) and EDC (516 mg, 2.69 mmol) in MeCN (10 mL) and EtOAc (10 mL) at 25° C., and the reaction mixture was stirred at 50° C. for 2 h. The solvent was removed under reduced pressure, and the residue was dissolved in $NaHCO_3$ (50 mL, aq) and EtOAc (100 mL). The phases were separated and the aqueous layer was extracted with EtOAc (4×75 mL). The combined organic layer was washed with water (3×50 mL), dried over $Na_2SO_4$, filtered and evaporated at reduced pressure. The crude product was purified by preparative HPLC, PrepMethod R, (gradient: 31-51%) to give the title compound (0.27 g, 65%) as a yellow solid; HRMS (ESI) m/z $[M+H]^+$ calcd for $C_{20}H_{19}F_3N_5O_3S$: 466.1156. found: 466.1152 $^1H$ NMR (300 MHz, DMSO-$d_6$) δ 9.00 (t, 1H), 8.68 (d, 1H), 7.92 (d, 1H), 7.43 (d, 1H), 7.33 (d, 1H), 7.19 (dd, 1H), 5.45-5.29 (m, 2H), 4.89 (d, 1H), 4.71 (d, 1H), 4.40 (dd, 2H), 4.31 (d, 2H), 4.05 (dd, 2H), 3.46-3.34 (m, overlapping with solvent).

Example 133: (R)—N-(2-(4-Cyanothiazolidin-3-yl)-2-oxoethyl)-6-(3-(2,2-difluoroethyl)-3-methylazetidin-1-yl)quinoline-4-carboxamide

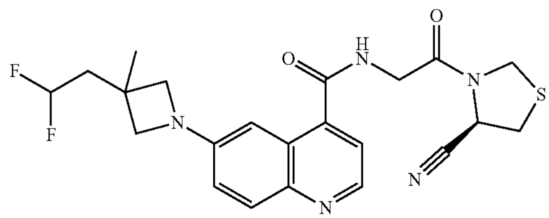 [SMILES: CC1(CC(F)F)CN(c2ccc3nccc(C(=O)NCC(=O)N4CSC[C@H]4C#N)c3c2)C1]

DIPEA (356 μL, 2.04 mmol) was added to a stirred suspension of 6-(3-(2,2-difluoroethyl)-3-methylazetidin-1-yl)quinoline-4-carboxylic acid Intermediate 254 (125 mg, 0.41 mmol), (R)-3-glycylthiazolidine-4-carbonitrile hydrochloride Intermediate 4 (127 mg, 0.61 mmol), HOBt (165 mg, 1.22 mmol) and EDC (235 mg, 1.22 mmol) in MeCN (5 mL) and EtOAc (5 mL) at 25° C., and the reaction mixture was stirred at 50° C. for 2 h. The solvent was removed under reduced pressure, and the residue was dissolved in $NaHCO_3$ (40 mL, aq) and EtOAc (100 mL). The phases were separated and the aqueous layer was extracted with EtOAc (4×100 mL). The combined organic layer was washed with water (3×50 mL), dried over $Na_2SO_4$, filtered and evaporated at reduced pressure. The crude product was purified by preparative HPLC, PrepMethod R, (gradient: 29-49%) to give the title compound (0.11 g, 59%) as a yellow solid; HRMS (ESI) m/z $[M+H]^+$ calcd for $C_{22}H_{24}F_2N_5O_2S$: 460.1614. found: 460.1582 $^1H$ NMR (300 MHz, DMSO-$d_6$) δ 8.95 (brs, 1H), 8.64 (d, 1H), 7.89 (d, 1H), 7.42 (d, 1H), 7.26-7.00 (m, 2H), 6.25 (t, 1H), 5.45-5.27 (m, 1H), 4.90 (d, 1H), 4.72 (d, 1H), 4.31 (d, 2H), 3.84 (d, 2H), 3.69 (d, 2H), 3.40-3.34 (m, overlapping with solvent), 2.24 (td, 2H), 1.43 (s, 3H).

Example 134: (R)—N-(2-(4-Cyanothiazolidin-3-yl)-2-oxoethyl)-6-(3-cyclopropyl-3-methylazetidin-1-yl)quinoline-4-carboxamide

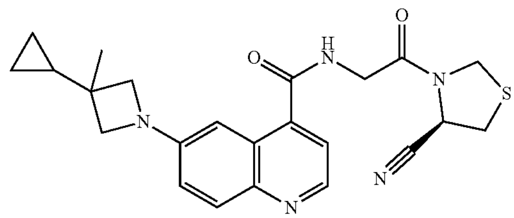 [SMILES: CC1(C2CC2)CN(c2ccc3nccc(C(=O)NCC(=O)N4CSC[C@H]4C#N)c3c2)C1]

DIPEA (247 μL, 1.42 mmol) was added to a stirred suspension of 6-(3-cyclopropyl-3-methylazetidin-1-yl)quinoline-4-carboxylic acid Intermediate 256 (80 mg, 0.28 mmol), (R)-3-glycylthiazolidine-4-carbonitrile hydrochloride Intermediate 4 (118 mg, 0.57 mmol), HOBt (115 mg, 0.85 mmol) and EDC (163 mg, 0.85 mmol) in MeCN (10 mL) and EtOAc (10 mL) at 20° C. and the reaction mixture was stirred at 50° C. for 2 h. The solvent was removed under reduced pressure and the residue was dissolved in $NaHCO_3$ (40 mL, aq) and EtOAc (100 mL). The phases were separated and the aqueous layer was extracted with EtOAc (4×50 mL). The combined organic layer was washed with water (3×25 mL), dried over $Na_2SO_4$, filtered and evaporated at reduced pressure. The crude product was purified by preparative HPLC, PrepMethod I, (gradient: 55-65%) to give the title compound (0.050 g, 40%) as a yellow solid; HRMS (ESI) m/z $[M+H]^+$ calcd for $C_{23}H_{26}N_5O_2S$: 436.1802. found: 436.1806; $^1$H NMR (400 MHz, DMSO-$d_6$) δ 8.96 (t, 1H), 8.62 (d, 1H), 7.88 (d, 1H), 7.40 (d, 1H), 7.18 (d, 1H), 7.09 (dd, 1H), 5.83-5.30 (m, 1H), 4.90 (d, 1H), 4.72 (d, 1H), 4.31 (d, 2H), 3.57 (s, 4H), 3.42-3.33 (m, overlapping with solvent), 1.33 (s, 3H), 1.10-0.98 (m, 1H), 0.49-0.39 (m, 2H), 0.35-0.20 (m, 2H).

Example 135: (R)—N-(2-(4-Cyanothiazolidin-3-yl)-2-oxoethyl)-6-(3-(difluoromethyl)-3-methylazetidin-1-yl)quinoline-4-carboxamide

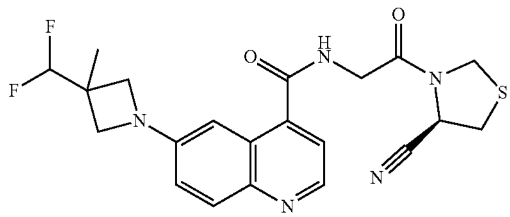 [SMILES: CC1(C(F)F)CN(c2ccc3nccc(C(=O)NCC(=O)N4CSC[C@H]4C#N)c3c2)C1]

DIPEA (284 μL, 1.63 mmol) was added to a stirred suspension of 6-(3-(difluoromethyl)-3-methylazetidin-1-yl)quinoline-4-carboxylic acid Intermediate 258 (95 mg, 0.33 mmol), (R)-3-glycylthiazolidine-4-carbonitrile hydrochloride Intermediate 4 (135 mg, 0.65 mmol), HOBt (132 mg, 0.98 mmol) and EDC (187 mg, 0.98 mmol) in MeCN (10 mL) and EtOAc (10 mL) at 20° C., and the reaction mixture was stirred at 50° C. for 2 h. The solvent was removed under reduced pressure, and the residue was dissolved in $NaHCO_3$ (40 mL, aq) and EtOAc (100 mL). The phases were separated and the aqueous layer was extracted with EtOAc (4×75 mL). The combined organic layer was washed with water (3×25 mL), dried over $Na_2SO_4$, filtered and evaporated at reduced pressure. The crude product was purified by preparative HPLC, PrepMethod A, (gradient: 32-62%) to give the title compound (0.083 g, 57%) as a yellow solid; HRMS (ESI) m/z $[M+H]^+$ calcd for $C_{21}H_{22}F_2N_5O_2S$: 446.1456. found: 446.1438; $^1$H NMR (300 MHz, DMSO-$d_6$) δ 8.98 (t, 1H), 8.65 (d, 1H), 7.90 (d, 1H), 7.42 (d, 1H), 7.26-7.10 (m, 2H), 6.29 (t, 1H), 5.33 (dd, 1H), 4.90 (d, 1H), 4.72 (d, 1H), 4.30 (d, 2H), 4.01 (d, 2H), 3.73 (d, 2H), 3.45-3.35 (m, 2H), 1.41 (s, 3H).

Example 136: (R)—N-(2-(4-Cyanothiazolidin-3-yl)-2-oxoethyl)-6-(3-(difluoromethoxy)-azetidin-1-yl)quinoline-4-carboxamide

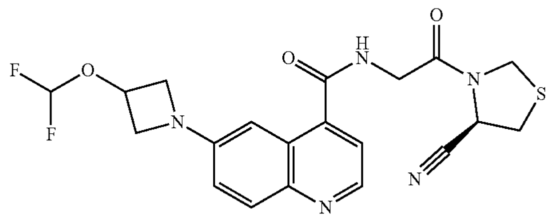 [SMILES: N#C[C@@H]1CSCN1C(=O)CNC(=O)c1ccnc2ccc(N3CC(OC(F)F)C3)cc12]

DIPEA (564 μL, 3.23 mmol) was added to a stirred suspension of 6-(3-(difluoromethoxy)azetidin-1-yl)quinoline-4-carboxylic acid Intermediate 260 (190 mg, 0.65 mmol), (R)-3-glycylthiazolidine-4-carbonitrile hydrochloride Intermediate 4 (201 mg, 0.97 mmol), HOBt (262 mg, 1.94 mmol) and EDC (371 mg, 1.94 mmol) in MeCN (5 mL) and EtOAc (5 mL) at 30° C., and the reaction mixture was stirred at 50° C. for 2 h. The solvent was removed under reduced pressure, and the residue was dissolved in $NaHCO_3$ (40 mL, aq) and EtOAc (100 mL). The phases were separated and the aqueous layer was extracted with EtOAc (5×75 mL). The combined organic layer was washed with water (3×50 mL), dried over $Na_2SO_4$, filtered and evaporated at reduced pressure. The crude product was purified by preparative HPLC, PrepMethod R, (gradient: 24-44%) to give the title compound (0.242 g, 84%) as a yellow solid; HRMS (ESI) m/z $[M+H]^+$ calcd for $C_{20}H_{20}F_2N_5O_3S$: 448.1250. found: 448.1246; $^1$H NMR (300 MHz, DMSO-$d_6$) δ 8.98 (t, 1H), 8.66 (d, 1H), 7.91 (d, 1H), 7.43 (d, 1H), 7.27 (d, 1H), 7.17 (dd, 1H), 6.81 (t, 1H), 5.34 (dd, 1H), 5.20-5.07 (m, 1H), 4.90 (d, 1H), 4.72 (d, 1H), 4.46-4.16 (m, 4H), 3.93 (dd, 2H), 3.45-3.36 (m, overlapping with solvent).

Example 137: (R)—N-(2-(4-Cyanothiazolidin-3-yl)-2-oxoethyl)-6-(3-ethyl-3-methyl-azetidin-1-yl)quinoline-4-carboxamide

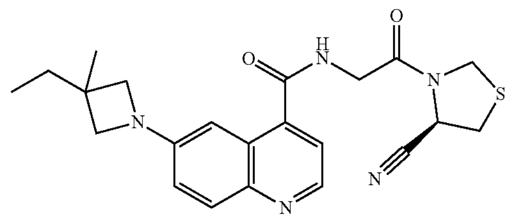 [SMILES: CCC1(C)CN(c2ccc3nccc(C(=O)NCC(=O)N4CSC[C@H]4C#N)c3c2)C1]

DIPEA (372 μL, 2.13 mmol) was added to a stirred suspension of 6-(3-ethyl-3-methylazetidin-1-yl)quinoline-4-carboxylic acid Intermediate 262 (115 mg, 0.43 mmol), (R)-3-glycylthiazolidine-4-carbonitrile hydrochloride Intermediate 4 (177 mg, 0.85 mmol), HOBt (172 mg, 1.28 mmol) and EDC (245 mg, 1.28 mmol) in MeCN (6 mL) and EtOAc (6 mL) at 20° C., and the reaction mixture was stirred at 50° C. for 2 h. The solvent was removed under reduced pressure, and the residue was dissolved in $NaHCO_3$ (30 mL, aq) and EtOAc (80 mL). The phases were separated and the aqueous layer was extracted with EtOAc (4×75 mL). The combined organic layer was washed with water (3×50 mL), dried over $Na_2SO_4$, filtered and evaporated at reduced pressure. The crude product was purified by preparative HPLC, PrepMethod I, (gradient: 60-78%) to give the title compound (0.110 g, 61%) as a yellow solid; HRMS (ESI) m/z $[M+H]^+$ calcd for $C_{22}H_{26}N_5O_2S$: 424.1802. found: 424.1802; $^1H$ NMR (400 MHz, DMSO-$d_6$) δ 9.02-8.90 (m, 1H), 8.61 (d, 1H), 7.87 (d, 1H), 7.39 (d, 1H), 7.17 (d, 1H), 7.10 (dd, 1H), 5.32 (dd, 1H), 4.89 (d, 1H), 4.71 (d, 1H), 4.30 (d, 2H), 3.70 (dd, 2H), 3.62 (d, 2H), 3.43 −3.34 (m, overlapping with solvent), 1.63 (q, 2H), 1.27 (s, 3H), 0.90 (t, 3H).

Example 138: (R)—N-(2-(4-Cyanothiazolidin-3-yl)-2-oxoethyl)-6-(3-ethyl-3-fluoro-azetidin-1-yl)quinoline-4-carboxamide

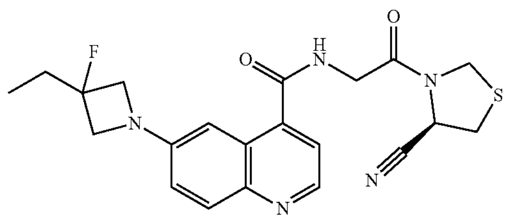 [SMILES: CCC1(F)CN(c2ccc3nccc(C(=O)NCC(=O)N4CSC[C@H]4C#N)c3c2)C1]

A solution of T3P (1.48 g, 2.33 mmol, 50% in EtOAc) in MeCN (8 mL) was added to a stirred solution of 6-(3-ethyl-3-fluoroazetidin-1-yl)quinoline-4-carboxylic acid Intermediate 264 (160 mg, 0.58 mmol), (R)-3-glycylthiazolidine-4-carbonitrile hydrochloride Intermediate 4 (121 mg, 0.87 mmol) and DIPEA (306 μL, 1.75 mmol) in EtOAc (8 mL) at 20° C., and the reaction mixture was stirred at 25° C. for 3 h. The reaction mixture was concentrated under reduced pressure, diluted with EtOAc (75 mL), and washed sequentially with water (25 mL) and sat brine (25 mL). The organic layer was dried over $Na_2SO_4$, filtered and evaporated at reduced pressure. The crude product was purified by preparative HPLC, PrepMethod R, (gradient: 28-48%) to give the title compound (0.050 g, 20%) as a yellow solid; HRMS (ESI) m/z $[M+H]^+$ calcd for $C_{21}H_{23}FN_5O_2S$: 428.1550. found: 428.1550; $^1H$ NMR (400 MHz, DMSO-$d_6$) δ 8.98 (t, 1H), 8.65 (d, 1H), 7.91 (d, 1H), 7.41 (d, 1H), 7.33 (d, 1H), 7.17 (dd, 1H), 5.34 (dd, 1H), 4.90 (d, 1H), 4.71 (d, 1H), 4.30 (d, 2H), 4.15-3.97 (m, 4H), 3.45-3.34 (m, 2H), 2.05-1.80 (m, 2H), 0.98 (t, 3H).

Example 139: (R)—N-(2-(4-Cyanothiazolidin-3-yl)-2-oxoethyl)-6-(2-azaspiro[3.4]octan-2-yl)quinoline-4-carboxamide

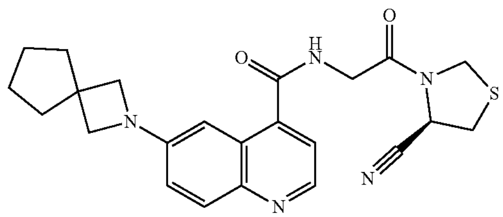 [SMILES: N#C[C@@H]1CSCN1C(=O)CNC(=O)c1ccnc2ccc(N3CC4(CCCC4)C3)cc12]

A solution of T3P (1.35 g, 2.13 mmol, 50% in EtOAc) in EtOAc (8 mL) was added to a stirred solution of 6-(2-azaspiro[3.4]octan-2-yl)quinoline-4-carboxylic acid Intermediate 266 (150 mg, 0.53 mmol), (R)-3-glycylthiazolidine-4-carbonitrile hydrochloride Intermediate 4 (110 mg, 0.53 mmol) and DIPEA (278 μL, 1.59 mmol) in MeCN (8 mL) at 25° C. and the reaction mixture was stirred at 25° C. for 2 h. The reaction mixture was concentrated under reduced pressure, diluted with EtOAc (75 mL), and washed sequentially with sat brine (25 mL) and water (25 mL). The organic layer was dried over $Na_2SO_4$, filtered and evaporated at reduced pressure. The crude product was purified by preparative HPLC, PrepMethod O, (gradient: 57-67%) to give the title compound (0.050 g, 22%) as a yellow solid; HRMS (ESI) m/z $[M+H]^+$ calcd for $C_{23}H_{26}N_5O_2S$: 436.1802. found: 436.1826; $^1H$ NMR (400 MHz, DMSO-$d_6$) δ 8.93 (t, 1H), 8.61 (d, 1H), 7.86 (d, 1H), 7.39 (d, 1H), 7.18 (d, 1H), 7.10 (dd, 1H), 5.32 (dd, 1H), 4.89 (d, 1H), 4.71 (d, 1H), 4.29 (d, 2H), 3.81 (s, 4H), 3.44-3.34 (m, overlapping with solvent), 1.89-1.71 (m, 4H), 1.69-1.50 (m, 4H).

Example 140: (R)—N-(2-(4-Cyanothiazolidin-3-yl)-2-oxoethyl)-6-(3-(2,2-difluoropropyl)-azetidin-1-yl) quinoline-4-carboxamide

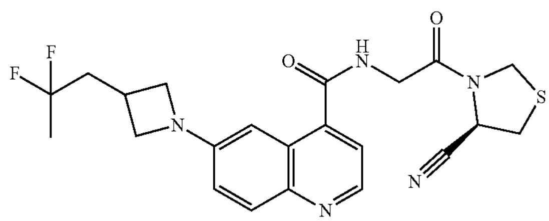 [SMILES: CC(F)(F)CC1CN(c2ccc3nccc(C(=O)NCC(=O)N4CSC[C@H]4C#N)c3c2)C1]

A solution of T3P (831 mg, 1.31 mmol, 50% in EtOAc) in EtOAc (8 mL) was added to a stirred solution of 6-(3-(2,2-difluoropropyl)azetidin-1-yl)quinoline-4-carboxylic acid Intermediate 268 (100 mg, 0.33 mmol), (R)-3-glycylthiazolidine-4-carbonitrile hydrochloride Intermediate 4 (68 mg, 0.49 mmol) and DIPEA (171 μL, 0.98 mmol) in MeCN (8 mL) at 25° C., and the reaction mixture was stirred at 25° C. for 3 h. The reaction mixture was concentrated under reduced pressure, diluted with EtOAc (100 mL), and washed sequentially with water (25 mL) and sat brine (25 mL). The organic layer was dried over $Na_2SO_4$, filtered and evaporated at reduced pressure. The crude product was purified by preparative HPLC, PrepMethod R, (gradient: 29-49%) to give the title compound (0.050 g, 33%) as a yellow solid; HRMS (ESI) m/z $[M+H]^+$ calcd for $C_{22}H_{24}F_2N_5O_2S$: 460.1614. found: 460.1600; $^1H$ NMR (400 MHz, DMSO-$d_6$) δ 8.95 (t, 1H), 8.62 (d, 1H), 7.87 (d, 1H), 7.41 (d, 1H), 7.17-7.07 (m, 2H), 5.31 (dd, 1H), 4.88 (d, 1H), 4.71 (d, 1H), 4.29 (d, 2H), 4.16 (t, 2H), 3.66 (t, 2H), 3.44-3.34 (m, overlapping with solvent), 3.12-2.95 (m, 1H), 2.28 (td, 2H), 1.63 (t, 3H).

Example 141: (R)—N-(2-(4-Cyanothiazolidin-3-yl)-2-oxoethyl)-6-(5,5-difluoro-2-azaspiro[3,4]octan-2-yl)quinoline-4-carboxamide

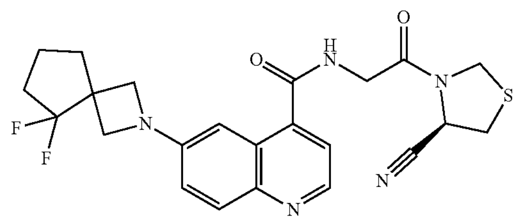 [SMILES: N#C[C@@H]1CSCN1C(=O)CNC(=O)c1ccnc2ccc(N3CC4(CCCC4(F)F)C3)cc12]

A solution of T3P (639 mg, 2.01 mmol, 50% in EtOAc) in EtOAc (8 mL) was added to a stirred solution of 6-(5,5-difluoro-2-azaspiro[3.4]octan-2-yl)quinoline-4-carboxylic acid Intermediate 270 (160 mg, 0.50 mmol), (R)-3-glycylthiazolidine-4-carbonitrile hydrochloride Intermediate 4 (104 mg, 0.75 mmol) and DIPEA (263 μL, 1.51 mmol) in MeCN (8.0 mL) at 20° C., and the reaction mixture was stirred at 25° C. for 3 h. The reaction mixture was concentrated under reduced pressure, diluted with EtOAc (125 mL), and washed sequentially with water (75 mL) and sat brine (75 mL). The organic layer was dried over $Na_2SO_4$, filtered and evaporated at reduced pressure. The crude product was purified by preparative HPLC, PrepMethod R, (gradient: 31-51%) to give the title compound (0.050 g, 21%) as a yellow solid; HRMS (ESI) m/z $[M+H]^+$ calcd for $C_{23}H_{24}F_2N_5O_2S$: 472.1614. found: 472.1612; $^1H$ NMR (400 MHz, DMSO-$d_6$) δ 8.97 (t, 1H), 8.64 (d, 1H), 7.90 (d, 1H), 7.40 (d, 1H), 7.31 (d, 1H), 7.16 (dd, 1H), 5.32 (dd, 1H), 4.89 (d, 1H), 4.71 (d, 1H), 4.30 (d, 2H), 4.12-4.00 (m, 2H), 3.84 (d, 2H), 3.48-3.34 (m, overlapping with solvent), 2.22-2.02 (m, 4H), 1.83 −1.65 (m, 2H).

Example 142: (R)—N-(2-(4-Cyanothiazolidin-3-yl)-2-oxoethyl)-6-(3-(3,3,3-trifluoropropyl)azetidin-1-yl)quinoline-4-carboxamide

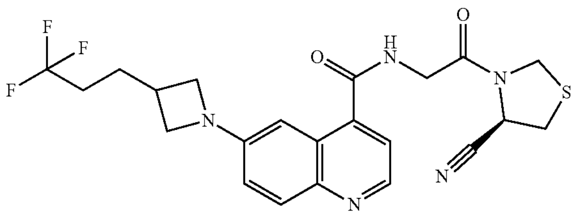 [SMILES: N#C[C@@H]1CSCN1C(=O)CNC(=O)c1ccnc2ccc(N3CC(CCC(F)(F)F)C3)cc12]

A solution of 6-(3-(3,3,3-trifluoropropyl)azetidin-1-yl) quinoline-4-carboxylic acid Intermediate 272 (110 mg, 0.34 mmol), (R)-3-glycylthiazolidine-4-carbonitrile hydrochloride Intermediate 4 (106 mg, 0.51 mmol), EDC (98 mg, 0.51 mmol), HOBt (78 mg, 0.51 mmol) and DIPEA (178 μL, 1.02 mmol) in MeCN (4 mL) and EtOAc (4 mL) was stirred at 50° C. for 2 h. The solvent was removed under reduced pressure, and the residue was diluted with EtOAc, and washed with water. The organic layer was dried over $Na_2SO_4$, filtered and evaporated at reduced pressure. The crude product was purified by preparative HPLC, PrepMethod F, (gradient: 28-38%) to give the title compound (0.110 g, 68%) as a yellow solid; HRMS (ESI) m/z $[M+H]^+$ calcd for $C_{22}H_{23}F_3N_5O_2S$: 478.1518. found: 478.1520; $^1H$ NMR (300 MHz, $CD_3OD$) δ 8.56 (d, 1H), 7.88 (d, 1H), 7.48 (d, 1H), 7.24 (s, 1H), 7.15 (dd, 1H), 5.33 (dd, 1H), 4.85-4.70 (m, overlapping with solvent), 4.38 (s, 2H), 4.25-4.10 (m, 2H), 3.70 (dd, 2H), 3.49-3.34 (m, 2H), 2.90-2.75 (m, 1H), 2.31-2.12 (m, 2H), 1.94 (q, 2H).

Example 143: (R)—N-(2-(4-Cyanothiazolidin-3-yl)-2-oxoethyl)-6-(3-fluoro-3-(trifluoromethyl)azetidin-1-yl)quinoline-4-carboxamide

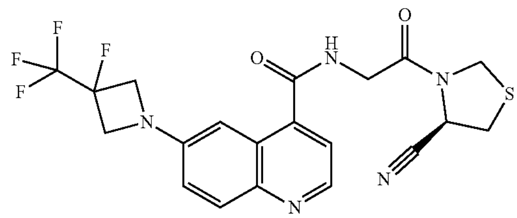 [SMILES: N#C[C@@H]1CSCN1C(=O)CNC(=O)c1ccnc2ccc(N3CC(F)(C(F)(F)F)C3)cc12]

A solution of 6-(3-fluoro-3-(trifluoromethyl)azetidin-1-yl)quinoline-4-carboxylic acid Intermediate 274 (100 mg, 0.32 mmol), (R)-3-glycylthiazolidine-4-carbonitrile hydrochloride Intermediate 4 (99 mg, 0.48 mmol), EDC (92 mg, 0.48 mmol), HOBt (73 mg, 0.48 mmol) and DIPEA (167 μL, 0.95 mmol) in MeCN (6 mL) and EtOAc (6 mL) was stirred at 50° C. for 2 h. The solvent was removed under reduced pressure, and the residue was diluted with EtOAc, and washed sequentially with water. The organic layer was dried over $Na_2SO_4$, filtered and evaporated at reduced pressure. The crude product was purified by preparative HPLC, PrepMethod F, (gradient: 31-41%) to give the title compound (110 mg, 74%) as a yellow solid; HRMS (ESI) m/z $[M+H]^+$ calcd for $C_{20}H_{18}F_4N_5O_2S$: 468.1112. found: 468.1124; $^1H$ NMR (300 MHz, $CD_3OD$) δ 8.66 (d, 1H), 7.97 (d, 1H), 7.56-7.49 (m, 2H), 7.26 (dd, 1H), 5.34 (dd, 1H), 4.85-4.66 (m, overlapping with solvent), 4.61-4.46 (m, 2H), 4.44-4.25 (m, 4H), 3.52-3.33 (m, 2H).

Example 144: (R)—N-(2-(4-Cyanothiazolidin-3-yl)-2-oxoethyl)-6-(3-(2,2-difluoroethyl)-azetidin-1-yl) quinoline-4-carboxamide

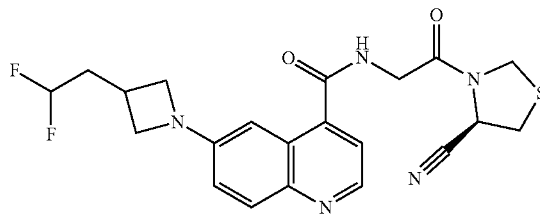

A solution of 6-(3-(2,2-difluoroethyl)azetidin-1-yl)quinoline-4-carboxylic acid Intermediate 276 (110 mg, 0.38 mmol), (R)-3-glycylthiazolidine-4-carbonitrile hydrochloride Intermediate 4 (117 mg, 0.56 mmol), EDC (108 mg, 0.56 mmol), HOBt (76 mg, 0.56 mmol) and DIPEA (197 μL, 1.13 mmol) in MeCN (4 mL) and EtOAc (4 mL) was stirred at 50° C. for 2 h. The solvent was removed under reduced pressure, and the residue was diluted with EtOAc, and washed sequentially with water. The organic layer was dried over $Na_2SO_4$, filtered and evaporated at reduced pressure. The crude product was purified by preparative HPLC, PrepMethod F, (gradient: 21-31%) to give the title compound (128 mg, 76%) as a yellow solid; HRMS (ESI) m/z $[M+H]^+$ calcd for $C_{21}H_{22}F_2N_5O_2S$: 446.1456. found: 446.1442; $^1H$ NMR (300 MHz, $CD_3OD$) δ 8.57 (d, 1H), 7.88 (d, 1H), 7.49 (d, 1H), 7.30-7.10 (m, 2H), 5.98 (tt, 1H), 5.40-5.25 (m, 1H), 4.85-4.70 (m, 2H), 4.45-4.30 (m, 2H), 4.22 (t, 2H), 3.82-3.72 (m, 2H), 3.51-3.34 (m, 2H), 3.08-2.95 (m, 1H), 2.35-2.12 (m, 2H).

Example 145: (R)—N-(2-(4-Cyanothiazolidin-3-yl)-2-oxoethyl)-6-(3-cyclopropylazetidin-1-yl)quinoline-4-carboxamide

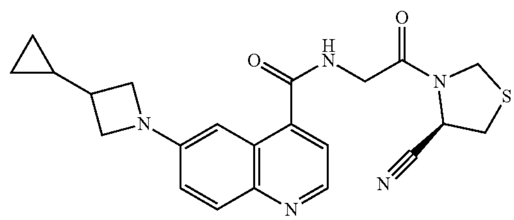 [SMILES: N#C[C@@H]1CSCN1C(=O)CNC(=O)c1ccnc2ccc(N3CC(C4CC4)C3)cc12]

A solution of 6-(3-cyclopropylazetidin-1-yl)quinoline-4-carboxylic acid Intermediate 278 (110 mg, 0.41 mmol), (R)-3-glycylthiazolidine-4-carbonitrile hydrochloride Intermediate 4 (128 mg, 0.61 mmol), EDC (118 mg, 0.61 mmol), HOBt (83 mg, 0.61 mmol) and DIPEA (215 μL, 1.23 mmol) in MeCN (6 mL) and EtOAc (6 mL) was stirred at 50° C. for 2 h. The solvent was removed under reduced pressure, the residue was diluted with EtOAc, and washed sequentially with water. The organic layer was dried over $Na_2SO_4$, filtered and evaporated at reduced pressure. The crude product was purified by preparative HPLC, PrepMethod C, gradient: 19-40%) to give the title compound (130 mg, 75%) as a yellow solid; HRMS (ESI) m/z $[M+H]^+$ calcd for $C_{22}H_{24}N_5O_2S$: 422.1646. found: 422.1638; $^1H$ NMR (300 MHz, $CD_3OD$) δ 8.55 (d, 1H), 7.87 (d, 1H), 7.49 (d, 1H), 7.22-7.09 (m, 2H), 5.39-5.31 (m, 1H), 4.85-4.70 (m, 2H), 4.38 (d, 2H), 4.12 (t, 2H), 3.72 (dd, 2H), 3.45-3.34 (m, 2H), 2.48-2.35 (m, 1H), 1.18-0.99 (m, 1H), 0.59-0.46 (m, 2H), 0.28-0.17 (m, 2H).

Example 146: (R)—N-(2-(4-Cyanothiazolidin-3-yl)-2-oxoethyl)-6-(3-(2-fluoroethyl)-azetidin-1-yl)quinoline-4-carboxamide

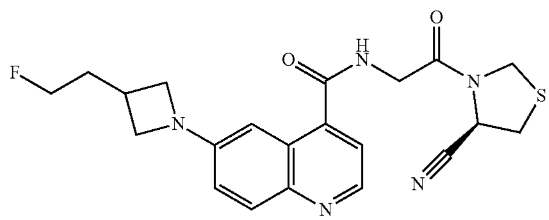 [SMILES: N#C[C@@H]1CSCN1C(=O)CNC(=O)c1ccnc2ccc(N3CC(CCF)C3)cc12]

A solution of 6-(3-(2-fluoroethyl)azetidin-1-yl)quinoline-4-carboxylic acid Intermediate 280 (100 mg, 0.36 mmol), (R)-3-glycylthiazolidine-4-carbonitrile hydrochloride Intermediate 4 (114 mg, 0.55 mmol), EDC (105 mg, 0.55 mmol), HOBt (84 mg, 0.55 mmol) and DIPEA (191 μL, 1.09 mmol) in MeCN (8 mL) and EtOAc (8 mL) was stirred at 50° C. for 2 h. The solvent was removed under reduced pressure, and the residue was diluted with EtOAc, and washed sequentially with water. The organic layer was dried over $Na_2SO_4$, filtered and evaporated at reduced pressure. The crude product was purified by preparative HPLC, PrepMethod F, (gradient: 18-28%) to give the title compound (120 mg, 77%) as a yellow solid; HRMS (ESI) m/z $[M+H]^+$ calcd for $C_{21}H_{23}FN_5O_2S$: 428.1550. found: 428.1558; $^1H$ NMR (300 MHz, $CD_3OD$) δ 8.56 (d, 1H), 7.88 (d, 1H), 7.49 (d, 1H), 7.25-7.10 (m, 2H), 5.37-5.29 (m, 1H), 4.86-4.73 (m, 2H), 4.60 (t, 1H), 4.49-4.35 (m, 3H), 4.20 (t, 2H), 3.74 (t, 2H), 3.55-3.36 (m, 2H), 3.00-2.85 (m, 1H), 2.11 (q, 1H), 2.03 (q, 1H).

Example 147: (R)—N-(2-(4-Cyanothiazolidin-3-yl)-2-oxoethyl)-6-(3-(1,1-difluoroethyl)-azetidin-1-yl)quinoline-4-carboxamide

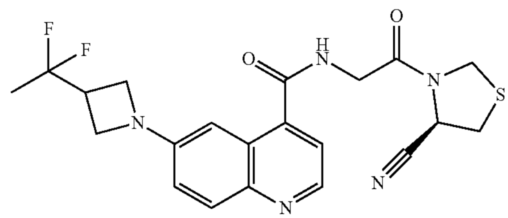 [SMILES: CC(F)(F)C1CN(c2ccc3nccc(C(=O)NCC(=O)N4CSC[C@H]4C#N)c3c2)C1]

A solution of 6-(3-(1,1-difluoroethyl)azetidin-1-yl)quinoline-4-carboxylic acid Intermediate 282 (100 mg, 0.34 mmol), (R)-3-glycylthiazolidine-4-carbonitrile hydrochloride Intermediate 4 (107 mg, 0.51 mmol), EDC (98 mg, 0.51 mmol), HOBt (79 mg, 0.51 mmol) and DIPEA (179 μL, 1.03 mmol) in MeCN (8 mL) and EtOAc (8 mL) was stirred at 50° C. for 2 h. The solvent was removed under reduced pressure, and the residue was diluted with EtOAc, and washed with water (3×10 mL). The organic layer was dried over $Na_2SO_4$, filtered and evaporated under reduced pressure. The crude product was triturated with MeOH (20 mL), the precipitate was collected by filtration, and dried under vacuum to give the title compound (115 mg, 75%) as a yellow solid; HRMS (ESI) m/z $[M+H]^+$ calcd for $C_{21}H_{22}F_2N_5O_2S$: 446.1456. found: 446.1448; $^1H$ NMR (300 MHz, DMSO-$d_6$) δ 8.97 (t, 1H), 8.62 (d, 1H), 7.88 (d, 1H), 7.39 (d, 1H), 7.24 (d, 1H), 7.12 (dd, 1H), 5.35-5.25 (m, 1H), 4.88 (d, 1H), 4.69 (d, 1H), 4.28 (d, 2H), 4.15-4.00 (m, 2H), 3.98-3.80 (m, 2H), 3.41-3.33 (m, overlapping with solvent), 1.66 (t, 3H).

Example 148: (R)—N-(2-(4-Cyanothiazolidin-3-yl)-2-oxoethyl)-6-(3-isopropylazetidin-1-yl)quinoline-4-carboxamide

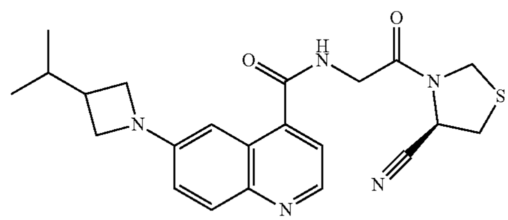 [SMILES: CC(C)C1CN(c2ccc3nccc(C(=O)NCC(=O)N4CSC[C@H]4C#N)c3c2)C1]

DIPEA (3.1 mL, 18 mmol) was added to a solution of 6-(3-isopropylazetidin-1-yl)quinoline-4-carboxylic acid Intermediate 284 (237 mg, 0.88 mmol), (R)-3-glycylthiazolidine-4-carbonitrile hydrochloride Intermediate 4 (273 mg, 1.31 mmol), HOBt (1.18 g, 8.75 mmol) and EDC (1.68 mg, 8.75 mmol) in MeCN (6 mL) and EtOAc (6 mL) at 25° C., and the reaction mixture was stirred at 50° C. for 2 h. The solvent was removed under reduced pressure, and the residue was diluted with sat $NaHCO_3$ (200 mL, aq), and extracted with EtOAc (3×200 mL). The combined organic layer was washed with water (3×50 mL), dried over $Na_2SO_4$, filtered and evaporated at reduced pressure. The crude product was purified by preparative HPLC, PrepMethod C, gradient: 22-38%) to give the title compound (183 mg, 49%) as an orange solid; HRMS (ESI) m/z $[M+H]^+$ calcd for $C_{22}H_{26}N_5O_2S$: 424.1802. found: 424.1798; $^1H$ NMR (300 MHz, DMSO-$d_6$) δ 8.95 (t, 1H), 8.61 (d, 1H), 7.87 (d, 1H), 7.40 (d, 1H), 7.18 (d, 1H), 7.10 (dd, 1H), 5.33 (dd, 1H), 4.90 (d, 1H), 4.72 (d, 1H), 4.30 (d, 2H), 4.10-3.98 (m, 2H), 3.70-3.52 (m, 2H), 3.48-3.38 (m, overlapping with solvent), 2.48-2.30 (m, 1H), 1.82-1.60 (m, 1H), 0.89 (d, 6H).

Example 149: (R)—N-(2-(4-Cyanothiazolidin-3-yl)-2-oxoethyl)-6-(6-methyl-2-azaspiro[3.3]heptan-2-yl)quinoline-4-carboxamide

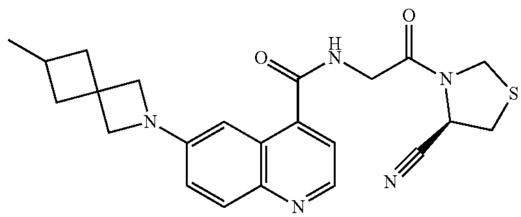 [SMILES: CC1CC2(C1)CN(c1ccc3nccc(C(=O)NCC(=O)N4CSC[C@H]4C#N)c3c1)C2]

DIPEA (4.2 mL, 24 mmol) was added to a solution of 6-(6-methyl-2-azaspiro[3.3]heptan-2-yl)quinoline-4-carboxylic acid Intermediate 286 (337 mg, 1.19 mmol), (R)-3-glycylthiazolidine-4-carbonitrile hydrochloride Intermediate 4 (372 mg, 1.79 mmol), HOBt (1.61 g, 11.9 mmol) and EDC (2.29 g, 11.9 mmol) in MeCN (5 mL) and EtOAc (5 mL) at 25° C., and the reaction mixture was stirred at 50° C. for 2 h. The solvent was removed under reduced pressure, and the residue was diluted with sat $NaHCO_3$(250 mL, aq), and extracted with EtOAc (3×250 mL). The combined organic layer was washed with water (3×50 mL), dried over $Na_2SO_4$, filtered and evaporated at reduced pressure. The crude product was purified by preparative HPLC, PrepMethod C, (gradient: 27-39%) to give the title compound (81 mg, 15%) as an orange solid; HRMS (ESI) m/z $[M+H]^+$ calcd for $C_{23}H_{26}N_5O_2S$: 436.1802. found: 436.1808; $^1H$ NMR (400 MHz, DMSO-$d_6$) δ 8.92 (t, 1H), 8.61 (d, 1H), 7.86 (d, 1H), 7.39 (d, 1H), 7.16 (d, 1H), 7.07 (dd, 1H), 5.33 (dd, 1H), 4.89 (d, 1H), 4.72 (d, 1H), 4.29 (d, 2H), 3.96 (s, 2H), 3.87 (s, 2H), 3.45-3.37 (m, overlapping with solvent), 2.41-2.19 (m, 3H), 1.86-1.70 (m, 2H), 1.05 (d, 3H).

Example 150: (R)—N-(2-(4-Cyanothiazolidin-3-yl)-2-oxoethyl)-6-(6-(trifluoromethyl)-2-azaspiro[3.3]heptan-2-yl)quinoline-4-carboxamide

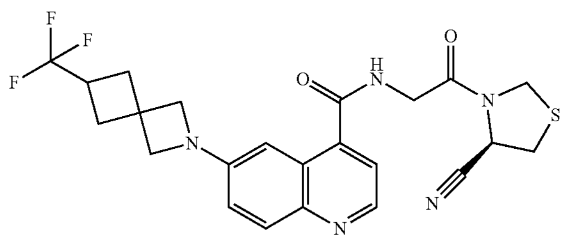 [SMILES: N#C[C@@H]1CSCN1C(=O)CNC(=O)c1ccnc2ccc(N3CC4(CC(C(F)(F)F)C4)C3)cc12]

DIPEA (2.39 mL, 13.7 mmol) was added to 6-(6-(trifluoromethyl)-2-azaspiro[3.3]heptan-2-yl)quinoline-4-carboxylic acid Intermediate 288 (230 mg, 0.68 mmol), (R)-3-glycylthiazolidine-4-carbonitrile hydrochloride Intermediate 4 (213 mg, 1.03 mmol), HOBt (924 mg, 6.84 mmol) and EDC (1.31 g, 6.84 mmol) in MeCN (6 mL) and EtOAc (6 mL) at 25° C., and the reaction mixture was stirred at 50° C. for 2 h. The solvent was removed under reduced pressure, and the residue was diluted with sat $NaHCO_3$ (300 mL, aq), and extracted with EtOAc (3×300 mL). The combined organic layer was washed with water (3×50 mL), dried over $Na_2SO_4$, filtered and evaporated at reduced pressure. The crude product was purified by preparative HPLC, PrepMethod C, (gradient: 26-40%) to give the title compound (185 mg, 55%) as an orange solid; HRMS (ESI) m/z $[M+H]^+$ calcd for $C_{23}H_{23}F_3N_5O_2S$: 490.1518. found: 490.1510; $^1H$ NMR (300 MHz, DMSO-$d_6$) δ 8.96 (t, 1H), 8.63 (d, 1H), 7.88 (d, 1H), 7.41 (d, 1H), 7.22-7.13 (m, 1H), 7.09 (dd, 1H), 5.34 (dd, 1H), 4.90 (d, 1H), 4.72 (d, 1H), 4.31 (d, 2H), 4.00 (s, 2H), 3.94 (s, 2H), 3.55-3.34 (m, overlapping with solvent), 3.21-3.05 (m, 1H), 2.60-2.40 (m, overlapping with solvent), 2.34-2.24 (m, 2H).

Example 151: (R)—N-(2-(4-Cyanothiazolidin-3-yl)-2-oxoethyl)-6-(3-methoxy-3-methyl-azetidin-1-yl)quinoline-4-carboxamide

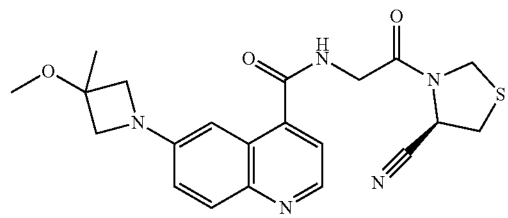 [SMILES: COC1(C)CN(c2ccc3nccc(C(=O)NCC(=O)N4CSC[C@H]4C#N)c3c2)C1]

TEA (3.13 mL, 22.5 mmol) was added to a solution of 6-(3-methoxy-3-methylazetidin-1-yl)quinoline-4-carboxylic acid Intermediate 290 (306 mg, 1.12 mmol), (R)-3-glycylthiazolidine-4-carbonitrile hydrochloride Intermediate 4 (350 mg, 1.69 mmol), HOBt (1.52 g, 11.2 mmol) and EDC (2.15 g, 11.2 mmol) in EtOAc (6 mL) and MeCN (6 mL) at 25° C., and the reaction mixture was stirred at 25° C. for 16 h. The solvent was removed under reduced pressure, and the residue was diluted with sat $NaHCO_3$(250 mL, aq), and extracted with EtOAc (3×250 mL). The combined organic layer was washed with water (3×50 mL), dried over $Na_2SO_4$, filtered and evaporated at reduced pressure. The crude product was purified by preparative HPLC, PrepMethod C, (gradient: 13-23%) to give the title compound (126 mg, 26%) as an orange solid; HRMS (ESI) m/z $[M+H]^+$ calcd for $C_{21}H_{24}N_5O_3S$: 426.1594. found: 426.1596; $^1H$ NMR (300 MHz, DMSO-$d_6$) δ 8.97 (t, 1H), 8.63 (d, 1H), 7.89 (d, 1H), 7.41 (d, 1H), 7.25 (d, 1H), 7.14 (dd, 1H), 5.34 (dd, 1H), 4.89 (d, 1H), 4.71 (d, 1H), 4.30 (d, 2H), 3.93-3.78 (m, 4H), 3.45-3.34 (m, overlapping with solvent), 3.22 (s, 3H), 1.51 (s, 3H).

Example 152: (R)—N-(2-(4-Cyanothiazolidin-3-yl)-2-oxoethyl)-6-(3-ethoxy-3-methyl-azetidin-1-yl)quinoline-4-carboxamide

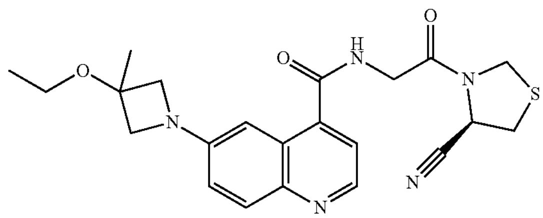 [SMILES: CCOC1(C)CN(c2ccc3nccc(C(=O)NCC(=O)N4CSC[C@H]4C#N)c3c2)C1]

DIPEA (3.98 mL, 22.8 mmol) was added to a solution of 6-(3-ethoxy-3-methylazetidin-1-yl)quinoline-4-carboxylic acid Intermediate 292 (326 mg, 1.14 mmol), (R)-3-glycylthiazolidine-4-carbonitrile hydrochloride Intermediate 4 (355 mg, 1.71 mmol), HOBt (1.54 g, 11.4 mmol) and EDC (2.19 g, 11.4 mmol) in MeCN (5 mL) and EtOAc (5 mL) at 25° C., and the reaction mixture was stirred at 50° C. for 2 h. The solvent was removed under reduced pressure, and the residue was diluted with sat $NaHCO_3$(250 mL, aq), and extracted with EtOAc (3×250 mL). The combined organic layer was washed with water (3×50 mL), dried over $Na_2SO_4$, filtered and evaporated at reduced pressure. The crude product was purified by preparative HPLC, PrepMethod C, (gradient: 13-28%) to give the title compound (251 mg, 49%) as an orange solid; HRMS (ESI) m/z $[M+H]^+$ calcd for $C_{22}H_{26}N_5O_3S$: 440.1750. found: 440.1754; $^1$H NMR (400 MHz, DMSO-$d_6$) δ 8.95 (t, 1H), 8.63 (d, 1H), 7.88 (d, 1H), 7.40 (d, 1H), 7.24 (d, 1H), 7.13 (dd, 1H), 5.33 (dd, 1H), 4.89 (d, 1H), 4.72 (d, 1H), 4.30 (d, 2H), 3.90-3.80 (m, 4H), 3.50-3.33 (m, overlapping with solvent), 1.51 (s, 3H), 1.13 (t, 3H).

Example 153: (R)—N-(2-(4-Cyanothiazolidin-3-yl)-2-oxoethyl)-6-(1-oxa-6-azaspiro[3.3]heptan-6-yl)quinoline-4-carboxamide

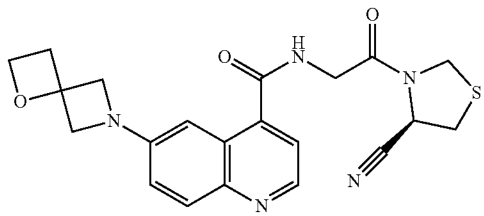 [SMILES: N#C[C@@H]1CSCN1C(=O)CNC(=O)c1ccnc2ccc(N3CC4(CCO4)C3)cc12]

DIPEA (620 μL, 3.55 mmol) was added to a stirred suspension of 6-(1-oxa-6-azaspiro[3.3]heptan-6-yl)quinoline-4-carboxylic acid Intermediate 294 (192 mg, 0.71 mmol), (R)-3-glycylthiazolidine-4-carbonitrile hydrochloride Intermediate 4 (251 mg, 1.21 mmol), HOBt (288 mg, 2.13 mmol) and EDC (409 mg, 2.13 mmol) in MeCN (10 mL) and EtOAc (10 mL) at 30° C., and the reaction mixture was stirred at 50° C. for 2 h. The solvent was removed under reduced pressure, and the residue was dissolved in a mixture of $NaHCO_3$ (40 mL, aq) and EtOAc (100 mL). The aqueous layer was extracted with EtOAc (4×75 mL). The combined organic layer was washed with water (3×50 mL), dried over $Na_2SO_4$, filtered and evaporated at reduced pressure. The crude product was purified by preparative HPLC, PrepMethod R, (gradient:15-35%) to give the title compound (90 mg, 30%) as a yellow solid; HRMS (ESI) m/z $[M+H]^+$ calcd for $C_{21}H_{22}N_5O_3S$: 424.1438. found: 424.1448; $^1$H NMR (400 MHz, DMSO-$d_6$) δ 9.10-8.90 (m, 1H), 8.65 (d, 1H), 7.89 (d, 1H), 7.42 (d, 1H), 7.24 (d, 1H), 7.13 (dd, 1H), 5.45-5.33 (m, 1H), 4.91 (d, 1H), 4.73 (d, 1H), 4.47 (t, 2H), 4.31 (d, 2H), 4.24 (d, 2H), 4.03 (d, 2H), 3.60-3.37 (m, 2H), 2.90 (t, 2H).

Example 154: (R)—N-(2-(4-Cyanothiazolidin-3-yl)-2-oxoethyl)-6-(3-ethyl-3-hydroxy-azetidin-1-yl)quinoline-4-carboxamide

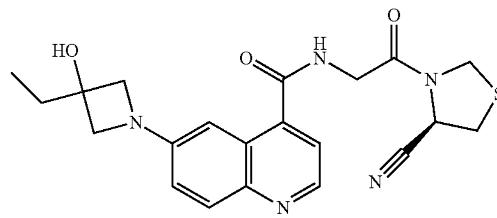

T3P (1.40 g, 2.20 mmol, 50% in EtOAc) was added to a solution of 6-(3-ethyl-3-hydroxyazetidin-1-yl)quinoline-4-carboxylic acid Intermediate 296 (150 mg, 0.55 mmol), (R)-3-glycylthiazolidine-4-carbonitrile hydrochloride Intermediate 4 (114 mg, 0.55 mmol) and DIPEA (289 μL, 1.65 mmol) in MeCN (8 mL) and EtOAc (8 mL) at 25° C., and the reaction mixture was stirred at 25° C. for 3 h. The reaction mixture was concentrated under reduced pressure, diluted with EtOAc (75 mL), and washed sequentially with sat brine (15 mL) and water (15 mL). The organic layer was dried over $Na_2SO_4$, filtered and evaporated at reduced pressure. The crude product was purified by preparative HPLC, PrepMethod R, (gradient: 15-35%) to give the title compound (50 mg, 21%) as a yellow solid; HRMS (ESI) m/z $[M+H]^+$ calcd for $C_{21}I\text{-}124N_5O_3S$: 426.1594. found: 426.1586; $^1$H NMR (400 MHz, DMSO-$d_6$) δ 8.95 (t, 1H), 8.61 (d, 1H), 7.87 (d, 1H), 7.39 (d, 1H), 7.17 (d, 1H), 7.12 (dd, 1H), 5.33 (dd, 1H), 4.89 (d, 1H), 4.71 (d, 1H), 4.29 (d, 2H), 4.00-3.85 (m, 2H), 3.71 (d, 2H), 3.50-3.34 (m, overlapping with solvent), 1.74 (q, 2H), 0.94 (t, 3H).

Example 155: (R)—N-(2-(4-Cyanothiazolidin-3-yl)-2-oxoethyl)-6-(6-fluoro-2-azaspiro[3,3]heptan-2-yl)quinoline-4-carboxamide

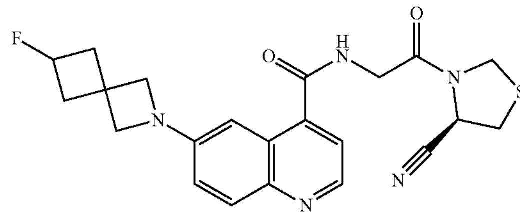 [SMILES: N#C[C@@H]1CSCN1C(=O)CNC(=O)c1ccnc2ccc(N3CC4(CC(F)C4)C3)cc12]

DIPEA (3.36 mL, 19.2 mmol) was added to a solution of 6-(6-fluoro-2-azaspiro[3.3]heptan-2-yl)quinoline-4-carboxylic acid Intermediate 298 (275 mg, 0.96 mmol), (R)-3-glycylthiazolidine-4-carbonitrile hydrochloride Intermediate 4 (299 mg, 1.44 mmol), HOBt (1.30 g, 9.61 mmol) and EDC (1.84 g, 9.61 mmol) in MeCN (6 mL) and EtOAc (6 mL) at 25° C., and the reaction mixture was stirred at 50° C. for 2 h. The reaction mixture was concentrated under reduced pressure, diluted with sat $NaHCO_3$(250 mL, aq), and extracted with EtOAc (3×250 mL). The combined organic layer was washed with water (3×50 mL), dried over $Na_2SO_4$, filtered and evaporated at reduced pressure. The crude product was purified by preparative HPLC, Prep-Method C, (gradient: 16-30%) to give the title compound (142 mg, 34%) as an orange solid; HRMS (ESI) m/z $[M+H]^+$ calcd for $C_{22}H_{23}FN_5O_2S$: 440.1550. found: 440.1556; $^1H$ NMR (300 MHz, DMSO-$d_6$) δ 8.94 (t, 1H), 8.63 (d, 1H), 7.88 (d, 1H), 7.41 (d, 1H), 7.23-7.02 (m, 2H), 5.34 (dd, 1H), 5.20 −4.80 (m, 2H), 4.75-4.59 (m, 1H), 4.30 (d, 2H), 3.96 (d, 4H), 3.46-3.39 (m, 2H), 2.73-2.58 (m, 2H), 2.45-2.25 (m, 2H).

Example 156: 6-((1RS,5RS)-6-Azabicyclo[3.2.0]heptan-6-yl)-N-(2-((R)-4-cyanothiazolidin-3-yl)-2-oxoethyl)quinoline-4-carboxamide

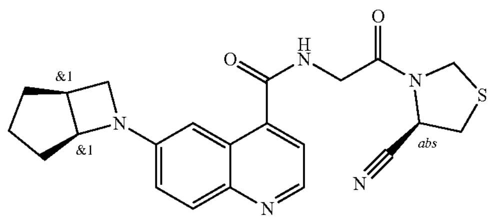 [SMILES: N#C[C@@H]1CSCN1C(=O)CNC(=O)c1ccnc2ccc(N3C[C@@H]4CCC[C@@H]43)cc12]

A solution of 6-(6-azabicyclo[3.2.0]heptan-6-yl)quinoline-4-carboxylic acid Intermediate 300 (100 mg, 0.37 mmol) in DMF (5 mL) was added to a mixture of (R)-3-glycylthiazolidine-4-carbonitrile hydrochloride Intermediate 4 (155 mg, 0.75 mmol), HATU (283 mg, 0.75 mmol) and DIPEA (193 mg, 1.49 mmol), and the reaction mixture was stirred at 25° C. for 6 h. The solvent was removed under reduced pressure, and the crude product was purified by preparative TLC (DCM:MeOH, 18:1), followed by preparative HPLC, PrepMethod T, (gradient: 30-50%) to give the title compound (86 mg, 55%) as a yellow solid; HRMS (ESI) m/z $[M+H]^+$ calcd for $C_{22}H_{24}N_5O_2S$: 422.1646. found: 422.1640; $^1H$ NMR (300 MHz, DMSO-$d_6$) δ 8.91 (t, 1H), 8.54 (d, 1H), 7.82 (d, 1H), 7.35 (d, 1H), 7.12-6.99 (m, 2H), 5.40-5.25 (m, 1H), 4.87 (d, 1H), 4.77-4.47 (m, 2H), 4.27 (d, 2H), 3.95 (t, 1H), 3.50 (dd, 1H), 3.41-3.33 (m, overlapping with solvent), 3.15-2.95 (m, 1H), 2.14-1.97 (m, 1H), 1.91-1.68 (m, 3H), 1.62 −1.33 (m, 2H).

Example 157: (R)—N-(2-(4-Cyanothiazolidin-3-yl)-2-oxoethyl)-6-(3-fluoro-3-(fluoromethyl)azetidin-1-yl)quinoline-4-carboxamide

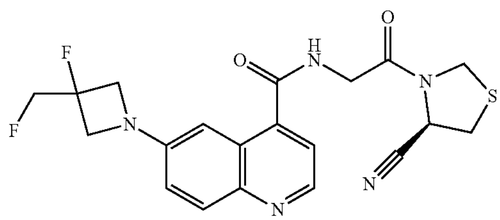 [SMILES: N#C[C@@H]1CSCN1C(=O)CNC(=O)c1ccnc2ccc(N3CC(F)(CF)C3)cc12]

DIPEA (565 μL, 3.23 mmol) was added to a stirred suspension of 6-(3-fluoro-3-(fluoromethyl)azetidin-1-yl)quinoline-4-carboxylic acid Intermediate 303 (90 mg, 0.32 mmol), (R)-3-glycylthiazolidine-4-carbonitrile hydrochloride Intermediate 4 (101 mg, 0.49 mmol), HOBt (248 mg, 1.62 mmol) and EDC (310 mg, 1.62 mmol) in MeCN (5 mL) and EtOAc (5 mL), and the reaction mixture was stirred at 18° C. for 15 h. The solvent was removed under reduced pressure, and the residue was dissolved in $NaHCO_3$ (30 mL, aq) and EtOAc (80 mL). The aqueous layer was extracted with EtOAc (5×75 mL) and the combined organic layer was washed with water (3×50 mL), dried over $Na_2SO_4$, filtered and evaporated at reduced pressure. The crude product was purified by preparative HPLC, PrepMethod R, (gradient: 22-42%) to give the title compound (35 mg, 25%) as a yellow solid; HRMS (ESI) m/z $[M+H]^+$ calcd for $C_{20}H_{20}F_2N_5O_2S$: 432.1300. found: 432.1294; $^1H$ NMR (300 MHz, DMSO-$d_6$) δ 9.10-8.90 (m, 1H), 8.68 (d, 1H), 7.94 (d, 1H), 7.44 (d, 1H), 7.35 (d, 1H), 7.22 (dd, 1H), 5.40-5.24 (m, 1H), 5.03-4.68 (m, 4H), 4.35-3.98 (m, 6H), 3.41 (m, overlapping with solvent).

Example 158: (R)—N-(2-(4-Cyanothiazolidin-3-yl)-2-oxoethyl)-6-(3-(2,2,2-trifluoroethyl)-azetidin-1-yl)quinoline-4-carboxamide

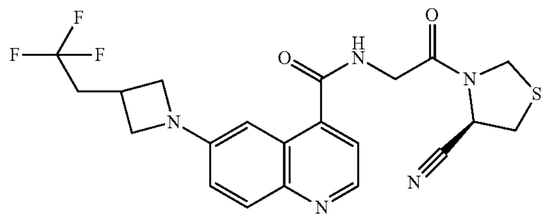 [SMILES: N#C[C@@H]1CSCN1C(=O)CNC(=O)c1ccnc2ccc(N3CC(CC(F)(F)F)C3)cc12]

DIPEA (1.80 mL, 10.3 mmol) was added to a stirred suspension of 6-(3-(2,2,2-trifluoroethyl)azetidin-1-yl)quinoline-4-carboxylic acid Intermediate 305 (320 mg, 1.03 mmol), (R)-3-glycylthiazolidine-4-carbonitrile hydrochloride Intermediate 4 (321 mg, 1.55 mmol), HOBt (790 mg, 5.16 mmol) and EDC (989 mg, 5.16 mmol) in MeCN (8 mL) and EtOAc (8 mL) at 28° C., and the reaction mixture was stirred at 50° C. for 2 h. The solvent was removed under reduced pressure and the residue was dissolved in $NaHCO_3$ (60 mL, aq) and EtOAc (100 mL). The aqueous layer was extracted with EtOAc (6×100 mL). The combined organic layer was washed with water (3×50 mL), dried over $Na_2SO_4$, filtered and evaporated at reduced pressure. The crude product was purified by preparative HPLC, PrepMethod R, (gradient: 32-45%) to give the title compound (250 mg, 52%) as a yellow solid; HRMS (ESI) m/z $[M+H]^+$ calcd for $C_{21}H_{21}F_3N_5O_2S$: 464.1362. found: 464.1360; $^1H$ NMR (300 MHz, DMSO-$d_6$) δ 8.94 (t, 1H), 8.62 (d, 1H), 7.87 (d, 1H), 7.40 (d, 1H), 7.18-7.07 (m, 2H), 5.30 (dd, 1H), 4.87 (d, 1H), 4.70 (d, 1H), 4.28 (d, 2H), 4.15 (t, 2H), 3.71 (t, 2H), 3.43-3.33 (m, 2H), 3.15-2.95 (m, 1H), 2.80-2.58 (m, 2H).

Example 159: N-(2-((R)-4-Cyanothiazolidin-3-yl)-2-oxoethyl)-6-((RS)-3,3-difluoro-2-methylazetidin-1-yl)quinoline-4-carboxamide

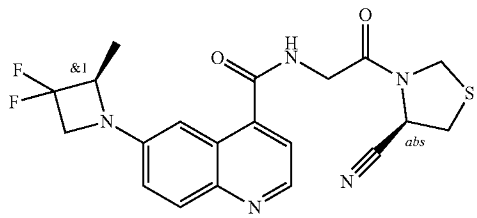 [SMILES: C[C@H]1N(c2ccc3nccc(C(=O)NCC(=O)N4CSC[C@H]4C#N)c3c2)CC1(F)F]

DIPEA (2.36 mL, 13.5 mmol) was added to a mixture of 6-(3,3-difluoro-2-methylazetidin-1-yl)quinoline-4-carboxylic acid Intermediate 307 (188 mg, 0.68 mmol), (R)-3-glycylthiazolidine-4-carbonitrile hydrochloride Intermediate 4 (210 mg, 1.01 mmol), HOBt (1.04 g, 6.76 mmol) and EDC (1.30 g, 6.76 mmol) in MeCN (5 mL) and EtOAc (5 mL) at 20° C., and the reaction mixture was stirred at 50° C. for 2 h. The solvent was removed under reduced pressure, and the reaction mixture was diluted with sat $NaHCO_3$(250 mL, aq), and extracted with EtOAc (4×250 mL). The combined organic layer was dried over $Na_2SO_4$, filtered and evaporated at reduced pressure. The crude product was purified by preparative HPLC, PrepMethod C, (gradient 25-50%) to give the title compound (169 mg, 58%) as an orange solid; HRMS (ESI) m/z $[M+H]^+$ calcd for $C_{20}H_{20}F_2N_5O_2S$: 432.1300. found: 432.1306; $^1H$ NMR (300 MHz, DMSO-$d_6$) δ 9.04 (brs, 1H), 8.72 (d, 1H), 7.96 (d, 1H), 7.56-7.50 (m, 1H), 7.45 (d, 1H), 7.27 (dd, 1H), 5.45-5.25 (m, 1H), 4.91 (d, 1H), 4.78-4.49 (m, 3H), 4.37-4.15 (m, 3H), 3.42-3.32 (m, overlapping with solvent), 1.52 (d, 3H).

Example 160: N-(2-((R)-4-Cyanothiazolidin-3-yl)-2-oxoethyl)-6-(6,6-difluoro-3-azabicyclo[3.1.0]hexan-3-yl)quinoline-4-carboxamide

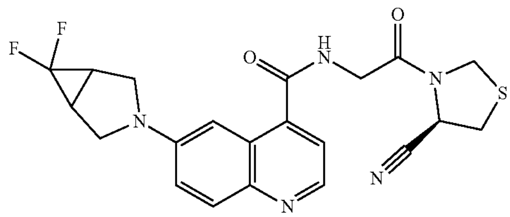 [SMILES: N#C[C@@H]1CSCN1C(=O)CNC(=O)c1ccnc2ccc(N3CC4C(C3)C4(F)F)cc12]

DIPEA (957 μL, 5.48 mmol) was added to a stirred suspension of 6-(6,6-difluoro-3-azabicyclo[3.1.0]hexan-3-yl)quinoline-4-carboxylic acid Intermediate 309 (153 mg, 0.27 mmol), (R)-3-glycylthiazolidine-4-carbonitrile hydrochloride Intermediate 4 (114 mg, 0.55 mmol), HOBt (210 mg, 1.37 mmol) and EDC (263 mg, 1.37 mmol) in MeCN (5 mL) and EtOAc (5 mL) at 12° C., and the reaction mixture was stirred at 50° C. for 2 h. The solvent was removed under reduced pressure, and the residue was dissolved in $NaHCO_3$ (30 mL, aq) and EtOAc (80 mL). The aqueous layer was extracted with EtOAc (5×75 mL). The combined organic layer was washed with water (3×50 mL), dried over $Na_2SO_4$, filtered and evaporated at reduced pressure. The crude product was purified by preparative HPLC, PrepMethod F, (gradient: 10-40%) to give the title compound (150 mg, 86%) as a yellow solid; HRMS (ESI) m/z $[M+H]^+$ calcd for $C_{21}H_{20}F_2N_5O_2S$: 444.1300. found: 444.1282; $^1H$ NMR (300 MHz, DMSO-$d_6$) δ 8.97 (t, 1H), 8.59 (d, 1H), 7.88 (d, 1H), 7.37 (d, 1H), 7.33-7.20 (m, 2H), 5.36-5.22 (m, 1H), 4.90 (d, 1H), 4.72 (d, 1H), 4.31-4.24 (m, 2H), 3.85-3.58 (m, 4H), 3.42-3.34 (m, overlapping with solvent), 2.80-2.60 (m, 2H).

Example 161: N-(2-((R)-4-Cyanothiazolidin-3-yl)-2-oxoethyl)-6-((R)-3-methoxy-pyrrolidin-1-yl)quinoline-4-carboxamide

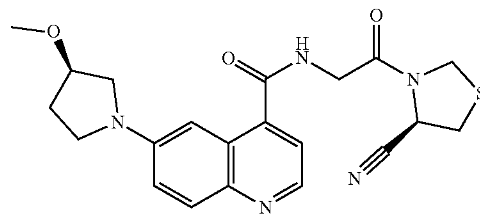

HATU (348 mg, 0.88 mmol), DIPEA (411 μL, 2.35 mmol) were added to a stirred solution of (R)-6-(3-methoxypyrrolidin-1-yl)quinoline-4-carboxylic acid Intermediate 311 (160 mg, 0.59 mmol) and), (R)-3-glycylthiazolidine-4-carbonitrile hydrochloride Intermediate 4 (122 mg, 0.59 mmol), in DMF (5 mL), and the reaction mixture was stirred at 25° C. for 2 h. The solvent was removed under reduced pressure, and the crude product was purified by preparative TLC (DCM:MeOH, 18:1), followed by preparative HPLC, PrepMethod F, (gradient: 1-35%) to give the title compound (108 mg, 42%) as a yellow solid; HRMS (ESI) m/z $[M+H]^+$ calcd for $C_{21}H_{24}N_5O_3S$: 426.1594. found: 426.1584; $^1H$ NMR (300 MHz, DMSO-$d_6$) δ 8.92 (t, 1H), 8.55 (d, 1H), 7.86 (d, 1H), 7.44-7.19 (m, 3H), 5.30 (dd, 1H), 4.88 (d, 1H), 4.70 (d, 1H), 4.38-4.23 (m, 2H), 4.18-4.01 (m, 1H), 3.60-3.18 (m, overlapping with solvent), 2.20-2.00 (m, 2H).

Example 162: (R)—N-(2-(4-Cyanothiazolidin-3-yl)-2-oxoethyl)-6-(3-oxa-9-azaspiro[5.5]undecan-9-yl)quinoline-4-carboxamide

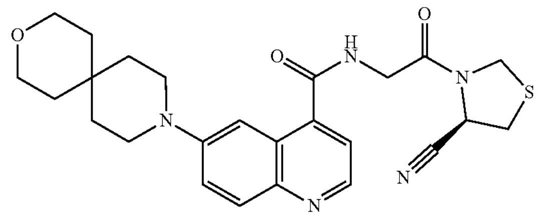 [SMILES: N#C[C@@H]1CSCN1C(=O)CNC(=O)c1ccnc2ccc(N3CCC4(CCOCC4)CC3)cc12]

A solution of 6-(3-oxa-9-azaspiro[5.5]undecan-9-yl)quinoline-4-carboxylic acid Intermediate 313 (100 mg, 0.31 mmol), (R)-3-glycylthiazolidine-4-carbonitrile hydrochloride Intermediate 4 (95 mg, 0.46 mmol), EDC (88 mg, 0.46 mmol), HOBt (70 mg, 0.46 mmol) and DIPEA (161 μL, 0.92 mmol) in MeCN (6 mL) and EtOAc (6 mL) was stirred at 50° C. for 2 h. The solvent was removed under reduced pressure, and the residue was diluted with EtOAc, and washed with water. The organic layer was dried over $Na_2SO_4$, filtered and evaporated at reduced pressure. The crude product was purified by preparative HPLC, PrepMethod F, (gradient: 30-40%) to give the title compound (75 mg, 51%) as a yellow solid; HRMS (ESI) m/z $[M+H]^+$ calcd for $C_{25}H_{30}N_5O_3S$: 480.2064. found: 480.2057; $^1$H NMR (300 MHz, $CD_3OD$) δ 8.62 (d, 1H), 7.90 (d, Hz, 1H), 7.78-7.62 (m, 2H), 7.48 (d, 1H), 5.35-5.27 (m, 1H), 4.90-4.80 (m, overlapping with solvent), 4.77 (d, 1H), 4.38 (s, 2H), 3.71 (t, 4H), 3.54-3.35 (m, 6H), 1.75 (t, 4H), 1.58 (t, 4H).

Example 163: (R)—N-(2-(4-Cyanothiazolidin-3-yl)-2-oxoethyl)-6-(5,8-dioxa-2-azaspiro[3.4]octan-2-yl)quinoline-4-carboxamide

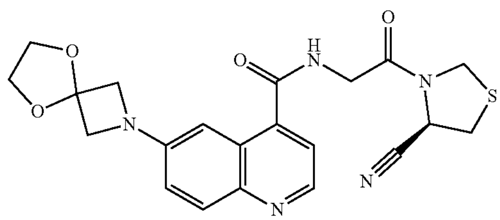 [SMILES: N#C[C@@H]1CSCN1C(=O)CNC(=O)c1ccnc2ccc(N3CC4(C3)OCCO4)cc12]

(R)-3-Glycylthiazolidine-4-carbonitrile hydrochloride Intermediate 4 (290 mg, 1.40 mmol), was added to a solution of 6-(5,8-dioxa-2-azaspiro[3.4]octan-2-yl)quinoline-4-carboxylic acid Intermediate 315 (200 mg, 0.70 mmol), HATU (531 mg, 1.40 mmol) and DIPEA (361 mg, 2.79 mmol) in DMF (5 mL), and the reaction mixture was stirred at 25° C. for 4 h. The solvent was evaporated at reduced pressure, and the residue was purified by preparative TLC (DCM:MeOH, 18:1), followed by preparative HPLC, PrepMethod B, (gradient: 18-38%) to give the title compound (50 mg, 16%) as a yellow solid; HRMS (ESI) m/z $[M+H]^+$ calcd for $C_{21}H_{22}N_5O_4S$: 440.1388. found: 440.1394; $^1$H NMR (300 MHz, DMSO-$d_6$) δ 8.95 (t, 1H), 8.63 (d, 1H), 7.89 (d, 1H), 7.39 (d, 1H), 7.30 (d, 1H), 7.14 (dd, 1H), (dd, 1H), 4.88 (d, 1H), 4.70 (d, 1H), 4.28 (d, 2H), 4.09 (s, 4H), 3.95 (s, 4H), 3.43-3.33 (m, 2H).

Example 164: (R)—N-(2-(4-Cyanothiazolidin-3-yl)-2-oxoethyl)-6-(5-azaspiro[2.3]hexan-5-yl)quinoline-4-carboxamide

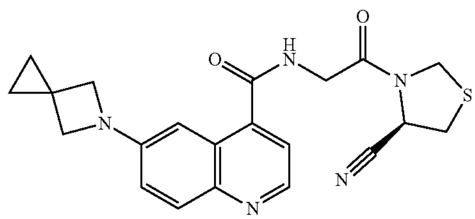 [SMILES: N#C[C@@H]1CSCN1C(=O)CNC(=O)c1ccnc2ccc(N3CC4(CC4)C3)cc12]

DIPEA (3.98 mL, 22.8 mmol) was added to a mixture of 6-(5-azaspiro[2.3]hexan-5-yl)quinoline-4-carboxylic acid Intermediate 317 (290 mg, 1.14 mmol), (R)-3-glycyl-thiazolidine-4-carbonitrile hydrochloride Intermediate 4 (474 mg, 2.28 mmol), HOBt (1746 mg, 11.40 mmol) and EDC (2186 mg, 11.40 mmol) in MeCN (3 mL) and EtOAc (3 mL) at 15° C., and the reaction mixture was stirred at 15° C. overnight. The solvent was removed under reduced pressure. The residue was diluted with $NaHCO_3$ (100 mL, aq), and extracted with EtOAc (5×100 mL). The combined organic layer was dried over $Na_2SO_4$, filtered and evaporated at reduced pressure. The crude product was purified by preparative HPLC, PrepMethod C, (gradient: 20-35%) to give the title compound (92 mg, 20%) as an orange solid; HRMS (ESI) m/z $[M+H]^+$ calcd for $C_{21}H_{22}N_5O_2S$: 408.1488. found: 408.1500; $^1$H NMR (300 MHz, DMSO-$d_6$) δ 9.05-8.90 (m, 1H), 8.63 (d, 1H), 7.89 (d, 1H), 7.41 (d, 1H), 7.25-7.16 (m, 1H), 7.12 (dd, 1H), 5.32 (dd, 1H), 4.88 (d, 2H), 4.70 (d, 1H), 4.29 (d, 2H), 4.06 (s, 4H), 3.41-3.35 (m, overlapping with solvent), 1.27-1.21 (m, 1H), 0.69 (s, 4H).

Example 165: (R)—N-(2-(4-Cyanothiazolidin-3-yl)-2-oxoethyl)-6-(3-hydroxy-3-methyl-azetidin-1-yl)quinoline-4-carboxamide

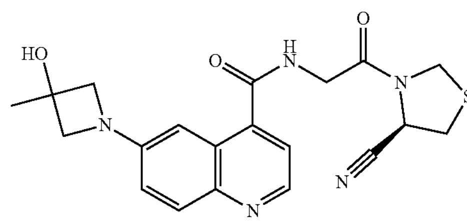

DIPEA (575 μL, 3.29 mmol) was added to a stirred suspension of 6-(3-hydroxy-3-methylazetidin-1-yl)quinoline-4-carboxylic acid Intermediate 319 (85 mg, 0.33 mmol), (R)-3-glycylthiazolidine-4-carbonitrile hydrochloride Intermediate 4 (137 mg, 0.66 mmol), HOBt (252 mg, 1.65 mmol) and EDC (315 mg, 1.65 mmol) in MeCN (3 mL) and EtOAc (3 mL) at 15° C., and the reaction mixture was stirred at 50° C. for 2 h. The solvent was removed under reduced pressure, and the residue was dissolved in $NaHCO_3$ (20 mL, aq) and EtOAc (60 mL). The aqueous layer was extracted with EtOAc (5×75 mL) and the combined organic layer was washed with water (3×25 mL). The combined aqueous layer was extracted with EtOAc (3×20 mL). The combined organic layer was dried over $Na_2SO_4$, filtered and evaporated at reduced pressure. The crude product was purified by preparative HPLC, PrepMethod R, (gradient: 15-35%) to give the title compound (20 mg, 15%) as a yellow solid; HRMS (ESI) m/z $[M+H]^+$ calcd for $C_{20}H_{22}N_5O_3S$: 412.1438. found: 412.1428; $^1$H NMR (300 MHz, DMSO-$d_6$) δ 8.95 (t, 1H), 8.61 (d, 1H), 7.87 (d, 1H), 7.39 (d, 1H), 7.22-7.06 (m, 2H), 5.60 (s, 1H), 5.39-5.24 (m, 1H), 4.89 (d, 1H), 4.72 (d, 1H), 4.29 (d, 2H), 3.89 (d, 2H), 3.76 (d, 2H), 3.48-3.33 (d, overlapping with solvent), 1.48 (s, 3H).

Example 166: (R)—N-(2-(4-Cyanothiazolidin-3-yl)-2-oxoethyl)-6-(2-oxa-6-azaspiro[3.3]heptan-6-yl)quinoline-4-carboxamide

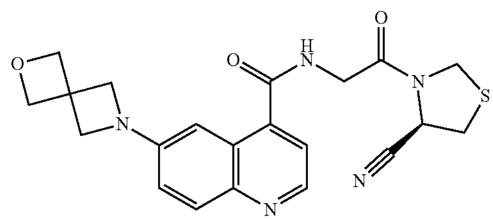 [SMILES: N#C[C@@H]1CSCN1C(=O)CNC(=O)c1ccnc2ccc(N3CC4(COC4)C3)cc12]

DIPEA (746 μL, 4.27 mmol) was added to a stirred suspension of 6-(2-oxa-6-azaspiro[3.3]heptan-6-yl)quinoline-4-carboxylic acid Intermediate 321 (231 mg, 0.85 mmol), (R)-3-glycylthiazolidine-4-carbonitrile hydrochloride Intermediate 4 (266 mg, 1.28 mmol), HOBt (346 mg, 2.56 mmol) and EDC (492 mg, 2.56 mmol) in MeCN (5 mL) and EtOAc (5 mL) at 25° C., and the reaction mixture was stirred at 50° C. for 2 h. The solvent was removed under reduced pressure. The residue was dissolved in $NaHCO_3$(40 mL, aq) and EtOAc (100 mL). The aqueous layer was extracted with EtOAc (6×75 mL) and the combined organic layer was washed with water (3×50 mL), dried over $Na_2SO_4$, filtered and evaporated at reduced pressure. The crude product was purified by preparative HPLC, PrepMethod R, (gradient: 20-45%) to give the title compound (80 mg, 22%) as a yellow solid; HRMS (ESI) m/z $[M+H]^+$ calcd for $C_{21}H_{22}N_5O_3S$: 424.1438. found: 424.1428; $^1H$ NMR (300 MHz, DMSO-$d_6$) δ 8.94 (t, 1H), 8.63 (d, 1H), 7.88 (d, 1H), 7.40 (d, 1H), 7.20 (d, 1H), 7.11 (dd, 1H), (dd, 1H), 4.89 (d, 1H), 4.84-4.64 (m, 5H), 4.30 (d, 2H), 4.13 (s, 4H), 3.41-3.36 (m, overlapping with solvent).

Example 167: N-(2-((R)-4-Cyanothiazolidin-3-yl)-2-oxoethyl)-6-((R)-3-hydroxy-3-methylpyrrolidin-1-yl)quinoline-4-carboxamide

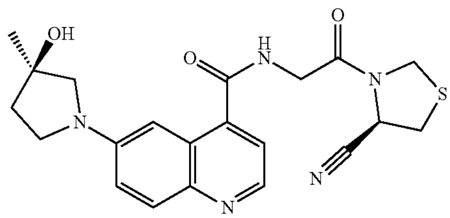 [SMILES: C[C@@]1(O)CCN(c2ccc3nccc(C(=O)NCC(=O)N4CSC[C@H]4C#N)c3c2)C1]

A solution of (R)-6-(3-hydroxy-3-methylpyrrolidin-1-yl) quinoline-4-carboxylic acid Intermediate 323 (150 mg, 0.55 mmol), (R)-3-glycylthiazolidine-4-carbonitrile hydrochloride Intermediate 4 (149 mg, 0.72 mmol), EDC (211 mg, 1.10 mmol), HOBt (169 mg, 1.10 mmol) and DIPEA (481 μL, 2.75 mmol) in EtOAc (5 mL) and MeCN (5 mL) was stirred at 50° C. for 2 h. The solvent was removed under reduced pressure, and the residue was diluted with EtOAc, and washed with water. The organic layer was dried over $Na_2SO_4$, filtered and evaporated at reduced pressure. The crude product was purified by preparative HPLC, PrepMethod C, (gradient: 9-19%) to give the title compound (120 mg, 50%) as an orange solid; HRMS (ESI) m/z $[M+H]^+$ calcd for $C_{21}$I-$124N_5O_3S$: 426.1594. found: 426.1604; $^1H$ NMR (300 MHz, $CD_3OD$) δ 8.49 (d, 1H), 7.87 (d, 1H), 7.46 (d, 1H), 7.31 (dd, 1H), 7.24 (d, 1H), 5.44-5.24 (m, 1H), 4.87-4.67 (m, overlapping with solvent), 4.38 (d, 2H), 3.72-3.51 (m, 2H), 3.49-3.33 (m, 4H), 2.12-1.97 (m, 2H), 1.48 (s, 3H).

Example 168: N-(2-((R)-4-Cyanothiazolidin-3-yl)-2-oxoethyl)-6-((S)-3-hydroxy-3-methylpyrrolidin-1-yl)quinoline-4-carboxamide

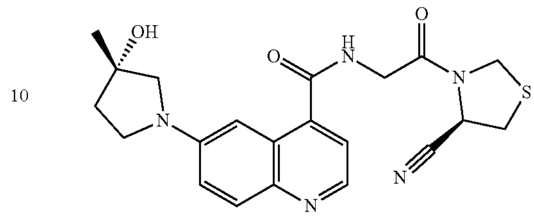

A solution of (S)-6-(3-hydroxy-3-methylpyrrolidin-1-yl) quinoline-4-carboxylic acid Intermediate 325 (150 mg, 0.55 mmol), (R)-3-glycylthiazolidine-4-carbonitrile hydrochloride Intermediate 4 (149 mg, 0.72 mmol), EDC (211 mg, 1.10 mmol), HOBt (169 mg, 1.10 mmol) and DIPEA (481 μL, 2.75 mmol) in EtOAc (5 mL) and MeCN (5 mL) was stirred at 50° C. for 2 h. The solvent was removed under reduced pressure, and the residue was diluted with EtOAc, and washed with water. The organic layer was dried over $Na_2SO_4$, filtered and evaporated at reduced pressure. The crude product was purified by preparative HPLC, PrepMethod C, (gradient (9-20%), to give the title compound (125 mg, 52%) as an orange solid; HRMS (ESI) m/z $[M+H]^+$ calcd for $C_{21}H_{24}N_5O_3S$: 426.1594. found: 426.1581; $^1H$ NMR (300 MHz, $CD_3OD$) δ 8.49 (d, 1H), 7.87 (d, 1H), 7.46 (d, 1H), 7.31 (dd, 1H), 7.24 (d, 1H), 5.44-5.24 (m, 1H), 4.87-4.67 (m, overlapping with solvent), 4.38 (d, 2H), 3.72-3.51 (m, 2H), 3.49-3.33 (m, 4H), 2.12-1.97 (m, 2H), 1.48 (s, 3H).

Example 169: (R)—N-(2-(4-Cyanothiazolidin-3-yl)-2-oxoethyl)-6-(6-(difluoromethyl)-pyridin-3-yl)quinoline-4-carboxamide

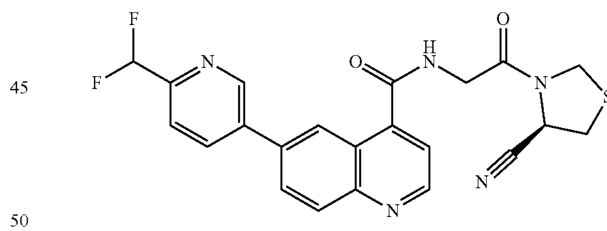

(R)-3-Glycylthiazolidine-4-carbonitrile hydrochloride Intermediate 4 (104 mg, 0.50 mmol) and DIPEA (0.13 mL, 0.75 mmol) were added to a suspension of 6-(6-(difluoromethyl)pyridin-3-yl)quinoline-4-carboxylic acid Intermediate 326 (75 mg, 0.25 mmol), HOBT (46 mg, 0.30 mmol) and EDC (0.072 g, 0.37 mmol) in EtOAc (1.18 mL) and MeCN (1.18 mL), and the reaction mixture was stirred at rt overnight. The reaction mixture was diluted with EtOAc and washed sequentially with sat $NaHCO_3$ (aq) and brine. The organic phase was dried using a phase separator, filtered and evaporated at reduced pressure. The crude product was purified by preparative SFC, PrepMethod SFC-G, (gradient: 20-25%), to give the title compound (17 mg, 15%); HRMS (ESI) m/z $[M+H]^+$ calcd for $C_{22}H_{18}F_2N_5O_2S$: 454.1144. found: 454.1140; $^1H$ NMR (600 MHz, DMSO-$d_6$) δ 9.29-9.17 (m, 2H), 9.05 (d, 1H), 8.92 (d, 1H), 8.56 (dd, 1H), 8.33

(dd, 1H), 8.25 (d, 1H), 7.88 (d, 1H), 7.65 (d, 1H), 7.05 (t, 1H), 5.39 (dd, 1H), 4.91 (d, 1H), 4.74 (d, 1H), 4.38 (t, 2H).

Example 170: (R)—N-(2-(4-Cyanothiazolidin-3-yl)-2-oxoethyl)-6-(1-cyclopropyl-1H-pyrazol-4-yl)quinoline-4-carboxamide

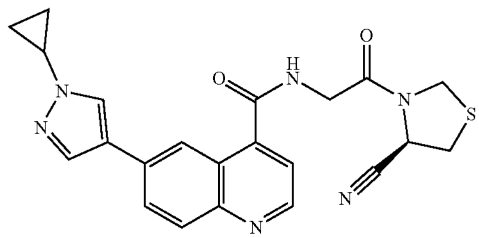 [SMILES: N#C[C@@H]1CSCN1C(=O)CNC(=O)c1ccnc2ccc(-c3cnn(C4CC4)c3)cc12]

DIPEA (1.42 mL, 8.13 mmol) was added to a suspension of 6-(1-cyclopropyl-1H-pyrazol-4-yl)quinoline-4-carboxylic acid Intermediate 327 (0.568 g, 2.03 mmol), (R)-3-glycylthiazolidine-4-carbonitrile hydrochloride Intermediate 4 (0.422 g, 2.03 mmol) and HATU (0.773 g, 2.03 mmol) in DCM (16 mL) and MeCN (4 mL), and the reaction mixture was stirred at rt overnight. The reaction mixture was diluted with EtOAc, and washed sequentially with sat $NaHCO_3$ (aq) and brine. The organic phase was dried, filtered and evaporated at reduced pressure, and the crude product was purified by preparative SFC, PrepMethod SFC-H, (gradient: 25-30%) to give the title compound (220 mg, 25%); HRMS (ESI) m/z $[M+H]^+$ calcd for $C_{22}H_{21}N_6O_2S$: 433.1442. found: 433.1454; $^1H$ NMR (600 MHz, DMSO-$d_6$) δ 9.10 (t, 1H), 8.95 (d, 1H), 8.53 (s, 1H), 8.36 (d, 1H), 8.27 (d, 1H), 8.13 (d, 1H), 7.98 (dd, 1H), 7.48 (d, 1H), 5.38 (dd, 1H), 4.90 (d, 1H), 4.73 (d, 1H), 4.33 (d, 2H), 3.79 (tt, 1H), 3.45-3.36 (m, overlapping with solvent), 1.15-1.11 (m, 2H), 1.05-0.99 (m, 2H).

Example 171: (R)—N-(2-(4-Cyanothiazolidin-3-yl)-2-oxoethyl)-6-(1,3-dimethyl-1H-pyrazol-4-yl)quinoline-4-carboxamide

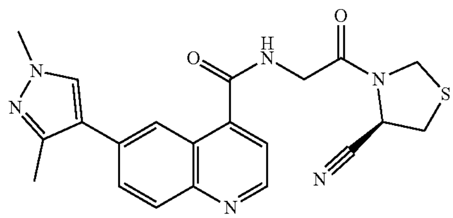 [SMILES: Cc1nn(C)cc1-c1ccc2nccc(C(=O)NCC(=O)N3CSC[C@H]3C#N)c2c1]

HATU (267 mg, 0.70 mmol) and DIPEA (0.294 mL, 1.68 mmol) were added to a suspension of 6-(1,3-dimethyl-1H-pyrazol-4-yl)quinoline-4-carboxylic acid Intermediate 328 (150 mg, 0.56 mmol) and (R)-3-glycylthiazolidine-4-carbonitrile hydrochloride Intermediate 4 (117 mg, 0.56 mmol) in EtOAc (3 mL) and MeCN (3 mL), and the reaction mixture was stirred at rt overnight. The reaction mixture was concentrated under reduced pressure and the crude product was purified by preparative HPLC, PrepMethod V, (gradient: 0-50%), to give the title compound (90 mg, 38%); HRMS (ESI) m/z $[M+H]^+$ calcd for $C_{21}H_{21}N_6O_2S$: 421.1442. found: 421.1456; $^1H$ NMR (600 MHz, DMSO-$d_6$) δ 9.12 (t, 1H), 8.92 (d, 1H), 8.45 (d, 1H), 8.14-8.06 (m, 2H), 7.94 (dd, 1H), 7.55 (d, 1H), 5.36 (dd, 1H), 4.91 (d, 1H), 4.73 (d, 1H), 4.34 (qd, 2H), 3.84 (s, 3H), 3.45-3.36 (m, overlapping with solvent), 2.40 (s, 3H).

Example 172: (R)—N-(2-(4-Cyanothiazolidin-3-yl)-2-oxoethyl)-6-(3,5-dimethyl-1-(tetrahydro-2H-pyran-4-yl)-1H-pyrazol-4-yl)quinoline-4-carboxamide

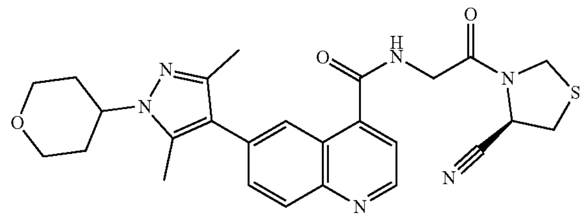 [SMILES: Cc1nn(C2CCOCC2)c(C)c1-c1ccc2nccc(C(=O)NCC(=O)N3CSC[C@H]3C#N)c2c1]

HATU (54 mg, 0.14 mmol) and DIPEA (60 µL, 0.34 mmol) were added to a suspension of 6-(3,5-dimethyl-1-(tetrahydro-2H-pyran-4-yl)-1H-pyrazol-4-yl)quinoline-4-carboxylic acid Intermediate 329 (40 mg, 0.11 mmol) and (R)-3-glycylthiazolidine-4-carbonitrile hydrochloride Intermediate 4 (24 mg, 0.11 mmol) in EtOAc (0.75 mL) and MeCN (0.75 mL), and the reaction mixture was stirred at rt overnight. The reaction mixture was concentrated under reduced pressure, and the residue was purified by preparative HPLC, PrepMethod F, (gradient: 5-95%), to give the title compound (15 mg, 26%); HRMS (ESI) m/z $[M+H]^+$ calcd for $C_{26}H_{29}N_6O_3S$: 505.2016. found: 505.2020; $^1H$ NMR (600 MHz, DMSO-$d_6$) δ 9.12 (t, 1H), 8.96 (d, 1H), 8.27 (d, 1H), 8.11 (d, 1H), 7.78 (dd, 1H), 7.56 (d, 1H), 5.31 (dd, 1H), 4.89 (d, 1H), 4.71 (d, 1H), 4.51-4.26 (m, 3H), 3.99 (dd, 2H), 3.49 (tt, 2H), 3.44-3.39 (m, overlapping with solvent), 2.35 (s, 3H), 2.23 (s, 3H), 2.08 (qt, 2H), 1.83 (tdd, 2H).

Example 173: (R)—N-(2-(4-Cyanothiazolidin-3-yl)-2-oxoethyl)-6-(1-(tetrahydro-2H-pyran-4-yl)-1H-pyrazol-4-yl)quinoline-4-carboxamide

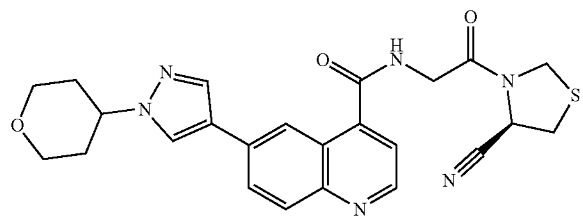 [SMILES: N#C[C@@H]1CSCN1C(=O)CNC(=O)c1ccnc2ccc(-c3cnn(C4CCOCC4)c3)cc12]

HATU (35 mg, 0.09 mmol) and DIPEA (0.039 mL, 0.22 mmol) were added to a suspension of 6-(1-(tetrahydro-2H-pyran-4-yl)-1H-pyrazol-4-yl)quinoline-4-carboxylic acid Intermediate 330 (24 mg, 0.07 mmol) and (R)-3-glycylthiazolidine-4-carbonitrile hydrochloride Intermediate 4 (15 mg, 0.07 mmol) in EtOAc (0.75 mL) and MeCN (0.75 mL), and the reaction mixture was stirred at rt overnight. The reaction mixture was concentrated under reduced pressure and the residue was purified by preparative SFC, PrepMethod SFC-G, (gradient: 0-50%) to give the title compound (11 mg, 31%); HRMS (ESI) m/z $[M+H]^+$ calcd for $C_{24}H_{25}N_6O_3S$: 477.1704. found: 477.1706; $^1H$ NMR (600 MHz, DMSO-$d_6$) δ 9.17 (t, 1H), 8.88 (d, 1H), 8.77 (d, 1H), 8.53 (s, 1H), 8.15-8.10 (m, 2H), 8.06 (d, 1H), 7.50 (d, 1H), 5.44 (dd, 1H), 4.94 (d, 1H), 4.75 (d, 1H), 4.52-4.44 (m, 1H), 4.38 (d, 2H), 4.05-3.95 (m, 2H), 3.54-3.39 (m, overlapping with solvent), 2.12-1.94 (m, 4H).

Example 174: (R)—N-(2-(4-Cyanothiazolidin-3-yl)-2-oxoethyl)-6-(1-methyl-1H-pyrazol-5-yl)quinoline-4-carboxamide

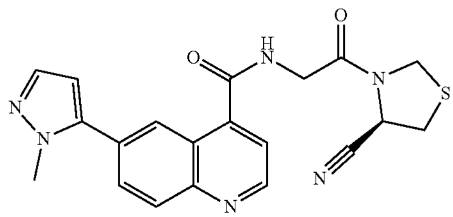 [SMILES: Cn1nccc1-c1ccc2nccc(C(=O)NCC(=O)N3CSC[C@H]3C#N)c2c1]

HATU (52 mg, 0.14 mmol) and DIPEA (0.058 mL, 0.33 mmol) were added to a suspension of 6-(1-methyl-1H-pyrazol-5-yl)quinoline-4-carboxylic acid Intermediate 331 (28 mg, 0.11 mmol) and (R)-3-glycylthiazolidine-4-carbonitrile hydrochloride Intermediate 4 (23 mg, 0.11 mmol) in EtOAc (0.7 mL) and MeCN (0.7 mL), and the reaction mixture was stirred at rt for 36 h. The reaction mixture was concentrated under reduced pressure and the crude product was purified by preparative SFC, PrepMethod SFC-H, (gradient: 22-27%) to give the title compound (16 mg, 36%); HRMS (ESI) m/z $[M+H]^+$ calcd for $C_{20}H_{19}N_6O_2S$: 407.1284. found: 407.1278; $^1H$ NMR (600 MHz, DMSO-$d_6$) δ 9.21 (t, 1H), 9.04 (d, 1H), 8.54 (brs, 1H), 8.20 (d, 1H), 8.00 (d, 1H), 7.64 (d, 1H), 7.54 (brs, 1H), 6.61 (brs, 1H), 5.36 (d, 1H), 4.90 (d, 1H), 4.72 (d, 1H), 4.34 (qd, 2H), 3.99 (s, 3H), 3.43-3.35 (m, overlapping with solvent).

Example 175: (R)—N-(2-(4-Cyanothiazolidin-3-yl)-2-oxoethyl)-6-(5,6,7,8-tetrahydroimidazo[1,2-a]pyridin-3-yl)quinoline-4-carboxamide

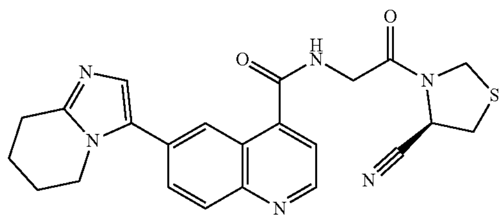 [SMILES: N#C[C@@H]1CSCN1C(=O)CNC(=O)c1ccnc2ccc(-c3cnc4n3CCCC4)cc12]

HATU (40 mg, 0.11 mmol) and DIPEA (0.045 mL, 0.26 mmol) were added to a suspension of 6-(5,6,7,8-tetrahydro-imidazo[1,2-c]pyridin-3-yl)quinoline-4-carboxylic acid Intermediate 333 (25 mg, 0.09 mmol) and (R)-3-glycylthiazolidine-4-carbonitrile hydrochloride Intermediate 4 (18 mg, 0.09 mmol) in EtOAc (0.5 mL) and MeCN (0.5 mL), and the reaction mixture was stirred at rt overnight. The reaction mixture was concentrated under reduced pressure, and the residue was purified by preparative SFC, PrepMethod SFC-H, (gradient: 27-32%), followed by preparative HPLC, PrepMethod N, (gradient: 5-45%) to give the title compound (5 mg, 13%): HRMS (ESI) m/z $[M+H]^+$ calcd for $C_{23}H_{23}N_6O_2S$: 447.1598. found: 447.1619; $^1H$ NMR (500 MHz, $CD_3OD$) δ 9.00 (d, 1H), 8.65 (s, 1H), 8.26 (s, 1H), 8.21 (d, 1H), 7.99 (d, 1H), 7.70 (d, 1H), 7.55 (s, 1H), 5.34-5.29 (m, 1H), 4.80-4.74 (m, overlapping with solvent), 4.51-4.21 (m, 4H), 3.52-3.33 (m, 2H), 3.07 (d, 2H), 2.18-2.02 (m, 4H).

Example 176: N-(2-((R)-4-Cyanothiazolidin-3-yl)-2-oxoethyl)-6-(14(RS)-tetrahydro-2H-pyran-2-yl)-1H-pyrazol-5-yl)quinoline-4-carboxamide

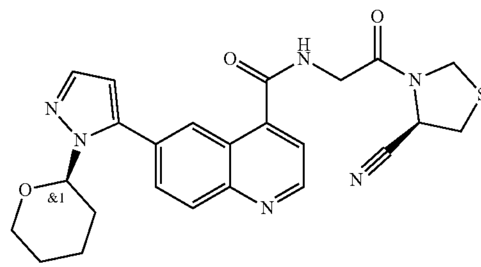

Step a) rac-(R)-6-(1-(Tetrahydro-2H-pyran-2-yl)-1H-pyrazol-5-yl)quinoline-4-carboxylic acid

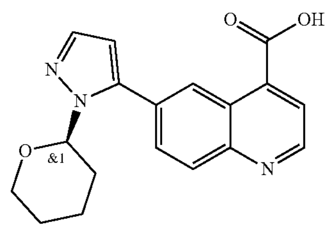 [SMILES: O=C(O)c1ccnc2ccc(-c3ccnn3[C@H]3CCCCO3)cc12]

A mixture of 1-(tetrahydro-2H-pyran-2-yl)-5-(4,4,5,5-tetramethyl-1,3,2-dioxaborolan-2-yl)-1H-pyrazole (77 mg, 0.28 mmol), 6-bromoquinoline-4-carboxylic acid (70 mg, mmol), $Cs_2CO_3$ (181 mg, 0.56 mmol) and Pd(dtbpf)$Cl_2$ (18 mg, 0.03 mmol) in 1,4-dioxane (1.5 mL) and water (0.37 mL) was stirred overnight. The reaction mixture was concentrated under reduced pressure to give the title compound (90 mg); MS (ESI) m/z $[M+H]^+$ 324.

Step b) N-(2-((R)-4-Cyanothiazolidin-3-yl)-2-oxoethyl)-6-(1-(tetrahydro-2H-pyran-2-yl)-1H-pyrazol-5-yl)quinoline-4-carboxamide HATU (132 mg, 0.35 mmol) and DIPEA (0.146 mL, 0.84 mmol) were added to a suspension of crude 6-(1-(tetrahydro-2H-pyran-2-yl)-1H-pyrazol-5-yl)quinoline-4-carboxylic acid (90 mg) and (R)-3-glycylthiazolidine-4-carbonitrile hydrochloride Intermediate 4 (58 mg, 0.28 mmol) in EtOAc (1 mL) and MeCN (1 mL), and the reaction mixture was stirred at rt overnight. The reaction mixture was concentrated under reduced pressure and the crude compound was purified by preparative SFC, PrepMethod SFC-C, (gradient: 27-32%), to give the title compound (74 mg, 56%); HRMS (ESI) m/z $[M+H]^+$ calcd for $C_{24}H_{25}N_6O_3S$: 477.1704. found: 477.1722; $^1H$ NMR (600 MHz, DMSO-$d_6$) δ 9.17 (t, 1H), 9.06 (d, 1H), 8.49 (s, 1H), 8.22 (d, 1H), 8.00-7.95 (m, 1H), 7.68-7.63 (m, 2H), 6.64 (dd, 1H), 5.35-

5.32 (m, 1H), 4.89 (dd, 1H), 4.72 (d, 1H), 4.40-4.27 (m, 2H), 4.04-3.97 (m, 1H), 3.58 (dt, 1H), 3.47-3.36 (m, overlapping with solvent), 2.48-2.37 (m, 1H), 1.94 (s, 1H), 1.85 (t, 1H), 1.63-1.47 (m, 3H).

Example 177: (R)—N-(2-(4-Cyanothiazolidin-3-yl)-2-oxoethyl)-6-(6-methylpyridin-3-yl)-quinoline-4-carboxamide

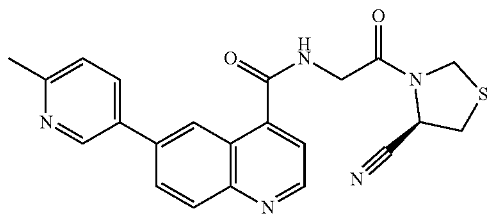 [SMILES: Cc1ccc(-c2ccc3nccc(C(=O)NCC(=O)N4CSC[C@H]4C#N)c3c2)cn1]

Step a) 6-(6-Methylpyridin-3-yl)quinoline-4-carboxylic acid

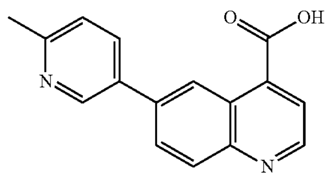 [SMILES: Cc1ccc(-c2ccc3nccc(C(=O)O)c3c2)cn1]

A mixture of 2-methyl-5-(4,4,5,5-tetramethyl-1,3,2-dioxaborolan-2-yl)pyridine (47 mg, 0.21 mmol), 6-bromoquinoline-4-carboxylic acid (54 mg, 0.21 mmol), $Cs_2CO_3$ (209 mg, 0.64 mmol) and Pd(dtbpf)$Cl_2$ (21 mg, 0.03 mmol) in 1,4-dioxane (1 mL) and water (0.25 mL) was stirred overnight. The reaction mixture was concentrated under reduced pressure to give the title compound (56 mg) as a crude; MS (ESI) m/z $[M+H]^+$ 263.

Step b) (R)—N-(2-(4-Cyanothiazolidin-3-yl)-2-oxoethyl)-6-(6-methylpyridin-3-yl)-quinoline-4-carboxamide HATU (101 mg, 0.26 mmol) and DIPEA (0.111 mL, 0.64 mmol) were added to a suspension of crude 6-(6-methylpyridin-3-yl)quinoline-4-carboxylic acid (56 mg) and (R)-3-glycylthiazolidine-4-carbonitrile hydrochloride Intermediate 4 (44 mg, 0, mmol) in EtOAc (1 mL) and MeCN (1 mL) and the solution was stirred at rt overnight. The reaction mixture was concentrated under reduced pressure and the crude product was purified by preparative HPLC, PrepMethod F, (gradient: 0-30%), to give the title compound (30 mg, 34%); HRMS (ESI) m/z $[M+H]^+$ calcd for $C_{22}H_{20}N_5O_2S$: 418.1332. found: 418.1328; $^1H$ NMR (600 MHz, DMSO-$d_6$) δ 9.20 (t, 1H), 9.01 (d, 1H), 8.96 (d, 1H), 8.78 (d, 1H), 8.26-8.17 (m, 3H), 7.62 (d, 1H), 7.42 (d, 1H), 5.38 (dd, 1H), 4.91 (d, 1H), 4.74 (d, 1H), 4.37 (d, 2H), 3.49-3.38 (m, overlapping with solvent), 2.55 (s, 3H).

Example 178: (R)—N-(2-(4-Cyanothiazolidin-3-yl)-2-oxoethyl)-6-(6-methoxypyridin-3-yl)quinoline-4-carboxamide

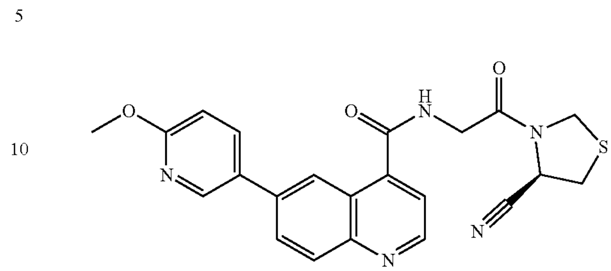

Step a) 6-(6-Methoxypyridin-3-yl)quinoline-4-carboxylic acid

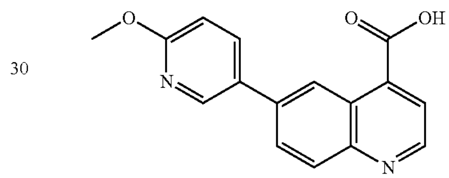

A mixture of 2-methoxy-5-(4,4,5,5-tetramethyl-1,3,2-dioxaborolan-2-yl)pyridine (49 mg, 0, mmol), 6-bromoquinoline-4-carboxylic acid (53 mg, 0.21 mmol), $Cs_2CO_3$ (206 mg, 0.63 mmol) and Pd(dtbpf)$Cl_2$ (21 mg, 0.03 mmol) in 1,4-dioxane (2 mL) and water (0.5 mL) was stirred overnight. The reaction mixture was evaporated at reduced pressure to give the crude title compound (58 mg); MS (ESI) m/z $[M+H]^+$ 281.

Step b) (R)—N-(2-(4-Cyanothiazolidin-3-yl)-2-oxoethyl)-6-(6-methoxypyridin-3-yl)quinoline-4-carboxamide HATU (98 mg, 0.26 mmol) and DIPEA (0.108 mL, 0.62 mmol) were added to a suspension of crude 6-(6-methoxypyridin-3-yl)quinoline-4-carboxylic acid (58 mg) and (R)-3-glycylthiazolidine-4-carbonitrile hydrochloride Intermediate 4 (43 mg, 0.21 mmol) in EtOAc (1 mL) and MeCN (1 mL), and the reaction mixture was stirred at rt overnight. The reaction mixture was concentrated under reduced pressure, and the crude product was purified by preparative SFC, PrepMethod SFC-C, (gradient: 25-30%), followed by PrepMethod SFC-E, (gradient: 20-25%), to give the title compound (23 mg, 25%); HRMS (ESI) m/z $[M+H]^+$ calcd for $C_{22}H_{20}N_5O_3S$: 434.1282. found: 434.1268; $^1H$ NMR (600 MHz, DMSO-$d_6$) δ 9.18 (t, 1H), 8.99 (d, 1H), 8.76 (d, 1H), 8.69 (d, 1H), 8.30 (dd, 1H), 8.26-8.15 (m, 2H), 7.60 (d, 1H), 7.00 (d, 1H), 5.38 (dd, 1H), 4.91 (d, 1H), 4.74 (d, 1H), 4.41-4.33 (m, 2H), 3.94 (s, 3H), 3.48-3.39 (m, overlapping with solvent).

Example 179: (R)-7-Chloro-N-(2-(4-cyanothiazolidin-3-yl)-2-oxoethyl)-6-morpholino-quinoline-4-carboxamide

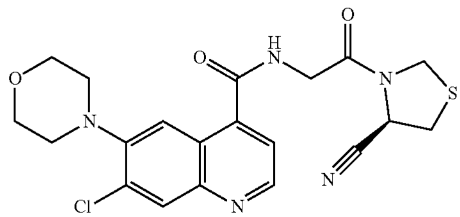 [SMILES: N#C[C@@H]1CSCN1C(=O)CNC(=O)c1ccnc2cc(Cl)c(N3CCOCC3)cc12]

DIPEA (107 μL, 0.61 mmol) was added to 7-chloro-6-morpholinoquinoline-4-carboxylic acid Intermediate 336 (60 mg, 0.20 mmol), (R)-3-glycylthiazolidine-4-carbonitrile hydrochloride Intermediate 4 (43 mg, 0.20 mmol) and T3P (521 mg, 0.82 mmol, 50% in EtOAc) in MeCN (5 mL) and EtOAc (5 ml), and the reaction mixture was stirred at for 3 h. The reaction mixture was concentrated under reduced pressure, diluted with EtOAc (50 mL), and washed sequentially with water (15 mL) and sat brine (15 mL). The organic layer was dried over $Na_2SO_4$, filtered and evaporated at reduced pressure. The crude product was purified by preparative HPLC, PrepMethod F, (gradient: 29-39%) to give the title compound (0.050 g, 55%) as a yellow solid; HRMS (ESI) m/z $[M+H]^+$ calcd for $C_{24}H_{21}ClN_5O_3S$: 446.1048. found: 446.1046; $^1H$ NMR (400 MHz, DMSO-$d_6$) δ 9.23-9.05 (m, 1H), 8.88 (d, 1H), 8.16 (s, 1H), 8.09 (s, 1H), 7.55 (d, 1H), 5.34 (dd, 1H), 4.90 (d, 1H), 4.72 (d, 1H), 4.41-4.27 (m, 2H), 3.81 (t, 4H), 3.45-3.34 (m, overlapping with solvent people), 3.20-3.05 (m, 4H).

Example 180: (R)-8-Chloro-N-(2-(4-cyanothiazolidin-3-yl)-2-oxoethyl)-6-morpholino-quinoline-4-carboxamide

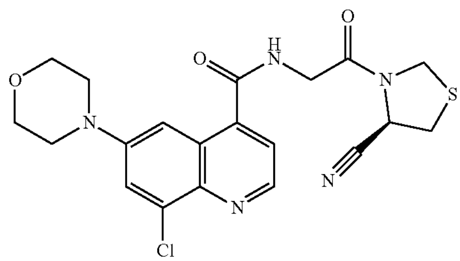 [SMILES: N#C[C@@H]1CSCN1C(=O)CNC(=O)c1ccnc2c(Cl)cc(N3CCOCC3)cc12]

A solution of T3P (608 mg, 0.96 mmol, 50% in EtOAc) in EtOAc (10 mL) was added to a stirred mixture of 8-chloro-6-morpholinoquinoline-4-carboxylic acid Intermediate 339 (70 mg, 0.24 mmol) and (R)-3-glycylthiazolidine-4-carbonitrile hydrochloride, Intermediate 4 (50 mg, 0.24 mmol) in MeCN (10 mL) at 20° C., and the reaction mixture was stirred at 25° C. for 3 h. The reaction mixture was concentrated under reduced pressure, diluted with EtOAc (50 mL), and washed sequentially with sat brine (20 mL) and water (15 mL). The organic layer was dried over $Na_2SO_4$, filtered and evaporated at reduced pressure. The crude product was purified by preparative HPLC, PrepMethod R, (gradient: 19-39%) to give the title compound (0.060 g, 56%) as a yellow solid; HRMS (ESI) m/z $[M+H]^+$ calcd for $C_{20}H_{21}ClN_5O_3S$: 446.1048. found: 446.1026; $^1H$ NMR (400 MHz, DMSO-$d_6$) δ 9.07 (t, 1H), 8.79 (d, 1H), 7.91 (d, 1H), 7.71 (d, 1H), 7.50 (d, 1H), 5.31 (dd, 1H), 4.89 (d, 1H), 4.70 (d, 1H), 4.39-4.22 (m, 2H), 3.78 (t, 4H), 3.45-3.34 (m, overlapping with solvent).

Example 181: (R)-6-(3-(Acetamidomethyl)-3-methylazetidin-1-yl)-N-(2-(4-cyano-thiazolidin-3-yl)-2-oxoethyl)quinoline-4-carboxamide

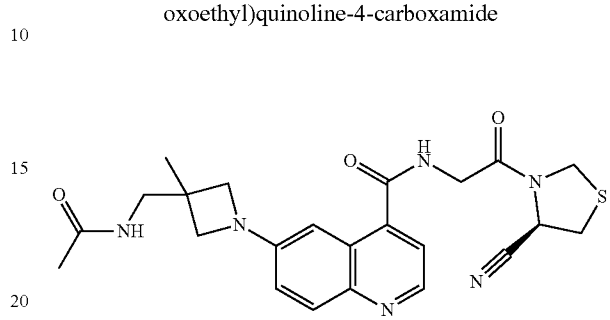

(R)-3-Glycylthiazolidine-4-carbonitrile hydrochloride Intermediate 4 (32 mg, 0.15 mmol) was added to a mixture of 6-(3-(acetamidomethyl)-3-methylazetidin-1-yl)quinoline-4-carboxylic acid Intermediate 341 (40 mg), HATU (73 mg, 0.19 mmol) and DIPEA (89 μL, 0.51 mmol) in MeCN (1.5 mL) and EtOAc (1.5 mL), and the reaction mixture was stirred at rt overnight. DCM (10 mL) and $NaHCO_3$(7 mL, aq) were added and the reaction mixture was filtered through a phase separator and evaporated under reduced pressure. The crude compound was purified by preparative HPLC, PrepMethod F, (gradient to give the title compound (3 mg, 6%); HRMS (ESI) m/z $[M+H]^+$ calcd for $C_{23}H_{27}N_6O_3S$: 467.1860. found: 467.1818; $^1H$ NMR (600 MHz, DMSO-$d_6$) δ 8.89 (t, 1H), 8.57 (d, 1H), 7.98 (t, 1H), 7.83 (d, 1H), 7.37 (d, 1H), 7.07-7.01 (m, 2H), 5.33-5.25 (m, 1H), 4.84 (d, 1H), 4.68 (d, 1H), 4.31-4.21 (m, 2H), 3.74 (dd, 2H), 3.52 (d, 2H), 3.45-3.30 (m, overlapping with solvent), 3.25 (d, 2H), 1.79 (s, 3H), 1.23 (s, 3H).

Example 182: (R)—N-(2-(4-Cyanothiazolidin-3-yl)-2-oxoethyl)-6-(3-fluoro-3-phenyl-azetidin-1-yl)quinoline-4-carboxamide

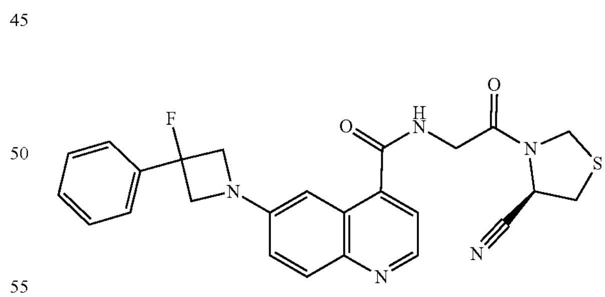

6-(3-Fluoro-3-phenylazetidin-1-yl)quinoline-4-carboxylic acid Intermediate 343 (22 mg, 0.07 mmol), HATU (39 mg, 0.10 mmol) and DIPEA (48 μL, 0.27 mmol) were mixed in MeCN (1 mL) and EtOAc (1 mL). (R)-3-Glycylthiazolidine-4-carbonitrile hydrochloride Intermediate 4 (17 mg, 0.08 mmol) was added and the reaction mixture was stirred at rt for 1 h. DCM (8 mL) and $NaHCO_3$ (5 mL, aq) were added, and the reaction mixture was stirred, filtered through a phase separator and evaporated under reduced pressure. The crude compound was purified by preparative SFC, PrepMethod SFC-E, (gradient: 30-35%), to give the title compound (2.4 mg, 7%); HRMS (ESI) m/z $[M+H]^+$ calcd for $C_{25}H_{23}FN_5O_2S$: 476.1550. found: 476.1560.

Example 183: (R)—N-(2-(4-Cyanothiazolidin-3-yl)-2-oxoethyl)-6-(3-(p-tolyl)azetidin-1-yl)quinoline-4-carboxamide

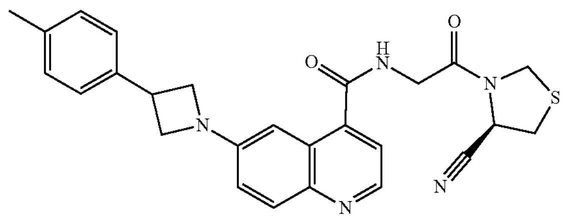 [SMILES: Cc1ccc(C2CN(c3ccc4nccc(C(=O)NCC(=O)N5CSC[C@H]5C#N)c4c3)C2)cc1]

6-(3-(p-Tolyl)azetidin-1-yl)quinoline-4-carboxylic acid Intermediate 345 (18 mg, 0.06 mmol), HATU (32 mg, 0.08 mmol) and DIPEA (40 μL, 0.23 mmol) were mixed in MeCN (0.5 mL) and EtOAc (0.5 mL). (R)-3-Glycylthiazolidine-4-carbonitrile hydrochloride Intermediate 4 (14 mg, 0.07 mmol) was added and the reaction mixture was stirred at rt for 1 h. DCM (5 mL) and $NaHCO_3$ (5 mL, aq) were added, and the reaction mixture was stirred, filtered through a phase separator, and evaporated under reduced pressure. The compound was purified by preparative HPLC, PrepMethod F, (gradient 5-95%) to give the title compound (85 mg, 32%); HRMS (ESI) m/z $[M+H]^+$ calcd for $C_{26}H_{26}N_5O_2S$: 472.1802. found: 472.1800; $^1H$ NMR (600 MHz, DMSO-$d_6$) δ 8.93 (t, 1H), 8.60 (d, 1H), 7.87 (d, 1H), 7.37 (d, 1H), 7.27-7.22 (m, 3H), 7.16-7.11 (m, 3H), 5.28 (dd, 1H), 4.84 (d, 1H), 4.67 (d, 1H), 4.37 (t, 2H), 4.25 (d, 2H), 3.99-3.85 (m, 3H), 3.35-3.25 (m, overlapping with water), 2.25 (s, 3H).

Example 184: (R)-6-(6-Acetyl-2,6-diazaspiro[3.3]heptan-2-yl)-N-(2-(4-cyanothiazolidin-3-yl)-2-oxoethyl)quinoline-4-carboxamide

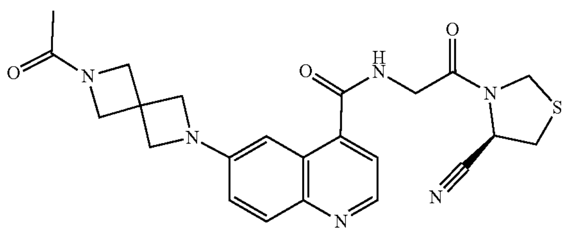 [SMILES: CC(=O)N1CC2(C1)CN(c1ccc3nccc(C(=O)NCC(=O)N4CSC[C@H]4C#N)c3c1)C2]

6-(6-Acetyl-2,6-diazaspiro[3.3]heptan-2-yl)quinoline-4-carboxylic acid Intermediate 347 (90 mg, 0.29 mmol), HATU (165 mg, 0.43 mmol) and DIPEA (202 μL, 1.16 mmol) were mixed in MeCN (2 mL) and EtOAc (2 mL). (R)-3-Glycylthiazolidine-4-carbonitrile hydrochloride Intermediate 4 (72 mg, 0.35 mmol) was added and the reaction mixture was stirred at rt for 3 h. DCM (15 mL) and $NaHCO_3$ (15 mL, aq) were added and the reaction mixture was stirred, filtered through a phase separator and evaporated under reduced pressure. The crude compound was purified by preparative HPLC, PrepMethod F, (gradient 5-95%), to give the title compound (37 mg, 28%); HRMS (ESI) m/z $[M+H]^+$ calcd for $C_{23}H_{25}N_6O_3S$: 465.1704. found: 465.1692; $^1H$ NMR (600 MHz, DMSO-$d_6$) δ 8.90 (t, 1H), 8.60 (d, 1H), 7.85 (d, 1H), 7.38 (d, 1H), 7.16 (d, 1H), 7.08 (dd, 1H), 5.31 (dd, 1H), 4.85 (d, 1H), 4.68 (d, 1H), 4.27 (s, 4H), 4.06 (s, 4H), 4.00 (s, 2H), 3.39-3.30 (m, 2H), δ 1.72 (s, 3H).

Example 185: (R)—N-(2-(4-Cyanothiazolidin-3-yl)-2-oxoethyl)-6-(3-(4-fluorophenyl)-azetidin-1-yl)quinoline-4-carboxamide

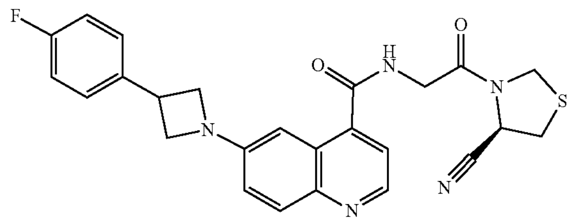 [SMILES: N#C[C@@H]1CSCN1C(=O)CNC(=O)c1ccnc2ccc(N3CC(c4ccc(F)cc4)C3)cc12]

6-(3-(4-Fluorophenyl)azetidin-1-yl)quinoline-4-carboxylic acid Intermediate 349 (80 mg, 0.25 mmol), HATU (142 mg, 0.37 mmol) and DIPEA (173 μL, 0.99 mmol) were mixed in MeCN (2 mL) and EtOAc (2 mL). (R)-3-Glycylthiazolidine-4-carbonitrile hydrochloride Intermediate 4 (62 mg, 0.30 mmol) was added and the reaction mixture was stirred at rt for 3 h. DCM (15 mL) and $NaHCO_3$ (15 mL, aq) were added, and the reaction mixture was stirred, filtered through a phase separator and evaporated under reduced pressure. The crude compound was purified by preparative HPLC, PrepMethod F, (gradient 5-95%) to give the title compound (60 mg, 51%); HRMS (ESI) m/z $[M+H]^+$ calcd for $C_{25}H_{23}FN_5O_2S$: 476.1550. found: 476.1550; $^1H$ NMR (600 MHz, DMSO-$d_6$) δ 8.97 (t, 1H), 8.64 (d, 1H), 7.90 (d, 1H), 7.46-7.38 (m, 3H), 7.28 (d, 1H), 7.20-7.11 (m, 3H), 5.28 (dd, 1H), 4.84 (d, 1H), 4.67 (d, 1H), 4.39 (t, 2H), 4.27 (d, 2H), 4.00 (p, 1H), 3.91 (dq, 2H), 3.37-3.27 (m, 2H).

Example 186: (R)—N-(2-(4-Cyanothiazolidin-3-yl)-2-oxoethyl)-6-(3-(m-tolyl)azetidin-1-yl)quinoline-4-carboxamide

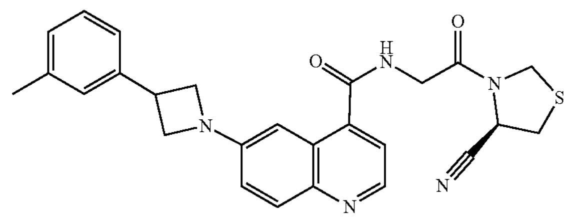 [SMILES: Cc1cccc(C2CN(c3ccc4nccc(C(=O)NCC(=O)N5CSC[C@H]5C#N)c4c3)C2)c1]

6-(3-(m-Tolyl)azetidin-1-yl)quinoline-4-carboxylic acid Intermediate 351 (90 mg, 0.28 mmol), HATU (161 mg, 0.42 mmol) and DIPEA (197 μL, 1.13 mmol) were mixed in MeCN (2 mL) and EtOAc (2 mL). (R)-3-Glycylthiazolidine-4-carbonitrile hydrochloride Intermediate 4 (70 mg, 0.34 mmol) was added and the reaction mixture was stirred at rt for 3 h. DCM (15 mL) and $NaHCO_3$ (15 mL, aq) were added, and the reaction mixture was stirred, filtered through a phase separator and evaporated under reduced pressure. The compound was purified by preparative HPLC, PrepMethod F, (gradient 5-95%) to give the title compound (58 mg, 51%); HRMS (ESI) m/z $[M+H]^+$ calcd for $C_{26}H_{26}N_5O_2S$: 472.1802. found: 472.1792: 471.18; $^1H$ NMR (600 MHz, DMSO-$d_6$) δ 8.97 (t, 1H), 8.64 (d, 1H), 7.89 (d, 1H), 7.43 (d, 1H), 7.27 (d, 1H), 7.23-7.12 (m, 4H), 7.03 (d, 1H), 5.28 (dd, 1H), 4.84 (d, 1H), 4.67 (d, 1H), 4.38 (t, 2H), 4.27 (d, 2H), 3.99-3.88 (m, 3H), 3.37-3.26 (m, 2H), 2.27 (s, 3H).

Example 187: (R)-6-(3-(4-Chlorobenzyl)azetidin-1-yl)-N-(2-(4-cyanothiazolidin-3-yl)-2-oxoethyl)quinoline-4-carboxamide

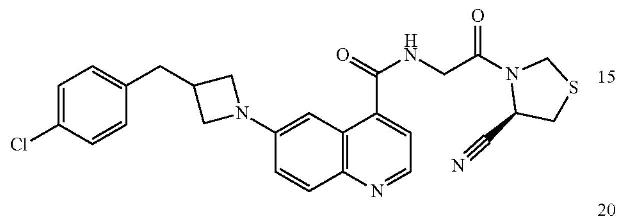

6-(3-(4-Chlorobenzyl)azetidin-1-yl)quinoline-4-carboxylic acid Intermediate 353 (80 mg, 0.23 mmol), HATU (129 mg, 0.34 mmol) and DIPEA (158 μL, 0.91 mmol) were mixed in MeCN (2 mL) and EtOAc (2 mL). (R)-3-Glycylthiazolidine-4-carbonitrile hydrochloride Intermediate 4 (56 mg, 0.27 mmol) was added and the reaction mixture was stirred at rt for 3 h. DCM (15 mL) and $NaHCO_3$ (15 mL, aq) were added, and the reaction mixture was stirred, filtered through a phase separator and evaporated under reduced pressure. The crude compound was purified by preparative HPLC, PrepMethod F, (gradient 5-95%) to give the title compound (18 mg, 16%); HRMS (ESI) m/z $[M+H]^+$ calcd for $C_{26}H_{25}ClN_5O_2S$: 506.1412. found: 506.1428; $^1H$ NMR (600 MHz, DMSO-$d_6$) δ 8.89 (t, 1H), 8.57 (d, 1H), 7.82 (d, 1H), 7.36 (d, 1H), 7.33-7.29 (m, 2H), 7.25 (d, 2H), 7.11-7.03 (m, 2H), 5.27-5.21 (m, 1H), 4.82 (d, 1H), 4.66 (d, 1H), 4.24 (d, 2H), 3.99 (q, 2H), 3.66-3.59 (m, 2H), 3.35-3.28 (m, 2H), 2.99 (dt, 1H), 2.90 (d, 2H).

Example 188: (R)—N-(2-(4-Cyanothiazolidin-3-yl)-2-oxoethyl)-6-(3-methyl-3-((methylsulfonyl)methyl)azetidin-1-yl)quinoline-4-carboxamide

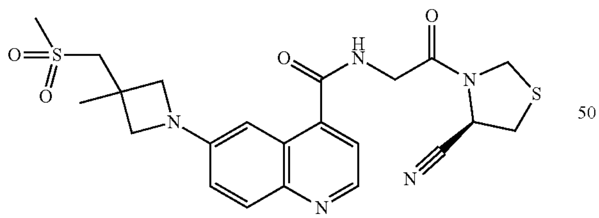

6-(3-Methyl-3-((methylsulfonyl)methyl)azetidin-1-yl)quinoline-4-carboxylic acid Intermediate 355 (55 mg, 0.16 mmol), HATU (94 mg, 0.25 mmol) and DIPEA (115 μL, 0.66 mmol) were mixed in MeCN (1.5 mL) and EtOAc (1.5 mL). (R)-3-Glycylthiazolidine-4-carbonitrile hydrochloride Intermediate 4 (41 mg, 0.20 mmol) was added and the reaction mixture was stirred at rt overnight. DCM (10 mL) and $NaHCO_3$(7 mL, aq) were added, and the reaction mixture was stirred, filtered through a phase separator, and evaporated under reduced pressure. The crude compound was purified by preparative SFC, PrepMethod SFC-E, (gradient 35-40%), to give the title compound (19 mg, 24%);

HRMS (ESI) m/z $[M+H]^+$ calcd for $C_{22}H_{26}N_5O_4S_2$: 488.1420. found: 488.1442; $^1H$ NMR (600 MHz, DMSO-$d_6$) δ 8.89 (t, 1H), 8.59 (d, 1H), 7.84 (d, 1H), 7.38 (d, 1H), 7.08 (dd, 2H), 5.28 (dd, 1H), 4.83 (d, 1H), 4.67 (d, 1H), 4.29-4.21 (m, 2H), 3.94 (d, 2H), 3.71 (d, 2H), 3.59 (s, 2H), 2.98 (s, 3H), 3.35-3.25 (m, overlapping with solvent), 1.56 (s, 3H).

Example 189: (R)—N-(2-(4-Cyanothiazolidin-3-yl)-2-oxoethyl)-6-(4-ethyl-4-hydroxy-piperidin-1-yl)quinoline-4-carboxamide

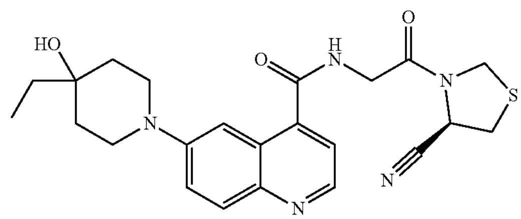 [SMILES: CCC1(O)CCN(c2ccc3nccc(C(=O)NCC(=O)N4CSC[C@H]4C#N)c3c2)CC1]

DIPEA (262 μL, 1.50 mmol) was added to a stirred suspension of 6-(4-ethyl-4-hydroxypiperidin-1-yl)quinoline-4-carboxylic acid Intermediate 357 (90 mg, 0.30 mmol), (R)-3-glycylthiazolidine-4-carbonitrile hydrochloride Intermediate 4 (124 mg, 0.60 mmol), HOBt (121 mg, 0.90 mmol) and EDC (172 mg, 0.90 mmol) in MeCN (5 mL) and EtOAc (5 mL) at 28° C. and the reaction mixture was stirred at 50° C. for 2 h. The reaction mixture was concentrated under reduced pressure and further diluted with sat $NaHCO_3$ (30 mL, aq) and EtOAc (100 mL). The aq layer was extracted with EtOAc (4×50 mL) and the combined organic layers was dried over $Na_2SO_4$, filtered and evaporated. The crude product was purified by preparative HPLC, PrepMethod F (gradient: 13-23%) to give the title compound (0.089 g, 64%) as a yellow solid; HRMS (ESI) m/z $[M+H]^+$ calcd for $C_{23}H_{28}N_5O_3S$: 454.1908. found: 454.1926; $^1H$ NMR (300 MHz, DMSO-$d_6$) δ 8.99 (t, 1H), 8.64 (d, 1H), 7.86 (d, 1H), 7.70-7.60 (m, 2H), 7.39 (d, 1H), 5.40-5.23 (m, 1H), 4.89 (d, 1H), 4.71 (d, 1H), 4.29 (d, 2H), 4.13 (brs, 1H), 3.67-3.51 (m, 2H), 3.50-3.15 (m, overlapping with solvent), 1.63-1.54 (m, 4H), 1.41 (q, 2H), 0.86 (t, 3H).

Example 190: (R)—N-(2-(4-Cyanothiazolidin-3-yl)-2-oxoethyl)-6-(4-hydroxy-4-methyl-piperidin-1-yl)quinoline-4-carboxamide

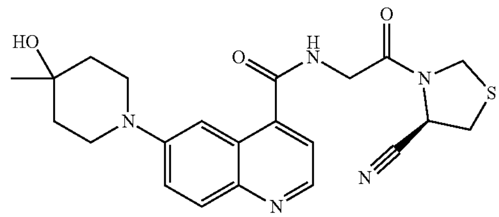 [SMILES: CC1(O)CCN(c2ccc3nccc(C(=O)NCC(=O)N4CSC[C@H]4C#N)c3c2)CC1]

DIPEA (183 μL, 1.05 mmol) was added to a stirred suspension of 6-(4-hydroxy-4-methylpiperidin-1-yl)quinoline-4-carboxylic acid Intermediate 359 (90 mg, 0.30 mmol), (R)-3-glycylthiazolidine-4-carbonitrile hydrochloride (109 mg, 0.52 mmol) Intermediate 4, HOBt (80 mg, 0.52 mmol) and EDC (100 mg, 0.52 mmol) in MeCN (5 mL)

and EtOAc (5 mL) at 28° C. and the reaction mixture was stirred at 50° C. for 2 h. The reaction mixture was concentrated under reduced pressure and was further diluted with EtOAc, and washed sequentially with $H_2O$. The organic layer was dried over $Na_2SO_4$, filtered and evaporated. The residue was purified by preparative HPLC, PrepMethod C (gradient: 10-16%) to give the title compound (0.075 g, 44%) as a yellow solid; HRMS (ESI) m/z $[M+H]^+$ calcd for $C_{22}H_{26}N_5O_3S$: 440.1750. found: 440.1760; $^1H$ NMR (300 MHz, $CD_3OD$) δ 8.61 (d, 1H), 7.90 (d, 1H), 7.75-7.63 (m, 2H), 7.50 (d, 1H), 5.34 (dd, 1H), 4.86-4.73 (m, 2H), 4.38 (d, 2H), 3.68-3.56 (m, 2H), 3.52-3.34 (m, overlapping with solvent), 1.85-1.65 (m, 4H), 1.26 (s, 3H).

Example 191: (R)—N-(2-(4-Cyanothiazolidin-3-yl)-2-oxoethyl)-6-(4-ethyl-4-methoxy-piperidin-1-yl)quinoline-4-carboxamide

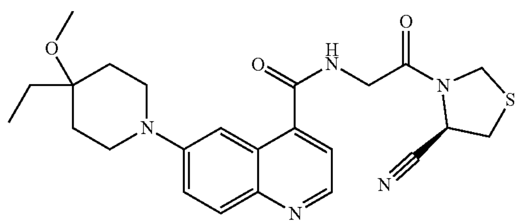 [SMILES: CCC1(OC)CCN(c2ccc3nccc(C(=O)NCC(=O)N4CSC[C@H]4C#N)c3c2)CC1]

DIPEA (142 μL, 0.81 mmol) was added to a stirred suspension of 6-(4-ethyl-4-methoxypiperidin-1-yl)quinoline-4-carboxylic acid Intermediate 361 (85 mg, 0.27 mmol), (R)-3-glycylthiazolidine-4-carbonitrile hydrochloride (84 mg, 0.41 mmol) Intermediate 4, HOBt (62 mg, 0.41 mmol) and EDC (78 mg, 0.41 mmol) in MeCN (5 mL) and EtOAc (5 mL) at 28° C. and the reaction mixture was stirred at 50° C. for 2 h. The reaction mixture was concentrated under reduced pressure and was further diluted with EtOAc (20 mL), and washed sequentially with $H_2O$ (2×15 mL). The organic layer was dried over $Na_2SO_4$, filtered and evaporated. The residue was purified by preparative HPLC, PrepMethod C, (gradient 20-31%) to give the title compound (0.075 g, 59%) as a yellow solid; HRMS (ESI) m/z $[M+H]^+$ calcd for $C_{24}H_{30}N_5O_3S$: 468.2064. found: 468.2066; $^1H$ NMR (400 MHz, $CD_3OD$) δ 8.62 (d, 1H), 7.90 (d, 1H), 7.75 (d, 1H), 7.68 (dd, 1H), 7.49 (d, 1H), 5.33 (dd, 1H), 4.85 (d, 1H), 4.77 (d, 1H), 4.39 (d, 2H), 3.75-3.63 (m, 2H), 3.51-3.32 (m, overlapping with solvent), 3.25-3.10 (m, 4H), 1.98-1.88 (m, 2H), 1.70 −1.50 (m, 4H), 0.88 (t, 3H).

Example 192: (R)—N-(2-(4-Cyanothiazolidin-3-yl)-2-oxoethyl)-6-(4-hydroxy-4-isopropyl-piperidin-1-yl)quinoline-4-carboxamide

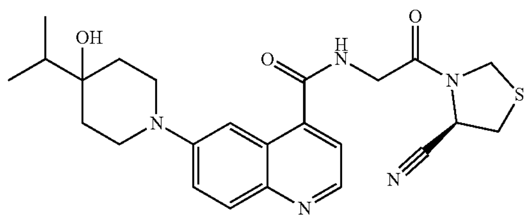 [SMILES: CC(C)C1(O)CCN(c2ccc3nccc(C(=O)NCC(=O)N4CSC[C@H]4C#N)c3c2)CC1]

DIPEA (389 μL, 2.23 mmol) was added to a stirred suspension of 6-(4-hydroxy-4-isopropylpiperidin-1-yl)quinoline-4-carboxylic acid Intermediate 363 (140 mg, 0.45 mmol), (R)-3-glycylthiazolidine-4-carbonitrile hydrochloride (185 mg, 0.89 mmol) Intermediate 4, HOBt (181 mg, 1.34 mmol) and EDC (256 mg, 1.34 mmol) in MeCN (5 mL) and EtOAc (5 mL) at 28° C. and the reaction mixture was stirred at 50° C. for 2 h. The reaction mixture was concentrated under reduced pressure and was further diluted with EtOAc (100 mL) and sat $NaHCO_3$ (30 mL, aq). The aq layer was extracted with EtOAc (4×50 mL). The organic layers were combined and washed with $H_2O$ (3×25 mL). The organic layer was dried over $Na_2SO_4$, filtered and evaporated. The residue was purified by preparative HPLC, PrepMethod F (gradient 18-28%) to give the title compound (0.12 g, 58%) as a yellow solid; HRMS (ESI) m/z $[M+H]^+$ calcd for $C_{24}H_{30}N_5O_3S$: 468.2064. found: 468.2068; $^1H$ NMR (300 MHz, DMSO-$d_6$) δ 8.99 (t, 1H), 8.65 (d, 1H), 7.86 (d, 1H), 7.70-7.59 (m, 2H), 7.39 (d, 1H), 5.40-5.25 (m, 1H), 4.89 (d, 1H), 4.71 (d, 1H), 4.30 (d, 2H), 4.00 (brs, 1H), 3.80-3.60 (m, 2H), 3.50-3.34 (m, overlapping with solvent), 3.21-3.08 (m, 2H), 1.68-1.45 (m, 5H), 0.86 (d, 6H).

Example 193: N-(2-((R)-4-Cyanothiazolidin-3-yl)-2-oxoethyl)-6-((3R,4S,5S)-4-hydroxy-3,4,5-trimethylpiperidin-1-yl)quinoline-4-carboxamide

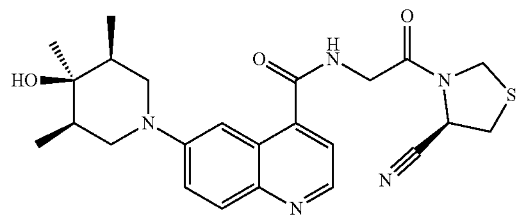 [SMILES: C[C@@H]1CN(c2ccc3nccc(C(=O)NCC(=O)N4CSC[C@H]4C#N)c3c2)C[C@H](C)[C@]1(C)O]

DIPEA (194 μL, 1.11 mmol) was added to a stirred suspension of 6-((3R,4s,5S)-4-hydroxy-3,4,5-trimethylpiperidin-1-yl)quinoline-4-carboxylic acid Intermediate 367 (70 mg, 0.22 mmol), (R)-3-glycylthiazolidine-4-carbonitrile hydrochloride (92 mg, 0.45 mmol) Intermediate 4, HOBt (90 mg, 0.67 mmol) and EDC (128 mg, 0.67 mmol) in MeCN (5 mL) and EtOAc (5 mL) at 25° C. and the reaction mixture was stirred at 25° C. for 15 h. The reaction mixture was concentrated under reduced pressure and was further diluted with EtOAc (100 mL) and sat $NaHCO_3$ (20 mL, aq). The aq layer was extracted with EtOAc (4×75 mL). The organic layers were combined and washed with $H_2O$ (3×25 mL). The organic layer was dried over $Na_2SO_4$, filtered and evaporated. The residue was purified by preparative HPLC, PrepMethod C, (gradient 15-25%) to give the title compound (0.078 g, 75%) as a yellow solid; HRMS (ESI) m/z $[M+H]^+$ calcd for $C_{24}H_{30}N_5O_3S$: 468.2064. found: 468.2072; $^1$NMR (300 MHz, DMSO-$d_6$) δ 8.98 (t, 1H), 8.61 (d, 1H), 7.83 (d, 1H), 7.68-7.58 (m, 2H), 7.34 (d, 1H), 5.80-5.22 (m, 1H), 4.87 (d, 1H), 4.70 (d, 1H), 4.27 (d, 2H), 4.00 (s, 1H), 3.65-3.45 (m, 2H), 3.44-3.34 (m, overlapping with solvent), 2.79 (t, 2H), 1.74-1.50 (m, 2H), 1.07 (s, 3H), 1.00-0.85 (m, 6H).

Example 194: 6-((1R,5S)-9-Oxa-3-azabicyclo[3.3.1]nonan-3-yl)-N-(2-((R)-4-cyano-thiazolidin-3-0)-2-oxoethyl)quinoline-4-carboxamide

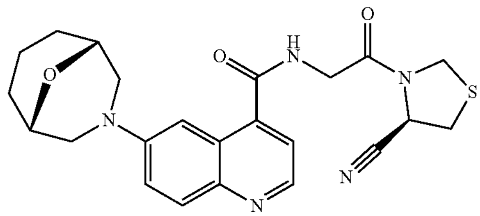 [SMILES: N#C[C@@H]1CSCN1C(=O)CNC(=O)c1ccnc2ccc(N3C[C@H]4CCC[C@@H](C3)O4)cc12]

HATU (0.110 g, 0.29 mmol) was added to a stirred mixture of 6-((1R,5S)-9-oxa-3-azabicyclo[3.3.1]nonan-3-yl)quinoline-4-carboxylic acid Intermediate 369 (0.098 g, 0.24 mmol) and DIPEA (0.210 mL, 1.20 mmol) in a mixture of MeCN (1.1 mL) and EtOAc (1.1 mL) at rt. The reaction was stirred for 1 min after which Intermediate 4 (R)-3-glycylthiazolidine-4-carbonitrile hydrochloride (0.060 g, 0.29 mmol) was added. The reaction was stirred for 1 h at rt. The reaction mixture was diluted with EtOAc (15 mL) and washed with sat $NaHCO_3$(8 mL, aq) followed by $H_2O$ (2×2 mL). The organic layer was dried over $Na_2SO_4$, filtered and concentrated. The residue was purified by flash chromatography (EtOAc:MeOH, gradient: 0% then 10%). The residue was further purified by preparative HPLC, PrepMethod G (gradient 5-35%) to give the title compound (0.053 g, 49%) as an orange solid; HRMS (ESI) m/z $[M+H]^+$ calcd for $C_{23}H_{26}N_5O_3S$: 452.1750. found: 452.1746; NMR (500 MHz, DMSO-$d_6$) δ 9.03 (t, 1H), 8.66 (d, 1H), 7.91 (d, 1H), 7.73-7.65 (m, 2H), 7.39 (d, 1H), 5.28-5.32 (m, 1H), 4.90 (d, 1H), 4.70 (d, 1H), 4.37-4.25 (m, 2H), 4.08-4.02 (m, 2H), 3.89 (d, 2H), 3.44-3.37 (m, 2H), 3.18-3.10 (m, 2H), 2.37-2.23 (m, 1H), 2.00 –1.89 (m, 2H), 1.84 –1.75 (m, 2H), 1.58-1.44 (m, 1H).

Example 195: (R)—N-(2-(4-Cyanothiazolidin-3-yl)-2-oxoethyl)-6-(4-fluoro-1-methyl-piperidin-4-yl)quinoline-4-carboxamide

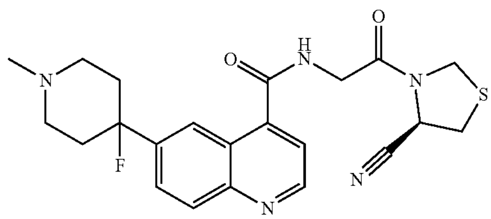 [SMILES: CN1CCC(F)(c2ccc3nccc(C(=O)NCC(=O)N4CSC[C@H]4C#N)c3c2)CC1]

DIPEA (200 μL, 1.14 mmol) was added to a stirred suspension of 6-(4-fluoro-1-methylpiperidin-4-yl)quinoline-4-carboxylic acid Intermediate 373 (110 mg, 0.38 mmol), (R)-3-glycylthiazolidine-4-carbonitrile hydrochloride (119 mg, 0.57 mmol) Intermediate 4, HOBt (88 mg, 0.57 mmol) and EDC (110 mg, 0.57 mmol) in MeCN (6 mL) and EtOAc (6 mL) at 25° C. and the reaction mixture was stirred at 50° C. for 2 h. The solvent was removed under reduced pressure. The reaction mixture was diluted with EtOAc and washed sequentially with $H_2O$. The organic layer was dried over $Na_2SO_4$, filtered and evaporated. The residue was purified by preparative HPLC, PrepMethod I (gradient 24-33%). The residue was further purified by preparative SFC, PrepMethod SFC-B to give the title compound (0.025 g, 15%) as a white solid; HRMS (ESI) m/z $[M+H]^+$ calcd for $C_{22}H_{25}FN_5O_2S$: 442.1708. found: 442.1698; $^1$H NMR (400 MHz, $CD_3OD$) δ 8.97 (d, 1H), 8.52 (s, 1H), 8.15 (d, 1H), 7.95 (dd, 1H), 7.71 (d, 1H), 5.68-5.38 (m, 1H), 4.87-4.72 (m, 2H), 4.52-4.36 (m, 2H), 3.57-3.35 (m, 2H), 3.00-2.83 (m, 2H), 2.65-2.50 (t, 2H), 2.49-2.36 (m, 5H), 2.25-2.06 (m, 2H).

Example 196: (R)—N-(2-(4-Cyanothiazolidin-3-yl)-2-oxoethyl)-6-(1H-pyrazol-5-yl)-quinoline-4-carboxamide

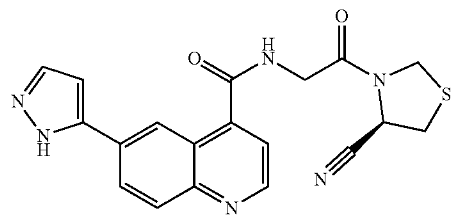 [SMILES: N#C[C@@H]1CSCN1C(=O)CNC(=O)c1ccnc2ccc(-c3ccn[nH]3)cc12]

To a suspension of 6-(1H-pyrazol-5-yl)quinoline-4-carboxylic acid Intermediate 374 (32 mg, 0.13 mmol) and (R)-3-glycylthiazolidine-4-carbonitrile hydrochloride Intermediate 4 (28 mg, 0.13 mmol) in EtOAc (0.7 mL) and MeCN (0.7 mL) was added HATU (64 mg, 0.17 mmol) and DIPEA (0.070 mL, 0.40 mmol). The solution was stirred at rt overnight and further stirred for 24 h. The reaction mixture was evaporated and the residue was purified by preparative SFC, PrepMethod SFC-C (gradient 27-32%) to give the title compound (8.9 mg, 17%); HRMS (ESI) m/z $[M+H]^+$ calcd for $C_{19}H_{17}N_6O_2S$: 393.1128. found: 393.1130; $^1$H NMR (500 MHz, $CD_3OD$) δ 8.91 (d, 1H), 8.87 (s, 1H), 8.34 (d, 1H), 8.13 (d, 1H), 7.72 (d, 1H), 7.66 (d, 1H), 7.06-7.02 (m, 1H), 5.43-5.38 (m, 1H), 4.89-4.70 (m, overlapping with solvent), 4.52-4.39 (m, 2H), 3.47-3.35 (m, 2H).

Example 197: (R)—N-(2-(4-Cyanothiazolidin-3-yl)-2-oxoethyl)-6-(1-isopropyl-1H-pyrazol-5-yl)quinoline-4-carboxamide

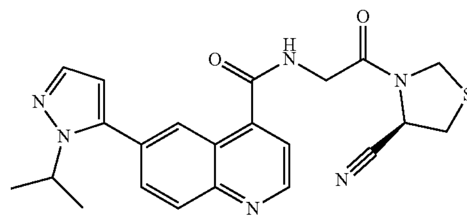

To a suspension of 6-(1-isopropyl-1H-pyrazol-5-yl)quinoline-4-carboxylic acid Intermediate 375 (56 mg, 0.20 mmol) and (R)-3-glycylthiazolidine-4-carbonitrile hydrochloride Intermediate 4 (41 mg, 0.20 mmol) in EtOAc (0.7 mL) and MeCN (0.7 mL) was added HATU (95 mg, 0.25 mmol) and DIPEA (0.104 mL, 0.60 mmol). The solution was stirred at rt overnight and further stirred for 24 h. The reaction mixture was evaporated and the residue was purified by preparative SFC, PrepMethod SFC-C (gradient 27-32%) to give the title compound (29 mg, 33%); HRMS (ESI) m/z $[M+H]^+$ calcd for $C_{22}H_{23}N_6O_2S$: 435.1598. found: 435.1590; $^1H$ NMR (600 MHz, DMSO-$d_6$) δ 9.15 (t, 1H), 8.87 (d, 1H), 8.73 (d, 1H), 8.46 (s, 1H), 8.13-8.08 (m, 2H), 8.05 (d, 1H), 7.49 (d, 1H), 5.42 (dd, 1H), 4.93 (d, 1H), 4.74 (d, 1H), 4.62-4.52 (m, 1H), 4.37 (d, 2H), 3.45-3.32 (m, overlapping with solvent), 1.52-1.46 (m, 6H).

Example 198: N-(2-((R)-4-Cyanothiazolidin-3-yl)-2-oxoethyl)-6-((RS)-3-fluoro-3-methylpyrrolidin-1-yl)quinoline-4-carboxamide

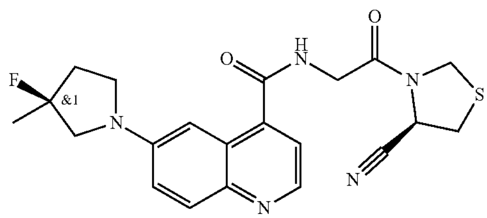 [SMILES: C[C@]1(F)CCN(c2ccc3nccc(C(=O)NCC(=O)N4CSC[C@H]4C#N)c3c2)C1]

DIPEA (614 μL, 3.51 mmol) was added to a solution of rac-(R)-6-(3-fluoro-3-methylpyrrolidin-1-yl)quinoline-4-carboxylic acid Intermediate 377 (439 mg, 0.35 mmol), (R)-3-glycylthiazolidine-4-carbonitrile hydrochloride Intermediate 4 (146 mg, 0.70 mmol) and HATU (401 mg, 1.05 mmol) in MeCN (5 mL) and EtOAc (5 mL). The reaction mixture was stirred at 10° C. overnight and then concentrated under reduced pressure. The reaction mixture was diluted with sat $NaHCO_3$ (50 mL, aq), and extracted with EtOAc (6×50 mL). The organic layers were combined and washed with brine (5×200 mL). The combined organic layers was dried over $Na_2SO_4$, filtered and evaporated. The crude product was purified by preparative HPLC, PrepMethod F (gradient: 15-25%) to give the title compound (0.064 g, 42%) as a yellow solid; HRMS (ESI) m/z $[M+H]^+$ calcd for $C_{21}H_{23}FN_5O_2S$: 428.1550. found: 428.1538; $^1H$ NMR (300 MHz, DMSO-$d_6$) δ 8.99 (t, 1H), 8.61 (d, 1H), 7.91 (d, 1H), 7.40 (d, 1H), 7.36-7.24 (m, 2H), 5.33 (dd, 1H), 4.89 (d, 1H), 4.71 (d, 1H), 4.37-4.26 (m, 2H), 3.68-3.34 (m, overlapping with solvent), 2.34-2.02 (m, 2H), 1.70 −1.57 (m, 3H).

Example 199: N-(2-((R)-4-Cyanothiazolidin-3-yl)-2-oxoethyl)-6-((R*)-2-cyclopropyl-pyrrolidin-1-yl)quinoline-4-carboxamide Isomer 1

Isomer 1

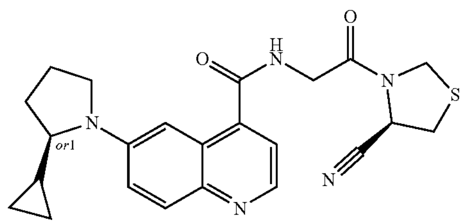

Example 200: N-(2-((R)-4-Cyanothiazolidin-3-yl)-2-oxoethyl)-6-((R*)-2-cyclopropyl-pyrrolidin-1-yl)quinoline-4-carboxamide Isomer 2

Isomer 2

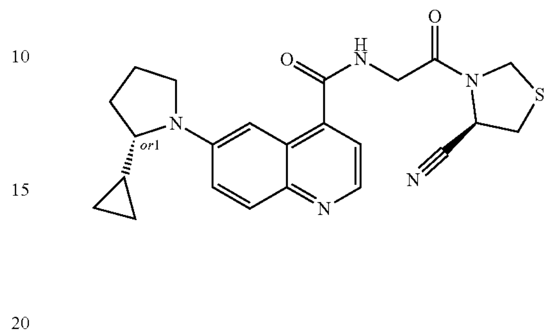

DIPEA (1.54 mL, 8.81 mmol) was added to a stirred suspension of rac-(R)-6-(2-cyclopropylpyrrolidin-1-yl)quinoline-4-carboxylic acid Intermediate 421 (335 mg, 0.44 mmol), (R)-3-glycylthiazolidine-4-carbonitrile hydrochloride Intermediate 4 (275 mg, 1.32 mmol), HOBt (472 mg, 3.08 mmol) and EDC (591 mg, 3.08 mmol in MeCN (5 mL) and EtOAc (5 mL). The reaction mixture was stirred at 10° C. overnight and then concentrated under reduced pressure. The residue was dissolved with a mixture of sat $NaHCO_3$(80 mL, aq) and EtOAc (100 mL). The aq layer was extracted with EtOAc (4×100 mL). The organic layers were combined and washed with $H_2O$ (3×75 mL). The aq layers were combined and extracted with EtOAc (3×25 mL). All organic layers were combined, dried over $Na_2SO_4$, filtered and evaporated. The residue was purified by preparative HPLC, PrepMethod C, (gradient: 23-35%). The isomers were separated by preparative chiral HPLC on a CHIRALPAK® IA column (5 μm, 250×20 ID mm) using an isocratic run of 30% MeOH in Hexane/DCM (0.5% 2M $NH_3$ in MeOH) 3/1 as mobile phase, and with a flow rate of mL/min;

the first eluting compound gave the title compound Isomer 1 Example 199 (0.030 g, 44%) as a yellow solid; HRMS (ESI) m/z $[M+H]^+$ calcd for $C_{23}H_{26}N_5O_2S$: 436.1802. found: 436.1798; $^1H$ NMR (300 MHz, DMSO-$d_6$) δ 8.89 (t, 1H), 8.54 (d, 1H), 7.83 (d, 1H), 7.43-7.24 (m, 3H), 5.40-5.25 (m, 1H), 4.90 (d, 1H), 4.72 (d, 1H), 4.27 (qd, 2H), 3.90-3.70 (m, 1H), 3.62-3.45 (m, 1H), 3.43-3.10 (m, overlapping with solvent), 2.19-1.80 (m, 4H), 1.02-0.87 (m, 1H), 0.60-0.41 (m, 2H), 0.40-0.24 (m, 1H), 0.22-0.08 (m, 1H);

and the second eluting compound gave the title compound Isomer 2 Example 200 (0.025 g, 37%) as a yellow solid; HRMS (ESI) m/z $[M+H]^+$ calcd for $C_{23}H_{26}N_5O_2S$: 436.1802. found: 436.1796; $^1H$ NMR (300 MHz, DMSO-$d_6$) δ 8.90 (t, 1H), 8.54 (d, 1H), 7.83 (d, 1H), 7.50-7.20 (m, 3H), 5.82-5.25 (m, 1H), 4.89 (d, 1H), 4.72 (d, 1H), 4.35-4.19 (m, 2H), 3.90-3.74 (m, 1H), 3.53 (t, 1H), 3.45-3.10 (m, overlapping with solvent), 2.17-1.71 (m, 4H), 1.05-0.85 (m, 1H), 0.58-0.40 (m, 2H), 0.40-0.27 (m, 1H), 0.23-0.08 (m, 1H).

Example 201: N-(2-((R)-4-Cyanothiazolidin-3-yl)-2-oxoethyl)-6-((R*)-3-methyl-2-oxopyrrolidin-1-yl) quinoline-4-carboxamide Isomer 1

Isomer 1

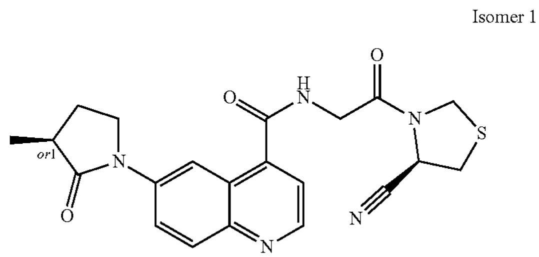 [SMILES: C[C@H]1CCN(c2ccc3nccc(C(=O)NCC(=O)N4CSC[C@H]4C#N)c3c2)C1=O]

Example 202: N-(2-((R)-4-Cyanothiazolidin-3-yl)-2-oxoethyl)-6-((R*)-3-methyl-2-oxopyrrolidin-1-yl) quinoline-4-carboxamide Isomer 2

Isomer 2

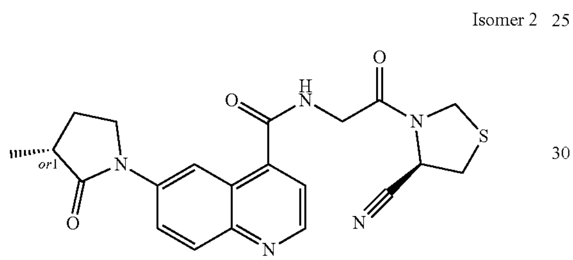

DIPEA (1874 μL, 10.73 mmol) was added to a stirred suspension of rac-(R)-6-(3-methyl-2-oxopyrrolidin-1-yl) quinoline-4-carboxylic acid Intermediate 379 (290 mg, 1.07 mmol), (R)-3-glycylthiazolidine-4-carbonitrile hydrochloride Intermediate 4 (446 mg, 2.15 mmol), HOBt (822 mg, 5.36 mmol) and EDC (1028 mg, 5.36 mmol) in MeCN (10 mL) and EtOAc (10 mL) at 15° C. The reaction mixture was stirred at 50° C. for 2 h and then concentrated under reduced pressure. The residue was dissolved with a mixture of sat $NaHCO_3$(60 mL, aq) and EtOAc (100 mL). The aq layer was extracted with EtOAc (5×100 mL). The organic layers were combined and washed with $H_2O$ (3×50 mL). The aq layers were combined and extracted with EtOAc (4×25 mL). All organic layers were combined, dried over $Na_2SO_4$, filtered and evaporated. The residue was purified by preparative HPLC, PrepMethod F (gradient: 15-35%). The isomers were separated by preparative chiral HPLC on a CHIRALPAK® IE Colum (5 μm, 250×20 ID mm) using an isocratic run of 50% MeOH in Hexane/DCM (0.5% 2M $NH_3$ in MeOH) 3/1 as mobile phase, and with a flow rate of 20 mL/min;

the first eluting compound gave the title compound Isomer 1 Example 201 (0.052 g, 49%) as a white solid; HRMS (ESI) m/z $[M+H]^+$ calcd for $C_2H_{22}N_5O_3S$: 424.1438. found: 424.1438; $^1H$ NMR (400 MHz, DMSO-$d_6$) δ 9.10 (t, 1H), 8.90 (d, 1H), 8.55 (dd, 1H), 8.30 (d, 1H), 8.08 (d, 1H), 7.56 (d, 1H), 5.40-5.30 (m, 1H), 4.90 (d, 1H), 4.72 (d, 1H), 4.33 (d, 2H), 3.98-3.74 (m, 2H), 3.44-3.35 (m, overlapping with solvent), 2.78-2.65 (m, 1H), 2.42-2.31 (m, 1H), 1.85-1.65 (m, 1H), 1.20 (d, 3H);

and the second eluting compound gave the title compound Isomer 2 Example 202 (0.048 g, 45%) as a white solid; HRMS (ESI) m/z $[M+H]^+$ calcd for $C_{21}H_{22}N_5O_3S$: 424.1438. found: 424.1418; $^1H$ NMR (400 MHz, DMSO-$d_6$) δ 9.10 (t, 1H), 8.90 (d, 1H), 8.55 (dd, 1H), 8.32 (d, 1H), 8.08 (d, 1H), 7.56 (d, 1H), 5.42-5.29 (m, 1H), 4.90 (d, 1H), 4.72 (d, 1H), 4.54-4.17 (m, 2H), 3.99-3.82 (m, 2H), 3.51-3.34 (m, overlapping with solvent), 2.78-2.61 (m, 1H), 2.43-2.25 (m, 1H), 1.85-1.65 (m, 1H), 1.20 (d, 3H).

Example 203: N-(2-((R)-4-Cyanothiazolidin-3-yl)-2-oxoethyl)-6-((R*)-3-methyl-2-oxopiperidin-1-yl) quinoline-4-carboxamide Isomer 1

Isomer 1

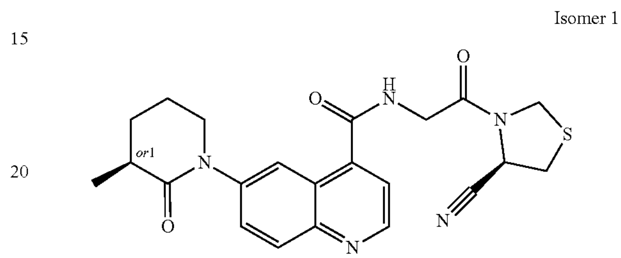

Example 204: N-(2-((R)-4-Cyanothiazolidin-3-yl)-2-oxoethyl)-6-((R*)-3-methyl-2-oxopiperidin-1-yl) quinoline-4-carboxamide Isomer 2

Isomer 2

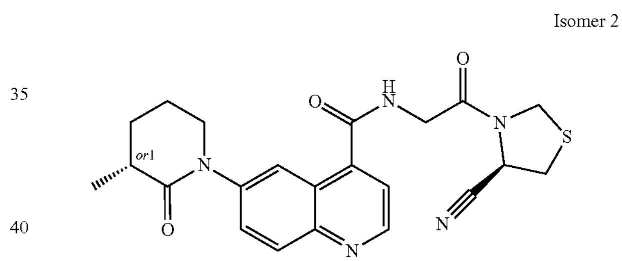

DIPEA (509 mg, 3.94 mmol) was added to a stirred suspension of rac-(R)-6-(3-methyl-2-oxopiperidin-1-yl)quinoline-4-carboxylic acid Intermediate 381 (280 mg, 0.98 mmol), (R)-3-glycylthiazolidine-4-carbonitrile hydrochloride Intermediate 4 (337 mg, 1.97 mmol), T3P (50% in EtOAc, 1253 mg, 3.94 mmol) in DMF (5 mL) under air. The reaction mixture was stirred at 25° C. for 6 h. The solvent was removed under reduced pressure. The residue was purified by preparative TLC (DCM:MeOH; 18:1). The residue was further purified by preparative HPLC, PrepMethod B (gradient: 18-38%). The isomers were separated by preparative chiral HPLC on a CHIRALPAK® IE column (5 μm, 250×20 ID mm) using an isocratic run of 50% MeOH in Hexane/DCM (0.5% 2 M $NH_3$ in MeOH) 3/1 as mobile phase, and with a flow rate of 20 mL/min;

the first eluting compound gave the title compound Isomer 1 Example 203 (0.025 g, 25%) as a white solid; HRMS (ESI) m/z $[M+H]^+$ calcd for $C_{22}H_{24}N_5O_3S$: 438.1594. found: 438.1592; $^1H$ NMR (300 MHz, DMSO-$d_6$) δ 9.11 (t, 1H), 8.94 (d, 1H), 8.35-8.20 (m, 1H), 8.01 (d, 1H), 7.75 (dd, 1H), 7.55 (d, 1H), 5.42-5.22 (m, 1H), 4.88 (d, 1H), 4.70 (d, 1H), 4.31 (d, 2H), 3.88-3.68 (m, 2H), 3.44-3.34 (m, overlapping with solvent), 2.63-2.53 (m, overlapping with solvent), 2.06-1.89 (m, 3H), 1.71-1.51 (m, 1H), 1.18 (d, 3H);

and the second eluting compound gave the title compound Isomer 2 Example 204 (0.071 g, 71%) as a white solid; HRMS (ESI) m/z $[M+H]^+$ calcd for $C_{22}H_{24}N_5O_3S$: 438.1594. found: 438.1588; $^1H$ NMR (300 MHz, DMSO-$d_6$) δ 9.12 (t, 1H), 8.94 (d, 1H), 8.40-8.20 (m, 1H), 8.01 (d, 1H), 7.75 (dd, 1H), 7.55 (d, 1H), 5.45-5.25 (m, 1H), 4.88 (d, 1H), 4.70 (d, 1H), 4.31 (d, 2H), 3.94-3.63 (m, 2H), 3.44-3.33 (m, overlapping with solvent), 2.61-2.52 (m, overlapping with solvent), 2.15-1.80 (m, 3H), 1.71-1.53 (m, 1H), 1.18 (d, 3H).

Example 205: (R)—N-(2-(4-Cyanothiazolidin-3-yl)-2-oxoethyl)-6-(4-fluoropiperidin-1-yl)-quinoline-4-carboxamide

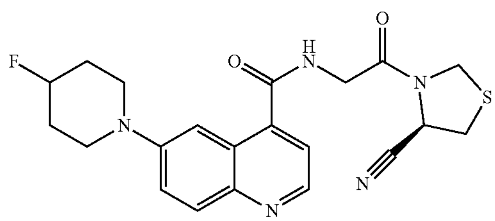 [SMILES: N#C[C@@H]1CSCN1C(=O)CNC(=O)c1ccnc2ccc(N3CCC(F)CC3)cc12]

DIPEA (6.11 mL, 35.0 mmol) was added to a solution of 6-(4-fluoropiperidin-1-yl)quinoline-4-carboxylic acid Intermediate 383 (600 mg, 0.87 mmol), (R)-3-glycylthiazolidine-4-carbonitrile hydrochloride Intermediate 4 (363 mg, 1.75 mmol), EDC (839 mg, 4.37 mmol) and HOBt (670 mg, 4.37 mmol) in MeCN (10 mL) and EtOAc (10 mL). The reaction mixture was stirred at 15° C. for 15 h and then concentrated under reduced pressure. The reaction mixture was diluted with EtOAc (100 mL) and sat $NaHCO_3$(60 mL, aq), and extracted with EtOAc (5×100 mL). The organic layer was dried over $Na_2SO_4$, filtered and evaporated. The crude product was purified by preparative HPLC, PrepMethod I (gradient: 40-52%) to give the title compound (0.21 g, 56%) as a yellow solid; HRMS (ESI) m/z $[M+H]^+$ calcd for $C_{21}H_{23}FN_5O_2S$: 428.1550. found: 428.1548; $^1H$ NMR (300 MHz, DMSO-$d_6$) δ 9.00 (t, 1H), 8.66 (d, 1H), 7.88 (d, 1H), 7.77-7.62 (m, 2H), 7.38 (d, 1H), 5.31 (dd, 1H), 5.01-4.54 (m, 3H), 4.43-4.16 (m, 2H), 3.70-3.33 (m, overlapping solvent), 2.13-1.90 (m, 2H), 1.89-1.71 (m, 2H).

Example 206: 6-(3-Azabicyclo[3.1.0]hexan-3-yl)-N-(2-((R)-4-cyanothiazolidin-3-yl)-2-oxoethyl)quinoline-4-carboxamide

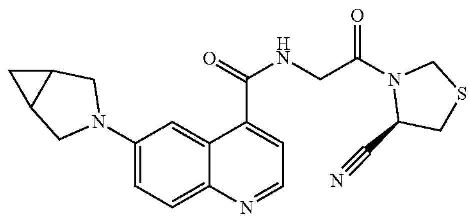 [SMILES: N#C[C@@H]1CSCN1C(=O)CNC(=O)c1ccnc2ccc(N3CC4CC4C3)cc12]

DIPEA (927 μL, 5.31 mmol) was added to a solution of 6-(3-azabicyclo[3.1.0]hexan-3-yl)quinoline-4-carboxylic acid Intermediate 385 (368 mg, 0.53 mmol), (R)-3-glycylthiazolidine-4-carbonitrile hydrochloride Intermediate 4 (221 mg, 1.06 mmol) and HATU (604 mg, 1.59 mmol) in MeCN (5 mL) and EtOAc (5 mL). The reaction mixture was stirred at 10° C. overnight and then concentrated under reduced pressure. The reaction mixture was diluted with sat $NaHCO_3$ (50 mL, aq), and extracted with EtOAc (6×50 mL). The organic layers were combined and washed with brine (5×200 mL). The combined organic layers was dried over $Na_2SO_4$, filtered and evaporated. The crude product was purified by preparative HPLC, PrepMethod P, (gradient: 15-25%) to give the title compound (0.132 g, 61%) as an orange solid; HRMS (ESI) m/z $[M+H]^+$ calcd for $C_{21}H_{22}N_5O_2S$: 408.1488. found: 408.1486; $^1H$ NMR (300 MHz, DMSO-$d_6$) δ 8.92 (t, 1H), 8.56 (d, 1H), 7.83 (d, 1H), 7.35 (d, 1H), 7.29 (dd, 1H), 7.23 (d, 1H), 5.74-5.31 (m, 1H), 4.89 (d, 1H), 4.72 (d, 1H), 4.27 (d, 2H), 3.75-3.55 (m, 2H), 3.39-3.32 (m, overlapping with solvent), 1.82-1.60 (m, 2H), 0.85-0.65 (m, 1H), 0.35-0.15 (m, 1H).

Example 207: N-(2-((R)-4-Cyanothiazolidin-3-yl)-2-oxoethyl)-6-((S)-3-methoxy-pyrrolidin-1-yl)quinoline-4-carboxamide

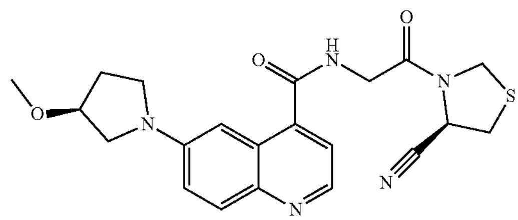 [SMILES: CO[C@H]1CCN(c2ccc3nccc(C(=O)NCC(=O)N4CSC[C@H]4C#N)c3c2)C1]

DIPEA (411 μL, 2.35 mmol) was added to a solution of (S)-6-(3-methoxypyrrolidin-1-yl)quinoline-4-carboxylic acid Intermediate 387 (160 mg, 0.59 mmol), (R)-3-glycylthiazolidine-4-carbonitrile hydrochloride Intermediate 4 (101 mg, 0.59 mmol) and HATU (335 mg, 0.88 mmol) in DMF (5 mL) The reaction mixture was stirred at 25° C. for 2 h under and then concentrated under reduced pressure. The crude product was purified by preparative TLC (DCM: MeOH; 18:1) and further purified by preparative HPLC, PrepMethod D (gradient: 25-33%) to give the title compound (0.049 g, 19%) as a yellow solid; HRMS (ESI) m/z $[M+H]^+$ calcd for $C_{21}$I-$124N_5O_3S$: 426.1594. found: 426.1584; $^1H$ NMR (300 MHz, DMSO-$d_6$) δ 8.93 (t, 1H), 8.56 (d, 1H), 7.86 (d, 1H), 7.39-7.19 (m, 3H), 5.31 (dd, 1H), 4.88 (d, 1H), 4.70 (d, 1H), 4.28 (d, 2H), 4.21-4.01 (m, 1H), 3.60-3.34 (m, overlapping with solvent), 2.20-1.99 (m, 2H).

Example 208: N-(2-((R)-4-Cyanothiazolidin-3-yl)-2-oxoethyl)-6-α1R,5S,6R)-6-(trifluoromethyl)-3-azabicyclo[3.1.0]hexan-3-yl)quinoline-4-carboxamide

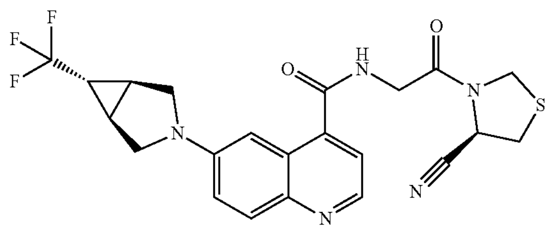 [SMILES: N#C[C@@H]1CSCN1C(=O)CNC(=O)c1ccnc2ccc(N3C[C@@H]4[C@H](C3)[C@H]4C(F)(F)F)cc12]

DIPEA (742 μL, 4.25 mmol) was added to a solution of 6-((1R,5S,60-6-(trifluoromethyl)-3-azabicyclo[3.1.0]hexan-3-yl)quinoline-4-carboxylic acid Intermediate 389 (349 mg, 0.42 mmol), (R)-3-glycylthiazolidine-4-carbonitrile hydrochloride Intermediate 4 (176 mg, 0.85 mmol), EDC (407 mg, 2.12 mmol) and HOBt (325 mg, 2.12 mmol) in MeCN (9 mL) and EtOAc (9 mL). The reaction mixture was stirred at 40° C. for 3 h and then concentrated under reduced pressure. The reaction mixture was diluted with EtOAc (100 mL) and washed with sat $NaHCO_3$ (3×200 mL, aq) and brine (3×200 mL). The organic layer was dried over $Na_2SO_4$, filtered and evaporated. The crude product was purified by preparative HPLC, PrepMethod C, (gradient: 20-55%) to give the title compound (0.201 g, 99%) as a yellow solid; HRMS (ESI) m/z $[M+H]^+$ calcd for $C_{22}H_{21}F_3N_5O_2S$: 476.1362. found: 476.1356; $^1H$ NMR (300 MHz, DMSO-$d_6$) δ 8.92 (t, 1H), 8.60 (d, 1H), 7.88 (m, 1H), 7.40-7.28 (m, 3H), 5.40-5.20 (m, 1H), 4.89 (d, 1H), 4.72 (d, 1H), 4.28 (d, 2H), 3.79 (d, 2H), 3.43-3.34 (m, overlapping with solvent), 2.33-2.10 (m, 2H), 1.98-1.73 (m, 1H).

Example 209: (R)-6-(7-Azabicyclo[2.2.1]heptan-7-yl)-N-(2-(4-cyanothiazolidin-3-yl)-2-oxoethyl)quinoline-4-carboxamide

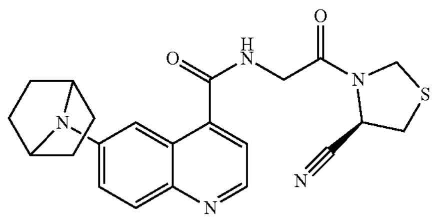 [SMILES: N#C[C@@H]1CSCN1C(=O)CNC(=O)c1ccnc2ccc(N3C4CCC3CC4)cc12]

DIPEA (560 μL, 3.21 mmol) was added to a suspension of 6-(7-azabicyclo[2.2.1]heptan-7-yl)quinoline-4-carboxylic acid Intermediate 391 (43 mg, 0.16 mmol), (R)-3-glycylthiazolidine-4-carbonitrile hydrochloride Intermediate 4 (67 mg, 0.32 mmol), EDC (307 mg, 1.60 mmol) and HOBt (245 mg, 1.60 mmol) in MeCN (3 mL) and EtOAc (3 mL). The reaction mixture was stirred at 10° C. for overnight and then concentrated under reduced pressure. The reaction mixture was diluted sat $NaHCO_3$ (100 mL, aq) and extracted with EtOAc (6×100 mL) and washed with brine (5×200 mL). The organic layer was dried over $Na_2SO_4$, filtered and evaporated. The crude product was purified by preparative HPLC, PrepMethod C, (gradient: 10-35%) to give the title compound (0.025 g, 37%) as a yellow solid; HRMS (ESI) m/z $[M+H]^+$ calcd for $C_{22}H_{24}N_5O_2S$: 422.1646. found: 422.1658; $^1H$ NMR (300 MHz, DMSO-$d_6$) δ 9.10-8.90 (m, 1H), 8.64 (d, 1H), 7.84 (d, 1H), 7.75-7.60 (m, 1H), 7.56 (dd, 1H), 7.36 (d, 1H), 5.34-5.28 (m, 1H), 4.88 (d, 1H), 4.70 (d, 1H), 4.43 (brs, 2H), 4.28 (d, 2H), 3.41-3.36 (m, overlapping with solvent), 1.85-1.64 (m, 4H), 1.58-1.35 (m, 4H).

Example 210: 6-((1RS,4SR)-2-Azabicyclo[2.2.1]heptan-2-yl)-N-(2-((R)-4-cyanothiazolidin-3-yl)-2-oxoethyl)quinoline-4-carboxamide

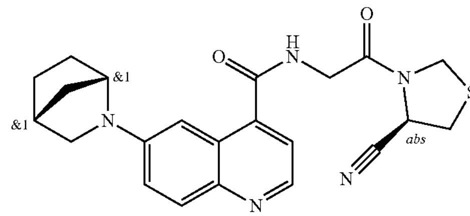

TEA (291 μL, 2.08 mmol) was added to a suspension of 6-(2-azabicyclo[2.2.1]heptan-2-yl)quinoline-4-carboxylic acid Intermediate 393 (75 mg, 0.10 mmol), (R)-3-glycylthiazolidine-4-carbonitrile hydrochloride Intermediate 4 (43 mg, 0.21 mmol), EDC (100 mg, 0.52 mmol) and HOBt (80 mg, 0.52 mmol) in MeCN (5 mL) and EtOAc (5 mL). The reaction mixture was stirred at 10° C. for overnight and then concentrated under reduced pressure. The reaction mixture was partitioned between sat $NaHCO_3$ (50 mL, aq) and EtOAc (100 mL), extracted with EtOAc (4×100 mL) and washed with brine (5×200 mL). The organic layer was dried over $Na_2SO_4$, filtered and evaporated. The crude product was purified by preparative HPLC, PrepMethod C, (gradient: 10-40%) to give the title compound (0.13 g) as a yellow solid; HRMS (ESI) m/z $[M+H]^+$ calcd for $C_{22}H_{24}N_5O_2S$: 422.1646. found: 422.1658; $^1H$ NMR (300 MHz, DMSO-$d_6$) δ 8.89 (t, 1H), 8.51 (d, 1H), 7.81 (d, 1H), 7.40-7.10 (m, 3H), 5.40-5.20 (m, 1H), 4.87 (d, 1H), 4.70 (d, 1H), 4.45-4.15 (m, 3H), 3.60-3.34 (m, overlapping with solvent), 2.85 (d, 1H), 2.61 (s, 1H), 1.80-1.42 (m, 5H), 1.40-1.15 (m, 1H).

Example 211: N-(2-((R)-4-cyanothiazolidin-3-yl)-2-oxoethyl)-6-((R)-2-methylpyrrolidin-1-yl)quinoline-4-carboxamide

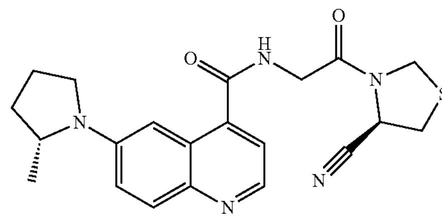

DIPEA (454 mg, 3.51 mmol) was added to a solution of (R)-6-(2-methylpyrrolidin-1-yl)quinoline-4-carboxylic acid Intermediate 395 (150 mg, 0.59 mmol), (R)-3-glycylthiazolidine-4-carbonitrile hydrochloride Intermediate 4 (150 mg, 0.88 mmol) and HATU (445 mg, 1.17 mmol) in MeCN (5 mL) and EtOAc (5 mL). The reaction mixture was stirred at 25° C. for 3 h and then concentrated under reduced pressure. The crude product was purified by preparative TLC (DCM:MeOH; 19:1) and further purified by preparative HPLC, PrepMethod F (gradient: 15-32%) to give the title compound (0.050 g, 21%) as an orange solid; HRMS (ESI) m/z $[M+H]^+$ calcd for $C_{21}H_{24}N_5O_2S$: 410.1646. found: 410.1634; $^1H$ NMR (400 MHz, DMSO-$d_6$) δ 8.92 (t, 1H), 8.55 (d, 1H), 7.86 (d, 1H), 7.39-7.29 (m, 2H), 7.25 (d, 1H), 5.40-5.20 (m, 1H), 4.89 (d, 1H), 4.73 (d, 1H), 4.29 (d, 2H), 4.15-4.00 (m, 1H), 3.55-3.20 (m, overlapping with solvent), 2.16-1.90 (m, 3H), 1.82 −1.65 (m, 1H), 1.17 (d, 3H).

Example 212: N-(2-((R)-4-Cyanothiazolidin-3-yl)-2-oxoethyl)-6-((S)-2-(methoxymethyl)-pyrrolidin-1-yl)quinoline-4-carboxamide

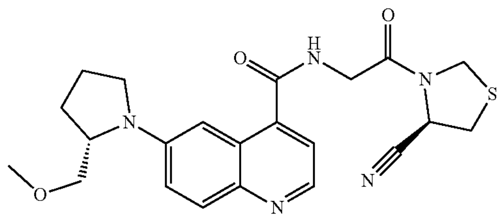 [SMILES: COC[C@@H]1CCCN1c1ccc2nccc(C(=O)NCC(=O)N3CSC[C@H]3C#N)c2c1]

DIPEA (549 μL, 3.14 mmol) was added to a suspension of (S)-6-(2-(methoxymethyl)pyrrolidin-1-yl)quinoline-4-carboxylic acid Intermediate 397 (150 mg, 0.52 mmol), (R)-3-glycylthiazolidine-4-carbonitrile hydrochloride Intermediate 4 (163 mg, 0.79 mmol), EDC (201 mg, 1.05 mmol) and HOBt (160 mg, 1.05 mmol) in MeCN (4 mL) and EtOAc (4 mL). The reaction mixture was stirred at 50° C. for 3 h and then concentrated under reduced pressure. The reaction mixture was diluted with EtOAc and washed with $H_2O$. The organic layer was dried over $Na_2SO_4$, filtered and evaporated. The crude product was purified by preparative HPLC, PrepMethod P, (gradient: 15-25%) to give the title compound (0.205 g, 89%) as a yellow solid; HRMS (ESI) m/z $[M+H]^+$ calcd for $C_{22}H_{26}N_5O_3S$: 440.1750. found: 440.1772; $^1H$ NMR (300 MHz, DMSO-$d_6$) δ 8.91 (t, 1H), 8.55 (d, 1H), 7.85 (d, 1H), 7.41-7.31 (m, 2H), 7.27 (d, 1H), 5.30 (dd, 1H), 4.87 (d, 1H), 4.70 (d, 1H), 4.27 (d, 2H), 4.06 (brs, 1H), 3.54-3.10 (m, overlapping with solvent), 2.13-1.93 (m, 4H).

Example 213: N-(2-((R)-4-Cyanothiazolidin-3-yl)-2-oxoethyl)-6-((3S,4S)-3,4-difluoro-pyrrolidin-1-yl) quinoline-4-carboxamide

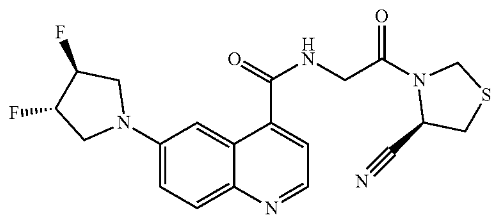 [SMILES: N#C[C@@H]1CSCN1C(=O)CNC(=O)c1ccnc2ccc(N3C[C@H](F)[C@@H](F)C3)cc12]

DIPEA (279 mg, 2.16 mmol) was added to a solution of 6-((3S,4S)-3,4-difluoropyrrolidin-1-yl)quinoline-4-carboxylic acid Intermediate 399 (100 mg, 0.36 mmol), (R)-3-glycylthiazolidine-4-carbonitrile hydrochloride Intermediate 4 (92 mg, 0.54 mmol) and HATU (273 mg, 0.72 mmol) in MeCN (2 mL) and EtOAc (2 mL). The reaction mixture was stirred at 25° C. for 3 h and then concentrated under reduced pressure. The crude product was purified by preparative TLC (DCM:MeOH; 20:1) and further purified by preparative HPLC, PrepMethod F (gradient: 17-35%) to give the title compound (0.063 g, 40%) as a red solid; HRMS (ESI) m/z $[M+H]^+$ calcd for $C_{20}H_{20}F_2N_5O_2S$: 432.1300. found: 432.1310; $^1H$ NMR (400 MHz, DMSO-$d_6$) δ 9.10 (t, 1H), 8.75 (d, 1H), 8.00 (d, 1H), 7.50-7.25 (m, 3H), −5.25 (m, 3H), 4.91 (d, 1H), 4.72 (d, 1H), 4.45-4.25 (m, 2H), 3.95-3.65 (m, 4H), 3.47-3.33 (m, overlapping with solvent).

Example 214: N-(2-((R)-4-Cyanothiazolidin-3-yl)-2-oxoethyl)-6-((3R,4R)-3,4-difluoro-pyrrolidin-1-yl) quinoline-4-carboxamide

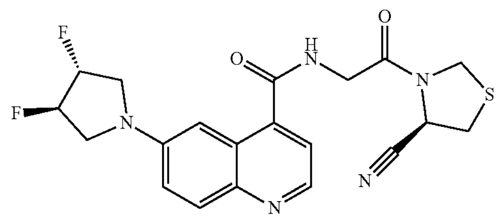 [SMILES: N#C[C@@H]1CSCN1C(=O)CNC(=O)c1ccnc2ccc(N3C[C@@H](F)[C@H](F)C3)cc12]

DIPEA (557 mg, 4.31 mmol) was added to a solution of rac-6-((3R,4R)-3,4-difluoropyrrolidin-1-yl)quinoline-4-carboxylic acid Intermediate 401 (200 mg, 0.72 mmol), (R)-3-glycylthiazolidine-4-carbonitrile hydrochloride Intermediate 4 (185 mg, 1.08 mmol) and HATU (547 mg, 1.44 mmol) in MeCN (4 mL) and EtOAc (4 mL). The reaction mixture was stirred at 25° C. for 3 h and then concentrated under reduced pressure. The crude product was purified by preparative TLC (DCM:MeOH; 20:1) and the isomers were separated by preparative chiral HPLC on a CHIRAL ART Cellulose-SB column (5 μm, 250×20 ID mm) using an isocratic run of 30% MeOH in Hexane/DCM (0.5% 2 M $NH_3$ in MeOH) 3/1 as mobile phase, and with a flow rate of 20 mL/min;

the first eluting compound gave the title compound Example 214 (0.080 g, 26%) as a yellow solid; HRMS (ESI) m/z $[M+H]^+$ calcd for $C_{20}H_{20}F_2N_5O_2S$: 432.1300. found: 432.1286; $^1H$ NMR (400 MHz, DMSO-$d_6$) δ 8.97 (t, 1H), 8.63 (d, 1H), 7.93 (d, 1H), 7.50-7.28 (m, 3H), 5.65-5.38 (m, 2H), 5.34 (dd, 1H), 4.90 (d, 1H), 4.72 (d, 1H), 4.37-4.27 (m, 2H), 3.92-3.68 (m, 4H), 3.49-3.34 (m, overlapping with solvent).

Example 215: (R)—N-(2-(4-Cyanothiazolidin-3-yl)-2-oxoethyl)-6-(2,4-dimethyloxazol-5-yl)quinoline-4-carboxamide

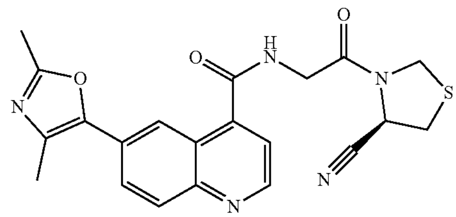 [SMILES: Cc1nc(C)c(-c2ccc3nccc(C(=O)NCC(=O)N4CSC[C@H]4C#N)c3c2)o1]

DIPEA (0.078 mL, 0.45 mmol) was added to a solution of 6-(2,4-dimethyloxazol-5-yl)quinoline-4-carboxylic acid Intermediate 402 (30 mg, 0.11 mmol), (R)-3-glycylthiazolidine-4-carbonitrile hydrochloride Intermediate 4 (23 mg, 0.11 mmol) and HATU (47 mg, 0.12 mmol) in DCM (4 mL). The reaction mixture was stirred at rt overnight. (R)-3-glycylthiazolidine-4-carbonitrile hydrochloride Intermediate 4 (23.22 mg, 0.11 mmol), HATU (14 mg, 0.04 mmol) and DIPEA (0.025 mL, 0.15 mmol) was added. The reaction mixture was stirred for 2 h and diluted with DMSO. The residue was purified by preparative HPLC, PrepMethod SFC-C (gradient: 20-25%) to give the title compound (37 mg, 79%). HRMS (ESI) m/z $[M+H]^+$ calcd for $C_{21}H_{20}N_5O_3S$: 422.1282. found: 422.1286; $^1H$ NMR (600 MHz, DMSO-$d_6$) δ 9.17 (t, 1H), 8.98 (d, 1H), 8.57 (d, 1H), 8.16 (d, 1H), 8.04 (dd, 1H), 7.62 (d, 1H), 5.33 (dd, 1H), 4.90 (d, 1H), 4.72 (d, 1H), 4.41-4.26 (m, 2H), 3.46-3.32 (m, overlapping with solvent), 2.48 (s, 3H), 2.40 (s, 3H).

Example 216: (R)—N-(2-(4-Cyanothiazolidin-3-yl)-2-oxoethyl)-6-(3,5-dimethylisoxazol-4-yl)quinoline-4-carboxamide

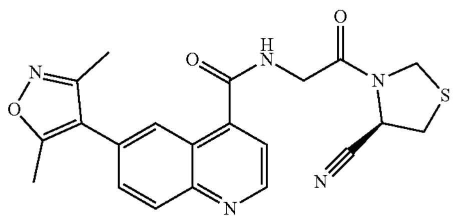 [SMILES: Cc1noc(C)c1-c1ccc2nccc(C(=O)NCC(=O)N3CSC[C@H]3C#N)c2c1]

DIPEA (0.98 mL, 5.6 mmol) was added to a solution of 6-(3,5-dimethylisoxazol-4-yl)quinoline-4-carboxylic acid Intermediate 403 (60 mg, 0.22 mmol), (R)-3-glycylthiazolidine-4-carbonitrile hydrochloride Intermediate 4 (56 mg, 0.27 mmol) and HATU (102 mg, 0.27 mmol) in DMF (2 mL). The reaction mixture was stirred at rt overnight. The reaction mixture was diluted with DCM (15 mL) and washed with sat $NaHCO_3$(8 mL, aq), passed through a phase separator and concentrated. The residue was purified by preparative HPLC, PrepMethod F (gradient: 5-95%) to give the title compound (57 mg, 60% over two-steps). HRMS (ESI) m/z $[M+H]^+$ calcd for $C_{21}H_{20}N_5O_3S$: 422.1282. found: 422.1298; $^1H$ NMR (600 MHz, DMSO-$d_6$) δ 9.17 (t, 1H), 9.01 (d, 1H), 8.43 (d, 1H), 8.17 (d, 1H), 7.87 (dd, 1H), 7.60 (d, 1H), 5.33 (dd, 1H), 4.89 (d, 1H), 4.71 (d, 1H), 4.32 (qd, 2H), 3.42-3.34 (m, overlapping with solvent), 2.54 (s, 6H).

Example 217: (R)—N-(2-(4-Cyanothiazolidin-3-yl)-2-oxoethyl)-6-(2-phenyl-1H-imidazol-1-yl)quinoline-4-carboxamide

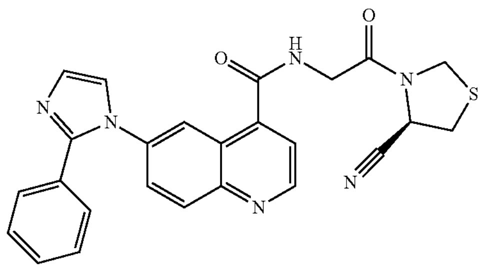 [SMILES: N#C[C@@H]1CSCN1C(=O)CNC(=O)c1ccnc2ccc(-n3ccnc3-c3ccccc3)cc12]

TEA (133 μL, 0.95 mmol) was added to a suspension of 6-(2-phenyl-1H-imidazol-1-yl)quinoline-4-carboxylic acid Intermediate 404 (30 mg, 0.10 mmol), (R)-3-glycylthiazolidine-4-carbonitrile hydrochloride Intermediate 4 (30 mg, 0.14 mmol, EDC (91 mg, 0.48 mmol) and HOBt (64 mg, 0.48 mmol) in MeCN (3 mL) and EtOAc (3 mL). The reaction mixture was stirred at 50° C. for 2 h and then concentrated under reduced pressure. The reaction mixture was diluted with EtOAc (60 mL) and sat $NaHCO_3$ (30 mL, aq), extracted with EtOAc (5×75 mL). The pooled organic layers were washed with $H_2O$ (3×25 mL), dried over $Na_2SO_4$, filtered and evaporated. The crude product was purified by preparative HPLC, PrepMethod C, (gradient: 5-35%) to give the title compound (0.023 g, 52%) as a grey solid; HRMS (ESI) m/z $[M+H]^+$ calcd for $C_{25}H_{21}N_6O_2S$: 469.1442. found: 469.1450; $^1H$ NMR (300 MHz, DMSO-$d_6$) δ 9.20-9.00 (m, 2H), 8.41 (d, 1H), 8.14-8.04 (m, 1H), 7.68 (d, 1H), 7.61-7.51 (m, 2H), 7.38-7.20 (m, 6H), 5.32 (dd, 1H), 4.85 (d, 1H), 4.68 (d, 1H), 4.28 (d, 2H), 3.37-3.33 (m, overlapping with solvent).

Example 218: (R)—N-(2-(4-Cyanothiazolidin-3-yl)-2-oxoethyl)-6-(3-phenyl-1H-pyrrol-1-yl)quinoline-4-carboxamide

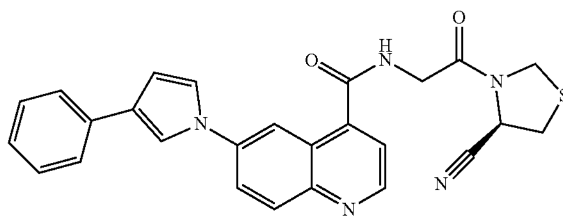

DIPEA (417 μL, 2.39 mmol) was added to a suspension of 6-(3-phenyl-1H-pyrrol-1-yl)quinoline-4-carboxylic acid Intermediate 405 (150 mg, 0.48 mmol), (R)-3-glycylthiazolidine-4-carbonitrile hydrochloride Intermediate 4 (149 mg, 0.72 mmol), EDC (183 mg, 0.95 mmol) and HOBt (129 mg, 0.95 mmol) in MeCN (5 mL) and EtOAc (5 mL). The reaction mixture was stirred at 50° C. for 2 h and then concentrated under reduced pressure. The reaction mixture was diluted with EtOAc (25 mL) and washed with $H_2O$ (3×10 mL). The organic layer was dried over $Na_2SO_4$, filtered and evaporated. The crude product was purified by preparative TLC (DCM: MeOH; 10:1) and further purified by preparative HPLC, PrepMethod C, (gradient: 40-60%) to give the title compound (0.105 g, 47%) as a grey solid; HRMS (ESI) m/z $[M+H]^+$ calcd for $C_{26}H_{22}N_5O_2S$: 468.1488. found: 468.1496; $^1H$ NMR (300 MHz, DMSO-$d_6$) δ 9.24 (t, 1H), 8.93 (d, 1H), 8.77-8.65 (m, 1H), 8.31-8.14 (m, 3H), 7.76-7.68 (m, 3H), 7.58 (d, 1H), 7.49-7.25 (m, 2H), 7.19 (t, 1H), 6.84-6.76 (m, 1H), 5.40 (dd, 1H), 4.94 (d, 1H), 4.74 (d, 1H), 4.55-4.23 (m, 2H), 3.52-3.37 (m, overlapping with solvent).

Example 219: (R)—N-(2-(4-Cyanothiazolidin-3-yl)-2-oxoethyl)-6-(4,5,6,7-tetrahydro-1H-indol-1-yl)quinoline-4-carboxamide

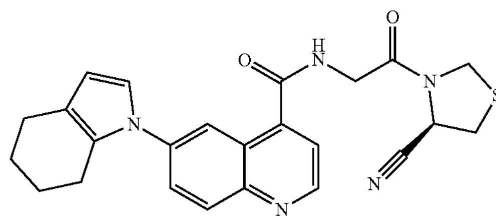

DIPEA (394 μL, 2.26 mmol) was added to a suspension of 6-(4,5,6,7-tetrahydro-1H-indol-1-yl)quinoline-4-carboxylic acid Intermediate 406 (50 mg, 0.15 mmol), (R)-3-glycylthiazolidine-4-carbonitrile hydrochloride Intermediate 4 (47 mg, 0.23 mmol), EDC (144 mg, 0.75 mmol) and HOBt (102 mg, 0.75 mmol) in MeCN (4 mL) and EtOAc (4 mL). The reaction mixture was stirred at 50° C. for 2 h and then concentrated under reduced pressure. The reaction mixture was diluted with EtOAc (60 mL) and sat $NaHCO_3$ (30 mL, aq), extracted with EtOAc (5×50 mL). The pooled organic layers were washed with $H_2O$ (3×20 mL), the aqueous layers were combined and extracted with EtOAc (3×20 mL) and all organic layers were pooled, dried over $Na_2SO_4$, filtered and evaporated. The crude product was purified by preparative HPLC, PrepMethod C, (gradient: 40-60%) to give the title compound (0.020 g, 30%) as a white solid; HRMS (ESI) m/z $[M+H]^+$ calcd for $C_{24}H_{24}N_5O_2S$: 446.1646. found: 446.1636; $^1H$ NMR (300 MHz, DMSO-$d_6$) δ 9.25-9.10 (m, 1H), 8.97 (d, 1H), 8.25 (d, 1H), 8.15 (d, 1H), 7.87 (dd, 1H), 7.61 (d, 1H), 6.99 (d, 1H), 6.04 (d, 1H), 5.30 (dd, 1H), 4.87 (d, 1H), 4.71 (d, 1H), 4.40-4.20 (m, 2H), 3.38-3.35 (m, overlapping with solvent), 2.80 −2.52 (m, overlapping with solvent), 1.78-1.66 (m, 4H).

Example 220: N-(2-((R)-4-Cyanothiazolidin-3-yl)-2-oxoethyl)-6-((R)-3-(hydroxymethyl)-pyrrolidin-1-yl)quinoline-4-carboxamide

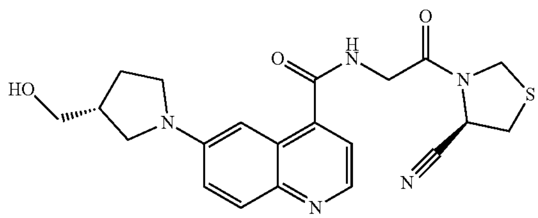 [SMILES: N#C[C@@H]1CSCN1C(=O)CNC(=O)c1ccnc2ccc(N3CC[C@@H](CO)C3)cc12]

DIPEA (192 μL, 1.10 mmol) was added to a suspension of (R)-6-(3-(hydroxymethyl)pyrrolidin-1-yl)quinoline-4-carboxylic acid Intermediate 408 (100 mg, 0.37 mmol), (R)-3-glycylthiazolidine-4-carbonitrile hydrochloride Intermediate 4 (76 mg, 0.37 mmol), T3P (50% in EtOAc, 934 mg, 1.47 mmol) in MeCN (5 mL) and EtOAc (5 mL). The reaction mixture was stirred at 20° C. for 5 h and then concentrated under reduced pressure. The reaction mixture was diluted with EtOAc (100 mL), washed with $H_2O$ (50 mL) and brine (50 mL). The organic layer was dried over $Na_2SO_4$, filtered and evaporated. The crude product was purified by preparative HPLC, PrepMethod C, (gradient: 1-25%) to give the title compound (0.027 g, 17%) as a yellow solid; HRMS (ESI) m/z $[M+H]^+$ calcd for $C_{21}$I-124$N_5O_3$S: 426.1594. found: 426.1580; $^1H$ NMR (400 MHz, DMSO-$d_6$) δ 8.92 (t, 1H), 8.56 (d, 1H), 7.86 (d, 1H), 7.37 (d, 1H), 7.29 (dd, 1H), 7.20 (d, 1H), 5.32 (dd, 1H), 4.89 (d, 1H), 4.77-4.68 (m, 2H), 4.30 (d, 2H), 3.53-3.32 (m, overlapping with solvent), 3.15 (dd, 1H), 2.50-2.42 (m, overlapping with solvent), 2.14-2.02 (m, 1H), 1.86-1.73 (m, 1H).

Example 221: N-(2-((R)-4-Cyanothiazolidin-3-yl)-2-oxoethyl)-6-((S)-3-(hydroxymethyl)-pyrrolidin-1-yl)quinoline-4-carboxamide

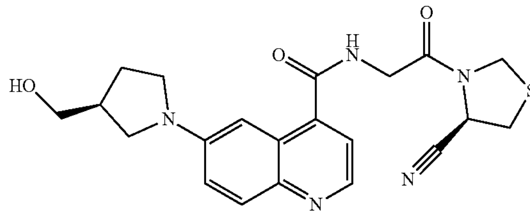

DIPEA (231 μL, 1.32 mmol) was added to a suspension of (S)-6-(3-(hydroxymethyl)pyrrolidin-1-yl)quinoline-4-carboxylic acid Intermediate 410 (120 mg, 0.44 mmol), (R)-3-glycylthiazolidine-4-carbonitrile hydrochloride Intermediate 4 (92 mg, 0.44 mmol), T3P (50% in EtOAc, 1.12 g, 1.76 mmol) in MeCN (5 mL) and EtOAc (5 mL). The reaction mixture was stirred at 20° C. for 5 h and then concentrated under reduced pressure. The reaction mixture was diluted with EtOAc (100 mL), washed with $H_2O$ (25 mL) and brine (25 mL). The organic layer was dried over $Na_2SO_4$, filtered and evaporated. The crude product was purified by preparative HPLC, PrepMethod C, (gradient: 5-23%) to give the title compound (0.032 g, 17%) as a yellow solid; HRMS (ESI) m/z $[M+H]^+$ calcd for $C_{21}H_{24}N_5O_3S$: 426.1594. found: 426.1596; $^1H$ NMR (400 MHz, DMSO-$d_6$) δ 8.92 (t, 1H), 8.56 (d, 1H), 7.86 (d, 1H), 7.37 (d, 1H), 7.29 (dd, 1H), 7.20 (d, 1H), 5.32 (dd, 1H), 4.89 (d, 1H), 4.80-4.65 (m, 2H), 4.30 (d, 2H), 3.50-3.32 (m, overlapping with solvent), 3.15 (dd, 1H), 2.50-2.42 (m, overlapping with solvent), 2.14-2.02 (m, 1H), 1.86-1.73 (m, 1H).

Example 222: (R)—N-(2-(4-Cyanothiazolidin-3-yl)-2-oxoethyl)-6-(1-thia-6-azaspiro[3,3]heptan-6-yl) quinoline-4-carboxamide

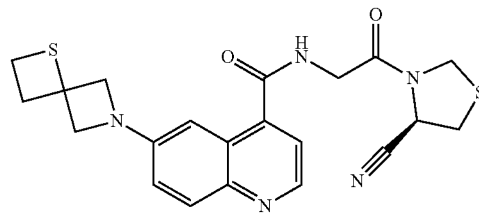

DIPEA (198 μL, 1.13 mmol) was added to a suspension of 6-(1-thia-6-azaspiro[3.3]heptan-6-yl)quinoline-4-carboxylic acid Intermediate 412 (65 mg, 0.23 mmol), (R)-3-glycylthiazolidine-4-carbonitrile hydrochloride Intermediate 4 (94 mg, 0.45 mmol), EDC (131 mg, 0.68 mmol) and HOBt (92 mg, 0.68 mmol) in MeCN (5 mL) and EtOAc (5 mL). The reaction mixture was stirred at 50° C. for 2 h and then concentrated under reduced pressure. The reaction mixture was diluted with EtOAc (80 mL) and sat $NaHCO_3$ (30 mL, aq), extracted with EtOAc (5×75 mL). The pooled organic layers were washed with $H_2O$ (3×50 mL), dried over $Na_2SO_4$, filtered and evaporated. The crude product was purified by preparative HPLC, PrepMethod B (gradient: 26-46%) to give the title compound (0.055 g, 55%) as a yellow solid; HRMS (ESI) m/z $[M+H]^+$ calcd for $C_{21}H_{22}N_5O_2S_2$: 440.1210. found: 440.1218; $^1H$ NMR (300 MHz, DMSO-$d_6$) δ 8.94 (t, 1H), 8.62 (d, 1H), 7.86 (d, 1H), 7.39 (d, 1H), 7.20 (d, 1H), 7.09 (dd, 1H), 5.51-5.29 (m, 1H), 4.88 (d, 1H), 4.71 (d, 1H), 4.33-4.18 (m, 4H), 4.08 (d, 2H), 3.41-3.36 (m, overlapping with solvent), 3.22-3.00 (m, 4H).

Example 223: (R)—N-(2-(4-Cyanothiazolidin-3-yl)-2-oxoethyl)-6-(4-fluoro-4-phenyl-piperidin-1-yl)quinoline-4-carboxamide

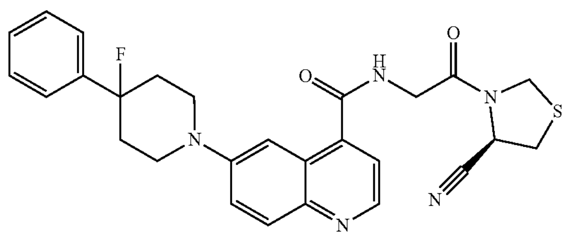 [SMILES: N#C[C@@H]1CSCN1C(=O)CNC(=O)c1ccnc2ccc(N3CCC(F)(c4ccccc4)CC3)cc12]

DIPEA (274 μL, 1.57 mmol) was added to a suspension of 6-(4-fluoro-4-phenylpiperidin-1-yl)quinoline-4-carboxylic acid Intermediate 415 (110 mg, 0.31 mmol), (R)-3-glycylthiazolidine-4-carbonitrile hydrochloride Intermediate 4 (98 mg, 0.47 mmol), EDC (120 mg, 0.63 mmol) and HOBt (85 mg, 0.63 mmol) in MeCN (5 mL) and EtOAc (5 mL). The reaction mixture was stirred at 50° C. for 2 h and then concentrated under reduced pressure. The reaction mixture was diluted with EtOAc (25 mL), washed with $H_2O$ (2×15 mL), dried over $Na_2SO_4$, filtered and evaporated. The crude product was purified by preparative HPLC, Prep-Method B (gradient: 59-66%) to give the title compound (0.060 g, 38%) as a yellow solid; HRMS (ESI) m/z $[M+H]^+$ calcd for $C_{27}H_{27}FN_5O_2S$: 504.1864. found: 504.1872; $^1H$ NMR (300 MHz, $CD_3OD$) δ 8.67 (d, 1H), 7.97 (d, 1H), 7.88 (d, 1H), 7.78 (dd, 1H), 7.53 (d, 1H), 7.50-7.25 (m, 5H), 5.33 (dd, 1H), 4.88-4.68 (m, overlapping with solvent), 4.41 (d, 2H), 4.17-3.99 (m, 2H), 3.58-3.33 (m, overlapping with solvent), 2.48-2.03 (m, 4H).

Example 224: N-(2-((R)-4-Cyanothiazolidin-3-yl)-2-oxoethyl)-6-((RS)-3,3-difluoro-4-hydroxypyrrolidin-1-yl)quinoline-4-carboxamide

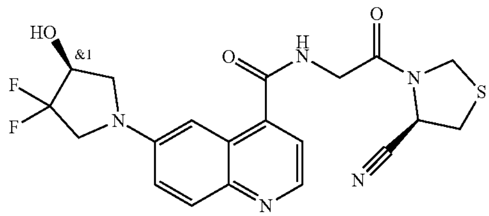 [SMILES: N#C[C@@H]1CSCN1C(=O)CNC(=O)c1ccnc2ccc(N3C[C@H](O)C(F)(F)C3)cc12]

TEA (142 μL, 1.02 mmol) was added to a suspension of rac-(R)-6-(3,3-difluoro-4-hydroxypyrrolidin-1-yl)quinoline-4-carboxylic acid Intermediate 417 (100 mg, 0.34 mmol), (R)-3-glycylthiazolidine-4-carbonitrile hydrochloride Intermediate 4 (71 mg, 0.34 mmol), EDC (98 mg, 0.51 mmol) and HOBt (69 mg, 0.51 mmol) in MeCN (5 mL) and EtOAc (5 mL). The reaction mixture was stirred at 20° C. for 16 h, diluted with EtOAc (75 mL), washed with sat $NaHCO_3$ (3×25 mL, aq), $H_2O$ (20 mL), brine (20 mL), dried over $Na_2SO_4$, filtered and concentrated under reduced pressure. The crude product was purified by preparative HPLC, Prep-Method C, (gradient: 5-30%) to give the title compound (0.055 g, 35%) as a yellow solid; HRMS (ESI) m/z $[M+H]^+$ calcd for $C_{20}H_{20}F_2N_5O_3S$: 448.1250. found: 448.1242; $^1H$ NMR (400 MHz, DMSO-$d_6$) δ 9.00 (t, 1H), 8.64 (d, 1H), 7.93 (d, 1H), 7.40 (d, 1H), 7.38-7.30 (m, 2H), 6.17 (d, 1H), 5.33 (dd, 1H), 4.90 (d, 1H), 4.72 (d, 1H), 4.40 (brs, 1H), 4.34-4.27 (d, 2H), 3.98-3.75 (m, 3H), 3.49-3.33 (m, overlapping with solvent).

Example 225: N-(2-((R)-4-Cyanothiazolidin-3-yl)-2-oxoethyl)-6-((3R*,4R*)-3,4-dimethylpyrrolidin-1-yl)quinoline-4-carboxamide Isomer 1

Isomer 1

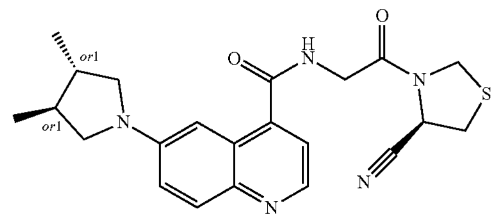

Example 226: N-(2-((R)-4-Cyanothiazolidin-3-yl)-2-oxoethyl)-6-((3R*,4R*)-3,4-dimethylpyrrolidin-1-yl)quinoline-4-carboxamide Isomer 2

Isomer 2

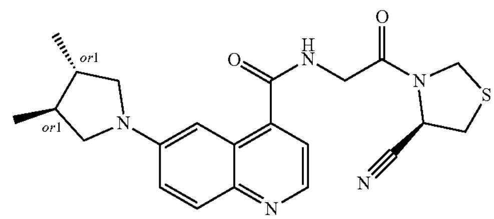

DIPEA (1.17 mL, 6.70 mmol) was added to a stirred suspension of rac-6-((3R,4R)-3,4-dimethylpyrrolidin-1-yl)quinoline-4-carboxylic acid Intermediate 419 (410 mg, 0.67 mmol), (R)-3-glycylthiazolidine-4-carbonitrile hydrochloride Intermediate 4 (209 mg, 1.00 mmol) and HATU (762 mg, 2.01 mmol) in MeCN (5 mL) and EtOAc (5 mL). The reaction mixture was stirred at 4° C. for 15 h and then concentrated under reduced pressure. The residue was dissolved with a mixture of sat $NaHCO_3$ (50 mL, aq) and EtOAc (100 mL). The aq layer was extracted with EtOAc (3×100 mL). The organic layers were combined and washed with $H_2O$ (3×75 mL). The aq layers were combined and extracted with EtOAc (4×25 mL). All organic layers were combined, dried over $Na_2SO_4$, filtered and evaporated. The residue was purified by preparative HPLC, PrepMethod F (gradient: 25-40%). The isomers were separated by preparative chiral HPLC on a CHIRAL ART Cellulose-SB column (5 μm, 250×20 ID mm) using an isocratic run of 50% MeOH in MTBE (0.5% 2 M $NH_3$ in MeOH) as mobile phase, and with a flow rate of 20 mL/min;

the first eluting compound gave the title compound Isomer 1 Example 225 (0.088 g, 37%) as a yellow solid; HRMS (ESI) m/z $[M+H]^+$ calcd for $C_{22}H_{26}N_5O_2S$: 424.1802. found: 424.1798; $^1H$ NMR (300 MHz, DMSO-$d_6$) δ 8.90 (t, 1H), 8.53 (d, 1H), 7.83 (d, 1H), 7.34 (d, 1H), 7.30-7.06 (m, 2H), 5.40-5.22 (m, 1H), 4.89 (d, 1H), 4.71 (d, 1H), 4.28 (d, 2H), 3.62 (dd, 2H), 3.42-3.33 (m, overlapping with solvent), 2.98 (t, 2H), 2.00-1.78 (m, 2H), 1.08 (d, 6H);

and the second eluting compound gave the title compound Isomer 2 Example 226 (0.088 g, 37%) as a yellow solid; HRMS (ESI) m/z $[M+H]^+$ calcd for $C_{22}H_{26}N_5O_2S$: 424.1802. found: 424.1808; $^1H$ NMR (300 MHz, DMSO-$d_6$) δ 8.91 (t, 1H), 8.53 (d, 1H), 7.83 (d, 1H), 7.34 (d, 1H), 7.29-7.09 (m, 2H), 5.40-5.27 (m, 1H), 4.89 (d, 1H), 4.71 (d, 1H), 4.40-4.20 (m, 2H), 3.70-3.53 (m, 2H), 3.45-3.34 (m, overlapping with solvent), 2.98 (t, 2H), 2.00-1.78 (m, 2H), 1.08 (d, 6H).

Example 227: (R)—N-(2-(4-Cyanothiazolidin-3-yl)-2-oxoethyl)-6-(1,5-dioxa-9-azaspiro[5.5]undecan-9-yl)quinoline-4-carboxamide

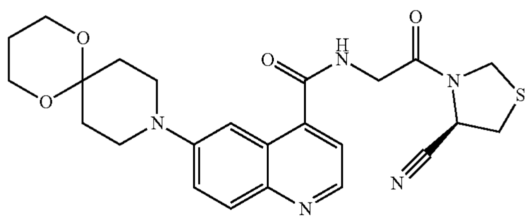 [SMILES: N#C[C@@H]1CSCN1C(=O)CNC(=O)c1ccnc2ccc(N3CCC4(CC3)OCCCO4)cc12]

DIPEA (586 μL, 3.36 mmol) was added to a solution of 6-(1,5-dioxa-9-azaspiro[5.5]undecan-9-yl)quinoline-4-carboxylic acid Intermediate 424 (220 mg, 0.67 mmol), (R)-3-glycylthiazolidine-4-carbonitrile hydrochloride Intermediate 4 (209 mg, 1.01 mmol), HOBt (272 mg, 2.01 mmol) and EDC (386 mg, 2.01 mmol) in MeCN (10 mL) and EtOAc (10 mL) at 15° C. The reaction mixture was stirred at 40° C. for 3 h. The solvent was removed under reduced pressure and the residue was diluted with sat $NaHCO_3$(aq, 200 mL). The aqueous phase was extracted with EtOAc (3×200 mL), and the combined organic layer was washed with water (3×50 mL), dried over $Na_2SO_4$, filtered and evaporated at reduced pressure. The crude product was purified by preparative HPLC, PrepMethod T, (gradient: 14-47%) to give the title compound (0.157 g, 49%) as a yellow solid; HRMS (ESI) m/z $[M+H]^+$ calcd for $C_{24}H_{28}N_5O_4S$: 482.1856. found: 482.1854; $^1H$ NMR (400 MHz, DMSO-$d_6$) δ 8.99 (t, 1H), 8.66 (d, 1H), 7.87 (d, 1H), 7.74-7.63 (m, 2H), 7.39 (d, 1H), 5.33 (dd, 1H), 4.90 (d, 1H), 4.72 (d, 1H), 4.30 (dd, 2H), 3.87 (t, 4H), 3.45-3.34 (m overlapping with solvent), 1.98-1.90 (m, 4H), 1.63 (p, 2H).

Example 228: (R)—N-(2-(4-Cyanothiazolidin-3-yl)-2-oxoethyl)-6-(1,4-dioxa-8-azaspiro[4.5]decan-8-yl)quinoline-4-carboxamide

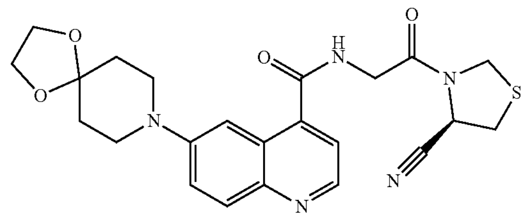 [SMILES: N#C[C@@H]1CSCN1C(=O)CNC(=O)c1ccnc2ccc(N3CCC4(CC3)OCCO4)cc12]

DIPEA (351 μL, 2.01 mmol) was added to a solution of 6-(1,4-dioxa-8-azaspiro[4.5]-decan-8-yl)quinoline-4-carboxylic acid Intermediate 426 (126 mg, 0.40 mmol), (R)-3-glycylthiazolidine-4-carbonitrile hydrochloride Intermediate 4 (125 mg, 0.60 mmol), HOBt (544 mg, 4.02 mmol) and EDC (771 mg, 4.02 mmol) in MeCN (6.0 mL) and EtOAc (6.0 mL) at 15° C. The reaction mixture was stirred at 15° C. for 16 h under an atmosphere of $N_2$ (g). The solvent was removed under reduced pressure, and the residue was diluted with sat $NaHCO_3$ (aq, 250 mL). The aqueous phase was extracted with EtOAc (3×250 mL), and the combined organic layer was washed with water (3×50 mL), dried over $Na_2SO_4$, filtered and evaporated at reduced pressure. The crude product was purified by preparative HPLC, PrepMethod C, (gradient 12-22%) to give the title compound (0.065 g, 34%) as a yellow solid; HRMS (ESI) m/z $[M+H]^+$ calcd for $C_{23}H_{26}N_5O_4S$: 468.1705. found: 468.1723; $^1H$ NMR (300 MHz, DMSO-d6) δ 9.03 (t, 1H), 8.67 (d, 1H), 7.89 (d, 1H), 7.78-7.64 (m, 2H), 7.40 (d, 1H), 5.33 (dd, 1H), 4.90 (d, 1H), 4.71 (d, 1H), 4.30 (d, 2H), 3.92 (s, 4H), 3.56-3.45 (m, 4H), 3.41-3.25 (m, overlapping with solvent), 1.76 (dd, 4H).

Example 229: (R)—N-(2-(4-Cyanothiazolidin-3-yl)-2-oxoethyl)-6-(2-oxa-7-azaspiro[3.5]-nonan-7-yl)quinoline-4-carboxamide

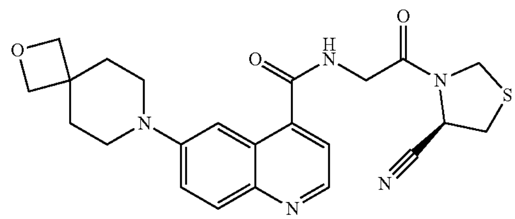 [SMILES: N#C[C@@H]1CSCN1C(=O)CNC(=O)c1ccnc2ccc(N3CCC4(CC3)COC4)cc12]

Step a) 6-(2-Oxa-7-azaspiro[3.5]nonan-7-yl)quinoline-4-carboxylic acid

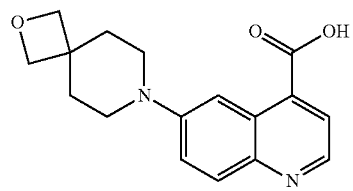 [SMILES: O=C(O)c1ccnc2ccc(N3CCC4(CC3)COC4)cc12]

NaOH (88 mg, 2.19 mmol) was added to a solution of methyl 6-(2-oxa-7-azaspiro[3.5]nonan-7-yl)quinoline-4-carboxylate Intermediate 427 (137 mg, 0.44 mmol) in MeOH (9.0 mL) and water (3.0 mL), and the reaction mixture was stirred at 15° C. for 2 h. The solvent was removed under reduced pressure. The residue was diluted with water (20 mL) and the pH was adjusted to 3 with aq HCl (1 M). The aqueous phase was extracted with EtOAc (10×50 mL), and the combined organic layer was dried over $Na_2SO_4$, filtered and evaporated to give the title compound (0.55 g) as a crude orange solid; MS (ESI) m/z $[M+H]^+$ 299.05.

Step b) (R)—N-(2-(4-Cyanothiazolidin-3-yl)-2-oxoethyl)-6-(2-oxa-7-azaspiro[3.5]nonan-7-yl)quinoline-4-carboxamide DIPEA (754 μL, 4.32 mmol) was added to 6-(2-oxa-7-azaspiro[3.5]nonan-7-yl)quinoline-4-carboxylic acid from Step a) (541 mg, 0.43 mmol), (R)-3-glycylthiazolidine-4-carbonitrile hydrochloride Intermediate 4 (134 mg, 0.65 mmol), HOBt (583 mg, 4.32 mmol) and EDC (827 mg, 4.32 mmol) in MeCN (5 mL) and EtOAc (5 mL) at 15° C. The reaction mixture was stirred at 15° C. for 16 h. The solvent was removed under reduced pressure, and the residue was diluted with sat $NaHCO_3$(aq, 250 mL), The aqueous phase was extracted with EtOAc (3×250 mL), and the combined organic layer was washed with water (3×50 mL), dried over $Na_2SO_4$, filtered and evaporated. The crude product was purified by preparative HPLC, PrepMethod R, (gradient: 15-35%) to give the title compound (0.171 g, 88%) as a yellow solid; HRMS (ESI) m/z $[M+H]^+$ calcd for $C_{23}H_{26}N_5O_3S$: 452.1750. found: 452.1724; $^1H$ NMR (400 MHz, DMSO-$d_6$) δ 8.99 (t, 1H), 8.67 (d, 1H), 7.87 (d, 1H), 7.71-7.62 (m, 2H), 7.39 (d, 1H), 5.33 (dd, 1H), 4.90 (d, 1H), 4.71 (d, 1H), 4.31 (s, 4H), 4.30 (dd, 2H), 3.40-3.27 (m, overlapping with solvent), 1.96-1.89 (m, 4H).

Example 230: (R)—N-(2-(4-cyanothiazolidin-3-yl)-2-oxoethyl)-6-(4-oxopiperidin-1-yl)quinoline-4-carboxamide

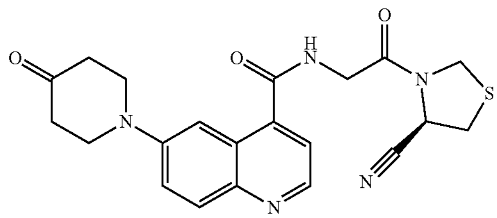 [SMILES: N#C[C@@H]1CSCN1C(=O)CNC(=O)c1ccnc2ccc(N3CCC(=O)CC3)cc12]

DIPEA (189 μL, 1.08 mmol) was added to a solution of 6-(1,5-dioxa-9-azaspiro[5.5]undecan-9-yl)quinoline-4-carboxylic acid Intermediate 424 (71 mg, 0.22 mmol), (R)-3-glycylthiazolidine-4-carbonitrile hydrochloride Intermediate 4 (67 mg, mmol), HOBt (292 mg, 2.16 mmol) and EDC (415 mg, 2.16 mmol) in MeCN (5 mL) and EtOAc (5 mL) at 15° C. The reaction mixture was stirred at 50° C. for 2 h. The solvent was removed under reduced pressure and the residue was diluted with sat $NaHCO_3$(aq, 200 mL). The aqueous phase was extracted with EtOAc (3×200 mL), and the combined organic layer was washed with water (3×50 mL), dried over $Na_2SO_4$, filtered and evaporated at reduced pressure. The crude product was purified by preparative HPLC, PrepMethod X, (gradient: 14-24%). The product containing fractions were collected and evaporated and the residue was lyophilized from a mixture of water/MeCN (×3) to give the title compound (57 mg, 61%) as a yellow solid; HRMS (ESI) m/z $[M+H]^+$ calcd for $C_{21}H_{22}N_5O_3S$: 424.1438. found: 424.1450; $^1H$ NMR (500 MHz, DMSO-$d_6$) δ 9.02 (t, 1H), 8.68 (d, 1H), 7.94 (d, 1H), 7.85 (d, 1H), 7.75 (dd, 1H), 7.40 (d, 1H), 5.32 (dd, 1H), 4.89 (d, 1H), 4.71 (d, 1H), 4.37-4.24 (m, 2H), 3.82 (t, 4H), 3.50-3.34 (m, overlapping with solvent), 2.49-2.46 (m, overlapping with solvent).

D. Biological Data

The hFAP protein used in the Examples was either commercially sourced or produced in insect cells as recombinant hFAP (Gp67-6HN-TEV-FAP (M39-A757), MW 89086.7 Da, or cd33-FAP (27-757)-6His, MW85926 Da). Recombinant hFAP protein was secreted from Sf21 cells in media, purified with affinity (batchmode, Ni excel resin, ÄKTA, GE Healthcare) and size exclusion chromatography (Superdex200, ÄKTA, GE Healthcare), concentrated to 19.5 mg/mL, snapfrozen in liquid $N_2$ and stored in −80° C.

Example 231: FAP Inhibition and Binding Assays

A. hFAP Inhibition Assay

Compounds were tested in a biochemical inhibition assay using hFAP enzyme at nM FAC (Proteros, 38-760 (PR-0071)) and the substrate Ala-Pro-AMC (ARI-3144) at μM FAC. 384 low volume black plates (Greiner #784076) were used. 4 μL, 0.48 nM enzyme solution (100 mM Tris HCl, 100 mM NaCl, 0.05% Chaps, pH 7.4) was added to nL compounds (in DMSO) at 10 CR, 3 fold dilution series from 50 μM FAC. Plates were incubated for 15 min at rt in dark. 4 μL, 40 μM substrate solution (100 mM Tris HCl, 100 mM NaCl, 0.05% Chaps, pH 7.4) was added to each well. Plates were centrifuged at 1000 rpm and incubated for 30 min at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound A (i.e., (S)—N-(2-(2-cyano-4,4-difluoropyrrolidin-1-yl)-2-oxoethyl)quinoline-4-carboxamide as reported in *J. Med. Chem.* 2014, 57, 3053) at 50 μM as 100% inhibitor control. Data for the compounds tested are reported in Table 1.

B. hFAP Inhibition Assay (Tight Binders)

Compounds were tested in a biochemical inhibition assay using human Fibroblast activation protein alpha (hFAP) enzyme at 2.4 pM FAC (Proteros, 38-760 (PR-0071) and the substrate Ala-Pro-AMC (ARI-3144) at 20 μM FAC. 384 low volume black plates (Greiner #784076) were used. 4 μL, 4.8 pM enzyme solution (100 mM Tris HCl, 100 mM NaCl, Chaps, pH 7.4) was added to 40 nL compounds (in DMSO) at 10 CR, 3 fold dilution series from 50 nM FAC. Plates were incubated for 15 min at rt in dark. 4 μL, 40 μM substrate solution (100 mM Tris HCl, 100 mM NaCl, 0.05% Chaps, pH 7.4) was added to each well. Plates were centrifuged at 1000 rpm and incubated for 2.5 h at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound A (i.e., (S)—N-(2-(2-cyano-4,4-difluoropyrrolidin-1-yl)-2-oxoethyl)quinoline-4-carboxamide as reported in J. Med. Chem. 2014, 57, 3053) at 50 μM as 100% inhibitor control. Data for the compounds tested are reported in Table 1.

C. hFAP Binding Assay

Compounds were tested in a direct binding assay using 8K surface plasmon resonance biosensor (GE Healthcare) at 20° C. Immobilization of hFAP (M39-A757) on a CMD200M sensor chip (Xantec) was performed using standard amine coupling procedure in immobilization buffer (10 mM HEPES, 150 mM NaCl, 0.05% Tween20, pH 7.4). The surface was washed with 10 mM NaOH, 1M NaCl before being activated with EDC/NHS (GE Healthcare), followed by immobilization of hFAP (in 10 mM Acetate pH 5.0). Finally, the surface was deactivated by ethanolamine Immobilization levels of hFAP were around 4000-6000 RU. The reference spot was treated as described, omitting the injection of hFAP. Compound concentration series were injected over the immobilized protein in increasing concentrations (2-500 nM) using single cycle kinetics in running buffer (20 mM TRIS, 150 mM NaCl, 0.05% Tween20, 1% DMSO, pH 7.4). Interaction models were fitted globally to the experimental traces, enabling determination of $k_{on}$, $k_{off}$ and $K_d$. Data for the compounds tested are reported in Table 1.

TABLE 1

| Example | hFAP inhibition assay $IC_{50}$ (nM)[1] | hFAP inhibition assay (tight binders) $IC_{50}$ (nM)[2] | hFAP Binding assay $K_d$ (nM)[3] | hFAP Binding assay $k_{(on)}$ ($M^{-1}s^{-1}$)[3] | hFAP Binding assay $k_{(off)}$ (1/s)[3] |
|---|---|---|---|---|---|
| 1 | | 0.099 | 0.18 | 730000 | 0.00014 |
| 2 | | 0.52 | 9.5 | 410000 | 0.0038 |
| 3 | 0.24 | 0.13 | 0.095 | 4100000 | 0.00040 |
| 4 | | 0.058 | 0.079 | 1200000 | 0.000094 |
| 5 | | 0.060 | 0.049 | NV | NV |
| 6 | | 0.51 | 0.38 | 40000000000 | 18 |
| 7 | | 0.16 | 0.10 | 740000 | 0.000075 |
| 8 | | 0.063 | 0.032 | 1300000 | 0.000034 |
| 9 | | 0.25 | 0.66 | 1200000 | 0.00076 |
| 10 | | 0.054 | 0.15 | 370000 | 0.000056 |
| 11 | | 0.057 | 0.044 | NV | NV |
| 12 | | 0.065 | 0.038 | 1900000 | 0.000064 |
| 13 | | 0.041 | 0.014 | 9200000 | 0.000076 |
| 14 | | 0.080 | 0.050 | 1300000 | 0.000064 |
| 15 | | 0.12 | 0.11 | 490000 | 0.000046 |
| 16 | | 0.11 | 0.054 | 740000 | 0.000041 |
| 17 | 0.22 | 0.085 | 0.015 | 8300000 | 0.00012 |
| 18 | 0.19 | 0.047 | 0.068 | 1400000 | 0.000059 |
| 19 | 0.66 | 0.38 | 0.15 | 430000 | 0.000066 |
| 20 | 0.74 | 0.43 | 0.030 | 4200000 | 0.00012 |
| 21 | 0.29 | 0.11 | 0.066 | 3000000 | 0.00020 |
| 22 | 0.34 | 0.12 | 0.050 | 940000 | 0.000047 |
| 23 | 0.31 | 0.20 | 0.085 | 2100000 | 0.00018 |
| 24 | 0.27 | 0.20 | 0.0094 | 25000000 | 0.00048 |
| 25 | 0.41 | 0.30 | 0.076 | 1400000 | 0.00011 |
| 26 | 0.31 | 0.10 | 0.056 | 1300000 | 0.000065 |
| 27 | 0.29 | 0.11 | 0.024 | 1100000 | 0.000026 |
| 28 | 0.26 | 0.10 | 0.11 | 1100000 | 0.00011 |
| 29 | 0.13 | 0.055 | 0.057 | 1100000 | 0.000061 |
| 30 | 0.28 | 0.12 | 0.042 | 5200000 | 0.00022 |
| 31 | 0.22 | 0.10 | 0.031 | 9700000 | 0.00024 |
| 32 | 0.30 | 0.16 | 0.022 | 1300000 | 0.000029 |
| 33 | 0.34 | 0.27 | 0.059 | 1100000 | 0.000052 |
| 34 | 0.27 | 0.22 | 0.057 | 2200000 | 0.000082 |
| 35 | 0.47 | 0.17 | 0.10 | 900000 | 0.00010 |
| 36 | 0.24 | 0.084 | 0.053 | 3000000 | 0.000090 |
| 37 | 0.22 | 0.19 | 0.028 | 1000000 | 0.000030 |
| 38 | | 0.10 | 0.11 | 520000 | 0.000078 |
| 39 | 0.28 | 0.10 | 0.040 | 4900000 | 0.00016 |
| 40 | 0.24 | 0.065 | 0.043 | 1300000 | 0.000046 |
| 41 | 0.33 | 0.16 | 0.093 | 680000 | 0.000064 |

TABLE 1-continued

| Example | hFAP inhibition assay $IC_{50}$ (nM)[1] | hFAP inhibition assay (tight binders) $IC_{50}$ (nM)[2] | hFAP Binding assay $K_d$ (nM)[3] | hFAP Binding assay $k_{(on)}$ ($M^{-1}s^{-1}$)[3] | hFAP Binding assay $k_{(off)}$ (1/s)[3] |
|---|---|---|---|---|---|
| 42 | | 0.053 | 0.030 | 1800000 | 0.000054 |
| 43 | | 0.045 | 0.0061 | 3200000 | 0.000019 |
| 44 | 0.22 | 0.074 | 0.042 | 1700000 | 0.000072 |
| 45 | 0.20 | 0.14 | 0.048 | 5400000 | 0.00018 |
| 46 | 0.29 | 0.082 | 0.020 | 3000000 | 0.000062 |
| 47 | 0.22 | 0.20 | 0.031 | 5600000 | 0.00016 |
| 48 | 0.29 | 0.11 | 0.067 | 1400000 | 0.000089 |
| 49 | 0.19 | 0.041 | 0.020 | 8800000 | 0.00017 |
| 50 | 0.34 | 0.069 | 0.071 | NV | NV |
| 51 | 0.21 | 0.064 | 0.021 | 5600000 | 0.00011 |
| 52 | 0.20 | 0.045 | 0.044 | 6800000 | 0.00019 |
| 53 | 0.27 | 0.18 | 0.074 | 680000 | 0.000050 |
| 54 | 0.22 | 0.062 | 0.045 | 6200000 | 0.00023 |
| 55 | 0.25 | 0.083 | 0.036 | 6700000 | 0.00025 |
| 56 | 0.44 | 0.19 | 0.14 | 540000 | 0.00011 |
| 57 | 0.26 | 0.098 | 0.022 | 8000000 | 0.00018 |
| 58 | 0.23 | 0.076 | 0.016 | 8800000000 | 0.091 |
| 59 | 0.27 | 0.061 | 0.087 | 2600000 | 0.00019 |
| 60 | 0.22 | 0.14 | 0.099 | 1700000 | 0.00017 |
| 61 | 0.21 | 0.060 | 0.062 | NV | NV |
| 62 | 0.25 | 0.058 | 0.12 | 710000 | 0.000085 |
| 63 | 0.33 | 0.19 | 0.030 | 4100000 | 0.000059 |
| 64 | 0.28 | 0.085 | 0.12 | 1300000 | 0.00015 |
| 65 | 0.28 | 0.17 | 0.055 | 6700000 | 0.00047 |
| 66 | | 0.077 | 0.035 | 26000000 | 0.00022 |
| 67 | 0.37 | 0.084 | 0.012 | 4900000 | 0.000046 |
| 68 | 0.37 | 0.10 | 0.11 | 1000000 | 0.00011 |
| 69 | 0.29 | 0.070 | 0.070 | 1400000 | 0.000093 |
| 70 | | 0.12 | 0.022 | 5400000 | 0.00014 |
| 71 | 0.22 | 0.068 | 0.050 | NV | NV |
| 72 | | 0.079 | 0.026 | 5200000 | 0.00016 |
| 73 | | 0.13 | 0.066 | 2400000 | 0.00016 |
| 74 | | 0.094 | 0.14 | 1100000 | 0.00016 |
| 75 | | 0.050 | 0.0063 | 2300000 | 0.000024 |
| 76 | | 0.080 | 0.051 | 1000000 | 0.000052 |
| 77 | | 0.051 | 0.014 | 4800000 | 0.000066 |
| 78 | | 0.097 | 0.12 | 880000 | 0.00010 |
| 79 | | 0.043 | 0.018 | 16000000 | 0.00012 |
| 80 | | 0.10 | 0.036 | 2400000 | 0.000088 |
| 81 | | 0.13 | 0.044 | 1400000 | 0.000063 |
| 82 | | 0.11 | 0.052 | 1400000 | 0.000071 |
| 83 | | 0.082 | 0.039 | 1700000 | 0.000064 |
| 84 | | 0.074 | 0.12 | 1200000 | 0.00011 |
| 85 | | 0.087 | 0.032 | 4000000 | 0.00011 |
| 86 | | 0.074 | 0.081 | 730000 | 0.000058 |
| 87 | 0.40 | 0.11 | 0.039 | 2800000 | 0.00011 |
| 88 | 0.31 | 0.074 | 0.082 | 4200000 | 0.00034 |
| 89 | | 0.096 | 0.053 | 3600000 | 0.00015 |
| 90 | 0.75 | 0.35 | 0.38 | 480000 | 0.00010 |
| 91 | | 0.088 | 0.072 | 3200000 | 0.00021 |
| 92 | | 0.074 | 0.047 | 2200000 | 0.00011 |
| 93 | | 0.091 | 0.047 | 1800000 | 0.000080 |
| 94 | | 0.071 | 0.074 | 1900000 | 0.000099 |
| 95 | | 0.16 | 0.024 | 2900000 | 0.000056 |
| 96 | | 0.17 | 0.067 | 4000000 | 0.00022 |
| 97 | | 0.23 | 0.11 | 690000 | 0.000076 |
| 98 | 0.27 | 0.11 | 0.0088 | 1600000 | 0.000015 |
| 99 | | 0.12 | 0.11 | 2100000 | 0.00020 |
| 100 | 0.50 | 0.27 | 0.73 | 3000000 | 0.0022 |
| 101 | 0.38 | 0.35 | 0.034 | 740000 | 0.000025 |
| 102 | 0.21 | 0.066 | 0.046 | 2000000 | 0.000080 |
| 103 | 0.31 | 0.11 | 0.033 | 3000000 | 0.00010 |
| 104 | 0.21 | 0.081 | 0.020 | 3000000 | 0.000061 |
| 105 | 0.37 | 0.088 | 0.082 | 890000 | 0.000068 |
| 106 | 0.23 | 0.080 | 0.075 | 1800000 | 0.00014 |
| 107 | 0.64 | 0.21 | 0.083 | 1900000 | 0.00016 |
| 108 | 0.28 | 0.12 | 0.038 | 1400000 | 0.000050 |
| 109 | | 1.2 | 8.5 | 1200000 | 0.0099 |
| 110 | | 0.054 | 0.019 | 2200000 | 0.000050 |
| 111 | | 0.064 | 0.055 | 1800000 | 0.000096 |
| 112 | | 0.20 | 0.31 | 440000 | 0.00014 |
| 113 | 0.25 | 0.12 | 0.031 | 1500000 | 0.000045 |

TABLE 1-continued

| Example | hFAP inhibition assay $IC_{50}$ (nM)[1] | hFAP inhibition assay (tight binders) $IC_{50}$ (nM)[2] | hFAP Binding assay $K_d$ (nM)[3] | hFAP Binding assay $k_{(on)}$ $(M^{-1}s^{-1})$[3] | hFAP Binding assay $k_{(off)}$ (1/s)[3] |
|---|---|---|---|---|---|
| 114 | | 0.072 | 0.062 | NV, NV | NV, NV |
| 115 | | 0.040 | 0.11 | NV, NV | NV, NV |
| 116 | | 0.16 | 0.15 | 7900000 | 0.0012 |
| 117 | | 0.061 | 0.060 | NV,NV | NV,NV |
| 118 | | 0.10 | 0.17 | NV | NV |
| 119 | | 0.16 | 0.39 | 610000 | 0.00031 |
| 120 | | 0.15 | 0.13 | NV | NV |
| 121 | | 0.15 | 0.012 | 1100000 | 0.000016 |
| 122 | | 0.049 | 0.033 | 1300000 | 0.000043 |
| 123 | 0.25 | 0.083 | 0.14 | 3000000 | 0.00042 |
| 124 | 0.24 | 0.055 | 0.094 | 3000000 | 0.00028 |
| 125 | 0.21 | 0.046 | 0.048 | 3000000 | 0.00014 |
| 126 | 0.32 | 0.081 | 0.11 | 1800000 | 0.00021 |
| 127 | 0.38 | 0.16 | 0.34 | 6000000 | 0.0020 |
| 128 | 0.45 | 0.24 | 0.15 | 5400000 | 0.00066 |
| 129 | 0.20 | 0.041 | 0.087 | 1400000 | 0.00012 |
| 130 | | 0.19 | 0.18 | 440000 | 0.000078 |
| 131 | | 0.12 | 0.033 | 1800000 | 0.00014 |
| 132 | | 0.41 | 0.52 | 270000 | 0.00014 |
| 133 | | 0.10 | 0.066 | 1200000 | 0.000073 |
| 134 | | 0.13 | 0.13 | 620000 | 0.000080 |
| 135 | | 0.11 | 0.013 | 1700000 | 0.000023 |
| 136 | | 0.061 | 0.036 | 2000000 | 0.000050 |
| 137 | | 0.11 | 0.013 | 9500000 | 0.000098 |
| 138 | | 0.047 | 0.028 | 2500000 | 0.000075 |
| 139 | | 0.32 | 0.015 | NV | NV |
| 140 | | 0.10 | 0.064 | 2600000 | 0.00016 |
| 141 | | 0.059 | 0.062 | 1400000 | 0.000078 |
| 142 | | 0.088 | 0.028 | 1800000 | 0.000055 |
| 143 | | 0.069 | 0.036 | 1600000 | 0.000057 |
| 144 | | 0.081 | 0.049 | 9100000 | 0.00051 |
| 145 | | 0.070 | 0.029 | 4500000 | 0.00013 |
| 146 | | 0.15 | 0.12 | 1400000 | 0.00017 |
| 147 | | 0.067 | 0.045 | 2800000 | 0.00012 |
| 148 | | 0.059 | 0.031 | 6600000 | 0.00020 |
| 149 | | 0.097 | 0.0087 | 4800000 | 0.000039 |
| 150 | | 0.50 | 0.16 | 280000 | 0.000043 |
| 151 | | 0.13 | 0.039 | 1500000 | 0.000053 |
| 152 | | 0.062 | 0.013 | 1000000 | 0.000014 |
| 153 | | 0.11 | 0.015 | 5300000 | 0.000085 |
| 154 | | 0.092 | 0.059 | 910000 | 0.000054 |
| 155 | | 0.086 | 0.016 | 3100000 | 0.000050 |
| 156 | | 0.22 | 0.056 | 1200000 | 0.000066 |
| 157 | | 0.37 | 0.065 | 1900000 | 0.00012 |
| 158 | | 0.10 | 0.10 | 3100000 | 0.00029 |
| 159 | | 0.073 | 0.039 | 2100000 | 0.000092 |
| 160 | | 0.050 | 0.068 | 1100000 | 0.000074 |
| 161 | | 0.052 | 0.022 | 14000000 | 0.00028 |
| 162 | | 0.053 | 0.018 | 1900000 | 0.000028 |
| 163 | | 0.079 | 0.034 | NV | NV |
| 164 | | 0.081 | 0.027 | 1400000 | 0.000036 |
| 165 | | 0.32 | 0.051 | 1200000 | 0.000063 |
| 166 | 0.34 | 0.22 | 0.030 | 2200000 | 0.000049 |
| 167 | | 0.091 | | | |
| 168 | | 0.16 | 0.032 | 1600000 | 0.000048 |
| 169 | 0.22 | 0.057 | 0.16 | 6200000 | 0.00096 |
| 170 | 0.24 | 0.063 | 0.017 | 10000000 | 0.00018 |
| 171 | 0.28 | 0.13 | 0.086 | 1000000 | 0.000092 |
| 172 | 0.55 | 0.26 | 0.036 | 2400000 | 0.000076 |
| 173 | 0.27 | 0.078 | 0.51 | 110000 | 0.000054 |
| 174 | 0.44 | 0.26 | 0.13 | 1900000 | 0.00024 |
| 175 | 0.34 | 0.12 | 0.086 | 1400000 | 0.00012 |
| 176 | 0.54 | 0.087 | 1.9 | 120000 | 0.00022 |
| 177 | 0.29 | 0.11 | 0.56 | 100000 | 0.000058 |
| 178 | 0.20 | 0.042 | 0.053 | 3100000 | 0.00017 |
| 179 | | 0.048 | 0.052 | 3200000 | 0.00016 |
| 180 | | 0.20 | 1.3 | 560000 | 0.00095 |
| 181 | 0.94 | 0.38 | 0.16 | 180000 | 0.000027 |
| 182 | 0.41 | 0.19 | 0.093 | 250000 | 0.000042 |
| 183 | 0.33 | 0.19 | 0.086 | NV | NV |
| 184 | 0.40 | 0.22 | 0.015 | 950000 | 0.000014 |
| 185 | 0.23 | 0.12 | 0.043 | NV | NV |
| 186 | 0.27 | 0.10 | 0.045 | NV | NV |
| 187 | 0.098 | 0.072 | 0.070 | 3100000 | 0.00022 |
| 188 | 0.28 | 0.19 | 0.011 | 2600000 | 0.000022 |
| 189 | | 0.056 | 0.020 | 2600000 | 0.000051 |
| 190 | | 0.069 | 0.020 | 1800000 | 0.000036 |
| 191 | | 0.038 | 0.022 | 1500000 | 0.000033 |
| 192 | | 0.051 | 0.0077 | 1300000 | 0.000014 |
| 193 | | 0.24 | 0.16 | 740000 | 0.00012 |
| 194 | | 0.046 | 0.066 | 1100000 | 0.000068 |
| 195 | | 0.39 | 0.33 | 190000 | 0.000061 |
| 196 | 0.19 | 0.066 | 0.080 | 3200000 | 0.00026 |
| 197 | 0.72 | 0.42 | 0.75 | 88000 | 0.000066 |
| 198 | | 0.056 | 0.038 | 2900000 | 0.00011 |
| 199 | | 0.30 | 0.10 | 2300000 | 0.00026 |
| 200 | | 0.24 | 0.090 | 2500000 | 0.00023 |
| 20 | | <0.025 | 0.059 | 1800000 | 0.00010 |
| 202 | | 0.044 | 0.043 | 1600000 | 0.000070 |
| 203 | | 0.26 | 0.15 | 440000 | 0.000063 |
| 204 | | 0.067 | 0.068 | 850000 | 0.000058 |
| 205 | 0.27 | 0.067 | 0.026 | 2100000 | 0.000046 |
| 206 | 0.22 | 0.065 | 0.033 | NV | NV |
| 207 | | 0.17 | 0.011 | 4600000 | 0.000053 |
| 208 | 0.22 | 0.11 | 0.046 | 5600000 | 0.00026 |
| 209 | 0.44 | 0.15 | 0.020 | 3200000 | 0.000042 |
| 210 | 0.44 | 0.18 | 0.026 | 3800000 | 0.000098 |
| 211 | 0.20 | 0.10 | 0.049 | 5900000 | 0.00020 |
| 212 | 0.29 | 0.26 | 0.10 | 3300000 | 0.00034 |
| 213 | 0.18 | 0.039 | 0.039 | 4400000 | 0.00017 |
| 214 | 0.20 | 0.079 | 0.043 | 2900000 | 0.000092 |
| 215 | 0.41 | 0.12 | 0.095 | 1800000 | 0.00017 |
| 216 | 2.4 | 1.7 | 0.27 | 5200000 | 0.00090 |
| 217 | | 0.67 | 0.71 | 1800000 | 0.0013 |
| 218 | | 0.068 | 0.48 | 670000 | 0.00032 |
| 219 | | 0.11 | 0.083 | 2400000 | 0.00020 |
| 220 | | 0.091 | 0.038 | 1600000 | 0.000050 |
| 221 | | 0.17 | 0.0048 | 8500000 | 0.000046 |
| 222 | | 0.087 | 0.022 | NV | NV |
| 223 | | 0.076 | 0.010 | 2500000 | 0.000026 |
| 224 | | 0.073 | 0.023 | 3000000 | 0.000068 |
| 225 | | 0.11 | 0.077 | NV | NV |
| 226 | | 0.20 | 0.044 | NV | NV |
| 228 | | 0.087 | | | |
| 229 | | 0.091 | 0.010 | 2400000 | 0.000026 |
| 230 | | 0.078 | | | |

[1] $IC_{50}$ is reported after single measurement (n = 1) or as geometric mean for multiple measurements (n = 2-3).

[2] $IC_{50}$ is reported after single measurement (n = 1) or as geometric mean for multiple measurements (n = 2-6).

[3] $K_d$ is reported after single measurement (n = 1) or as geometric mean for multiple measurements (n = 2-4). $k_{(on)}$ and $k_{(off)}$ are reported after single measurement (n = 1) or as an average for multiple measurements (n = 2-4). NV is not valid.

D. FAP Plasma Inhibition Assay

This assay was adapted from the method described in Example 237 for detection of FAP target engagement enzyme activity in plasma. Plasma (anticoagulant K2EDTA) wa used as the enzyme source: Human plasma (Pooled from AZ Biobank), Mouse plasma (AZ AST Biobank), and Cynomolgus plasma (BioIVT, #NHPOOPLK2FNN, lot CYN222895). 384-Well black fluotrack PS plates (Greiner 781076) were used. 20 μL diluted plasma (Cynomolgus and Human plasma dilution 1:40, Mouse plasma dilution 1:67) in buffer (PBS, 0.1% BSA) was added to 0.6 μL compounds (in DMSO). Compounds were tested using 10 CR, 3 fold dilution series from 500 nM FAC. Two replicates for each assay point were run on the same plate. A fluorescence blank read was taken before substrate addition. Substrate, Ala-Pro-AMC (ARI-3144) stock solution (20 mM in DMSO) was diluted in buffer (PBS, 0.1% BSA) to 150 μM concentration and 20 μL added giving 75 μM FAC. Plates were incubated for 40 min at rt in the dark. The plates were read on a Beckman Paradigm® reader with excitation 360 nm and emission 465 nm. Data were analyzed in Excel (IDBS XLfit Add-In) using a one site dose response model (4-parameter logistic fit). $IC_{50}$ values were determined by plotting % inhibition versus log compound concentration. Raw data signals were normalized using 1.5% DMSO in diluted plasma as 0% control and 1.5% DMSO in buffer (no plasma) as 100% inhibitor control. Data for the compounds tested are reported in Table 2.

TABLE 2

| Example | FAP Human Plasma $IC_{50}$ (nM)[1] | FAP Mouse Plasma $IC_{50}$ (nM)[2] | FAP Cyno Plasma $IC_{50}$ (nM)[3] |
|---|---|---|---|
| 2 | 8.1 | 7.3 | 9.2 |
| 8 | 0.10 | 0.20 | 0.20 |
| 9 | 0.60 | 0.60 | 0.60 |
| 16 | 0.20 | 0.40 | 0.20 |
| 24 | 0.20 | 0.40 | 0.30 |
| 27 | 0.20 | 0.50 | 0.30 |
| 28 | 0.20 | 0.50 | 0.30 |
| 50 | 0.30 | 0.50 | 0.30 |
| 67 | 0.36 | 0.52 | 0.40 |
| 68 | 0.30 | 0.50 | 0.30 |
| 69 | 0.20 | 0.30 | 0.20 |
| 70 | 0.20 | 0.30 | 0.20 |
| 71 | 0.20 | 0.20 | 0.20 |
| 72 | 0.20 | 0.20 | 0.20 |
| 74 | 0.20 | 0.30 | 0.20 |
| 82 | 0.30 | 0.40 | 0.30 |
| 88 | 0.20 | 0.30 | 0.20 |
| 98 | 0.20 | 0.40 | 0.30 |
| 102 | 0.20 | 0.20 | 0.20 |
| 112 | 0.60 | 0.80 | 0.50 |
| 113 | 0.20 | 0.50 | 0.40 |
| 147 | 0.10 | 0.20 | 0.10 |
| 151 | 0.20 | 0.40 | 0.30 |
| 157 | 0.30 | 0.60 | 0.40 |
| 163 | 0.10 | 0.20 | 0.20 |
| 166 | 0.30 | 0.60 | 0.30 |
| 170 | 0.30 | 0.50 | |
| 171 | 0.20 | 0.30 | |
| 172 | 0.20 | 0.60 | |
| 173 | 0.10 | 0.20 | |
| 174 | 0.20 | 0.40 | |
| 175 | 0.20 | 0.40 | |
| 178 | 0.10 | 0.10 | |
| 181 | 0.30 | 0.90 | 0.50 |
| 184 | 0.20 | 0.60 | 0.30 |
| 195 | 0.90 | 1.4 | 1 |
| 196 | 0.10 | 0.20 | |
| 203 | 0.40 | 0.50 | 0.40 |
| 204 | 0.20 | 0.30 | 0.20 |
| 205 | 0.30 | 0.30 | 0.30 |

[1]$IC_{50}$ is reported after single measurement (n = 1) or as geometric mean for multiple measurements (n = 4).
[2]$IC_{50}$ is reported after single measurement (n = 1) or as geometric mean for multiple measurements (n = 4).
[3]$IC_{50}$ is reported after single measurement (n = 1).

Example 232: hPrep Inhibition Assay

Compounds were tested in a biochemical inhibition assay using Prolyl endopeptidase, Prolyl Oligopeptidase (hPREP) enzyme at 0.6 nM FAC (R&D Systems, 4308-SE) and the substrate Z-Gly-Pro-amino-methylcoumarin (Bachem, 1-1145) at 50 μM FAC. 384 Low volume black plates (Greiner #784076) were used. 4 μL, 1.2 nM enzyme solution (25 mM Tris HCl, 250 mM NaCl, 0.01% Triton X-100, 5 mM Glutathione, pH 7.5) was added to 40 nL compounds (in DMSO) at 10 CR, 3 fold dilution series from 50 μM FAC. Plates were incubated for 15 min at rt in dark. 4 μL, 100 μM substrate solution (25 mM Tris HCl, 250 mM NaCl, 0.01% Triton X-100, 5 mM Glutathione, pH 7.5) was added to each well. Plates were centrifuged at 1000 rpm and incubated for 20 min at rt in dark. The plates were read on a PHERAstar® reader with excitation 340 nm and emission 460 nm. Data were analyzed in Genedata Screener®. $IC_{50}$ values were determined by plotting % inhibition versus log compound concentration and using a one site dose response model. Raw data signals were normalized using 0.5% DMSO as 0% control and Reference Compound B (i.e., (R)—N-(2-(4-cyanothiazolidin-3-yl)-2-oxoethyl)-7-methylquinoline-4-carboxamide) at 50 μM as 100% inhibitor control. Data for the compounds tested are reported in Table 3.

TABLE 3

| Example | PREP $IC_{50}$ (nM)[1] |
|---|---|
| 1 | 410 |
| 2 | 1700 |
| 3 | 690 |
| 4 | 1100 |
| 5 | 220 |
| 6 | 200 |
| 7 | 510 |
| 8 | 1400 |
| 9 | 980 |
| 10 | 940 |
| 11 | 140 |
| 12 | 510 |
| 13 | 380 |
| 14 | 1200 |
| 15 | 2100 |
| 16 | 1600 |
| 17 | 160 |
| 18 | 570 |
| 19 | 160 |
| 20 | 430 |
| 21 | 93 |
| 22 | 470 |
| 23 | 160 |
| 24 | 510 |
| 25 | 370 |
| 26 | 580 |
| 27 | 660 |
| 28 | 580 |
| 29 | 500 |
| 30 | 510 |
| 31 | 760 |
| 32 | 450 |
| 33 | 220 |
| 34 | 430 |
| 35 | 1700 |
| 36 | 400 |
| 37 | 270 |
| 38 | 480 |
| 39 | 500 |
| 40 | 280 |
| 41 | 640 |
| 42 | 880 |
| 43 | 1000 |
| 44 | 540 |
| 45 | 190 |
| 46 | 110 |
| 47 | 270 |
| 48 | 170 |
| 49 | 340 |
| 50 | 540 |
| 51 | 130 |
| 52 | 400 |
| 53 | 170 |
| 54 | 300 |
| 55 | 440 |
| 56 | 220 |
| 57 | 160 |
| 58 | 180 |
| 59 | 30 |
| 60 | 86 |
| 61 | 390 |

TABLE 3-continued

| Example | PREP $IC_{50}$ (nM)[1] |
|---|---|
| 62 | 280 |
| 63 | 400 |
| 64 | 610 |
| 65 | 100 |
| 66 | 490 |
| 67 | 1200 |
| 68 | 1700 |
| 69 | 2000 |
| 70 | 1100 |
| 71 | 1400 |
| 72 | 1900 |
| 73 | 1800 |
| 74 | 2300 |
| 75 | 490 |
| 76 | 510 |
| 77 | 470 |
| 78 | 890 |
| 79 | 630 |
| 80 | 1500 |
| 81 | 1700 |
| 82 | 930 |
| 83 | 640 |
| 84 | 710 |
| 85 | 720 |
| 86 | 360 |
| 87 | 760 |
| 88 | 1200 |
| 89 | 1300 |
| 90 | 1100 |
| 91 | 260 |
| 92 | 2400 |
| 93 | 1900 |
| 94 | 1800 |
| 95 | 740 |
| 96 | 880 |
| 97 | 890 |
| 98 | 790 |
| 99 | 1100 |
| 100 | 170 |
| 101 | 380 |
| 102 | 680 |
| 103 | 580 |
| 104 | 650 |
| 105 | 590 |
| 106 | 520 |
| 107 | 1100 |
| 108 | 1000 |
| 109 | 4400 |
| 110 | 1100 |
| 111 | 1200 |
| 112 | 3600 |
| 113 | 490 |
| 114 | 230 |
| 115 | 130 |
| 116 | 230 |
| 117 | 170 |
| 118 | 360 |
| 119 | 76 |
| 120 | 25 |
| 121 | 88 |
| 122 | 840 |
| 123 | 740 |
| 124 | 220 |
| 125 | 120 |
| 126 | 260 |
| 127 | 130 |
| 128 | 110 |
| 129 | 330 |
| 130 | 540 |
| 131 | 360 |
| 132 | 3700 |
| 133 | 370 |
| 134 | 620 |
| 135 | 500 |
| 136 | 300 |
| 137 | 340 |
| 138 | 470 |

TABLE 3-continued

| Example | PREP $IC_{50}$ (nM)[1] |
|---|---|
| 139 | 1000 |
| 140 | 840 |
| 141 | 460 |
| 142 | 530 |
| 143 | 460 |
| 144 | 460 |
| 145 | 250 |
| 146 | 450 |
| 147 | 570 |
| 148 | 420 |
| 149 | 470 |
| 150 | 2000 |
| 151 | 1000 |
| 152 | 690 |
| 153 | 540 |
| 154 | 590 |
| 155 | 380 |
| 156 | 310 |
| 157 | 1200 |
| 158 | 560 |
| 159 | 280 |
| 160 | 210 |
| 161 | 470 |
| 162 | 280 |
| 163 | 980 |
| 164 | 240 |
| 165 | 670 |
| 166 | 1700 |
| 167 | 1000 |
| 168 | 630 |
| 169 | 440 |
| 170 | 260 |
| 171 | 270 |
| 172 | 540 |
| 173 | 940 |
| 174 | 87 |
| 175 | 760 |
| 176 | 560 |
| 177 | 360 |
| 178 | 120 |
| 179 | 470 |
| 180 | 590 |
| 181 | 1600 |
| 182 | 210 |
| 183 | 140 |
| 184 | 1100 |
| 185 | 130 |
| 186 | 150 |
| 187 | 38 |
| 188 | 430 |
| 189 | 440 |
| 190 | 690 |
| 191 | 550 |
| 192 | 200 |
| 193 | 360 |
| 194 | 460 |
| 195 | 1200 |
| 196 | 84 |
| 197 | 1900 |
| 198 | 410 |
| 199 | 170 |
| 200 | 130 |
| 201 | 610 |
| 202 | 550 |
| 203 | 3500 |
| 204 | 920 |
| 205 | 640 |
| 206 | 330 |
| 207 | 430 |
| 208 | 210 |
| 209 | 540 |
| 210 | 220 |
| 211 | 110 |
| 212 | 330 |
| 213 | 470 |
| 214 | 280 |
| 215 | 250 |

TABLE 3-continued

| Example | PREP $IC_{50}$ (nM)[1] |
|---|---|
| 216 | 190 |
| 217 | 310 |
| 218 | 390 |
| 219 | 230 |
| 220 | 390 |
| 221 | 410 |
| 222 | 490 |
| 223 | 86 |
| 224 | 670 |
| 225 | 470 |
| 226 | 660 |
| 227 | 600 |
| 228 | 1200 |
| 229 | 320 |
| 230 | 600 |
| B[2] | 5.2 |
| C[3] | 7.1 |

[1] $IC_{50}$ is reported after single measurement (n = 1) or as geometric mean for multiple measurements (n = 2-9).
[2] Reference Compound B: (R)-N-(2-(4-cyanothiazolidin-3-yl)-2-oxoethyl)-7-methylquinoline-4-carboxamide
[3] Reference Compound C: (R)-N-(2-(4-cyanothiazolidin-3-yl)-2-oxoethyl)-quinoline-4-carboxamide

Example 233: hDPP Inhibition Assays

A. hDPP7 Inhibition Assay

Compounds were tested in a biochemical inhibition assay using human dipeptidylpeptidase 7 (hDPP7) enzyme at 15 nM FAC (BPS Bioscience, #80070) and the substrate Ala-Pro-amino-methylcoumarin (BPS Bioscience, #80305) at 5 μM FAC. The enzymatic reactions were conducted in duplicate at rt for 30 min in 50 μL DPP assay buffer (BPS Bioscience, #80300). Compound solutions (in DMSO) at 10 CR, 3 fold dilution series were prepared in assay buffer ten-fold higher than the final concentration, and 5 μL of the dilution was added to a 50 μL reaction so that the highest compound concentration was 100 μM FAC and the concentration of DMSO was 1% in all wells. The plates were read on a Tecan Infinite M1000 microplate reader with excitation 340 nm and emission 460 nm. Data were analyzed in Graph Pad Prism. $IC_{50}$ values were determined by plotting % inhibition versus log compound concentration and using a one site dose response model. Raw data signals were normalized using 1% DMSO as 0% control and no enzyme as 100% inhibitor control. Data for the compounds tested are reported in Table 4.

B. hDPP8 Inhibition Assay

Compounds were tested in a biochemical inhibition assay using human dipeptidylpeptidase 8 (hDPP8) enzyme at 1.5 nM FAC (BPS Bioscience, #80080) and the substrate Ala-Pro-amino-methylcoumarin (BPS Bioscience #80305) at 5 μM FAC. The enzymatic reactions were conducted in duplicate at rt for 30 min in 50 μL DPP assay buffer (BPS Bioscience, #80300). Compound solutions (in DMSO) at 10 CR, 3 fold dilution series were prepared in assay buffer ten-fold higher than the final concentration, and 5 μL of the dilution was added to a 50 μL reaction so that the highest compound concentration was 100 μM FAC and the concentration of DMSO was 1% in all wells. The plates were read on a Tecan Infinite M1000 microplate reader with excitation 340 nm and emission 460 nm. Data were analyzed in Graph Pad Prism. $IC_{50}$ values were determined by plotting % inhibition versus log compound concentration and using a one site dose response model. Raw data signals were normalized using 1% DMSO as 0% control and no enzyme as 100% inhibitor control. Data for the compounds tested are reported in Table 4.

C. hDPP9 Inhibition Assay

Compounds were tested in a biochemical inhibition assay using human dipeptidylpeptidase 9 (hDPP9) enzyme at 0.4 nM FAC (BPS Bioscience, #80090) and the substrate Ala-Pro-amino-methylcoumarin (BPS Bioscience #80305) at 5 μM FAC. The enzymatic reactions were conducted in duplicate at rt for 30 min in 50 μL DPP assay buffer (BPS Bioscience, #80300). Compound solutions (in DMSO) at 10 CR, 3 fold dilution series were prepared in assay buffer ten-fold higher than the final concentration, and 5 μL of the dilution was added to a 50 μL reaction so that the highest compound concentration was 100 μM FAC and the concentration of DMSO was 1% in all wells. The plates were read on a Tecan Infinite M1000 microplate reader with excitation 340 nm and emission 460 nm. Data were analyzed in Graph Pad Prism. $IC_{50}$ values were determined by plotting % inhibition versus log compound concentration and using a one site dose response model. Raw data signals were normalized using 1% DMSO as 0% control and no enzyme as 100% inhibitor control. Data for the compounds tested are reported in Table 4.

TABLE 4

| Example | hDPP7 $IC_{50}$ (nM)[1] | hDPP8 $IC_{50}$ (nM)[1] | hDPP9 $IC_{50}$ (nM)[1] |
|---|---|---|---|
| 8 | >100000 | 3300 | 400 |
| 9 | >100000 | 5100 | 640 |
| 27 | >100000 | 4300 | 1100 |
| 67 | 33000 | 13000 | 1900 |
| 68 | >100000 | 6600 | 1500 |
| 69 | >100000 | 7500 | 950 |
| 70 | >100000 | 4700 | 1400 |
| 71 | >100000 | 5900 | 1900 |
| 72 | >100000 | 6600 | 2500 |
| 80 | >100000 | 3500 | 1400 |
| 110 | >100000 | 430 | 250 |
| 111 | >100000 | 950 | 410 |
| 151 | >100000 | 3800 | 2000 |
| 163 | >100000 | 3900 | 1500 |
| 171 | >100000 | 3000 | 630 |

[1] $IC_{50}$ is reported after single measurement (n = 1).

Example 234: Metabolic Stability Assays

A. Aldehyde Oxidase (AO) Metabolism Assay 1

AO-mediated metabolism was measured essentially as described in *Drug Metab. Disp.* 2010, 38,1322. Human liver cytosol (Corning life sciences, UltraPool Human Cytosol 150, Product 452115) in phosphate buffer, pH 7.4, was pre-incubated for 5 min at 37° C. shaking at 900 rpm. The reactions were initiated by addition of pre-diluted test compounds including positive control, zaleplon, and incubated at 37° C. with final conditions 2.5 mg/mL human liver cytosolic fraction, 1 μM test compound, 0.01% DMSO and 0.09% MeCN. The samples were incubated for 120 min with time points taken at 0, 10, 30, 60, 90 and 120 min. The aliquots (25 μL) were precipitated with 100 μL MeCN containing internal standard (44(2'-(1H-tetrazol-5-yl)-[1,1'-biphenyl]-4-yl)methoxy)-2-ethylquinoline, (*J Med Chem* 1992, 35, 4027), centrifuged at 3500 rpm for 10 min and the supernatant diluted 1 in 7 (v/v) with ultra-pure HPLC water before analysis by LC-MS/MS. All incubations were carried out in duplicate. The in vitro elimination rate constant corresponding to parent compound depletion was determined for each reaction using the 1st order decay calculation in Microsoft Excel Sheet. In some cases the experiment was conducted additionally in presence of an aldehyde oxidase inhibitor: The cytosol mix was pre-incubated with 3 μM raloxifene shaking at 900 rpm for min at 37° C. prior to addition of test compound. Data for the compounds tested are reported in Table 5.

B. Aldehyde Oxidase (AO) Metabolism Assay 2

AO-mediated metabolism was measured essentially as described in *Drug Metab. Disp.* 2010, 38,1322. Human liver cytosol (BioreclamationIVT, stored at −80° C. prior to use, protein concentration 2.5 mg/mL) and 0.1 M phosphate buffer (with 0.1 mM EDTA) pH 7.4 is pre-incubated at 37° C. The reaction was initiated by addition of test compound (final substrate concentration 1 μM, final DMSO concentration 0.3% and final incubation volume 500 μL). Phthalazine (known to be metabolized by AO) was used as a control compound. Test compounds were incubated for 0, 5, 15, 30, 60 and 120 min. The reactions were stopped by removing an aliquot of incubate into organic solvent containing internal standard at the appropriate time points. The termination plates were centrifuged at 2500 rpm for 30 min at 4° C. to precipitate the protein. Sample supernatants were combined in cassettes of up to four compounds and analyzed using generic LC MS/MS conditions. From a plot of ln peak area ratio (compound peak area/internal standard peak area) against time, the gradient of the line was determined. Subsequently, half-life and intrinsic clearance were calculated using the equations below:

Elimination rate constant ($k$)=(−gradient)

Half-life ($t_{1/2}$)(min)=0.693/$k$

Intrinsic clearance ($CL_{int}$)(μL/min/mg protein)=$V$×0.693/$t_{1/2}$ where V=Incubation volume (jut)/protein (mg)

The percentage of the parent compound remaining at each time point, along with the intrinsic clearance value ($CL_{int}$), half-life and standard error of the $CL_{int}$ were reported. Data for the compounds tested are reported in Table 5.

TABLE 5

| Example | AO-assay 1 $CL_{int}$ (μL/min/mg)[1] | AO-assay 2 $CL_{int}$ (μL/min/mg)[1] |
|---|---|---|
| 8 | 0.50 | |
| 9 | <0.50 | |
| 22 | | 0.07 |
| 27 | | 0.12 |
| 40 | | 1.1 |
| 47 | | 1.3 |
| 67 | <0.50 | 0.25 |
| 68 | <0.50 | |
| 69 | <0.50 | |
| 71 | | 0.56 |
| 107 | | 0 |
| 129 | | 0.76 |
| 151 | | 0.32 |
| 163 | | 0.30 |
| 170 | <0.50 | 0.18 |
| 171 | <0.50 | |
| 172 | <0.50 | |
| 173 | | 0.58 |
| 175 | 0.60 | |
| 196 | <0.50 | |
| 205 | | 0.68 |
| Compound A[2] | 3.8 | |
| Compound C[3] | 5.3 | |

[1]$CL_{int}$ is reported after single measurement (n = 1).
[2]Compound A ((S)-N-(2-(2-cyano-4,4-difluoropyrrolidin-1-yl)-2-oxoethyl)quinoline-4-carboxamide, *J Med Chem* 2014, 57, 3053)
[3]Compound C (R)-N-(2-(4-cyanothiazolidin-3-yl)-2-oxoethyl)quinoline-4-carboxamide C. Human Liver Microsomes (HLM)

Metabolic stability in HLM was measured as described in *J Comput Aided Mol Des* 2015, 29, 795. Data for the compounds tested are reported in Table 6.

D. Rat Hepatocytes (rHep)

Metabolic stability in rat hepatocytes was measured as described in *J Comput Aided Mol Des* 2015, 29, 795. Data for the compounds tested are reported in Table 6.

E. Human Hepatocytes (hHep)

Metabolic stability in human hepatocytes was measured as described in *Xenobiotica* 2010, 40, 637. Data for the compounds tested are reported in Table 6.

TABLE 6

| Example | HLM $CL_{int}$[1] (μL/min/mg) | rHep $CL_{int}$[2] (μL/min/1E6) | hHep $CL_{int}$[3] (μL/min/1E6) |
|---|---|---|---|
| 1 | 14 | 4.9 | <1 |
| 2 | 22 | 3 | <1 |
| 3 | 75 | 28 | |
| 4 | 50 | 14 | |
| 5 | 93 | 32 | |
| 6 | NV | 100 | |
| 7 | 31 | 2.6 | |
| 8 | <3 | 2.7 | <1 |
| 9 | 21 | 4.3 | <1 |
| 10 | 130 | 41 | |
| 11 | <3 | 2.5 | |
| 12 | 6.4 | <1 | |
| 13 | 12 | 5.4 | |
| 14 | <3 | <1 | |
| 15 | 43 | 11 | |
| 16 | <3 | <1 | |
| 17 | 48 | 16 | |
| 18 | 22 | 6 | 3.7 |
| 19 | 190 | 63 | |
| 20 | 290 | 120 | |
| 21 | 15 | 17 | <1 |
| 22 | 21 | 14 | 2.9 |
| 23 | 25 | 27 | |
| 24 | 14 | 20 | <1 |
| 25 | 23 | 14 | |
| 26 | 31 | 7.6 | |
| 27 | 16 | 8.3 | <1.4 |
| 28 | <3 | 13 | 2.6 |
| 29 | 18 | 4.5 | <1 |
| 30 | <3 | 7.2 | <1 |
| 31 | 45 | 14 | |
| 32 | 40 | 19 | 4.1 |
| 33 | 92 | 44 | |
| 34 | 38 | 33 | |
| 35 | 63 | 64 | |
| 36 | 48 | 19 | |
| 37 | 66 | 30 | |
| 38 | >300 | >300 | |
| 39 | 120 | 31 | |
| 40 | 23 | 15 | <1 |
| 41 | 30 | 12 | |
| 42 | 21 | 7.6 | 2.7 |
| 43 | 36 | 9.1 | |
| 44 | 220 | 160 | |
| 45 | 260 | 160 | |
| 46 | 190 | 72 | |
| 47 | 32 | 33 | |
| 48 | 89 | 51 | |
| 49 | 58 | 48 | |
| 50 | 13 | 20 | 1.7 |
| 51 | 14 | 24 | |
| 52 | 22 | 21 | |
| 53 | 120 | 71 | |
| 54 | 57 | 49 | |
| 55 | 55 | 63 | |
| 56 | >300 | 160 | |
| 57 | >300 | >300 | |
| 58 | 140 | 72 | |
| 59 | >300 | 91 | |
| 60 | 210 | 120 | |

TABLE 6-continued

| Example | HLM $CL_{int}$[1] (μL/min/mg) | rHep $CL_{int}$[2] (μL/min/1E6) | hHep $CL_{int}$[3] (μL/min/1E6) |
|---|---|---|---|
| 61 | 47 | 26 | |
| 62 | 31 | 46 | |
| 63 | 180 | 30 | |
| 64 | 56 | 29 | |
| 65 | 150 | 110 | |
| 66 | <3 | <1 | |
| 67 | <5.2 | 3.4 | <1 |
| 68 | 12 | 5.2 | <1 |
| 69 | 5.6 | 2.6 | <1 |
| 70 | 18 | 5.9 | 2 |
| 71 | 7 | 4 | <1 |
| 72 | 9.7 | 2.7 | <1 |
| 73 | 32 | 11 | |
| 74 | 28 | 13 | <1 |
| 75 | 9 | 6.7 | |
| 76 | 4.2 | 3.5 | |
| 77 | 7.1 | 5.4 | |
| 78 | 23 | 12 | 1.2 |
| 79 | 21 | 6.2 | |
| 80 | 7.5 | 2 | <1 |
| 81 | 17 | 8.1 | |
| 82 | 39 | 11 | |
| 83 | 70 | 9.2 | |
| 84 | 64 | 26 | |
| 85 | 260 | 35 | |
| 86 | 160 | 44 | |
| 87 | 52 | 12 | |
| 88 | 22 | 8.6 | <1 |
| 89 | 16 | 7.1 | <1 |
| 90 | 100 | 20 | 4.6 |
| 91 | <3 | 8 | |
| 92 | 14 | 1.7 | <1 |
| 93 | <3 | 2.6 | |
| 94 | 7.1 | 2.2 | <1 |
| 95 | 63 | 13 | |
| 96 | 71 | 15 | |
| 97 | 32 | 19 | |
| 98 | 26 | 13 | 1.8 |
| 99 | 16 | 8.1 | 1.9 |
| 100 | NV | 280 | |
| 101 | 8.6 | 2.3 | |
| 102 | 12 | 10 | 1.2 |
| 103 | 54 | 23 | |
| 104 | 130 | 28 | |
| 105 | 180 | 18 | |
| 106 | 47 | 21 | |
| 107 | 42 | 8.1 | 2.8 |
| 108 | 53 | 12 | |
| 109 | | | |
| 110 | 39 | 3.3 | |
| 111 | 20 | <1 | |
| 112 | <3 | <1 | <1 |
| 113 | <3 | 11 | <1.5 |
| 114 | 170 | 36 | |
| 115 | 120 | 20 | |
| 116 | 98 | 15 | |
| 117 | 170 | 29 | |
| 118 | 41 | 21 | |
| 119 | 68 | 27 | |
| 120 | 100 | 27 | |
| 121 | 43 | 13 | |
| 122 | <3 | <1 | |
| 123 | 32 | 7.1 | 1.6 |
| 124 | 12 | 14 | |
| 125 | 14 | 7.4 | |
| 126 | 16 | 10 | |
| 127 | 11 | 8.2 | |
| 128 | 27 | 11 | |
| 129 | <3 | 1.4 | |
| 130 | 54 | 11 | |
| 131 | 97 | 16 | |
| 132 | 38 | 8.5 | |
| 133 | 40 | 8.8 | |
| 134 | 210 | 74 | |
| 135 | 23 | 6.8 | |
| 136 | <3 | 4.8 | |
| 137 | 70 | 17 | |
| 138 | 20 | 33 | |
| 139 | 72 | 13 | |
| 140 | 32 | 7.7 | |
| 141 | 54 | 11 | |
| 142 | 43 | 6.7 | |
| 143 | 40 | 13 | |
| 144 | 14 | 7 | |
| 145 | 40 | 10 | |
| 146 | 11 | 4.3 | |
| 147 | 17 | 2.9 | |
| 148 | 53 | 12 | |
| 149 | 56 | 7 | |
| 150 | 49 | 5 | |
| 151 | 10 | 4.5 | <1 |
| 152 | 23 | 8.2 | |
| 153 | <3 | <1 | |
| 154 | <3 | 2.7 | |
| 155 | 19 | 3.2 | |
| 156 | 140 | 120 | |
| 157 | 7.3 | <1 | <1 |
| 158 | 17 | 4.7 | |
| 159 | 61 | 47 | |
| 160 | 45 | 33 | |
| 161 | 6.7 | 8.5 | |
| 162 | 44 | 3.4 | |
| 163 | 5.6 | <1 | <1 |
| 164 | 22 | 8.1 | |
| 165 | <3 | <1 | |
| 166 | <3 | <1 | <1 |
| 167 | <3 | <1 | |
| 168 | | | |
| 169 | 18 | 8.8 | |
| 170 | 4.9 | 4.2 | 1.3 |
| 171 | 7 | 3.1 | <1 |
| 172 | 22 | 3.7 | <1 |
| 173 | 12 | 2.2 | |
| 174 | 12 | 7.2 | |
| 175 | 10 | 9.7 | |
| 176 | 92 | 15 | |
| 177 | 13 | 7.4 | |
| 178 | 16 | 7.2 | |
| 179 | 140 | 47 | |
| 180 | 110 | 3 | |
| 181 | <3 | 2 | <1 |
| 182 | 100 | 26 | |
| 183 | 49 | 19 | |
| 184 | <3 | <1 | <1 |
| 185 | 58 | 15 | |
| 186 | 70 | 24 | |
| 187 | 190 | 140 | |
| 188 | 3.1 | 1.8 | <1 |
| 189 | 11 | <1 | |
| 190 | <3 | <1 | |
| 191 | 94 | 5.3 | |
| 192 | 28 | 2.9 | |
| 193 | 53 | 11 | |
| 194 | 78 | 44 | |
| 195 | <3 | 1.8 | |
| 196 | <3 | 4.7 | |
| 197 | 15 | 5.3 | |
| 198 | 20 | 22 | |
| 199 | >300 | 250 | |
| 200 | >300 | >300 | |
| 201 | <3 | <1 | |
| 202 | 7.7 | <1 | |
| 203 | 12 | 2.9 | |
| 204 | 8 | 1.8 | |
| 205 | 26 | 17 | <1.1 |
| 206 | 46 | 130 | |
| 207 | <3 | 1.4 | |
| 208 | 72 | 12 | |
| 209 | 170 | 52 | |
| 210 | 220 | 250 | |
| 211 | 200 | 190 | |
| 212 | 110 | 57 | |

TABLE 6-continued

| Example | HLM $CL_{int}$[1] (μL/min/mg) | rHep $CL_{int}$[2] (μL/min/1E6) | hHep $CL_{int}$[3] (μL/min/1E6) |
|---|---|---|---|
| 213 | 31 | 19 | |
| 214 | 27 | 15 | |
| 215 | 8 | 3.9 | |
| 216 | 58 | 17 | |
| 217 | >300 | 37 | |
| 218 | 37 | 18 | |
| 219 | 160 | 75 | |
| 220 | <3 | 4.4 | |
| 221 | <3 | 3.8 | |
| 222 | 40 | 4.2 | |
| 223 | 57 | 51 | |
| 224 | <3 | <1 | |
| 225 | 110 | 37 | |
| 226 | 94 | 44 | |
| 227 | 17 | 2.8 | |
| 228 | <3 | 9 | <1 |
| 229 | <3 | 15 | |
| 230 | <3 | 2.8 | |

[1] $CL_{int}$ is reported after single measurement (n = 1) or as an average for multiple measurements (n = 2-3).
[2] $CL_{int}$ is reported after single measurement (n = 1) or as geometric mean for multiple measurements (n = 2-3).
[3] $CL_{int}$ is reported after single measurement (n = 1) or as geometric mean for multiple measurements (n = 2).

Example 235: Caco-2 Cell Permeability

Caco-2 cell permeability was measured as described in *Mol Pharm* 2017, 14, 1601. Data for the compounds tested are reported in Table 7.

TABLE 7

| Example | Caco2 AB Intrinsic $P_{app}$[1] (1E−6 · cm/s) | Caco2 Bidirectional (ABBA) A to B $P_{app}$[1] (1E−6 · cm/s) | Caco2 Bidirectional (ABBA) B to A $P_{app}$[1] (1E−6 · cm/s) | Caco2 Bi-directional (ABBA) Efflux Ratio |
|---|---|---|---|---|
| 1 | | 4.7 | 29 | 6.1 |
| 2 | 23 | 0.98 | 31 | 32 |
| 4 | | 1.6 | 28 | 18 |
| 5 | | 1.9 | 32 | 17 |
| 7 | | 0.34 | 20 | 59 |
| 8 | 17 | 1.8 | 28 | 16 |
| 9 | 18 | 1.9 | 23 | 12 |
| 11 | | 0.34 | 9.8 | 29 |
| 12 | | 0.29 | 19 | 65 |
| 14 | | 0.15 | 2.4 | 16 |
| 15 | | 0.30 | 13 | 45 |
| 16 | | 0.16 | 4.2 | 26 |
| 18 | 13 | 0.90 | 31 | 34 |
| 21 | | 3.7 | 23 | 6.2 |
| 22 | 41 | 6.9 | 26 | 3.8 |
| 24 | | 3.5 | 33 | 9.3 |
| 27 | 30 | 4.9 | 29 | 5.9 |
| 28 | 21 | 1.6 | 20 | 12 |
| 29 | 26 | 3.7 | 37 | 10 |
| 30 | 15 | 3.1 | 30 | 9.6 |
| 32 | | 8.7 | 28 | 3.3 |
| 33 | | 7.5 | 19 | 2.5 |
| 40 | 20 | 3 | 28 | 9.3 |
| 41 | 16 | | | |
| 42 | | 2.8 | 33 | 12 |
| 50 | | 0.83 | 27 | 32 |
| 67 | 6 | 1 | 19 | 19 |
| 68 | 16 | 2.5 | 21 | 8.3 |
| 69 | 7.6 | 0.79 | 22 | 28 |
| 70 | | 1.4 | 26 | 18 |
| 71 | | 0.78 | 23 | 30 |
| 72 | | 1.3 | 24 | 19 |
| 74 | | 1.8 | 53 | 29 |
| 75 | | 0.77 | 17 | 21 |

TABLE 7-continued

| Example | Caco2 AB Intrinsic $P_{app}$[1] (1E−6 · cm/s) | Caco2 Bidirectional (ABBA) A to B $P_{app}$[1] (1E−6 · cm/s) | Caco2 Bidirectional (ABBA) B to A $P_{app}$[1] (1E−6 · cm/s) | Caco2 Bi-directional (ABBA) Efflux Ratio |
|---|---|---|---|---|
| 76 | | 0.64 | 20 | 31 |
| 77 | | 0.57 | 16 | 29 |
| 78 | | 1.2 | 27 | 21 |
| 79 | | 1.1 | 33 | 29 |
| 80 | | 0.81 | 25 | 31 |
| 81 | | 1 | 25 | 24 |
| 87 | | 1.4 | 29 | 21 |
| 88 | 13 | 1.3 | 29 | 23 |
| 89 | 5.4 | 0.38 | 18 | 47 |
| 90 | | 1.2 | 19 | 16 |
| 91 | | 0.90 | 30 | 33 |
| 92 | | 0.12 | 4.2 | 35 |
| 93 | | 0.33 | 17 | 50 |
| 94 | | 0.15 | 4.4 | 29 |
| 97 | | 0.52 | 23 | 45 |
| 98 | 8.6 | 0.71 | 18 | 25 |
| 99 | | 0.46 | 21 | 46 |
| 102 | 9 | 0.97 | 21 | 22 |
| 107 | | 0.78 | 25 | 32 |
| 108 | | 1.4 | 22 | 16 |
| 111 | | 0.17 | 10 | 61 |
| 112 | <0.24 | 0.51 | 3 | 6 |
| 113 | 20 | 1.9 | 23 | 12 |
| 122 | | 0.20 | 10 | 50 |
| 123 | 14 | 0.17 | 29 | 170 |
| 124 | | 0.65 | 39 | 59 |
| 128 | | 0.57 | 26 | 45 |
| 129 | | 0.39 | 21 | 54 |
| 135 | | 4.4 | 29 | 6.5 |
| 138 | | 5.5 | 32 | 5.8 |
| 147 | | 2.7 | 40 | 15 |
| 151 | 9.5 | 2.6 | 30 | 11 |
| 152 | | 3.2 | 25 | 7.8 |
| 153 | | 0.82 | 23 | 28 |
| 154 | | 0.32 | 12 | 37 |
| 155 | | 4.2 | 27 | 6.5 |
| 157 | | 2 | 29 | 15 |
| 163 | 8.7 | 0.99 | 22 | 22 |
| 165 | 0.51 | | | |
| 166 | 2 | 0.56 | 13 | 24 |
| 167 | | 0.13 | 9.5 | 74 |
| 170 | 10 | 1.4 | 24 | 17 |
| 171 | 3.8 | 0.27 | 22 | 81 |
| 172 | | 0.26 | 21 | 84 |
| 173 | | 0.18 | 24 | 130 |
| 174 | | 0.54 | 25 | 46 |
| 175 | | 0.52 | 6.4 | 12 |
| 177 | | 1.3 | 22 | 17 |
| 181 | <0.20 | 0.24 | 3.3 | 13 |
| 184 | 0.10 | 0.25 | 0.78 | 3.1 |
| 188 | 0.28 | 0.18 | 3.7 | 21 |
| 189 | | 0.29 | 13 | 46 |
| 190 | | 0.32 | 7.6 | 24 |
| 192 | | 0.51 | 39 | 76 |
| 195 | | 0.40 | 4.8 | 12 |
| 196 | | 0.63 | 10 | 17 |
| 198 | | 3.4 | 36 | 11 |
| 201 | 4.8 | | | |
| 202 | 5.2 | | | |
| 203 | | 0.40 | 8 | 20 |
| 204 | | 0.44 | 8.5 | 19 |
| 205 | 25 | 3.4 | 23 | 6.9 |
| 207 | | 2.3 | 30 | 13 |
| 215 | | 0.48 | 29 | 59 |
| 216 | | 0.62 | 40 | 65 |
| 220 | | 0.29 | 16 | 56 |
| 224 | 1.2 | | | |
| 228 | 0.9 | 25 | 27 | 0.9 |
| 229 | 0.7 | 22 | 32 | 0.7 |
| 230 | 2 | 34 | 17 | 2 |

[1] $P_{app}$ is reported after single measurement (n = 1) or as an average for multiple measurement (n = 2-4).

Example 236: Kinetic Solubility

Kinetic solubility was measured as described in *Comput Aided Mol Des* 2015, 29, 795. Data for the compounds tested are reported in Table 8.

TABLE 8

| Example | Solubility (μM)[1] |
|---|---|
| 1 | >1000 |
| 2 | 83 |
| 3 | 700 |
| 4 | 55 |
| 5 | 11 |
| 6 | 120 |
| 7 | >1000 |
| 8 | 680 |
| 9 | 310 |
| 10 | 270 |
| 11 | 170 |
| 12 | 830 |
| 13 | 27 |
| 14 | 830 |
| 15 | 890 |
| 16 | 170 |
| 17 | 250 |
| 18 | 93 |
| 19 | 480 |
| 20 | 900 |
| 21 | 390 |
| 22 | 460 |
| 23 | 63 |
| 24 | 500 |
| 25 | 130 |
| 26 | 15 |
| 27 | 720 |
| 28 | 73 |
| 29 | 560 |
| 30 | >1000 |
| 31 | 180 |
| 32 | 240 |
| 33 | 85 |
| 34 | 770 |
| 35 | 600 |
| 36 | <98 |
| 37 | 210 |
| 38 | 33 |
| 39 | 22 |
| 40 | 290 |
| 41 | 620 |
| 42 | 850 |
| 43 | 52 |
| 44 | 140 |
| 45 | 340 |
| 46 | 190 |
| 47 | 57 |
| 48 | 18 |
| 49 | 13 |
| 50 | 33 |
| 51 | 56 |
| 52 | 57 |
| 53 | 2.6 |
| 54 | 13 |
| 55 | 11 |
| 56 | 5.9 |
| 57 | 150 |
| 58 | 5.8 |
| 59 | 40 |
| 60 | 160 |
| 61 | 670 |
| 62 | 640 |
| 63 | 690 |
| 64 | 130 |
| 65 | 49 |
| 66 | 210 |
| 67 | >860 |
| 68 | 180 |
| 69 | >1000 |
| 70 | 580 |

TABLE 8-continued

| Example | Solubility (μM)[1] |
|---|---|
| 71 | 990 |
| 72 | >1000 |
| 73 | 310 |
| 74 | 180 |
| 75 | 930 |
| 76 | >1000 |
| 77 | 850 |
| 78 | 190 |
| 79 | 610 |
| 80 | 980 |
| 81 | 900 |
| 82 | 970 |
| 83 | 840 |
| 84 | 940 |
| 85 | 800 |
| 86 | 640 |
| 87 | 910 |
| 88 | >980 |
| 89 | 910 |
| 90 | >1000 |
| 91 | >1000 |
| 92 | 810 |
| 93 | 300 |
| 94 | 920 |
| 95 | 960 |
| 96 | >1000 |
| 97 | 950 |
| 98 | >1000 |
| 99 | 800 |
| 100 | 36 |
| 101 | >1000 |
| 102 | >1000 |
| 103 | >1000 |
| 104 | 930 |
| 105 | >1000 |
| 106 | 700 |
| 107 | >1000 |
| 108 | 880 |
| 109 | |
| 110 | 950 |
| 111 | 330 |
| 112 | 670 |
| 113 | 71 |
| 114 | 4.5 |
| 115 | 0.59 |
| 116 | 490 |
| 117 | 25 |
| 118 | 20 |
| 119 | 1 |
| 120 | 0.92 |
| 121 | 44 |
| 122 | >1000 |
| 123 | 280 |
| 124 | 38 |
| 125 | 38 |
| 126 | 400 |
| 127 | 120 |
| 128 | 960 |
| 129 | 58 |
| 130 | 16 |
| 131 | 140 |
| 132 | 13 |
| 133 | <380 |
| 134 | 71 |
| 135 | 310 |
| 136 | 21 |
| 137 | 74 |
| 138 | 260 |
| 139 | 50 |
| 140 | 39 |
| 141 | 140 |
| 142 | 1.8 |
| 143 | 33 |
| 144 | 18 |
| 145 | 5.3 |
| 146 | 24 |
| 147 | 40 |

TABLE 8-continued

| Example | Solubility (μM)[1] |
|---|---|
| 148 | 3.4 |
| 149 | 130 |
| 150 | 77 |
| 151 | 850 |
| 152 | 810 |
| 153 | 930 |
| 154 | 850 |
| 155 | 400 |
| 156 | 100 |
| 157 | 62 |
| 158 | 8.9 |
| 159 | 550 |
| 160 | 1.8 |
| 161 | 84 |
| 162 | 140 |
| 163 | 160 |
| 164 | 64 |
| 165 | >1000 |
| 166 | >910 |
| 167 | 240 |
| 168 | |
| 169 | 26 |
| 170 | 11 |
| 171 | 320 |
| 172 | 100 |
| 173 | 32 |
| 174 | 800 |
| 175 | 640 |
| 176 | 800 |
| 177 | 40 |
| 178 | 6 |
| 179 | 110 |
| 180 | 170 |
| 181 | >1000 |
| 182 | 230 |
| 183 | 19 |
| 184 | 930 |
| 185 | 7 |
| 186 | 130 |
| 187 | 19 |
| 188 | 990 |
| 189 | 840 |
| 190 | >1000 |
| 191 | 400 |
| 192 | 530 |
| 193 | 940 |
| 194 | 480 |
| 195 | 830 |
| 196 | 700 |
| 197 | 6 |
| 198 | 38 |
| 199 | 85 |
| 200 | 81 |
| 201 | 90 |
| 202 | 140 |
| 203 | 540 |
| 204 | 480 |
| 205 | 270 |
| 206 | 26 |
| 207 | 280 |
| 208 | 1.6 |
| 209 | 970 |
| 210 | 150 |
| 211 | 110 |
| 212 | 16 |
| 213 | 100 |
| 214 | 230 |
| 215 | 350 |
| 216 | 710 |
| 217 | 410 |
| 218 | <0.16 |
| 219 | 2.5 |
| 220 | 460 |
| 221 | 360 |
| 222 | 120 |
| 223 | <1.6 |
| 224 | 50 |
| 225 | 2.2 |
| 226 | 4.5 |
| 227 | 852 |
| 228 | 879 |
| 229 | >1000 |
| 230 | >1000 |

[1]Solubility is reported after single measurement (n = 1) or as an average for multiple measurements (n = 2-3).

Example 237: FAP Target Engagement Enzyme Activity in Mouse Plasma

The effect of test compound on FAP enzyme activity in mouse plasma was evaluated in an enzymatic assay using the Fibroblast Activation Protein alpha (FAP) specific fluorogenic substrate dipeptide-Coumarin, Ala-Pro-AMC, (ARI-3144). In this assay, FAP cleaves Ala-Pro-AMC to release free AMC which is measured as a fluorescent signal that correlates with enzyme activity.

Male C57Bl/6 mice (Charles River, Germany), 8 weeks of age, were single housed in a temperature-controlled room with a 12-hour light/dark cycle (06:00-18:00 light). The mice had ad libitum access to water and rodent chow diet (R70, Lactamin, Kimstad, Sweden), and were acclimated for 5 days upon arrival. After acclimation, all mice received a single oral dose of test compound (3 or 10 mg/kg). Blood samples for whole blood compound exposure measurements were taken at 0.25, 0.5, 1, 2, 4, 8 and 24 h post oral dosing. Samples were collected in EDTA capillary tubes (20 μL, K2E, REF 19.447) and were transferred to a 96-deep well plate (NUNC, Thermo Discher Scientific) and stored at −20° C. until further analyses were performed. Blood samples for plasma FAP enzyme activity measurements were taken at 0.25, 0.5, 1, 2, 8 and 24 h post dosing. 25 μL of whole blood was collected in EDTA Microvette® CB 300 (K2E, REF 16.444.100) tubes, and were centrifuged at 4,000×g for min 10 μL of plasma was then transferred to PCR tubes and stored at −20° C. until further analysis was performed. All blood samples were taken by vena saphena puncture.

Recombinant human FAP (PB-17-1837, construct PL-17-0278, cd33-FAP (27-757)-6His, Mw85926 Da) was used as a standard for this assay. Protein was secreted from Sf21 cells (insect cells) in media, purified with affinity (batch mode, Ni excel resin) and size exclusion chromatography (Superdex200), concentrated and aliquoted to be frozen in liquid $N_2$ for storage at −80° C. Recombinant FAP was diluted in protein buffer (25 mM Tris/HCl, pH 7.6, 150 mM NaCl, 5% glycerol, 1 mM EDTA, 0.25 mM TCEP) and 5 μL aliquots (0.1 mg/mL, 1.15 μM) were stored at −80° C. Standards were prepared using 2-fold dilution steps, 8 concentrations, 4 replicates (FAC: 1.2 nM, 0.6 nM, 0.3 nM . . . ). The plates were read on a Beckman Paradigm reader with excitation 360 nm and emission 465 nm. Fluorescence measurements were performed with kinetic read every 5 minutes for 60 min at room temperature. Data were analyzed in Excel (IDBS XLfit Add-In) using a Linear Regression (y=k*x+m) model to prepare a human recombinant FAP standard curve.

On the day of the assay, plasma was diluted (1:2) to 20 μL volume in buffer (PBS, BSA) and 7.5 μL was transferred to the assay plate (384-well black, fluotrack PS, Greiner 781076). Ala-Pro-AMC (stock solution in 10 mM DMSO) was diluted in buffer (PBS, 0.1% BSA) to 150 μM concentration (180 μL stock solution to 12 mL buffer) and 7.5 μL added to the assay plate followed by a pipetting mix. The plates were read on a Beckman Paradigm reader with excitation 360 nm and emission 465 nm. Fluorescence measurements were performed with kinetic read every 5 minutes for 60 minutes at room temperature. As noted above, FAP cleaves Ala-Pro-AMC to release free AMC which is measured as a fluorescent signal.

The in vivo potency $IC_{50}$ of each test compound was then estimated by relating the plasma exposure C of the compound to target engagement E in plasma using the following equation:

$$E = E_0\left(1 - \frac{I_{max}C}{IC_{50} + C}\right)$$

where $E_0$ is the FAP baseline in plasma prior to dosing and $I_{max}$ is the maximum effect of the compound. Data from each target engagement experiment were considered separately and therefore slightly different estimates of FAP baseline for each compound were obtained. Full inhibition was achieved for all tested compounds at the earlier timepoints and therefore the parameter $I_{max}$ was fixed to 1 for all compounds. The parameter estimation was done in Phoenix WinNonlin Certara build 8.1.0.3530 with the algorithm 'Naïve pooled' as parameter estimation method. In vivo $IC_{50}$ estimates for the test compounds are reported in Table 9.

TABLE 9

| Example | In vivo Mouse $IC_{50}$ (nM)[1] |
|---|---|
| 27 | 1.4 |
| 67 | 0.18 |
| 68 | 19 |
| 69 | 2.1 |
| 71 | 2.8 |
| 72 | 7.2 |
| 80 | 9.0 |
| 113 | 2.0 |
| 151 | 3.3 |
| 163 | 3.0 |
| 169 | 1.4 |
| 170 | 8.7 |
| 171 | 2.5 |
| 205 | 1.2 |

Although specific embodiments and examples have been described above, these embodiments and examples are only illustrative and do not limit the scope of the disclosure. Changes and modifications can be made in accordance with ordinary skill in the art without departing from the disclosure in its broader aspects as defined in the following claims. For example, any embodiment described herein can be combined with any other suitable embodiment described herein to provide additional embodiments.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present disclosure. It is also understood that such values inherently contain variability necessarily resulting from the standard deviations found in their respective testing measurements.

One skilled in the art will also readily recognize that where members are grouped together in a common manner, such as in a Markush group, the present disclosure encompasses not only the entire group listed as a whole, but each member of the group individually and all possible subgroups of the main group. Additionally, for all purposes, the present disclosure encompasses not only the main group, but also the main group absent one or more of the group members. The present disclosure also envisages the explicit exclusion or disclaimer of one or more of any of the group members in the claimed disclosure.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_{(1-6)}$, includes the subranges $C_{(2-6)}$, $C_{(3-6)}$, $C_{(3-5)}$, $C_{(4-6)}$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

Reference to a "step" in this disclosure is used for convenience purposes only and does not categorize, define or limit the disclosure as set forth herein.

What is claimed is:

1. A compound having the structure of Formula (I):

(I)

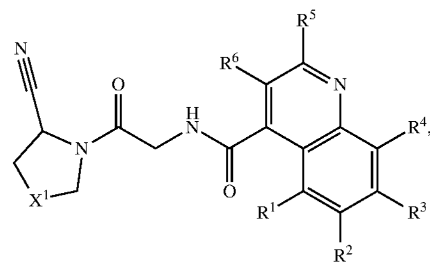

or a pharmaceutically acceptable salt thereof, wherein:

$X^1$ is selected from the group consisting of —S—, —S(O)—, and —S(O)$_2$—;

$R^1$ is selected from the group consisting of hydrogen, halogen, hydroxy, $C_{1-3}$-alkyl, and $C_{1-6}$-alkoxy;

$R^2$ is selected from the group consisting of:

(a) heterocyclyl containing a total of 4 to 10 ring atoms, wherein the heterocyclyl ring: (i) is a saturated, partially saturated, or completely unsaturated monocyclic or fused bicyclic ring, (ii) has one, two, or three nitrogen ring atoms with the remaining ring atoms being carbon, and (iii) is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$ alkyl, $C_{1-6}$-alkoxy, $C_{3-6}$-cycloalkoxy, $C_{1-3}$- alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkyl-carbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy;

(b) heterocyclyl containing a total of 5 to 10 ring atoms, wherein the heterocyclyl ring: (i) is a saturated, partially saturated, or completely unsaturated monocyclic or fused bicyclic ring, (ii) has (a) one nitrogen ring atom and one oxygen ring atom with the remaining ring atoms being carbon, or (b) one nitrogen ring atom and one sulfur ring atom with the remaining ring atoms being carbon, and (iii) is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen; and (c) spiro heterocyclyl containing a total of 6 to 11 ring atoms, wherein the spiro heterocyclyl: (i) contains two saturated rings, (ii) has: (a) one or two nitrogen ring atoms with the remaining ring atoms being carbon, (b) one or two nitrogen ring atoms and one or two oxygen ring atoms with the remaining ring atoms being carbon, or (c) one nitrogen ring atom and one sulfur ring atom with the remaining ring atoms being carbon, and (iii) is optionally substituted with one or more substituents independently selected from the group consisting of halogen, oxo, $C_{1-6}$-alkyl, $C_{1-6}$-haloalkyl, $C_{1-6}$-alkoxy, $C_{1-6}$-haloalkoxy, and $C_{1-6}$-alkylcarbonyl;

$R^3$ is selected from the group consisting of hydrogen, halogen, and $C_{1-3}$-alkyl;

$R^4$ is selected from the group consisting of hydrogen, halogen, and $C_{1-3}$-alkyl;

$R^5$ is selected from the group consisting of hydrogen, halogen, and $C_{1-3}$-alkyl; and $R^6$ is selected from the group consisting of hydrogen, halogen, and $C_{1-3}$-alkyl.

2. The compound of claim 1, or a pharmaceutically acceptable salt thereof, which is a compound having the structure of Formula (II):

(II)

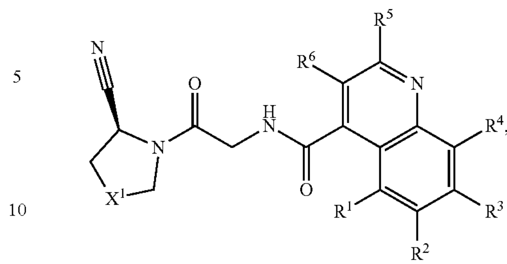

or a pharmaceutically acceptable salt thereof, wherein $X^1$, $R^1$, $R^2$, $R^3$, $R^4$, $R^5$, and $R^6$ are as defined in claim 1.

3. The compound of claim 2, or a pharmaceutically acceptable salt thereof, wherein $X^1$ is —S—.

4. The compound of claim 1, or a pharmaceutically acceptable salt thereof, which is a compound having the structure of Formula (III-A):

(III-A)

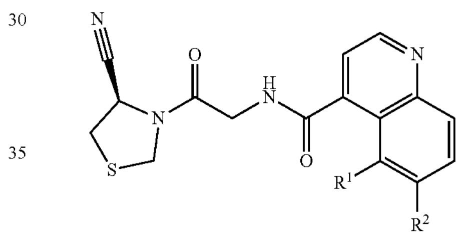

or a pharmaceutically acceptable salt thereof, wherein $R^1$ and $R^2$ are as defined in claim 1.

5. The compound of claim 1, or a pharmaceutically acceptable salt thereof, which is a compound having the structure of Formula (III-B):

(III-B)

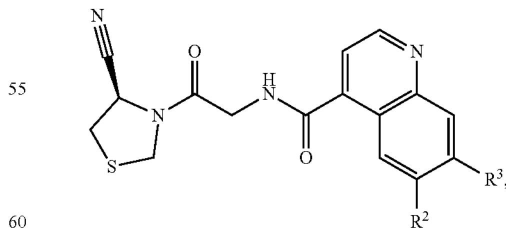

or a pharmaceutically acceptable salt thereof, wherein $R^2$ and $R^3$ are as defined in claim 1.

6. The compound of claim 1, or a pharmaceutically acceptable salt thereof, which is a compound having the structure of Formula (III-C):

(III-C)

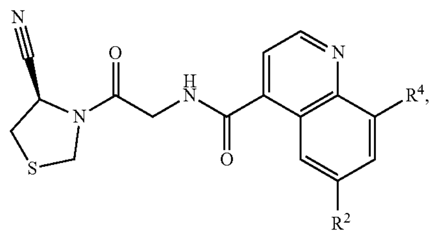

or a pharmaceutically acceptable salt thereof, wherein $R^2$ and $R^4$ are as defined in claim 1.

7. The compound of claim 1, or a pharmaceutically acceptable salt thereof, which is a compound having the structure of Formula (III-D):

(III-D)

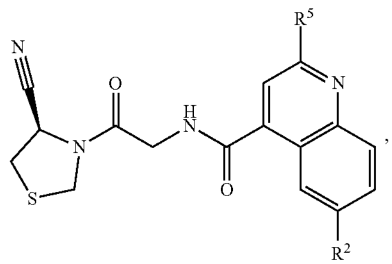

or a pharmaceutically acceptable salt thereof, wherein $R^2$ and $R^5$ are as defined in claim 1.

8. The compound of claim 1, or a pharmaceutically acceptable salt thereof, which is a compound having the structure of Formula (III-E):

(III-E)

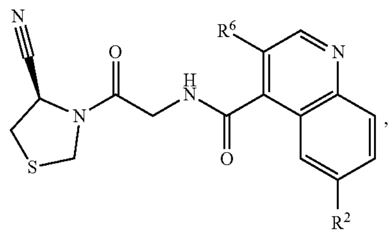

or a pharmaceutically acceptable salt thereof, wherein $R^2$ and $R^6$ are as defined in claim 1.

9. The compound of claim 2, or a pharmaceutically acceptable salt thereof, which is a compound having the structure of Formula (IV-A):

(IV-A)

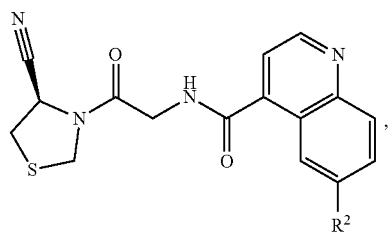

or a pharmaceutically acceptable salt thereof, wherein $R^2$ is as defined in claim 1.

10. The compound of claim 1, or a pharmaceutically acceptable salt thereof, wherein $R^2$ is heterocyclyl containing a total of 4 to 10 ring atoms, wherein the heterocyclyl ring: (i) is a saturated, partially saturated, or completely unsaturated monocyclic or fused bicyclic ring, (ii) has one, two, or three nitrogen ring atoms with the remaining ring atoms being carbon, and (iii) is optionally substituted with one or more substituents independently selected from the group consisting of halogen, hydroxy, oxo, cyano, $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl, and wherein: (a) the $C_{1-6}$-alkyl, $C_{3-6}$-cycloalkyl, $C_{3-6}$-cycloalkyl-$C_{1-3}$-alkyl, $C_{1-6}$-alkoxy, $C_{3-6}$-cycloalkoxy, $C_{1-3}$-alkoxy-$C_{1-3}$-alkyl, $C_{1-3}$-alkoxy-$C_{2-3}$-alkoxy, $C_{1-3}$-alkoxy-$C_{2-3}$-alkoxy-$C_{1-3}$-alkyl, $C_{1-3}$-alkylcarbonyl, $C_{3-6}$-cycloalkylcarbonyl, $C_{1-3}$-alkylcarbonylamino-$C_{1-3}$-alkyl, $C_{1-3}$-alkylsulfonyl-$C_{1-3}$-alkyl, phenyl, tolyl, $C_{1-3}$-alkoxyphenyl, phenyl-$C_{1-3}$-alkyl, $C_{1-3}$-alkoxyphenyl-$C_{1-3}$-alkyl, azetidinyl, pyrrolidinyl, piperidinyl, morpholinyl, tetrahydrofuranyl, tetrahydropyranyl, and tetrahydrooxepanyl may be further substituted with one or more halogen, and (b) the $C_{1-6}$-alkyl may be further substituted with one or more hydroxy.

11. The compound of claim 1, or a pharmaceutically acceptable salt thereof, wherein $R^2$ is heterocyclyl containing a total of 5 to 10 ring atoms, wherein the heterocyclyl ring: (i) is a saturated, partially saturated, or completely unsaturated monocyclic or fused bicyclic ring, (ii) has (a) one nitrogen ring atom and one oxygen ring atom with the remaining ring atoms being carbon, or (b) one nitrogen ring atom and one sulfur ring atom with the remaining ring atoms being carbon, and (iii) is optionally substituted with one or more substituents independently selected from the group consisting of halogen, cyano, oxo, $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl, and wherein the $C_{1-6}$-alkyl, $C_{3-6}$-cycloalkyl, $C_{1-6}$-alkoxy, $C_{1-3}$-alkoxy-$C_{1-3}$-alkyl, $C_{1-3}$-alkylcarbonyl-$C_{1-3}$-alkyl, and $C_{1-3}$-alkylsulfonyl-$C_{1-3}$-alkyl may be further substituted with one or more halogen.

12. The compound of claim 1, or a pharmaceutically acceptable salt thereof, wherein $R^2$ is spiro heterocyclyl containing a total of 6 to 11 ring atoms, wherein the spiro heterocyclyl: (i) contains two saturated rings, (ii) has: (a) one or two nitrogen ring atoms with the remaining ring atoms being carbon, (b) one or two nitrogen ring atoms and one or two oxygen ring atoms with the remaining ring atoms being carbon, or (c) one nitrogen ring atom and one sulfur ring atom with the remaining ring atoms being carbon, and (iii) is optionally substituted with one or more substituents independently selected from the group consisting of halogen, oxo, $C_{1-6}$-alkyl, $C_{1-6}$-haloalkyl, $C_{1-6}$-alkoxy, $C_{1-6}$-haloalkoxy, and $C_{1-6}$-alkylcarbonyl.

13. The compound of claim 1, or a pharmaceutically acceptable salt thereof, which is a compound having the structure of Formula (V):

(V)

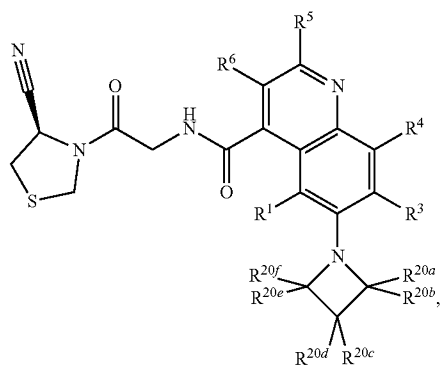

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{20a}$ and $R^{20b}$ are independently selected from the group consisting of hydrogen and $C_{1-3}$-alkyl;

$R^{20c}$ and $R^{20d}$ are independently selected from the group consisting of hydrogen, fluoro, hydroxy, $C_{1-3}$-alkyl, $C_{3-6}$-cycloalkyl, $C_{3-6}$-cycloalkyl-$C_{1-3}$-alkyl, $C_{1-3}$-alkoxy, $C_{3-6}$-cycloalkoxy, $C_{1-3}$-alkoxy-$C_{1-3}$-alkyl, phenyl, tolyl, phenyl-$C_{1-3}$-alkyl, morpholinyl, $C_{1-3}$-alkylsulfonyl-$C_{1-3}$-alkyl, and $C_{1-3}$-alkyl-carbonylamino-$C_{1-3}$-alkyl; and wherein the $C_{1-3}$-alkyl, $C_{3-6}$-cycloalkyl, $C_{3-6}$-cycloalkyl-$C_{1-3}$-alkyl, $C_{1-3}$-alkoxy, $C_{3-6}$-cycloalkoxy, $C_{1-3}$-alkoxy-$C_{1-3}$-alkyl, phenyl, and phenyl-$C_{1-3}$-alkyl may be further substituted with one or more halogen; and $R^{20e}$ and $R^{20f}$ are independently selected from the group consisting of hydrogen and $C_{1-3}$-alkyl.

14. The compound of claim 1, or a pharmaceutically acceptable salt thereof, which is a compound having the structure of Formula (VI):

(VI)

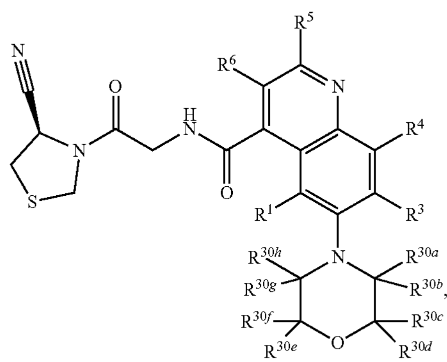

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{30a}$ and $R^{30b}$ are independently selected from the group consisting of hydrogen, $C_{1-3}$-alkyl, halo-$C_{1-3}$-alkyl, and $C_{1-3}$-alkoxy-$C_{1-3}$-alkyl;

$R^{30c}$ and $R^{30d}$ are independently selected from the group consisting of hydrogen, halogen, $C_{1-3}$-alkyl, halo-$C_{1-3}$-alkyl, $C_{1-3}$-alkoxy-$C_{1-3}$-alkyl, and $C_{1-3}$-alkylsulfonyl-$C_{1-3}$-alkyl;

$R^{30e}$ and $R^{30f}$ are independently selected from the group consisting of hydrogen, halogen, $C_{1-3}$-alkyl, halo-$C_{1-3}$-alkyl, $C_{1-3}$-alkoxy-$C_{1-3}$-alkyl, and $C_{1-3}$-alkylsulfonyl-$C_{1-3}$-alkyl; and $R^{30g}$ and $R^{30h}$ are independently selected from the group consisting of hydrogen, $C_{1-3}$-alkyl, halo-$C_{1-3}$-alkyl, and $C_{1-3}$-alkoxy-$C_{1-3}$-alkyl.

15. The compound of claim 1, or a pharmaceutically acceptable salt thereof, which is a compound having the structure of Formula (VII):

(VII)

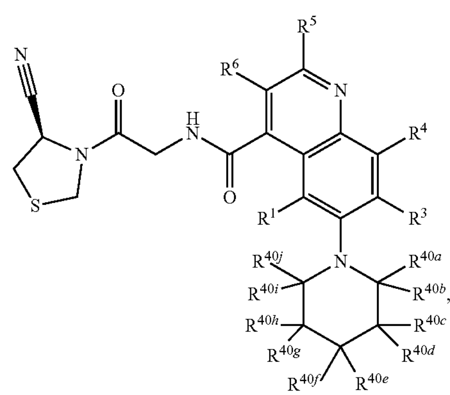

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{40a}$ and $R^{40b}$ are independently selected from the group consisting of hydrogen, $C_{1-3}$-alkyl, and halo-$C_{1-3}$-alkyl;

$R^{40c}$ and $R^{40d}$ are independently selected from the group consisting of hydrogen, fluoro, $C_{1-3}$-alkyl, halo-$C_{1-3}$-alkyl, and $C_{1-3}$-alkoxy;

$R^{40e}$ and $R^{40f}$ are independently selected from the group consisting of hydrogen, fluoro, hydroxy, oxo, $C_{1-3}$-alkyl, halo-$C_{1-3}$-alkyl, cyclopropyl, and $C_{1-3}$-alkoxy;

$R^{40g}$ and $R^{40h}$ are independently selected from the group consisting of hydrogen, fluoro, $C_{1-3}$-alkyl, halo-$C_{1-3}$-alkyl, and $C_{1-3}$-alkoxy; and $R^{40i}$ and $R^{40j}$ are independently selected from the group consisting of hydrogen, $C_{1-3}$-alkyl, and halo-$C_{1-3}$-alkyl.

16. The compound of claim 1, or a pharmaceutically acceptable salt thereof, which is a compound having the structure of Formula (VIII):

(VIII)

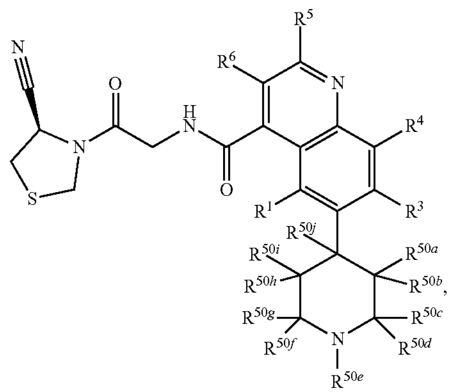

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{50a}$ and $R^{50b}$ are independently selected from the group consisting of hydrogen, fluoro, $C_{1-3}$-alkyl, halo-$C_{1-3}$-alkyl, and $C_{1-3}$-alkoxy;

$R^{50c}$ and $R^{50d}$ are independently selected from the group consisting of hydrogen, $C_{1-3}$-alkyl, and halo-$C_{1-3}$-alkyl, or together are oxo;

$R^{50e}$ is selected from the group consisting of hydrogen, $C_{1-3}$-alkyl, halo-$C_{1-3}$-alkyl, $C_{1-3}$-alkoxy-$C_{2-3}$-alkyl, $C_{1-3}$-alkyl-carbonyl, and $C_{3-6}$-cycloalkyl-carbonyl;

$R^{50f}$ and $R^{50g}$ are independently selected from the group consisting of hydrogen, $C_{1-3}$-alkyl, and halo-$C_{1-3}$-alkyl, or together are oxo;

$R^{50h}$ and $R^{50i}$ are independently selected from the group consisting of hydrogen, fluoro, $C_{1-3}$-alkyl, halo-$C_{1-3}$-alkyl, and $C_{1-3}$-alkoxy; and $R^{50j}$ is selected from the group consisting of hydrogen and fluoro.

17. The compound of claim 1, or a pharmaceutically acceptable salt thereof, which is a compound having the structure of Formula (IX):

(IX)

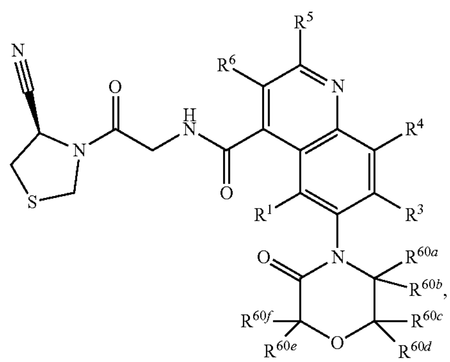

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{60a}$ and $R^{60b}$ are independently selected from the group consisting of hydrogen and $C_{1-3}$-alkyl;

$R^{60c}$ and $R^{60d}$ are independently selected from the group consisting of hydrogen and $C_{1-3}$-alkyl; and $R^{60e}$ and $R^{60f}$ are independently selected from the group consisting of hydrogen and $C_{1-3}$-alkyl.

18. The compound of claim 1, or a pharmaceutically acceptable salt thereof, which is a compound having the structure of Formula (X):

(X)

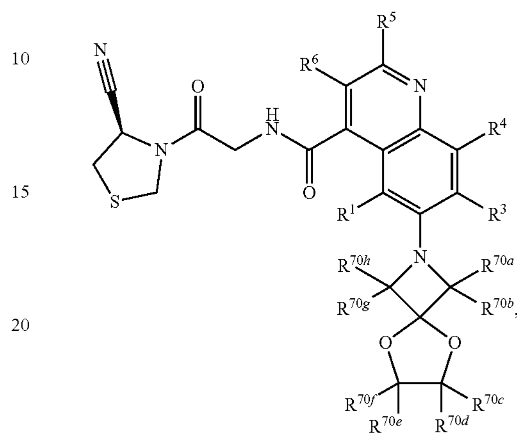

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{70a}$ and $R^{70b}$ are independently selected from the group consisting of hydrogen and $C_{1-3}$-alkyl;

$R^{70c}$ and $R^{70d}$ are independently selected from the group consisting of hydrogen and $C_{1-3}$-alkyl;

$R^{70e}$ and $R^{70f}$ are independently selected from the group consisting of hydrogen and $C_{1-3}$-alkyl; and $R^{70g}$ and $R^{70h}$ are independently selected from the group consisting of hydrogen and $C_{1-3}$-alkyl.

19. The compound of claim 1, or a pharmaceutically acceptable salt thereof, which is a compound having the structure of Formula (XI):

(XI)

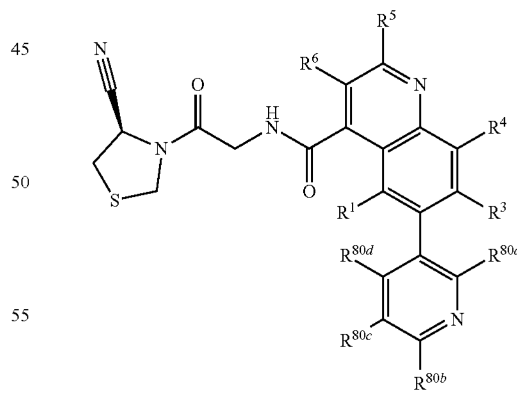

or a pharmaceutically acceptable salt thereof, wherein:

$R^1$, $R^3$, $R^4$, $R^5$, and $R^6$ are independently selected from the group consisting of hydrogen, chloro, fluoro, and methyl;

$R^{80a}$ is selected from the group consisting of hydrogen, fluoro, $C_{1-3}$-alkyl, halo-$C_{1-3}$-alkyl, and $C_{1-3}$-alkoxy;

$R^{80b}$ is selected from the group consisting of hydrogen, fluoro, $C_{1-3}$-alkyl, halo-$C_{1-3}$-alkyl, and $C_{1-3}$-alkoxy;

$R^{80c}$ is selected from the group consisting of hydrogen, fluoro, $C_{1-3}$-alkyl, halo-$C_{1-3}$-alkyl, and $C_{1-3}$-alkoxy; and $R^{80d}$ is selected from the group consisting of hydrogen, fluoro, $C_{1-3}$-alkyl, halo-$C_{1-3}$-alkyl, and $C_{1-3}$-alkoxy.

20. A pharmaceutical composition comprising a compound of claim 1, or a pharmaceutically acceptable salt thereof, and one or more pharmaceutically acceptable excipients.

* * * * *